US011045540B2

(12) United States Patent
Ciaramella

(10) Patent No.: US 11,045,540 B2
(45) Date of Patent: Jun. 29, 2021

(54) VARICELLA ZOSTER VIRUS (VZV) VACCINE

(71) Applicant: ModernaTX, Inc., Cambridge, MA (US)

(72) Inventor: Giuseppe Ciaramella, Sudbury, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/494,162

(22) PCT Filed: Mar. 15, 2018

(86) PCT No.: PCT/US2018/022643
§ 371 (c)(1),
(2) Date: Sep. 13, 2019

(87) PCT Pub. No.: WO2018/170270
PCT Pub. Date: Sep. 20, 2018

(65) Prior Publication Data

US 2020/0069793 A1 Mar. 5, 2020

Related U.S. Application Data

(60) Provisional application No. 62/490,112, filed on Apr. 26, 2017, provisional application No. 62/471,809, filed on Mar. 15, 2017.

(51) Int. Cl.

| | |
|---|---|
| ***A61K 39/25*** | (2006.01) |
| ***A61K 31/7105*** | (2006.01) |
| ***C12N 15/86*** | (2006.01) |
| ***A61K 9/127*** | (2006.01) |
| ***A61K 39/00*** | (2006.01) |
| ***A61K 49/00*** | (2006.01) |
| ***B82Y 5/00*** | (2011.01) |
| ***A61K 9/51*** | (2006.01) |
| ***A61K 47/28*** | (2006.01) |
| ***A61K 47/54*** | (2017.01) |

(52) U.S. Cl.
CPC .............. *A61K 39/25* (2013.01); *A61K 9/127* (2013.01); *A61K 9/51* (2013.01); *A61K 31/7105* (2013.01); *A61K 39/0012* (2013.01); *A61K 49/0091* (2013.01); *B82Y 5/00* (2013.01); *C12N 15/86* (2013.01); *A61K 9/1271* (2013.01); *A61K 9/1272* (2013.01); *A61K 47/28* (2013.01); *A61K 47/543* (2017.08); *A61K 47/544* (2017.08); *C12N 2710/16722* (2013.01); *C12N 2710/16734* (2013.01)

(58) Field of Classification Search
CPC ...... A61K 39/25; A61K 9/51; A61K 49/0091; A61K 39/0012; A61K 9/127; A61K 31/7105; A61K 47/544; A61K 47/543; A61K 47/28; A61K 9/1272; A61K 9/1271; B82Y 5/00; C12N 15/86; C12N 2710/16722; C12N 2710/16734; C07K 14/005; A61P 31/22
See application file for complete search history.

(56) References Cited

U.S. PATENT DOCUMENTS

| | | | |
|---|---|---|---|
| 6,500,419 B1 | 12/2002 | Hone et al. | |
| 6,514,948 B1 | 2/2003 | Raz et al. | |
| 6,610,044 B2 | 8/2003 | Mathiesen | |
| 7,001,890 B1 | 2/2006 | Wagner et al. | |
| 8,058,069 B2 * | 11/2011 | Yaworski ............. | A61K 31/713 435/458 |
| 8,569,256 B2 | 10/2013 | Heyes et al. | |
| 8,609,142 B2 | 12/2013 | Troiano et al. | |
| 8,613,954 B2 | 12/2013 | Zale et al. | |
| 8,617,608 B2 | 12/2013 | Zale et al. | |
| 8,710,200 B2 | 4/2014 | Schrum et al. | |
| 8,734,832 B2 | 5/2014 | O'Hagan et al. | |
| 8,734,853 B2 | 5/2014 | Sood et al. | |
| 8,754,062 B2 | 6/2014 | De Fougerolles et al. | |
| 8,822,663 B2 | 9/2014 | Schrum et al. | |
| 8,999,380 B2 | 4/2015 | Bancel et al. | |
| 9,221,891 B2 | 12/2015 | Bancel et al. | |
| 9,283,287 B2 | 3/2016 | Bancel et al. | |
| 9,303,079 B2 | 4/2016 | Bancel et al. | |
| 9,464,124 B2 | 10/2016 | Bancel et al. | |
| 9,512,456 B2 | 12/2016 | Wang et al. | |
| 9,597,380 B2 | 3/2017 | Chakraborty et al. | |

(Continued)

FOREIGN PATENT DOCUMENTS

| | | |
|---|---|---|
| AU | 652831 B2 | 9/1994 |
| CA | 2473135 A1 | 6/2003 |

(Continued)

OTHER PUBLICATIONS

Chen S, Tam YYC, Lin PJC, Sung MMH, Tam YK, Cullis PR. Influence of particle size on the in vivo potency of lipid nanoparticle formulations of siRNA. J Control Release. Aug. 10, 2016;235:236-244. Epub May 26, 2016.*

(Continued)

*Primary Examiner* — Rachel B Gill

(74) *Attorney, Agent, or Firm* — Wolf, Greenfield & Sacks, P.C.

(57) ABSTRACT

Aspects of the disclosure relate to nucleic acid vaccines. The vaccines include at least one RNA polynucleotides having an open reading frame encoding at least one varicella zoster virus (VZV) antigen. Methods for preparing and using such vaccines are also described.

20 Claims, 21 Drawing Sheets

Specification includes a Sequence Listing.

(56) References Cited

U.S. PATENT DOCUMENTS 9,868,691 B2 1/2018 Benenato et al.
9,872,900 B2 1/2018 Ciaramella et al.
10,064,934 B2 9/2018 Ciaramella et al.
10,064,935 B2 9/2018 Ciaramella et al.
10,124,055 B2 11/2018 Ciaramella et al.
10,207,010 B2 2/2019 Besin et al.
10,273,269 B2 4/2019 Ciaramella
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,653,712 B2 5/2020 Hoge
10,653,767 B2 5/2020 Ciaramella et al.
10,695,419 B2 6/2020 Ciaramella et al.
2001/0001066 A1 5/2001 Cezayirli et al.
2003/0032615 A1 2/2003 Felgner et al.
2005/0032730 A1 2/2005 Von Der Mulbe et al.
2005/0059624 A1 3/2005 Hoerr et al.
2005/0250723 A1 11/2005 Hoerr et al.
2006/0172003 A1 8/2006 Meers et al.
2006/0172966 A1 8/2006 Lipford et al.
2007/0280929 A1 12/2007 Hoerr et al.
2010/0130588 A1* 5/2010 Yaworski ........... C12N 15/1137 514/44 A
2010/0189729 A1 7/2010 Hoerr et al.
2010/0203076 A1 8/2010 Fotin-Mleczek et al.
2010/0239608 A1 9/2010 Von Der Mulbe et al.
2010/0303851 A1 12/2010 Hoerr et al.
2011/0117125 A1* 5/2011 Hope ................. A61K 31/7088 424/204.1
2011/0250225 A1 10/2011 Fotin-Mleczek et al.
2011/0269950 A1 11/2011 Von Der Mulbe et al.
2011/0311472 A1 12/2011 Hoerr et al.
2012/0101148 A1* 4/2012 Aking ..................... A61P 43/00 514/44 A
2012/0189700 A1 7/2012 Aguilar et al.
2012/0258046 A1 10/2012 Mutske
2013/0102034 A1 4/2013 Schrum et al.
2013/0121988 A1 5/2013 Hoerr et al.
2013/0142818 A1 6/2013 Baumhof et al.
2013/0171241 A1 7/2013 Geall
2013/0183355 A1 7/2013 Jain et al.
2013/0189351 A1 7/2013 Geall
2013/0195867 A1 8/2013 Hoerr et al.
2013/0195968 A1 8/2013 Geall et al.
2013/0195969 A1 8/2013 Geall et al.
2013/0202684 A1 8/2013 Geall et al.
2013/0236533 A1 9/2013 Von Andrian et al.
2013/0236974 A1 9/2013 De Fougerolles
2013/0245103 A1 9/2013 de Fougerolles et al.
2013/0259923 A1 10/2013 Bancel et al.
2013/0266640 A1 10/2013 De Fougerolles et al.
2013/0295043 A1 11/2013 Kallen et al.
2013/0336998 A1 12/2013 Kallen et al.
2014/0065228 A1 3/2014 Yaworski et al.
2014/0134201 A1 5/2014 Tureci et al.
2014/0147432 A1 5/2014 Bancel et al.
2014/0148502 A1 5/2014 Bancel et al.
2014/0193482 A1 7/2014 Bancel et al.
2014/0206752 A1 7/2014 Afeyan et al.
2014/0220083 A1 8/2014 Brito et al.
2014/0271829 A1 9/2014 Lilja et al.
2014/0378538 A1 12/2014 Bancel
2015/0051268 A1 2/2015 Bancel et al.
2015/0141499 A1 5/2015 Bancel et al.
2015/0307542 A1 10/2015 Roy et al.
2015/0315541 A1 11/2015 Bancel et al.
2016/0024140 A1 1/2016 Issa et al.
2016/0024141 A1 1/2016 Issa et al.
2016/0032273 A1 2/2016 Shahrokh et al.
2016/0038612 A1 2/2016 Hoge et al.
2016/0317647 A1 11/2016 Ciaramella et al.
2017/0202979 A1 7/2017 Chakraborty et al.
2017/0130255 A1 10/2017 Wang et al.
2017/0340724 A1 11/2017 Ciaramella et al.
2017/0340725 A1 11/2017 Ciaramella et al.
2018/0000953 A1 1/2018 Almarsson et al.
2018/0002393 A1 1/2018 Bancel et al.
2018/0006700 A1 1/2018 Heineman et al.
2018/0028645 A1 2/2018 Ciaramella et al.
2018/0028664 A1 2/2018 Besin et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0271970 A1 9/2018 Ciaramella et al.
2018/0273977 A1 9/2018 Mousavi et al.
2018/0274009 A1 9/2018 Marquardt et al.
2018/0280496 A1 10/2018 Ciaramella et al.
2018/0289792 A1 10/2018 Ciaramella et al.
2018/0303929 A1 10/2018 Ciaramella et al.
2018/0311336 A1 11/2018 Ciaramella et al.
2018/0311343 A1 11/2018 Huang et al.
2018/0312549 A1 11/2018 Ciaramella
2018/0318409 A1 11/2018 Valiante et al.
2018/0363019 A1 12/2018 Hoge
2018/0371047 A1 12/2018 Ticho et al.
2019/0002890 A1 1/2019 Martini et al.
2019/0008938 A1 1/2019 Ciaramella et al.
2019/0085368 A1 3/2019 Bancel et al.
2019/0099481 A1 4/2019 Ciaramella et al.
2019/0175517 A1 6/2019 Martini et al.
2019/0192646 A1 6/2019 Cohen et al.
2019/0192653 A1 6/2019 Hoge et al.
2019/0275170 A1 9/2019 Benenato et al.
2019/0298658 A1 10/2019 Benenato
2019/0314493 A1 10/2019 Ciaramella et al.
2019/0336595 A1 11/2019 Ciaramella
2019/0351040 A1 11/2019 Valiante et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0069793 A1 3/2020 Ciaramella
2020/0069794 A1 3/2020 Ciaramella et al.
2020/0071689 A1 3/2020 Miracco
2020/0109420 A1 4/2020 Brito et al.
2020/0129608 A1 4/2020 Ciaramella et al.
2020/0129615 A1 4/2020 Ciaramella et al.
2020/0239869 A1 7/2020 Issa et al.
2020/0254086 A1 8/2020 Hoge et al.
2020/0282047 A1 9/2020 Ciaramella et al.

FOREIGN PATENT DOCUMENTS

EP 1083232 B1 2/2005
EP 1301614 B1 11/2006
EP 1383556 B1 10/2007
EP 1905844 A2 2/2008
EP 1026253 B2 12/2012
EP 2188379 B1 1/2013
WO WO 1990/011092 A1 10/1990
WO WO 1991/007425 A1 5/1991
WO WO 1995/027069 A1 3/1995
WO WO 1999/052503 A2 10/1999
WO WO 2001/021810 A1 3/2001
WO WO 2004/058166 A2 7/2004
WO WO 2005/007689 A1 1/2005
WO WO 2008/014979 A3 2/2008
WO WO 2008/052770 A2 5/2008
WO WO 2008/083949 A2 7/2008
WO WO 2010/037408 A1 4/2010
WO WO 2010/042877 A1 4/2010
WO WO 2010/054406 A1 5/2010
WO WO 2010/088927 A1 8/2010
WO WO 2010/115046 A2 10/2010
WO WO 2011/005799 A2 1/2011
WO WO 2011/069529 A1 6/2011
WO WO 2011/069586 A1 6/2011
WO WO 2011/144358 A1 11/2011
WO WO 2012/006369 A2 1/2012
WO WO 2012/006380 A2 1/2012
WO WO 2012/019630 A1 2/2012
WO WO 2012/019780 A1 2/2012

(56) References Cited

FOREIGN PATENT DOCUMENTS

WO WO 2012/051211 A1 4/2012
WO WO 2012/075040 A2 6/2012
WO WO 2012/089225 A1 7/2012
WO WO 2012/106377 A3 8/2012
WO WO 2012/113513 A1 8/2012
WO WO 2012/116714 A1 9/2012
WO WO 2012/116715 A1 9/2012
WO WO 2012/116810 A1 9/2012
WO WO 2012/116811 A1 9/2012
WO WO 2013/006837 A1 1/2013
WO WO 2013/006838 A1 1/2013
WO WO 2013/006842 A2 1/2013
WO WO 2013/030778 A2 3/2013
WO WO 2013/052167 A2 4/2013
WO WO 2013/055905 A1 4/2013
WO WO 2013/056132 A2 4/2013
WO WO 2013/059496 A1 4/2013
WO WO-2013086373 A1 * 6/2013 ........... C07C 229/16
WO WO 2013/113502 A1 8/2013
WO WO 2013/174409 A1 11/2013
WO WO 2014/071963 A1 5/2014
WO WO 2014/072061 A1 5/2014
WO WO 2014/093924 A1 6/2014
WO WO 2014/127917 A1 8/2014
WO WO 2014/152027 A1 9/2014
WO WO 2014/160243 A1 10/2014
WO WO 2015/013551 A1 1/2015
WO WO 2015/024667 A1 2/2015
WO WO 2015/024668 A2 2/2015
WO WO 2015/164674 A1 10/2015
WO WO 2015/189425 A1 12/2015
WO WO-2015199952 A1 * 12/2015 ........... A61K 9/1272
WO WO 2016/164762 A1 10/2016
WO WO 2016/176330 A1 11/2016
WO WO 2016/201377 A1 12/2016
WO WO 2016/203025 A1 12/2016
WO WO 2017/015457 A1 1/2017
WO WO 2017/015463 A1 1/2017
WO WO 2017/019935 A1 2/2017
WO WO 2017/020026 A1 2/2017
WO WO 2017/031232 A1 2/2017
WO WO 2017/031241 A1 2/2017
WO WO-2017049245 A2 * 3/2017 ........... C07C 279/24
WO WO 2017/062513 A1 4/2017
WO WO 2017/066789 A1 4/2017
WO WO 2017/070601 A1 4/2017
WO WO 2017/070616 A1 4/2017
WO WO 2017/070618 A1 4/2017
WO WO 2017/070620 A1 4/2017
WO WO 2017/070622 A1 4/2017
WO WO 2017/070623 A1 4/2017
WO WO-2017070624 A1 * 4/2017 .............. A61P 11/00
WO WO-2017070626 A2 * 4/2017 ......... C07K 16/1027
WO WO 2017/201333 A1 11/2017
WO WO 2017/201340 A1 11/2017
WO WO 2017/201342 A1 11/2017
WO WO 2017/201347 A1 11/2017
WO WO 2017/201349 A1 11/2017
WO WO 2018/053209 A1 3/2018
WO WO 2018/075980 A1 4/2018
WO WO 2018/078053 A1 5/2018
WO WO 2018/081459 A1 5/2018
WO WO 2018/081462 A1 5/2018
WO WO 2018/089851 A1 5/2018
WO WO 2018/107088 A1 6/2018
WO WO 2018/111967 A1 6/2018
WO WO 2018/144082 A1 8/2018
WO WO 2018/144778 A1 8/2018
WO WO 2018/170245 A1 9/2018
WO WO 2018/170256 A1 9/2018
WO WO 2018/170260 A1 9/2018
WO WO 2018/170270 A1 9/2018
WO WO 2018/170347 A1 9/2018
WO WO 2018/175783 A1 9/2018
WO WO 2018/187590 A1 10/2018
WO WO 2018/200737 A1 11/2018
WO WO 2018/232355 A1 12/2018
WO WO 2018/232357 A1 12/2018
WO WO 2019/036670 A1 2/2019
WO WO 2019/036682 A1 2/2019
WO WO 2019/036683 A1 2/2019
WO WO 2019/036685 A1 2/2019
WO WO 2019/103993 A1 5/2019
WO WO 2019/148101 A1 8/2019
WO WO 2020/006242 A1 1/2020
WO WO 2020/056370 A1 3/2020
WO WO 2020/061284 A1 3/2020
WO WO 2020/061295 A1 3/2020
WO WO 2020/061367 A1 3/2020
WO WO-2020061367 A1 * 3/2020 ........... C07C 311/51
WO WO 2020/097291 A1 5/2020
WO WO 2020/172239 A1 8/2020
WO WO 2020/185811 A1 9/2020
WO WO 2020/190750 A1 9/2020

OTHER PUBLICATIONS

Hassett KJ, Benenato KE, Jacquinet E, Lee A, Woods A, Yuzhakov O, Himansu S, Deterling J, Geilich BM, Ketova T, Mihai C, Lynn A, et. al. Optimization of Lipid Nanoparticles for Intramuscular Administration of mRNA Vaccines. Mol Ther Nucleic Acids. Apr. 15, 2019;15:1-11. Epub Feb. 7, 2019.*

Depledge DP, Yamanishi K, Gomi Y, Gershon AA, Breuer J. Deep Sequencing of Distinct Preparations of the Live Attenuated Varicella-Zoster Virus Vaccine Reveals a Conserved Core of Attenuating Single-Nucleotide Polymorphisms. J Virol. Sep. 12, 2016;90 (19):8698-704.*

John S, Yuzhakov O, Woods A, Deterling J, Hassett K, Shaw CA, Ciaramella G. Multi-antigenic human cytomegalovirus mRNA vaccines that elicit potent humoral and cell-mediated immunity. Vaccine. Mar. 14, 2018;36(12): 1689-1699. doi: 10.1016/j.vaccine.2018.01.029. Epub Feb. 15, 2018.*

Freer G, Pistello M. Varicella-zoster virus infection: natural history, clinical manifestations, immunity and current and future vaccination strategies. New Microbiol. Apr. 2018;41(2):95-105. Epub Mar. 2, 2018.*

Cunningham AL. The herpes zoster subunit vaccine. Expert Opin Biol Ther. 2016;16(2):265-71. doi: 10.1517/14712598.2016.1134481. PMID: 26865048.*

Woodward M, Marko A, Galea S, Eagel B, Straus W. Varicella Virus Vaccine Live: A 22-Year Review of Postmarketing Safety Data. Open Forum Infect Dis. Aug. 1, 2019;6(8):ofz295. (Year: 2019).*

Shah RA, Limmer AL, Nwannunu CE, Patel RR, Mui UN, Tyring SK. Shingrix for Herpes Zoster: A Review. Skin Therapy Lett. Jul. 2019;24(4):5-7.*

Monslow MA, Elbashir S, Sullivan NL, Thiriot DS, Ahl P, et. al. Immunogenicity generated by mRNA vaccine encoding VZV gE antigen is comparable to adjuvanted subunit vaccine and better than live attenuated vaccine in nonhuman primates. Vaccine. Aug. 10, 2020;38(36):5793-5802. Epub Jul. 20, 2020. (Year: 2020).*

Richner JM, Himansu S, Dowd KA, Butler SL, Salazar V, Fox JM, Julander JG, Tang WW, Shresta S, Pierson TC, Ciaramella G, Diamond MS. Modified mRNA Vaccines Protect against Zika Virus Infection. Cell. Mar. 9, 2017;168(6): 1114-1125.e10. Epub Feb. 17, 2017. Erratum in: Cell. Mar. 23, 2017; 169(1):176. (Year: 2017).*

Bahl K, Senn JJ, Yuzhakov O, Bulychev A, Brito LA, Hassett KJ, Laska ME, Smith M, Almarsson Ö, et. al. Preclinical and Clinical Demonstration of Immunogenicity by mRNA Vaccines against H10N8 and H7N9 Influenza Viruses. Mol Ther. Jun. 7, 2017;25(6): 1316-1327. Epub Apr. 27, 2017. (Year: 2017).*

McKay PF, Hu K, Blakney AK, Samnuan K, Brown JC, Penn R, Zhou J, Bouton CR, Rogers P, Polra K, Lin PJC, Barbosa C, Tam YK, Barclay WS, Shattock RJ. Self-amplifying RNA SARS-CoV-2 lipid nanoparticle vaccine candidate induces high neutralizing antibody titers in mice. Nat Commun. Jul. 9, 2020;11 (1):3523. (Year: 2020).*

Sabnis S, Kumarasinghe ES, Salerno T, Mihai C, Ketova T, Senn JJ, Lynn A, Bulychev A, et. al. A Novel Amino Lipid Series for mRNA

(56) References Cited

OTHER PUBLICATIONS

Delivery: Improved Endosomal Escape and Sustained Pharmacology and Safety in Non-human Primates. Mol Ther. Jun. 6, 2018;26(6): 1509-1519. Mar. 14, 2018. (Year: 2018).*
International Search Report and Written Opinion for Application No. PCT/US2018/022643, dated Jun. 26, 2018.
Alconada et al., A tyrosine-based motif and a casein kinase II phosphorylation site regulate the intracellular trafficking of the varicella-zoster virus glycoprotein I, a protein localized in the trans-Golgi network. EMBO J. Nov. 15, 1996;15(22):6096-110.
Anderson et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Azarkh et al. Synthesis and decay of varicella zoster virus transcripts. J Neurovirol. Jun. 2011;17(3):281-7. doi: 10.1007/s13365-011-0029-2. Epub Apr. 12, 2011.
Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.
Bose et al., Influence of cationic lipid concentration on properties of lipid-polymer hybrid nanospheres for gene delivery. Int J Nanomedicine. Sep. 2, 2015;10:5367-82. doi:. 10.2147/IJN.S87120. eCollection 2015.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Cheng et al., Multifunctional triblock copolymers for intracellular messenger RNA delivery. Biomaterials. Oct. 2012; 33(28): 6868-6876.
Cu et al., Enhanced Delivery and Potency of Self-Amplifying mRNA Vaccines by Electroporation in Situ, Vaccines, 2013, 1, 367-383. Abstract Only.
De Jong et al., Drug delivery and nanoparticles:applications and hazards. Int J Nanomedicine. 2008;3(2):133-49.
Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.
Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Hecker, Nonviral, cationic lipid-mediated delivery of mRNA. Methods Mol Biol. 2013;969:73-88. doi: 10.1007/978-1-62703-260-5_5.
Hess et al., Vaccination with mRNAs encoding tumor-associated antigens and granulocyte-macrophage colony-stimulating factor efficiently primes CTL responses, but is insufficient to overcome tolerance to a model tumor/self antigen. Cancer Immunol Immunother. Jun. 2006;55(6):672-83. Epub Aug. 20, 2005.
Holtkamp et al., Modification of antigen-encoding RNA increases stability, translational efficacy, and T-cell stimulatory capacity of dendritic cells. Blood. Dec. 15, 2006;108(13):4009-17.
Hsu et al., Cationic lipid nanoparticles for therapeutic delivery of siRNA and miRNA to murine liver tumor. Nanomedicine. Nov. 2013;9(8):1169-80. doi: 10.1016/j.nano.2013.05.007. Epub May 30, 2013.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.
Kuhn et al., mRNA as a versatile tool for exogenous protein expression. Current Gene Therapy. Oct. 2012; 12 (5): 347-361.
Leitner et al., DNA and RNA-based vaccines: principles, progress and prospects. Vaccine. Dec. 10, 1999;18 (9-10):765-77.
Leroueil et al., Wide varieties of cationic nanoparticles induce defects in supported lipid bilayers. Nano Lett. Feb. 2008;8(2):420-4. doi: 10.1021/nl0722929. Epub Jan. 25, 2008.
Li et al., Developing lipid nanoparticle-based siRNA therapeutics for hepatocellular carcinoma using an integrated approach. Mol Cancer Ther. Nov. 2013;12(11):2308-18. doi: 10.1158/1535-7163.MCT-12-0983-T. Epub Aug. 13, 2013.
Lian et al., Trends and developments in liposome drug delivery systems. J Pharm Sci. Jun. 2001;90(6):667-80.
Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.
Lin et al., Lipid-based nanoparticles in the systemic delivery of siRNA. Nanomedicine (Lond). Jan. 2014;9(1):105-20. doi: 10.2217/nnm.13.192.
Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.
Lorenzi et al., Intranasal vaccination with messenger RNA as a new approach in gene therapy: Use against tuberculosis. BMC Biotechnol. Oct. 2010; 10(77): 1-11.
Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Martinon et al., Induction of virus-specific cytotoxic T lymphocytes in vivo by liposome-entrapped mRNA. EurJ Immunol. Jul. 1993;23(7):1719-22.
McKenzie et al., Nucleic acid vaccines: tasks and tactics. Immunol Res. 2001 ;24(3):225-44.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mol Ther. Apr. 2000;2(2):176-81.
Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.
Moffat et al., Functions of the C-terminal domain of varicella-zoster virus glycoprotein E in viral replication in vitro and skin and T-cell tropism in vivo. J Virol. Nov. 2004;78(22):12406-15.

(56) References Cited

OTHER PUBLICATIONS

Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Pollard et al., Type I IFN counteracts the induction of antigen-specific immune responses by lipid-based delivery of mRNA vaccines. Mol Ther. Jan. 2013; 21 (1): 251-259.
Schirrmacher et al., Intra-pinna anti-tumor vaccination with self-replicating infectious RNA or with DNA encoding a model tumor antigen and a cytokine. Gene Ther. Jul. 2000;7(13):1137-47.
Schott et al., Viral and non-viral approaches for transient delivery of mRNA and proteins. Current Gene Ther. 2011; 11 (5): 382-398.
Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni et al., Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Vassilev et al., Microparticle-mediated RNA immunization against bovine viral diarrhea virus. Vaccine. Feb. 28, 2001;19(15-16):2012-9.
Wang et al., Essential role played by the C-terminal domain of glycoprotein I in envelopment of varicella-zoster virus in the trans-Golgi network: interactions of glycoproteins with tegument. J Virol. Jan. 2001;75(1):323-40.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Wong et al., An mRNA vaccine for influenza. Nat Biotechnol. Dec. 2012;30(12):1202-4. doi: 10.1038/nbt.2439.
Xue et al., Lipid-Based Nanocarriers for RNA Delivery. Curr Pharm Des. 2015;21(22):3140-7.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ying et al., Cancer therapy using a self-replicating RNA vaccine. Nat Med. Jul. 1999;5(7):823-7.
Zhu et al., Targeting of glycoprotein I (gE) of varicella-zoster virus to the trans-Golgi network by an AYRV sequence and an acidic amino acid-rich patch in the cytosolic domain of the molecule. J Virol. Oct. 1996;70(10):6563-75.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Reichmuth et al., mRNA Vaccine Delivery Using Lipid Nanoparticles. Ther Deliv. 2016;7(5):319-34. doi: 10.4155/tde-2016-0006.

* cited by examiner

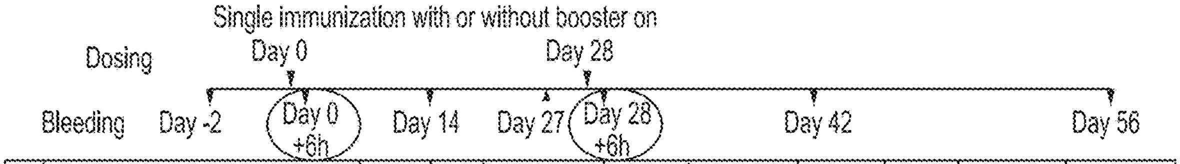

| G# | Antigen | Route | N= | Dosage (ug) | Dose Vol (ul) | 1st dose | 2nd dose | LNP | mRNA Conc. (mg/ml) | Volume +Overage |
|---|---|---|---|---|---|---|---|---|---|---|
| 1 | VZV-gE-oka-hIgkappa (G5; cap1) | IM | 8 | 10 | 50 | Day 0 | | MC3 | 0.2 | 1x600 ul |
| 2 | VZV-gE-oka-hIgkappa (G5; cap1) | IM | 8 | 10 | 50 | Day 0 | Day 28 | MC3 | 0.2 | 2x600 ul |
| 3 | VZV-gE-oka-hIgkappa (G5; cap1) | ID | 8 | 10 | 50 | Day 0 | | MC3 | 0.2 | 1x600 ul |
| 4 | VZV-gE-oka-hIgkappa (G5; cap1) | ID | 8 | 10 | 50 | Day 0 | Day 28 | MC3 | 0.2 | 2x600 ul |
| 5 | VZV-gE-oka (G0; cap1) | IM | 8 | 10 | 50 | Day 0 | | MC3 | 0.2 | 1x600 ul |
| 6 | VZV-gE-oka (G0; cap1) | IM | 8 | 10 | 50 | Day 0 | Day 28 | MC3 | 0.2 | 2x600 ul |
| 7 | VZV-gE-oka (G0; cap1) | ID | 8 | 10 | 50 | Day 0 | | MC3 | 0.2 | 1x600 ul |
| 8 | VZV-gE-oka (G0; cap1) | ID | 8 | 10 | 50 | Day 0 | Day 28 | MC3 | 0.2 | 2x600 ul |
| 9 | VZV-gE-oka (G5; cap1) | IM | 8 | 10 | 50 | Day 0 | | MC3 | 0.2 | 1x600 ul |
| 10 | VZV-gE-oka (G5; cap1) | IM | 8 | 10 | 50 | Day 0 | Day 28 | MC3 | 0.2 | 2x600 ul |
| 11 | VZV-gE-oka (G5; cap1) | ID | 8 | 10 | 50 | Day 0 | | MC3 | 0.2 | 1x600 ul |
| 12 | VZV-gE-oka (G5; cap1) | ID | 8 | 10 | 50 | Day 0 | Day 28 | MC3 | 0.2 | 2x600 ul |
| 13 | Negative control (PBS) | IM | 6 | / | 50 | Day 0 | | PBS | / | 1x600 ul |
| 14 | Negative control (PBS) | IM | 6 | / | 50 | Day 0 | Day 28 | PBS | / | 2x600 ul |
| 15 | Positive control (Varivax) | SC | 6 | 54 (pfu) | 50 | Day 0 | | | / | 1x1250 ul |
| 16 | Positive control (Varivax) | SC | 6 | 54 (pfu) | 50 | Day 0 | Day 28 | | / | |
| 17 | Positive control (Varivax) | SC | 4 | 675 (pfu) | 100 | Day 0 | | | / | 4x220 ul |
| 18 | Positive control (Varivax) | SC | 4 | 675 (pfu) | 100 | Day 0 | Day 28 | | / | |

Fig. 3

Anti GM130 (CST D6B1) - green
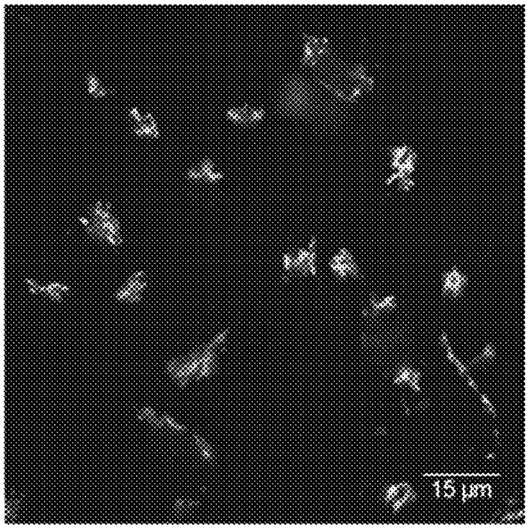
Fig. 8A
Anti Golgin-97 (CST D8P2K) - green
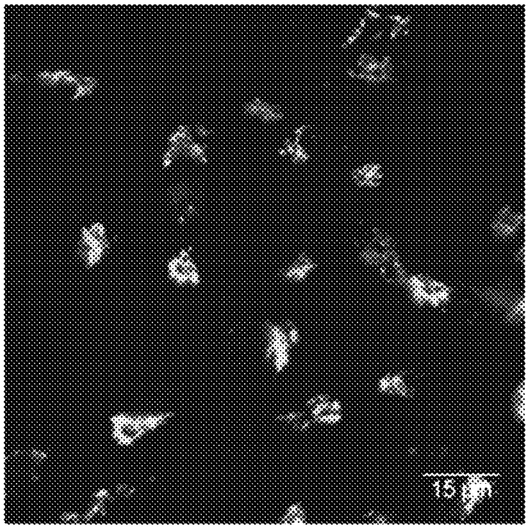
Fig. 8B
Anti GE Abcam 52549 - green
Untransfected Control
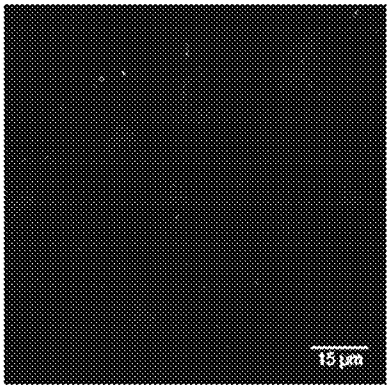
SE-VZV-GE-delete-562
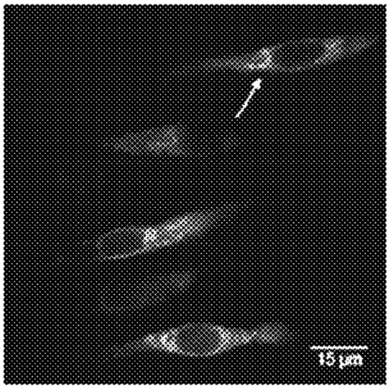
SE-VZV-GE-full_with_AEAADA
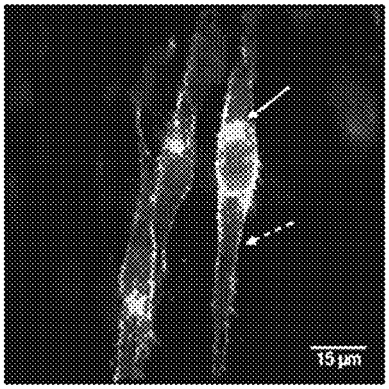
→ Perinuclear (Golgi ?) localization
⇢ Cell membrane localization
Fig. 9A
Fig. 9B
Fig. 9C

VARICELLA ZOSTER VIRUS (VZV) VACCINE

RELATED APPLICATIONS

This application is a national stage filing under 35 U.S.C. § 371 of international application number PCT/US2018/022643, filed Mar. 15, 2018, which was published under PCT Article 21(2) in English and claims the benefit under 35 U.S.C. § 119(e) of U.S. provisional application No. 62/471,809, filed Mar. 15, 2017, and U.S. provisional application No. 62/490,112, filed Apr. 26, 2017, each of which is incorporated by reference herein in its entirety.

BACKGROUND

Varicella is an acute infectious disease caused by varicella zoster virus (VZV). Varicella zoster virus is one of eight herpesviruses known to infect humans and vertebrates. VZV is also known as chickenpox virus, varicella virus, zoster virus, and human herpesvirus type 3 (HHV-3). VZV only affects humans, and commonly causes chickenpox in children, teens and young adults and herpes zoster (shingles) in adults (rarely in children). The primary VZV infection, which results in chickenpox (varicella), may result in complications, including viral or secondary bacterial pneumonia. Even when the clinical symptoms of chickenpox have resolved, VZV remains dormant in the nervous system of the infected person (virus latency) in the trigeminal and dorsal root ganglia. In about 10-20% of cases, VZV reactivates later in life, travelling from the sensory ganglia back to the skin where it produces a disease (rash) known as shingles or herpes zoster. VZV can also cause a number of neurologic conditions ranging from aseptic meningitis to encephalitis. Other serious complications of VZV infection include postherpetic neuralgia, Mollaret's meningitis, zoster multiplex, thrombocytopenia, myocarditis, arthritis, and inflammation of arteries in the brain leading to stroke, myelitis, herpes ophthalmicus, or zoster sine herpete. In rare instances, VZV affects the geniculate ganglion, giving lesions that follow specific branches of the facial nerve. Symptoms may include painful blisters on the tongue and ear along with one sided facial weakness and hearing loss.

Varicella cases have declined 97% since 1995, mostly due to vaccination. However, an estimated 500,000 to 1 million episodes of herpes zoster (shingles) occur annually in just the United States. The lifetime risk of herpes zoster is estimated to be at least 32%, with increasing age and cellular immunosuppression being the most important risk factors. In fact, it is estimated that 50% of persons living until the age of 85 will develop herpes zoster.

A live attenuated VZV Oka strain vaccine is available and is marketed in the United States under the trade name VARIVAX® (Merck). A similar, but not identical, VZV vaccine is marketed globally as VARILRIX® (GlaxoSmithKline). Since its approval in 1995, it has been added to the recommended vaccination schedules for children in Australia, the United States, and several other countries. In 2007, the Advisory Committee on Immunization Practices (ACIP) recommended a second dose of vaccine before school entry to ensure the maintenance of high levels of varicella immunity. In 2001-2005, outbreaks were reported in schools with high varicella vaccination coverage, indicating that even in settings where most children were vaccinated and the vaccine performed as expected, varicella outbreaks could not be prevented with the one-dose vaccination policy. As a result, two-dose vaccination is the adopted protocol; however, even with two doses of vaccine, there are reported incidences of breakthrough varicella. Furthermore, varicella vaccination has raised concerns that the immunity induced by the vaccine may not be lifelong, possibly leaving adults vulnerable to more severe disease as the immunity from their childhood immunization wanes.

In 2005, the FDA approved the combined live attenuated combination measles-mumps-rubella-varicella (MMRV) vaccine PROQUAD™ (Merck) for use in persons 12 months to 12 years in age. While the attenuated measles, mumps, and rubella vaccine viruses in MMRV are identical and of equal titer to those in the MMR vaccine, the titer of Oka/Merck VZV is higher in MMRV vaccine than in single-antigen varicella vaccine.

In 2006, the United States Food and Drug Administration approved ZOSTAVAX® (Merck) for the prevention of shingles (herpes zoster) in persons 60 years or older (currently 50-59 years of age is approved). ZOSTAVAX® contains the same Oka/Merck varicella zoster virus used in the varicella and MMRV vaccines, but at a much higher titer (>10-fold higher viral dose) than that present in both of these vaccines, as the concentrated formulation is designed to elicit an immune response in older adults whose immunity to VZV wanes with advancing age.

Although the varicella vaccine has been shown to be safe in healthy individuals, there is evidence that immunity to VZV infection conferred by the vaccine wanes over time, rendering the vaccinated individuals susceptible to shingles, a more serious condition. In addition, there have been reports that individuals have developed chicken pox or shingles from the varicella vaccination. The vaccine may establish a latent infection in neural ganglia, which can then reactivate to cause herpes zoster.

Moreover, live attenuated virus is not suitable for all subjects, including pregnant women and persons with moderate or severe acute illnesses. Also, varicella is not suitable or approved for immunocompromised patients, including persons with immunosuppression due to leukemia, lymphoma, generalized malignancy, immune deficiency disease or immunosuppressive therapy. Likewise, persons with moderate or severe cellular immunodeficiency resulting from infection with human immunodeficiency virus (HIV) including those diagnosed with acquired immunodeficiency syndrome (AIDS) should not receive the varicella vaccine. Thus, despite the high risk of morbidity and mortality associated with herpes zoster in immunocompromised individuals, this population is not eligible for vaccination with a live attenuated vaccine, such as ZOSTAVAX®.

There are one million cases of herpes zoster in the U.S. each year. An estimated $1 billion is spent annually on direct medical costs for herpes zoster in the US and treatment for herpes zoster is not always effective or available.

Deoxyribonucleic acid (DNA) vaccination is one technique used to stimulate humoral and cellular immune responses to foreign antigens, such as VZV antigens. The direct injection of genetically engineered DNA (e.g., naked plasmid DNA) into a living host results in a small number of host cells directly producing an antigen, resulting in a protective immunological response. With this technique, however, comes potential problems, including the possibility of insertional mutagenesis, which could lead to the activation of oncogenes or the inhibition of tumor suppressor genes.

SUMMARY

Provided herein is a ribonucleic acid (RNA) vaccine that builds on the knowledge that RNA (e.g., messenger RNA (mRNA)) can safely direct the body's cellular machinery to produce nearly any protein of interest, from native proteins to antibodies and other entirely novel protein constructs that can have therapeutic activity inside and outside of cells. The varicella zoster virus (VZV) RNA vaccines of the present disclosure may be used to induce a balanced immune response against VZV comprising both cellular and humoral immunity, without many of the risks associated with attenuated virus vaccination.

The RNA (e.g., mRNA) vaccines may be utilized in various settings depending on the prevalence of the infection or the degree or level of unmet medical need. The RNA (e.g., mRNA) vaccines may be utilized to treat and/or prevent a VZV of various genotypes, strains, and isolates. The RNA (e.g., mRNA) vaccines have superior properties in that they produce much larger antibody titers and produce responses earlier than commercially available anti-viral therapeutic treatments. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Various VZV amino acid sequences encompasses by the present disclosure are provided in Tables 1-9. RNA (e.g., mRNA) vaccines as provided herein may include at least one RNA polynucleotide encoding at least one of the VZV glycoproteins provided in Table 1, or a fragment, homolog (e.g., having at least 80%, 85%, 90%, 95%, 98% or 99% identity) or variant or derivative thereof.

Some embodiments of the present disclosure provide VZV vaccines that include at least one ribonucleic acid (RNA) polynucleotide having an open reading frame encoding at least one VZV antigenic polypeptide. Some embodiments of the present disclosure provide VZV vaccines that include at least one RNA polynucleotide having an open reading frame encoding two or more VZV antigenic polypeptides. Some embodiments of the present disclosure provide VZV vaccines that include two or more RNA polynucleotides having an open reading frame encoding two or more VZV antigenic polypeptides.

In some embodiments, an antigenic polypeptide is a VZV glycoprotein. For example, a VZV glycoprotein may be VZV gE, gI, gB, gH, gK, gL, gC, gN, or gM. In some embodiments, the antigenic polypeptide is a VZV gE polypeptide. In some embodiments, the antigenic polypeptide is a VZV gI polypeptide. In some embodiments, the antigenic polypeptide is a VZV gB polypeptide. In some embodiments, the antigenic polypeptide is a VZV gH polypeptide. In some embodiments, the antigenic polypeptide is a VZV gK polypeptide. In some embodiments, the antigenic polypeptide is a VZV gL polypeptide. In some embodiments, the antigenic polypeptide is a VZV gC polypeptide. In some embodiments, the antigenic polypeptide is a VZV gN polypeptide. In some embodiments, the antigenic polypeptide is a VZV gM polypeptide. In some embodiments, the VZV glycoprotein is encoded by a nucleic acid sequence of SEQ ID NO: 1 or SEQ ID NO: 2.

In some embodiments, the VZV glycoprotein is a variant gE polypeptide. In some embodiments, the variant VZV gE polypeptide is a truncated polypeptide lacking the anchor domain (ER retention domain). In some embodiments, the truncated VZV gE polypeptide comprises (or consists of, or consists essentially of) amino acids 1-561 of VZV gE polypeptide. In some embodiments, the truncated VZV gE polypeptide comprises (or consists of, or consists essentially of) amino acids 1-561 of SEQ ID NO: 10. In some embodiments, the truncated VZV gE polypeptide comprises (or consists of, or consists essentially of) amino acids 1-573 of SEQ ID NO: 18. In some embodiments, the truncated VZV gE polypeptide comprises (or consists of, or consists essentially of) amino acids 1-573 of SEQ ID NO: 10. In some embodiments, the variant VZV gE polypeptide is a truncated polypeptide lacking the carboxy terminal tail domain. In some embodiments, the truncated VZV gE polypeptide comprises (or consists of, or consists essentially of) amino acids 1-573 of VZV gE polypeptide. In some embodiments, the truncated VZV gE polypeptide comprises (or consists of, or consists essentially of) amino acids 1-573 of SEQ ID NO: 34.

In some embodiments, the variant VZV gE polypeptide has at least one mutation in one or more motif(s) associated with ER retention, wherein the mutation(s) in one or more motif(s) results in decreased retention of the VZV gE polypeptide in the ER and/or golgi. In some embodiments, the variant VZV gE polypeptide has at least one mutation in one or more motif(s) associated with targeting gE to the golgi or trans-golgi network (TGN), wherein the mutation(s) in one or more motif(s) results in decreased targeting or localization of the VZV gE polypeptide to the golgi or TGN. In some embodiments, the variant VZV gE polypeptide has at least one mutation in one or more motif(s) associated with the internalization of VZV gE or the endocytosis of gE, wherein the mutation(s) in one or more motif(s) results in decreased endocytosis of the VZV gE polypeptide. In some embodiments, the variant VZV gE polypeptide has at least one mutation in one or more phosphorylated acidic motif(s), such as SSTT (SEQ ID NO: 122). In some embodiments, the variant VZV gE polypeptide is a full-length VZV gE polypeptide having a Y582G mutation. In some embodiments, the variant VZV gE polypeptide is a full-length VZV gE polypeptide having a Y569A mutation. In some embodiments, the variant VZV gE polypeptide is a full-length VZV gE polypeptide having a Y582G mutation and a Y569A mutation. In some embodiments, the variant VZV gE polypeptide is an antigenic fragment comprising amino acids 1-573 of VZV gE and having a Y569A mutation. In some embodiments, the variant VZV gE polypeptide is an antigenic fragment comprising SEQ ID NO: 38.

In some embodiments, the variant VZV gE polypeptide is a full-length VZV gE polypeptide having an Igκ sequence. In some embodiments, the variant VZV gE polypeptide is SEQ ID NO: 14. In some embodiments, the variant VZV gE polypeptide is a full-length VZV gE polypeptide having an A-E-A-A-D-A sequence (SEQ ID NO: 58) that replaces SESTDT (SEQ ID NO: 59). This is a replacement of the Ser/Thr-rich "SSTT" (SEQ ID NO: 122) acidic cluster with an Ala-rich sequence. In some embodiments, the variant VZV gE polypeptide is SEQ ID NO: 26. In some embodiments in which the VZV gE polypeptide has an A-E-A-A-D-A sequence (SEQ ID NO: 58), the variant VZV gE polypeptide also has at least one mutation in one or more motif(s) associated with ER/golgi retention, TGN localization, or endocytosis (e.g., has a Y582G mutation, a Y569A mutation, or both a Y582G mutation and a Y569A mutation) and/or has at least one mutation in one or more phosphorylated acidic motif(s), such as a SSTT (SEQ ID NO: 122) motif. In some embodiments, the variant VZV gE polypeptide is or comprises the amino acid sequence of SEQ ID NO: 30.

In some embodiments, the variant VZV gE polypeptide is a full-length VZV gE polypeptide having an additional sequence at the C-terminus that aids in secretion of the polypeptide or its localization to the cell membrane. In some embodiments, the variant VZV gE polypeptide is a full-length VZV gE polypeptide having an IgKappa sequence at the C-terminus. In some embodiments, the VZV gE polypeptide has additional sequence at the C-terminus that aids in secretion (e.g., has an IgKappa sequence at the C-terminus) and has at least one mutation in one or more motif(s) associated with ER retention, TGN localization, or endocytosis (e.g., has a Y582G mutation, a Y569A mutation, or both a Y582G mutation and a Y569A mutation) and/or has at least one mutation in one or more phosphorylated acidic motif(s), such as the SSTT (SEQ ID NO: 122) motif. In some embodiments, the variant VZV gE polypeptide is a truncated polypeptide lacking the anchor domain (ER retention domain) and having an additional sequence at the C-terminus that aids in secretion of the polypeptide (e.g., an IgKappa sequence at the C-terminus). In some embodiments, the truncated VZV gE polypeptide comprises amino acids 1-561 and has an IgKappa sequence at the C-terminus. In some embodiments, the variant polypeptide is SEQ ID NO: 22. In some embodiments, the variant VZV gE polypeptide is a truncated polypeptide lacking the carboxy terminal tail domain and having an additional sequence at the C-terminus that aids in secretion of the polypeptide, for example, having an IgKappa sequence at the C-terminus. In some embodiments, the truncated VZV gE polypeptide comprises amino acids 1-573 and has an IgKappa sequence at the C-terminus.

In some embodiments, the antigenic polypeptide comprises two or more glycoproteins. In some embodiments, the two or more glycoproteins are encoded by a single RNA polynucleotide. In some embodiments, the two or more glycoproteins are encoded by two or more RNA polynucleotides, for example, each glycoprotein is encoded by a separate RNA polynucleotide. In some embodiments, the two or more glycoproteins can be any combination of VZV gE, gI, gB, gH, gK, gL, gC, gN, and gM polypeptides. In some embodiments, the two or more glycoproteins can be any combination of VZV gE and at least one of gI, gB, gH, gK, gL, gC, gN, and gM polypeptides. In some embodiments, the two or more glycoproteins can be any combination of VZV gI and at least one of gE, gB, gH, gK, gL, gC, gN, and gM polypeptides. In some embodiments, the two or more glycoproteins can be any combination of VZV gE, gI, and at least one of gB, gH, gK, gL, gC, gN, and gM polypeptides.

In some embodiments, the two or more VZV glycoproteins are gE and gI. In some embodiments, the two or more VZV glycoproteins are gE and gB. In some embodiments, the two or more VZV glycoproteins are gI and gB. In some embodiments, the two or more VZV glycoproteins are gE, gI, and gB. In some embodiments, the two or more VZV glycoproteins are gE and gH. In some embodiments, the two or more VZV glycoproteins are gI and gH. In some embodiments, the two or more VZV glycoproteins are gE, gI, and gH. In some embodiments, the two or more VZV glycoproteins are gE and gK. In some embodiments, the two or more VZV glycoproteins are gI and gK. In some embodiments, the two or more VZV glycoproteins are gE, gI, and gK. In some embodiments, the two or more VZV glycoproteins are gE and gL. In some embodiments, the two or more VZV glycoproteins are gI and gL. In some embodiments, the two or more VZV glycoproteins are gE, gI, and gL. In some embodiments, the two or more VZV glycoproteins are gE and gC. In some embodiments, the two or more VZV glycoproteins are gI and gC. In some embodiments, the two or more VZV glycoproteins are gE, gI, and gC. In some embodiments, the two or more VZV glycoproteins are gE and gN. In some embodiments, the two or more VZV glycoproteins are gI and gN. In some embodiments, the two or more VZV glycoproteins are gE, gI, and gN. In some embodiments, the two or more VZV glycoproteins are gE and gM. In some embodiments, the two or more VZV glycoproteins are gI and gM. In some embodiments, the two or more VZV glycoproteins are gE, gI, and gM.

In some embodiments, the vaccine comprises any two or more VZV glycoproteins (e.g., any of the variant VZV gE disclosed in the preceding paragraphs and in the Examples and Figures), and the VZV gE is a variant gE, such as any of the variant VZV gE glycoproteins disclosed herein, for example, any of the variant VZV gE disclosed in the preceding paragraphs and in the Examples and Figures.

In some embodiments, the VZV vaccine includes two or more RNA polynucleotides having an open reading frame encoding two or more VZV antigenic polypeptides (either encoded by a single RNA polynucleotide or encoded by two or more RNA polynucleotides, for example, each glycoprotein encoded by a separate RNA polynucleotide), and the two or more VZV glycoproteins are a variant gE (e.g., any of the variant gE polypeptides disclosed herein in the preceding paragraphs) and a VZV glycoprotein selected from gI, gB, gH, gK, gL, gC, gN, and gM polypeptides. In some embodiments, the two or more VZV glycoproteins are a variant gE (e.g., any of the variant gE polypeptides disclosed herein in the preceding paragraphs) and gI. In some embodiments, the glycoproteins are VZV gI and variant VZV gE, and the variant VZV gE polypeptide is a truncated polypeptide lacking the anchor domain (ER retention domain) (e.g., a truncated VZV gE polypeptide comprising amino acids 1-561 of SEQ ID NO: 10). In some embodiments, the glycoproteins are VZV gI and variant VZV gE, and the variant VZV gE polypeptide is a truncated polypeptide lacking the carboxy terminal tail domain (e.g., a truncated VZV gE polypeptide comprising amino acids 1-573 of SEQ ID NO: 18). In some embodiments, the glycoproteins are VZV gI and variant VZV gE, and the variant VZV gE polypeptide has at least one mutation in one or more motif(s) associated with ER retention, TGN localization, and/or endocytosis (e.g., the variant VZV gE has a Y582G mutation, a Y569A mutation, or both a Y582G mutation and a Y569A mutation) and/or has at least one mutation in one or more phosphorylated acidic motif(s), such as SSTT (SEQ ID NO: 122) motif. In some embodiments, the glycoproteins are VZV gI and variant VZV gE, and the variant VZV gE polypeptide is an antigenic fragment comprising amino acids 1-573 of VZV gE and having a Y569A mutation. In some embodiments, the glycoproteins are VZV gI and variant VZV gE, and the variant VZV gE polypeptide is a full-length VZV gE polypeptide having an A-E-A-A-D-A (SEQ ID NO: 58) sequence. In some embodiments, the glycoproteins are VZV gI and variant VZV gE, and the qVZV gE polypeptide has an A-E-A-A-D-A (SEQ ID NO: 58) sequence and a Y582G mutation, a Y569A mutation, or both a Y582G mutation and a Y569A mutation. In some embodiments, the glycoproteins are VZV gI and variant VZV gE, and the VZV gE polypeptide is a full-length VZV gE polypeptide having an additional sequence at the C-terminus that aids in secretion of the polypeptide (e.g., an IgKappa sequence). In some embodiments, the glycoproteins are VZV gI and variant VZV gE, and the VZV gE polypeptide is a full-length VZV gE polypeptide having an IgKappa sequence and a Y582G mutation, a Y569A mutation, or both a Y582G mutation and a Y569A mutation. In some embodiments, the glycoproteins are VZV gI and variant VZV gE, and the VZV gE polypeptide is a truncated VZV gE polypeptide lacking the anchor domain (ER retention domain) and having an IgKappa sequence. In some embodiments, the variant VZV gE polypeptide is a truncated polypeptide comprising amino acids 1-561 or amino acids 1-573 and having an IgKappa sequence at the C-terminus.

In any of the above-described embodiments, the VZV vaccine may further comprise a live attenuated VZV, a whole inactivated VZV, or a VZV virus-like particle (VLP). In some embodiments, the live attenuated VZV, whole inactivated VZV, or VZV VLP is selected from or derived from the following strains and genotypes: VZV E1 strain, genotypes E1_32_5, E1_Kel, E1_Dumas, E1_Russia 1999, E1_SD, E1_MSP, E1_36, E1_49, E1_BC, E1_NH29; VZV E2 strain, genotypes E2_03-500, E2_2, E2_11, E2_HJO; VZV J strain, genotype pOka; VZV M1 strain, genotype M1_CA123; VZV M2 strain, genotypes M2_8 and M2_DR; and VZV M4 strain, genotypes Spain 4242, France 4415, and Italy 4053.

Alternate RNA vaccines comprising RNA polynucleotides encoding other viral protein components of VZV, for example, tegument proteins are encompassed by the present disclosure. Thus, some embodiments of the present disclosure provide VZV vaccines that include at least one ribonucleic acid (RNA) polynucleotide having an open reading frame encoding at least one VZV tegument protein. Some embodiments of the present disclosure provide VZV vaccines that include at least one RNA polynucleotide having an open reading frame encoding at least one VZV tegument protein and at least one VZV glycoprotein. Some embodiments of the present disclosure provide VZV vaccines that include at least one RNA polynucleotide having an open reading frame encoding at least one VZV tegument protein and at least one RNA polynucleotide having an open reading frame encoding at least one VZV glycoprotein. In some embodiments, RNA vaccines comprise RNA (e.g., mRNA) polynucleotide(s) encoding one or more VZV tegument protein(s) and one or more VZV glycoprotein(s) selected from VZV gE, gI, gB, gH, gK, gL, gC, gN, and gM polypeptides. In some embodiments, the VZV glycoprotein is a VZV gE polypeptide. In some embodiments, the VZV glycoprotein is a VZV gI polypeptide. In some embodiments, the VZV glycoprotein is a variant VZV gE polypeptide, such as any of the variant VZV gE polypeptides disclosed herein. In some embodiments, the VZV glycoproteins are VZV gE glycoproteins and VZV gI glycoproteins.

In some embodiments, at least one RNA polynucleotide is encoded by at least one nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 41 and homologs having at least 80% (e.g., 85%, 90%, 95%, 98%, 99%) identity with a nucleic acid sequence selected from SEQ ID NO: 1-8 and 41. In some embodiments, at least one RNA polynucleotide is encoded by at least one nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 41 and homologs having at least 90% (e.g., 90%, 91%, 92%, 93%, 94%, 95%, 96%, 97%, 98%, 99%, 99.8% or 99.9%) identity with a nucleic acid sequence selected from SEQ ID NO: 1-8 and 41. In some embodiments, at least one RNA polynucleotide is encoded by at least one fragment of a nucleic acid sequence (e.g., a fragment having an antigenic sequence or at least one epitope) selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 41 and homologs having at least 80% (e.g., 85%, 90%, 95%, 98%, 99%) identity with a nucleic acid sequence selected from SEQ ID NO: 1-8 and 41. In some embodiments, at least one RNA polynucleotide is encoded by at least one epitope of a nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 41.

In some embodiments, at least one RNA polynucleotide is a gE polypeptide encoded by SEQ ID NO: 1. In some embodiments, at least one RNA polynucleotide is a gI polypeptide encoded by SEQ ID NO: 2. In some embodiments, at least one RNA polynucleotide is a truncated gE polypeptide encoded by SEQ ID NO: 3. In some embodiments, at least one RNA polynucleotide is a truncated gE polypeptide encoded by SEQ ID NO: 5. In some embodiments, at least one RNA polynucleotide is a truncated gE polypeptide having Y569A mutation encoded by SEQ ID NO: 6. In some embodiments, at least one RNA polynucleotide is a gE polypeptide having an AEAADA sequence SEQ ID NO: 58 encoded by SEQ ID NO: 7. In some embodiments, at least one RNA polynucleotide is a gE polypeptide having a Y582G mutation and a AEAADA sequence (SEQ ID NO: 58) encoded by SEQ ID NO: 8. In some embodiments, at least one RNA polynucleotide is a gE polypeptide encoded by SEQ ID NO: 41.

In some embodiments, at least one RNA (e.g., mRNA) polynucleotide encodes an antigenic polypeptide having at least 90% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 95% identity to the amino acid sequence of any one of SEQ ID NO: 10, 14, 18, 22, 26, 30, 34, 38, 42 and 45-55. In some embodiments, at least one RNA polynucleotide encodes an antigenic polypeptide having at least 96% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 97% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 98% identity to the amino acid sequence of any one of SEQ ID NO: 10, 14, 18, 22, 26, 30, 34, 38, 42 and 45-55. In some embodiments, at least one RNA (e.g., mRNA) polynucleotide encodes an antigenic polypeptide having at least 99% identity to the amino acid sequence of any one of SEQ ID NO: 10, 14, 18, 22, 26, 30, 34, 38, 42 and 45-55.

In some embodiments, the open reading frame from which the VZV polypeptide is encoded is codon-optimized. In some embodiments, the at least one RNA polynucleotide encodes an antigenic protein of any one of SEQ ID NO: 10, 14, 18, 22, 26, 30, 34, 38, 42 and 45-55, and wherein the RNA polynucleotide is codon-optimized mRNA. In some embodiments, the at least one RNA polynucleotide comprises a mRNA sequence identified by any one of SEQ ID NO: 92-108. In some embodiments, the mRNA sequence identified by any one of SEQ ID NO: 92-108 is codon optimized to encode antigenic VZV polypeptides that are as immunogenic, or more immunogenic than, the antigenic VZV polypeptides encoded by any one of SEQ ID NO: 92-108.

In some embodiments, the at least one RNA (e.g., mRNA) polynucleotide encodes an antigenic protein of SEQ ID NO:

10, wherein the RNA (e.g., mRNA) polynucleotide has less than 80% identity to wild-type mRNA sequence. In some embodiments, the at least one RNA polynucleotide encodes an antigenic protein of SEQ ID NO: 10, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 42, wherein the RNA e.g., mRNA) polynucleotide has less than 80% identity to wild-type mRNA sequence. In some embodiments, the at least one RNA (e.g., mRNA) polynucleotide encodes an antigenic protein of SEQ ID NO: 42, wherein the RNA polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 14, wherein the RNA (e.g., mRNA) polynucleotide has less than 80% identity to wild-type mRNA sequence. In some embodiments, the at least one RNA (e.g., mRNA) polynucleotide encodes an antigenic protein of SEQ ID NO: 14, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 26, wherein the RNA polynucleotide has less than 80% identity to wild-type mRNA sequence. In some embodiments, the at least one RNA (e.g., mRNA) polynucleotide encodes an antigenic protein of SEQ ID NO: 26, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide encodes an antigenic protein of SEQ ID NO: 30, wherein the RNA polynucleotide has less than 80% identity to wild-type mRNA sequence. In some embodiments, the at least one RNA polynucleotide encodes an antigenic protein of SEQ ID NO: 30, wherein the RNA (e.g., mRNA) polynucleotide has greater than 80% identity to wild-type mRNA sequence, but does not include wild-type mRNA sequence. In some embodiments, the at least one RNA (e.g., mRNA) polynucleotide is encoded by a sequence selected from any one of SEQ ID NO: 1-8 and SEQ ID NO 41 and includes at least one chemical modification.

In some embodiments, the VZV vaccine is multivalent. In some embodiments, the RNA polynucleotide comprises a polynucleotide sequence derived from VZV E1 strain, including, for example, any one or more of genotypes E1_32_5, E1_Kel, E1_Dumas, E1_Russia 1999, E1_SD, E1_MSP, E1_36, E1_49, E1_BC, and E1_NH29. In some embodiments, the RNA (e.g., mRNA) polynucleotide comprises a polynucleotide sequence derived from VZV E2 strain, including, for example, any one or more of genotypes E2_03-500, E2_2, E2_11, and E2_HJO. In some embodiments, the RNA (e.g., mRNA) polynucleotide comprises a polynucleotide sequence derived from VZV J strain, including, for example, genotype pOka. In some embodiments, the RNA (e.g., mRNA) polynucleotide comprises a polynucleotide sequence derived from VZV M1 strain, including, for example, genotype M1_CA123. In some embodiments, the RNA (e.g., mRNA) polynucleotide comprises a polynucleotide sequence derived from VZV M2 strain, including, for example, genotypes M2_8 and M2_DR. In some embodiments, the RNA (e.g., mRNA) polynucleotide comprises a polynucleotide sequence derived from VZV M4 strain, including, for example, any one or more of genotypes Spain 4242, France 4415, and Italy 4053.

Some embodiments of the present disclosure provide a VZV vaccine that includes at least one ribonucleic acid (RNA) polynucleotide having an open reading frame encoding at least one VZV antigenic polypeptide and at least one 5' terminal cap. In some embodiments, a 5' terminal cap is 7mG(5')ppp(5')N1mpNp. Some embodiments of the present disclosure provide a VZV vaccine that includes at least one RNA (e.g., mRNA) polynucleotide having an open reading frame encoding at least one VZV antigenic polypeptide, wherein the at least one RNA (e.g., mRNA) polynucleotide has at least one chemical modification. In some embodiments, the at least one RNA (e.g., mRNA) polynucleotide further comprises a second chemical modification. In some embodiments, the at least one RNA (e.g., mRNA) polynucleotide having at least one chemical modification has a 5' terminal cap. In some embodiments, the at least one chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, every (100%) of the uridines of the at least one RNA polynucleotide comprises a chemical modification, such as a N1-methylpseudouridine modification or a N1-ethylpseudouridine modification.

Some embodiments of the present disclosure provide a VZV vaccine that includes at least one ribonucleic acid (RNA) polynucleotide having an open reading frame encoding at least one VZV antigenic polypeptide, wherein at least 80% (e.g., 85%, 90%, 95%, 98%, 99%, 100%) of the uracil in the open reading frame have a chemical modification, optionally wherein the vaccine is formulated in a lipid nanoparticle. In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, 100% of the uracil in the open reading frame are modified to include N1-methyl pseudouridine.

Some embodiments of the present disclosure provide a VZV vaccine that is formulated within a cationic lipid nanoparticle. In some embodiments, the cationic lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z,15Z)—N,N-dimethyl-2-nonylhenicosa-12,15-dien-1-amine, and N,N-dimethyl-1-[(1S,2R)-2-octylcyclopropyl]heptadecan-8-amine.

In some embodiments, the lipid is

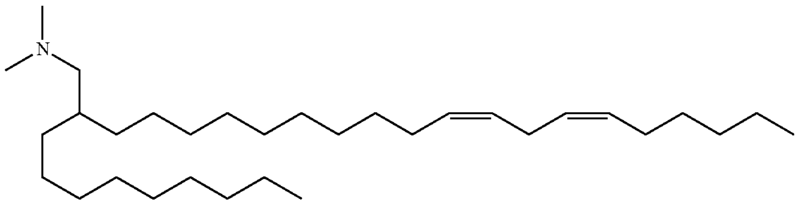

In some embodiments, the lipid is

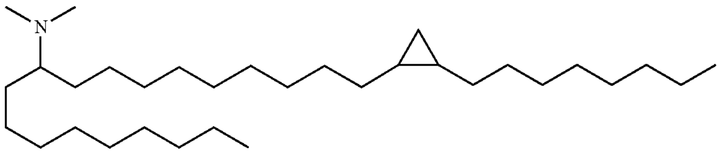

In some embodiments, at least one cationic lipid selected from compounds of Formula (I):

(I)

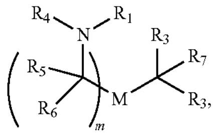

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, —N(R)$R_8$, —O$(CH_2)_n$OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)N$(R)_2$, —C(═$NR_9$)R, —C(O)N(R)OR, and —C(R)N$(R)_2$ C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S$(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S$(O)_2$R, —S$(O)_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_n$Q, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_n$N$(R)_2$, —C(O)OR, —OC(O)R, —$CX_3$, —$CX_2$H, —$CXH_2$, —CN, —C(O)N$(R)_2$, —N(R)C(O)R, —N(R)S$(O)_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(═$NR_9$)N$(R)_2$, —N(R)C(═$CHR_9$)N$(R)_2$, —OC(O)N$(R)_2$, —N(R)C(O)OR, —N(OR)C(O)R, —N(OR)S$(O)_2$R, —N(OR)C(O)OR, —N(OR)C(O)N$(R)_2$, —N(OR)C(S)N$(R)_2$, —N(OR)C(═$NR_9$)N$(R)_2$, —N(OR)C(═$CHR_9$)N$(R)_2$, —C(═$NR_9$)N$(R)_2$, —C(═$NR_9$)R, —C(O)N(R)OR, and a 5- to 14-membered heterocycloalkyl having one or more heteroatoms selected from N, O, and S which is substituted with one or more substituents selected from oxo (═O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{1-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(═NR$_9$)N(R)$_2$, —N(R)C(═CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═NR$_9$)N(R)$_2$, —N(OR)C(═CHR$_9$)N(R)$_2$, —C(═NR$_9$)R, —C(O)N(R)OR, and —C(═NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(═NR$_9$)N(R)$_2$, —N(R)C(═CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═NR$_9$)N(R)$_2$, —N(OR)C(═CHR$_9$)N(R)$_2$, —C(═NR$_9$)R, —C(O)N(R)OR, and —C(═NR$_9$)N(R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is $—(CH_2)_nQ$ or $—(CH_2)_nCHQR$, where Q is $—N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-4}$ alkenyl, —R*YR", —YR", and —R*OR", or $R_2$ and $R_3$, together with the atom to which they are attached, form a heterocycle or carbocycle;

$R_4$ is selected from the group consisting of $—(CH_2)_nQ$, $—(CH_2)_nCHQR$, —CHQR, and $—CQ(R)_2$, where Q is $—N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

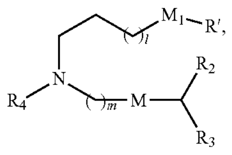

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or $—(CH_2)_nQ$, in which Q is OH, $—NHC(S)N(R)_2$, $—NHC(O)N(R)_2$, —N(R)C(O)R, $—N(R)S(O)_2R$, $—N(R)R_8$, $—NHC(=NR_9)N(R)_2$, $—NHC(=CHR_9)N(R)_2$, $—OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, the cationic lipid nanoparticle has a molar ratio of about 20-60% cationic lipid, about 5-25% non-cationic lipid, about 25-55% sterol, and about 0.5-15% PEG-modified lipid. In some embodiments, the nanoparticle has a polydispersity value of less than 0.4. In some embodiments, the nanoparticle has a net neutral charge at a neutral pH value. In some embodiments, the nanoparticle has a mean diameter of 50-200 nm.

Some embodiments of the present disclosure provide methods of inducing an antigen specific immune response in a subject, comprising administering to the subject a VZV RNA (e.g., mRNA) vaccine in an amount effective to produce an antigen specific immune response. In some embodiments, an antigen specific immune response comprises a T cell response or a B cell response. In some embodiments, an antigen specific immune response comprises a T cell response and a B cell response. In some embodiments, a method of producing an antigen specific immune response involves a single administration of the vaccine. In some embodiments, a method further includes administering to the subject a booster dose of the vaccine. In some embodiments, a vaccine is administered to the subject by intradermal or intramuscular injection.

Also provided herein are VZV RNA (e.g., mRNA) vaccines for use in a method of inducing an antigen specific immune response in a subject, the method comprising administering the vaccine to the subject in an amount effective to produce an antigen specific immune response.

Further provided herein are uses of VZV RNA (e.g., mRNA) vaccines in the manufacture of a medicament for use in a method of inducing an antigen specific immune response in a subject, the method comprising administering the vaccine to the subject in an amount effective to produce an antigen specific immune response.

Some aspects of the present disclosure provide methods of preventing or treating VZV infection comprising administering to a subject the VZV RNA (e.g., mRNA) vaccine of the present disclosure. In some embodiments, the VZV RNA (e.g., mRNA) vaccine is formulated in an effective amount to produce an antigen specific immune response in a subject.

Some embodiments of the present disclosure provide methods of inducing an antigen specific immune response in a subject, the methods comprising administering to a subject a VZV RNA (e.g., mRNA) vaccine as provided herein in an effective amount to produce an antigen specific immune response in a subject.

In some embodiments, an anti-VZV antigenic polypeptide antibody titer produced in the subject is increased by at least 1 log relative to a control. In some embodiments, the anti-VZV antigenic polypeptide antibody titer produced in the subject is increased by 1-3 log relative to a control.

In some embodiments, the anti-VZV antigenic polypeptide antibody titer produced in the subject is increased at least 2 times relative to a control. In some embodiments, the anti-VZV antigenic polypeptide antibody titer produced in the subject is increased at least 5 times relative to a control. In some embodiments, the anti-VZV antigenic polypeptide antibody titer produced in the subject is increased at least 10 times relative to a control. In some embodiments, the anti-VZV antigenic polypeptide antibody titer produced in the subject is increased 2-10 times relative to a control.

In some embodiments, the control is an anti-VZV antigenic polypeptide antibody titer produced in a subject who has not been administered VZV vaccine. In some embodiments, the control is an anti-VZV antigenic polypeptide antibody titer produced in a subject who has been administered a live attenuated or inactivated VZV vaccine. In some embodiments, the control is an anti-VZV antigenic polypeptide antibody titer produced in a subject who has been administered a recombinant or purified VZV protein vaccine. In some embodiments, the control is an anti-VZV antigenic polypeptide antibody titer produced in a subject who has been administered an VZV virus-like particle (VLP) vaccine.

In some embodiments, the effective amount is a dose equivalent to at least a 2-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 4-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 10-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 100-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to at least a 1000-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a dose equivalent to a 2-fold to 1000-fold reduction in the standard of care dose of a recombinant VZV protein vaccine, wherein an anti-VZV antigenic polypeptide antibody titer produced in the subject is equivalent to an anti-VZV antigenic polypeptide antibody titer produced in a control subject administered the standard of care dose of a recombinant or purified VZV protein vaccine, a live attenuated or inactivated VZV vaccine, or a VZV VLP vaccine.

In some embodiments, the effective amount is a total dose of 25 μg to 1000 μg, or 50 μg to 1000 μg or 25 to 200 μs. In some embodiments, the effective amount is a total dose of 50 μg, 100 μg, 200 μg, 400 μg, 800 μg, or 1000 μg. In some embodiments, the effective amount is a total dose of 200 μg. In some embodiments, the effective amount is a total dose of 50 μg to 400 μg. In some embodiments, the effective amount is a total dose of 50 μg, 100 μg, 150 μg, 200 μg, 250 μg, 300 μg, 350 μg or 400 μg. In some embodiments, the effective amount is a dose of 25 μg administered to the subject a total of two times. In some embodiments, the effective amount is a dose of 50 μg administered to the subject a total of two times. In some embodiments, the effective amount is a dose of 100 μg administered to the subject a total of two times. In some embodiments, the effective amount is a dose of 200 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments, the efficacy (or effectiveness) of the VZV RNA (e.g., mRNA) vaccine against VZV is greater than 60%.

Vaccine efficacy may be assessed using standard analyses (see, e.g., Weinberg et al., *J Infect Dis.* 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100;\ \text{and}$$

$$\text{Efficacy}=(1-\text{RR})\times 100.$$

Likewise, vaccine effectiveness may be assessed using standard analyses (see, e.g., Weinberg et al., *J Infect Dis.* 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, the efficacy (or effectiveness) of the VZV RNA (e.g., mRNA) vaccine against VZV is greater than 65%. In some embodiments, the efficacy (or effectiveness) of the vaccine against VZV is greater than 70%. In some embodiments, the efficacy (or effectiveness) of the vaccine against VZV is greater than 75%. In some embodiments, the efficacy (or effectiveness) of the vaccine against VZV is greater than 80%. In some embodiments, the efficacy (or effectiveness) of the vaccine against VZV is greater than 85%. In some embodiments, the efficacy (or effectiveness) of the vaccine against VZV is greater than 90%.

In some embodiments, the vaccine immunizes the subject against VZV up to 1 year (e.g. for a single VZV season). In some embodiments, the vaccine immunizes the subject against VZV for up to 2 years. In some embodiments, the vaccine immunizes the subject against VZV for more than 2 years. In some embodiments, the vaccine immunizes the subject against VZV for more than 3 years. In some embodiments, the vaccine immunizes the subject against VZV for more than 4 years. In some embodiments, the vaccine immunizes the subject against VZV for 5-10 years.

In some embodiments, the subject administered an VZV RNA (e.g., mRNA) vaccine is between the ages of about 12 months old and about 10 years old (e.g., about 1, 2, 3, 4, 5, 6, 7, 8, 9 or 10 years old). In some embodiments, the subject administered an VZV RNA (e.g., mRNA) vaccine is between the ages of about 12 months old and about 15 months old (e.g., about 12, 12.5, 13, 13.5, 14, 14.5 or 15 months old). In some embodiments, the subject administered an VZV RNA (e.g., mRNA) vaccine is between the ages of about 4 years old and about 6 years old (e.g., about 4, 4.5, 5, 5.6, or 6 years old).

In some embodiments, the subject is a young adult between the ages of about 20 years and about 50 years (e.g., about 20, 25, 30, 35, 40, 45 or 50 years old).

In some embodiments, the subject is an elderly subject about 60 years old, about 70 years old, or older (e.g., about 60, 65, 70, 75, 80, 85 or 90 years old).

In some embodiments, the subject has been exposed to VZV, is infected with (has) VZV, or is at risk of infection by VZV.

In some embodiments, the subject is immunocompromised (has an impaired immune system, e.g., has an immune disorder or autoimmune disorder).

Some aspects of the present disclosure provide varicella zoster virus (VZV) RNA (e.g., mRNA) vaccines containing a signal peptide linked to a VZV antigenic polypeptide. Thus, in some embodiments, the VZV RNA (e.g., mRNA) vaccines contain at least one ribonucleic acid (RNA) polynucleotide having an open reading frame encoding a signal peptide linked to a VZV antigenic peptide. Also provided herein are nucleic acids encoding the VZV RNA (e.g., mRNA) vaccines disclosed herein.

Other aspects of the present disclosure provide varicella zoster virus (VZV) vaccines containing a signal peptide linked to a VZV antigenic polypeptide. In some embodiments, the VZV antigenic polypeptide is a VZV glycoprotein. In some embodiments, the VZV glycoprotein is selected from VZV gE, gI, gB, gH, gK, gL, gC, gN, and gM. In some embodiments, the VZV glycoprotein is VZV gE or a variant VZV gE polypeptide.

In some embodiments, the signal peptide is a IgE signal peptide. In some embodiments, the signal peptide is an IgE HC (Ig heavy chain epsilon-1) signal peptide. In some embodiments, the signal peptide has the sequence MDWTWILFLVAAATRVHS (SEQ ID NO: 56). In some embodiments, the signal peptide is an IgGx signal peptide. In some embodiments, the signal peptide has the sequence METPAQLLFLLLLWLPDTTG (SEQ ID NO: 57). In some embodiments, the signal peptide is selected from: a Japanese encephalitis PRM signal sequence (MLGSNSGQRVVFTILLLLVAPAYS; SEQ ID NO: 109), VSVg protein signal sequence (MKCLLYLAFLFIGVNCA; SEQ ID NO: 110) and Japanese encephalitis JEV signal sequence (MWLVSLAIVTACAGA; SEQ ID NO: 111).

Further provided herein are nucleic acids encoding VZV vaccines disclosed herein. Such VZV vaccines include at least one ribonucleic acid (RNA) (e.g., mRNA) polynucleotide having an open reading frame encoding a signal peptide linked to a VZV antigenic polypeptide. In some embodiments, the VZV antigenic peptide is a VZV glycoprotein. In some embodiments, the VZV glycoprotein is selected from VZV gE, gI, gB, gH, gK, gL, gC, gN, and gM. In some embodiments, the VZV antigenic peptide is a VZV gE or a variant of the gE polypeptide.

In some embodiments, an effective amount of an VZV RNA (e.g., mRNA) vaccine (e.g., a single dose of the VZV vaccine) results in a 2 fold to 200 fold (e.g., about 2, 3, 4, 5, 6, 7, 8, 9, 10, 20, 30, 40, 50, 60, 70, 80, 90, 100, 110, 120, 130, 140, 150, 160, 170, 180, 190 or 200 fold) increase in serum neutralizing antibodies against VZV, relative to a control. In some embodiments, a single dose of the VZV RNA (e.g., mRNA) vaccine results in an about 5 fold, 50 fold, or 150 fold increase in serum neutralizing antibodies against VZV, relative to a control. In some embodiments, a single dose of the VZV RNA (e.g., mRNA) vaccine results in an about 2 fold to 10 fold, or an about 40 to 60 fold increase in serum neutralizing antibodies against VZV, relative to a control.

In some embodiments, efficacy of RNA vaccines RNA (e.g., mRNA) can be significantly enhanced when combined with a flagellin adjuvant, in particular, when one or more antigen-encoding mRNAs is combined with an mRNA encoding flagellin.

RNA (e.g., mRNA) vaccines combined with the flagellin adjuvant (e.g., mRNA-encoded flagellin adjuvant) have superior properties in that they may produce much larger antibody titers and produce responses earlier than commercially available vaccine formulations. While not wishing to be bound by theory, it is believed that the RNA vaccines, for example, as mRNA polynucleotides, are better designed to produce the appropriate protein conformation upon translation, for both the antigen and the adjuvant, as the RNA (e.g., mRNA) vaccines co-opt natural cellular machinery. Unlike traditional vaccines, which are manufactured ex vivo and may trigger unwanted cellular responses, RNA (e.g., mRNA) vaccines are presented to the cellular system in a more native fashion.

Some embodiments of the present disclosure provide RNA (e.g., mRNA) vaccines that include at least one RNA (e.g., mRNA) polynucleotide having an open reading frame encoding at least one antigenic polypeptide and at least one RNA (e.g., mRNA polynucleotide) having an open reading frame encoding a flagellin adjuvant.

In some embodiments, at least one flagellin polypeptide (e.g., encoded flagellin polypeptide) is a flagellin protein. In some embodiments, at least one flagellin polypeptide (e.g., encoded flagellin polypeptide) is an immunogenic flagellin fragment. In some embodiments, at least one flagellin polypeptide and at least one antigenic polypeptide are encoded by a single RNA (e.g., mRNA) polynucleotide. In other embodiments, at least one flagellin polypeptide and at least one antigenic polypeptide are each encoded by a different RNA polynucleotide.

In some embodiments at least one flagellin polypeptide has at least 80%, at least 85%, at least 90%, or at least 95% identity to a flagellin polypeptide having a sequence of any one of SEQ ID NO: 115-117.

In some embodiments the nucleic acid vaccines described herein are chemically modified. In other embodiments the nucleic acid vaccines are unmodified.

In some embodiments, the RNA polynucleotide is any one of SEQ ID NO: 1-8 and 41 and includes at least one chemical modification. In other embodiments, the RNA polynucleotide is any one of SEQ ID NO: 1-8 and 41 and does not include any nucleotide modifications, or is unmodified. In yet other embodiments, the at least one RNA polynucleotide encodes an antigenic protein of any one of SEQ ID NO: 10, 14, 18, 22, 26, 30, 34, 38, 42 and 45-55 and includes at least one chemical modification. In other embodiments, the RNA polynucleotide encodes an antigenic protein of any one of SEQ ID NO: 10, 14, 18, 22, 26, 30, 34, 38, 42 and 45-55 and does not include any nucleotide modifications, or is unmodified.

In some embodiments, the RNA polynucleotide comprises a sequence of any one of SEQ ID NO: 142-150. In some embodiments, the RNA polynucleotide comprises a sequence of any one of SEQ ID NO: 142-150 and includes at least one chemical modification. In other embodiments, the RNA polynucleotide comprises a sequence of any one of SEQ ID NO: 142-150 and does not include any nucleotide modifications, or is unmodified.

Yet other aspects provide compositions for and methods of vaccinating a subject comprising administering to the subject a nucleic acid vaccine comprising one or more RNA polynucleotides having an open reading frame encoding a first antigenic VZV polypeptide, wherein the RNA polynucleotide does not include a stabilization element, and wherein an adjuvant is not co-formulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 μg/kg and 400 μg/kg of the nucleic acid vaccine is administered to the subject. In some embodiments the dosage of the RNA polynucleotide is 1-5 μg, 5-10 μg, 10-15 μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide.

In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no chemical modification, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between bug and 400 μg of one or more RNA polynucleotides having an open reading frame comprising at least one chemical modification or optionally no chemical modification, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a VZV strain in an individual or population of individuals comprising administering to said individual or population an antigenic memory booster nucleic acid vaccine comprising (a) at least one RNA polynucleotide, said polynucleotide comprising at least one chemical modification or optionally no chemical modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no modified nucleotides (unmodified), the open reading frame encoding a first antigenic polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. The data demonstrated the effectiveness of both chemically modified and unmodified RNA vaccines of the invention. Surprisingly, in contrast to prior art reports that it was preferable to use chemically unmodified mRNA formulated in a carrier for the production of vaccines, it was discovered herein that chemically modified mRNA-LNP vaccines required a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding a VZV antigenic polypeptide in an effective amount to vaccinate the subject.

In other aspects the invention encompasses a method of treating a young subject age 17 years or younger comprising administering to the subject a nucleic acid vaccine comprising one or more RNA polynucleotides having an open reading frame encoding a VZV antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding a VZV antigenic polypeptide in an effective amount to vaccinate the subject.

In preferred aspects, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3 depicts the study design and injection schedule for the immunization of BALB/C mice with MC3 formulated mRNA encoded VZV gE antigens.

FIGS. 8A and 8B show confocal microscopy of human melanoma (MeWo) cells stained with an antibodies to show the golgi apparatus.

FIGS. 9A-9C show confocal microscopy of MeWo cells stained with antibodies against VZV gE to show VZV gE expression and trafficking. The sequence AEAADA depicted in FIG. 9C is SEQ ID NO: 58.

FIGS. 11A and 11B is SEQ ID NO: 58.

FIGS. 12A and 12B is SEQ ID NO: 58.

FIG. 13 is SEQ ID NO: 58.

FIG. 14A is SEQ ID NO: 58.

FIGS. 15A and 15B is SEQ ID NO: 58.

FIG. 22A shows the injection schedule for Table 6. FIG. 22B shows the injection table for Table 7.

DETAILED DESCRIPTION

Figure 1:
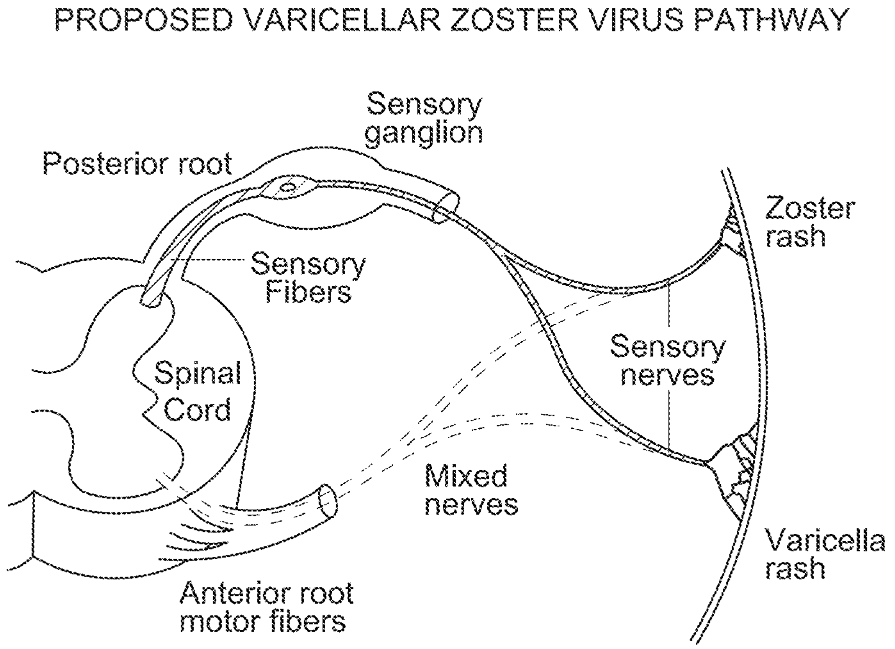
FIG. 1 is a schematic depicting a proposed Varicella zoster virus pathway.

Embodiments of the present disclosure provide RNA (e.g., mRNA) vaccines that include at least one RNA (e.g., mRNA) polynucleotide encoding a varicella zoster virus (VZV) antigen. There are at least five clades of varicella zoster virus (VZV). Clades 1 and 3 include European/North American strains; clade 2 includes Asian strains, especially from Japan; and Clade 5 appears to be based in India. Clade 4 includes some strains from Europe, but its geographic origins need further clarification. Phylogenetic analysis of VZV genomic sequences resolves wild-type strains into 9 genotypes (E1, E2, J, M1, M2, M3, M4, VIII and IX). Sequence analysis of 342 clinical varicella and zoster specimens from 18 European countries identified the following distribution of VZV genotypes: E1, 221 (65%); E2, 87 (25%); M1, 20 (6%); M2, 3 (1%); M4, and 11 (3%). No M3 or J strains were observed. Of 165 clinical varicella and zoster isolates from Australia and New Zealand, 67 of 127 eastern Australian isolates were E1, 30 were E2, 16 were J, 10 were M1, and 4 were M2; 25 of 38 New Zealand isolates were E1, 8 were E2, and 5 were M1.

VZV is an alphaherpesvirus that exists as a spherical multilayered structure approximately 200 nm in diameter. The viral genome is surrounded by a protein capsid structure that is covered by an amorphous layer of tegument proteins. These two structures are surrounded by a lipid envelope that is studded with viral glycoproteins, each about 8 nm in length, that are displayed on the exterior of the virion, and encloses the 100 nm nucleocapsid which is comprised of 162 hexameric and pentameric capsomeres arranged in an icosahedral form. The tegument, which is comprised of virally-encoded proteins and enzymes, is located in the space between the nucleocapsid and the viral envelope. The viral envelope is acquired from host cell membranes and contains viral-encoded glycoproteins.

The VZV genome is a single, linear, duplex DNA molecule of 124,884 base pairs having at least 70 open reading frames. The genome has 2 predominant isomers, depending on the orientation of the S segment, P (prototype) and IS (inverted S), which are present with equal frequency for a total frequency of 90-95%. The L segment can also be inverted resulting in a total of four linear isomers (IL and ILS).

VZV is closely related to the herpes simplex viruses (HSV), sharing much genome homology. The VZV genome is the smallest of the human herpesviruses and encodes at least 71 unique proteins (ORF0-ORF68) with three more opening reading frames (ORF69-ORF71) that duplicate earlier open reading frames (ORF64-62, respectively). Only a fraction of the encoded proteins form the structure of the virus particle. Among those proteins are nine glycoproteins: ORFS (gK), ORF9A (gN), ORF14 (gC), ORF31 (gB), ORF37 (gH), ORF50 (gM), ORF60 (gL), ORF67 (gI), and ORF68 (gE). The known envelope glycoproteins (gB, gC, gE, gH, gI, gK, gL, gN, and gM) correspond with those in HSV; however, there is no equivalent of HSV gD. VZV also fails to produce the LAT (latency-associated transcripts) that play an important role in establishing HSV latency (herpes simplex virus). The encoded glycoproteins gE, gI, gB, gH, gK, gL, gC, gN, and gM function in different steps of the viral replication cycle. The most abundant glycoprotein found in infected cells, as well as in the mature virion, is glycoprotein E (gE, ORF 68), which is a major component of the virion envelope and is essential for viral replication. Glycoprotein I (gI, ORG 67) forms a complex with gE in infected cells, which facilitates the endocytosis of both glycoproteins and directs them to the trans-Golgi network (TGN) where the final viral envelope is acquired. Glycoprotein I (gI) is required within the TGN for VZV envelopment and for efficient membrane fusion during VZV replication. VZV gE and gI are found complexed together on the infected host cell surface. Glycoprotein B (ORF 31), which is the second most prevalent glycoprotein and thought to play a role in virus entry, binds to neutralizing antibodies. Glycoprotein H is thought to have a fusion function facilitating cell to cell spread of the virus. Antibodies to gE, gB, and gH are prevalent after natural infection and following vaccination and have been shown to neutralize viral activity in vitro.

Embodiments of the present disclosure provide RNA (e.g., mRNA) vaccines that include at least one polynucleotide encoding at least one VZV antigenic polypeptide. The VZV RNA vaccines provided herein may be used to induce a balanced immune response, comprising both cellular and humoral immunity, without many of the risks associated with DNA vaccines and live attenuated vaccines. The various RNA (e.g., mRNA) vaccines disclosed herein produced an immune response in BALB/C mice, the results of which are discussed in detail in the Examples section. Specifically, RNA (e.g., mRNA) polynucleotide vaccines having an open reading frame encoding one or more of a variety of VZV antigens produced significant immune response, relative to a traditional VZV vaccine (e.g. attenuated VZV virus). The VZV RNA (e.g., mRNA) polynucleotide vaccines disclosed herein encoding either VZV gE or variant VZV gE demonstrated significant immune response after two administrations when administered intramuscularly (IM) or intradermally (ID). The VZV glycoproteins and tegument proteins have been shown to be antigenic. VZV glycoproteins, fragments thereof, and epitopes thereof are encompassed within the present disclosure.

The entire contents of International Application No. PCT/US2015/027400, International Publication No. WO2015/164674A, are incorporated herein by reference.

It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the invention generate a more rapid immune response with fewer doses of antigen than other vaccines tested. The mRNA-LNP formulations of the invention also produce quantitatively and qualitatively better immune responses than vaccines formulated in a different carriers. The data described herein demonstrate that the formulations of the invention produced significant unexpected improvements over existing VZV antigen vaccines, including significantly higher levels of IgG production by mRNA chemically modified and unmodified VZV vaccines formulated in LNP compared to VARIVAX and ZOSTAVAX. The onset of IgG production was significantly more rapid for the chemically modified LNP mRNA vaccines than the unmodified or commercially available vaccines tested.

Additionally, the mRNA-LNP formulations of the invention are superior to other vaccines even when the dose of mRNA is lower than other vaccines. The data demonstrate that all gE variants LNP mRNA vaccines induced much stronger immune response than ZOSTAVAX® after the two 10 μg doses as well as after the two 2 μg doses. When the sera were diluted more than 100 fold, the antibody titer is higher in VZV gE LNP mRNA vaccinated mice sera than in ZOSTAVAX® vaccinated mice sera, suggesting that the VZV gE LNP mRNA vaccines induced much stronger immune response than ZOSTAVAX® in mice.

The results in mice were consistent with the immunogenicity observed in non-human primates. Rhesus monkeys were primed with chemically modified VZV LNP mRNA vaccines or ZOSTAVAX®. The mRNA vaccines provided higher anti-gE titers than ZOSTAVAX® and produced reasonable frequency of CD4 T-cells producing IFNγ, IL-2 or TNFα cells, unlike the ZOSTAVAX® group. The data also demonstrated that a single dose of mRNA vaccination after ZOSTAVAX® exposure was equivalent to two doses of mRNA vaccination in inducing comparable T-cell responses.

Some of the LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Antigens/Antigenic Polypeptides

In some embodiments, an antigenic polypeptide is a VZV glycoprotein. For example, a VZV glycoprotein may be VZV gE, gI, gB, gH, gK, gL, gC, gN, or gM. In some embodiments, the antigenic polypeptide is a VZV gE polypeptide. In some embodiments, the antigenic polypeptide is a VZV gI polypeptide. In some embodiments, the antigenic polypeptide is a VZV gB polypeptide. In some embodiments, the antigenic polypeptide is a VZV gH polypeptide. In some embodiments, the antigenic polypeptide is a VZV gK polypeptide. In some embodiments, the antigenic polypeptide is a VZV gL polypeptide. In some embodiments, the antigenic polypeptide is a VZV gC polypeptide. In some embodiments, the antigenic polypeptide is a VZV gN polypeptide. In some embodiments, the antigenic polypeptide is a VZV gM polypeptide.

In some embodiments, the antigenic polypeptide comprises two or more glycoproteins. The two or more glycoproteins can be encoded by a single RNA polynucleotide or can be encoded by two or more RNA polynucleotides, for example, each glycoprotein encoded by a separate RNA polynucleotide. In some embodiments, the two or more glycoproteins can be any combination of VZV gE, gI, gB, gH, gK, gL, gC, gN, and gM polypeptides. In some embodiments, the two or more glycoproteins can be any combination of VZV gE and a glycoprotein selected from gI, gB, gH, gK, gL, gC, gN, and gM polypeptides. In some embodiments, the two or more glycoproteins can be any combination of VZV gI and a glycoprotein selected from gE, gB, gH, gK, gL, gC, gN, and gM polypeptides. In some embodiments, the two or more glycoproteins can be any combination of VZV gE, gI, and a glycoprotein selected from gB, gH, gK, gL, gC, gN, and gM polypeptides. In some embodiments, the two or more VZV glycoproteins are gE and gI. Alternate RNA vaccines comprising RNA polynucleotides encoding other viral protein components of VZV, for example, tegument proteins are encompassed by the present disclosure. Thus, some embodiments of the present disclosure provide VZV vaccines that include at least one ribonucleic acid (RNA) polynucleotide having an open reading frame encoding at least one VZV tegument protein. In some embodiments, the antigenic polypeptide is a VZV tegument protein. In other embodiments, the antigenic fragment(s) of the VZV vaccine may be at least one VZV tegument polypeptide and at least one VZV glycoprotein polypeptide, for example any VZV glycoprotein selected from gE, gI, gB, gH, gK, gL, gC, gN, and gM.

The present disclosure includes variant VZV antigenic polypeptides. In some embodiments, the variant VZV antigenic polypeptide is a variant VZV gE polypeptide. The variant VZV gE polypeptides are designed to avoid ER/golgi retention of polypeptides, leading to increased surface expression of the antigen. In some embodiments, the variant gE polypeptides are truncated to remove the ER retention portion or the cytoplasmic tail portion of the polypeptide. In some embodiments, the variant VZV gE polypeptides are mutated to reduce VZV polypeptide localization to the ER/golgi/TGN. Such modifications inhibit ER trapping and, as such, expedite trafficking to the cell membrane.

Thus, in some embodiments, the VZV glycoprotein is a variant gE polypeptide. VZV gE has targeting sequences for the TGN in its C-terminus and is transported from the ER to the TGN in infected and gE-transfected cells. Most gE in the TGN appears to be retrieved by endocytosis from the plasma membrane and delivered to the TGN by endosomes, which is followed by recycling to the plasma membranes. gE is accumulated in TGN, along with other VZV proteins (e.g., tegument proteins) associated with the production of fully enveloped VZV virions. Thus, mutations to reduce TGN localization and endocytosis aids in the trafficking of gE to the cell membrane.

The variant VZV gE polypeptide can be any truncated polypeptide lacking the anchor domain (ER retention domain). For example, the variant VZV gE polypeptide can be a truncated VZV gE polypeptide comprising at least amino acids 1-124, including, for example, amino acids 1-124, 1-140, 1-160, 1-200, 1-250, 1-300, 1-350, 1-360, 1-400, 1-450, 1-500, 1-511, 1-550, and 1-561, as well as polypeptide fragments having fragment sizes within the recited size ranges. In one embodiment, the truncated VZV gE polypeptide comprises amino acids 1-561 of SEQ ID NO: 10. In some embodiments, the variant VZV gE polypeptide is a truncated polypeptide lacking the carboxy terminal tail domain. Thus in some embodiments, the truncated VZV gE polypeptide comprises amino acids 1-573 of SEQ ID NO: 10.

In some embodiments, the variant VZV gE polypeptide has at least one mutation in one or more motif(s) associated with ER retention, wherein the mutation(s) in one or more motif(s) results in decreased retention of the VZV gE polypeptide in the ER and/or golgi. In some embodiments, the variant VZV gE polypeptide has at least one mutation in one or more phosphorylated acidic motif(s). For example, the variant VZV gE polypeptide can be a full-length VZV gE polypeptide having a Y582G mutation, a Y569A mutation, or both a Y582G mutation and a Y569A mutation. Alternatively, the variant VZV gE polypeptide can be an antigenic fragment comprising, for example, amino acids 1-573 of VZV gE and having a Y569A mutation. Alternatively, the variant VZV gE polypeptide can be an antigenic fragment having mutation in an acidic phosphorylation motif, such as an SST motif. For example, the variant VZV gE polypeptide can be an antigenic fragment having AEAADA sequence (SEQ ID NO: 58).

In some embodiments, the variant VZV gE polypeptide is a full-length VZV gE polypeptide having additional sequence at the C-terminus which aids in secretion of the polypeptide. For example, the variant VZV gE polypeptide can be a full-length VZV gE polypeptide having an IgKappa sequence at the C-terminus. In some embodiments, the VZV gE polypeptide has additional sequence at the C-terminus that aids in secretion (I., an IgKappa sequence at the C-terminus) and the variant VZV gE polypeptide has at least one mutation in one or more motif(s) associated with ER retention, TGN localization, and/or endocytosis (e.g., a Y582G mutation, a Y569A mutation, or both a Y582G mutation and a Y569A mutation) and/or at least one mutation in one or more phosphorylated acidic motif(s). In some embodiments, the variant VZV gE polypeptide is a truncated polypeptide lacking the anchor domain (ER retention domain) and having an additional sequence at the C-terminus which aids in secretion of the polypeptide, for example, an IgKappa sequence at the C-terminus. In some embodiments, the truncated VZV gE polypeptide comprises amino acids 1-561 of SEQ ID NO: 10 and has an IgKappa sequence at the C-terminus. In some embodiments, the variant VZV gE polypeptide is a truncated polypeptide lacking the carboxy terminal tail domain and having an additional sequence at the C-terminus that aids in secretion of the polypeptide (e.g., having an IgKappa sequence at the C-terminus). In some embodiments, the truncated VZV gE polypeptide comprises amino acids 1-573 of SEQ ID NO: 10 and has an IgKappa sequence at the C-terminus.

In some embodiments, a VZV antigenic polypeptide is longer than 25 amino acids and shorter than 50 amino acids. The term "antigenic polypeptide" and "antigenic protein" includes immunogenic fragments and epitopes thereof. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain or multichain polypeptides such as antibodies or insulin and may be associated or linked. Most commonly, disulfide linkages are found in multichain polypeptides. The term polypeptide may also apply to amino acid polymers in which at least one amino acid residue is an artificial chemical analogue of a corresponding naturally-occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, a "variant mimic" contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic. For example, phenylalanine may act as an inactivating substitution for tyrosine, or alanine may act as an inactivating substitution for serine.

"Orthologs" refers to genes in different species that evolved from a common ancestral gene by speciation. Normally, orthologs retain the same function in the course of evolution. Identification of orthologs is critical for reliable prediction of gene function in newly sequenced genomes.

"Analogs" is meant to include polypeptide variants that differ by one or more amino acid alterations, for example, substitutions, additions or deletions of amino acid residues that still maintain one or more of the properties of the parent or starting polypeptide.

"Paralogs" are genes (or proteins) related by duplication within a genome. Orthologs retain the same function in the course of evolution, whereas paralogs evolve new functions, even if these are related to the original one.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant," but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support. In alternative embodiments, sequences for (or encoding) signal sequences, termination sequences, transmembrane domains, linkers, multimerization domains (such as, e.g., foldon regions) and the like may be substituted with alternative sequences that achieve the same or a similar function. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an RNA (e.g., mRNA) vaccine.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue, such as lysine, arginine or histidine for another, or the substitution of one acidic residue, such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein, when referring to polypeptides the terms "site" as it pertains to amino acid based embodiments, is used synonymously with "amino acid residue" and "amino acid side chain." As used herein, when referring to polynucleotides the terms "site" as it pertains to nucleotide based embodiments, is used synonymously with "nucleotide." A site represents a position within a peptide or polypeptide or polynucleotide that may be modified, manipulated, altered, derivatized or varied within the polypeptide or polynucleotide based molecules.

As used herein, the terms "termini" or "terminus," when referring to polypeptides or polynucleotides, refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N-termini and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids that are 40%, 50%, 60%, 70%, 80%, 90%, 95%, or 100% identical to any of the sequences described herein can be utilized in accordance with the present disclosure. In some embodiments, a polypeptide includes 2, 3, 4, 5, 6, 7, 8, 9, 10, or more mutations, as shown in any of the sequences provided or referenced herein. In some embodiments, a protein fragment is longer than 25 amino acids and shorter than 50 amino acids.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity," as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication.

Nucleic Acids/Polynucleotides

Varicella zoster virus (VZV) vaccines, as provided herein, comprise at least one (one or more) ribonucleic acid (RNA, e.g., mRNA) polynucleotide having an open reading frame encoding at least one VZV antigenic polypeptide. The term "nucleic acid," in its broadest sense, includes any compound and/or substance that comprises a polymer of nucleotides. These polymers are referred to as polynucleotides.

In some embodiments, at least one RNA polynucleotide of a VZV vaccine is encoded by at least one nucleic acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 41.

In some embodiments, at least one RNA (e.g., mRNA) polynucleotide of a VZV vaccine is encoded by at least one fragment of a nucleic acid sequence (e.g., a fragment having an antigenic sequence or at least one epitope) selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 41.

Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The skilled artisan will appreciate that, except where otherwise noted, polynucleotide sequences set forth in the instant application will recite "T"s in a representative DNA sequence, but where the sequence represents RNA (e.g., mRNA), the "T"s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U."

It should be understood that the mRNA polynucleotides of the vaccines as provided herein are synthetic molecules, i.e., they are not naturally-occurring molecules. That is, the mRNA polynucleotides of the present disclosure are isolated mRNA polynucleotides. As is known in the art, "isolated polynucleotides" refer to polynucleotides that are substantially physically separated from other cellular material (e.g., separated from cells and/or systems that produce the polynucleotides) or from other material that hinders their use in the vaccines of the present disclosure. Isolated polynucleotides are substantially pure in that they have been substantially separated from the substances with which they may be associated in living or viral systems. Thus, mRNA polynucleotide vaccines are not associated with living or viral systems, such as cells or viruses. The mRNA polynucleotide vaccines do not include viral components (e.g., viral capsids, viral enzymes, or other viral proteins, for example, those needed for viral-based replication), and the mRNA polynucleotide vaccines are not packaged within, encapsulated within, linked to, or otherwise associated with a virus or viral particle. In some embodiments, the mRNA vaccines comprise a lipid nanoparticle that consists of, or consists essentially of, one or more mRNA polynucleotides (e.g., mRNA polynucleotides encoding one or more VZV antigen(s)).

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features, which serve to overcome existing problems of effective polypeptide expression using nucleic-acid based therapeutics. In some embodiments, the RNA is a messenger RNA (mRNA) having an open reading frame encoding at least one VZV antigen. In some embodiments, the RNA (e.g., mRNA) further comprises a (at least one) 5' UTR, 3' UTR, a polyA tail and/or a 5' cap.

In some embodiments, a RNA polynucleotide (e.g., mRNA) of a VZV vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA polynucleotide (e.g., mRNA) of a VZV RNA (e.g., mRNA) vaccine encodes at least 10, 20, 30, 40, 50, 60, 70, 80, 90 or 100 antigenic polypeptides. In some embodiments, a RNA polynucleotide (e.g., mRNA) of a VZV vaccine encodes at least 100 antigenic polypeptides, or at least 200 antigenic polypeptides. In some embodiments, a RNA polynucleotide (e.g., mRNA) of a VZV vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides (e.g., mRNAs) of the present disclosure, in some embodiments, are codon optimized. Codon optimization methods are known in the art and may be used as provided herein. For example, any one or more of the sequences SEQ ID NO: 11, 15, 19, 23, 27, 31, 35, 39, 62, 66, 70, 74, 78, 82, 86, 90 or any one or more of the sequences of SEQ ID NO: 92-108 may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence (e.g., a codon-optimized sequence any one of SEQ ID NO: 92-108) shares less than 95% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide)). In some embodiments, a codon optimized sequence shares between 65% and 75% or about 80% sequence identity to a naturally-occurring or wild-type sequence (e.g., a naturally-occurring or wild-type mRNA sequence encoding a polypeptide or protein of interest (e.g., an antigenic protein or polypeptide)).

In some embodiments, a codon-optimized sequence (e.g., a codon-optimized sequence of any one of SEQ ID NO: 92-108) encodes an antigenic polypeptide that is as immunogenic as, or more immunogenic than (e.g., at least 10%, at least 20%, at least 30%, at least 40%, at least 50%, at least 100%, or at least 200% more), than an antigenic polypeptide encoded by a (non-codon-optimized) sequence of any one of SEQ ID NO: 92-108.

In some embodiments, the VZV vaccine includes at least one RNA polynucleotide having an open reading frame encoding at least one VZV antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O—Me-m7G(5') ppp(5') G [the ARCA cap]; G(5')ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G (5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

When transfected into mammalian cells, the modified mRNAs have a stability of between 12-18 hours, or greater than 18 hours, e.g., 24, 36, 48, 60, 72, or greater than 72 hours.

In some embodiments a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Signal Peptides

In some embodiments, antigenic polypeptides encoded by VZV polynucleotides comprise a signal peptide. Signal peptides, comprising the N-terminal 15-60 amino acids of proteins, are typically needed for the translocation across the membrane on the secretory pathway and thus universally control the entry of most proteins both in eukaryotes and prokaryotes to the secretory pathway. Signal peptides generally include of three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodominance of certain signal peptides are much more versatile than previously anticipated.

Signal peptides typically function to facilitate the targeting of newly synthesized protein to the endoplasmic reticulum (ER) for processing. ER processing produces a mature Envelope protein, wherein the signal peptide is cleaved, typically by a signal peptidase of the host cell. A signal peptide may also facilitate the targeting of the protein to the cell membrane. VZV vaccines of the present disclosure may comprise, for example, RNA polynucleotides encoding an artificial signal peptide, wherein the signal peptide coding sequence is operably linked to and is in frame with the coding sequence of the VZV antigenic polypeptide. Thus, VZV vaccines of the present disclosure, in some embodiments, produce an antigenic polypeptide comprising a VZV antigenic polypeptide fused to a signal peptide. In some embodiments, a signal peptide is fused to the N-terminus of the VZV antigenic polypeptide. In some embodiments, a signal peptide is fused to the C-terminus of the VZV antigenic polypeptide.

In some embodiments, the signal peptide fused to the VZV antigenic polypeptide is an artificial signal peptide. In some embodiments, an artificial signal peptide fused to the VZV antigenic polypeptide encoded by the VZV RNA (e.g., mRNA) vaccine is obtained from an immunoglobulin protein, e.g., an IgE signal peptide or an IgG signal peptide. In some embodiments, a signal peptide fused to the VZV antigenic polypeptide encoded by a VZV RNA (e.g., mRNA) vaccine is an Ig heavy chain epsilon-1 signal peptide (IgE HC SP) having the sequence of: MDWTWILFLVAAATRVHS (SEQ ID NO: 56). In some embodiments, a signal peptide fused to a VZV antigenic polypeptide encoded by the VZV RNA (e.g., mRNA) vaccine is an IgGk chain V-III region HAH signal peptide (IgGk SP) having the sequence of METPAQLLFLLLLWLPDTTG (SEQ ID NO: 57). In some embodiments, the VZV antigenic polypeptide encoded by a VZV RNA (e.g., mRNA) vaccine has an amino acid sequence set forth in one of 10, 14, 18, 22, 26, 30, 34, 38, 42 and 45-55 fused to a signal peptide of any one of SEQ ID NO: 56, 57, 109, 110 and 111. The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature VZV antigenic polypeptide produce by VZV RNA vaccine of the present disclosure typically does not comprise a signal peptide.

Chemical Modifications

RNA (e.g., mRNA) vaccines of the present disclosure comprise, in some embodiments, at least one ribonucleic acid (RNA) polynucleotide having an open reading frame encoding at least one respiratory syncytial virus (VZV) antigenic polypeptide, wherein said RNA comprises at least one chemical modification.

The terms "chemical modification" and "chemically modified" refer to modification with respect to adenosine (A), guanosine (G), uridine (U), thymidine (T) or cytidine (C) ribonucleosides or deoxyribonucleosides in at least one of their position, pattern, percent or population. Generally, these terms do not refer to the ribonucleotide modifications in naturally occurring 5'-terminal mRNA cap moieties.

Modifications of polynucleotides include, without limitation, those described herein, and include, but are expressly not limited to, those modifications that comprise chemical modifications. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

With respect to a polypeptide, the term "modification" refers to a modification relative to the canonical set of 20 amino acids. Polypeptides, as provided herein, are also considered "modified" if they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those polynucleotides having at least one chemical modification. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides), including but not limited to chemical modification, that are useful in the compositions, vaccines, methods and synthetic processes of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-

Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; T-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-0-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio)pseudouracil; 2'deoxy uridine; 2'fluorouridine; 2-(thio)uracil; 2,4-(dithio)psuedouracil; 2'methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2'deoxyuridine; 2'fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio) uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; P seudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxyl-ethoxy}-ethoxy)-propionyl]pseudouridine TP; 1-{3-[2-(2-Aminoethoxy)-ethoxy]-propionyl}pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP;

1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2'methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (w), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (ml A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl) pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQObase, preQ1base, and combinations of two or more thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polyribonucleotide (e.g., RNA polyribonucleotide, such as mRNA polyribonucleotide) includes a combination of at least two (e.g., 2, 3, 4 or more) of the aforementioned modified nucleobases. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polyribonucleotide includes a combination of at least two (e.g., 2, 3, 4 or more) of the aforementioned modified nucleobases, including but not limited to chemical modifications.

In some embodiments, polynucleotides (e.g., RNA polynucleotides, such as mRNA polynucleotides) comprise pseudouridine (ψ) and 5-methyl-cytidine (m5C). In some embodiments, the polyribonucleotides (e.g., RNA, such as mRNA) comprise 1-methyl-pseudouridine (m1ψ). In some embodiments, the polyribonucleotides (e.g., RNA, such as mRNA) comprise 1-ethyl-pseudouridine (e1ψ). In some embodiments, the polyribonucleotides (e.g., RNA, such as mRNA) comprise 1-methyl-pseudouridine (m1ψ) and 5-methyl-cytidine (m5C). In some embodiments, the polyribonucleotides (e.g., RNA, such as mRNA) comprise 1-ethyl-pseudouridine (e1ψ) and 5-methyl-cytidine (m5C). In some embodiments, the polyribonucleotides (e.g., RNA, such as mRNA) comprise 2-thiouridine (s2U). In some embodiments, the polyribonucleotides (e.g., RNA, such as mRNA) comprise 2-thiouridine and 5-methyl-cytidine (m5C). In some embodiments, the polyribonucleotides (e.g., RNA, such as mRNA) comprise methoxy-uridine (mo5U). In some embodiments, the polyribonucleotides (e.g., RNA, such as mRNA) comprise 5-methoxy-uridine (mo5U) and 5-methyl-cytidine (m5C). In some embodiments, the polyribonucleotides (e.g., RNA, such as mRNA) comprise 2'-O-methyl uridine. In some embodiments, the polyribonucleotides (e.g., RNA, such as mRNA) comprise 2'-O-methyl uridine and 5-methyl-cytidine (m5C). In some embodiments, the polyribonucleotides (e.g., RNA, such as mRNA) comprise N6-methyl-adenosine (m6A). In some embodiments, the polyribonucleotides (e.g., RNA, such as mRNA) comprise N6-methyl-adenosine (m6A) and 5-methyl-cytidine (m5C).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 1-methyl-pseudouridine, meaning that all uridine residues in the mRNA sequence are replaced with 1-methyl-pseudouridine. Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and nucleosides having a modified uridine include 1-methyl-pseudouridine (m1ψ), 1-ethyl-pseudouridine (e1ψ), 5-methoxy uridine, 2-thio uridine, 5-cyano uridine, 2'-O-methyl uridine and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (mil), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, and 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Thus, in some embodiments, the RNA vaccines comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine (yr), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridineor 5-bromo-uridine), 3-methyl-uridine ($m^3U$), 5-methoxy-uridine ($mo^5U$), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($rm^5U$), 1-taurinomethyl-pseudouridine, 5-taurinomethyl-2-thio-uridine ($\tau m^5s^2U$), 1-taurinomethyl-4-thio-pseudouridine, 5-methyl-uridine ($m^5U$, i.e., having the nucleobase deoxythymine), 1-methyl-pseudouridine ($m^1\psi$), 1-ethyl-pseudouridine ($e1\psi$), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Urn), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4{}_2Cm$), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2$ $m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl-N6-threonylcarbamoyl-adenosine ($m^6t^6A$), 2-methylthio-N6-threonylcarbamoyl-adenosine ($ms^2g^6A$), N6,N6-dimethyl-adenosine ($m^6{}_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methyl-thio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6{}_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine (G+), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2{}_2G$), N2,7-dimethyl-guanosine ($m^{2,7}G$), N2,N2,7-dimethyl-guanosine ($m^{2.2.7}$8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2{}_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), 2'-O-ribosylguanosine (phosphate) (Gr(p)), 1-thio-guanosine, 06-methyl-guanosine, 2'-F-ara-guanosine, and 2'-F-guanosine.

In Vitro Transcription of RNA (e.g., mRNA)

VZV vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, the at least one RNA polynucleotide has at least one chemical modification. The at least one chemical modification may include, but is expressly not limited to, any modification described herein.

In vitro transcription of RNA is known in the art and is described in International Publication WO2014/152027, which is incorporated by reference herein in its entirety. For example, in some embodiments, the RNA transcript is generated using a non-amplified, linearized DNA template in an in vitro transcription reaction to generate the RNA transcript. In some embodiments the RNA transcript is capped via enzymatic capping. In some embodiments the RNA transcript is purified via chromatographic methods, e.g., use of an oligo dT substrate. Some embodiments exclude the use of DNase. In some embodiments the RNA transcript is synthesized from a non-amplified, linear DNA template coding for the gene of interest via an enzymatic in vitro transcription reaction utilizing a T7 phage RNA polymerase and nucleotide triphosphates of the desired chemistry. Any number of RNA polymerases or variants may be used in the method of the present invention. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides.

In some embodiments a non-amplified, linearized plasmid DNA is utilized as the template DNA for in vitro transcription. In some embodiments, the template DNA is isolated DNA. In some embodiments, the template DNA is cDNA. In some embodiments, the cDNA is formed by reverse transcription of a RNA polynucleotide, for example, but not limited to VZV RNA, e.g. VZV mRNA. In some embodiments, Cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5 ' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA or RNA beginning with a start codon (e.g., methionine (ATG or AUG)), and ending with a stop codon (e.g., TAA, TAG or TGA, or UAA, UAG or UGA) and typically encodes a polypeptide (e.g., protein). It will be understood that the sequences disclosed herein may further comprise additional elements, e.g., 5' and 3' UTRs, but that those elements, unlike the ORF, need not necessarily be present in a vaccine of the present disclosure.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

Methods of Treatment

Provided herein are compositions (e.g., pharmaceutical compositions), methods, kits and reagents for prevention and/or treatment of VZV in humans and other mammals. VZV RNA vaccines can be used as therapeutic or prophylactic agents. They may be used in medicine to prevent and/or treat infectious disease. In exemplary aspects, the VZV RNA vaccines of the invention are used to provide prophylactic protection from varicella and herpes zoster. Varicella is an acute infectious disease caused by VZV. The primary varicella zoster virus infection that results in chickenpox (varicella) may result in complications, including viral or secondary bacterial pneumonia. Even when the clinical symptoms of chickenpox have resolved, VZV remains dormant in the nervous system of the infected person in the trigeminal and dorsal root ganglia and may reactivate later in life, travelling from the sensory ganglia back to the skin where it produces a disease (rash) known as shingles or herpes zoster, and can also cause a number of neurologic conditions ranging from aseptic meningitis to encephalitis. The VZV vaccines of the present disclosure can be used to prevent and/or treat both the primary infection (Chicken pox) and also the re-activated viral infection (shingles or herpes zoster) and may be particularly useful for prevention and/or treatment of immunocompromised and elderly patients to prevent or to reduce the severity and/or duration of herpes zoster.

Prophylactic protection from VZV can be achieved following administration of a VZV RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against a VZV is provided in aspects of the present disclosure. The method involves administering to the subject a VZV RNA vaccine comprising at least one RNA (e.g., mRNA) polynucleotide having an open reading frame encoding at least one VZV antigenic polypeptide, thereby inducing in the subject an immune response specific to VZV antigenic polypeptide, wherein anti-antigenic polypeptide antibody titer in the subject is increased following vaccination relative to anti-antigenic polypeptide antibody titer in a subject vaccinated with a prophylactically effective dose of a traditional vaccine against the VZV. An "anti-antigenic polypeptide antibody" is a serum antibody the binds specifically to the antigenic polypeptide.

A prophylactically effective dose is a therapeutically effective dose that prevents infection with the virus at a clinically acceptable level. In some embodiments, the therapeutically effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, VLP vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

A method of eliciting an immune response in a subject against a VZV is provided in aspects of the invention. The method involves administering to the subject a VZV RNA vaccine comprising at least one RNA polynucleotide having an open reading frame encoding at least one VZV antigenic polypeptide, thereby inducing in the subject an immune response specific to VZV antigenic polypeptide, wherein anti-antigenic polypeptide antibody titer in the subject is increased following vaccination relative to anti-antigenic polypeptide antibody titer in a subject vaccinated with a prophylactically effective dose of a traditional vaccine against the VZV. An "anti-antigenic polypeptide antibody" is a serum antibody the binds specifically to the antigenic polypeptide.

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc.

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the VZV.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the VZV.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the VZV.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the VZV.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the VZV.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the VZV.

A method of eliciting an immune response in a subject against a VZV is provided in other aspects of the invention. The method involves administering to the subject a VZV RNA vaccine comprising at least one RNA polynucleotide having an open reading frame encoding at least one VZV antigenic polypeptide, thereby inducing in the subject an immune response specific to VZV antigenic polypeptide, wherein the immune response in the subject is equivalent to an immune response in a subject vaccinated with a traditional vaccine against the VZV at 2 times to 100 times the dosage level relative to the RNA vaccine.

In some embodiments the immune response in the subject is equivalent to an immune response in a subject vaccinated with a traditional vaccine at twice the dosage level relative to the VZV RNA vaccine.

In some embodiments the immune response in the subject is equivalent to an immune response in a subject vaccinated with a traditional vaccine at three times the dosage level relative to the VZV RNA vaccine.

In some embodiments the immune response in the subject is equivalent to an immune response in a subject vaccinated with a traditional vaccine at 4 times the dosage level relative to the VZV RNA vaccine.

In some embodiments the immune response in the subject is equivalent to an immune response in a subject vaccinated with a traditional vaccine at 5 times the dosage level relative to the VZV RNA vaccine.

In some embodiments the immune response in the subject is equivalent to an immune response in a subject vaccinated with a traditional vaccine at 10 times the dosage level relative to the VZV RNA vaccine.

In some embodiments the immune response in the subject is equivalent to an immune response in a subject vaccinated with a traditional vaccine at 50 times the dosage level relative to the VZV RNA vaccine.

In some embodiments the immune response in the subject is equivalent to an immune response in a subject vaccinated with a traditional vaccine at 100 times the dosage level relative to the VZV RNA vaccine.

In some embodiments the immune response in the subject is equivalent to an immune response in a subject vaccinated with a traditional vaccine at 10 times to 1000 times the dosage level relative to the VZV RNA vaccine.

In some embodiments the immune response in the subject is equivalent to an immune response in a subject vaccinated with a traditional vaccine at 100 times to 1000 times the dosage level relative to the VZV RNA vaccine.

In other embodiments the immune response is assessed by determining [protein]antibody titer in the subject.

In other aspects the invention is a method of eliciting an immune response in a subject against a VZV by administering to the subject a VZV RNA vaccine comprising at least one RNA polynucleotide having an open reading frame encoding at least one VZV antigenic polypeptide, thereby inducing in the subject an immune response specific to VZV antigenic polypeptide, wherein the immune response in the subject is induced 2 days to 10 weeks earlier relative to an immune response induced in a subject vaccinated with a prophylactically effective dose of a traditional vaccine against the VZV. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of v eliciting an immune response in a subject against a VZV by administering to the subject a VZV RNA vaccine having an open reading frame encoding a first antigenic polypeptide, wherein the RNA polynucleotide does not include a stabilization element, and wherein an adjuvant is not co-formulated or co-administered with the vaccine.

Flagellin Adjuvants

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. Typhimurium, H. Pylori, V. Cholera, S. marcesens, S. flexneri, T. Pallidum, L. pneumophila, B. burgdorferei, C. difficile, R. meliloti, A. tumefaciens, R. lupini, B. clarridgeiae, P. Mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identify to a flagellin protein or immunogenic fragments thereof. Exemplary flagellin proteins include flagellin from *Salmonella typhi* (UniPro Entry number: Q56086), *Salmonella typhimurium* (A0A0C$_9$DG09), *Salmonella enteritidis* (A0A0C9BAB7), and *Salmonella choleraesuis* (Q6V2X8), and SEQ ID NO: 115-117. In some embodiments, the flagellin polypeptide has at least 60%, 70%, 75%, 80%, 90%, 95%, 97%, 98%, or 99% sequence identify to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region, "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains D0 through D3. D0 and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 (in *Salmonella typhimurium* FliC flagellin. Within the 13 amino acids in the 88-100 region, at least 6 substitutions are permitted between *Salmonella* flagellin and other flagellin proteins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 118).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides and the other encoding the flagellin polypeptide. The at least two RNA polynucleotides may be co-formulated in a carrier such as a lipid nanoparticle.

Therapeutic and Prophylactic Compositions

Provided herein are compositions (e.g., pharmaceutical compositions), methods, kits and reagents for prevention, treatment or diagnosis of VZV in humans and other mammals, for example. VZV RNA (e.g., mRNA) vaccines can be used as therapeutic or prophylactic agents. They may be used in medicine to prevent and/or treat infectious disease. In some embodiments, the VZV vaccines of the invention can be envisioned for use in the priming of immune effector cells, for example, to activate peripheral blood mononuclear cells (PBMCs) ex vivo, which are then infused (re-infused) into a subject.

In exemplary embodiments, a VZV vaccine containing RNA polynucleotides as described herein can be administered to a subject (e.g., a mammalian subject, such as a human subject), and the RNA polynucleotides are translated in vivo to produce an antigenic polypeptide.

The VZV RNA vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue or organism is contacted with an effective amount of a composition containing a VZV RNA vaccine that contains a polynucleotide that has at least one a translatable region encoding an antigenic polypeptide.

An "effective amount" of the VZV RNA vaccine is provided based, at least in part, on the target tissue, target cell type, means of administration, physical characteristics of the polynucleotide (e.g., size, and extent of modified nucleosides) and other components of the VZV RNA vaccine, and other determinants. In general, an effective amount of the VZV RNA vaccine composition provides an induced or boosted immune response as a function of antigen production in the cell. In general, an effective amount of the VZV RNA vaccine containing RNA polynucleotides having at least one chemical modifications are preferably more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of VZV.

VZV RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

VZV RNA (e.g., mRNA) vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, VZV RNA vaccines may be administered intramuscularly, intranasally or intradermally, similarly to the administration of inactivated vaccines known in the art.

The VZV RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers and produce responses early than commercially available anti-virals.

Provided herein are pharmaceutical compositions including VZV RNA vaccines and RNA vaccine compositions and/or complexes optionally in combination with one or more pharmaceutically acceptable excipients.

VZV RNA (e.g., mRNA) vaccines may be formulated or administered alone or in conjunction with one or more other components. For instance, VZV RNA vaccines (vaccine compositions) may comprise other components including, but not limited to, adjuvants.

In some embodiments, VZV RNA vaccines do not include an adjuvant (they are adjuvant free).

VZV RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, VZV RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigenic polypeptides.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

VZV RNA vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with VZV RNA vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

In some embodiments, the RNA vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Nanoparticle Formulations

In some embodiments, VZV RNA (e.g., mRNA) vaccines are formulated in a nanoparticle. In some embodiments, VZV RNA vaccines are formulated in a lipid nanoparticle. In some embodiments, VZV RNA vaccines are formulated in a lipid-polycation complex, referred to as a cationic lipid nanoparticle. The formation of the lipid nanoparticle may be accomplished by methods known in the art and/or as described in U.S. Publication No. 2012/0178702, herein incorporated by reference in its entirety. As a non-limiting example, the polycation may include a cationic peptide or a polypeptide such as, but not limited to, polylysine, polyornithine and/or polyarginine and the cationic peptides described in International Publication No. WO2012/013326 or U.S. Publication No. US2013/0142818; each of which is herein incorporated by reference in its entirety. In some embodiments, VZV RNA vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (*Nature Biotech.* 2010 28:172-176; herein incorporated by reference in its entirety), the lipid nanoparticle formulation is composed of 57.1% cationic lipid, 7.1 dipalmitoylphosphatidylcholine, 34.3% cholesterol, and 1.4% PEG-c-DMA. As another example, changing the composition of the cationic lipid was shown to more effectively deliver siRNA to various antigen presenting cells (Basha et al. *Mol Ther.* 2011 19:2186-2200; herein incorporated by reference in its entirety).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from $C_{14}$ to $C_{18}$ to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, $C_{12-200}$ and DLin-KC2-DMA.

In some embodiments, a VZV RNA (e.g., mRNA) vaccine formulation is a nanoparticle that comprises at least one lipid. The lipid may be selected from, but is not limited to, DLin-DMA, DLin-K-DMA, 98N12-5, $C_{12-200}$, DLin-MC3-

DMA, DLin-KC2-DMA, DODMA, PLGA, PEG, PEG-DMG, (12Z,15Z)—N,N-dimethyl-2-nonylhenicosa-12,15-dien-1-amine, N,N-dimethyl-1-[(1S,2R)-2-octylcyclopropyl]heptadecan-8-amine, PEGylated lipids and amino alcohol lipids.

In some embodiments, the cationic lipid is

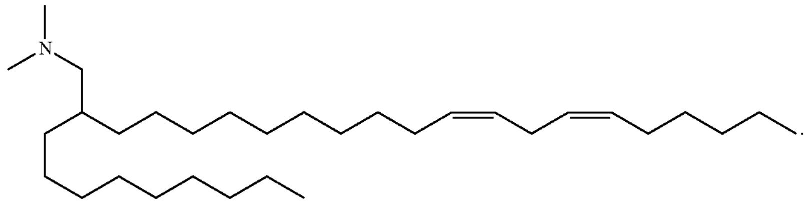 [SMILES: CCCCC/C=C\C/C=C\CCCCCCCCCC(CCCCCCCCC)CN(C)C]

In some embodiments, the cationic lipid is

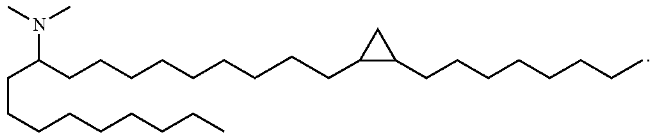 [SMILES: CCCCCCCCCC(CCCCCCCCCC1CC1CCCCCCCC)N(C)C]

In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in U.S. Publication No. US2013/0150625, herein incorporated by reference in its entirety. As a non-limiting example, the cationic lipid may be 2-amino-3-[(9Z,12Z)-octadeca-9,12-dien-1-yloxy]-2-[[(9Z,2Z)-octadeca-9,12-dien-1-yloxy]methyl]propan-1-ol (Compound 1 in US2013/0150625); 2-amino-3-[(9Z)-octadec-9-en-1-yloxy]-2-{[(9Z)-octadec-9-en-1-yloxy]methyl}propan-1-ol (Compound 2 in US2013/0150625); 2-amino-3-[(9Z,12Z)-octadeca-9,12-dien-1-yloxy]-2-[(octyloxy)methyl]propan-1-ol (Compound 3 in US2013/0150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US2013/0150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate, and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate; (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% cationic lipid: 5-25% neutral lipid (non-cationic lipid): 25-55% sterol; 0.5-15% PEG-lipid.

In some embodiments, a lipid nanoparticle formulation includes 25% to 75% on a molar basis of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-$C_{14}$ or $C_{14}$-PEG), PEG-cDMA (further discussed in Reyes et al. J. Controlled Release, 107, 276-287 (2005) the content of which is herein incorporated by reference in its entirety).

In some embodiments, lipid nanoparticle formulations include 25-75% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from the group consisting of 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 7.5% of the neutral lipid, 31% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 10% of the neutral lipid, 38.5% of the sterol, and 1.5% of the PEG or PEG-modified lipid on a molar basis.

In some embodiments, lipid nanoparticle formulations include 50% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 15% of the neutral lipid, 40% of the sterol, and 5% of the PEG or PEG-modified lipid on a molar basis.

In some embodiments, lipid nanoparticle formulations include 57.2% of a cationic lipid selected from the group consisting of 2,2-dilinoleyl-4-dimethylaminoethyl[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate, 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (J. Controlled Release, 107, 276-287 (2005), the content of which is herein incorporated by reference in its entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid: 5-45% neutral lipid: 20-55% cholesterol: 0.5-15% PEG-modified lipid. In some embodiments, lipid nanoparticle formulations consists essentially of a lipid mixture in a molar ratio of 20-60% cationic lipid: 5-25% neutral lipid (non-cationic lipid): 25-55% cholesterol: 0.5-15% PEG-modified lipid.

In some embodiments, the molar lipid ratio is 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Choi/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51: 8529-8533; and Maier et al. (2013) *Molecular Therapy* 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and di((Z)-non-2-en-1-yl) 9-((4-(dimethylamino)butanoyl)oxy)heptadecanedioate.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and di((Z)-non-2-en-1-yl) 9-((4-(dimethylamino)butanoyl)oxy)heptadecanedioate.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid di((Z)-non-2-en-1-yl) 9-((4-(dimethylamino)butanoyl) oxy)heptadecanedioate, 10% of the non-cationic lipid DSPC, 2.5% of the PEG lipid PEG-DMG and 32.5% of the structural lipid cholesterol.

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding VZV), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Liposomes, Lipoplexes, and Lipid Nanoparticles

In some embodiments, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the RNA vaccines may be formulated in a lyophilized gel-phase liposomal composition as described in U.S. Publication No. US2012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. US2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water soluble conjugate. The polymer conjugate may have a structure as described in U.S. Publication No. 2013/0059360, the content of which is herein incorporated by reference in its entirety. In some aspects, polymer conjugates with the polynucleotides of the present invention may be made using the methods and/or segmented polymeric reagents described in U.S. Publication No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In some aspects, the conjugate may be a "self" peptide designed from the human membrane protein CD47 (e.g., the "self" particles described by Rodriguez et al (*Science* 2013, 339, 971-975), herein incorporated by reference in its entirety). As shown by Rodriguez et al. the self peptides delayed macrophage-mediated clearance of nanoparticles which enhanced delivery of the nanoparticles. In other aspects, the conjugate may be the membrane protein CD47 (e.g., see Rodriguez et al. *Science* 2013, 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In other embodiments, the nanoparticle may comprise PEG and a conjugate of CD47 or a derivative thereof. In yet other embodiments, the nanoparticle may comprise both the "self" peptide described above and the membrane protein CD47.

In some embodiments, a "self" peptide and/or CD47 protein may be conjugated to a virus-like particle or pseudovirion, as described herein for delivery of the RNA vaccines of the present invention.

In other embodiments, RNA vaccine pharmaceutical compositions comprising the polynucleotides of the present invention and a conjugate, which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Publication No. US2013/0184443, the content of which is herein incorporated by reference in its entirety.

The nanoparticle formulations may be a carbohydrate nanoparticle comprising a carbohydrate carrier and a RNA vaccine. As a non-limiting example, the carbohydrate carrier may include, but is not limited to, an anhydride-modified phytoglycogen or glycogen-type material, phytoglycogen octenyl succinate, phytoglycogen beta-dextrin, anhydride-modified phytoglycogen beta-dextrin. (See e.g., International Publication No. WO2012/109121, the content of which is herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in U.S. Publication No. US2013/0183244, the content of which is herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in U.S. Publication No. US2013/0210991, the content of which is herein incorporated by reference in its entirety.

In other embodiments, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbo.

In some embodiments, an immune response may be elicited by delivering a lipid nanoparticle which may include a nanospecies, a polymer and an immunogen. (U.S. Publication No. 2012/0189700 and International Publication No. WO2012/099805, each of which is herein incorporated by reference in its entirety).

The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm to 500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. *Adv Drug Deliv Rev.* 2009 61(2): 158-171; each of which is herein incorporated by reference in its entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Publication No. WO2013/110028, the content of each of which is herein incorporated by reference in its entirety.

The lipid nanoparticle engineered to penetrate mucus may comprise a polymeric material (e.g., a polymeric core) and/or a polymer-vitamin conjugate and/or a tri-block copolymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Publication No. WO2013/116804, the content of which is herein incorporated by reference in its entirety. The polymeric material may additionally be irradiated. As a non-limiting example, the polymeric material may be gamma irradiated (see e.g., International Publication No. WO2012/082165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a copolymer such as, but not limited to, a block co-polymer (such as a branched polyether-polyamide block copolymer described in International Publication No. WO2013/012476, herein incorporated by reference in its entirety), and (poly(ethylene glycol))-(poly(propylene oxide))-(poly(ethylene glycol)) triblock copolymer (see e.g., U.S. Publication 2012/0121718, U.S. Publication 2010/0003337 and U.S. Pat. No. 8,263,665, each of which is herein incorporated by reference in its entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int. Ed.* 2011 50:25972600, the content of which is herein incorporated by reference in its entirety). A non-limiting scalable method to produce nanoparticles which can penetrate human mucus is described by Xu et al. (see e.g., *J Control Release* 2013, 170(2):279-86, the content of which is herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

In some embodiments, the RNA (e.g., mRNA) vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. *Cancer Biology & Therapy* 2006 5(12)1708-1713, herein incorporated by reference in its entirety)) and hyaluronan-coated liposomes (Quiet Therapeutics, Israel).

In some embodiments, the RNA vaccines may be formulated in a lyophilized gel-phase liposomal composition as described in U.S. Publication No. U52012/0060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Publication No. WO2013/033438 or U.S. Publication No. 2013/0196948, the content of each of which is herein incorporated by reference in its entirety. As a non-limiting example, the phosphate conjugates may include a compound of any one of the formulas described in International Publication No. WO2013/033438, herein incorporated by reference in its entirety.

The nanoparticle formulation may comprise a polymer conjugate. The polymer conjugate may be a water soluble conjugate. The polymer conjugate may have a structure as described in U.S. Application No. 2013/0059360, the content of which is herein incorporated by reference in its entirety. In some aspects, polymer conjugates with the polynucleotides of the present invention may be made using the methods and/or segmented polymeric reagents described in U.S. Patent Application No. 2013/0072709, herein incorporated by reference in its entirety. In other aspects, the polymer conjugate may have pendant side groups comprising ring moieties such as, but not limited to, the polymer conjugates described in U.S. Publication No. US2013/0196948, the content of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In some aspects, the conjugate may be a "self" peptide designed from the human membrane protein CD47 (e.g., the "self" particles described by Rodriguez et al. (*Science* 2013, 339, 971-975), herein incorporated by reference in its entirety). As shown by Rodriguez et al. the self peptides delayed macrophage-mediated clearance of nanoparticles which enhanced delivery of the nanoparticles. In other aspects, the conjugate may be the membrane protein CD47 (e.g., see Rodriguez et al. *Science* 2013, 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles that comprise a conjugate to enhance the delivery of the nanoparticles of the present disclosure in a subject. The conjugate may be the CD47 membrane or the conjugate may be derived from the CD47 membrane protein, such as the "self" peptide described previously. In other aspects the nanoparticle may comprise PEG and a conjugate of CD47 or a derivative thereof. In yet other aspects, the nanoparticle may comprise both the "self" peptide described above and the membrane protein CD47.

In other aspects, a "self" peptide and/or CD47 protein may be conjugated to a virus-like particle or pseudovirion, as described herein for delivery of the RNA vaccines of the present invention.

In other embodiments, RNA vaccine pharmaceutical compositions comprising the polynucleotides of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in U.S. Publication No. US2013/0184443, the content of which is herein incorporated by reference in its entirety.

The nanoparticle formulations may be a carbohydrate nanoparticle comprising a carbohydrate carrier and a RNA (e.g., mRNA) vaccine. As a non-limiting example, the carbohydrate carrier may include, but is not limited to, an anhydride-modified phytoglycogen or glycogen-type material, phytoglycogen octenyl succinate, phytoglycogen beta-dextrin, anhydride-modified phytoglycogen beta-dextrin. (See e.g., International Publication No. WO2012/109121; the content of which is herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in U.S. Publication No. US2013/0183244, the content of which is herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in U.S. Publication No. US2013/0210991, the content of which is herein incorporated by reference in its entirety.

In other embodiments, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbo.

In some embodiments, an immune response may be elicited by delivering a lipid nanoparticle which may include a nanospecies, a polymer and an immunogen (U.S. Publication No. 2012/0189700 and International Publication No. WO2012/099805, each of which is herein incorporated by reference in its entirety).

The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. *PNAS* 2007 104(5):1482-487; Lai et al. *Adv Drug Deliv Rev.* 2009 61(2): 158-171; each of which is herein incorporated by reference in its entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Publication No. WO2013/110028, the content of each of which is herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Publication No. WO2013/116804, the content of which is herein incorporated by reference in its entirety. The polymeric material may additionally be irradiated. As a non-limiting example, the polymeric material may be gamma irradiated (see e.g., International Publication No. WO2012/082165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a copolymer such as, but not limited to, a block co-polymer (such as a branched polyether-polyamide block copolymer described in International Publication No. WO2013/012476, herein incorporated by reference in its entirety), and (poly(ethylene glycol))-(poly(propylene oxide))-(poly(ethylene glycol)) triblock copolymer (see e.g., U.S. Publication 2012/0121718 and U.S. Publication 2010/0003337 and U.S. Pat. No. 8,263,665; each of which is herein incorporated by reference in its entirety). The copolymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. *Angew. Chem. Int. Ed.* 2011 50:25972600; the content of which is herein incorporated by reference in its entirety). A non-limiting scalable method to produce nanoparticles which can penetrate human mucus is described by Xu et al. (see e.g., *J Control Release* 2013, 170(2):279-86, the content of which is herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle (see e.g., U.S. Publication 2010/0215580 and U.S. Publication 2008/0166414 and US2013/0164343 the content of each of which is herein incorporated by reference in its entirety).

In some embodiments, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In other embodiments, the mucus penetrating lipid nanoparticles may be a hypotonic formulation comprising a mucosal penetration enhancing coating. The formulation may be hypotonic for the epithelium to which it is being delivered.

Non-limiting examples of hypotonic formulations may be found in International Publication No. WO2013/110028, the content of which is herein incorporated by reference in its entirety.

In some embodiments, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (see e.g., Ensign et al. *Biomaterials* 2013, 34(28):6922-9, the content of which is herein incorporated by reference in its entirety).

In some embodiments, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. *Cancer Res.* 2008 68:9788-9798; Strumberg et al. *Int J Clin Pharmacol Ther* 2012 50:76-78; Santel et al., *Gene Ther* 2006 13:1222-1234; Santel et al., *Gene Ther* 2006 13:1360-1370; Gutbier et al., *Pulm Pharmacol. Ther.* 2010 23:334-344; Kaufmann et al. *Microvasc Res* 2010 80:286-293; Weide et al. *J Immunother.* 2009 32:498-507; Weide et al. *J Immunother.* 2008 31:180-188; Pascolo, *Expert Opin. Biol. Ther.* 4:1285-1294; Fotin-Mleczek et al., 2011 *J. Immunother.* 34:1-15; Song et al., *Nature Biotechnol.* 2005, 23:709-717; Peer et al., *Proc Natl Acad Sci USA.* 2007 6; 104:4095-4100; deFougerolles *Hum Gene Ther.* 2008 19:125-132; each of which is incorporated herein by reference in its entirety).

In some embodiments, such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. *Mol Ther.* 2010 18:1357-1364; Song et al., *Nat Biotechnol.* 2005 23:709-717; Judge et al., *J Clin Invest.* 2009 119:661-673; Kaufmann et al., *Microvasc Res* 2010 80:286-293; Santel et al., *Gene Ther* 2006 13:1222-1234; Santel et al., *Gene Ther* 2006 13:1360-1370; Gutbier et al., *Pulm Pharmacol. Ther.* 2010 23:334-344; Basha et al., *Mol. Ther.* 2011 19:2186-2200; Fenske and Cullis, *Expert Opin Drug Deliv.* 2008 5:25-44; Peer et al., *Science.* 2008 319:627-630; Peer and Lieberman, *Gene Ther.* 2011 18:1127-1133; each of which is incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. *Mol Ther.* 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., *Curr Drug Discov Technol.* 2011 8:197-206; Musacchio and Torchilin, *Front Biosci.* 2011 16:1388-1412; Yu et al., *Mol Membr Biol.* 2010 27:286-298; Patil et al., *Crit Rev Ther Drug Carrier Syst.* 2008 25:1-61; Benoit et al., *Biomacromolecules.* 2011 12:2708-2714; Zhao et al., *Expert Opin Drug Deliv.* 2008 5:309-319; Akinc et al., *Mol Ther.* 2010 18:1357-1364; Srinivasan et al., *Methods Mol Biol.* 2012 820:105-116; Ben-Arie et al., *Methods Mol Biol.* 2012 757:497-507; Peer 2010 *J Control Release.* 20:63-68; Peer et al., *Proc Natl Acad Sci USA.* 2007 104:4095-4100; Kim et al., *Methods Mol Biol.* 2011 721:339-353; Subramanya et al., *Mol Ther.* 2010 18:2028-2037; Song et al., *Nat Biotechnol.* 2005 23:709-717; Peer et al., *Science.* 2008 319:627-630; Peer and Lieberman, *Gene Ther.* 2011 18:1127-1133; each of which is incorporated herein by reference in its entirety).

In some embodiments, the RNA (e.g., mRNA) vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In other embodiments, the lipid nanoparticle may be a self-assembly lipid-polymer nanoparticle (see Zhang et al., *ACS Nano,* 2008, 2 (8), pp 1696-1702; the content of which is herein incorporated by reference in its entirety). As a non-limiting example, the SLN may be the SLN described in International Publication No. WO2013/105101, the content of which is herein incorporated by reference in its entirety. As another non-limiting example, the SLN may be made by the methods or processes described in International Publication No. WO2013/105101, the content of which is herein incorporated by reference in its entirety.

Liposomes, lipoplexes, or lipid nanoparticles may be used to improve the efficacy of polynucleotides directed protein production as these formulations may be able to increase cell transfection by the RNA vaccine; and/or increase the translation of encoded protein. One such example involves the use of lipid encapsulation to enable the effective systemic delivery of polyplex plasmid DNA (Heyes et al., *Mol Ther.* 2007 15:713-720; herein incorporated by reference in its entirety). The liposomes, lipoplexes, or lipid nanoparticles may also be used to increase the stability of the polynucleotide.

In some embodiments, the RNA (e.g., mRNA) vaccines of the present invention can be formulated for controlled release and/or targeted delivery. As used herein, "controlled release" refers to a pharmaceutical composition or compound release profile that conforms to a particular pattern of release to effect a therapeutic outcome. In some embodiments, the RNA vaccines may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the present disclosure are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012/131104 and WO2012/131106; the contents of each of which is herein incorporated by reference in its entirety).

In other embodiments, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc. Deerfield, Ill.), PEG-based sealants, and COSEAL® (Baxter International, Inc Deerfield, Ill.).

In other embodiments, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the RNA vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA (e.g., mRNA) vaccine controlled release and/or targeted delivery formulation may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In other embodiments, the degradable polyesters may include a PEG conjugation to form a PEGylated polymer.

In some embodiments, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In other embodiments, the RNA vaccine controlled release delivery formulation comprising at least one polynucleotide may be the controlled release polymer system described in U.S. Publication No. 2013/0130348, herein incorporated by reference in its entirety.

In some embodiments, the RNA (e.g., mRNA)vaccines of the present invention may be encapsulated in a therapeutic nanoparticle, referred to herein as "therapeutic nanoparticle RNA vaccines." Therapeutic nanoparticles may be formulated by methods described herein and known in the art such as, but not limited to, International Publication Nos. WO2010/005740, WO2010/030763, WO2010/005721, WO2010/005723, WO2012/054923, U.S. Publication Nos. US2011/0262491, US2010/0104645, US2010/0087337, US2010/0068285, US2011/0274759, US2010/0068286, US2012/0288541, US2013/0123351 and US2013/0230567 and U.S. Pat. Nos. 8,206,747, 8,293,276, 8,318,208 and 8,318,211, the content of each of which is herein incorporated by reference in its entirety. In other embodiments, therapeutic polymer nanoparticles may be identified by the methods described in U.S. Publication No. US2012/0140790, the content of which is herein incorporated by reference in its entirety.

In some embodiments, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present invention (see International Publication No. 2010/075072 and U.S. Publication Nos. US2010/0216804, US2011/0217377 and US2012/0201859, each of which is herein incorporated by reference in its entirety). In another non-limiting example, the sustained release formulation may comprise agents which permit persistent bioavailability such as, but not limited to, crystals, macromolecular gels and/or particulate suspensions (see U.S. Publication No. US2013/0150295, the content of which is herein incorporated by reference in its entirety).

In some embodiments, the therapeutic nanoparticle RNA vaccines may be formulated to be target specific. As a non-limiting example, the therapeutic nanoparticles may include a corticosteroid (see International Publication No. WO2011/084518, herein incorporated by reference in its entirety). As a non-limiting example, the therapeutic nanoparticles may be formulated in nanoparticles described in International Publication Nos. WO2008/121949, WO2010/005726, WO2010/005725, WO2011/084521 and U.S. Publication Nos. US2010/0069426, US2012/0004293 and US2010/0104655, each of which is herein incorporated by reference in its entirety.

In some embodiments, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In yet other embodiments, the diblock copolymer may be a high-X diblock copolymer such as those described in International Publication No. WO2013/120052, the content of which is herein incorporated by reference in its entirety.

As a non-limiting example, the therapeutic nanoparticle comprises a PLGA-PEG block copolymer (see U.S. Publication No. US2012/0004293 and U.S. Pat. No. 8,236,330, each of which is herein incorporated by reference in its entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012/166923, the content of each of which is herein incorporated by reference in its entirety). In yet another non-limiting example, the therapeutic nanoparticle is a stealth nanoparticle or a target-specific stealth nanoparticle as described in U.S. Publication No. 2013/0172406, the content of which is herein incorporated by reference in its entirety.

In some embodiments, the therapeutic nanoparticle may comprise a multiblock copolymer (see e.g., U.S. Pat. Nos. 8,263,665 and 8,287,910 and U.S. Publication No. 2013/0195987, the content of each of which is herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) used as a TGF-betal gene delivery vehicle in Lee et al. "Thermosensitive Hydrogel as a TGF-β1 Gene Delivery Vehicle Enhances Diabetic Wound Healing." *Pharmaceutical Research,* 2003 20(12): 1995-2000; and used as a controlled gene delivery system in Li et al. "Controlled Gene Delivery System Based on Thermosensitive Biodegradable Hydrogel" *Pharmaceutical Research* 2003 20(6):884-888; and Chang et al., "Non-ionic amphiphilic biodegradable PEG-PLGA-PEG copolymer enhances gene delivery efficiency in rat skeletal muscle." *J Controlled Release.* 2007 118:245-253; each of which is herein incorporated by reference in its entirety). The RNA (e.g., mRNA) vaccines of the present disclosure may be formulated in lipid nanoparticles comprising the PEG-PLGA-PEG block copolymer.

In some embodiments, the block copolymers described herein may be included in a polyion complex comprising a non-polymeric micelle and the block copolymer. (see e.g., U.S. Publication No. 2012/0076836, herein incorporated by reference in its entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In some embodiments, the therapeutic nanoparticles may comprise at least one poly(vinyl ester) polymer. The poly(vinyl ester) polymer may be a copolymer such as a random copolymer. As a non-limiting example, the random copolymer may have a structure such as those described in International Publication No. WO2013/032829 or U.S. Publication No. 2013/0121954, the content of which is herein incorporated by reference in its entirety. In some aspects, the poly(vinyl ester) polymers may be conjugated to the polynucleotides described herein.

In some embodiments, the therapeutic nanoparticle may comprise at least one diblock copolymer. The diblock copolymer may be, but it not limited to, a poly(lactic) acid-poly(ethylene)glycol copolymer (see e.g., International Publication No. WO2013/044219; herein incorporated by reference in its entirety). As a non-limiting example, the therapeutic nanoparticle may be used to treat cancer (see International publication No. WO2013/044219, herein incorporated by reference in its entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethyleneimine, poly(amidoamine) dendrimers, poly(beta-amino esters) (see e.g., U.S.

Pat. No. 8,287,849, herein incorporated by reference in its entirety) and combinations thereof. In other embodiments, the nanoparticles described herein may comprise an amine cationic lipid such as those described in International Publication No. WO2013/059496, the content of which is herein incorporated by reference in its entirety. In some aspects the cationic lipids may have an amino-amine or an amino-amide moiety.

In some embodiments, the therapeutic nanoparticles may comprise at least one degradable polyester, which may contain polycationic side chains. Degradable polyesters include, but are not limited to, poly(serine ester), poly(L-lactide-co-L-lysine), poly(4-hydroxy-L-proline ester), and combinations thereof. In other embodiments, the degradable polyesters may include a PEG conjugation to form a PEGylated polymer.

In other embodiments, the therapeutic nanoparticle may include a conjugation of at least one targeting ligand. The targeting ligand may be any ligand known in the art such as, but not limited to, a monoclonal antibody (Kirpotin et al, *Cancer Res.* 2006 66:6732-6740, herein incorporated by reference in its entirety).

In some embodiments, the therapeutic nanoparticle may be formulated in an aqueous solution, which may be used to target cancer (see International Publication No. WO2011/084513 and U.S. Publication No. 2011/0294717, each of which is herein incorporated by reference in its entirety).

In some embodiments, the therapeutic nanoparticle RNA vaccines, e.g., therapeutic nanoparticles comprising at least one RNA vaccine may be formulated using the methods described by Podobinski et al in U.S. Pat. No. 8,404,799, the content of which is herein incorporated by reference in its entirety.

In some embodiments, the RNA (e.g., mRNA) vaccines may be encapsulated in, linked to and/or associated with synthetic nanocarriers. Synthetic nanocarriers include, but are not limited to, those described in International Publication Nos. WO2010/005740, WO2012/149454 and WO2013/019669, and U.S. Publication Nos. US2011/0262491, US2010/0104645, US2010/0087337 and US2012/0244222, each of which is herein incorporated by reference in its entirety. The synthetic nanocarriers may be formulated using methods known in the art and/or described herein. As a non-limiting example, the synthetic nanocarriers may be formulated by the methods described in International Publication Nos. WO2010/005740, WO2010/030763 and WO2012/13501, and U.S. Publication Nos. US2011/0262491, US2010/0104645, US2010/0087337 and US2012/024422, each of which is herein incorporated by reference in its entirety. In other embodiments, the synthetic nanocarrier formulations may be lyophilized by methods described in International Publication No. WO2011/072218 and U.S. Pat. No. 8,211,473, the content of each of which is herein incorporated by reference in its entirety. In yet other embodiments, formulations of the present invention, including, but not limited to, synthetic nanocarriers, may be lyophilized or reconstituted by the methods described in U.S. Publication No. 2013/0230568, the content of which is herein incorporated by reference in its entirety.

In some embodiments, the synthetic nanocarriers may contain reactive groups to release the polynucleotides described herein (see International Publication No. WO2012/092552 and U.S.

Publication No. US2012/0171229, each of which is herein incorporated by reference in its entirety).

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Publication No. WO2010/123569 and U.S. Publication No. 2011/0223201, each of which is herein incorporated by reference in its entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA vaccines after 24 hours and/or at a pH of 4.5 (see International Publication Nos. WO2010/138193 and WO2010/138194 and U.S. Publication Nos. US2011/0020388 and US2011/0027217, each of which is herein incorporated by reference in their entireties).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Publication No. WO2010/138192 and U.S. Publication No. 2010/0303850, each of which is herein incorporated by reference in its entirety.

In some embodiments, the RNA vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encode at least one antigen. As a non-limiting example, the synthetic nanocarrier may include at least one antigen and an excipient for a vaccine dosage form (see International Publication No. WO2011/150264 and U.S. Publication No. 2011/0293723, each of which is herein incorporated by reference in its entirety). As another non-limiting example, a vaccine dosage form may include at least two synthetic nanocarriers with the same or different antigens and an excipient (see International Publication No. WO2011/150249 and U.S. Publication No. 2011/0293701, each of which is herein incorporated by reference in its entirety). The vaccine dosage form may be selected by methods described herein, known in the art and/or described in International Publication No. WO2011/150258 and U.S. Publication No. US2012/0027806, each of which is herein incorporated by reference in its entirety).

In some embodiments, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (see e.g., U.S. Pat. No. 8,241,610; herein incorporated by reference in its entirety). In other embodiments, the synthetic nanocarrier may comprise at least one polynucleotide and an adjuvant. As a non-limiting example, the synthetic nanocarrier comprising and adjuvant may be formulated by the methods described in International Publication No. WO2011/150240 and U.S. Publication No. US2011/0293700, each of which is herein incorporated by reference in its entirety.

In some embodiments, the synthetic nanocarrier may encapsulate at least one polynucleotide which encodes a peptide, fragment or region from a virus. As a non-limiting example, the synthetic nanocarrier may include, but is not limited to, the nanocarriers described in International Publication Nos. WO2012/024621, WO2012/02629, WO2012/024632 and U.S. Publication No. US2012/0064110, US2012/0058153 and US2012/0058154, each of which is herein incorporated by reference in its entirety.

In some embodiments, the synthetic nanocarrier may be coupled to a polynucleotide which may be able to trigger a humoral and/or cytotoxic T lymphocyte (CTL) response (See e.g., International Publication No. WO2013/019669, herein incorporated by reference in its entirety).

In some embodiments, the RNA vaccine may be encapsulated in, linked to and/or associated with zwitterionic lipids. Non-limiting examples of zwitterionic lipids and methods of using zwitterionic lipids are described in U.S. Publication No. 2013/0216607, the content of which is herein incorporated by reference in its entirety. In some aspects, the zwitterionic lipids may be used in the liposomes and lipid nanoparticles described herein.

In some embodiments, the RNA vaccine may be formulated in colloid nanocarriers as described in U.S. Publication No. 2013/0197100, the content of which is herein incorporated by reference in its entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Publication No. 2012/0282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA vaccine may be delivered using smaller LNPs. Such particles may comprise a diameter from below 0.1 μm up to 100 nm such as, but not limited to, less than 0.1 μm, less than 1.0 μm, less than 5 μm, less than 10 μm, less than 15 μm, less than 20 μm, less than 25 μm, less than 30 μm, less than 35 μm, less than 40 μm, less than 50 μm, less than 55 μm, less than 60 μm, less than 65 μm, less than 70 μm, less than 75 μm, less than 80 μm, less than 85 μm, less than 90 μm, less than 95 μm, less than 100 μm, less than 125 μm, less than 150 μm, less than 175 μm, less than 200 μm, less than 225 μm, less than 250 μm, less than 275 μm, less than 300 μm, less than 325 μm, less than 350 μm, less than 375 μm, less than 400 μm, less than 425 μm, less than 450 μm, less than 475 μm, less than 500 μm, less than 525 μm, less than 550 μm, less than 575 μm, less than 600 μm, less than 625 μm, less than 650 μm, less than 675 μm, less than 700 μm, less than 725 μm, less than 750 μm, less than 775 μm, less than 800 μm, less than 825 μm, less than 850 μm, less than 875 μm, less than 900 μm, less than 925 μm, less than 950 μm, or less than 975 μm.

In other embodiments, RNA (e.g., mRNA) vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nm, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigital micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. *Molecular Therapy-Nucleic Acids.* 2012. 1:e37; Chen, D. et al., Rapid discovery of potent siRNA-containing lipid nanoparticles enabled by controlled microfluidic formulation. *J Am Chem Soc.* 2012. 134(16):6948-51; each of which is herein incorporated by reference in its entirety).

In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In some embodiments, the RNA vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In some embodiments, the RNA (e.g., mRNA) vaccines of the present disclosure may be formulated in lipid nanoparticles created using microfluidic technology (see Whitesides, George M. The Origins and the Future of Microfluidics. *Nature,* 2006 442: 368-373; and Abraham et al. Chaotic Mixer for Microchannels. *Science,* 2002 295: 647-651; each of which is herein incorporated by reference in its entirety). As a non-limiting example, controlled microfluidic formulation includes a passive method for mixing streams of steady pressure-driven flows in micro channels at a low Reynolds number (see e.g., Abraham et al. Chaotic Mixer for Microchannels. *Science,* 2002 295: 647651; which is herein incorporated by reference in its entirety).

In some embodiments, the RNA (e.g., mRNA) vaccines of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the RNA (e.g., mRNA) vaccines of the invention may be formulated for delivery using the drug encapsulating microspheres described in International Publication No. WO2013/063468 or U.S. Pat. No. 8,440,614, each of which is herein incorporated by reference in its entirety. The microspheres may comprise a compound of the formula (I), (II), (III), (IV), (V) or (VI) as described in International Publication No. WO2013/063468, the content of which is herein incorporated by reference in its entirety. In other aspects, the amino acid, peptide, polypeptide, lipids (APPL) are useful in delivering the RNA vaccines of the invention to cells (see International Publication No. WO2013/063468, the contents of which is herein incorporated by reference in its entirety).

In some embodiments, the RNA (e.g., mRNA) vaccines of the present disclosure may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some aspects, the lipid nanoparticle may be a limit size lipid nanoparticle described in International Publication No. WO2013/059922, the content of which is herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a $C_8$-$C_{20}$ fatty acid diacylphophatidylcholine, and 1-palmitoyl-2-oleoyl phosphatidylcholine (POPC). In other aspects the limit size lipid nanoparticle may comprise a polyethylene glycol-lipid such as, but not limited to, DLPE-PEG, DMPE-PEG, DPPC-PEG and DSPE-PEG.

In some embodiments, the RNA vaccines may be delivered, localized and/or concentrated in a specific location using the delivery methods described in International Publication No. WO2013063530, the content of which is herein incorporated by reference in its entirety. As a non-limiting example, a subject may be administered an empty polymeric particle prior to, simultaneously with or after delivering the RNA vaccines to the subject. The empty polymeric particle undergoes a change in volume once in contact with the subject and becomes lodged, embedded, immobilized or entrapped at a specific location in the subject.

In some embodiments, the RNA vaccines may be formulated in an active substance release system (see e.g., U.S. Publication No. US2013/0102545, the contents of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA (e.g., mRNA) vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Publication No. WO2013/052167, herein incorporated by reference in its entirety. As another non-limiting example, the nanoparticle described in International Publication No. WO2013/052167, herein incorporated by reference in its entirety, may be used to deliver the RNA vaccines described herein.

In some embodiments, the RNA vaccines may be formulated in porous nanoparticle-supported lipid bilayers (protocells). Protocells are described in International Publication No. WO2013/056132, the content of which is herein incorporated by reference in its entirety.

In some embodiments, the RNA vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the content of which is herein incorporated by reference in its entirety. As another non-limiting example, the polymer nanoparticle for oral and parenteral formulations may be made by the methods described in European Patent No. EP2073848B1, the content of which is herein incorporated by reference in its entirety.

In other embodiments, the RNA (e.g., mRNA) vaccines described herein may be formulated in nanoparticles used in imaging. The nanoparticles may be liposome nanoparticles such as those described in U.S. Publication No. 2013/

0129636, herein incorporated by reference in its entirety. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., U.S. Publication No US2013/0129636, the contents of which is herein incorporated by reference in its entirety).

In some embodiments, the nanoparticles which may be used in the present invention are formed by the methods described in U.S. Patent Application No. 2013/0130348, the contents of which is herein incorporated by reference in its entirety.

The nanoparticles of the present invention may further include nutrients such as, but not limited to, those which deficiencies can lead to health hazards from anemia to neural tube defects (see e.g., the nanoparticles described in International Patent Publication No. WO2013/072929, the contents of which is herein incorporated by reference in its entirety). As a non-limiting example, the nutrient may be iron in the form of ferrous, ferric salts or elemental iron, iodine, folic acid, vitamins or micronutrients.

In some embodiments, the RNA (e.g., mRNA) vaccines of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the RNA (e.g., mRNA) vaccines of the present invention to the pulmonary system (see e.g., U.S. Pat. No. 8,440,231, the contents of which is herein incorporated by reference in its entirety).

The RNA (e.g., mRNA) vaccines of the present invention may be formulated in polyanhydride nanoparticles such as, but not limited to, those described in U.S. Pat. No. 8,449,916, the contents of which is herein incorporated by reference in its entirety. The nanoparticles and microparticles of the present invention may be geometrically engineered to modulate macrophage and/or the immune response. In some aspects, the geometrically engineered particles may have varied shapes, sizes and/or surface charges in order to incorporated the polynucleotides of the present invention for targeted delivery such as, but not limited to, pulmonary delivery (see e.g., International Publication No. WO2013/082111, the content of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No. WO2013/082111, the contents of which is herein incorporated by reference in its entirety.

In some embodiments, the nanoparticles of the present invention may be water soluble nanoparticles such as, but not limited to, those described in International Publication No. WO2013/090601, the content of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments the nanoparticles of the present invention may be developed by the methods described in U.S. Publication No. US2013/0172406, the content of which is herein incorporated by reference in its entirety.

In some embodiments, the nanoparticles of the present invention are stealth nanoparticles or target-specific stealth nanoparticles such as, but not limited to, those described in U.S. Publication No. 2013/0172406, the content of which is herein incorporated by reference in its entirety. The nanoparticles of the present invention may be made by the methods described in U.S. Publication No. 2013/0172406, the content of which is herein incorporated by reference in its entirety.

In other embodiments, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in U.S. Publication No. 2013/0171646, the content of which is herein incorporated by reference in its entirety. The nanoparticle may comprise a nucleic acid such as, but not limited to, polynucleotides described herein and/or known in the art.

At least one of the nanoparticles of the present invention may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Publication No. WO2013/123523, the content of which is herein incorporated by reference in its entirety.

In some embodiments, a nanoparticle comprises compounds of Formula (I):

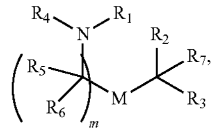

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, —N(R)

$R_8$, —$O(CH_2)_nOR$, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)$S(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and —C(R)$N(R)_2$ C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —C(O)$N(R)_2$, —N(R)C(O)R, —N(R)$S(O)_2R$, —N(R)C(O)$N(R)_2$, —N(R)C(S)$N(R)_2$, —$CRN(R)_2C(O)OR$, —N(R)$R_8$, —$O(CH_2)_nOR$, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)$S(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH—)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —C(O)$N(R)_2$, —N(R)C(O)R, —N(R)$S(O)_2R$, —N(R)C(O)$N(R)_2$, —N(R)C(S)$N(R)_2$, —$CRN(R)_2C(O)OR$, —N(R)$R_8$, —$O(CH_2)_nOR$, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)$S(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH (OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2$R, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2$H, —$CXH_2$, —CN, —$C(O)N(R)_2$, —N(R)C(O)R, —$N(R)S(O)_2$R, —$N(R)C(O)N(R)_2$, —$N(R)C(S)N(R)_2$, —$CRN(R)_2$C(O)OR, —$N(R)R_8$, —$O(CH_2)_n$OR, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2$R, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H; $R_8$ is selected from the group consisting of $C_{3-6}$ carbocycle and heterocycle; $R_9$ is selected from the group consisting of H, CN, $NO_2$, $C_{1-6}$ alkyl, —OR, —$S(O)_2$R, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5; each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R'' is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

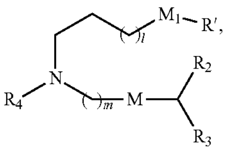

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or $-(CH_2)_nQ$, in which Q is OH, $-NHC(S)N(R)_2$, $-NHC(O)N(R)_2$, $-N(R)C(O)R$, $-N(R)S(O)_2R$, $-N(R)R_8$, $-NHC(=NR_9)N(R)_2$, $-NHC(=CHR_9)N(R)_2$, $-OC(O)N(R)_2$, $-N(R)C(O)OR$, heteroaryl or heterocycloalkyl; M and M' are independently selected from $-C(O)O-$, $-OC(O)-$, $-C(O)N(R')-$, $-P(O)(OR')O-$, $-S-S-$, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

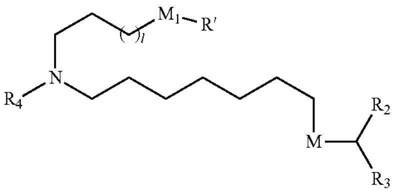

or a salt or isomer thereof, wherein 1 is selected from 1, 2, 3, 4, and 5; $M_1$ is a bond or M'; $R_4$ is unsubstituted $C_{1-3}$ alkyl, or $-(CH_2)_nQ$, in which n is 2, 3, or 4, and Q is OH, $-NHC(S)N(R)_2$, $-NHC(O)N(R)_2$, $-N(R)C(O)R$, $-N(R)S(O)_2R$, $-N(R)R_8$, $-NHC(=NR_9)N(R)_2$, $-NHC(=CHR_9)N(R)_2$, $-OC(O)N(R)_2$, $-N(R)C(O)OR$, heteroaryl or heterocycloalkyl; M and M' are independently selected from $-C(O)O-$, $-OC(O)-$, $-C(O)N(R')-$, $-P(O)(OR')O-$, $-S-S-$, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

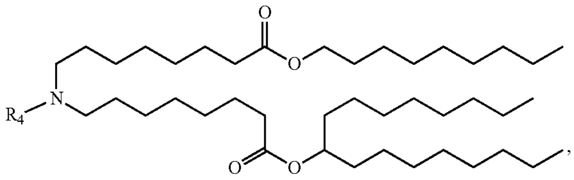

(IIb)

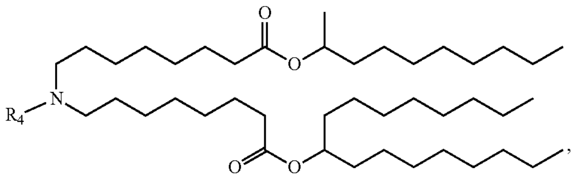

(IIc)

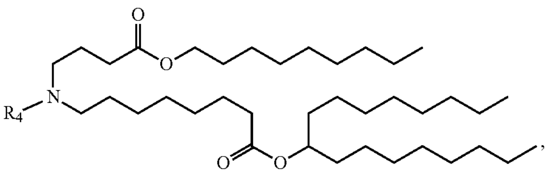

or (IIe)

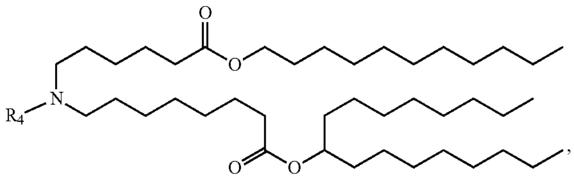

or a salt or isomer thereof, wherein $R_4$ is as described herein.

In some embodiments, a subset of compounds of Formula (I) includes those of Formula (IId):

(IId)

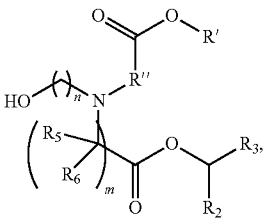

or a salt or isomer thereof, wherein n is 2, 3, or 4; and m, R', R'', and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)
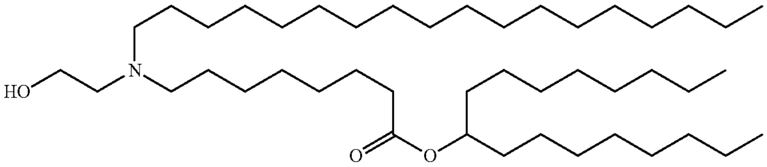,
(Compound 2)
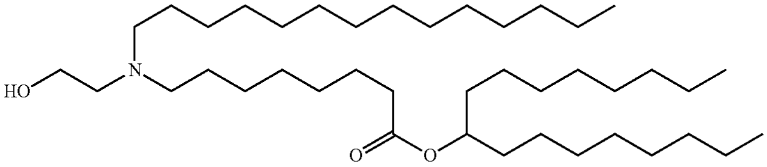,
(Compound 3)
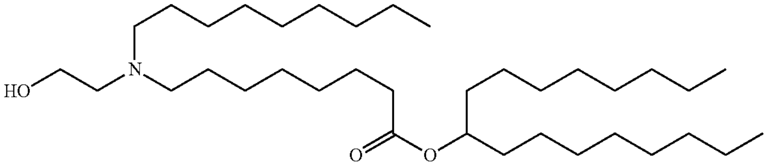,
(Compound 4)
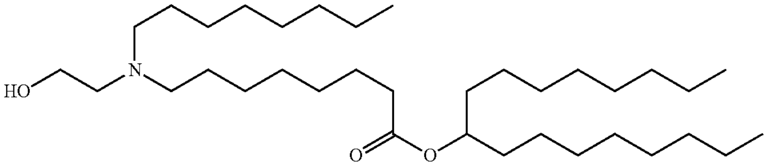,
(Compound 5)
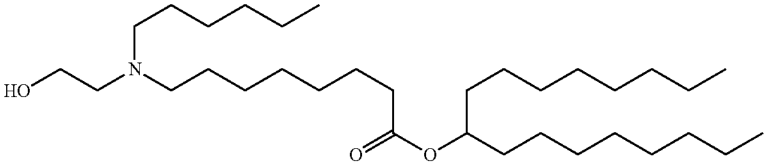,
(Compound 6)
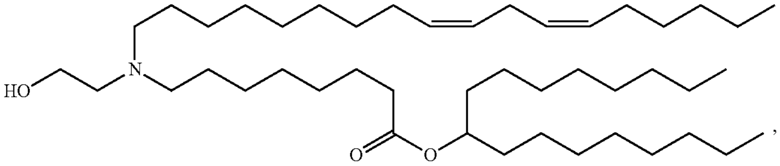,
(Compound 7)
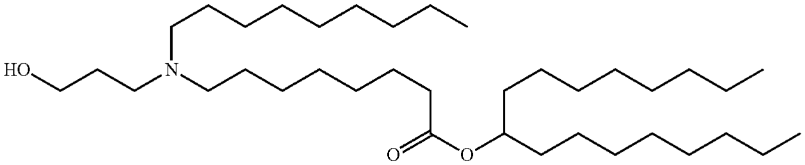,
(Compound 8)
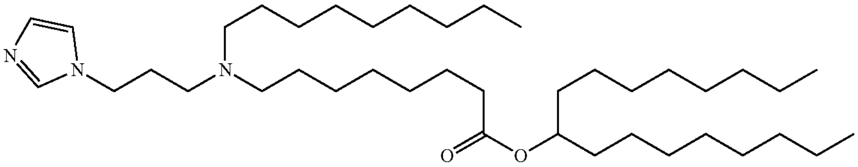,
(Compound 9)
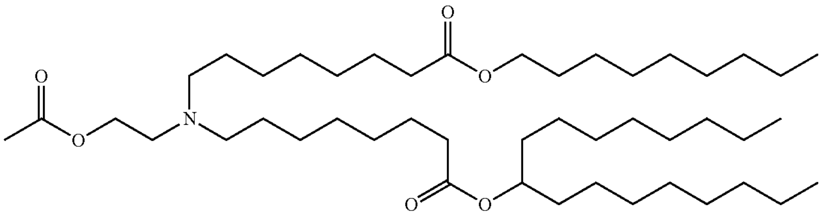, -continued
(Compound 10)
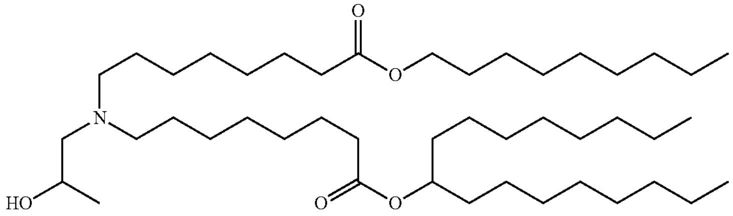
,
(Compound 11)
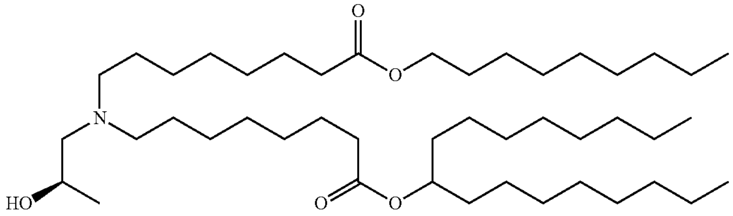
,
(Compound 12)
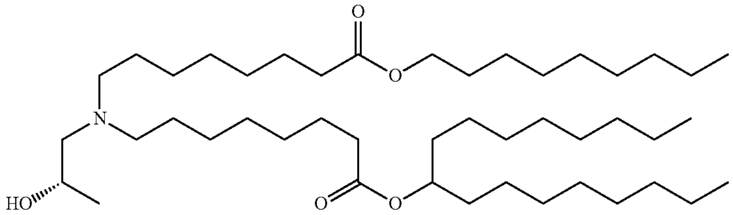
,
(Compound 13)
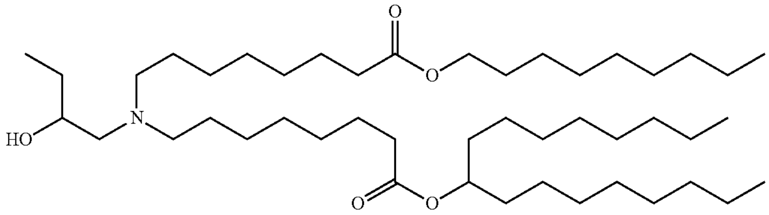
,
(Compound 14)
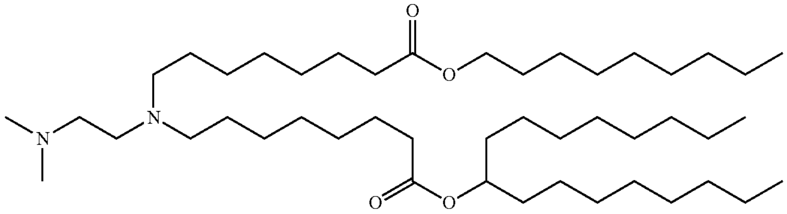
(Compound 15)
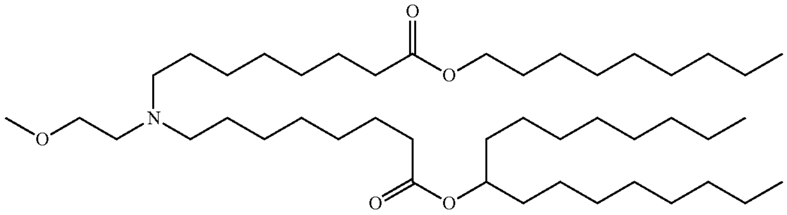
,
(Compound 16)
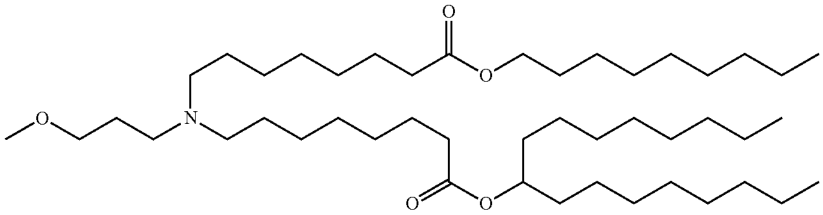
, -continued
(Compound 17)
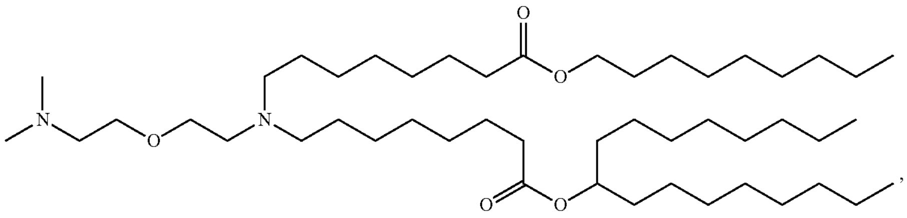
(Compound 18)
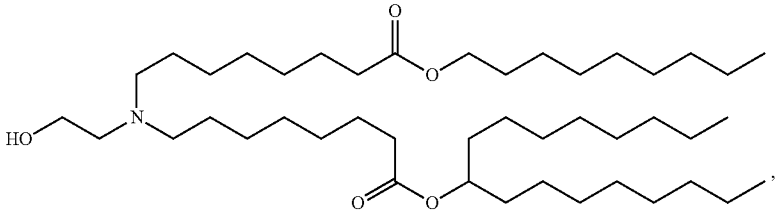
(Compound 19)
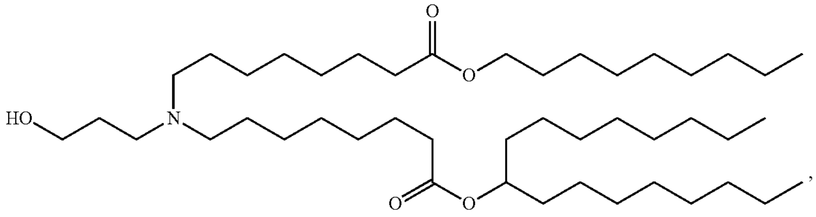
(Compound 20)
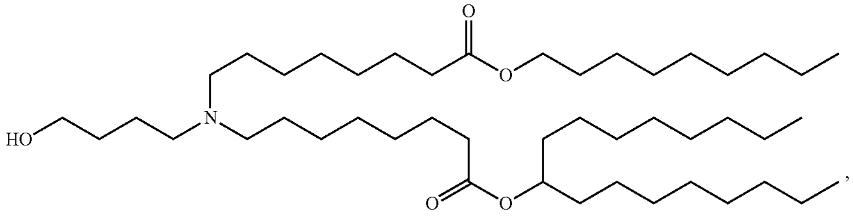
(Compound 21)
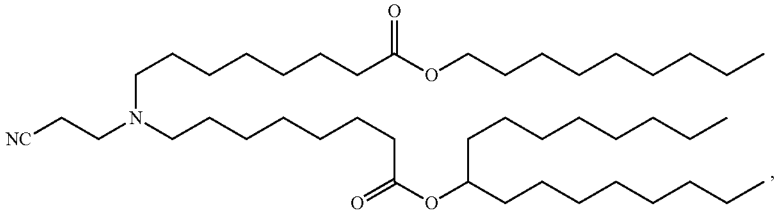
(Compound 22)
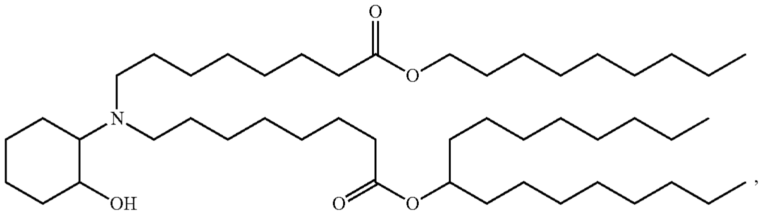
(Compound 23)
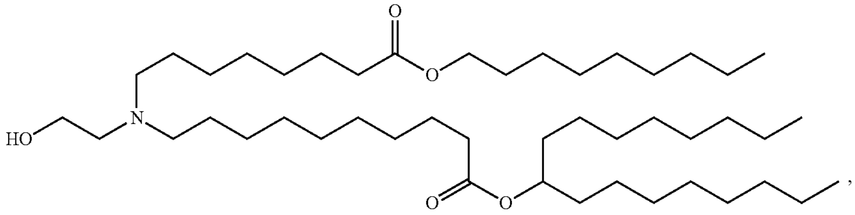

-continued
(Compound 24)
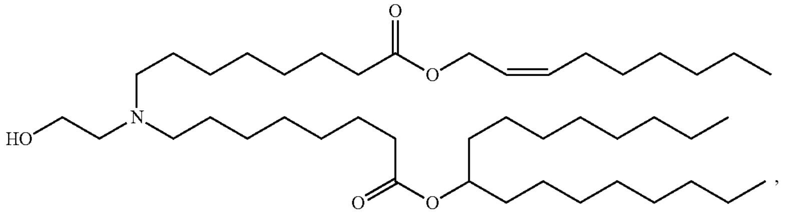
(Compound 25)
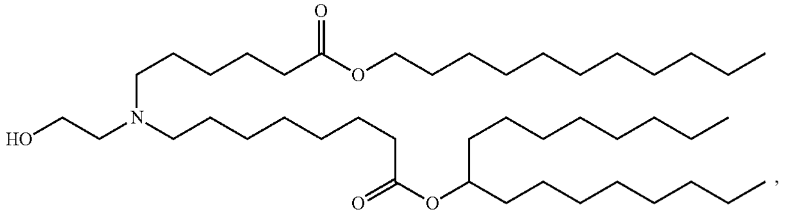
(Compound 26)
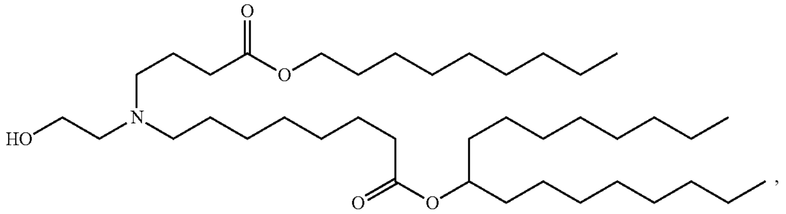
(Compound 27)
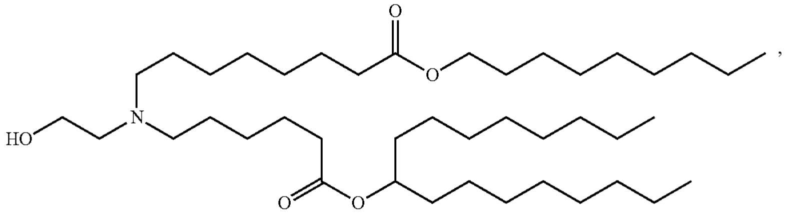
(Compound 28)
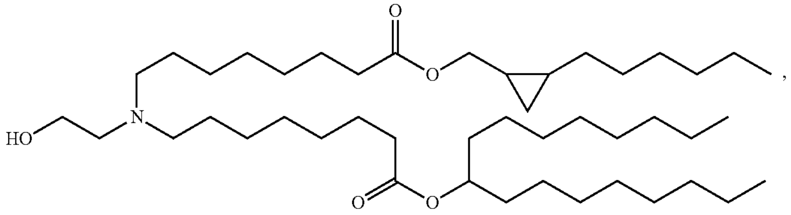
(Compound 29)
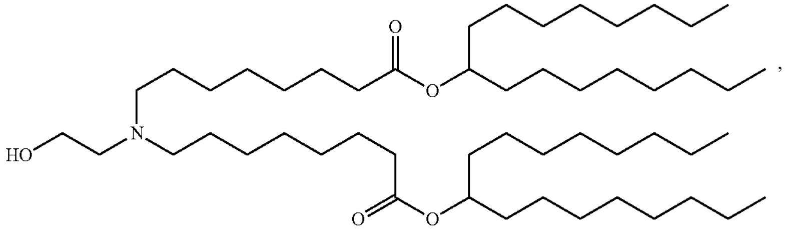
(Compound 30)
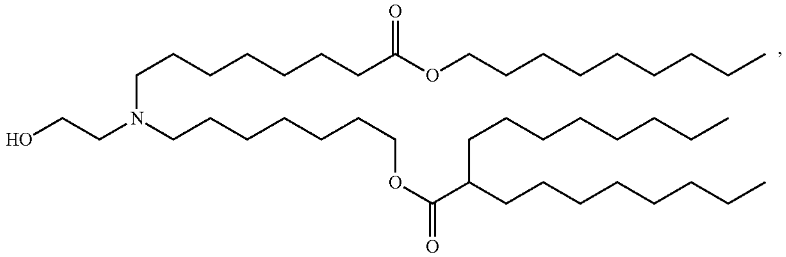

-continued
(Compound 31)
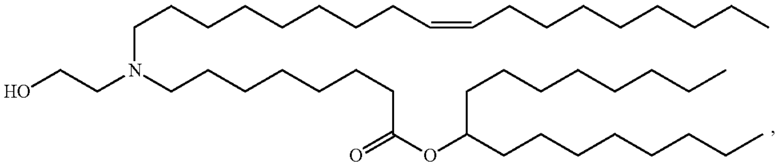
,
(Compound 32)
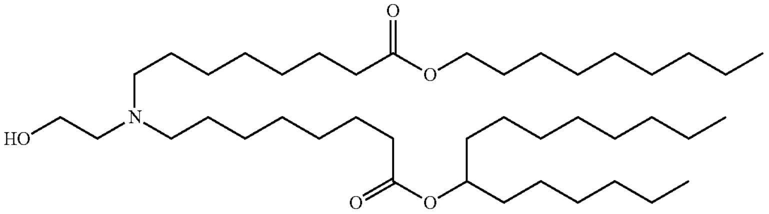
,
(Compound 33)
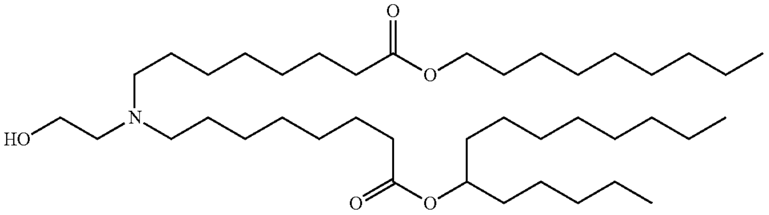
,
(Compound 34)
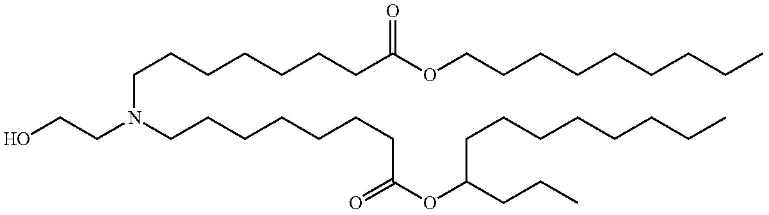
,
(Compound 35)
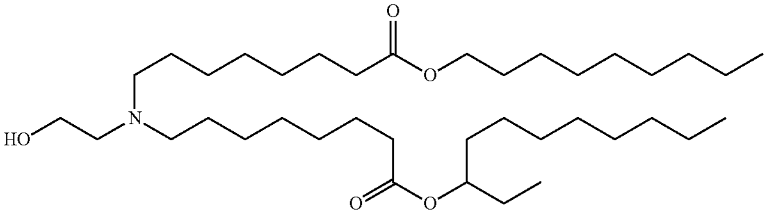
,
(Compound 36)
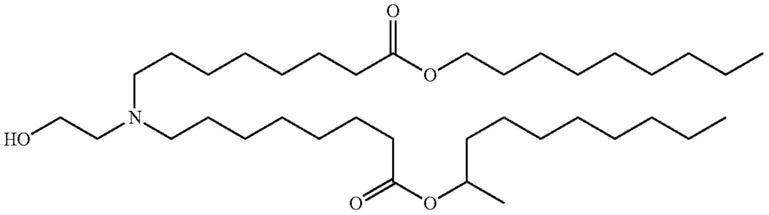
,
(Compound 37)
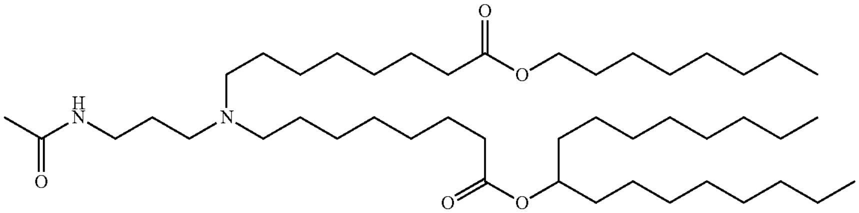
, -continued
(Compound 38)
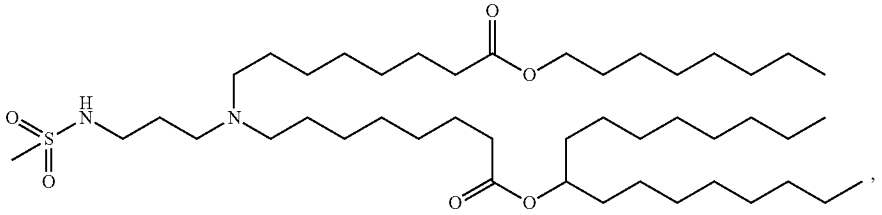
(Compound 39)
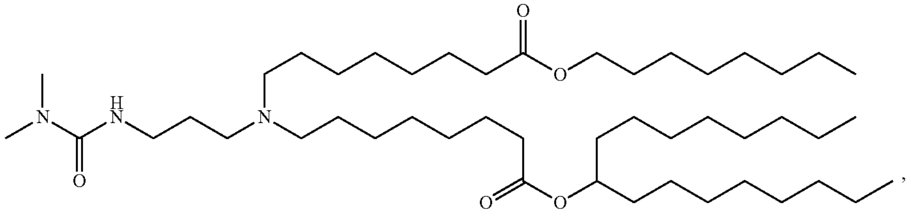
(Compound 40)
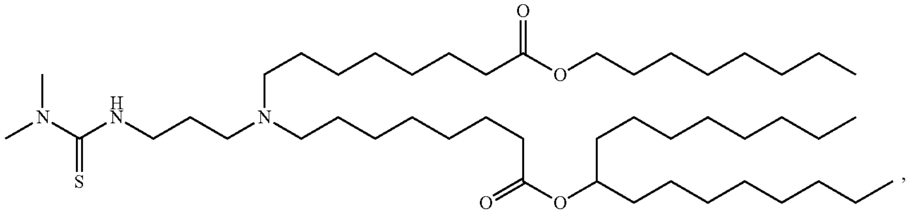
(Compound 41)
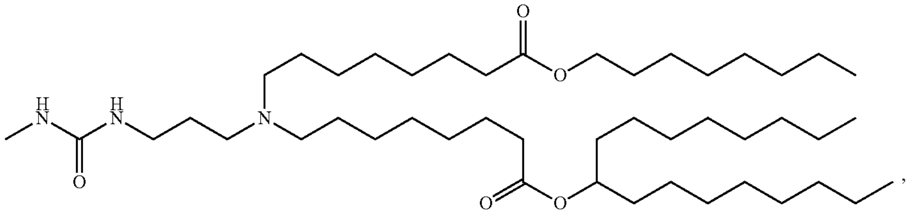
(Compound 42)
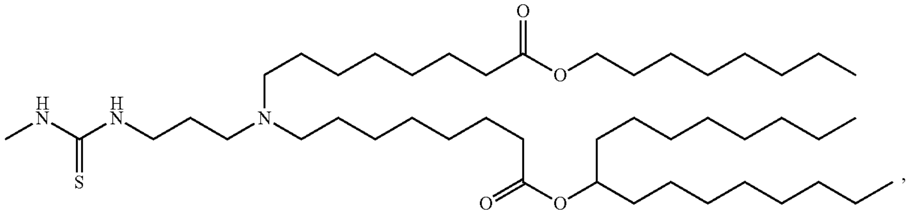
(Compound 43)
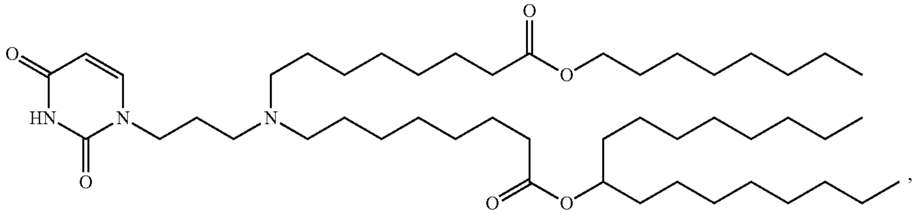
(Compound 44)
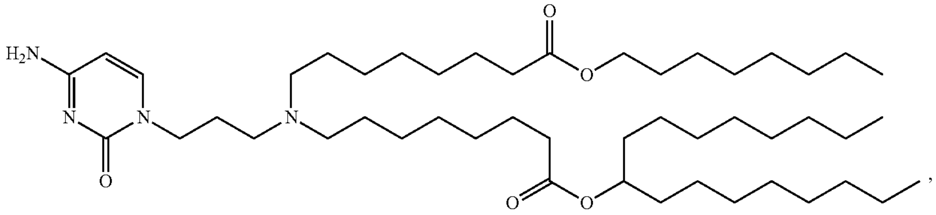

-continued
(Compound 45)
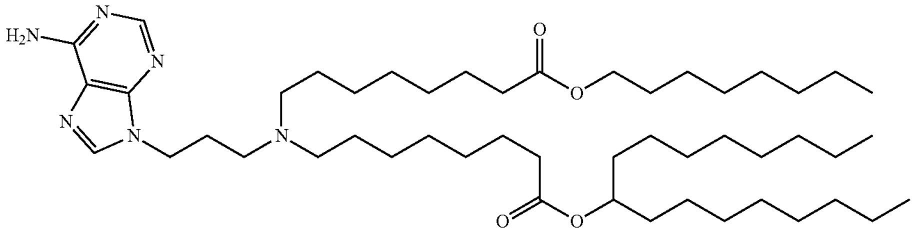
,
(Compound 46)
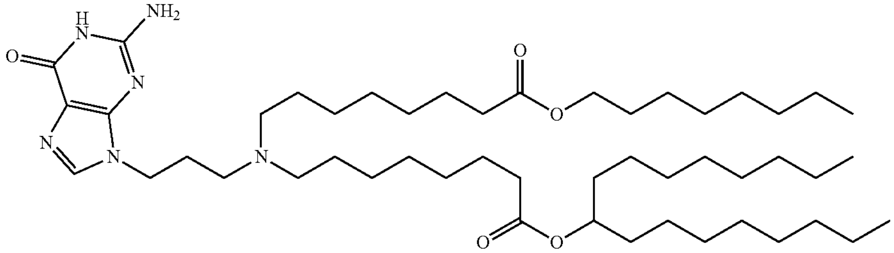
,
(Compound 47)
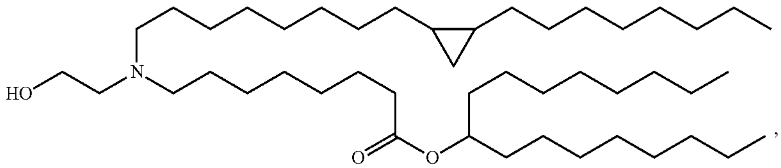
,
(Compound 48)
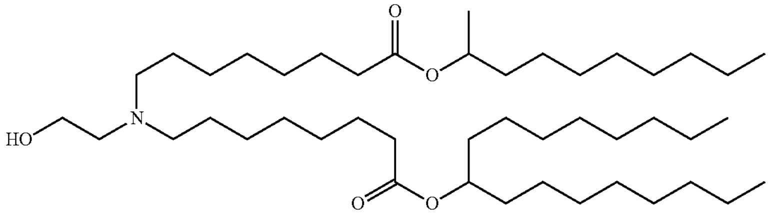
,
(Compound 49)
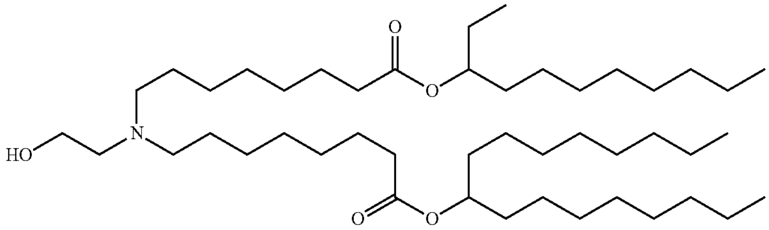
,
(Compound 50)
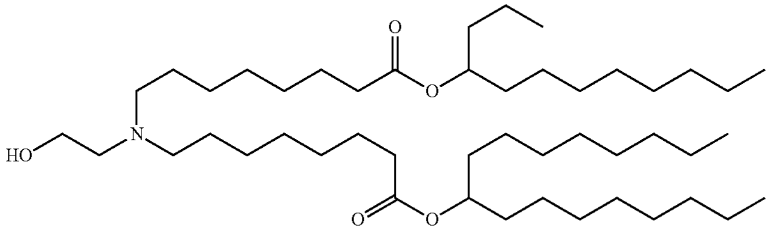
,
(Compound 51)
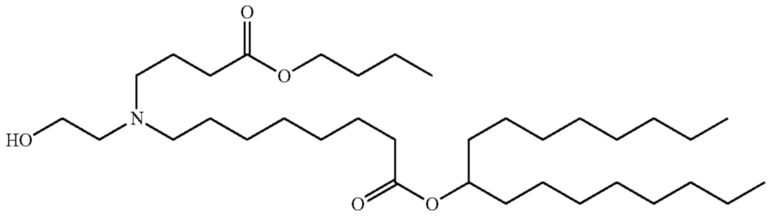
, -continued
(Compound 52)
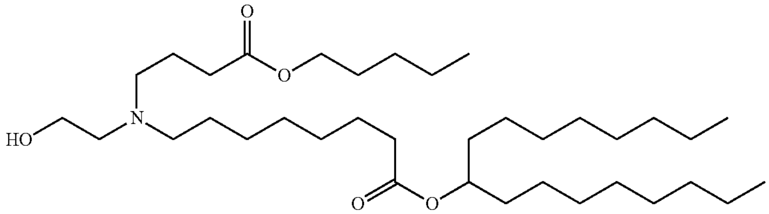
,
(Compound 53)
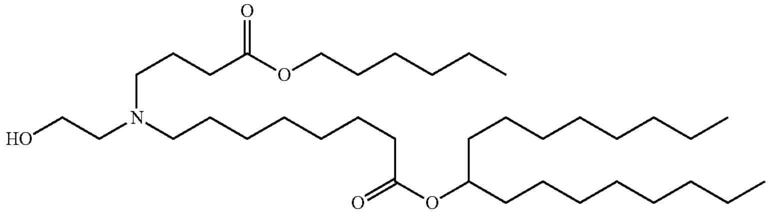
,
(Compound 54)
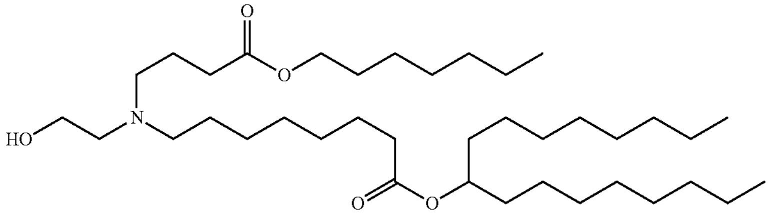
,
(Compound 55)
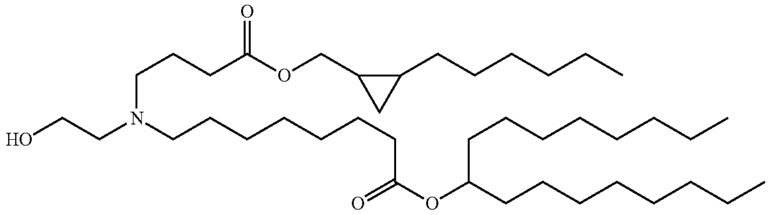
,
(Compound 56)
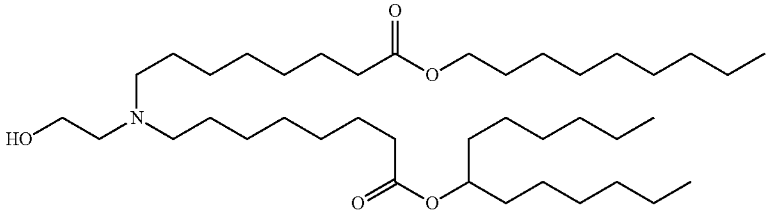
,
(Compound 57)
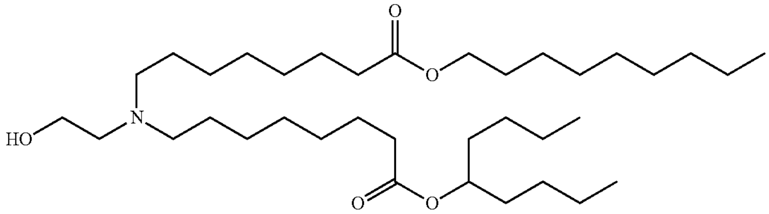
,
(Compound 58)
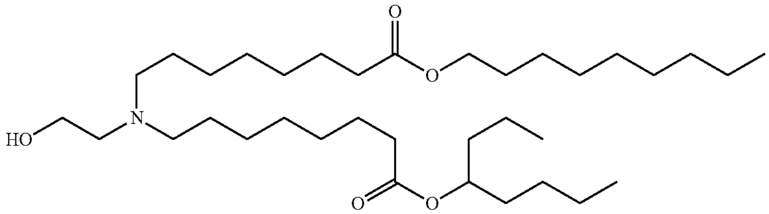
, -continued
(Compound 59)
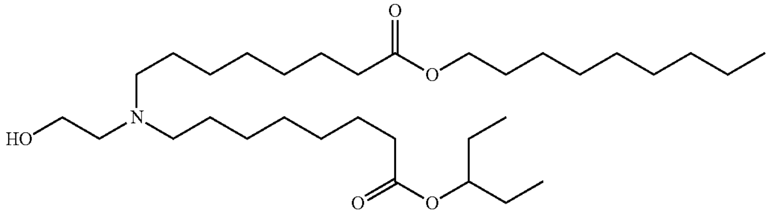
,
(Compound 60)
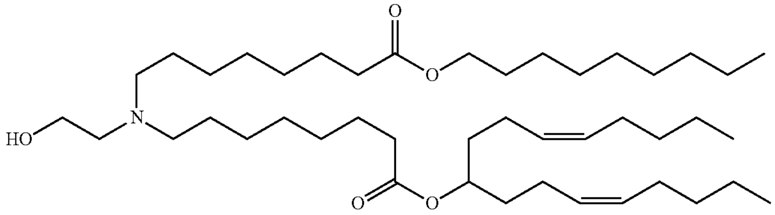
, and
(Compound 61)
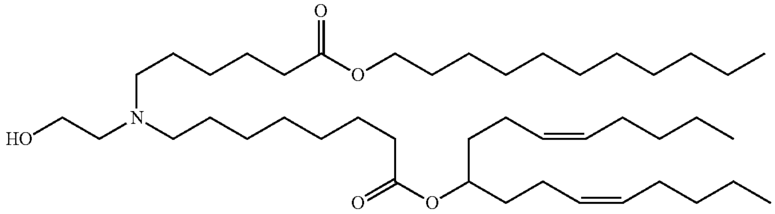
.
In further embodiments, the compound of Formula (I) is selected from the group consisting of:
(Compound 62)
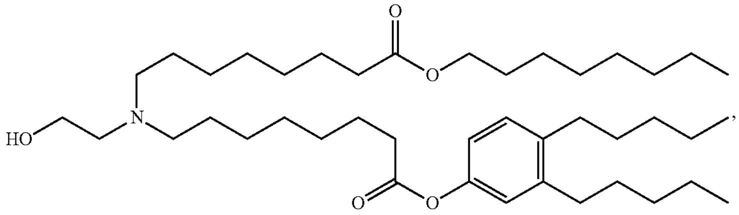
,
(Compound 63)
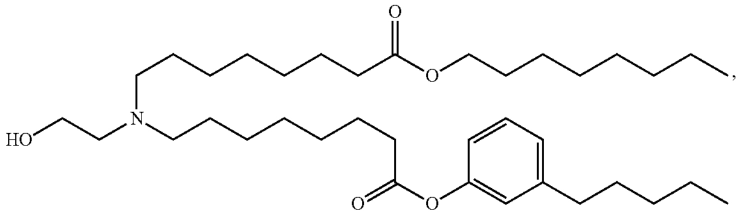
, and
(Compound 64)
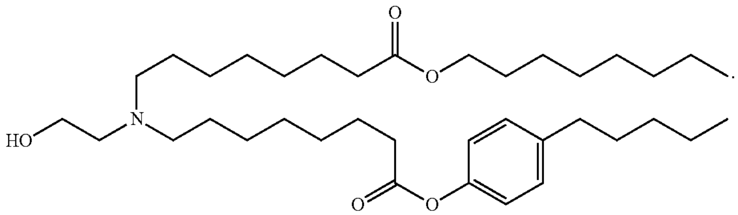
.

In some embodiments, the compound of Formula (I) is selected from the group consisting of:
(Compound 65)
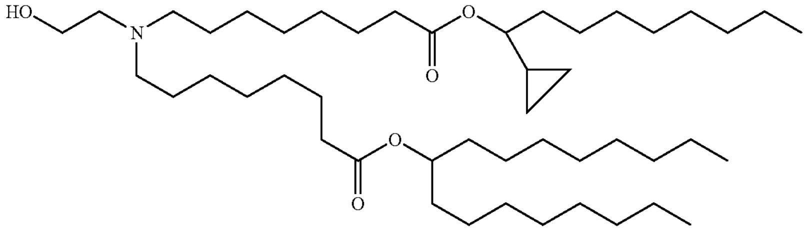
,
(Compound 66)
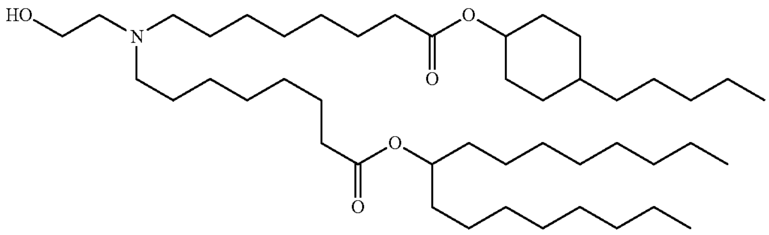
,
(Compound 67)
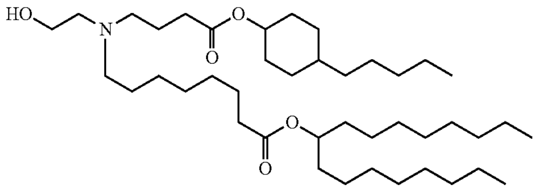
,
(Compound 68)
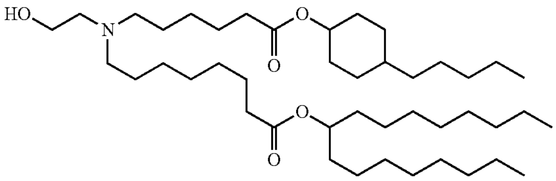
,
(Compound 69)
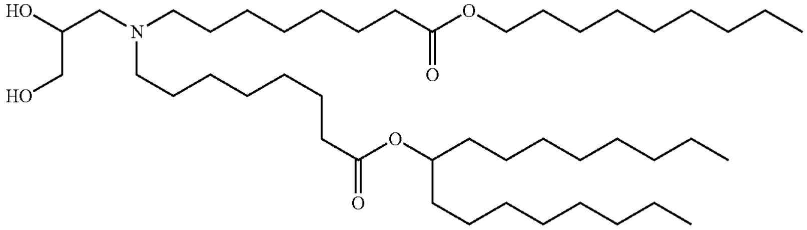
,
(Compound 70)
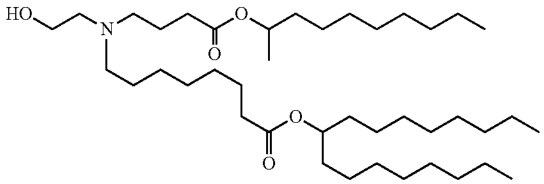
,
(Compound 71)
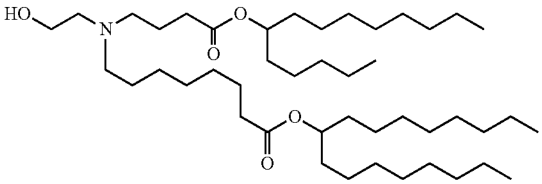
,
(Compound 72)
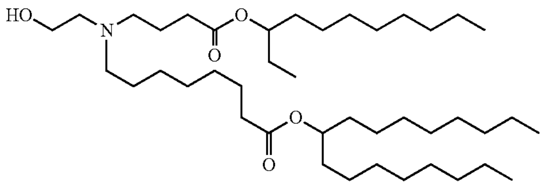
,
(Compound 73)
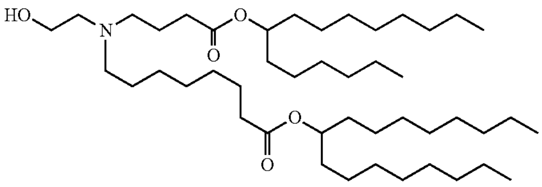
,
(Compound 74)
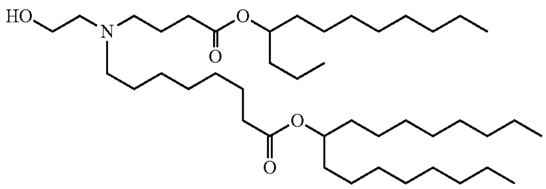
,
(Compound 75)
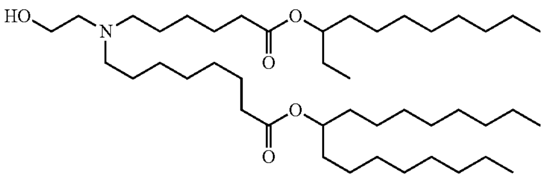
, -continued
(Compound 76)
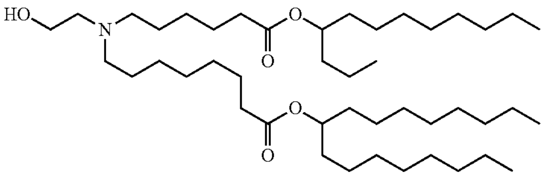
,
(Compound 77)
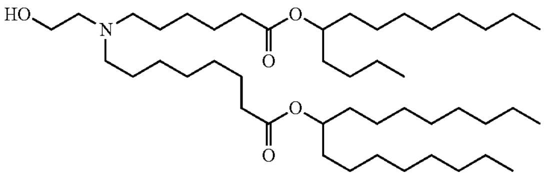
,
(Compound 78)
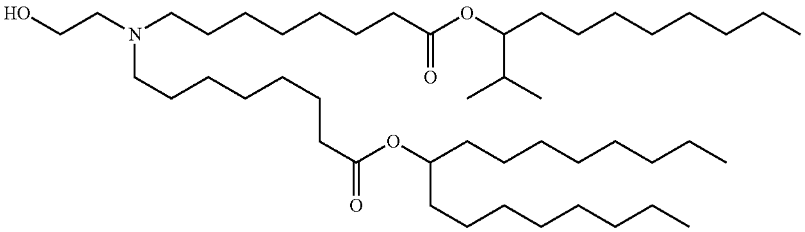
,
(Compound 79)
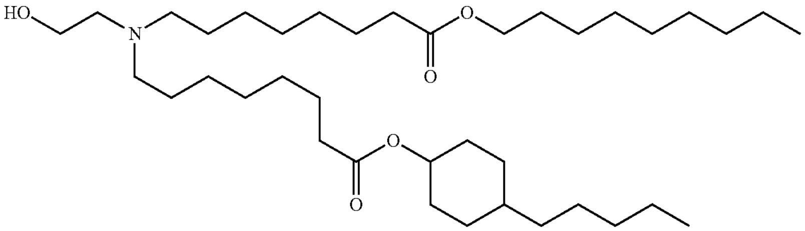
,
(Compound 80)
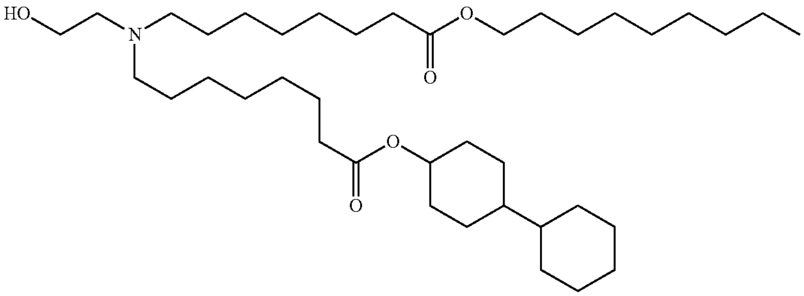
,
(Compound 81)
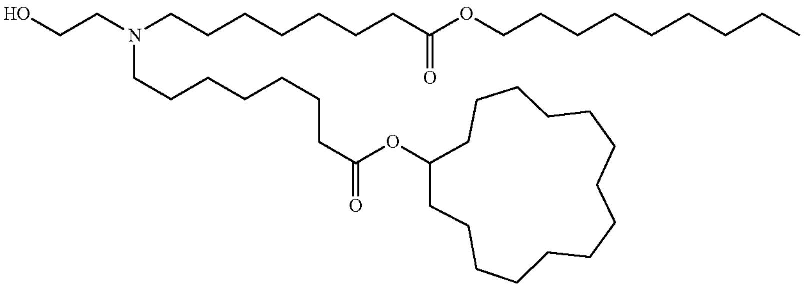
,
(Compound 82)
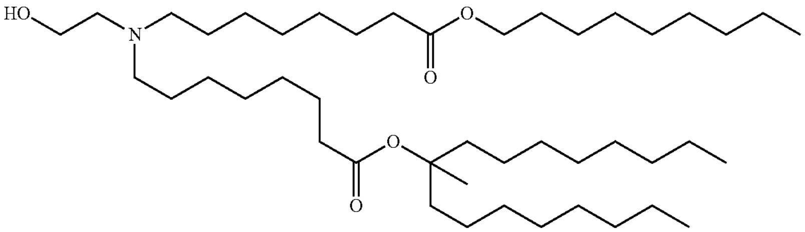
, -continued
(Compound 83)
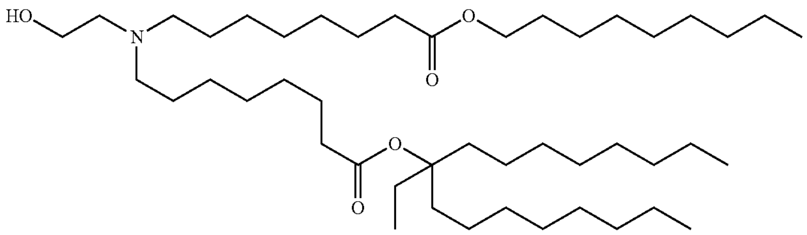
,
(Compound 84)
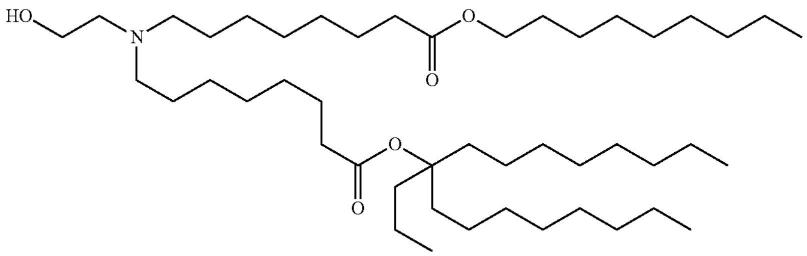
,
(Compound 85)
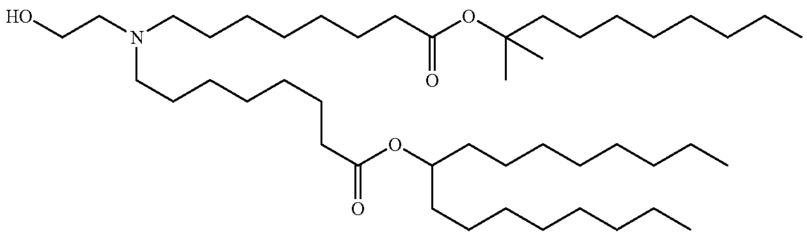
,
(Compound 86)
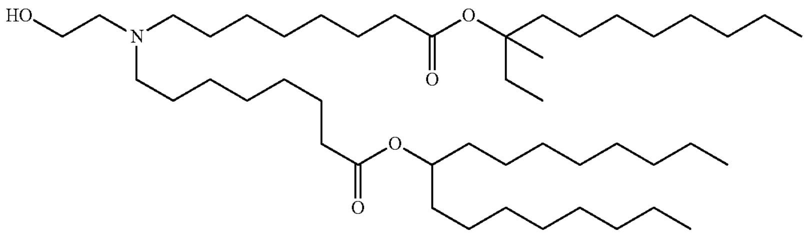
,
(Compound 87)
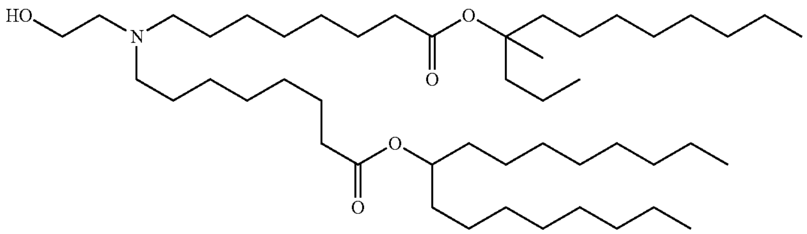
,
(Compound 88)
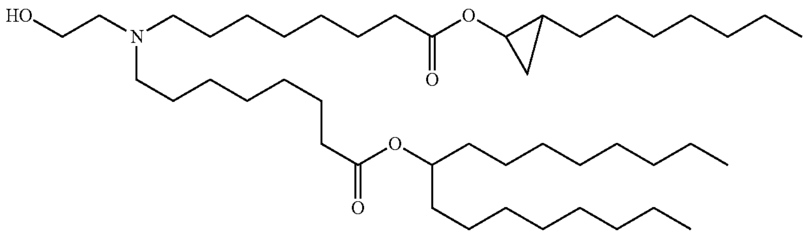
, -continued
(Compound 89)
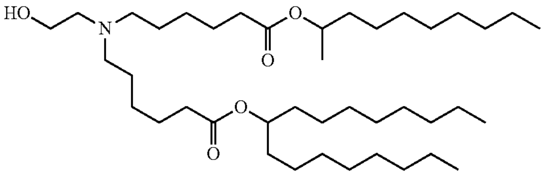
,
(Compound 90)
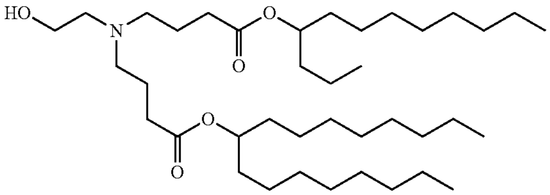
,
(Compound 91)
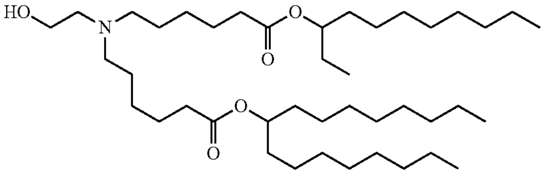
,
(Compound 92)
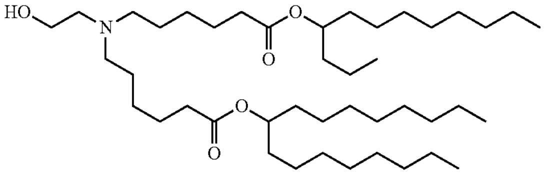
,
(Compound 93)
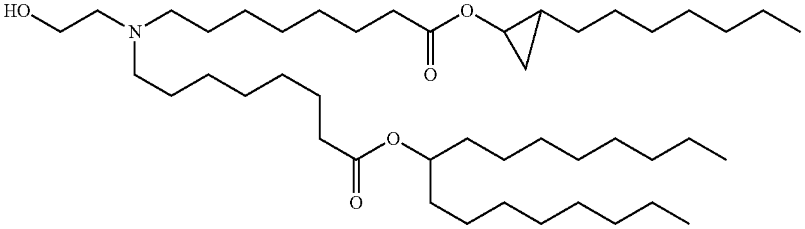
,
(Compound 94)
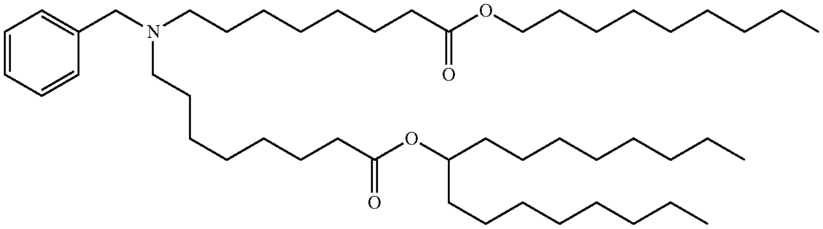
,
(Compound 95)
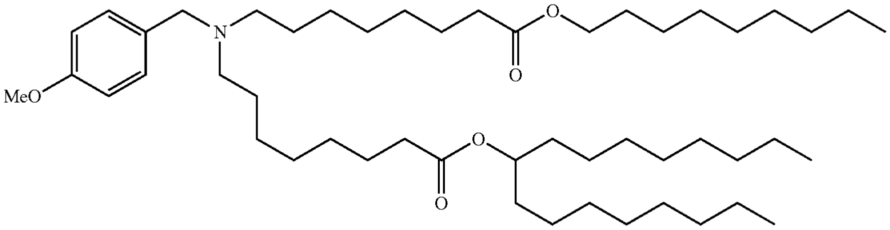
,
(Compound 96)
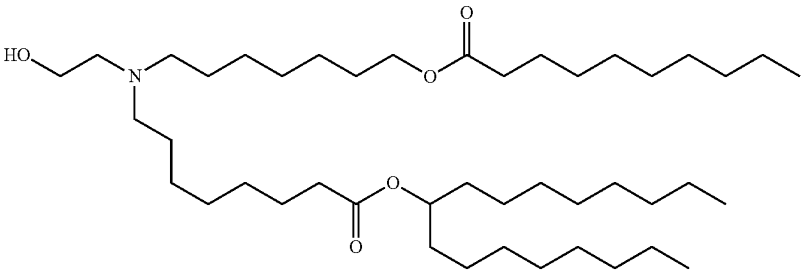
, -continued
(Compound 97)
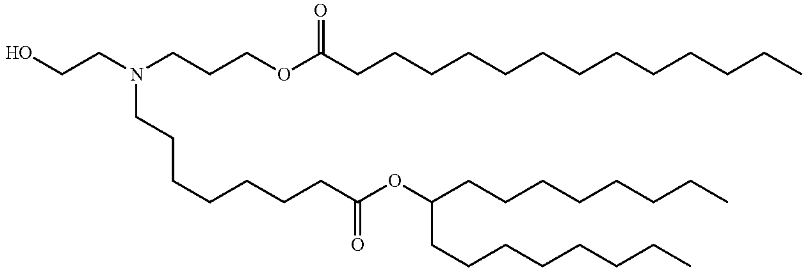
,
(Compound 98)
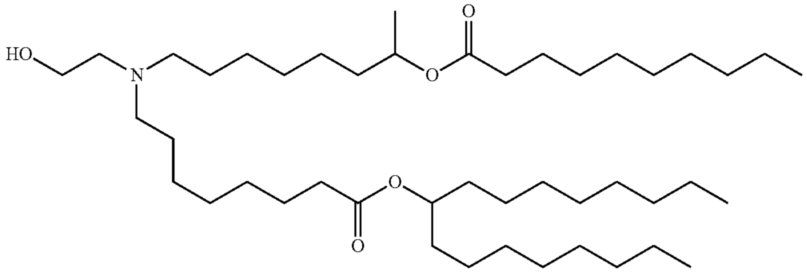
,
(Compound 99)
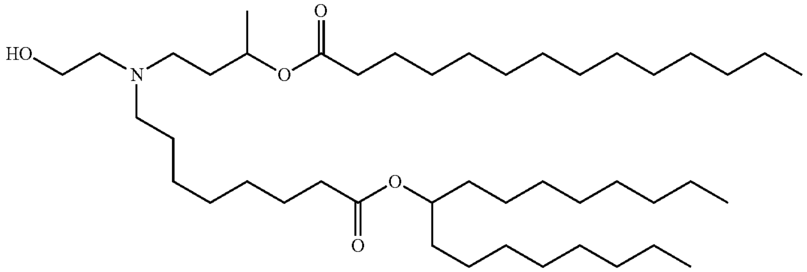
,
(Compound 100)
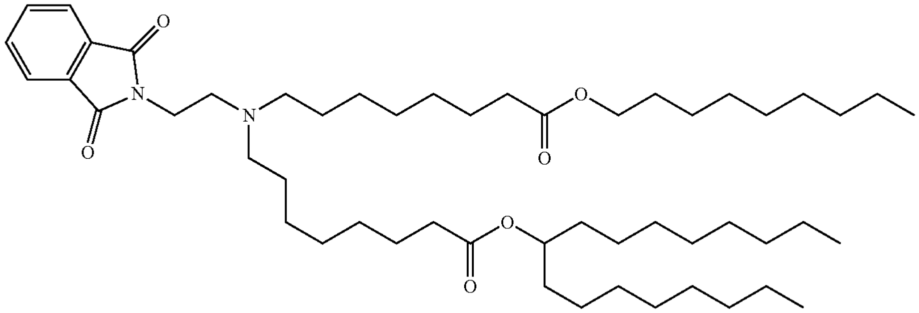
,
(Compound 101)
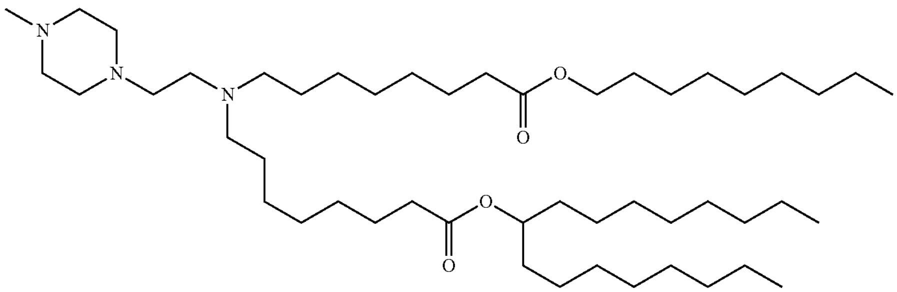
, -continued
(Compound 102)
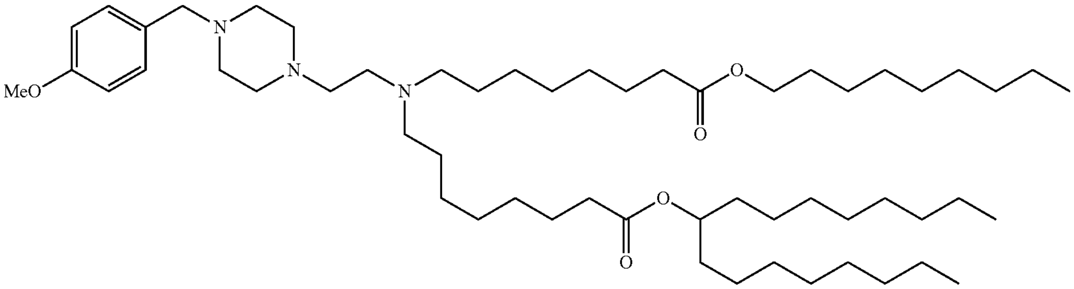
,
(Compound 103)
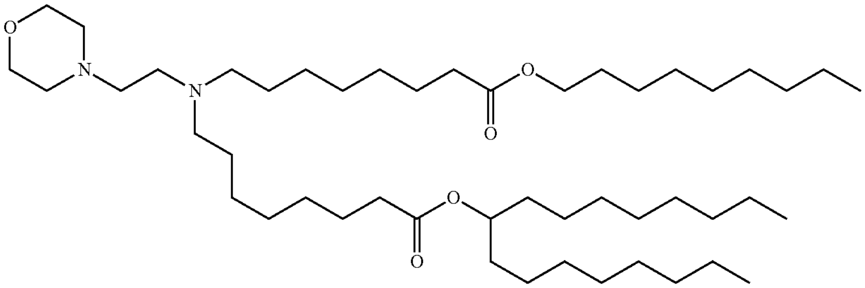
,
(Compound 104)
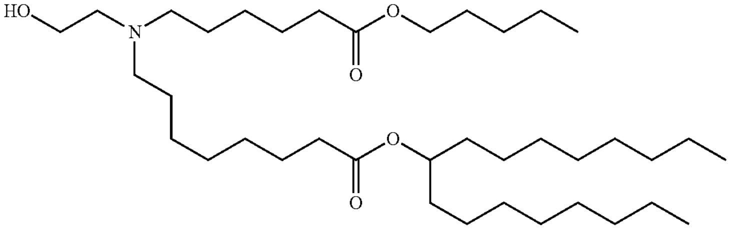
,
(Compound 105)
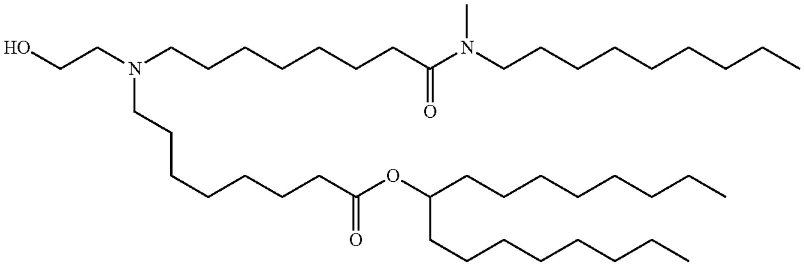
,
(Compound 106)
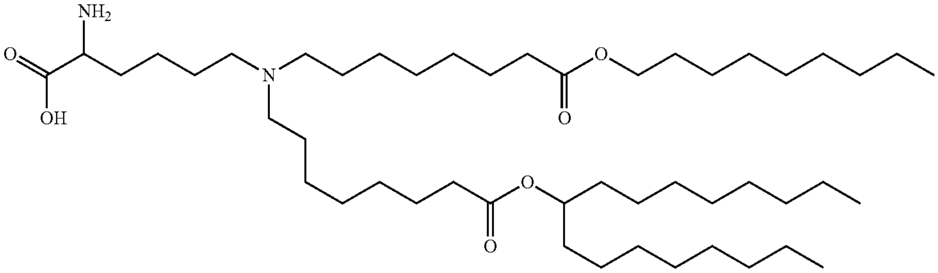
,
(Compound 107)
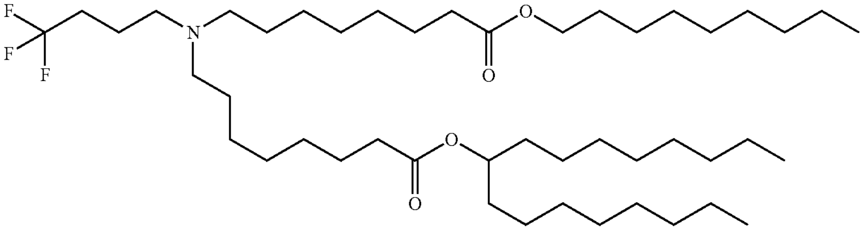
, -continued
(Compound 108)
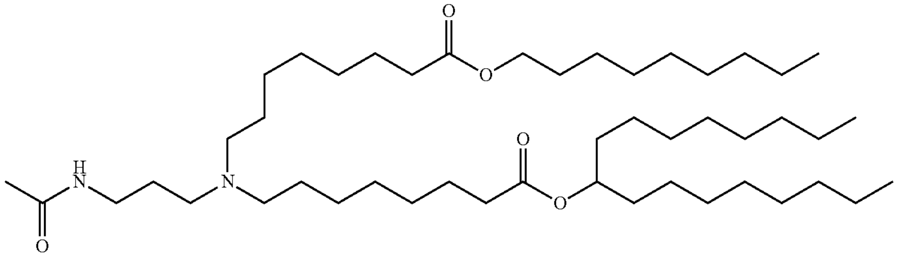
,
(Compound 109)
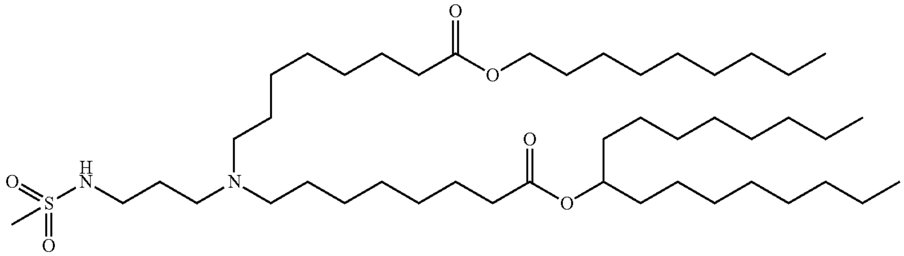
,
(Compound 110)
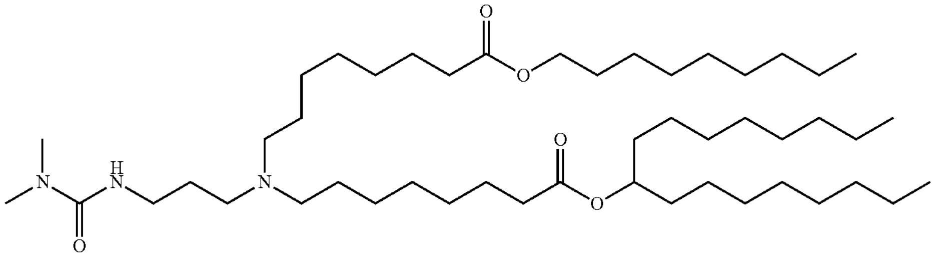
,
(Compound 111)
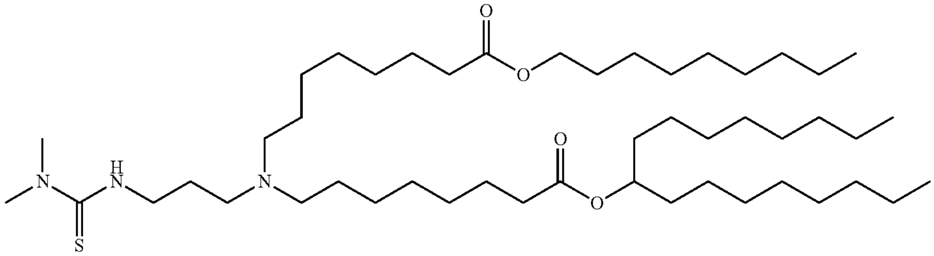
,
(Compound 112)
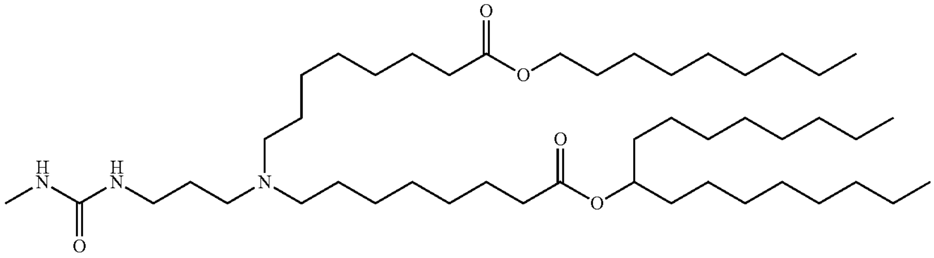
,
(Compound 113)
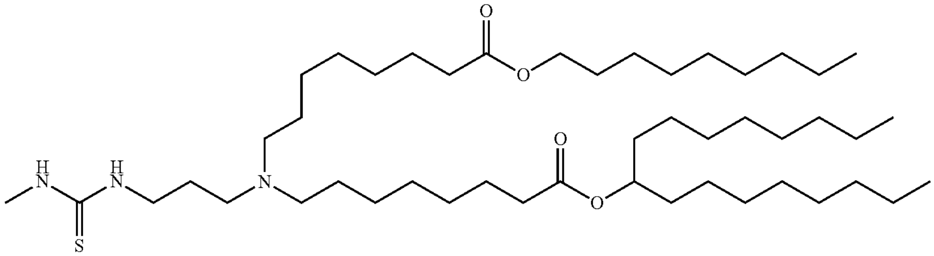
, -continued
(Compound 114)
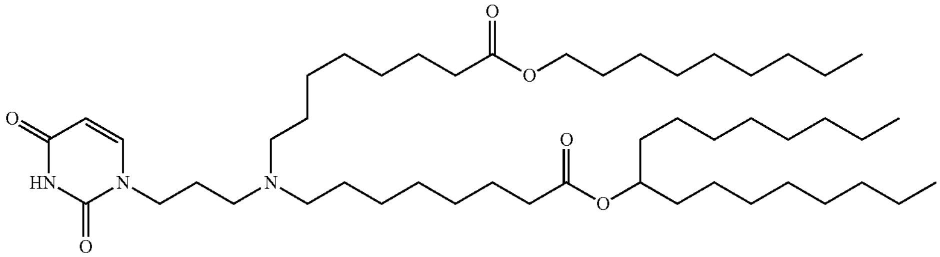
,
(Compound 115)
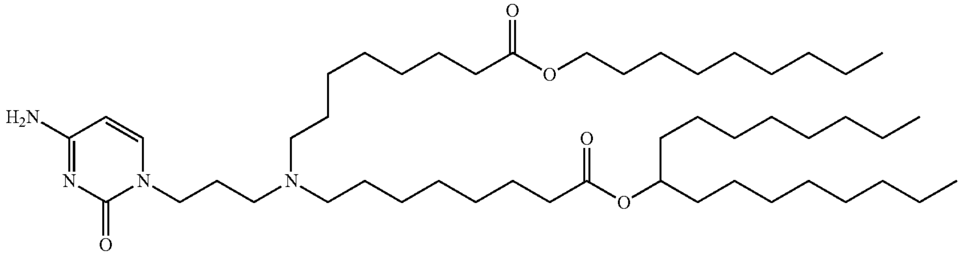
,
(Compound 116)
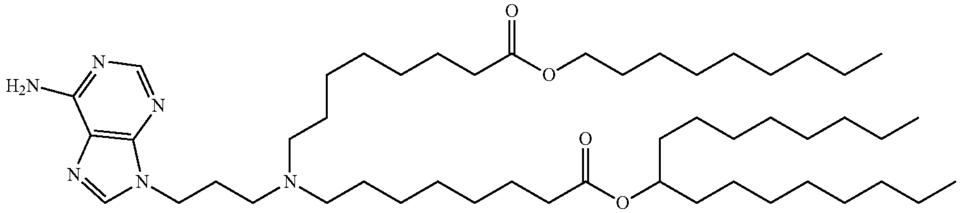
,
(Compound 117)
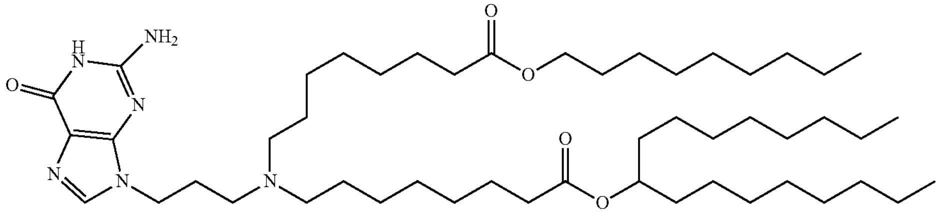
,
(Compound 118)
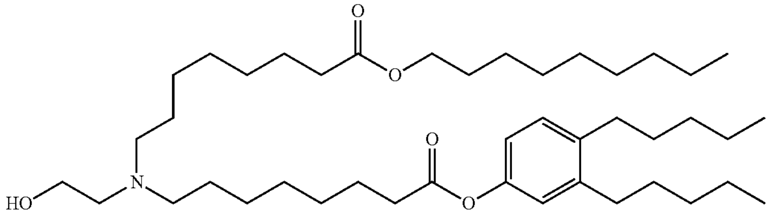
,
(Compound 119)
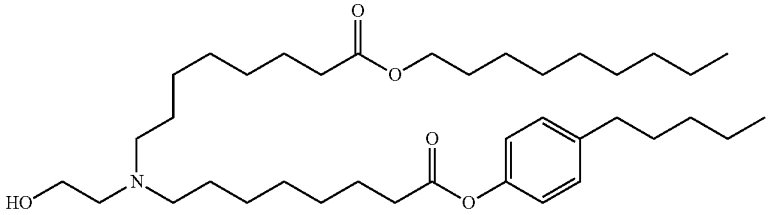
,
(Compound 120)
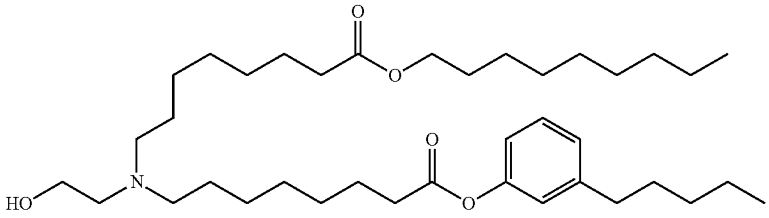
, -continued
(Compound 121)
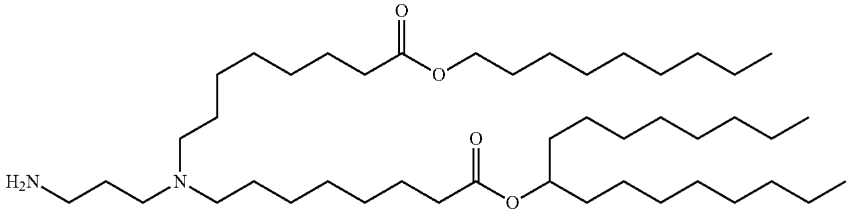
,
(Compound 122)
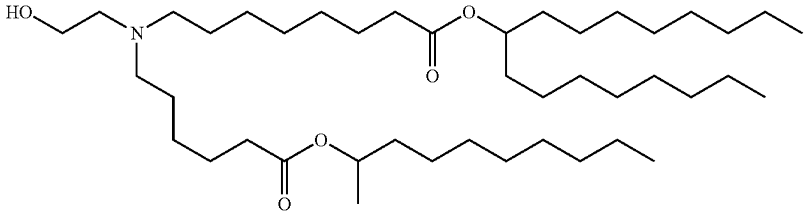
,
(Compound 123)
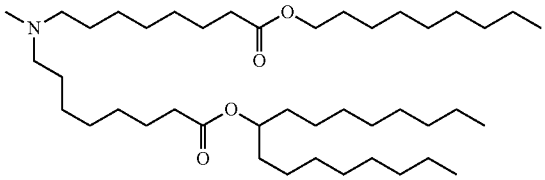
,
(Compound 124)
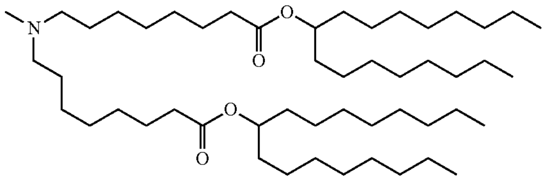
,
(Compound 125)
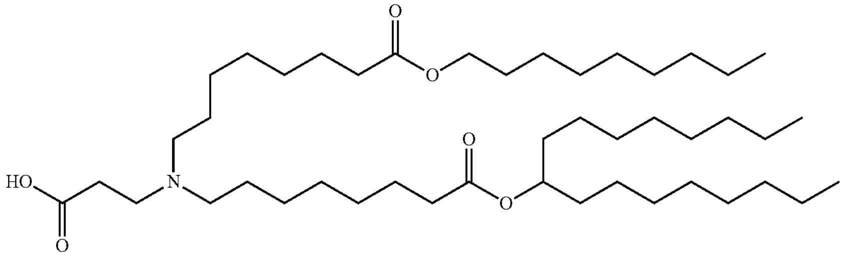
,
(Compound 126)
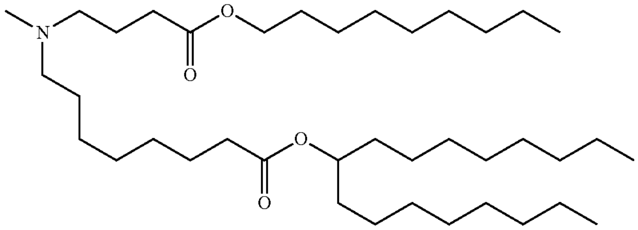
,
(Compound 127)
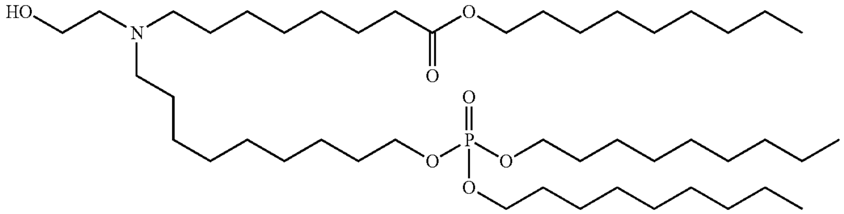
,
(Compound 128)
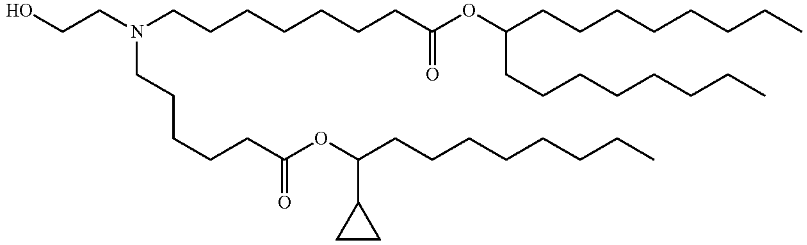
, -continued
(Compound 129)
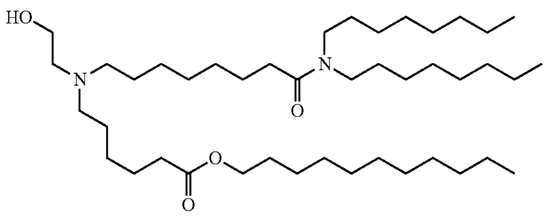
,
(Compound 130)
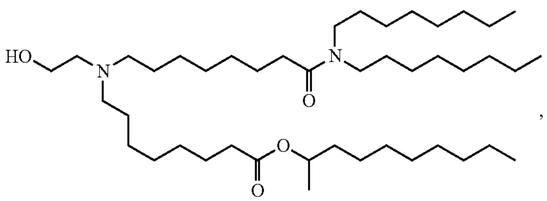
,
(Compound 131)
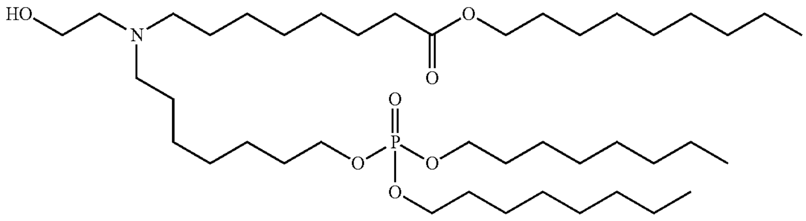
,
(Compound 132)
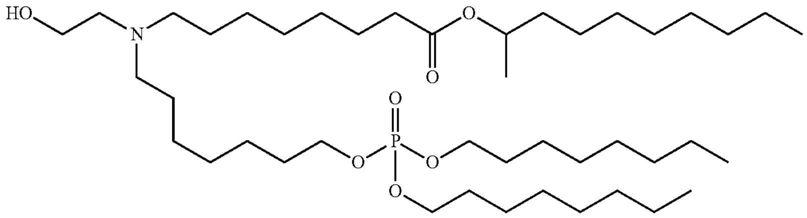
,
(Compound 133)
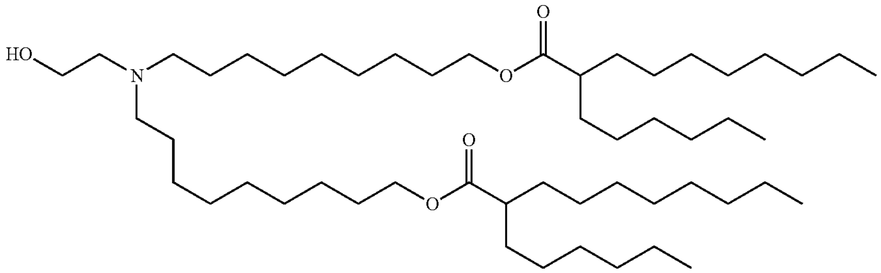
,
(Compound 134)
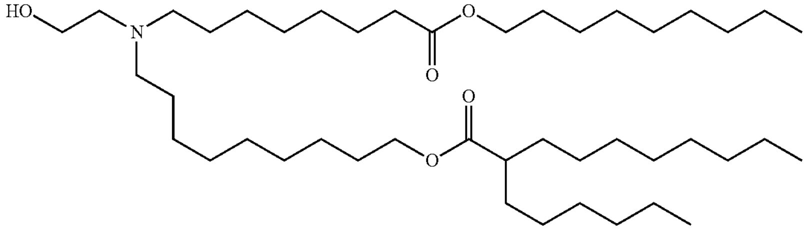
,
(Compound 135)
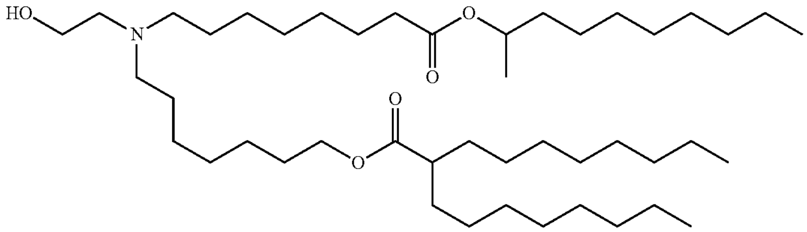
,
(Compound 136)
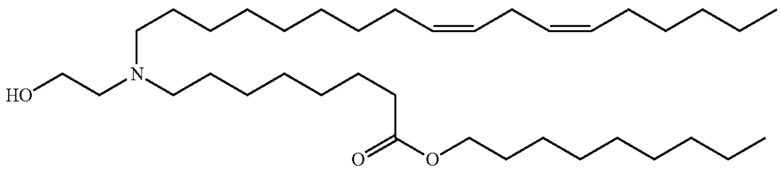
, -continued
(Compound 137)
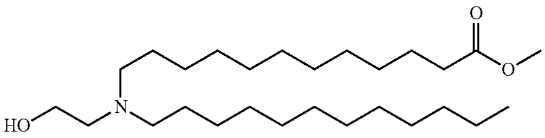,
(Compound 138)
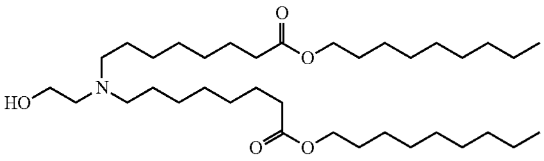,
(Compound 139)
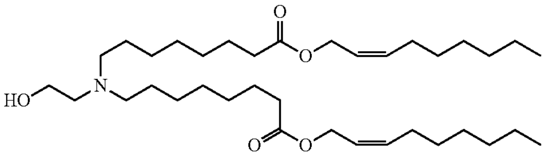,
(Compound 140)
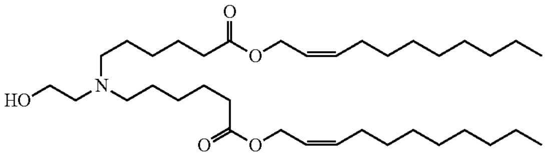,
(Compound 141)
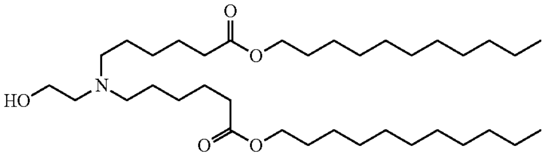,
(Compound 142)
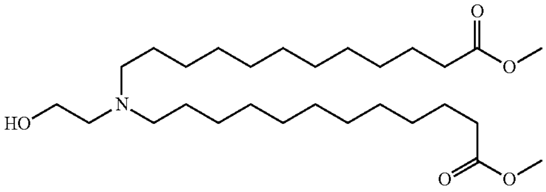,
(Compound 143)
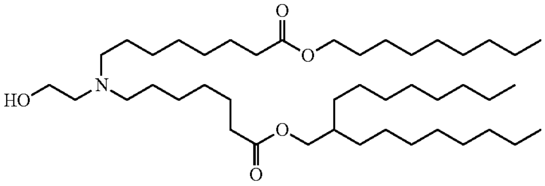,
(Compound 144)
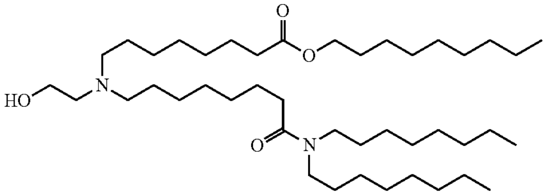,
(Compound 145)
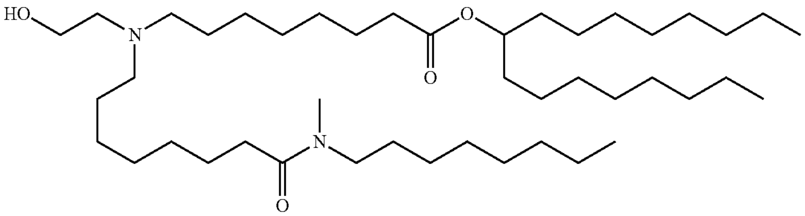,
(Compound 146)
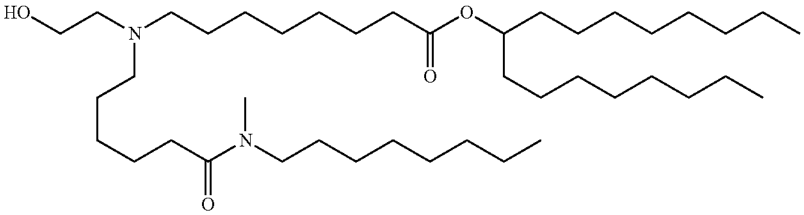,
(Compound 147)
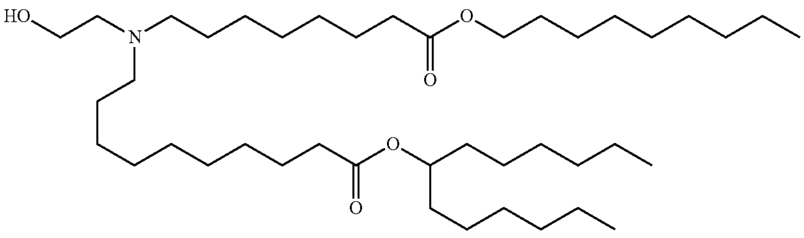, -continued
(Compound 148)
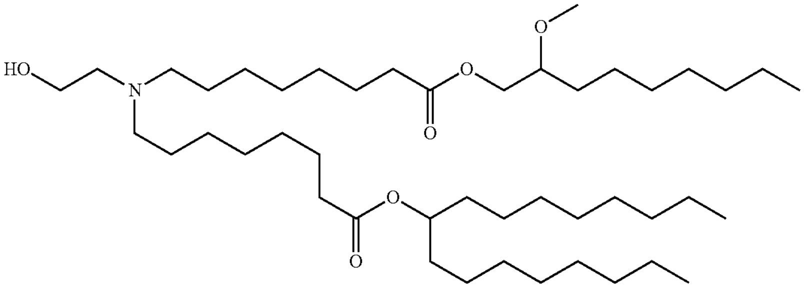
,
(Compound 149)
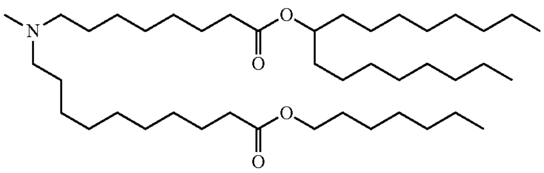
,
(Compound 150)
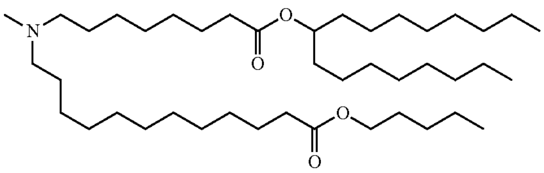
,
(Compound 151)
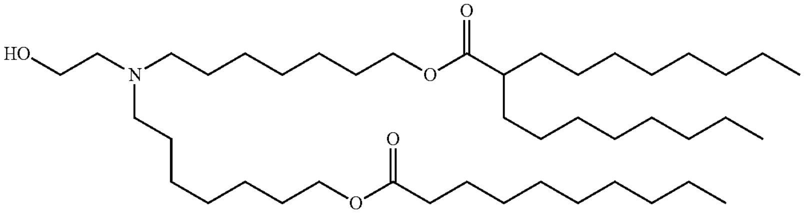
,
(Compound 152)
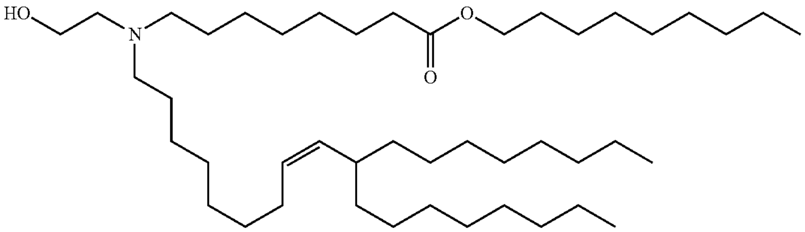
,
(Compound 153)
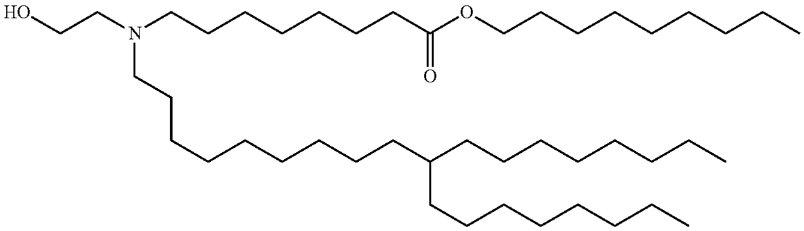
,
(Compound 154)
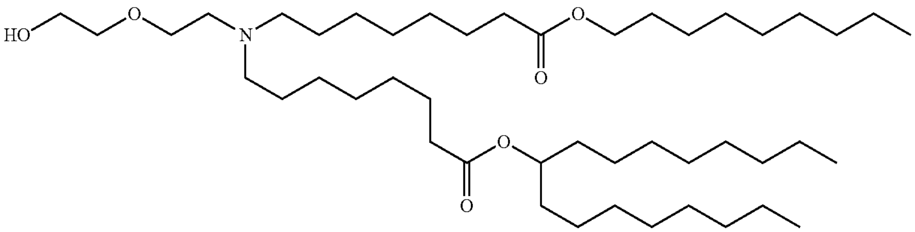
, -continued
(Compound 155)
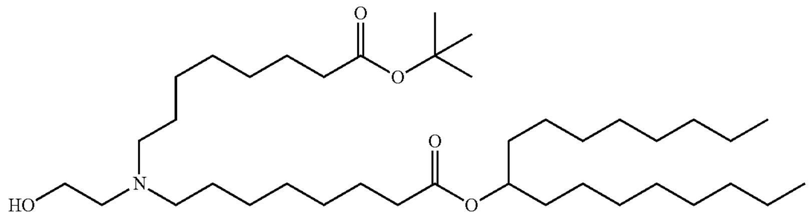
,
(Compound 156)
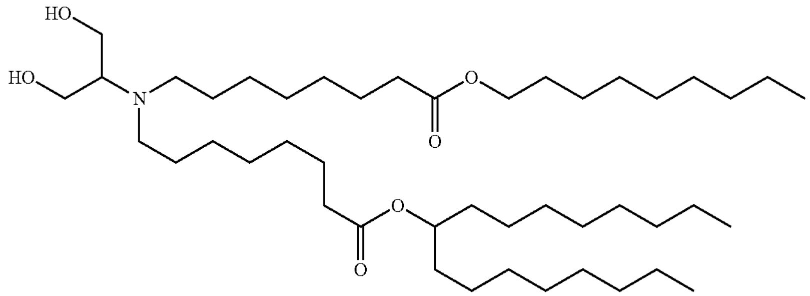
,
(Compound 157)
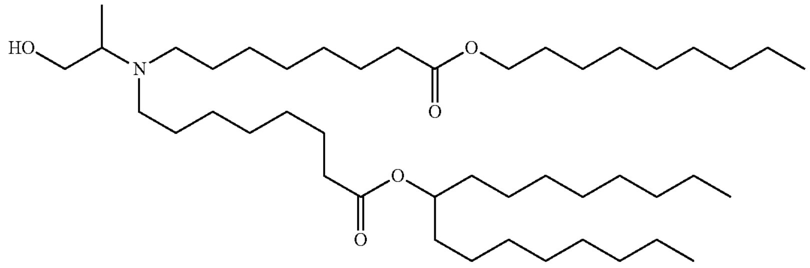
,
(Compound 158)
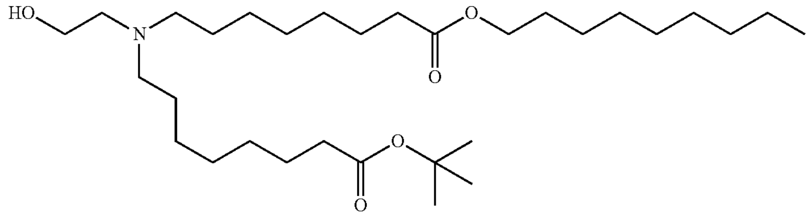
,
(Compound 159)
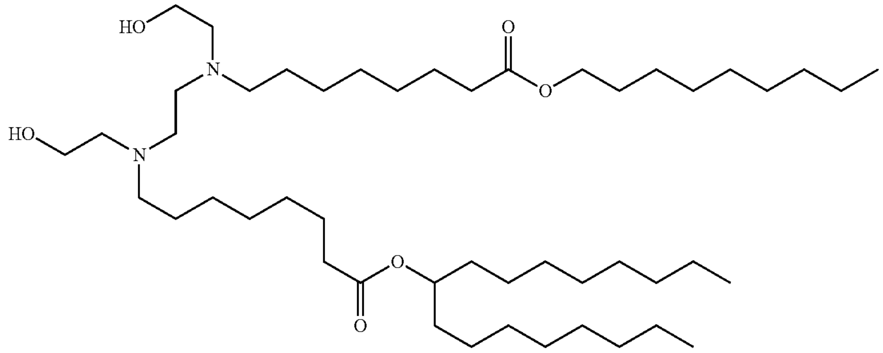
, -continued
(Compound 160)
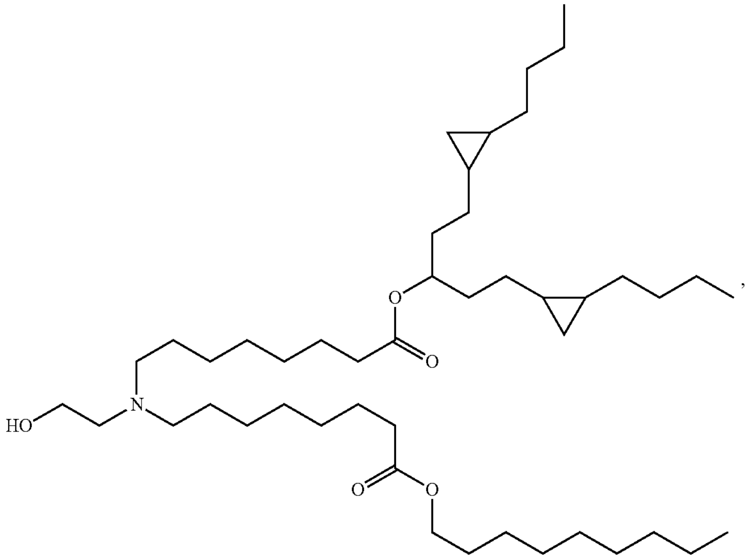
,
(Compound 161)
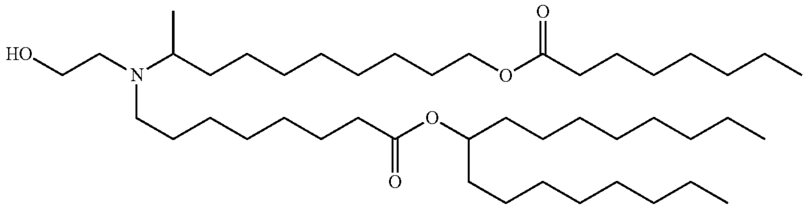
,
(Compound 162)
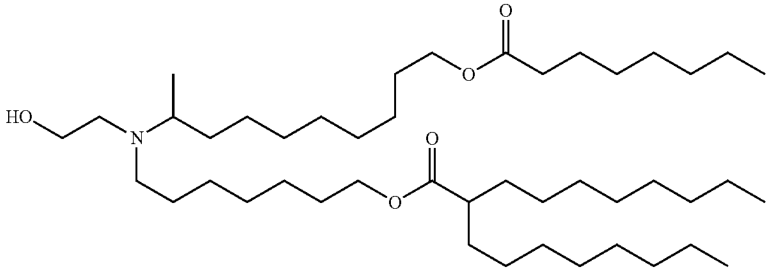
,
(Compound 163)
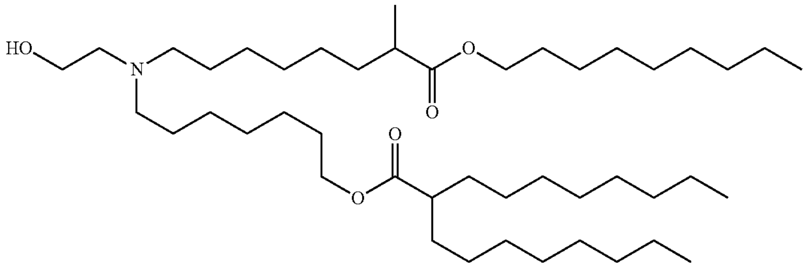
,
(Compound 164)
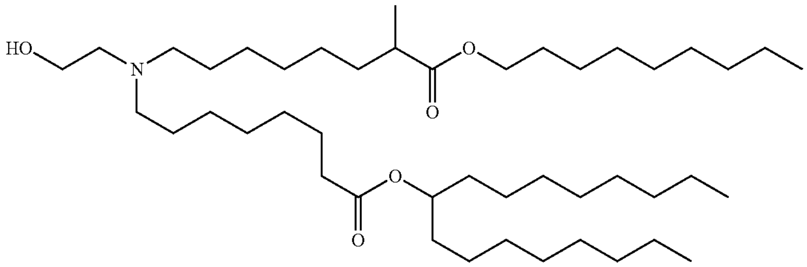
, -continued
(Compound 165)
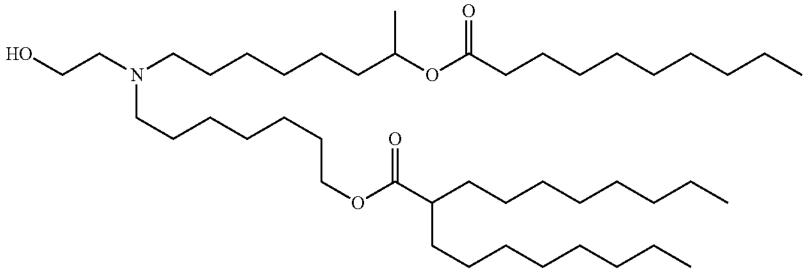
,
(Compound 166)
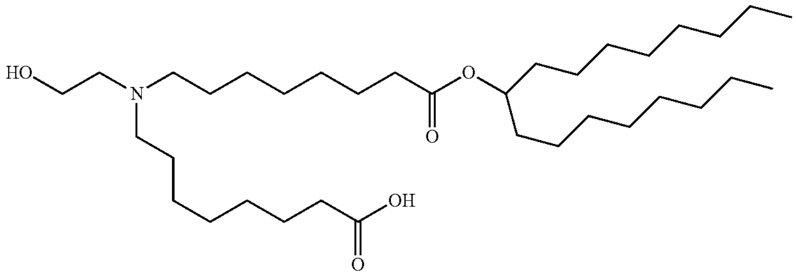
,
(Compound 167)
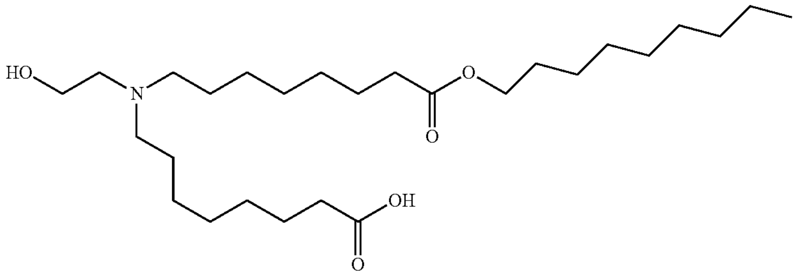
,
(Compound 168)
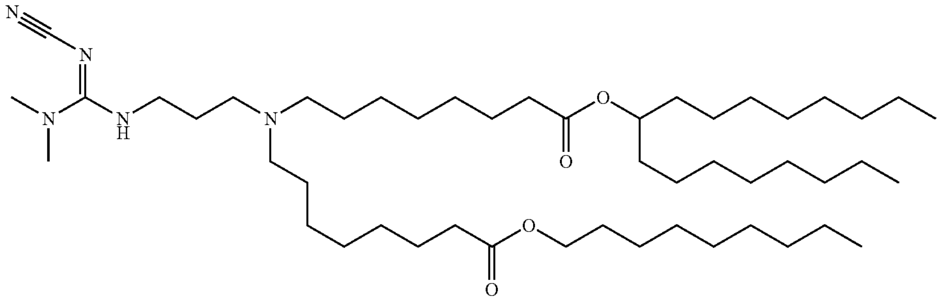
,
(Compound 169)
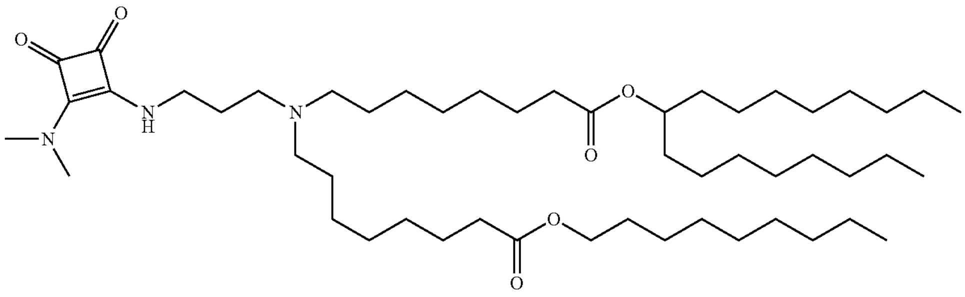
, -continued
(Compound 170)
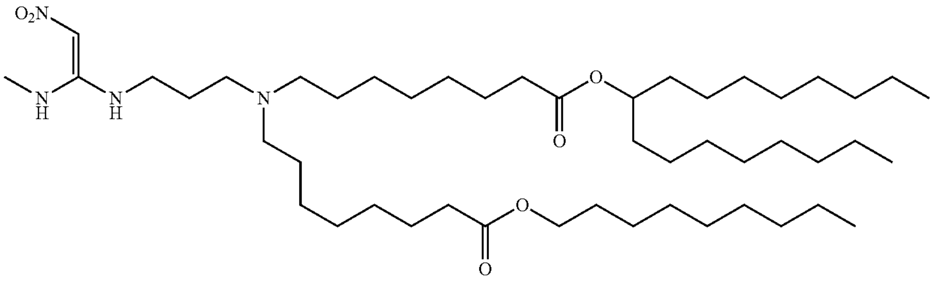
,
(Compound 171)
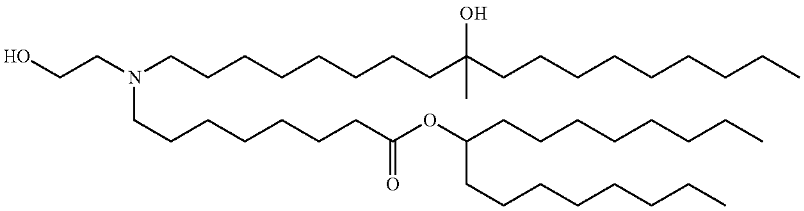
,
(Compound 172)
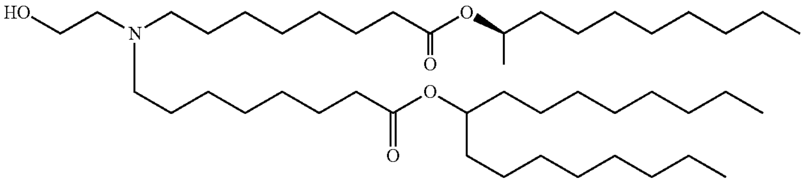
,
(Compound 173)
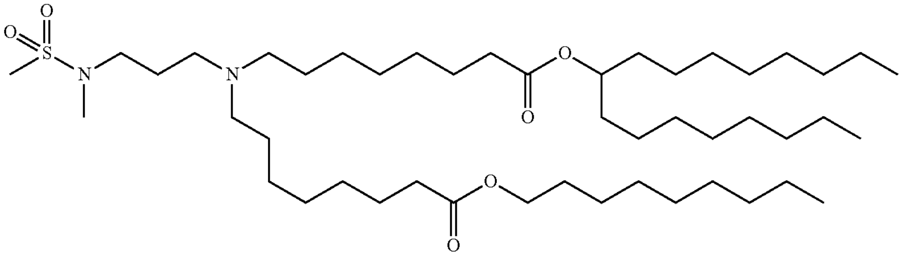
,
(Compound 174)
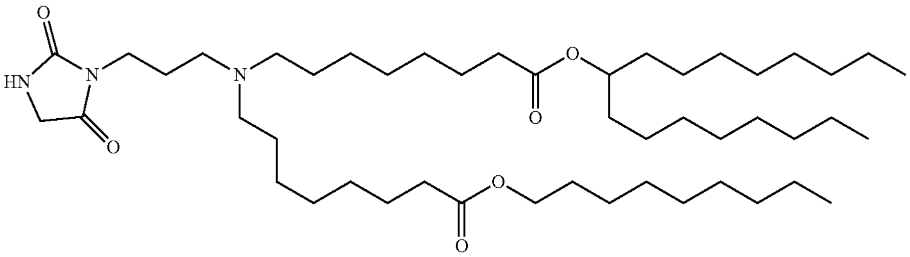
,
(Compound 175)
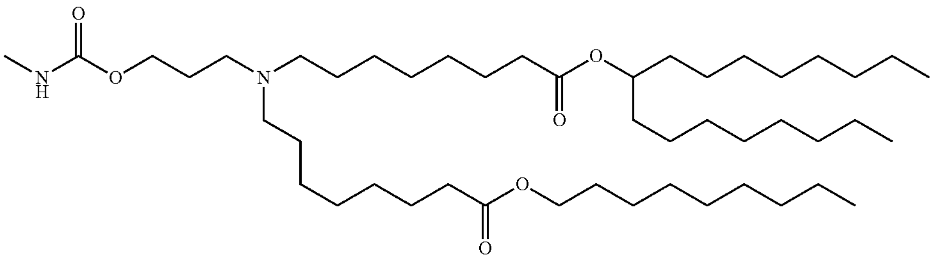
, -continued
(Compound 176)
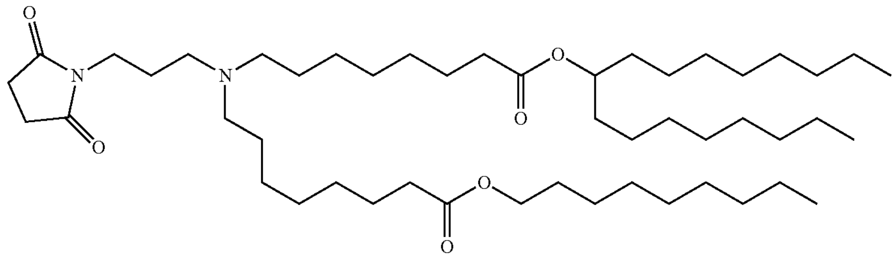
,
(Compound 177)
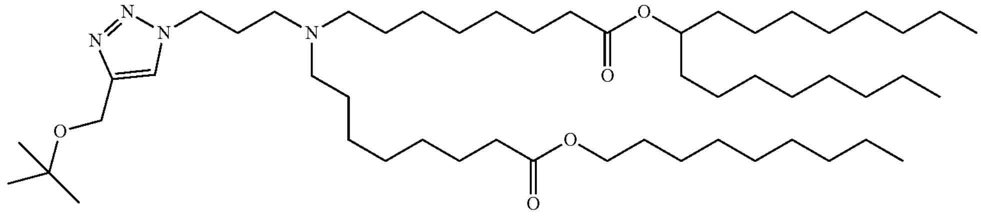
,
(Compound 178)
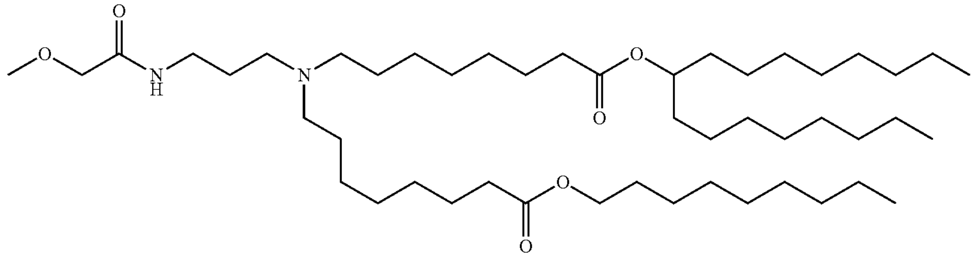
,
(Compound 179)
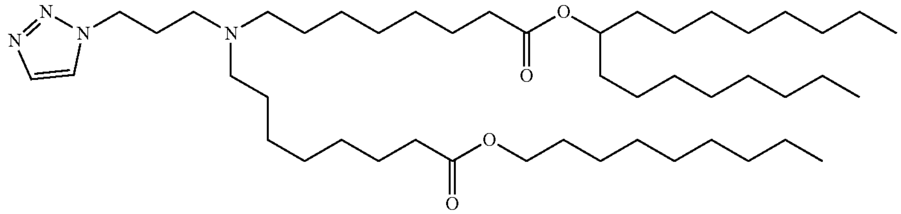
,
(Compound 180)
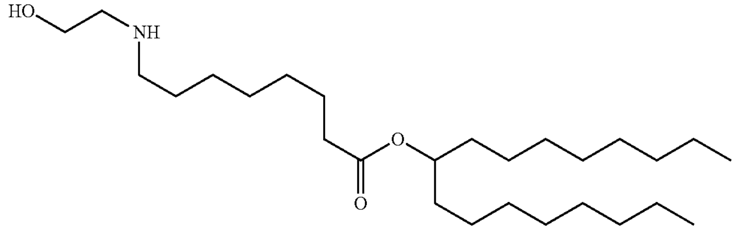
,
(Compound 181)
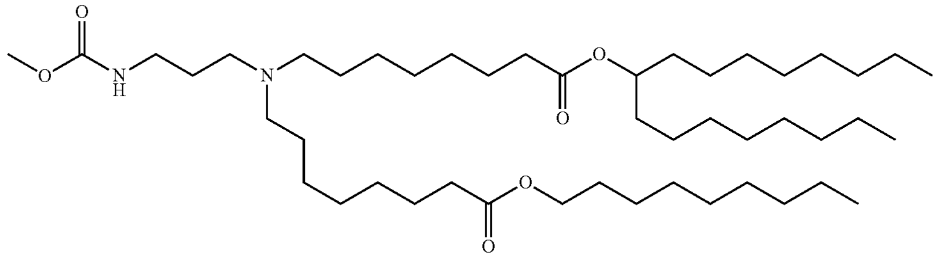
, -continued
(Compound 182)
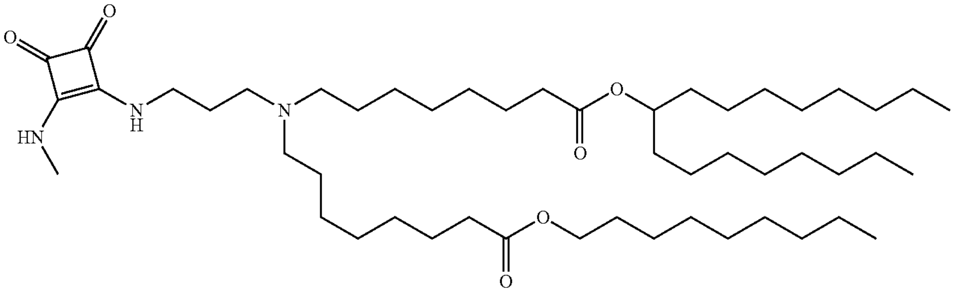
,
(Compound 183)
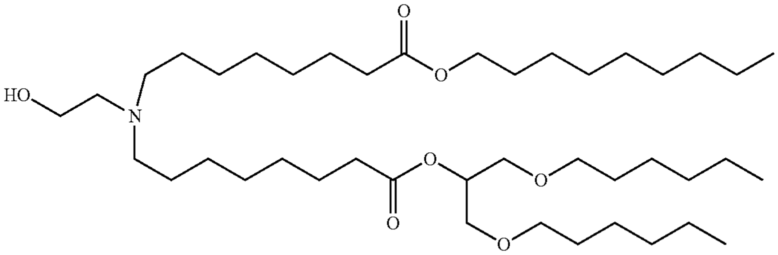
,
(Compound 184)
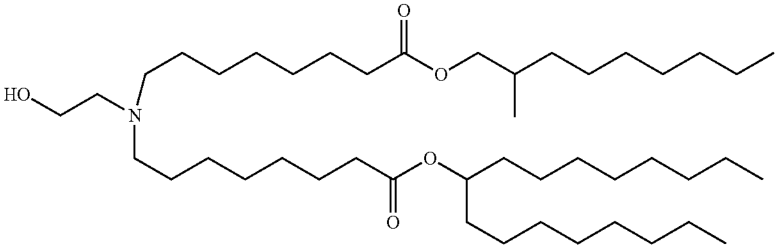
,
(Compound 185)
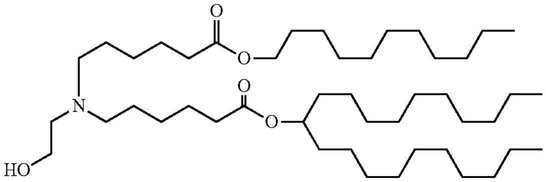
,
(Compound 186)
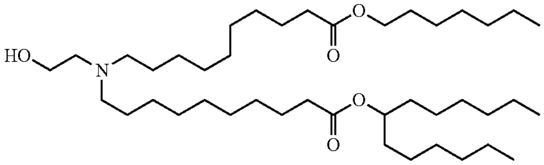
,
(Compound 187)
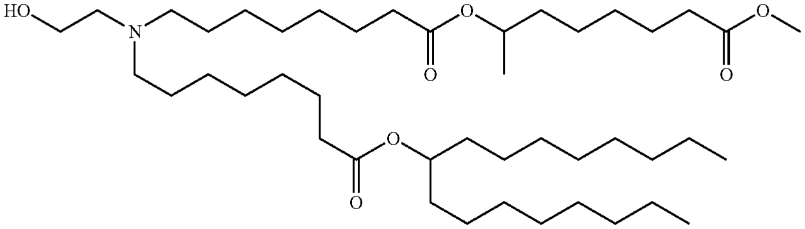
,
(Compound 188)
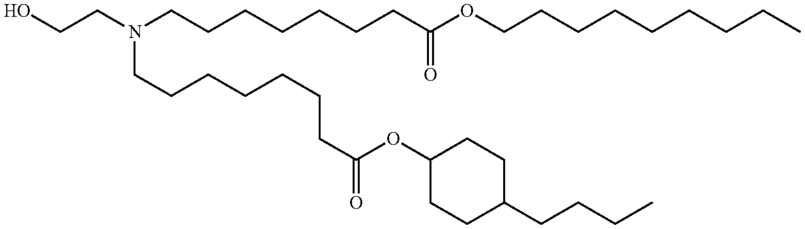
, -continued
(Compound 189)
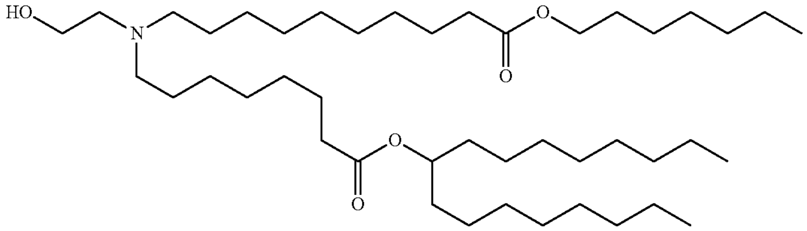
,
(Compound 190)
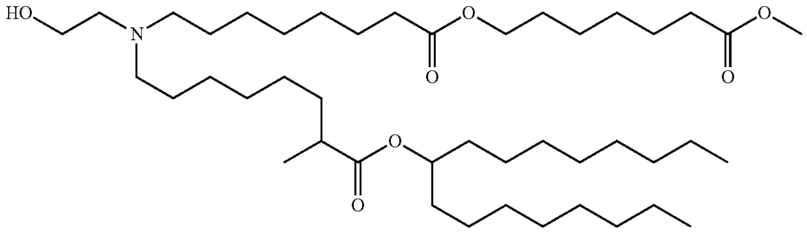
,
(Compound 191)
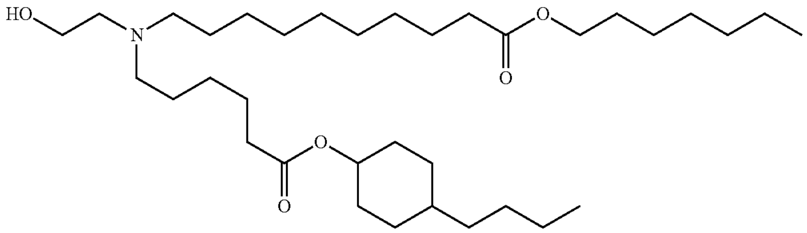
,
(Compound 192)
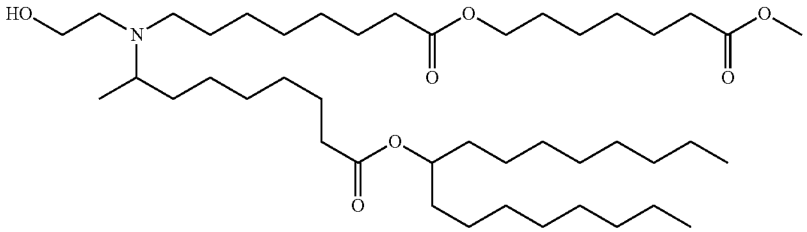
,
(Compound 193)
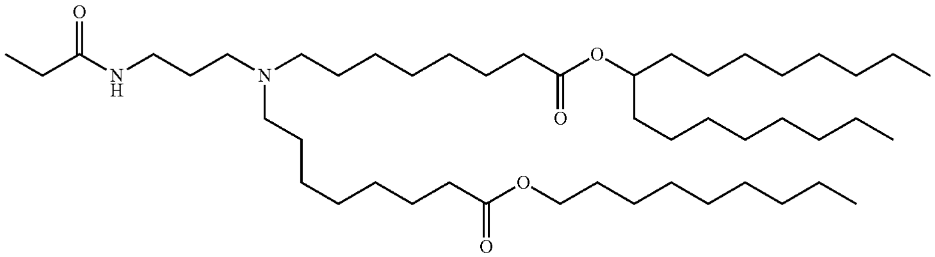
,
(Compound 194)
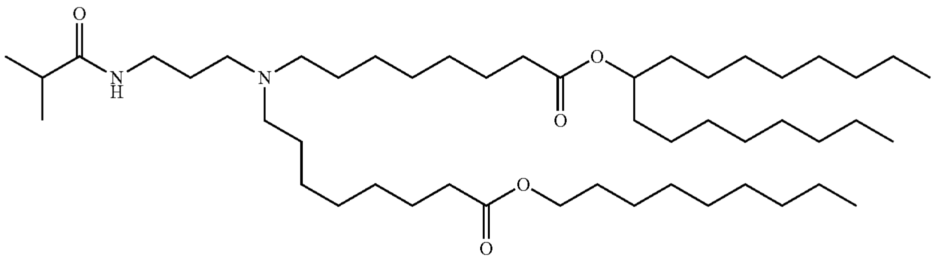
, -continued
(Compound 195)
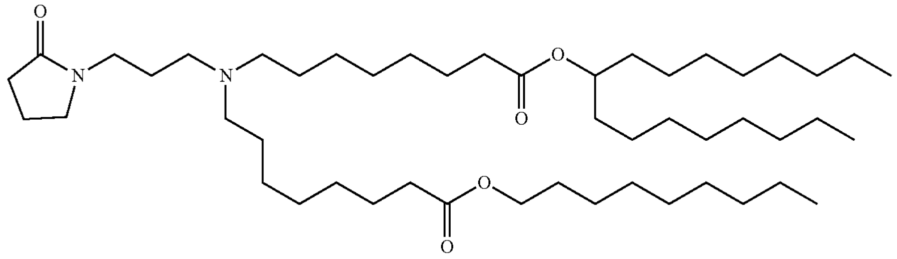
,
(Compound 196)
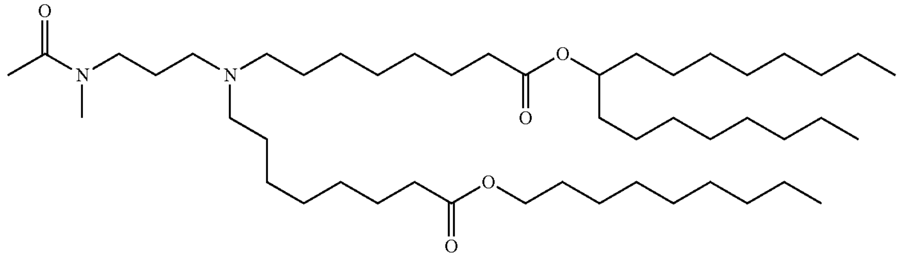
,
(Compound 197)
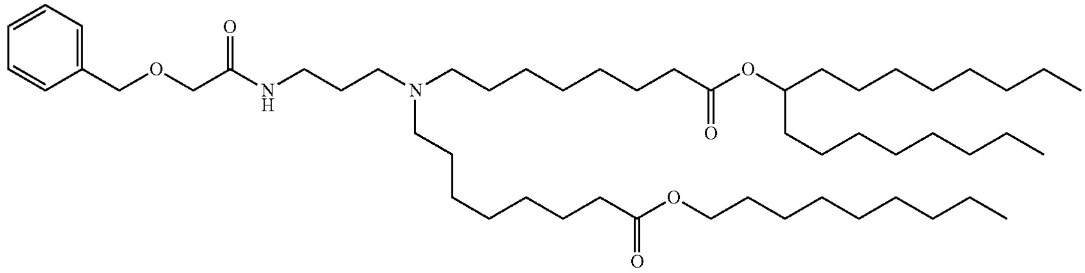
,
(Compound 198)
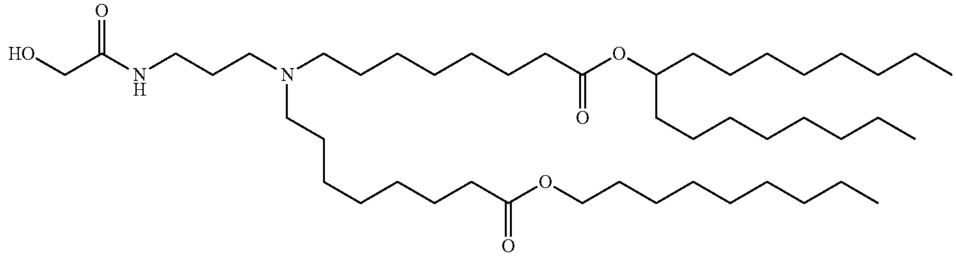
,
(Compound 199)
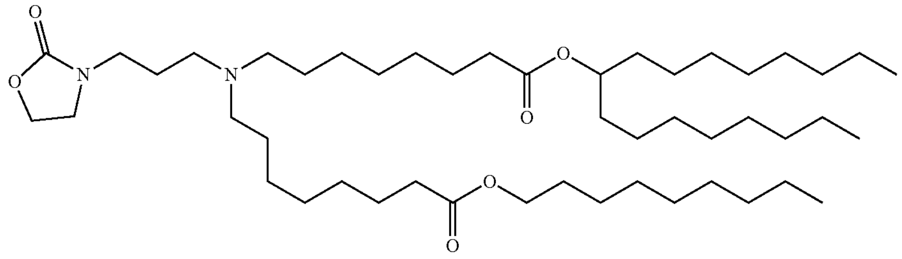
,
(Compound 200)
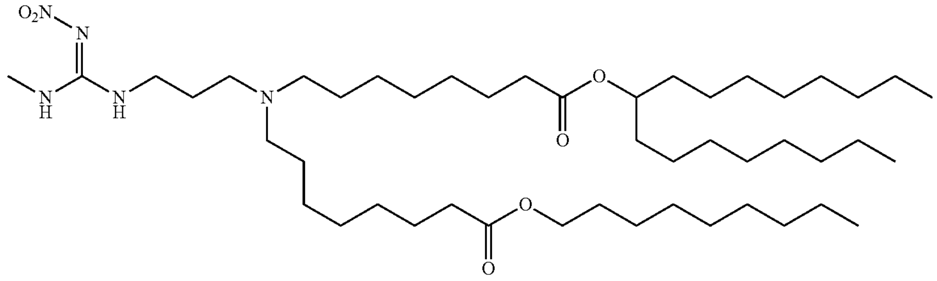
, -continued
(Compound 201)
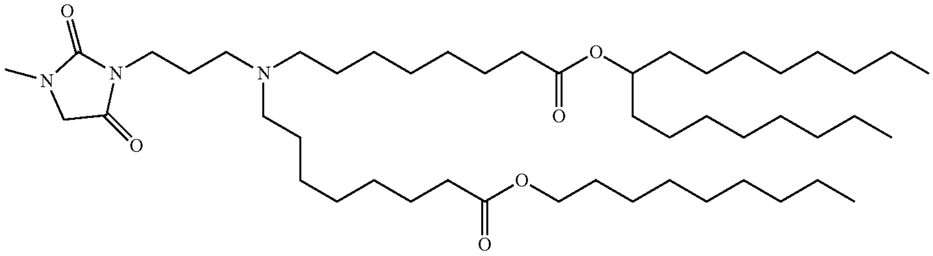
,
(Compound 202)
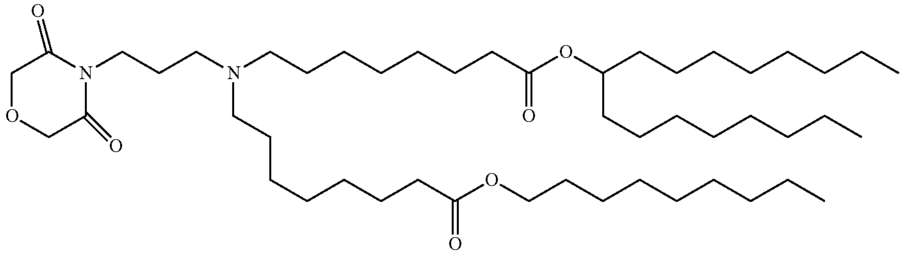
,
(Compound 203)
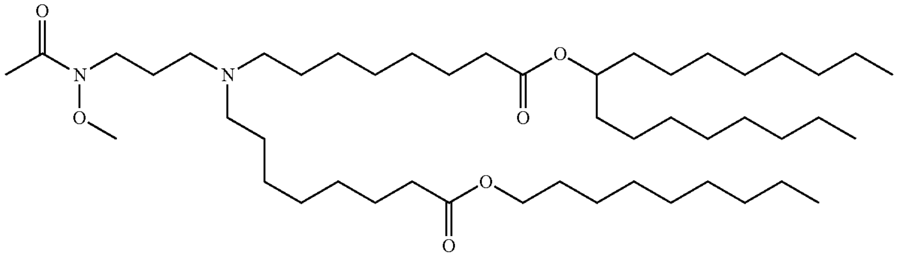
,
(Compound 204)
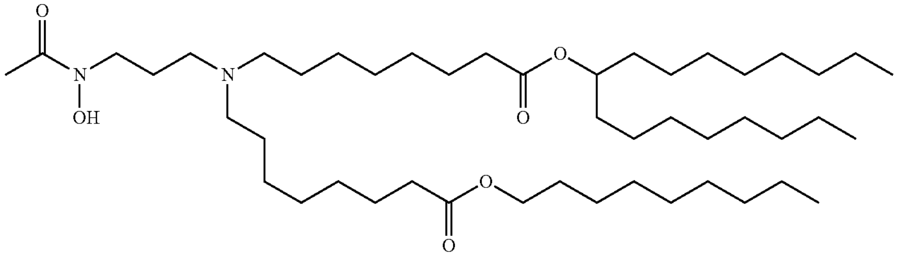
,
(Compound 205)
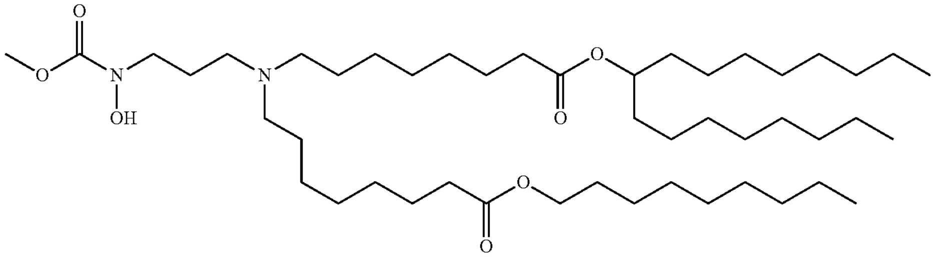
,
(Compound 206)
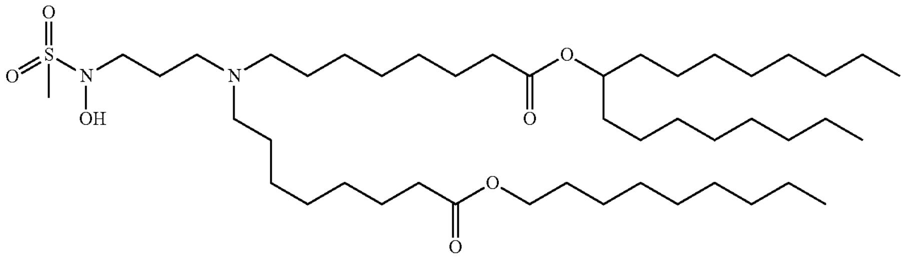
, -continued
(Compound 207)
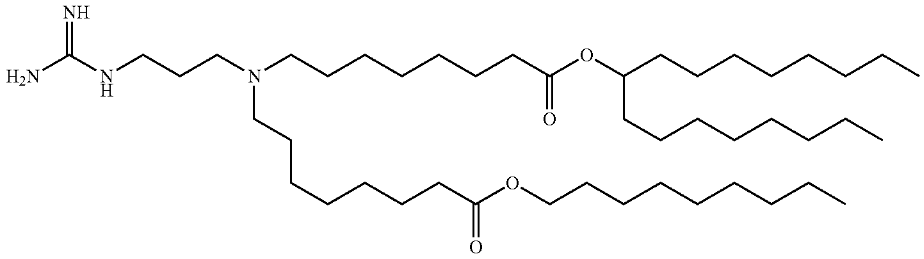
,
(Compound 208)
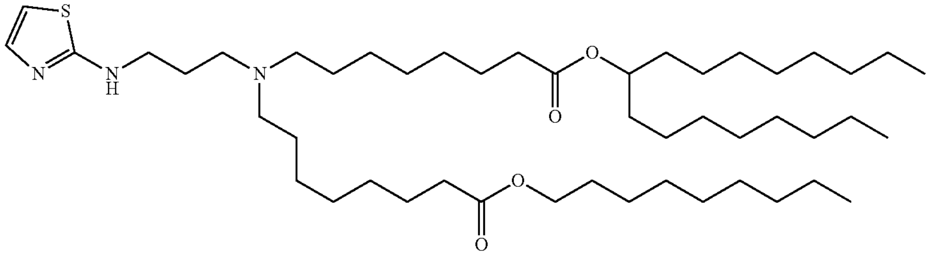
,
(Compound 209)
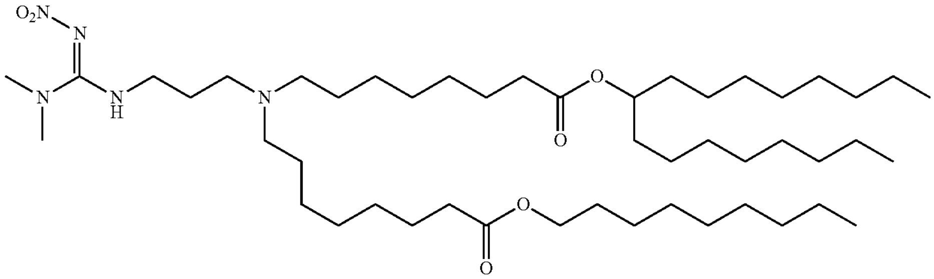
,
(Compound 210)
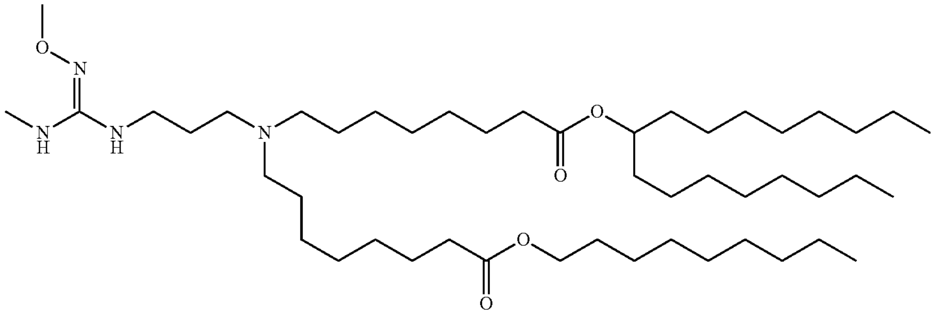
,
(Compound 211)
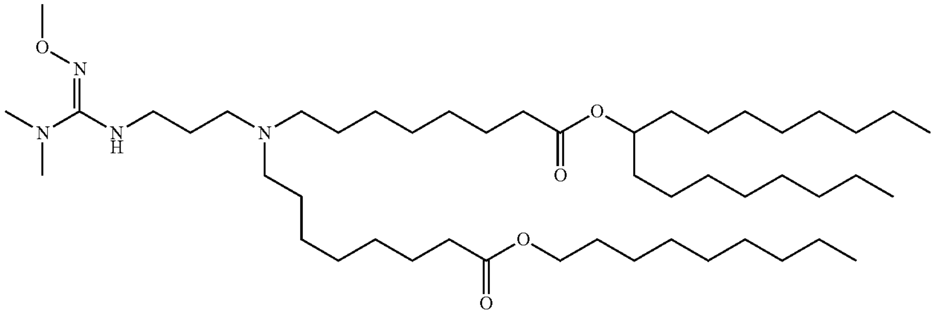
, -continued
(Compound 212)
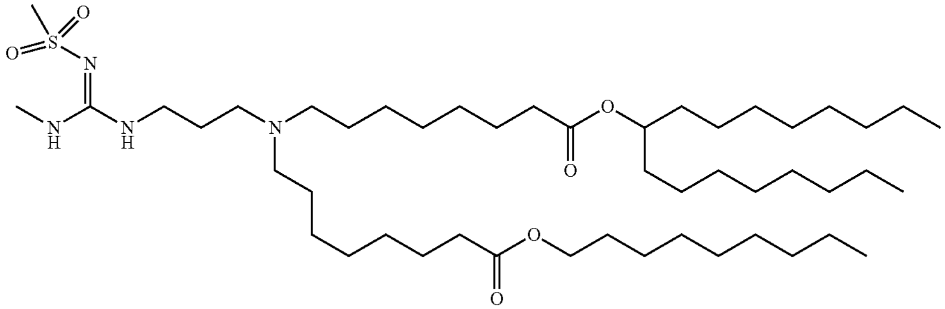
,
(Compound 213)
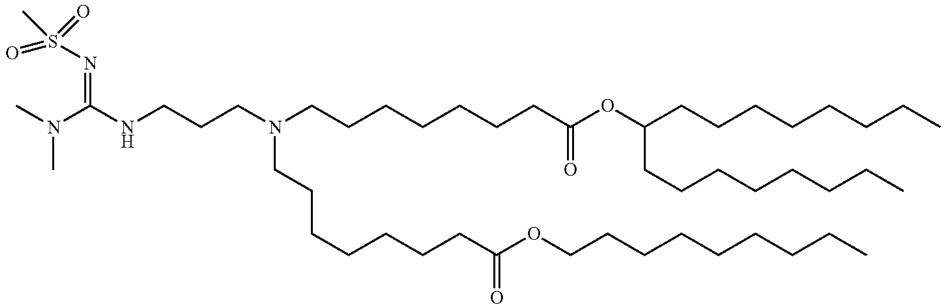
,
(Compound 214)
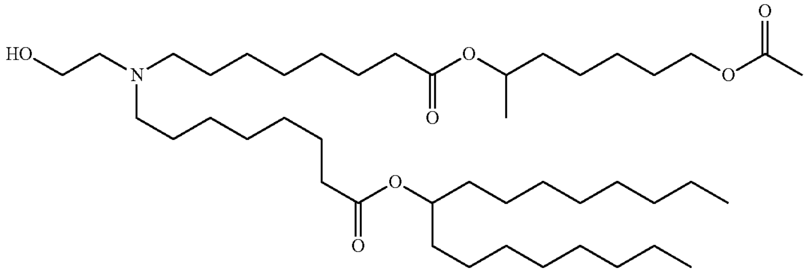
,
(Compound 215)
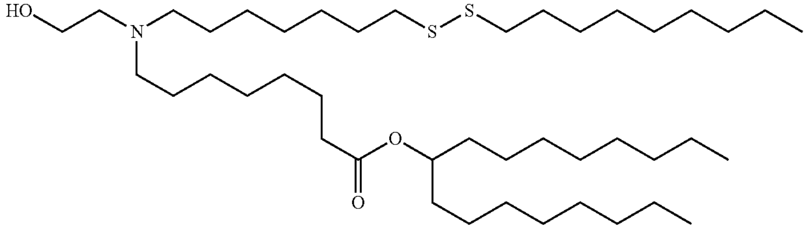
,
(Compound 216)
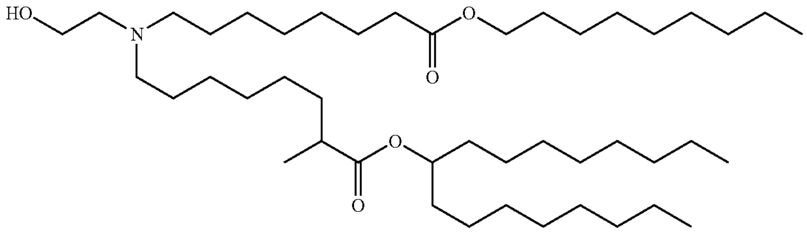
,
(Compound 217)
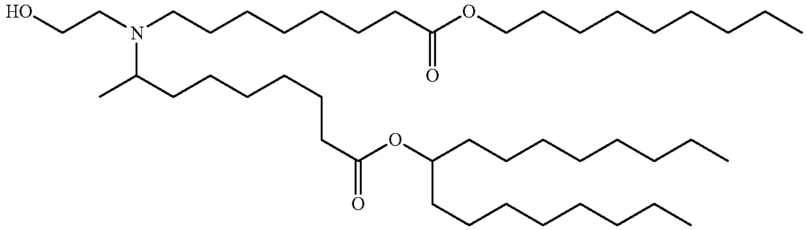
, -continued
(Compound 218)
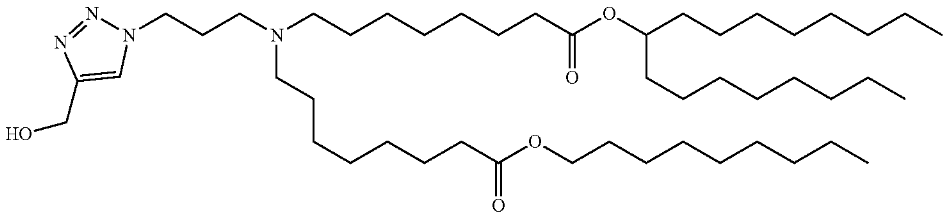
,
(Compound 219)
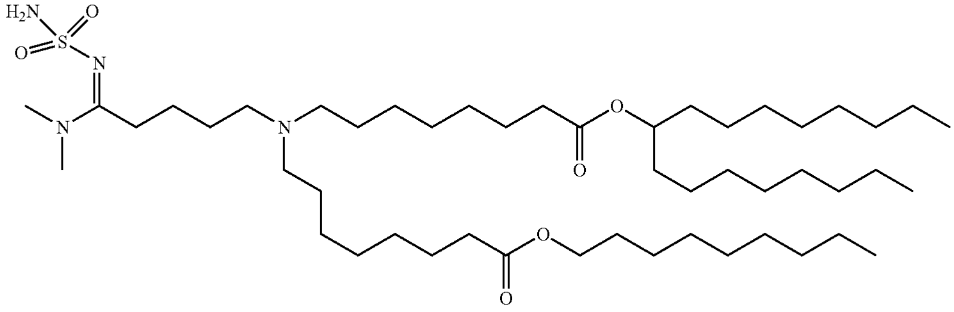
,
(Compound 220)
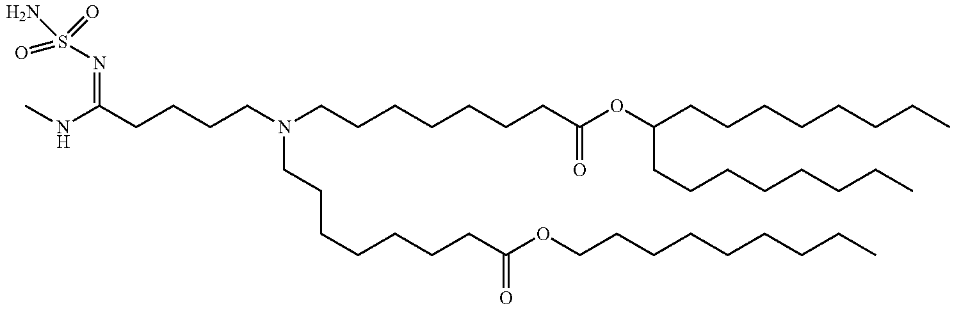
,
(Compound 221)
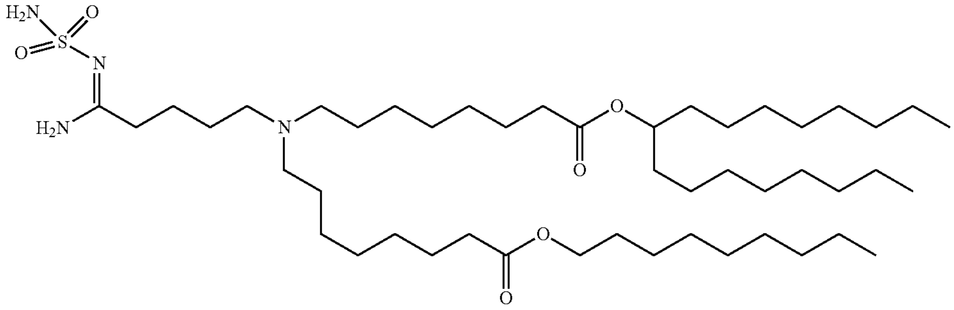
,
(Compound 222)
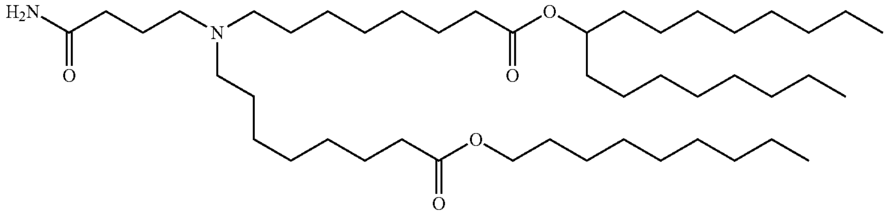
,
(Compound 223)
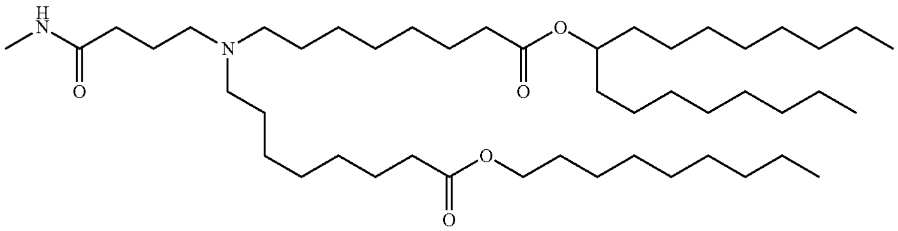
, -continued
(Compound 224)
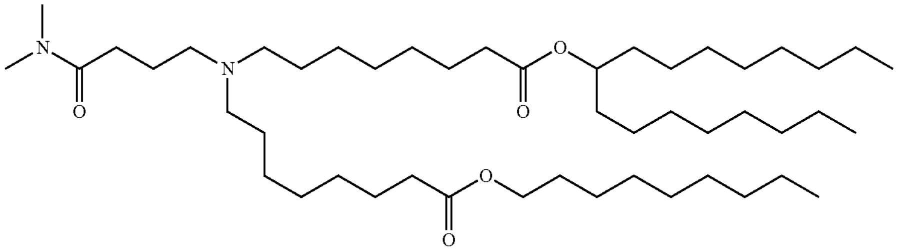
,
(Compound 225)
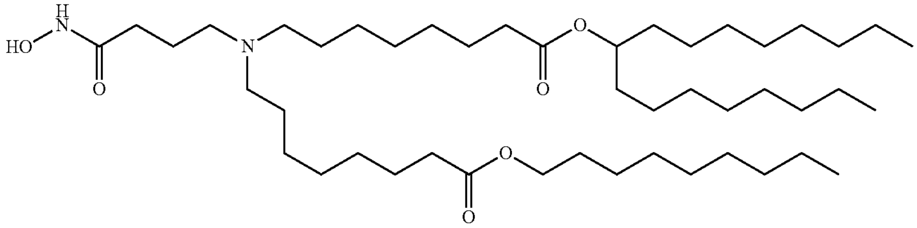
,
(Compound 226)
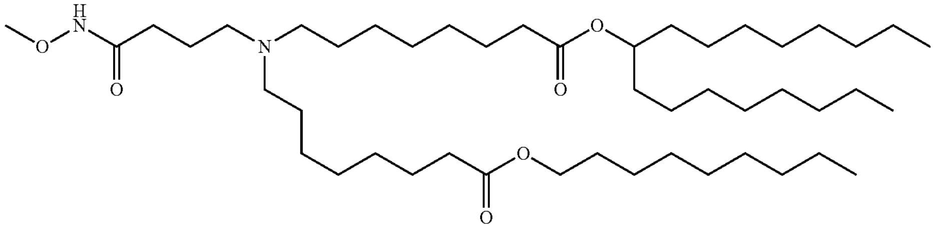
,
(Compound 227)
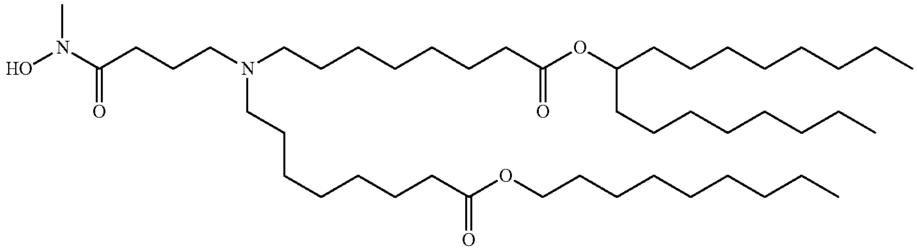
,
(Compound 228)
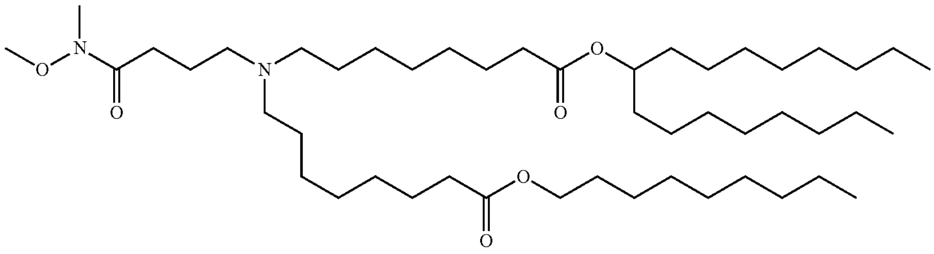
,
(Compound 229)
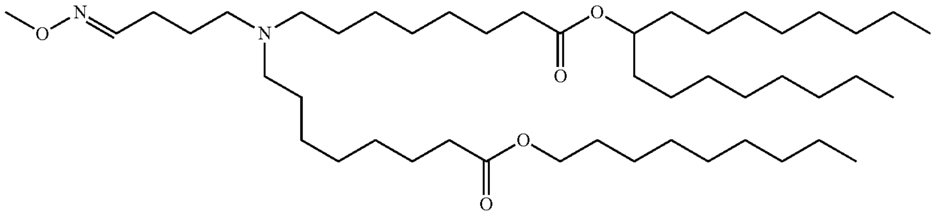
, -continued (Compound 230)

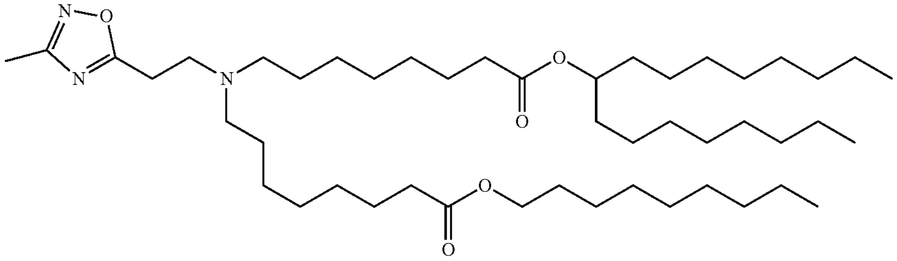

, (Compound 231)

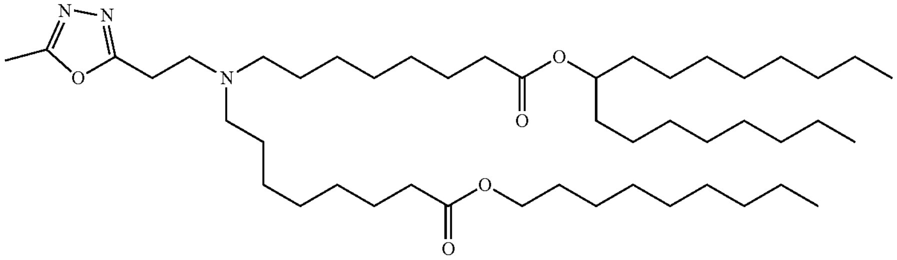

, (Compoumd 232)

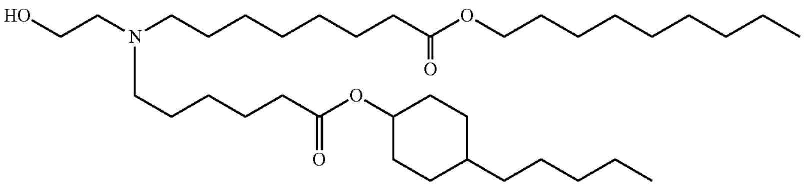

, and salts and isomers thereof.

In some embodiments, a nanoparticle comprises the following compound:

(Compound 233)

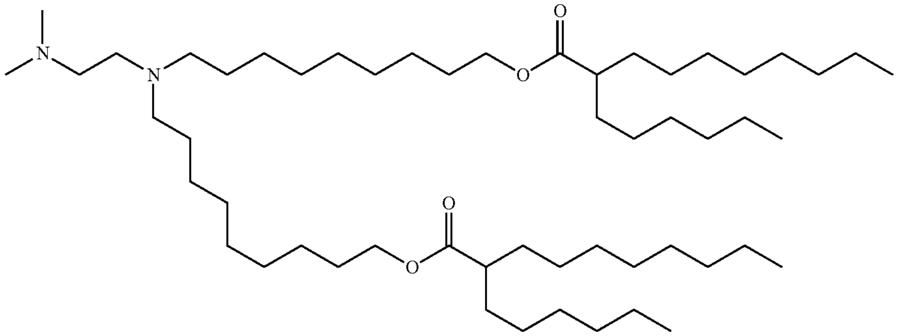

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

In some embodiments, the disclosure features a pharmaceutical composition comprising a nanoparticle composition according to the preceding embodiments and a pharmaceutically acceptable carrier. For example, the pharmaceutical composition is refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition is a solution that is refrigerated for storage and/or shipment at, for example, about −20° C., −30° C., −40° C., −50° C., −60° C., −70° C., or −80° C.

In some embodiments, the disclosure provides a method of delivering a therapeutic and/or prophylactic (e.g., RNA, such as mRNA) to a cell (e.g., a mammalian cell). This method includes the step of administering to a subject (e.g., a mammal, such as a human) a nanoparticle composition including (i) a lipid component including a phospholipid (such as a polyunsaturated lipid), a PEG lipid, a structural lipid, and a compound of Formula (I), (IA), (II), (IIa), (IIb), (IIc), (IId) or (IIe) and (ii) a therapeutic and/or prophylactic, in which administering involves contacting the cell with the nanoparticle composition, whereby the therapeutic and/or prophylactic is delivered to the cell.

In some embodiments, the disclosure provides a method of producing a polypeptide of interest in a cell (e.g., a mammalian cell). The method includes the step of contacting the cell with a nanoparticle composition including (i) a lipid component including a phospholipid (such as a polyunsaturated lipid), a PEG lipid, a structural lipid, and a compound of Formula (I), (IA), (II), (IIa), (IIb), (IIe), (IId) or (IIe) and (ii) an mRNA encoding the polypeptide of interest, whereby the mRNA is capable of being translated in the cell to produce the polypeptide.

In some embodiments, the disclosure provides a method of treating a disease or disorder in a mammal (e.g., a human) in need thereof. The method includes the step of administering to the mammal a therapeutically effective amount of a nanoparticle composition including (i) a lipid component including a phospholipid (such as a polyunsaturated lipid), a PEG lipid, a structural lipid, and a compound of Formula (I), (IA), (II), (IIa), (IIb), (IIe), (IId) or (IIe) and (ii) a therapeutic and/or prophylactic (e.g., an mRNA). In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disclosure provides a method of delivering (e.g., specifically delivering) a therapeutic and/or prophylactic to a mammalian organ (e.g., a liver, spleen, lung, or femur). This method includes the step of administering to a subject (e.g., a mammal) a nanoparticle composition including (i) a lipid component including a phospholipid, a PEG lipid, a structural lipid, and a compound of Formula (I), (IA), (II), (IIa), (IIb), (IIc), (IId) or (IIe) and (ii) a therapeutic and/or prophylactic (e.g., an mRNA), in which administering involves contacting the cell with the nanoparticle composition, whereby the therapeutic and/or prophylactic is delivered to the target organ (e.g., a liver, spleen, lung, or femur).

In some embodiments, the disclosure features a method for the enhanced delivery of a therapeutic and/or prophylactic (e.g., an mRNA) to a target tissue (e.g., a liver, spleen, lung, or femur). This method includes administering to a subject (e.g., a mammal) a nanoparticle composition, the composition including (i) a lipid component including a compound of Formula (I), (IA), (II), (IIa), (IIb), (IIc), (IId) or (IIe), a phospholipid, a structural lipid, and a PEG lipid; and (ii) a therapeutic and/or prophylactic, the administering including contacting the target tissue with the nanoparticle composition, whereby the therapeutic and/or prophylactic is delivered to the target tissue.

In some embodiments, the disclosure features a method of lowering immunogenicity comprising introducing the nanoparticle composition of the disclosure into cells, wherein the nanoparticle composition reduces the induction of the cellular immune response of the cells to the nanoparticle composition, as compared to the induction of the cellular immune response in cells induced by a reference composition which comprises a reference lipid instead of a compound of Formula (I), (IA), (II), (IIa), (IIb), (IIc), (IId) or (IIe). For example, the cellular immune response is an innate immune response, an adaptive immune response, or both.

The disclosure also includes methods of synthesizing a compound of Formula (I), (IA), (II), (IIa), (IIb), (IIc), (IId) or (IIe) and methods of making a nanoparticle composition including a lipid component comprising the compound of Formula (I), (IA), (II), (IIa), (IIb), (IIc), (IId) or (IIe).

Modes of Vaccine Administration

VZV RNA (e.g., mRNA) vaccines may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. VZV RNA (e.g., mRNA) vaccines compositions are typically formulated in dosage unit form for ease of administration and uniformity of dosage. It will be understood, however, that the total daily usage of VZV RNA (e.g., mRNA)vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, VZV RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013/078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, VZV RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, VZV RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, VZV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a VZV RNA (e.g., mRNA) vaccine composition may be administered three or four times.

In some embodiments, VZV RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the VZV RNA (e.g., mRNA) vaccine for use in a method of vaccinating a subject is administered the subject a single dosage of between 10 mg/kg and 400 μg/kg of the nucleic acid vaccine in an effective amount to vaccinate the subject. In some embodiments the RNA vaccine for use in a method of vaccinating a subject is administered the subject a single dosage of between 10 mg and 400 μg of the nucleic acid vaccine in an effective amount to vaccinate the subject. In some embodiments, a VZV RNA (e.g., mRNA) vaccine for use in a method of vaccinating a subject is administered to the subject as a single dosage of 25-1000 μg (e.g., a single dosage of mRNA encoding an VZV antigen). In some embodiments, a VZV RNA vaccine is administered to the subject as a single dosage of 25, 50, 100, 150, 200, 250, 300, 350, 400, 450, 500, 550, 600, 650, 700, 750, 800, 850, 900, 950 or 1000 μg. For example, a VZV RNA vaccine may be administered to a subject as a single dose of 25-100, 25-500, 50-100, 50-500, 50-1000, 100-500, 100-1000, 250-500, 250-1000, or 500-1000 μg. In some embodiments, a VZV RNA (e.g., mRNA) vaccine for use in a method of vaccinating a subject is administered to the subject as two dosages, the combination of which equals 25-1000 μg of the VZV RNA (e.g., mRNA) vaccine.

A VZV RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

VZV RNA Vaccine Formulations and Methods of Use

Some aspects of the present disclosure provide formulations of the VZV RNA (e.g., mRNA) vaccine, wherein the VZV RNA vaccine is formulated in an effective amount to produce an antigen specific immune response in a subject (e.g., production of antibodies specific to an anti-VZV antigenic polypeptide). "An effective amount" is a dose of an VZV RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-VZV antigenic polypeptide antibody titer produced in a subject administered a VZV RNA (e.g., mRNA) vaccine as provided herein. An antibody titer is a measurement of the amount of antibodies within a subject, for example, antibodies that are specific to a particular antigen (e.g., an anti-VZV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the VZV RNA (e.g., mRNA) vaccine.

In some embodiments, an anti-VZV antigenic polypeptide antibody titer produced in a subject is increased by at least 1 log relative to a control. For example, anti-VZV antigenic polypeptide antibody titer produced in a subject may be increased by at least 1.5, at least 2, at least 2.5, or at least 3 log relative to a control. In some embodiments, the anti-VZV antigenic polypeptide antibody titer produced in the subject is increased by 1, 1.5, 2, 2.5 or 3 log relative to a control. In some embodiments, the anti-VZV antigenic polypeptide antibody titer produced in the subject is increased by 1-3 log relative to a control. For example, the anti-VZV antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-VZV antigenic polypeptide antibody titer produced in a subject is increased at least 2 times relative to a control. For example, the anti-VZV antigenic polypeptide antibody titer produced in a subject may be increased at least 3 times, at least 4 times, at least 5 times, at least 6 times, at least 7 times, at least 8 times, at least 9 times, or at least 10 times relative to a control. In some embodiments, the anti-VZV antigenic polypeptide antibody titer produced in the subject is increased 2, 3, 4, 5, 6, 7, 8, 9, or 10 times relative to a control. In some embodiments, the anti-VZV antigenic polypeptide antibody titer produced in a subject is increased 2-10 times relative to a control. For example, the anti-VZV antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-VZV antigenic polypeptide antibody titer produced in a subject who has not been administered a VZV RNA (e.g., mRNA) vaccine. In some embodiments, a control is an anti-VZV antigenic polypeptide antibody titer produced in a subject who has been administered a live attenuated VZV vaccine. An attenuated vaccine is a vaccine produced by reducing the virulence of a viable (IIve). An attenuated virus is altered in a manner that renders it harmless or less virulent relative to live, unmodified virus. In some embodiments, a control is an anti-VZV antigenic polypeptide antibody titer produced in a subject administered inactivated VZV vaccine. In some embodiments, a control is an anti-VZV antigenic polypeptide antibody titer produced in a subject administered a recombinant or purified VZV protein vaccine. Recombinant protein vaccines typically include protein antigens that either have been produced in a heterologous expression system (e.g., bacteria or yeast) or purified from large amounts of the pathogenic organism. In some embodiments, a control is an anti-VZV antigenic polypeptide antibody titer produced in a subject who has been administered a VZV virus-like particle (VLP) vaccine (e.g., particles that contain viral capsid protein but lack a viral genome and, therefore, cannot replicate/produce progeny virus). In some embodiments, the control is a VLP VZV vaccine that comprises prefusion or postfusion F proteins, or that comprises a combination of the two.

In some embodiments, an effective amount of a VZV RNA (e.g., mRNA) vaccine is a dose that is reduced compared to the standard of care dose of a recombinant VZV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified VZV protein vaccine, or a live attenuated or inactivated VZV vaccine, or a VZV VLP vaccine, that a physician/clinician or other medical professional would administer to a subject to treat or prevent VZV, or a VZV-related condition, while following the standard of care guideline for treating or preventing VZV, or a VZV-related condition.

In some embodiments, the anti-VZV antigenic polypeptide antibody titer produced in a subject administered an effective amount of a VZV RNA vaccine is equivalent to an anti-VZV antigenic polypeptide antibody titer produced in a control subject administered a standard of care dose of a recombinant or purified VZV protein vaccine, or a live attenuated or inactivated VZV vaccine, or a VZV VLP vaccine.

In some embodiments, an effective amount of a VZV RNA (e.g., mRNA) vaccine is a dose equivalent to an at least 2-fold reduction in a standard of care dose of a recombinant or purified VZV protein vaccine. For example, an effective amount of a VZV RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified VZV protein vaccine. In some embodiments, an effective amount of a VZV RNA vaccine is a dose equivalent to an at least 100-fold, at least 500-fold, or at least 1000-fold reduction in a standard of care dose of a recombinant or purified VZV protein vaccine. In some embodiments, an effective amount of a VZV RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified VZV protein vaccine. In some embodiments, the anti-VZV antigenic polypeptide antibody titer produced in a subject administered an effective amount of a VZV RNA vaccine is equivalent to an anti-VZV antigenic polypeptide antibody titer produced in a control subject administered the standard of care dose of a recombinant or protein VZV protein vaccine, or a live attenuated or inactivated VZV vaccine, or a VZV VLP vaccine. In some embodiments, an effective amount of a VZV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified VZV protein vaccine, wherein the anti-VZV antigenic polypeptide antibody titer produced in the subject is equivalent to an anti-VZV antigenic polypeptide antibody titer produced in a control subject administered the standard of care dose of a recombinant or purified VZV protein vaccine, or a live attenuated or inactivated VZV vaccine, or a VZV VLP vaccine.

In some embodiments, the effective amount of a VZV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 300-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant VZV protein vaccine. In some embodiments, such as the foregoing, the anti-VZV antigenic polypeptide antibody titer produced in the subject is equivalent to an anti-VZV antigenic polypeptide antibody titer produced in a control subject administered the standard of care dose of a recombinant or purified VZV protein vaccine, or a live attenuated or inactivated VZV vaccine, or a VZV VLP vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant VZV protein vaccine. In some embodiments, such as the foregoing, an anti-VZV antigenic polypeptide antibody titer produced in the subject is equivalent to an anti-VZV antigenic polypeptide antibody titer produced in a control subject administered the standard of care dose of a recombinant or purified VZV protein vaccine, or a live attenuated or inactivated VZV vaccine, or a VZV VLP vaccine.

In some embodiments, the effective amount of a VZV RNA (e.g., mRNA) vaccine is a total dose of 50-1000 μg. In some embodiments, the effective amount of a VZV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of a VZV RNA (e.g., mRNA) vaccine is a total dose of 50, 100, 150, 200, 250, 300, 350, 400, 450, 500, 550, 600, 650, 700, 750, 800, 850, 900, 950 or 1000 pig. In some embodiments, the effective amount is a dose of 25-500 μg administered to the subject a total of two times. In some embodiments, the effective amount of a VZV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of a VZV RNA (e.g., mRNA) vaccine is a total dose of 25, 50, 100, 150, 200, 250, 300, 350, 400, 450, or 500 μg administered to the subject a total of two times.

Additional Embodiments

1. A varicella zoster virus (VZV) vaccine, comprising:
   at least one messenger ribonucleic acid (mRNA) polynucleotide having a 5' terminal cap, an open reading frame encoding at least one VZV antigenic polypeptide, and a 3' polyA tail.
2. The vaccine of paragraph 1, wherein the at least one mRNA polynucleotide is encoded by a sequence identified by SEQ ID NO: 11.
3. The vaccine of paragraph 1, wherein the at least one mRNA polynucleotide comprises a sequence identified by SEQ ID NO: 92.
4. The vaccine of paragraph 1, wherein the at least one antigenic polypeptide comprises a sequence identified by SEQ ID NO: 10.
5. The vaccine of paragraph 1, wherein the at least one mRNA polynucleotide is encoded by a sequence identified by SEQ ID NO: 15.
6. The vaccine of paragraph 1, wherein the at least one mRNA polynucleotide comprises a sequence identified by SEQ ID NO: 93.
7. The vaccine of paragraph 1, wherein the at least one antigenic polypeptide comprises a sequence identified by SEQ ID NO: 14.
8. The vaccine of paragraph 1, wherein the at least one mRNA polynucleotide is encoded by a sequence identified by SEQ ID NO: 19.
9. The vaccine of paragraph 1, wherein the at least one mRNA polynucleotide comprises a sequence identified by SEQ ID NO: 94.
10. The vaccine of paragraph 1, wherein the at least one antigenic polypeptide comprises a sequence identified by SEQ ID NO: 18.
11. The vaccine of paragraph 1, wherein the at least one mRNA polynucleotide is encoded by a sequence identified by SEQ ID NO: 23.
12. The vaccine of paragraph 1, wherein the at least one mRNA polynucleotide comprises a sequence identified by SEQ ID NO: 95.
13. The vaccine of paragraph 1, wherein the at least one antigenic polypeptide comprises a sequence identified by SEQ ID NO: 22.
14. The vaccine of paragraph 1, wherein the at least one mRNA polynucleotide is encoded by a sequence identified by SEQ ID NO: 27.
15. The vaccine of paragraph 1, wherein the at least one mRNA polynucleotide comprises a sequence identified by SEQ ID NO: 96.
16. The vaccine of paragraph 1, wherein the at least one antigenic polypeptide comprises a sequence identified by SEQ ID NO: 26.
17. The vaccine of paragraph 1, wherein the at least one mRNA polynucleotide is encoded by a sequence identified by SEQ ID NO: 31.

18. The vaccine of paragraph 1, wherein the at least one mRNA polynucleotide comprises a sequence identified by SEQ ID NO: 97.
19. The vaccine of paragraph 1, wherein the at least one antigenic polypeptide comprises a sequence identified by SEQ ID NO: 30.
20. The vaccine of paragraph 1, wherein the at least one mRNA polynucleotide is encoded by a sequence identified by SEQ ID NO: 35.
21. The vaccine of paragraph 1, wherein the at least one mRNA polynucleotide comprises a sequence identified by SEQ ID NO: 98.
22. The vaccine of paragraph 1, wherein the at least one antigenic polypeptide comprises a sequence identified by SEQ ID NO: 34.
23. The vaccine of paragraph 1, wherein the at least one mRNA polynucleotide is encoded by a sequence identified by SEQ ID NO: 39.
24. The vaccine of paragraph 1, wherein the at least one mRNA polynucleotide comprises a sequence identified by SEQ ID NO: 99.
25. The vaccine of paragraph 1, wherein the at least one antigenic polypeptide comprises a sequence identified by SEQ ID NO: 38.
26. The vaccine of paragraph 1, wherein the at least one mRNA polynucleotide is encoded by a sequence identified by SEQ ID NO: 62.
27. The vaccine of paragraph 1, wherein the at least one mRNA polynucleotide comprises a sequence identified by SEQ ID NO: 101.
28. The vaccine of paragraph 26 or 27, wherein the at least one antigenic polypeptide comprises a sequence identified by SEQ ID NO: 38.
29. The vaccine of paragraph 1, wherein the at least one mRNA polynucleotide is encoded by a sequence identified by SEQ ID NO: 66.
30. The vaccine of paragraph 1, wherein the at least one mRNA polynucleotide comprises a sequence identified by SEQ ID NO: 102.
31. The vaccine of paragraph 30 or 31, wherein the at least one antigenic polypeptide comprises a sequence identified by SEQ ID NO: 38.
32. The vaccine of paragraph 1, wherein the at least one mRNA polynucleotide is encoded by a sequence identified by SEQ ID NO: 70.
33. The vaccine of paragraph 1, wherein the at least one mRNA polynucleotide comprises a sequence identified by SEQ ID NO: 103.
34. The vaccine of paragraph 32 or 33, wherein the at least one antigenic polypeptide comprises a sequence identified by SEQ ID NO: 38.
35. The vaccine of paragraph 1, wherein the at least one mRNA polynucleotide is encoded by a sequence identified by SEQ ID NO: 74.
36. The vaccine of paragraph 1, wherein the at least one mRNA polynucleotide comprises a sequence identified by SEQ ID NO: 104.
37. The vaccine of paragraph 35 or 36, wherein the at least one antigenic polypeptide comprises a sequence identified by SEQ ID NO: 38.
38. The vaccine of paragraph 1, wherein the at least one mRNA polynucleotide is encoded by a sequence identified by SEQ ID NO: 78.
39. The vaccine of paragraph 1, wherein the at least one mRNA polynucleotide comprises a sequence identified by SEQ ID NO: 105.
40. The vaccine of paragraph 38 or 39, wherein the at least one antigenic polypeptide comprises a sequence identified by SEQ ID NO: 38.
41. The vaccine of paragraph 1, wherein the at least one mRNA polynucleotide is encoded by a sequence identified by SEQ ID NO: 82.
42. The vaccine of paragraph 1, wherein the at least one mRNA polynucleotide comprises a sequence identified by SEQ ID NO: 106.
43. The vaccine of paragraph 41 or 42, wherein the at least one antigenic polypeptide comprises a sequence identified by SEQ ID NO: 38.
44. The vaccine of paragraph 1, wherein the at least one mRNA polynucleotide is encoded by a sequence identified by SEQ ID NO: 86.
45. The vaccine of paragraph 1, wherein the at least one mRNA polynucleotide comprises a sequence identified by SEQ ID NO: 107, 134, or 148.
46. The vaccine of paragraph 44 or 45, wherein the at least one antigenic polypeptide comprises a sequence identified by SEQ ID NO: 38.
47. The vaccine of paragraph 1, wherein the at least one mRNA polynucleotide is encoded by a sequence identified by SEQ ID NO: 90.
48. The vaccine of paragraph 1, wherein the at least one mRNA polynucleotide comprises a sequence identified by SEQ ID NO: 108.
49. The vaccine of paragraph 47 or 48, wherein the at least one antigenic polypeptide comprises a sequence identified by SEQ ID NO: 38.
50. The vaccine of any one of paragraphs 1-49, wherein the 5' terminal cap is or comprises 7mG(5')ppp(5')N1mpNp.
51. The vaccine of any one of paragraphs 1-50, wherein 100% of the uracil in the open reading frame is modified to include N1-methyl pseudouridine at the 5-position of the uracil.
52. The vaccine of any one of paragraphs 1-51, wherein the vaccine is formulated in a lipid nanoparticle comprising: DLin-MC3-DMA; cholesterol; 1,2-Distearoyl-sn-glycero-3-phosphocholine (DSPC); and polyethylene glycol (PEG)2000-DMG.
53. The vaccine of paragraph 52, wherein the lipid nanoparticle further comprises trisodium citrate buffer, sucrose and water.
54. A varicella zoster virus (VZV) vaccine, comprising:
at least one messenger ribonucleic acid (mRNA) polynucleotide having a 5' terminal cap 7mG(5')ppp(5')N1mpNp, a sequence identified by SEQ ID NO: 92 and a 3' polyA tail, wherein the uracil nucleotides of the sequence identified by SEQ ID NO: 92 are modified to include N1-methyl pseudouridine at the 5-position of the uracil nucleotide.
55. A varicella zoster virus (VZV) vaccine, comprising:
at least one messenger ribonucleic acid (mRNA) polynucleotide having a 5' terminal cap 7mG(5')ppp(5')N1mpNp, a sequence identified by SEQ ID NO: 93 and a 3' polyA tail, wherein the uracil nucleotides of the sequence identified by SEQ ID NO: 93 are modified to include N1-methyl pseudouridine at the 5-position of the uracil nucleotide.
56. A varicella zoster virus (VZV) vaccine, comprising:
at least one messenger ribonucleic acid (mRNA) polynucleotide having a 5' terminal cap 7mG(5')ppp(5')N1mpNp, a sequence identified by SEQ ID NO: 94 and a 3' polyA tail, wherein the uracil nucleotides of the sequence identified by SEQ ID NO: 94 are modified to include N1-methyl pseudouridine at the 5-position of the uracil nucleotide.

57. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 95 and a 3' polyA tail, wherein the uracil nucleotides of the sequence identified by SEQ ID NO: 95 are modified to include N1-methyl pseudouridine at the 5-position of the uracil nucleotide.

58. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 96 and a 3' polyA tail, wherein the uracil nucleotides of the sequence identified by SEQ ID NO: 96 are modified to include N1-methyl pseudouridine at the 5-position of the uracil nucleotide.

59. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 97 and a 3' polyA tail, wherein the uracil nucleotides of the sequence identified by SEQ ID NO: 97 are modified to include N1-methyl pseudouridine at the 5-position of the uracil nucleotide.

60. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 98 and a 3' polyA tail, wherein the uracil nucleotides of the sequence identified by SEQ ID NO: 98 are modified to include N1-methyl pseudouridine at the 5-position of the uracil nucleotide.

61. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 99 and a 3' polyA tail, wherein the uracil nucleotides of the sequence identified by SEQ ID NO: 99 are modified to include N1-methyl pseudouridine at the 5-position of the uracil nucleotide.

62. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 101 and a 3' polyA tail, wherein the uracil nucleotides of the sequence identified by SEQ ID NO: 101 are modified to include N1-methyl pseudouridine at the 5-position of the uracil nucleotide.

63. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 102 and a 3' polyA tail, wherein the uracil nucleotides of the sequence identified by SEQ ID NO: 102 are modified to include N1-methyl pseudouridine at the 5-position of the uracil nucleotide.

64. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 103 and a 3' polyA tail, wherein the uracil nucleotides of the sequence identified by SEQ ID NO: 103 are modified to include N1-methyl pseudouridine at the 5-position of the uracil nucleotide.

65. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 104 and a 3' polyA tail, wherein the uracil nucleotides of the sequence identified by SEQ ID NO: 104 are modified to include N1-methyl pseudouridine at the 5-position of the uracil nucleotide.

66. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 105 and a 3' polyA tail, wherein the uracil nucleotides of the sequence identified by SEQ ID NO: 105 are modified to include N1-methyl pseudouridine at the 5-position of the uracil nucleotide.

67. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 106 and a 3' polyA tail, wherein the uracil nucleotides of the sequence identified by SEQ ID NO: 106 are modified to include N1-methyl pseudouridine at the 5-position of the uracil nucleotide.

68. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 107, 134, or 148 and a 3' polyA tail, wherein the uracil nucleotides of the sequence identified by SEQ ID NO: 107 or 134 are modified to include N1-methyl pseudouridine at the 5-position of the uracil nucleotide.

69. A varicella zoster virus (VZV) vaccine, comprising: at least one messenger ribonucleic acid (mRNA) polynucleotide having a 5' terminal cap 7mG(5')ppp(5')N1mpNp, a sequence identified by SEQ ID NO: 108 and a 3' polyA tail, wherein the uracil nucleotides of the sequence identified by SEQ ID NO: 108 are modified to include N1-methyl pseudouridine at the 5-position of the uracil nucleotide.

70. The vaccine of any one of claims 54-69, wherein the vaccine is formulated in a lipid nanoparticle comprising DLin-MC3-DMA, cholesterol, 1,2-Distearoyl-sn-glycero-3-phosphocholine (DSPC), and polyethylene glycol (PEG)2000-DMG.

71. The vaccine of any one of paragraphs 1-70 formulated in a lipid nanoparticle comprising at least one cationic lipid selected from compounds of Formula (I):

(I)

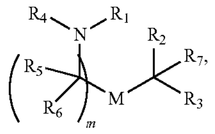

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —N(R)S$(O)_2R$, —N(R)C(O)$N(R)_2$, —N(R)C(S)$N(R)_2$, —N(R)$R_8$, —$O(CH_2)_nOR$, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)S$(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and —C(R)N$(R)_2$ C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

72. The vaccine of paragraph 71, wherein a subset of compounds of Formula (I) includes those in which when $R_4$ is —$(CH_2)_nQ$, —$(CH_2)_nCHQR$, —CHQR, or —CQ$(R)_2$, then (i) Q is not —$N(R)_2$ when n is 1, 2, 3, 4 or 5, or (ii) Q is not 5, 6, or 7-membered heterocycloalkyl when n is 1 or 2.

73. The vaccine of paragraph 71, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S$(O)_2R$, —N(R)C(O)$N(R)_2$, —N(R)C(S)$N(R)_2$, —CRN$(R)_2$C(O)OR, —N(R)$R_8$, —$O(CH_2)_nOR$, —N(R)C(=$NR_9$)$N(R)_2$, —N(R)C(=$CHR_9$)$N(R)_2$, —OC(O)N$(R)_2$, —N(R)C(O)OR, —N(OR)C(O)R, —N(OR)S$(O)_2$R, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_3$-6 carbocycle;

each X is independently selected from the group consisting of F, Cl, Br, and I; and m is selected from 5, 6, 7, 8, 9, 10, 11, 12, and 13, or salts or isomers thereof.

74. The vaccine of paragraph 71, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —CQ$(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —N(R)S$(O)_2R$, —N(R)C(O)$N(R)_2$, —N(R)C(S)$N(R)_2$, —CRN$(R)_2$C(O)OR, —N(R)$R_8$, —$O(CH_2)_nOR$, —N(R)C(=$NR_9$)$N(R)_2$, —N(R)C(=$CHR_9$)$N(R)_2$, —OC(O)N$(R)_2$, —N(R)C(O)OR, —N(OR)C(O)R, —N(OR)S$(O)_2$R, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —CQ$(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_1$-12 alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

75. The vaccine of paragraph 71, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_2$-14 alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_n$Q, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

76. The vaccine of paragraph 71, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_n$Q or —$(CH_2)_n$CHQR, where Q is —$N(R)_2$, and n is selected from 3, 4, and 5; each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

77. The vaccine of paragraph 71, wherein a subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_n$Q, —$(CH_2)_n$CHQR, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

78. The vaccine of paragraph 71, wherein a subset of compounds of Formula (I) includes those of Formula (IA):

(IA)

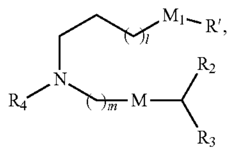

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N$(R)_2$, —NHC(O)N$(R)_2$, —N(R)C(O)R, —N(R)$S(O)_2$R, —N(R)$R_8$, —NHC(=N$R_9$)N$(R)_2$, —NHC(=CH$R_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Broad Spectrum VZV Vaccines

It is envisioned that there may be situations where persons are at risk for infection with more than one strain of VZV. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one strain of VZV, a combination vaccine can be administered that includes RNA encoding at least one antigenic polypeptide protein (or antigenic portion thereof) of a first VZV and further includes RNA encoding at least one antigenic polypeptide protein (or antigenic portion thereof) of a second VZV. RNAs (mRNAs) can be co-formulated, for example, in a single lipid nanoparticle (LNP) or can be formulated in separate LNPs destined for co-administration.

Multiprotein and Multicomponent Vaccines

The present disclosure encompasses VZV vaccines comprising multiple RNA (e.g., mRNA) polynucleotides, each encoding a single antigenic polypeptide, as well as VZV vaccines comprising a single RNA polynucleotide encoding more than one antigenic polypeptide (e.g., as a fusion polypeptide). Thus, it should be understood that a vaccine composition comprising a RNA (e.g., mRNA) polynucleotide having an open reading frame encoding a first VZV antigenic polypeptide and a RNA polynucleotide (e.g., mRNA) having an open reading frame encoding a second VZV antigenic polypeptide encompasses (a) vaccines that comprise a first RNA polynucleotide encoding a first VZV antigenic polypeptide and a second RNA polynucleotide encoding a second VZV antigenic polypeptide, and (b) vaccines that comprise a single RNA polynucleotide encoding a first and second VZV antigenic polypeptide (e.g., as a fusion polypeptide). VZV RNA vaccines of the present disclosure, in some embodiments, comprise 2-10 (e.g., 2, 3, 4, 5, 6, 7, 8, 9 or 10), or more, RNA polynucleotides having an open reading frame, each of which encodes a different VZV antigenic polypeptide (or a single RNA polynucleotide encoding 2-10, or more, different VZV antigenic polypeptides). In some embodiments, a VZV RNA vaccine comprises a RNA polynucleotide having an open reading frame encoding a VZV gE protein, a RNA polynucleotide having an open reading frame encoding a VZV gI protein, a RNA polynucleotide having an open reading frame encoding a VZV gB protein, a RNA polynucleotide having an open reading frame encoding a VZV gH protein, a RNA polynucleotide having an open reading frame encoding a VZV gK protein, a RNA polynucleotide having an open reading frame encoding a VZV gL protein, a RNA polynucleotide having an open reading frame encoding a VZV gC protein, a RNA polynucleotide having an open reading frame encoding a VZV gN protein, and a RNA polynucleotide having an open reading frame encoding a VZV gM protein. In some embodiments, a VZV RNA vaccine comprises a RNA polynucleotide having an open reading frame encoding a VZV gE and a RNA polynucleotide having an open reading frame encoding a VZV gI protein. In some embodiments, a VZV RNA vaccine comprises a RNA polynucleotide having an open reading frame encoding a VZV gE protein or a gE variant.

In some embodiments, a RNA polynucleotide encodes a VZV antigenic polypeptide fused to a signal peptide (e.g., SEQ ID NO: 56, 57, 109, 110, or 111). The signal peptide may be fused at the N-terminus or the C-terminus of the antigenic polypeptide.

EXAMPLES

Example 1: Manufacture of Polynucleotides

According to the present disclosure, the manufacture of polynucleotides and/or parts or regions thereof may be accomplished utilizing the methods taught in International Publication WO2014/152027, entitled "Manufacturing Methods for Production of RNA Transcripts," the contents of which is incorporated herein by reference in its entirety.

Purification methods may include those taught in International Publication WO2014/152030 and International Publication WO2014/152031, each of which is incorporated herein by reference in its entirety.

Detection and characterization methods of the polynucleotides may be performed as taught in International Publication WO2014/144039, which is incorporated herein by reference in its entirety.

Characterization of the polynucleotides of the disclosure may be accomplished using polynucleotide mapping, reverse transcriptase sequencing, charge distribution analysis, detection of RNA impurities, or any combination of two or more of the foregoing. "Characterizing" comprises determining the RNA transcript sequence, determining the purity of the RNA transcript, or determining the charge heterogeneity of the RNA transcript, for example. Such methods are taught in, for example, International Publication WO2014/144711 and International Publication WO2014/144767, the content of each of which is incorporated herein by reference in its entirety.

Example 2: Chimeric Polynucleotide Synthesis

According to the present disclosure, two regions or parts of a chimeric polynucleotide may be joined or ligated using triphosphate chemistry. A first region or part of 100 nucleotides or less is chemically synthesized with a 5' monophosphate and terminal 3'desOH or blocked OH, for example. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

For ligation methods, ligation with DNA T4 ligase, followed by treatment with DNase should readily avoid concatenation.

The entire chimeric polynucleotide need not be manufactured with a phosphate-sugar backbone. If one of the regions or parts encodes a polypeptide, then such region or part may comprise a phosphate-sugar backbone.

Ligation is then performed using any known click chemistry, orthoclick chemistry, solulink, or other bioconjugate chemistries known to those in the art.

Synthetic Route

The chimeric polynucleotide may be made using a series of starting segments. Such segments include:

(a) a capped and protected 5' segment comprising a normal 3'OH (SEG. 1)

(b) a 5' triphosphate segment, which may include the coding region of a polypeptide and a normal 3'OH (SEG. 2)

(c) a 5' monophosphate segment for the 3' end of the chimeric polynucleotide (e.g., the tail) comprising cordycepin or no 3'OH (SEG. 3)

After synthesis (chemical or IVT), segment 3 (SEG. 3) may be treated with cordycepin and then with pyrophosphatase to create the 5' monophosphate.

Segment 2 (SEG. 2) may then be ligated to SEG. 3 using RNA ligase. The ligated polynucleotide is then purified and treated with pyrophosphatase to cleave the diphosphate. The treated SEG. 2-SEG. 3 construct may then be purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA may be performed using 2×KAPA HIFI™ HotStart ReadyMix by Kapa Biosystems (Woburn, Mass.). This system includes 2×KAPA ReadyMix 12.5 μl; Forward Primer (10 μM) 0.75 μl; Reverse Primer (10 μM) 0.75 μl; Template cDNA 100 ng; and $dH_2O$ diluted to 25.0 μl. The reaction conditions may be at 95° C. for 5 min. The reaction may be performed for 25 cycles of 98° C. for 20 sec, then 58° C. for 15 sec, then 72° C. for 45 sec, then 72° C. for 5 min, then 4° C. to termination.

The reaction may be cleaned up using Invitrogen's PURELINK™ PCR Micro Kit (Carlsbad, Calif.) per manufacturer's instructions (up to 5 μg). Larger reactions may require a cleanup using a product with a larger capacity. Following the cleanup, the cDNA may be quantified using the NANODROP™ and analyzed by agarose gel electrophoresis to confirm that the cDNA is the expected size. The cDNA may then be submitted for sequencing analysis before proceeding to the in vitro transcription reaction.

Example 4: In Vitro Transcription (IVT)

The in vitro transcription reaction generates RNA polynucleotides. Such polynucleotides may comprise a region or part of the polynucleotides of the disclosure, including chemically modified RNA (e.g., mRNA) polynucleotides. The chemically modified RNA polynucleotides can be uniformly modified polynucleotides. The in vitro transcription reaction utilizes a custom mix of nucleotide triphosphates (NTPs). The NTPs may comprise chemically modified NTPs, or a mix of natural and chemically modified NTPs, or natural NTPs.

A typical in vitro transcription reaction includes the following:

| | | |
|---|---|---|
| 1) | Template cDNA | 1.0 μg |
| 2) | 10x transcription buffer (400 mM Tris-HCl pH 8.0, 190 mM $MgCl_2$, 50 mM DTT, 10 mM Spermidine) | 2.0 μl |
| 3) | Custom NTPs (25 mM each) | 0.2 μl |
| 4) | RNase Inhibitor | 20 U |
| 5) | T7 RNA polymerase | 3000 U |
| 6) | $dH_20$ | up to 20.0 μl. and |
| 7) | Incubation at 37° C. for 3 hr-5 hrs. | |

The crude IVT mix may be stored at 4° C. overnight for cleanup the next day. 1 U of RNase-free DNase may then be used to digest the original template. After 15 minutes of incubation at 37° C., the mRNA may be purified using Ambion's MEGACLEAR™ Kit (Austin, Tex.) following the manufacturer's instructions. This kit can purify up to 500 μg of RNA.

Following the cleanup, the RNA polynucleotide may be quantified using the NANODROP™ and analyzed by agarose gel electrophoresis to confirm the RNA polynucleotide is the proper size and that no degradation of the RNA has occurred.

Example 5: Enzymatic Capping

Capping of a RNA polynucleotide is performed as follows where the mixture includes: IVT RNA 60 μg-180 μg and $dH_2O$ up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The RNA polynucleotide may then be purified using Ambion's MEGACLEAR™ Kit (Austin, Tex.) following the manufacturer's instructions. Following the cleanup, the RNA may be quantified using the NANODROP™ (ThermoFisher, Waltham, Mass.) and analyzed by agarose gel electrophoresis to confirm the RNA polynucleotide is the proper size and that no degradation of the RNA has occurred. The RNA polynucleotide product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing capped IVT RNA (100 μl); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 μg). Poly-A Polymerase may be a recombinant enzyme expressed in yeast.

It should be understood that the processivity or integrity of the polyA tailing reaction may not always result in an exact size polyA tail. Hence, polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the present disclosure.

Example 7: Capping Assays

Protein Expression Assay

Polynucleotides (e.g., mRNA) encoding a polypeptide, containing any of the caps taught herein, can be transfected into cells at equal concentrations. The amount of protein secreted into the culture medium can be assayed by ELISA at 6, 12, 24 and/or 36 hours post-transfection. Synthetic polynucleotides that secrete higher levels of protein into the medium correspond to a synthetic polynucleotide with a higher translationally-competent cap structure.

Purity Analysis Synthesis

RNA (e.g., mRNA) polynucleotides encoding a polypeptide, containing any of the caps taught herein can be compared for purity using denaturing Agarose-Urea gel electrophoresis or HPLC analysis. RNA polynucleotides with a single, consolidated band by electrophoresis correspond to the higher purity product compared to polynucleotides with multiple bands or streaking bands. Chemically modified RNA polynucleotides with a single HPLC peak also correspond to a higher purity product. The capping reaction with a higher efficiency provides a more pure polynucleotide population.

Cytokine Analysis

RNA (e.g., mRNA) polynucleotides encoding a polypeptide, containing any of the caps taught herein can be transfected into cells at multiple concentrations. The amount of pro-inflammatory cytokines, such as TNF-alpha and IFN-beta, secreted into the culture medium can be assayed by ELISA at 6, 12, 24 and/or 36 hours post-transfection. RNA polynucleotides resulting in the secretion of higher levels of pro-inflammatory cytokines into the medium correspond to a polynucleotides containing an immune-activating cap structure.

Capping Reaction Efficiency

RNA (e.g., mRNA) polynucleotides encoding a polypeptide, containing any of the caps taught herein can be analyzed for capping reaction efficiency by LC-MS after nuclease treatment. Nuclease treatment of capped polynucleotides yield a mixture of free nucleotides and the capped 5'-5-triphosphate cap structure detectable by LC-MS. The amount of capped product on the LC-MS spectra can be expressed as a percent of total polynucleotide from the reaction and correspond to capping reaction efficiency. The cap structure with a higher capping reaction efficiency has a higher amount of capped product by LC-MS.

Example 8: Agarose Gel Electrophoresis of Modified RNA or RT PCR Products

Individual RNA polynucleotides (200-400 ng in a 20 μl volume) or reverse transcribed PCR products (200-400 ng) may be loaded into a well on a non-denaturing 1.2% Agarose E-Gel (Invitrogen, Carlsbad, Calif.) and run for 12-15 minutes, according to the manufacturer protocol.

Example 9: NANODROP™ Modified RNA Quantification and UV Spectral Data

Chemically modified RNA polynucleotides in TE buffer (1 μl) are used for NANODROP™ UV absorbance readings to quantitate the yield of each polynucleotide from an chemical synthesis or in vitro transcription reaction.

Example 10: Formulation of Modified mRNA Using Lipidoids

RNA (e.g., mRNA) polynucleotides may be formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may be used as a starting point. After formation of the particle, polynucleotide is added and allowed to integrate with the complex. The encapsulation efficiency is determined using a standard dye exclusion assays.

Example 11: Exemplary Nucleic Acid Encoding gE RNA Polynucleotide for Use in a VZV Vaccine The following sequence is an exemplary sequence that can be used to encode a VZV RNA polynucleotide gE for use in a VZV vaccine. A VZV vaccine may comprise, for example, at least one RNA polynucleotide encoded by at least one of the following sequence or by at least one fragment of the following sequence. In some embodiments, the mRNA further comprises a 5' cap, for example, any of the caps disclosed herein, e.g., a cap having sequence m7G(5')ppp(5')G-2'-O-methyl. In some embodiments, the mRNA does not have a cap sequence. In some embodiments, the mRNA has at least one chemical modification, for example, any of the chemical modifications disclosed herein, e.g., N1-methylpseudouridine modification or N1-ethylpseudouridine modification. In other embodiments, the mRNA does not have chemical modification.

Each of the sequences described herein encompasses a chemically modified sequence or an unmodified sequence which includes no modified nucleotides.

VZV gE-full-length Oka strain:

(SEQ ID NO: 1)

TCAAGCTTTTGGACCCTCGTACAGAAGCTAATACGACTCACTATAGGGAAATAAGAGAGAAAAGA

AGAGTAAGAAGAAATATAAGAGCCACCATGGGGACAGTGAATAAGCCGGTTGTGGGCGTGCTTAT

GGGCTTTGGGATTATTACCGGTACATTACGAATTACCAATCCAGTGCGCGCCAGTGTGCTGCGTTA

CGACGACTTTCACATTGACGAGGATAAGCTGGATACTAACAGCGTGTACGAACCTTATTACCACTC

AGATCATGCCGAATCAAGCTGGGTTAATAGAGGAGAAAGCAGCCGAAAAGCCTACGACCACAACT

CACCTTATATTTGGCCCAGAAACGATTATGACGGTTTCCTGGAAAACGCACATGAACACCATGGAG

TCTACAACCAAGGCAGGGGAATCGACAGTGGCGAGCGTCTTATGCAGCCAACACAGATGTCGGCA

CAGGAGGATCTCGGTGATGACACCGGCATACACGTGATTCCCACATTAAACGGCGACGACAGACA

TAAGATCGTCAATGTGGATCAGCGTCAGTATGGGGATGTCTTTAAAGGCGATTTGAATCCAAAGCC

CCAAGGACAGAGACTGATCGAGGTCTCTGTAGAAGAAAATCACCCCTTCACTTTGCGCGCTCCAAT

CCAGAGGATTTACGGGGTGCGTTATACCGAAACTTGGAGTTTCTTGCCGTCACTGACGTGTACGGG

GGATGCCGCCCCCGCAATCCAGCACATCTGTCTGAAACACACCACATGCTTTCAGGACGTGGTTGT

GGATGTGGATTGCGCGGAAAACACAAAAGAAGACCAACTCGCCGAAATCAGCTATCGTTTTCAGG

GTAAAAAAGAGGCCGACCAACCGTGGATTGTTGTGAATACGAGCACGCTCTTCGATGAGCTTGAA

CTCGATCCCCCCGGAAATCGAGCCTGGGGTTCTAAAAGTGTTGAGGACCGAGAAGCAGTACCTCGG

GGTTTATATCTGGAATATGAGAGGCTCCGATGGCACCTCTACCTACGCAACGTTTCTGGTTACCTG

GAAGGGAGACGAGAAGACACGGAATCCAACGCCCGCTGTGACCCCTCAGCCTAGGGGAGCCGAA

TTCCACATGTGGAACTATCACTCCCATGTATTCAGTGTGGGTGACACTTTCAGCCTGGCCATGCAC

CTGCAGTATAAGATTCACGAGGCACCCTTCGACCTCCTGCTGGAGTGGTTGTACGTACCTATTGAT

CCCACTTGTCAGCCCATGCGCCTGTACTCCACTTGCTTGTACCACCCCAATGCACCACAGTGTCTAT

CACACATGAACTCCGGGTGTACCTTTACTTCACCCCATCTTGCCCAGCGGGTCGCCAGCACAGTGT

ATCAGAACTGTGAGCATGCTGACAACTATACTGCTTATTGCCTCGGAATATCCCATATGGAGCCAA

GCTTCGGGCTCATACTGCACGATGGTGGTACGACACTCAAGTTCGTGGACACCCCCGAAAGCCTTT

CTGGCTTGTACGTGTTCGTGGTCTACTTCAATGGACATGTGGAGGCAGTGGCTTACACAGTGGTTT

CGACAGTTGATCACTTTGTAAATGCCATTGAGGAACGCGGCTTCCCGCCTACAGCGGGCCAGCCCC

CTGCGACAACAAAACCAAAAGAGATTACGCCCGTTAATCCTGGGACTAGTCCATTGCTGAGGTAT

GCCGCCTGGACTGGCGGTCTGGCGGCCGTGGTACTTCTGTGTTTAGTCATATTTCTGATCTGTACCG

CTAAACGTATGCGGGTCAAGGCTTACCGTGTTGACAAGTCTCCTTACAATCAGTCAATGTACTATG

CAGGACTCCCTGTTGACGATTTCGAAGACTCAGAGAGTACAGACACAGAAGAAGAATTCGGAAAC

GCTATAGGTGGCTCTCACGGAGGTAGCTCGTATACAGTGTACATCGATAAAACCAGATGATAATA

GGCTGGAGCCTCGGTGGCCATGCTTCTTGCCCCTTGGGCCTCCCCCCAGCCCCTCCTCCCCTTCCTG

CACCCGTACCCCCGTGGTCTTTGAATAAAGTCTGAGTGGGCGGC

VZV gE-full-length Oka strain (mRNA):

(SEQ ID NO: 123)

UCAAGCUUUUGGACCCUCGUACAGAAGCUAAUACGACUCACUAUAGGGAAAUAAGAGAGAAAA

-continued

GAAGAGUAAGAAGAAAUAUAAGAGCCACCAUGGGGACAGUGAAUAAGCCGGUUGUGGGCGUGC

UUAUGGGCUUUGGGAUUAUUACCGGUACAUUACGAAUUACCAAUCCAGUGCGCGCCAGUGUGC

UGCGUUACGACGACUUUCACAUUGACGAGGAUAAGCUGGAUACUAACAGCGUGUACGAACCUU

AUUACCACUCAGAUCAUGCCGAAUCAAGCUGGGUUAAUAGAGGAGAAAGCAGCCGAAAAGCCU

ACGACCACAACUCACCUUAUAUUUGGCCCAGAAACGAUUAUGACGGUUUCCUGGAAAACGCAC

AUGAACACCAUGGAGUCUACAACCAAGGCAGGGGAAUCGACAGUGGCGAGCGUCUUAUGCAGC

CAACACAGAUGUCGGCACAGGAGGAUCUCGGUGAUGACACCGGCAUACACGUGAUUCCCACAU

UAAACGGCGACGACAGACAUAAGAUCGUCAAUGUGGAUCAGCGUCAGUAUGGGGAUGUCUUUA

AAGGCGAUUUGAAUCCAAAGCCCCAAGGACAGAGACUGAUCGAGGUCUCUGUAGAAGAAAAUC

ACCCCUUCACUUUGCGCGCUCCAAUCCAGAGGAUUUACGGGGUGCGUUAUACCGAAACUUGGA

GUUUCUUGCCGUCACUGACGUGUACGGGGGAUGCCGCCCCCGCAAUCCAGCACAUCUGUCUGAA

ACACACCACAUGCUUUCAGGACGUGGUUGUGGAUGUGGAUUGCGCGGAAAACACAAAAGAAGA

CCAACUCGCCGAAAUCAGCUAUCGUUUUCAGGGUAAAAAAGAGGCCGACCAACCGUGGAUUGU

UGUGAAUACGAGCACGCUCUUCGAUGAGCUUGAACUCGAUCCCCCGGAAAUCGAGCCUGGGGU

UCUAAAAGUGUUGAGGACCGAGAAGCAGUACCUCGGGGUUUAUAUCUGGAAUAUGAGAGGCUC

CGAUGGCACCUCUACCUACGCAACGUUUCUGGUUACCUGGAAGGGAGACGAGAAGACACGGAA

UCCAACGCCCGCUGUGACCCCUCAGCCUAGGGGAGCCGAAUUCCACAUGUGGAACUAUCACUCC

CAUGUAUUCAGUGUGGGUGACACUUUCAGCCUGGCCAUGCACCUGCAGUAUAAGAUUCACGAG

GCACCCUUCGACCUCCUGCUGGAGUGGUUGUACGUACCUAUUGAUCCCACUUGUCAGCCCAUGC

GCCUGUACUCCACUUGCUUGUACCACCCCAAUGCACCACAGUGUCUAUCACACAUGAACUCCGG

GUGUACCUUUACUUCACCCCAUCUUGCCCAGCGGGUCGCCAGCACAGUGUAUCAGAACUGUGAG

CAUGCUGACAACUAUACUGCUUAUUGCCUCGGAAUAUCCCAUAUGGAGCCAAGCUUCGGGCUC

AUACUGCACGAUGGUGGUACGACACUCAAGUUCGUGGACACCCCCGAAAGCCUUUCUGGCUUG

UACGUGUUCGUGGUCUACUUCAAUGGACAUGUGGAGGCAGUGGCUUACACAGUGGUUUCGACA

GUUGAUCACUUUGUAAAUGCCAUUGAGGAACGCGGCUUCCCGCCUACAGCGGGCCAGCCCCCUG

CGACAACAAAACCAAAAGAGAUUACGCCCGUUAAUCCUGGGACUAGUCCAUUGCUGAGGUAUG

CCGCCUGGACUGGCGGUCUGGCGGCCGUGGUACUUCUGUGUUUAGUCAUAUUUCUGAUCUGUA

CCGCUAAACGUAUGCGGGUCAAGGCUUACCGUGUUGACAAGUCUCCUUACAAUCAGUCAAUGU

ACUAUGCAGGACUCCCUGUUGACGAUUUCGAAGACUCAGAGAGUACAGACACAGAAGAAGAAU

UCGGAAACGCUAUAGGUGGCUCUCACGGAGGUAGCUCGUAUACAGUGUACAUCGAUAAAACCA

GAUGAUAAUAGGCUGGAGCCUCGGUGGCCAUGCUUCUUGCCCCUUGGGCCUCCCCCCAGCCCCU

CCUCCCCUUCCUGCACCCGUACCCCCGUGGUCUUUGAAUAAAGUCUGAGUGGGCGGC

Example 12: Exemplary Nucleic Acid Encoding gI RNA Polynucleotide for Use in a VZV Vaccine The following sequence is an exemplary sequence that can be used to encode a VZV RNA polynucleotide gI for use in a VZV RNA (e.g., mRNA) vaccine. The gI polypeptide forms a complex with gE in infected cells which facilitates the endocytosis of both glycoproteins and directs them to the trans-Golgi network (TGN) where the final viral envelope is acquired. A VZV vaccine may comprise, for example, at least one RNA (e.g., mRNA) polynucleotide encoded by at least one of the following sequence or by at least one fragment of the following sequence. In some embodiments, the mRNA further comprises a 5' cap, for example, any of the caps disclosed herein, e.g., a cap having sequence m7G(5')ppp(5')G-2'-O-methyl. In other embodiments, the mRNA does not have a cap sequence. In some embodiments, the mRNA has at least one chemical modification, for example, any of the chemical modifications disclosed herein, e.g., N1-methylpseudouridine modification or N1-ethylpseudouridine modification. In other embodiments, the mRNA does not have chemical modification.

VZV-GI-full length (Oka strain):

(SEQ ID NO: 2)

TCAAGCTTTTGGACCCTCGTACAGAAGCTAATACGACTCACTATAGGGAAATAAGAGAGAAAAGA

AGAGTAAGAAGAAATATAAGAGCCACCATGTTTTTAATCCAATGTTTGATATCGGCCGTTATATTT

TACATACAAGTGACCAACGCTTTGATCTTCAAGGGCGACCACGTGAGCTTGCAAGTTAACAGCAGT

CTCACGTCTATCCTTATTCCCATGCAAAATGATAATTATACAGAGATAAAAGGACAGCTTGTCTTT

ATTGGAGAGCAACTACCTACCGGGACAAACTATAGCGGAACACTGGAACTGTTATACGCGGATAC

GGTGGCGTTTTGTTTCCGGTCAGTACAAGTAATAAGATACGACGGATGTCCCCGGATTAGAACGAG

CGCTTTTATTTCGTGTAGGTACAAACATTCGTGGCATTATGGTAACTCAACGGATCGGATATCAAC

AGAGCCGGATGCTGGTGTAATGTTGAAAATTACCAAACCGGGAATAAATGATGCTGGTGTGTATG

TACTTCTTGTTCGGTTAGACCATAGCAGATCCACCGATGGTTTCATTCTTGGTGTAAATGTATATAC

AGCGGGCTCGCATCACAACATTCACGGGGTTATCTACACTTCTCCATCTCTACAGAATGGATATTC

TACAAGAGCCCTTTTTCAACAAGCTCGTTTGTGTGATTTACCCGCGACACCCAAAGGGTCCGGTAC

CTCCCTGTTTCAACATATGCTTGATCTTCGTGCCGGTAAATCGTTAGAGGATAACCCTTGGTTACAT

GAGGACGTTGTTACGACAGAAACTAAGTCCGTTGTTAAGGAGGGGATAGAAAATCACGTATATCC

AACGGATATGTCCACGTTACCCGAAAAGTCCCTTAATGATCCTCCAGAAAATCTACTTATAATTAT

TCCTATAGTAGCGTCTGTCATGATCCTCACCGCCATGGTTATTGTTATTGTAATAAGCGTTAAGCGA

CGTAGAATTAAAAAACATCCAATTTATCGCCCAAATACAAAAACAAGAAGGGGCATACAAAATGC

GACACCAGAATCCGATGTGATGTTGGAGGCCGCCATTGCACAACTAGCAACGATTCGCGAAGAAT

CCCCCCCACATTCCGTTGTAAACCCGTTTGTTAAATAGTGATAATAGGCTGGAGCCTCGGTGGCCA

TGCTTCTTGCCCCTTGGGCCTCCCCCCAGCCCCTCCTCCCCTTCCTGCACCCGTACCCCCGTGGTCTT

TGAATAAAGTCTGAGTGGGCGGC

VZV-GI-full length (Oka strain)(mRNA):

(SEQ ID NO: 124)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGUUUUUAAUCCAAUGUUUGAUAUCGGCCGUUA

UAUUUUACAUACAAGUGACCAACGCUUUGAUCUUCAAGGGCGACCACGUGAGCUUGCAAGUUA

ACAGCAGUCUCACGUCUAUCCUUAUUCCCAUGCAAAAUGAUAAUUAUACAGAGAUAAAAGGAC

AGCUUGUCUUUAUUGGAGAGCAACUACCUACCGGGACAAACUAUAGCGGAACACUGGAACUGU

UAUACGCGGAUACGGUGGCGUUUUGUUUCCGGUCAGUACAAGUAAUAAGAUACGACGGAUGUC

CCCGGAUUAGAACGAGCGCUUUUAUUUCGUGUAGGUACAAACAUUCGUGGCAUUAUGGUAACU

CAACGGAUCGGAUAUCAACAGAGCCGGAUGCUGGUGUAAUGUUGAAAAUUACCAAACCGGGAA

UAAAUGAUGCUGGUGUGUAUGUACUUCUUGUUCGGUUAGACCAUAGCAGAUCCACCGAUGGUU

UCAUUCUUGGUGUAAAUGUAUAUACAGCGGGCUCGCAUCACAACAUUCACGGGGUUAUCUACA

CUUCUCCAUCUCUACAGAAUGGAUAUUCUACAAGAGCCCUUUUUCAACAAGCUCGUUUGUGUG

-continued

```
AUUUACCCGCGACACCCAAAGGGUCCGGUACCUCCCUGUUUCAACAUAUGCUUGAUCUUCGUGC

CGGUAAAUCGUUAGAGGAUAACCCUUGGUUACAUGAGGACGUUGUUACGACAGAAACUAAGUC

CGUUGUUAAGGAGGGGAUAGAAAAUCACGUAUAUCCAACGGAUAUGUCCACGUUACCCGAAAA

GUCCCUUAAUGAUCCUCCAGAAAAUCUACUUAUAAUUAUUCCUAUAGUAGCGUCUGUCAUGAU

CCUCACCGCCAUGGUUAUUGUUAUUGUAAUAAGCGUUAAGCGACGUAGAAUUAAAAAACAUCC

AAUUUAUCGCCCAAAUACAAAAACAAGAAGGGGCAUACAAAAUGCGACACCAGAAUCCGAUGU

GAUGUUGGAGGCCGCCAUUGCACAACUAGCAACGAUUCGCGAAGAAUCCCCCCCACAUUCCGUU

GUAAACCCGUUUGUUAAAUAGUGAUAAUAGGCUGGAGCCUCGGUGGCCAUGCUUCUUGCCCCU

UGGGCCUCCCCCCAGCCCCUCCUCCCCUUCCUGCACCCGUACCCCCGUGGUCUUUGAAUAAAGU

CUGAGUGGGCGGC
```

Figure 4:
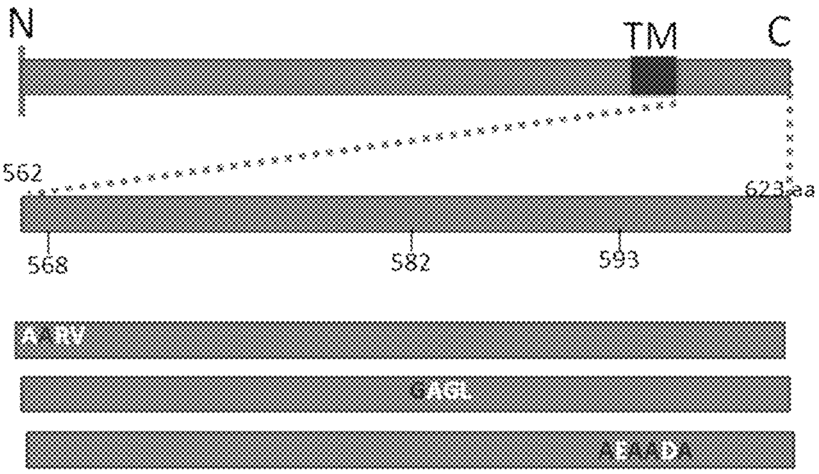
FIG. 4 is a schematic showing various variant VZV gE antigens. This figure depicts SEQ ID NOs: 120, 132, and 58 from top to bottom, respectively.

Example 13: mRNAs Encoding Variant gE Antigens Having Different C-Terminal Sequence for Use in a VZV Vaccine VZV is enveloped in the trans-golgi network. Glycoprotein I (gI) forms a complex with gE in infected cells which facilitates the endocytosis of both glycoproteins and directs them to the trans-Golgi network (TGN) where the final viral envelope is acquired. mRNAs encoding gE antigens having different C-terminal variant sequence were designed to avoid gE being trapped in the ER/golgi/TGN, leading to an increase in the localization of gE antigen to the plasma membrane and improved immune-stimulating capabilities. A schematic of the gE antigen is shown in FIG. 4.

Several different gE variant mRNA sequences (Oka strain) were engineered:

(1) gE variant mRNA encoding a truncated polypeptide having the terminal 62 amino acids of the C terminal region deleted (SEQ ID NO: 17-20). The resultant polypeptide has reduced localization to the trans-golgi network and reduced endocytosis.

(2) gE variant mRNA encoding a truncated polypeptide having the terminal 62 amino acids of the C terminal region deleted and also having the signal peptide replaced with IgKappa, which results in a secreted form of the truncated gE polypeptide (SEQ ID NO: 21-24). The resultant polypeptide has reduced localization to the trans-golgi network and reduced endocytosis.

(3) gE variant mRNA encoding a truncated polypeptide having the terminal 50 amino acids of the C terminal region deleted (SEQ ID NO: 33-36). The resultant polypeptide has reduced localization to the trans-golgi network and reduced endocytosis.

(4) gE variant mRNA encoding a truncated polypeptide having the terminal 50 amino acids of the C terminal region deleted and also having the point mutation Y569A (SEQ ID NO: 37-40). The "AYRV" motif (SEQ ID NO: 119) is a trafficking motif which targets the gE polypeptide to the trans-golgi network. Thus, mutating the AARV sequence SEQ ID NO: 120 to AYRV SEQ ID NO: 119 results in reduced localization of the gE polypeptide to the trans-golgi network.

(5) gE variant mRNA encoding full-length gE polypeptide with an AEAADA (SEQ ID NO: 58) sequence (SEQ ID NO: 25-28). The A-E-A-A-D-A (SEQ ID NO: 58) sequence replaces SESTDT (SEQ ID NO: 59). This is a replacement of the Ser/Thr-rich "SSTT" (SEQ ID NO: 122) acidic cluster with an Ala-rich sequence. This reduces CKII phosphorylation, which in turn results in reduced localization of the gE polypeptide to the trans-golgi network.

(6) gE variant mRNA encoding full-length gE polypeptide with an AEAADA (SEQ ID NO: 58) sequence and also having the point mutation Y582G (SEQ ID NO: 29-32). The "YAGL" (SEQ ID NO: 121) motif is an endocytosis motif which enhances localization of the gE polypeptide to the trans-golgi network. Thus, mutating the GAGL sequence (SEQ ID NO: 132) to YAGL (SEQ ID NO: 121) results in reduced endocytosis of the resultant polypeptide.

Each of these variants have modifications that reduce localization of the encoded gE protein to the trans-golgi network and enhance trafficking to the plasma membrane. Table 1 summarizes mRNAs encoding the variant gE antigens having different C-terminal sequence. In some embodiments, the variant mRNA further comprises a 5' cap, for example, any of the caps disclosed herein, e.g., a cap having sequence m7G(5')ppp(5')G-2'-O-methyl. In some embodiments, the variant mRNA does not have a 5' cap. In some embodiments, the variant mRNA has at least one chemical modification, for example, any of the chemical modifications disclosed herein, e.g., N1-methylpseudouridine modification or N1-ethylpseudouridine modification. In some embodiments, the mRNA does not have chemical modification. The sequences encoding the mRNA variants are provided beneath the table.

TABLE 1

| mRNA Constructs | | | |
|---|---|---|---|
| SEQ ID NO: | Name of mRNA construct | Description | Function |
| 3 (DNA) and 125 (mRNA) | VZV-GE-delete-562 | Truncated VZV gE sequence-deletion from aa 562 (62 aa deletion from C terminal domain) | The C-terminal sequence targets gE to the trans-Golgi network (TGN); truncation assists in reducing gE localization to TGN |
| 4 (DNA) and 126 (mRNA) | VZV-GE-delete-562-IgKappa | Secreted form of truncated VZV gE sequence-deletion from aa 562 (62 aa deletion from C terminal domain) | The C-terminal sequence targets gE to the trans-Golgi networks (TGN); truncation assists in |

TABLE 1-continued

| mRNA Constructs | | | |
|---|---|---|---|
| SEQ ID NO: | Name of mRNA construct | Description | Function |
| | | and signal peptide replaced with IgKappa | reducing gE localization to TGN |
| 5 (DNA) and 127 (mRNA) | VZV-GE-delete-574 | Truncated VZV gE sequence-deletion from aa 574 (50 aa deletion from C terminal domain) | The C-terminal sequence targets gE to the trans-Golgi network (TGN); truncation assists in reducing gE localization to TGN |
| 6 (DNA) and 128 (mRNA) | VZV-GE-delete-574-Y569A | Truncated VZV gE sequence-deletion from aa 574 (50 aa deletion from C terminal domain) and Y569 A point mutation | The C-terminal sequence targets gE to the trans-Golgi network (TGN); the AYRV (SEQ ID NO: 119) sequence is required for targeting gE to the TGN; truncation/mutation reduces localization to TGN) |
| 7 (DNA) and 129 (mRNA) | VZV-GE-full-length-AEAADA (SEQ ID NO: 58) | VZV gE full length sequence with AEAADA (SEQ ID NO: 58) sequence | AEAADA (SEQ ID NO: 58) replaces SSTT (SEQ ID NO: 122) (acid cluster) comprising a phosphorylation motif, which phosphorylation assists in localizing gE to the TGN; mutation reduces localization of gE to TGN |
| 8 (DNA) and 130 (mRNA) | VZV-GE-full-AEAADA length-(SEQ ID NO: 58)-Y582G | VZV gE-full length sequence with AEAADA sequence (SEQ ID NO: 58) and Y582G point mutation | Mutations assist in reducing endocytosis and localization of gE to the TGN |

VZV-GE-delete-562

(SEQ ID NO: 3)

```
TCAAGCTTTTGGACCCTCGTACAGAAGCTAATACGACTCACTATAGGGAAATAAGAGAGAAAAGA
AGAGTAAGAAGAAATATAAGAGCCACCATGGGGACAGTTAATAAACCTGTGGTGGGGGTATTGAT
GGGGTTCGGAATTATCACGGGAACGTTGCGTATAACGAATCCGGTCAGAGCATCCGTCTTGCGATA
CGATGATTTTCACATCGATGAAGACAAACTGGATACAAACTCCGTATATGAGCCTTACTACCATTC
AGATCATGCGGAGTCTTCATGGGTAAATCGGGGAGAGTCTTCGCGAAAAGCGTACGATCATAACT
CACCTTATATATGGCCACGTAATGATTATGATGGATTTTTAGAGAACGCACACGAACACCATGGGG
TGTATAATCAGGGCCGTGGTATCGATAGCGGGGAACGGTTAATGCAACCCACACAAATGTCTGCA
CAGGAGGATCTTGGGGACGATACGGGCATCCACGTTATCCCTACGTTAAACGGCGATGACAGACA
TAAAATTGTAAATGTGGACCAACGTCAATACGGTGACGTGTTTAAAGGAGATCTTAATCCAAAAC
CCCAAGGCCAAAGACTCATTGAGGTGTCAGTGGAAGAAAATCACCCGTTTACTTTACGCGCACCG
ATTCAGCGGATTTATGGAGTCCGGTACACCGAGACTTGGAGCTTTTTGCCGTCATTAACCTGTACG
GGAGACGCAGCGCCCGCCATCCAGCATATATGTTTAAAACATACAACATGCTTTCAAGACGTGGT
GGTGGATGTGGATTGCGCGGAAAATACTAAAGAGGATCAGTTGGCCGAAATCAGTTACCGTTTTC
AAGGTAAGAAGGAAGCGGACCAACCGTGGATTGTTGTAAACACGAGCACACTGTTTGATGAACTC
GAATTAGACCCCCCCGAGATTGAACCGGGTGTCTTGAAAGTACTTCGGACAGAAAAACAATACTT
GGGTGTGTACATTTGGAACATGCGCGGCTCCGATGGTACGTCTACCTACGCCACGTTTTTGGTCAC
CTGGAAAGGGGATGAAAAAACAAGAAACCCTACGCCCGCAGTAACTCCTCAACCAAGAGGGGCT
GAGTTTCATATGTGGAATTACCACTCGCATGTATTTTCAGTTGGTGATACGTTTAGCTTGGCAATGC
ATCTTCAGTATAAGATACATGAAGCGCCATTTGATTTGCTGTTAGAGTGGTTGTATGTCCCCATCG
ATCCTACATGTCAACCAATGCGGTTATATTCTACGTGTTTGTATCATCCCAACGCACCCCAATGCCT
CTCTCATATGAATTCCGGTTGTACATTTACCTCGCCACATTTAGCCCAGCGTGTTGCAAGCACAGTG
TATCAAAATTGTGAACATGCAGATAACTACACCGCATATTGTCTGGGAATATCTCATATGGAGCCT
AGCTTTGGTCTAATCTTACACGACGGGGGCACCACGTTAAAGTTTGTAGATACACCCGAGAGTTTG
```

-continued

TCGGGATTATACGTTTTTGTGGTGTATTTTAACGGGCATGTTGAAGCCGTAGCATACACTGTTGTAT

CCACAGTAGATCATTTTGTAAACGCAATTGAAGAGCGTGGATTTCCGCCAACGGCCGGTCAGCCAC

CGGCGACTACTAAACCCAAGGAAATTACCCCCGTAAACCCCGGAACGTCACCACTTCTACGATAT

GCCGCATGGACCGGAGGGCTTGCAGCAGTAGTACTTTTATGTCTCGTAATATTTTTAATCTGTACG

GCTTGATGATAATAGGCTGGAGCCTCGGTGGCCATGCTTCTTGCCCCTTGGGCCTCCCCCCAGCCC

CTCCTCCCCTTCCTGCACCCGTACCCCCGTGGTCTTTGAATAAAGTCTGAGTGGGCGGC

VZV-GE-delete-562 (mRNA)

(SEQ ID NO: 125)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGGGGACAGUUAAUAAACCUGUGGUGGGGGUAU

UGAUGGGGUUCGGAAUUAUCACGGGAACGUUGCGUAUAACGAAUCCGGUCAGAGCAUCCGUCU

UGCGAUACGAUGAUUUUCACAUCGAUGAAGACAAACUGGAUACAAACUCCGUAUAUGAGCCUU

ACUACCAUUCAGAUCAUGCGGAGUCUUCAUGGGUAAAUCGGGGAGAGUCUUCGCGAAAAGCGU

ACGAUCAUAACUCACCUUAUAUAUGGCCACGUAAUGAUUAUGAUGGAUUUUUAGAGAACGCAC

ACGAACACCAUGGGGUGUAUAAUCAGGGCCGUGGUAUCGAUAGCGGGGAACGGUUAAUGCAAC

CCACACAAAUGUCUGCACAGGAGGAUCUUGGGGACGAUACGGGCAUCCACGUUAUCCCUACGU

UAAACGGCGAUGACAGACAUAAAAUUGUAAAUGUGGACCAACGUCAAUACGGUGACGUGUUUA

AAGGAGAUCUUAAUCCAAAACCCCAAGGCCAAAGACUCAUUGAGGUGUCAGUGGAAGAAAAUC

ACCCGUUUACUUUACGCGCACCGAUUCAGCGGAUUUAUGGAGUCCGGUACACCGAGACUUGGA

GCUUUUUGCCGUCAUUAACCUGUACGGGAGACGCAGCGCCCGCCAUCCAGCAUAUAUGUUUAA

AACAUACAACAUGCUUUCAAGACGUGGUGGUGGAUGUGGAUUGCGCGGAAAAUACUAAAGAGG

AUCAGUUGGCCGAAAUCAGUUACCGUUUUCAAGGUAAGAAGGAAGCGGACCAACCGUGGAUUG

UUGUAAACACGAGCACACUGUUUGAUGAACUCGAAUUAGACCCCCCCGAGAUUGAACCGGGUG

UCUUGAAAGUACUUCGGACAGAAAAACAAUACUUGGGUGUGUACAUUUGGAACAUGCGCGGCU

CCGAUGGUACGUCUACCUACGCCACGUUUUUGGUCACCUGGAAAGGGGAUGAAAAAACAAGAA

ACCCUACGCCCGCAGUAACUCCUCAACCAAGAGGGGCUGAGUUUCAUAUGUGGAAUUACCACUC

GCAUGUAUUUUCAGUUGGUGAUACGUUUAGCUUGGCAAUGCAUCUUCAGUAUAAGAUACAUGA

AGCGCCAUUUGAUUUGCUGUUAGAGUGGUUGUAUGUCCCCAUCGAUCCUACAUGUCAACCAAU

GCGGUUAUAUUCUACGUGUUUGUAUCAUCCCAACGCACCCCAAUGCCUCUCUCAUAUGAAUUCC

GGUUGUACAUUUACCUCGCCACAUUUAGCCCAGCGUGUUGCAAGCACAGUGUAUCAAAAUUGU

GAACAUGCAGAUAACUACACCGCAUAUUGUCUGGGAAUAUCUCAUAUGGAGCCUAGCUUUGGU

CUAAUCUUACACGACGGGGGCACCACGUUAAAGUUUGUAGAUACACCCGAGAGUUUGUCGGGA

UUAUACGUUUUUGUGGUGUAUUUUAACGGGCAUGUUGAAGCCGUAGCAUACACUGUUGUAUCC

ACAGUAGAUCAUUUUGUAAACGCAAUUGAAGAGCGUGGAUUUCCGCCAACGGCCGGUCAGCCA

CCGGCGACUACUAAACCCAAGGAAAUUACCCCCGUAAACCCCGGAACGUCACCACUUCUACGAU

AUGCCGCAUGGACCGGAGGGCUUGCAGCAGUAGUACUUUUAUGUCUCGUAAUAUUUUUAAUCU

GUACGGCUUGAUGAUAAUAGGCUGGAGCCUCGGUGGCCAUGCUUCUUGCCCCUUGGGCCUCCCC

CCAGCCCCUCCUCCCCUUCCUGCACCCGUACCCCCGUGGUCUUUGAAUAAAGUCUGAGUGGGCG

GC

-continued

VZV-GE-delete-562-IgKappa (SEQ ID NO: 4)

TCAAGCTTTTGGACCCTCGTACAGAAGCTAATACGACTCACTATAGGGAAATAAGAGAGAAAAGA

AGAGTAAGAAGAAATATAAGAGCCACCATGGAAACCCCGGCGCAGCTGCTGTTTCTGCTGCTGCT

GTGGCTGCCGGATACCACCGGCTCCGTCTTGCGATACGATGATTTTCACATCGATGAAGACAAACT

GGATACAAACTCCGTATATGAGCCTTACTACCATTCAGATCATGCGGAGTCTTCATGGGTAAATCG

GGGAGAGTCTTCGCGAAAAGCGTACGATCATAACTCACCTTATATATGGCCACGTAATGATTATGA

TGGATTTTTAGAGAACGCACACGAACACCATGGGGTGTATAATCAGGGCCGTGGTATCGATAGCG

GGGAACGGTTAATGCAACCCACACAAATGTCTGCACAGGAGGATCTTGGGGACGATACGGGCATC

CACGTTATCCCTACGTTAAACGGCGATGACAGACATAAAATTGTAAATGTGGACCAACGTCAATA

CGGTGACGTGTTTAAAGGAGATCTTAATCCAAAACCCCAAGGCCAAAGACTCATTGAGGTGTCAG

TGGAAGAAAATCACCCGTTTACTTTACGCGCACCGATTCAGCGGATTTATGGAGTCCGGTACACCG

AGACTTGGAGCTTTTTGCCGTCATTAACCTGTACGGGAGACGCAGCGCCCCGCCATCCAGCATATAT

GTTTAAAACATACAACATGCTTTCAAGACGTGGTGGTGGATGTGGATTGCGCGGAAAATACTAAA

GAGGATCAGTTGGCCGAAATCAGTTACCGTTTTCAAGGTAAGAAGGAAGCGGACCAACCGTGGAT

TGTTGTAAACACGAGCACACTGTTTGATGAACTCGAATTAGACCCCCCCGAGATTGAACCGGGTGT

CTTGAAAGTACTTCGGACAGAAAAACAATACTTGGGTGTGTACATTTGGAACATGCGCGGCTCCG

ATGGTACGTCTACCTACGCCACGTTTTTGGTCACCTGGAAAGGGGATGAAAAAACAAGAAACCCT

ACGCCCGCAGTAACTCCTCAACCAAGAGGGGCTGAGTTTCATATGTGGAATTACCACTCGCATGTA

TTTTCAGTTGGTGATACGTTTAGCTTGGCAATGCATCTTCAGTATAAGATACATGAAGCGCCATTTG

ATTTGCTGTTAGAGTGGTTGTATGTCCCCATCGATCCTACATGTCAACCAATGCGGTTATATTCTAC

GTGTTTGTATCATCCCAACGCACCCCAATGCCTCTCTCATATGAATTCCGGTTGTACATTTACCTCG

CCACATTTAGCCCAGCGTGTTGCAAGCACAGTGTATCAAAATTGTGAACATGCAGATAACTACACC

GCATATTGTCTGGGAATATCTCATATGGAGCCTAGCTTTGGTCTAATCTTACACGACGGGGGCACC

ACGTTAAAGTTTGTAGATACACCCGAGAGTTTGTCGGGATTATACGTTTTTGTGGTGTATTTTAACG

GGCATGTTGAAGCCGTAGCATACACTGTTGTATCCACAGTAGATCATTTTGTAAACGCAATTGAAG

AGCGTGGATTTCCGCCAACGGCCGGTCAGCCACCGGCGACTACTAAACCCAAGGAAATTACCCCC

GTAAACCCCGGAACGTCACCACTTCTACGATATGCCGCATGGACCGGAGGGCTTGCAGCAGTAGT

ACTTTTATGTCTCGTAATATTTTTAATCTGTACGGCTTGATGATAATAGGCTGGAGCCTCGGTGGCC

ATGCTTCTTGCCCCTTGGGCCTCCCCCCAGCCCCTCCTCCCCTTCCTGCACCCGTACCCCCGTGGTC

TTTGAATAAAGTCTGAGTGGGCGGC

VZV-GE-delete-562-IgKappa (mRNA)

(SEQ ID NO: 126)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGGAAACCCCGGCGCAGCUGCUGUUUCUGCUGC

UGCUGUGGCUGCCGGAUACCACCGGCUCCGUCUUGCGAUACGAUGAUUUUCACAUCGAUGAAG

ACAAACUGGAUACAAACUCCGUAUAUGAGCCUUACUACCAUUCAGAUCAUGCGGAGUCUUCAU

GGGUAAAUCGGGGAGAGUCUUCGCGAAAAGCGUACGAUCAUAACUCACCUUAUAUAUGGCCAC

GUAAUGAUUAUGAUGGAUUUUUAGAGAACGCACACGAACACCAUGGGGUGUAUAAUCAGGGCC

GUGGUAUCGAUAGCGGGGAACGGUUAAUGCAACCCACACAAAUGUCUGCACAGGAGGAUCUUG

GGGACGAUACGGGCAUCCACGUUAUCCCUACGUUAAACGGCGAUGACAGACAUAAAAUUGUAA

AUGUGGACCAACGUCAAUACGGUGACGUGUUUAAAGGAGAUCUUAAUCCAAAACCCCAAGGCC

-continued

AAAGACUCAUUGAGGUGUCAGUGGAAGAAAAUCACCCGUUUACUUUACGCGCACCGAUUCAGC

GGAUUUAUGGAGUCCGGUACACCGAGACUUGGAGCUUUUUGCCGUCAUUAACCUGUACGGGAG

ACGCAGCGCCCGCCAUCCAGCAUAUAUGUUUAAAACAUACAACAUGCUUUCAAGACGUGGUGG

UGGAUGUGGAUUGCGCGGAAAAUACUAAAGAGGAUCAGUUGGCCGAAAUCAGUUACCGUUUUC

AAGGUAAGAAGGAAGCGGACCAACCGUGGAUUGUUGUAAACACGAGCACACUGUUUGAUGAAC

UCGAAUUAGACCCCCCCGAGAUUGAACCGGGUGUCUUGAAAGUACUUCGGACAGAAAAACAAU

ACUUGGGUGUGUACAUUUGGAACAUGCGCGGCUCCGAUGGUACGUCUACCUACGCCACGUUUU

UGGUCACCUGGAAAGGGGAUGAAAAAACAAGAAACCCUACGCCCGCAGUAACUCCUCAACCAA

GAGGGGCUGAGUUUCAUAUGUGGAAUUACCACUCGCAUGUAUUUCAGUUGGUGAUACGUUUA

GCUUGGCAAUGCAUCUUCAGUAUAAGAUACAUGAAGCGCCAUUUGAUUUGCUGUUAGAGUGGU

UGUAUGUCCCCAUCGAUCCUACAUGUCAACCAAUGCGGUUAUAUUCUACGUGUUUGUAUCAUC

CCAACGCACCCCAAUGCCUCUCUCAUAUGAAUUCCGGUUGUACAUUUACCUCGCCACAUUUAGC

CCAGCGUGUUGCAAGCACAGUGUAUCAAAAUUGUGAACAUGCAGAUAACUACACCGCAUAUUG

UCUGGGAAUAUCUCAUAUGGAGCCUAGCUUUGGUCUAAUCUUACACGACGGGGGCACCACGUU

AAAGUUUGUAGAUACACCCGAGAGUUUGUCGGGAUUAUACGUUUUUGUGGUGUAUUUUAACGG

GCAUGUUGAAGCCGUAGCAUACACUGUUGUAUCCACAGUAGAUCAUUUUGUAAACGCAAUUGA

AGAGCGUGGAUUUCCGCCAACGGCCGGUCAGCCACCGGCGACUACUAAACCCAAGGAAAUUACC

CCCGUAAACCCCGGAACGUCACCACUUCUACGAUAUGCCGCAUGGACCGGAGGGCUUGCAGCAG

UAGUACUUUUAUGUCUCGUAAUAUUUUUAAUCUGUACGGCUUGAUGAUAAUAGGCUGGAGCCU

CGGUGGCCAUGCUUCUUGCCCCUUGGGCCUCCCCCCAGCCCCUCCUCCCCUUCCUGCACCCGUAC

CCCCGUGGUCUUUGAAUAAAGUCUGAGUGGGCGGC

VZV-GE- delete-574

(SEQ ID NO: 5)

TCAAGCTTTTGGACCCTCGTACAGAAGCTAATACGACTCACTATAGGGAAATAAGAGAGAAAAGA

AGAGTAAGAAGAAATATAAGAGCCACCATGGGGACAGTTAATAAACCTGTGGTGGGGGTATTGAT

GGGGTTCGGAATTATCACGGGAACGTTGCGTATAACGAATCCGGTCAGAGCATCCGTCTTGCGATA

CGATGATTTTCACATCGATGAAGACAAACTGGATACAAACTCCGTATATGAGCCTTACTACCATTC

AGATCATGCGGAGTCTTCATGGGTAAATCGGGGAGAGTCTTCGCGAAAAGCGTACGATCATAACT

CACCTTATATATGGCCACGTAATGATTATGATGGATTTTTAGAGAACGCACACGAACACCATGGGG

TGTATAATCAGGGCCGTGGTATCGATAGCGGGGAACGGTTAATGCAACCCACACAAATGTCTGCA

CAGGAGGATCTTGGGGACGATACGGGCATCCACGTTATCCCTACGTTAAACGGCGATGACAGACA

TAAAATTGTAAATGTGGACCAACGTCAATACGGTGACGTGTTTAAAGGAGATCTTAATCCAAAAC

CCCAAGGCCAAAGACTCATTGAGGTGTCAGTGGAAGAAAATCACCCGTTTACTTTACGCGCACCG

ATTCAGCGGATTTATGGAGTCCGGTACACCGAGACTTGGAGCTTTTTGCCGTCATTAACCTGTACG

GGAGACGCAGCGCCCGCCATCCAGCATATATGTTTAAAACATACAACATGCTTTCAAGACGTGGT

GGTGGATGTGGATTGCGCGGAAAATACTAAAGAGGATCAGTTGGCCGAAATCAGTTACCGTTTTC

AAGGTAAGAAGGAAGCGGACCAACCGTGGATTGTTGTAAACACGAGCACACTGTTTGATGAACTC

GAATTAGACCCCCCCGAGATTGAACCGGGTGTCTTGAAAGTACTTCGGACAGAAAAACAATACTT

GGGTGTGTACATTTGGAACATGCGCGGCTCCGATGGTACGTCTACCTACGCCACGTTTTTGGTCAC

CTGGAAAGGGGATGAAAAAACAAGAAACCCTACGCCCGCAGTAACTCCTCAACCAAGAGGGGCT

GAGTTTCATATGTGGAATTACCACTCGCATGTATTTTCAGTTGGTGATACGTTTAGCTTGGCAATGC

ATCTTCAGTATAAGATACATGAAGCGCCATTTGATTTGCTGTTAGAGTGGTTGTATGTCCCCATCG

-continued

ATCCTACATGTCAACCAATGCGGTTATATTCTACGTGTTTGTATCATCCCAACGCACCCCAATGCCT

CTCTCATATGAATTCCGGTTGTACATTTACCTCGCCACATTTAGCCCAGCGTGTTGCAAGCACAGTG

TATCAAAATTGTGAACATGCAGATAACTACACCGCATATTGTCTGGGAATATCTCATATGGAGCCT

AGCTTTGGTCTAATCTTACACGACGGGGGCACCACGTTAAAGTTTGTAGATACACCCGAGAGTTTG

TCGGGATTATACGTTTTTGTGGTGTATTTTAACGGGCATGTTGAAGCCGTAGCATACACTGTTGTAT

CCACAGTAGATCATTTTGTAAACGCAATTGAAGAGCGTGGATTTCCGCCAACGGCCGGTCAGCCAC

CGGCGACTACTAAACCCAAGGAAATTACCCCCGTAAACCCCGGAACGTCACCACTTCTACGATAT

GCCGCATGGACCGGAGGGCTTGCAGCAGTAGTACTTTTATGTCTCGTAATATTTTTAATCTGTACG

GCTAAACGAATGAGGGTTAAAGCCTATAGGGTAGACAAGTGATGATAATAGGCTGGAGCCTCGGT

GGCCATGCTTCTTGCCCCTTGGGCCTCCCCCCAGCCCCTCCTCCCCTTCCTGCACCCGTACCCCCGT

GGTCTTTGAATAAAGTCTGAGTGGGCGGC

VZV-GE- delete-574 (mRNA)

(SEQ ID NO: 127)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGGGGACAGUUAAUAAACCUGUGGUGGGGGUAU

UGAUGGGGUUCGGAAUUAUCACGGGAACGUUGCGUAUAACGAAUCCGGUCAGAGCAUCCGUCU

UGCGAUACGAUGAUUUUCACAUCGAUGAAGACAAACUGGAUACAAACUCCGUAUAUGAGCCUU

ACUACCAUUCAGAUCAUGCGGAGUCUUCAUGGGUAAAUCGGGGAGAGUCUUCGCGAAAAGCGU

ACGAUCAUAACUCACCUUAUAUAUGGCCACGUAAUGAUUAUGAUGGAUUUUUAGAGAACGCAC

ACGAACACCAUGGGGUGUAUAAUCAGGGCCGUGGUAUCGAUAGCGGGGAACGGUUAAUGCAAC

CCACACAAAUGUCUGCACAGGAGGAUCUUGGGGACGAUACGGGCAUCCACGUUAUCCCUACGU

UAAACGGCGAUGACAGACAUAAAAUUGUAAAUGUGGACCAACGUCAAUACGGUGACGUGUUUA

AAGGAGAUCUUAAUCCAAAACCCCAAGGCCAAAGACUCAUUGAGGUGUCAGUGGAAGAAAAUC

ACCCGUUUACUUUACGCGCACCGAUUCAGCGGAUUUAUGGAGUCCGGUACACCGAGACUUGGA

GCUUUUUGCCGUCAUUAACCUGUACGGGAGACGCAGCGCCCGCCAUCCAGCAUAUAUGUUUAA

AACAUACAACAUGCUUUCAAGACGUGGUGGUGGAUGUGGAUUGCGCGGAAAAUACUAAAGAGG

AUCAGUUGGCCGAAAUCAGUUACCGUUUUCAAGGUAAGAAGGAAGCGGACCAACCGUGGAUUG

UUGUAAACACGAGCACACUGUUUGAUGAACUCGAAUUAGACCCCCCCGAGAUUGAACCGGGUG

UCUUGAAAGUACUUCGGACAGAAAAACAAUACUUGGGUGUGUACAUUUGGAACAUGCGCGGCU

CCGAUGGUACGUCUACCUACGCCACGUUUUUGGUCACCUGGAAAGGGGAUGAAAAAACAAGAA

ACCCUACGCCCGCAGUAACUCCUCAACCAAGAGGGGCUGAGUUUCAUAUGUGGAAUUACCACUC

GCAUGUAUUUUCAGUUGGUGAUACGUUUAGCUUGGCAAUGCAUCUUCAGUAUAAGAUACAUGA

AGCGCCAUUUGAUUUGCUGUUAGAGUGGUUGUAUGUCCCCAUCGAUCCUACAUGUCAACCAAU

GCGGUUAUAUUCUACGUGUUUGUAUCAUCCCAACGCACCCCAAUGCCUCUCUCAUAUGAAUUCC

GGUUGUACAUUUACCUCGCCACAUUUAGCCCAGCGUGUUGCAAGCACAGUGUAUCAAAAUUGU

GAACAUGCAGAUAACUACACCGCAUAUUGUCUGGGAAUAUCUCAUAUGGAGCCUAGCUUUGGU

CUAAUCUUACACGACGGGGGCACCACGUUAAAGUUUGUAGAUACACCCGAGAGUUUGUCGGGA

UUAUACGUUUUUGUGGUGUAUUUUAACGGGCAUGUUGAAGCCGUAGCAUACACUGUUGUAUCC

ACAGUAGAUCAUUUUGUAAACGCAAUUGAAGAGCGUGGAUUUCCGCCAACGGCCGGUCAGCCA

CCGGCGACUACUAAACCCAAGGAAAUUACCCCCGUAAACCCCGGAACGUCACCACUUCUACGAU

AUGCCGCAUGGACCGGAGGGCUUGCAGCAGUAGUACUUUUAUGUCUCGUAAUAUUUUUAAUCU

-continued

GUACGGCUAAACGAAUGAGGGUUAAAGCCUAUAGGGUAGACAAGUGAUGAUAAUAGGCUGGAG

CCUCGGUGGCCAUGCUUCUUGCCCCUUGGGCCUCCCCCCAGCCCCUCCUCCCCUUCCUGCACCCG

UACCCCCGUGGUCUUUGAAUAAAGUCUGAGUGGGCGGC

VZV-GE- delete-574-Y569A (SEQ ID NO: 6)

TCAAGCTTTTGGACCCTCGTACAGAAGCTAATACGACTCACTATAGGGAAATAAGAGAGAAAAGA

AGAGTAAGAAGAAATATAAGAGCCACCATGGGGACAGTTAATAAACCTGTGGTGGGGGTATTGAT

GGGGTTCGGAATTATCACGGGAACGTTGCGTATAACGAATCCGGTCAGAGCATCCGTCTTGCGATA

CGATGATTTTCACATCGATGAAGACAAACTGGATACAAACTCCGTATATGAGCCTTACTACCATTC

AGATCATGCGGAGTCTTCATGGGTAAATCGGGGAGAGTCTTCGCGAAAAGCGTACGATCATAACT

CACCTTATATATGGCCACGTAATGATTATGATGGATTTTTAGAGAACGCACACGAACACCATGGGG

TGTATAATCAGGGCCGTGGTATCGATAGCGGGGAACGGTTAATGCAACCCACACAAATGTCTGCA

CAGGAGGATCTTGGGGACGATACGGGCATCCACGTTATCCCTACGTTAAACGGCGATGACAGACA

TAAAATTGTAAATGTGGACCAACGTCAATACGGTGACGTGTTTAAAGGAGATCTTAATCCAAAAC

CCCAAGGCCAAAGACTCATTGAGGTGTCAGTGGAAGAAAATCACCCGTTTACTTTACGCGCACCG

ATTCAGCGGATTTATGGAGTCCGGTACACCGAGACTTGGAGCTTTTTGCCGTCATTAACCTGTACG

GGAGACGCAGCGCCCGCCATCCAGCATATATGTTTAAAACATACAACATGCTTTCAAGACGTGGT

GGTGGATGTGGATTGCGCGGAAAATACTAAAGAGGATCAGTTGGCCGAAATCAGTTACCGTTTTC

AAGGTAAGAAGGAAGCGGACCAACCGTGGATTGTTGTAAACACGAGCACACTGTTTGATGAACTC

GAATTAGACCCCCCCGAGATTGAACCGGGTGTCTTGAAAGTACTTCGGACAGAAAAACAATACTT

GGGTGTGTACATTTGGAACATGCGCGGCTCCGATGGTACGTCTACCTACGCCACGTTTTTGGTCAC

CTGGAAAGGGGATGAAAAAACAAGAAACCCTACGCCCGCAGTAACTCCTCAACCAAGAGGGGCT

GAGTTTCATATGTGGAATTACCACTCGCATGTATTTTCAGTTGGTGATACGTTTAGCTTGGCAATGC

ATCTTCAGTATAAGATACATGAAGCGCCATTTGATTTGCTGTTAGAGTGGTTGTATGTCCCCATCG

ATCCTACATGTCAACCAATGCGGTTATATTCTACGTGTTTGTATCATCCCAACGCACCCCAATGCCT

CTCTCATATGAATTCCGGTTGTACATTTACCTCGCCACATTTAGCCCAGCGTGTTGCAAGCACAGTG

TATCAAAATTGTGAACATGCAGATAACTACACCGCATATTGTCTGGGAATATCTCATATGGAGCCT

AGCTTTGGTCTAATCTTACACGACGGGGGCACCACGTTAAAGTTTGTAGATACACCCGAGAGTTTG

TCGGGATTATACGTTTTTGTGGTGTATTTTAACGGGCATGTTGAAGCCGTAGCATACACTGTTGTAT

CCACAGTAGATCATTTTGTAAACGCAATTGAAGAGCGTGGATTTCCGCCAACGGCCGGTCAGCCAC

CGGCGACTACTAAACCCAAGGAAATTACCCCCGTAAACCCCGGAACGTCACCACTTCTACGATAT

GCCGCATGGACCGGAGGGCTTGCAGCAGTAGTACTTTTATGTCTCGTAATATTTTTAATCTGTACG

GCTAAACGAATGAGGGTTAAAGCCGCCAGGGTAGACAAGTGATGATAATAGGCTGGAGCCTCGGT

GGCCATGCTTCTTGCCCCTTGGGCCTCCCCCCAGCCCCTCCTCCCCTTCCTGCACCCGTACCCCCGT

GGTCTTTGAATAAAGTCTGAGTGGGCGGC

VZV-GE- delete-574-Y569A(mRNA)

(SEQ ID NO: 128)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGGGGACAGUUAAUAAACCUGUGGUGGGGGUAU

UGAUGGGGUUCGGAAUUAUCACGGGAACGUUGCGUAUAACGAAUCCGGUCAGAGCAUCCGUCU

UGCGAUACGAUGAUUUUCACAUCGAUGAAGACAAACUGGAUACAAACUCCGUAUAUGAGCCUU

ACUACCAUUCAGAUCAUGCGGAGUCUUCAUGGGUAAAUCGGGGAGAGUCUUCGCGAAAAGCGU

ACGAUCAUAACUCACCUUAUAUAUGGCCACGUAAUGAUUAUGAUGGAUUUUUAGAGAACGCAC

-continued

ACGAACACCAUGGGGUGUAUAAUCAGGGCCGUGGUAUCGAUAGCGGGGAACGGUUAAUGCAAC
CCACACAAAUGUCUGCACAGGAGGAUCUUGGGGACGAUACGGGCAUCCACGUUAUCCCUACGU
UAAACGGCGAUGACAGACAUAAAAUUGUAAAUGUGGACCAACGUCAAUACGGUGACGUGUUUA
AAGGAGAUCUUAAUCCAAAACCCCAAGGCCAAAGACUCAUUGAGGUGUCAGUGGAAGAAAAUC
ACCCGUUUACUUUACGCGCACCGAUUCAGCGGAUUUAUGGAGUCCGGUACACCGAGACUUGGA
GCUUUUUGCCGUCAUUAACCUGUACGGGAGACGCAGCGCCCGCCAUCCAGCAUAUAUGUUUAA
AACAUACAACAUGCUUUCAAGACGUGGUGGUGGAUGUGGAUUGCGCGGAAAAUACUAAAGAGG
AUCAGUUGGCCGAAAUCAGUUACCGUUUUCAAGGUAAGAAGGAAGCGGACCAACCGUGGAUUG
UUGUAAACACGAGCACACUGUUUGAUGAACUCGAAUUAGACCCCCCCGAGAUUGAACCGGGUG
UCUUGAAAGUACUUCGGACAGAAAAACAAUACUUGGGUGUGUACAUUUGGAACAUGCGCGGCU
CCGAUGGUACGUCUACCUACGCCACGUUUUUGGUCACCUGGAAAGGGGAUGAAAAAACAAGAA
ACCCUACGCCCGCAGUAACUCCUCAACCAAGAGGGGCUGAGUUUCAUAUGUGGAAUUACCACUC
GCAUGUAUUUUCAGUUGGUGAUACGUUUAGCUUGGCAAUGCAUCUUCAGUAUAAGAUACAUGA
AGCGCCAUUUGAUUUGCUGUUAGAGUGGUUGUAUGUCCCCAUCGAUCCUACAUGUCAACCAAU
GCGGUUAUAUUCUACGUGUUUGUAUCAUCCCAACGCACCCCAAUGCCUCUCUCAUAUGAAUUCC
GGUUGUACAUUUACCUCGCCACAUUUAGCCCAGCGUGUUGCAAGCACAGUGUAUCAAAAUUGU
GAACAUGCAGAUAACUACACCGCAUAUUGUCUGGGAAUAUCUCAUAUGGAGCCUAGCUUUGGU
CUAAUCUUACACGACGGGGGCACCACGUUAAAGUUUGUAGAUACACCCGAGAGUUUGUCGGGA
UUAUACGUUUUUGUGGUGUAUUUUAACGGGCAUGUUGAAGCCGUAGCAUACACUGUUGUAUCC
ACAGUAGAUCAUUUUGUAAACGCAAUUGAAGAGCGUGGAUUUCCGCCAACGGCCGGUCAGCCA
CCGGCGACUACUAAACCCAAGGAAAUUACCCCCGUAAACCCCGGAACGUCACCACUUCUACGAU
AUGCCGCAUGGACCGGAGGGCUUGCAGCAGUAGUACUUUUAUGUCUCGUAAUAUUUUUAAUCU
GUACGGCUAAACGAAUGAGGGUUAAAGCCGCCAGGGUAGACAAGUGAUGAUAAUAGGCUGGAG
CCUCGGUGGCCAUGCUUCUUGCCCCUUGGGCCUCCCCCCAGCCCCUCCUCCCCUUCCUGCACCCG
UACCCCCGUGGUCUUUGAAUAAAGUCUGAGUGGGCGGC

VZV-gE-full length-AEAADA (SEQ ID NO: 58)

(SEQ ID NO: 7)

TCAAGCTTTTGGACCCTCGTACAGAAGCTAATACGACTCACTATAGGGAAATAAGAGAGAAAAGA
AGAGTAAGAAGAAATATAAGAGCCACCATGGGGACAGTTAATAAACCTGTGGTGGGGGTATTGAT
GGGGTTCGGAATTATCACGGGAACGTTGCGTATAACGAATCCGGTCAGAGCATCCGTCTTGCGATA
CGATGATTTTCACATCGATGAAGACAAACTGGATACAAACTCCGTATATGAGCCTTACTACCATTC
AGATCATGCGGAGTCTTCATGGGTAAATCGGGGAGAGTCTTCGCGAAAAGCGTACGATCATAACT
CACCTTATATATGGCCACGTAATGATTATGATGGATTTTTAGAGAACGCACACGAACACCATGGGG
TGTATAATCAGGGCCGTGGTATCGATAGCGGGGAACGGTTAATGCAACCCACACAAATGTCTGCA
CAGGAGGATCTTGGGGACGATACGGGCATCCACGTTATCCCTACGTTAAACGGCGATGACAGACA
TAAAATTGTAAATGTGGACCAACGTCAATACGGTGACGTGTTTAAAGGAGATCTTAATCCAAAAC
CCCAAGGCCAAAGACTCATTGAGGTGTCAGTGGAAGAAAATCACCCGTTTACTTTACGCGCACCG
ATTCAGCGGATTTATGGAGTCCGGTACACCGAGACTTGGAGCTTTTTGCCGTCATTAACCTGTACG
GGAGACGCAGCGCCCGCCATCCAGCATATATGTTTAAAACATACAACATGCTTTCAAGACGTGGT
GGTGGATGTGGATTGCGCGGAAAATACTAAAGAGGATCAGTTGGCCGAAATCAGTTACCGTTTTC
AAGGTAAGAAGGAAGCGGACCAACCGTGGATTGTTGTAAACACGAGCACACTGTTTGATGAACTC

-continued

GAATTAGACCCCCCCGAGATTGAACCGGGTGTCTTGAAAGTACTTCGGACAGAAAAACAATACTT

GGGTGTGTACATTTGGAACATGCGCGGCTCCGATGGTACGTCTACCTACGCCACGTTTTTGGTCAC

CTGGAAAGGGGATGAAAAAACAAGAAACCCTACGCCCGCAGTAACTCCTCAACCAAGAGGGGCT

GAGTTTCATATGTGGAATTACCACTCGCATGTATTTTCAGTTGGTGATACGTTTAGCTTGGCAATGC

ATCTTCAGTATAAGATACATGAAGCGCCATTTGATTTGCTGTTAGAGTGGTTGTATGTCCCCATCG

ATCCTACATGTCAACCAATGCGGTTATATTCTACGTGTTTGTATCATCCCAACGCACCCCAATGCCT

CTCTCATATGAATTCCGGTTGTACATTTACCTCGCCACATTTAGCCCAGCGTGTTGCAAGCACAGTG

TATCAAAATTGTGAACATGCAGATAACTACACCGCATATTGTCTGGGAATATCTCATATGGAGCCT

AGCTTTGGTCTAATCTTACACGACGGGGGCACCACGTTAAAGTTTGTAGATACACCCGAGAGTTTG

TCGGGATTATACGTTTTTGTGGTGTATTTTAACGGGCATGTTGAAGCCGTAGCATACACTGTTGTAT

CCACAGTAGATCATTTTGTAAACGCAATTGAAGAGCGTGGATTTCCGCCAACGGCCGGTCAGCCAC

CGGCGACTACTAAACCCAAGGAAATTACCCCCGTAAACCCCGGAACGTCACCACTTCTACGATAT

GCCGCATGGACCGGAGGGCTTGCAGCAGTAGTACTTTTATGTCTCGTAATATTTTTAATCTGTACG

GCTAAACGAATGAGGGTTAAAGCCTATAGGGTAGACAAGTCCCCGTATAACCAAAGCATGTATTA

CGCTGGCCTTCCAGTGGACGATTTCGAGGACGCCGAAGCCGCCGATGCCGAAGAAGAGTTTGGTA

ACGCGATTGGAGGGAGTCACGGGGGTTCGAGTTACACGGTGTATATAGATAAGACCCGGTGATGA

TAATAGGCTGGAGCCTCGGTGGCCATGCTTCTTGCCCCTTGGGCCTCCCCCCAGCCCCTCCTCCCCT

TCCTGCACCCGTACCCCCGTGGTCTTTGAATAAAGTCTGAGTGGGCGGC

VZV-gE-full length-AEAADA (SEQ ID NO: 58)(mRNA)

(SEQ ID NO: 129)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGGGGACAGUUAAUAAACCUGUGGUGGGGGUAU

UGAUGGGGUUCGGAAUUAUCACGGGAACGUUGCGUAUAACGAAUCCGGUCAGAGCAUCCGUCU

UGCGAUACGAUGAUUUUCACAUCGAUGAAGACAAACUGGAUACAAACUCCGUAUAUGAGCCUU

ACUACCAUUCAGAUCAUGCGGAGUCUUCAUGGGUAAAUCGGGGAGAGUCUUCGCGAAAAGCGU

ACGAUCAUAACUCACCUUAUAUAUGGCCACGUAAUGAUUAUGAUGGAUUUUUAGAGAACGCAC

ACGAACACCAUGGGGUGUAUAAUCAGGGCCGUGGUAUCGAUAGCGGGGAACGGUUAAUGCAAC

CCACACAAAUGUCUGCACAGGAGGAUCUUGGGGACGAUACGGGCAUCCACGUUAUCCCUACGU

UAAACGGCGAUGACAGACAUAAAAUUGUAAAUGUGGACCAACGUCAAUACGGUGACGUGUUUA

AAGGAGAUCUUAAUCCAAAACCCCAAGGCCAAAGACUCAUUGAGGUGUCAGUGGAAGAAAAUC

ACCCGUUUACUUUACGCGCACCGAUUCAGCGGAUUUAUGGAGUCCGGUACACCGAGACUUGGA

GCUUUUUGCCGUCAUUAACCUGUACGGGAGACGCAGCGCCCGCCAUCCAGCAUAUAUGUUUAA

AACAUACAACAUGCUUUCAAGACGUGGUGGUGGAUGUGGAUUGCGCGGAAAAUACUAAAGAGG

AUCAGUUGGCCGAAAUCAGUUACCGUUUUCAAGGUAAGAAGGAAGCGGACCAACCGUGGAUUG

UUGUAAACACGAGCACACUGUUUGAUGAACUCGAAUUAGACCCCCCCGAGAUUGAACCGGGUG

UCUUGAAAGUACUUCGGACAGAAAAACAAUACUUGGGUGUGUACAUUUGGAACAUGCGCGGCU

CCGAUGGUACGUCUACCUACGCCACGUUUUUGGUCACCUGGAAAGGGGAUGAAAAAACAAGAA

ACCCUACGCCCGCAGUAACUCCUCAACCAAGAGGGGCUGAGUUUCAUAUGUGGAAUUACCACUC

GCAUGUAUUUUCAGUUGGUGAUACGUUUAGCUUGGCAAUGCAUCUUCAGUAUAAGAUACAUGA

AGCGCCAUUUGAUUUGCUGUUAGAGUGGUUGUAUGUCCCCAUCGAUCCUACAUGUCAACCAAU

GCGGUUAUAUUCUACGUGUUUGUAUCAUCCCAACGCACCCCAAUGCCUCUCUCAUAUGAAUUCC

GGUUGUACAUUUACCUCGCCACAUUUAGCCCAGCGUGUUGCAAGCACAGUGUAUCAAAAUUGU

-continued

GAACAUGCAGAUAACUACACCGCAUAUUGUCUGGGAAUAUCUCAUAUGGAGCCUAGCUUUGGU

CUAAUCUUACACGACGGGGGCACCACGUUAAAGUUUGUAGAUACACCCGAGAGUUUGUCGGGA

UUAUACGUUUUUGUGGUGUAUUUUAACGGGCAUGUUGAAGCCGUAGCAUACACUGUUGUAUCC

ACAGUAGAUCAUUUUGUAAACGCAAUUGAAGAGCGUGGAUUUCCGCCAACGGCCGGUCAGCCA

CCGGCGACUACUAAACCCAAGGAAAUUACCCCCGUAAACCCCGGAACGUCACCACUUCUACGAU

AUGCCGCAUGGACCGGAGGGCUUGCAGCAGUAGUACUUUUAUGUCUCGUAAUAUUUUUAAUCU

GUACGGCUAAACGAAUGAGGGUUAAAGCCUAUAGGGUAGACAAGUCCCCGUAUAACCAAAGCA

UGUAUUACGCUGGCCUUCCAGUGGACGAUUUCGAGGACGCCGAAGCCGCCGAUGCCGAAGAAG

AGUUUGGUAACGCGAUUGGAGGGAGUCACGGGGGUUCGAGUUACACGGUGUAUAUAGAUAAGA

CCCGGUGAUGAUAAUAGGCUGGAGCCUCGGUGGCCAUGCUUCUUGCCCCUUGGGCCUCCCCCCA

GCCCCUCCUCCCCUUCCUGCACCCGUACCCCCGUGGUCUUUGAAUAAAGUCUGAGUGGGCGGC

VZV-GE-full-AEAADA (SEQ ID NO: 58)-Y582G (SEQ ID NO: 8)

TCAAGCTTTTGGACCCTCGTACAGAAGCTAATACGACTCACTATAGGGAAATAAGAGAGAAAAGA

AGAGTAAGAAGAAATATAAGAGCCACCATGGGGACAGTTAATAAACCTGTGGTGGGGGTATTGAT

GGGGTTCGGAATTATCACGGGAACGTTGCGTATAACGAATCCGGTCAGAGCATCCGTCTTGCGATA

CGATGATTTTCACATCGATGAAGACAAACTGGATACAAACTCCGTATATGAGCCTTACTACCATTC

AGATCATGCGGAGTCTTCATGGGTAAATCGGGGAGAGTCTTCGCGAAAAGCGTACGATCATAACT

CACCTTATATATGGCCACGTAATGATTATGATGGATTTTTAGAGAACGCACACGAACACCATGGGG

TGTATAATCAGGGCCGTGGTATCGATAGCGGGGAACGGTTAATGCAACCCACACAAATGTCTGCA

CAGGAGGATCTTGGGGACGATACGGGCATCCACGTTATCCCTACGTTAAACGGCGATGACAGACA

TAAAATTGTAAATGTGGACCAACGTCAATACGGTGACGTGTTTAAAGGAGATCTTAATCCAAAAC

CCCAAGGCCAAAGACTCATTGAGGTGTCAGTGGAAGAAAATCACCCGTTTACTTTACGCGCACCG

ATTCAGCGGATTTATGGAGTCCGGTACACCGAGACTTGGAGCTTTTTGCCGTCATTAACCTGTACG

GGAGACGCAGCGCCCGCCATCCAGCATATATGTTTAAAACATACAACATGCTTTCAAGACGTGGT

GGTGGATGTGGATTGCGCGGAAAATACTAAAGAGGATCAGTTGGCCGAAATCAGTTACCGTTTTC

AAGGTAAGAAGGAAGCGGACCAACCGTGGATTGTTGTAAACACGAGCACACTGTTTGATGAACTC

GAATTAGACCCCCCCGAGATTGAACCGGGTGTCTTGAAAGTACTTCGGACAGAAAAACAATACTT

GGGTGTGTACATTTGGAACATGCGCGGCTCCGATGGTACGTCTACCTACGCCACGTTTTTGGTCAC

CTGGAAAGGGGATGAAAAAACAAGAAACCCTACGCCCGCAGTAACTCCTCAACCAAGAGGGGCT

GAGTTTCATATGTGGAATTACCACTCGCATGTATTTTCAGTTGGTGATACGTTTAGCTTGGCAATGC

ATCTTCAGTATAAGATACATGAAGCGCCATTTGATTTGCTGTTAGAGTGGTTGTATGTCCCCATCG

ATCCTACATGTCAACCAATGCGGTTATATTCTACGTGTTTGTATCATCCCAACGCACCCCAATGCCT

CTCTCATATGAATTCCGGTTGTACATTTACCTCGCCACATTTAGCCCAGCGTGTTGCAAGCACAGTG

TATCAAAATTGTGAACATGCAGATAACTACACCGCATATTGTCTGGGAATATCTCATATGGAGCCT

AGCTTTGGTCTAATCTTACACGACGGGGGCACCACGTTAAAGTTTGTAGATACACCCGAGAGTTTG

TCGGGATTATACGTTTTTGTGGTGTATTTTAACGGGCATGTTGAAGCCGTAGCATACACTGTTGTAT

CCACAGTAGATCATTTTGTAAACGCAATTGAAGAGCGTGGATTTCCGCCAACGGCCGGTCAGCCAC

CGGCGACTACTAAACCCAAGGAAATTACCCCCGTAAACCCCGGAACGTCACCACTTCTACGATAT

GCCGCATGGACCGGAGGGCTTGCAGCAGTAGTACTTTTATGTCTCGTAATATTTTTAATCTGTACG

GCTAAACGAATGAGGGTTAAAGCCTATAGGGTAGACAAGTCCCCGTATAACCAAAGCATGTATGG

-continued

CGCTGGCCTTCCAGTGGACGATTTCGAGGACGCCGAAGCCGCCGATGCCGAAGAAGAGTTTGGTA

ACGCGATTGGAGGGAGTCACGGGGGTTCGAGTTACACGGTGTATATAGATAAGACCCGGTGATGA

TAATAGGCTGGAGCCTCGGTGGCCATGCTTCTTGCCCCTTGGGCCTCCCCCCAGCCCCTCCTCCCCT

TCCTGCACCCGTACCCCCGTGGTCTTTGAATAAAGTCTGAGTGGGCGGC

VZV-GE-full-AEAADA (SEQ ID NO: 58)-Y582G(mRNA)

(SEQ ID NO: 130)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGGGGACAGUUAAUAAACCUGUGGUGGGGGUAU

UGAUGGGGUUCGGAAUUAUCACGGGAACGUUGCGUAUAACGAAUCCGGUCAGAGCAUCCGUCU

UGCGAUACGAUGAUUUUCACAUCGAUGAAGACAAACUGGAUACAAACUCCGUAUAUGAGCCUU

ACUACCAUUCAGAUCAUGCGGAGUCUUCAUGGGUAAAUCGGGGAGAGUCUUCGCGAAAAGCGU

ACGAUCAUAACUCACCUUAUAUAUGGCCACGUAAUGAUUAUGAUGGAUUUUUAGAGAACGCAC

ACGAACACCAUGGGGUGUAUAAUCAGGGCCGUGGUAUCGAUAGCGGGGAACGGUUAAUGCAAC

CCACACAAAUGUCUGCACAGGAGGAUCUUGGGGACGAUACGGGCAUCCACGUUAUCCCUACGU

UAAACGGCGAUGACAGACAUAAAAUUGUAAAUGUGGACCAACGUCAAUACGGUGACGUGUUUA

AAGGAGAUCUUAAUCCAAAACCCCAAGGCCAAAGACUCAUUGAGGUGUCAGUGGAAGAAAAUC

ACCCGUUUACUUUACGCGCACCGAUUCAGCGGAUUUAUGGAGUCCGGUACACCGAGACUUGGA

GCUUUUUGCCGUCAUUAACCUGUACGGGAGACGCAGCGCCCGCCAUCCAGCAUAUAUGUUUAA

AACAUACAACAUGCUUUCAAGACGUGGUGGUGGAUGUGGAUUGCGCGGAAAAUACUAAAGAGG

AUCAGUUGGCCGAAAUCAGUUACCGUUUUCAAGGUAAGAAGGAAGCGGACCAACCGUGGAUUG

UUGUAAACACGAGCACACUGUUUGAUGAACUCGAAUUAGACCCCCCCGAGAUUGAACCGGGUG

UCUUGAAAGUACUUCGGACAGAAAAACAAUACUUGGGUGUGUACAUUUGGAACAUGCGCGGCU

CCGAUGGUACGUCUACCUACGCCACGUUUUUGGUCACCUGGAAAGGGGAUGAAAAAACAAGAA

ACCCUACGCCCGCAGUAACUCCUCAACCAAGAGGGGCUGAGUUUCAUAUGUGGAAUUACCACUC

GCAUGUAUUUUCAGUUGGUGAUACGUUUAGCUUGGCAAUGCAUCUUCAGUAUAAGAUACAUGA

AGCGCCAUUUGAUUUGCUGUUAGAGUGGUUGUAUGUCCCCAUCGAUCCUACAUGUCAACCAAU

GCGGUUAUAUUCUACGUGUUUGUAUCAUCCCAACGCACCCCAAUGCCUCUCUCAUAUGAAUUCC

GGUUGUACAUUUACCUCGCCACAUUUAGCCCAGCGUGUUGCAAGCACAGUGUAUCAAAAUUGU

GAACAUGCAGAUAACUACACCGCAUAUUGUCUGGGAAUAUCUCAUAUGGAGCCUAGCUUUGGU

CUAAUCUUACACGACGGGGGCACCACGUUAAAGUUUGUAGAUACACCCGAGAGUUUGUCGGGA

UUAUACGUUUUUGUGGUGUAUUUUAACGGGCAUGUUGAAGCCGUAGCAUACACUGUUGUAUCC

ACAGUAGAUCAUUUUGUAAACGCAAUUGAAGAGCGUGGAUUUCCGCCAACGGCCGGUCAGCCA

CCGGCGACUACUAAACCCAAGGAAAUUACCCCCGUAAACCCCGGAACGUCACCACUUCUACGAU

AUGCCGCAUGGACCGGAGGGCUUGCAGCAGUAGUACUUUUAUGUCUCGUAAUAUUUUUAAUCU

GUACGGCUAAACGAAUGAGGGUUAAAGCCUAUAGGGUAGACAAGUCCCCGUAUAACCAAAGCA

UGUAUGGCGCUGGCCUUCCAGUGGACGAUUUCGAGGACGCCGAAGCCGCCGAUGCCGAAGAAG

AGUUUGGUAACGCGAUUGGAGGGAGUCACGGGGGUUCGAGUUACACGGUGUAUAUAGAUAAGA

CCCGGUGAUGAUAAUAGGCUGGAGCCUCGGUGGCCAUGCUUCUUGCCCCUUGGGCCUCCCCCCA

GCCCCUCCUCCCCUUCCUGCACCCGUACCCCCGUGGUCUUUGAAUAAAGUCUGAGUGGGCGGC

VZV_gE_Oka_hIgkappa (SEQ ID NO: 41)

TCAAGCTTTTGGACCCTCGTACAGAAGCTAATACGACTCACTATAGGGAAATAAGAGAGAAAAGA

AGAGTAAGAAGAAATATAAGAGCCACCATGGAGACTCCCGCTCAGCTACTGTTCCTCCTGCTCCTT

-continued

TGGCTGCCTGATACTACAGGCTCTGTTTTGCGGTACGACGACTTTCACATCGATGAGGACAAGCTC

GACACTAATAGCGTGTATGAGCCCTACTACCATTCAGATCACGCCGAGTCCTCTTGGGTGAACAGG

GGTGAAAGTTCTAGGAAAGCCTATGATCACAACAGCCCTTATATTTGGCCACGGAATGATTACGAC

GGATTTCTCGAAAATGCCCACGAGCATCACGGAGTGTACAACCAGGGCCGTGGAATCGACTCTGG

GGAGAGATTGATGCAACCTACACAGATGAGCGCCCAGGAAGATCTCGGGGATGATACAGGAATTC

ACGTTATCCCTACATTAAACGGAGATGACCGCCACAAAATCGTCAATGTCGATCAAAGACAGTAT

GGAGATGTGTTCAAAGGCGATCTCAACCCTAAGCCGCAGGGCCAGAGACTCATTGAGGTGTCTGT

CGAAGAGAACCACCCTTTCACTCTGCGCGCTCCCATTCAGAGAATCTATGGAGTTCGCTATACGGA

GACTTGGTCATTCCTTCCTTCCCTGACATGCACCGGAGACGCCGCCCCTGCCATTCAGCACATATG

CCTGAAACATACCACCTGTTTCCAGGATGTGGTGGTTGATGTTGATTGTGCTGAAAATACCAAGGA

AGACCAACTGGCCGAGATTAGTTACCGGTTCCAAGGGAAAAAGGAAGCCGACCAGCCATGGATTG

TGGTTAATACAAGCACTCTGTTCGATGAGCTCGAGCTGGATCCCCCCGAGATAGAACCCGGAGTTC

TGAAAGTGCTCCGGACAGAAAAACAATATCTGGGAGTCTACATATGGAACATGCGCGGTTCCGAT

GGGACCTCCACTTATGCAACCTTTCTCGTCACGTGGAAGGGAGATGAGAAAACTAGGAATCCCAC

ACCCGCTGTCACACCACAGCCAAGAGGGGCTGAGTTCCATATGTGGAACTATCATAGTCACGTGTT

TAGTGTCGGAGATACGTTTTCATTGGCTATGCATCTCCAGTACAAGATTCATGAGGCTCCCTTCGAT

CTGTTGCTTGAGTGGTTGTACGTCCCGATTGACCCGACCTGCCAGCCCATGCGACTGTACAGCACC

TGTCTCTACCATCCAAACGCTCCGCAATGTCTGAGCCACATGAACTCTGGGTGTACTTTCACCAGT

CCCCACCTCGCCCAGCGGGTGGCCTCTACTGTTTACCAGAACTGTGAGCACGCCGACAACTACACC

GCATACTGCCTCGGTATTTCTCACATGGAACCCTCCTTCGGACTCATCCTGCACGATGGGGGCACT

ACCCTGAAGTTCGTTGATACGCCAGAATCTCTGTCTGGGCTCTATGTTTTCGTGGTCTACTTCAATG

GCCATGTCGAGGCCGTGGCCTATACTGTCGTTTCTACCGTGGATCATTTTGTGAACGCCATCGAAG

AACGGGGATTCCCCCCTACGGCAGGCCAGCCGCCTGCAACCACCAAGCCCAAGGAAATAACACCA

GTGAACCCTGGCACCTCACCTCTCCTAAGATATGCCGCGTGGACAGGGGGACTGGCGGCAGTGGT

GCTCCTCTGTCTCGTGATCTTTCTGATCTGTACAGCCAAGAGGATGAGGGTCAAGGCTTATAGAGT

GGACAAGTCCCCCTACAATCAGTCAATGTACTACGCCGGCCTTCCCGTTGATGATTTTGAGGATTC

CGAGTCCACAGATACTGAGGAAGAGTTCGGTAACGCTATAGGCGGCTCTCACGGGGGTTCAAGCT

ACACGGTTTACATTGACAAGACACGCTGATAATAGGCTGGAGCCTCGGTGGCCATGCTTCTTGCCC

CTTGGGCCTCCCCCCAGCCCCTCCTCCCCTTCCTGCACCCGTACCCCCGTGGTCTTTGAATAAAGTC

TGAGTGGGCGGC

VZV_gE_Oka_hIgkappa (mRNA)

(SEQ ID NO: 131)

UCAAGCUUUUGGACCCUCGUACAGAAGCUAAUACGACUCACUAUAGGGAAAUAAGAGAGAAAA

GAAGAGUAAGAAGAAAUAUAAGAGCCACCAUGGAGACUCCCGCUCAGCUACUGUUCCUCCUGC

UCCUUUGGCUGCCUGAUACUACAGGCUCUGUUUUGCGGUACGACGACUUUCACAUCGAUGAGG

ACAAGCUCGACACUAAUAGCGUGUAUGAGCCCUACUACCAUUCAGAUCACGCCGAGUCCUCUUG

GGUGAACAGGGGUGAAAGUUCUAGGAAAGCCUAUGAUCACAACAGCCCUUAUAUUUGGCCACG

GAAUGAUUACGACGGAUUUCUCGAAAAUGCCCACGAGCAUCACGGAGUGUACAACCAGGGCCG

UGGAAUCGACUCUGGGGAGAGAUUGAUGCAACCUACACAGAUGAGCGCCCAGGAAGAUCUCGG

GGAUGAUACAGGAAUUCACGUUAUCCCUACAUUAAACGGAGAUGACCGCCACAAAAUCGUCAA

UGUCGAUCAAAGACAGUAUGGAGAUGUGUUCAAAGGCGAUCUCAACCCUAAGCCGCAGGGCCA

-continued

GAGACUCAUUGAGGUGUCUGUCGAAGAGAACCACCCUUUCACUCUGCGCGCUCCCAUUCAGAG

AAUCUAUGGAGUUCGCUAUACGGAGACUUGGUCAUUCCUUCCUUCCCUGACAUGCACCGGAGA

CGCCGCCCCUGCCAUUCAGCACAUAUGCCUGAAACAUACCACCUGUUUCCAGGAUGUGGUGGUU

GAUGUUGAUUGUGCUGAAAAUACCAAGGAAGACCAACUGGCCGAGAUUAGUUACCGGUUCCAA

GGGAAAAAGGAAGCCGACCAGCCAUGGAUUGUGGUUAAUACAAGCACUCUGUUCGAUGAGCUC

GAGCUGGAUCCCCCCGAGAUAGAACCCGGAGUUCUGAAAGUGCUCCGGACAGAAAAACAAUAU

CUGGGAGUCUACAUAUGGAACAUGCGCGGUUCCGAUGGGACCUCCACUUAUGCAACCUUUCUC

GUCACGUGGAAGGGAGAUGAGAAAACUAGGAAUCCCACACCCGCUGUCACACCACAGCCAAGA

GGGGCUGAGUUCCAUAUGUGGAACUAUCAUAGUCACGUGUUUAGUGUCGGAGAUACGUUUUCA

UUGGCUAUGCAUCUCCAGUACAAGAUUCAUGAGGCUCCCUUCGAUCUGUUGCUUGAGUGGUUG

UACGUCCCGAUUGACCCGACCUGCCAGCCCAUGCGACUGUACAGCACCUGUCUCUACCAUCCAA

ACGCUCCGCAAUGUCUGAGCCACAUGAACUCUGGGUGUACUUUCACCAGUCCCCACCUCGCCCA

GCGGGUGGCCUCUACUGUUUACCAGAACUGUGAGCACGCCGACAACUACACCGCAUACUGCCUC

GGUAUUUCUCACAUGGAACCCUCCUUCGGACUCAUCCUGCACGAUGGGGGCACUACCCUGAAGU

UCGUUGAUACGCCAGAAUCUCUGUCUGGGCUCUAUGUUUUCGUGGUCUACUUCAAUGGCCAUG

UCGAGGCCGUGGCCUAUACUGUCGUUUCUACCGUGGAUCAUUUUGUGAACGCCAUCGAAGAAC

GGGGAUUCCCCCCUACGGCAGGCCAGCCGCCUGCAACCACCAAGCCCAAGGAAAUAACACCAGU

GAACCCUGGCACCUCACCUCUCCUAAGAUAUGCCGCGUGGACAGGGGGACUGGCGGCAGUGGU

GCUCCUCUGUCUCGUGAUCUUUCUGAUCUGUACAGCCAAGAGGAUGAGGGUCAAGGCUUAUAG

AGUGGACAAGUCCCCCUACAAUCAGUCAAUGUACUACGCCGGCCUUCCCGUUGAUGAUUUUGA

GGAUUCCGAGUCCACAGAUACUGAGGAAGAGUUCGGUAACGCUAUAGGCGGCUCUCACGGGGG

UUCAAGCUACACGGUUUACAUUGACAAGACACGCUGAUAAUAGGCUGGAGCCUCGGUGGCCAU

GCUUCUUGCCCCUUGGGCCUCCCCCCAGCCCCUCCUCCCCUUCCUGCACCCGUACCCCCGUGGUC

UUUGAAUAAAGUCUGAGUGGGCGGC

TABLE 2

Sequences of Variant VZV gE Constructs

| mRNA Name(s) | Sequence, NT(5' UTR, ORF, 3' UTR) | ORF Sequence, AA | ORF Sequence, NT | mRNA Sequence (assumes T100 tail) |
|---|---|---|---|---|
| | SEQ ID NO: 9 | SEQ ID NO: 10 | SEQ ID NO: 11 | SEQ ID NO: 12 |
| VZV_gE_ | TCAAGCTTTTGG | MGTVNKPVVGVLMGFGI | ATGGGGACAGTGAATAA | G*GGGAAATAAG |
| Oka | ACCCTCGTACAG | ITGTLRITNPVRASVLR | GCCGGTTGTGGGCGTGC | AGAGAAAAGAAG |
| | AAGCTAATACGA | YDDFHIDEDKLDTNSVY | TTATGGGCTTTGGGATT | AGTAAGAAGAAA |
| | CTCACTATAGGG | EPYYHSDHAESSWVNRG | ATTACCGGTACATTACG | TATAAGAGCCAC |
| | AAATAAGAGAGA | ESSRKAYDHNSPYIWPR | AATTACCAATCCAGTGC | CATGGGGACAGT |
| | AAAGAAGAGTAA | NDYDGFLENAHEHHGVY | GCGCCAGTGTGCTGCGT | GAATAAGCCGGT |
| | GAAGAAATATAA | NQGRGIDSGERLMQPTQ | TACGACGACTTTCACAT | TGTGGGCGTGCT |
| | GAGCCACCATGG | MSAQEDLGDDTGIHVIP | TGACGAGGATAAGCTGG | TATGGGCTTTGG |
| | GGACAGTGAATA | TLNGDDRHKIVNVDQRQ | ATACTAACAGCGTGTAC | GATTATTACCGG |
| | AGCCGGTTGTGG | YGDVFKGDLNPKPQGQR | GAACCTTATTACCACTC | TACATTACGAAT |
| | GCGTGCTTATGG | LIEVSVEENHPFTLRAP | AGATCATGCCGAATCAA | TACCAATCCAGT |
| | GCTTTGGGATTA | IQRIYGVRYTETWSFLP | GCTGGGTTAATAGAGGA | GCGCGCCAGTGT |
| | TTACCGGTACAT | SLTCTGDAAPAIQHICL | GAAAGCAGCCGAAAAGC | GCTGCGTTACGA |
| | TACGAATTACCA | KHTTCFQDVVVDVDCAE | CTACGACCACAACTCAC | CGACTTTCACAT |
| | ATCCAGTGCGCG | NTKEDQLAEISYRFQGK | CTTATATTTGGCCCAGA | TGACGAGGATAA |
| | CCAGTGTGCTGC | KEADQPWIVVNTSTLFD | AACGATTATGACGGTTT | GCTGGATACTAA |
| | GTTACGACGACT | ELELDPPEIEPGVLKVL | CCTGGAAAACGCACATG | CAGCGTGTACGA |
| | TTCACATTGACG | RTEKQYLGVYIWNMRGS | AACACCATGGAGTCTAC | ACCTTATTACCA |
| | AGGATAAGCTGG | DGTSTYATFLVTWKGDE | AACCAAGGCAGGGGAAT | CTCAGATCATGC |
| | ATACTAACAGCG | KTRNPTPAVTPQPRGAE | CGACAGTGGCGAGCGTC | CGAATCAAGCTG |
| | TGTACGAACCTT | FHMWNYHSHVFSVGDTF | TTATGCAGCCAACACAG | GGTTAATAGAGG |

TABLE 2-continued

| | | | |
|---|---|---|---|
| ATTACCACTCAG | SLAMHLQYKIHEAPFDL | ATGTCGGCACAGGAGGA | AGAAAGCAGCCG |
| ATCATGCCGAAT | LLEWLYVPIDPTCQPMR | TCTCGGTGATGACACCG | AAAAGCCTACGA |
| CAAGCTGGGTTA | LYSTCLYHPNAPQCLSH | GCATACACGTGATTCCC | CCACAACTCACC |
| ATAGAGGAGAAA | MNSGCTFTSPHLAQRVA | ACATTAAACGGCGACGA | TTATATTTGGCC |
| GCAGCCGAAAAG | STVYQNCEHADNYTAYC | CAGACATAAGATCGTCA | CAGAAACGATTA |
| CCTACGACCACA | LGISHMEPSFGLILHDG | ATGTGGATCAGCGTCAG | TGACGGTTTCCT |
| ACTCACCTTATA | GTTLKFVDTPESLSGLY | TATGGGGATGTCTTTAA | GGAAAACGCACA |
| TTTGGCCCAGAA | VFVVYFNGHVEAVAYTV | AGGCGATTTGAATCCAA | TGAACACCATGG |
| ACGATTATGACG | VSTVDHFVNAIEERGFP | AGCCCCAAGGACAGAGA | AGTCTACAACCA |
| GTTTCCTGGAAA | PTAGQPPATTKPKEITP | CTGATCGAGGTCTCTGT | AGGCAGGGGAAT |
| ACGCACATGAAC | VNPGTSPLLRYAAWTGG | AGAAGAAAATCACCCCT | CGACAGTGGCGA |
| ACCATGGAGTCT | LAAVVLLCLVIFLICTA | TCACTTTGCGCGCTCCA | GCGTCTTATGCA |
| ACAACCAAGGCA | KRMRVKAYRVDKSPYNQ | ATCCAGAGGATTTACGG | GCCAACACAGAT |
| GGGGAATCGACA | SMYYAGLPVDDFEDSES | GGTGCGTTATACCGAAA | GTCGGCACAGGA |
| GTGGCGAGCGTC | TDTEEEFGNAIGGSHGG | CTTGGAGTTTCTTGCCG | GGATCTCGGTGA |
| TTATGCAGCCAA | SSYTVYIDKTR | TCACTGACGTGTACGGG | TGACACCGGCAT |
| CACAGATGTCGG | | GGATGCCGCCCCCGCAA | ACACGTGATTCC |
| CACAGGAGGATC | | TCCAGCACATCTGTCTG | CACATTAAACGG |
| TCGGTGATGACA | | AAACACACCACATGCTT | CGACGACAGACA |
| CCGGCATACACG | | TCAGGACGTGGTTGTGG | TAAGATCGTCAA |
| TGATTCCCACAT | | ATGTGGATTGCGCGGAA | TGTGGATCAGCG |
| TAAACGGCGACG | | AACACAAAAGAAGACCA | TCAGTATGGGGA |
| ACAGACATAAGA | | ACTCGCCGAAATCAGCT | TGTCTTTAAAGG |
| TCGTCAATGTGG | | ATCGTTTTCAGGGTAAA | CGATTTGAATCC |
| ATCAGCGTCAGT | | AAAGAGGCCGACCAACC | AAAGCCCCAAGG |
| ATGGGGATGTCT | | GTGGATTGTTGTGAATA | ACAGAGACTGAT |
| TTAAAGGCGATT | | CGAGCACGCTCTTCGAT | CGAGGTCTCTGT |
| TGAATCCAAAGC | | GAGCTTGAACTCGATCC | AGAAGAAAATCA |
| CCCAAGGACAGA | | CCCGGAAATCGAGCCTG | CCCCTTCACTTT |
| GACTGATCGAGG | | GGGTTCTAAAAGTGTTG | GCGCGCTCCAAT |
| TCTCTGTAGAAG | | AGGACCGAGAAGCAGTA | CCAGAGGATTTA |
| AAAATCACCCCT | | CCTCGGGGTTTATATCT | CGGGGTGCGTTA |
| TCACTTTGCGCG | | GGAATATGAGAGGCTCC | TACCGAAACTTG |
| CTCCAATCCAGA | | GATGGCACCTCTACCTA | GAGTTTCTTGCC |
| GGATTTACGGGG | | CGCAACGTTTCTGGTTA | GTCACTGACGTG |
| TGCGTTATACCG | | CCTGGAAGGGAGACGAG | TACGGGGGATGC |
| AAACTTGGAGTT | | AAGACACGGAATCCAAC | CGCCCCCGCAAT |
| TCTTGCCGTCAC | | GCCCGCTGTGACCCCTC | CCAGCACATCTG |
| TGACGTGTACGG | | AGCCTAGGGGAGCCGAA | TCTGAAACACAC |
| GGGATGCCGCCC | | TTCCACATGTGGAACTA | CACATGCTTTCA |
| CCGCAATCCAGC | | TCACTCCCATGTATTCA | GGACGTGGTTGT |
| ACATCTGTCTGA | | GTGTGGGTGACACTTTC | GGATGTGGATTG |
| AACACACCACAT | | AGCCTGGCCATGCACCT | CGCGGAAAACAC |
| GCTTTCAGGACG | | GCAGTATAAGATTCACG | AAAAGAAGACCA |
| TGGTTGTGGATG | | AGGCACCCTTCGACCTC | ACTCGCCGAAAT |
| TGGATTGCGCGG | | CTGCTGGAGTGGTTGTA | CAGCTATCGTTT |
| AAAACACAAAAG | | CGTACCTATTGATCCCA | TCAGGGTAAAAA |
| AAGACCAACTCG | | CTTGTCAGCCCATGCGC | AGAGGCCGACCA |
| CCGAAATCAGCT | | CTGTACTCCACTTGCTT | ACCGTGGATTGT |
| ATCGTTTTCAGG | | GTACCACCCCAATGCAC | TGTGAATACGAG |
| GTAAAAAAGAGG | | CACAGTGTCTATCACAC | CACGCTCTTCGA |
| CCGACCAACCGT | | ATGAACTCCGGGTGTAC | TGAGCTTGAACT |
| GGATTGTTGTGA | | CTTTACTTCACCCCATC | CGATCCCCCGGA |
| ATACGAGCACGC | | TTGCCCAGCGGGTCGCC | AATCGAGCCTGG |
| TCTTCGATGAGC | | AGCACAGTGTATCAGAA | GGTTCTAAAAGT |
| TTGAACTCGATC | | CTGTGAGCATGCTGACA | GTTGAGGACCGA |
| CCCCGGAAATCG | | ACTATACTGCTTATTGC | GAAGCAGTACCT |
| AGCCTGGGGTTC | | CTCGGAATATCCCATAT | CGGGGTTTATAT |
| TAAAAGTGTTGA | | GGAGCCAAGCTTCGGGC | CTGGAATATGAG |
| GGACCGAGAAGC | | TCATACTGCACGATGGT | AGGCTCCGATGG |
| AGTACCTCGGGG | | GGTACGACACTCAAGTT | CACCTCTACCTA |
| TTTATATCTGGA | | CGTGGACACCCCCGAAA | CGCAACGTTTCT |
| ATATGAGAGGCT | | GCCTTTCTGGCTTGTAC | GGTTACCTGGAA |
| CCGATGGCACCT | | GTGTTCGTGGTCTACTT | GGGAGACGAGAA |
| CTACCTACGCAA | | CAATGGACATGTGGAGG | GACACGGAATCC |
| CGTTTCTGGTTA | | CAGTGGCTTACACAGTG | AACGCCCGCTGT |
| CCTGGAAGGGAG | | GTTTCGACAGTTGATCA | GACCCCTCAGCC |
| ACGAGAAGACAC | | CTTTGTAAATGCCATTG | TAGGGGAGCCGA |
| GGAATCCAACGC | | AGGAACGCGGCTTCCCG | ATTCCACATGTG |
| CCGCTGTGACCC | | CCTACAGCGGGCCAGCC | GAACTATCACTC |
| CTCAGCCTAGGG | | CCCTGCGACAACAAAAC | CCATGTATTCAG |
| GAGCCGAATTCC | | CAAAAGAGATTACGCCC | TGTGGGTGACAC |
| ACATGTGGAACT | | GTTAATCCTGGGACTAG | TTTCAGCCTGGC |
| ATCACTCCCATG | | TCCATTGCTGAGGTATG | CATGCACCTGCA |
| TATTCAGTGTGG | | CCGCCTGGACTGGCGGT | GTATAAGATTCA |
| GTGACACTTTCA | | CTGGCGGCCGTGGTACT | CGAGGCACCCTT |
| GCCTGGCCATGC | | TCTGTGTTTAGTCATAT | CGACCTCCTGCT |
| ACCTGCAGTATA | | TTCTGATCTGTACCGCT | GGAGTGGTTGTA |
| AGATTCACGAGG | | AAACGTATGCGGGTCAA | CGTACCTATTGA |
| CACCCTTCGACC | | GGCTTACCGTGTTGACA | TCCCACTTGTCA |

TABLE 2-continued

| | | |
|---|---|---|
| TCCTGCTGGAGT | AGTCTCCTTACAATCAG | GCCCATGCGCCT |
| GGTTGTACGTAC | TCAATGTACTATGCAGG | GTACTCCACTTG |
| CTATTGATCCCA | ACTCCCTGTTGACGATT | CTTGTACCACCC |
| CTTGTCAGCCCA | TCGAAGACTCAGAGAGT | CAATGCACCACA |
| TGCGCCTGTACT | ACAGACACAGAAGAAGA | GTGTCTATCACA |
| CCACTTGCTTGT | ATTCGGAAACGCTATAG | CATGAACTCCGG |
| ACCACCCCAATG | GTGGCTCTCACGGAGGT | GTGTACCTTTAC |
| CACCACAGTGTC | AGCTCGTATACAGTGTA | TTCACCCCATCT |
| TATCACACATGA | CATCGATAAAACCAGA | TGCCCAGCGGGT |
| ACTCCGGGTGTA | | CGCCAGCACAGT |
| CCTTTACTTCAC | | GTATCAGAACTG |
| CCCATCTTGCCC | | TGAGCATGCTGA |
| AGCGGGTCGCCA | | CAACTATACTGC |
| GCACAGTGTATC | | TTATTGCCTCGG |
| AGAACTGTGAGC | | AATATCCCATAT |
| ATGCTGACAACT | | GGAGCCAAGCTT |
| ATACTGCTTATT | | CGGGCTCATACT |
| GCCTCGGAATAT | | GCACGATGGTGG |
| CCCATATGGAGC | | TACGACACTCAA |
| CAAGCTTCGGGC | | GTTCGTGGACAC |
| TCATACTGCACG | | CCCCGAAAGCCT |
| ATGGTGGTACGA | | TTCTGGCTTGTA |
| CACTCAAGTTCG | | CGTGTTCGTGGT |
| TGGACACCCCCG | | CTACTTCAATGG |
| AAAGCCTTTCTG | | ACATGTGGAGGC |
| GCTTGTACGTGT | | AGTGGCTTACAC |
| TCGTGGTCTACT | | AGTGGTTTCGAC |
| TCAATGGACATG | | AGTTGATCACTT |
| TGGAGGCAGTGG | | TGTAAATGCCAT |
| CTTACACAGTGG | | TGAGGAACGCGG |
| TTTCGACAGTTG | | CTTCCCGCCTAC |
| ATCACTTTGTAA | | AGCGGGCCAGCC |
| ATGCCATTGAGG | | CCCTGCGACAAC |
| AACGCGGCTTCC | | AAAACCAAAAGA |
| CGCCTACAGCGG | | GATTACGCCCGT |
| GCCAGCCCCCTG | | TAATCCTGGGAC |
| CGACAACAAAAC | | TAGTCCATTGCT |
| CAAAAGAGATTA | | GAGGTATGCCGC |
| CGCCCGTTAATC | | CTGGACTGGCGG |
| CTGGGACTAGTC | | TCTGGCGGCCGT |
| CATTGCTGAGGT | | GGTACTTCTGTG |
| ATGCCGCCTGGA | | TTTAGTCATATT |
| CTGGCGGTCTGG | | TCTGATCTGTAC |
| CGGCCGTGGTAC | | CGCTAAACGTAT |
| TTCTGTGTTTAG | | GCGGGTCAAGGC |
| TCATATTTCTGA | | TTACCGTGTTGA |
| TCTGTACCGCTA | | CAAGTCTCCTTA |
| AACGTATGCGGG | | CAATCAGTCAAT |
| TCAAGGCTTACC | | GTACTATGCAGG |
| GTGTTGACAAGT | | ACTCCCTGTTGA |
| CTCCTTACAATC | | CGATTTCGAAGA |
| AGTCAATGTACT | | CTCAGAGAGTAC |
| ATGCAGGACTCC | | AGACACAGAAGA |
| CTGTTGACGATT | | AGAATTCGGAAA |
| TCGAAGACTCAG | | CGCTATAGGTGG |
| AGAGTACAGACA | | CTCTCACGGAGG |
| CAGAAGAAGAAT | | TAGCTCGTATAC |
| TCGGAAACGCTA | | AGTGTACATCGA |
| TAGGTGGCTCTC | | TAAAACCAGATG |
| ACGGAGGTAGCT | | ATAATAGGCTGG |
| CGTATACAGTGT | | AGCCTCGGTGGC |
| ACATCGATAAAA | | CATGCTTCTTGC |
| CCAGATGATAAT | | CCCTTGGGCCTC |
| AGGCTGGAGCCT | | CCCCCAGCCCCT |
| CGGTGGCCATGC | | CCTCCCCTTCCT |
| TTCTTGCCCCTT | | GCACCCGTACCC |
| GGGCCTCCCCCC | | CCGTGGTCTTTG |
| AGCCCCTCCTCC | | AATAAAGTCTGA |
| CCTTCCTGCACC | | GTGGGCGGCAAA |
| CGTACCCCCGTG | | AAAAAAAAAAAA |
| GTCTTTGAATAA | | AAAAAAAAAAAA |
| AGTCTGAGTGGG | | AAAAAAAAAAAA |
| CGGC | | AAAAAAAAAAAA |
| | | AAAAAAAAAAAA |
| | | AAAAAAAAAAAA |
| | | AAAAAAAAAAAA |
| | | AAAAAAAAAAAA |
| | | ATCTAG |

TABLE 2-continued

| | SEQ ID NO: 13 | SEQ ID NO: 14 | SEQ ID NO: 15 | SEQ ID NO: 16 |
|---|---|---|---|---|
| VZV_gE_ Oka_hIg kappa | TCAAGCTTTTGG ACCCTCGTACAG AAGCTAATACGA CTCACTATAGGG AAATAAGAGAGA AAAGAAGAGTAA GAAGAAATATAA GAGCCACCATGG AGACTCCCGCTC AGCTACTGTTCC TCCTGCTCCTTT GGCTGCCTGATA CTACAGGCTCTG TTTTGCGGTACG ACGACTTTCACA TCGATGAGGACA AGCTCGACACTA ATAGCGTGTATG AGCCCTACTACC ATTCAGATCACG CCGAGTCCTCTT GGGTGAACAGGG GTGAAAGTTCTA GGAAAGCCTATG ATCACAACAGCC CTTATATTTGGC CACGGAATGATT ACGACGGATTTC TCGAAAATGCCC ACGAGCATCACG GAGTGTACAACC AGGGCCGTGGAA TCGACTCTGGGG AGAGATTGATGC AACCTACACAGA TGAGCGCCCAGG AAGATCTCGGGG ATGATACAGGAA TTCACGTTATCC CTACATTAAACG GAGATGACCGCC ACAAAATCGTCA ATGTCGATCAAA GACAGTATGGAG ATGTGTTCAAAG GCGATCTCAACC CTAAGCCGCAGG GCCAGAGACTCA TTGAGGTGTCTG TCGAAGAGAACC ACCCTTTCACTC TGCGCGCTCCCA TTCAGAGAATCT ATGGAGTTCGCT ATACGGAGACTT GGTCATTCCTTC CTTCCCTGACAT GCACCGGAGACG CCGCCCCTGCCA TTCAGCACATAT GCCTGAAACATA CCACCTGTTTCC AGGATGTGGTGG TTGATGTTGATT GTGCTGAAAATA CCAAGGAAGACC AACTGGCCGAGA TTAGTTACCGGT TCCAAGGGAAAA AGGAAGCCGACC AGCCATGGATTG TGGTTAATACAA GCACTCTGTTCG ATGAGCTCGAGC TGGATCCCCCCG AGATAGAACCCG GAGTTCTGAAAG TGCTCCGGACAG | METPAQLLFLLLLWLPD TTGSVLRYDDFHIDEDK LDTNSVYEPYYHSDHAE SSWVNRGESSRKAYDHN SPYIWPRNDYDGFLENA HEHHGVYNQGRGIDSGE RLMQPTQMSAQEDLGDD TGIHVIPTLNGDDRHKI VNVDQRQYGDVFKGDLN PKPQGQRLIEVSVEENH PFTLRAPIQRIYGVRYT ETWSFLPSLTCTGDAAP AIQHICLKHTTCFQDVV VDVDCAENTKEDQLAEI SYRFQGKKEADQPWIVV NTSTLFDELELDPPEIE PGVLKVLRTEKQYLGVY IWNMRGSDGTSTYATFL VTWKGDEKTRNPTPAVT PQPRGAEFHMWNYHSHV FSVGDTFSLAMHLQYKI HEAPFDLLLEWLYVPID PTCQPMRLYSTCLYHPN APQCLSHMNSGCTFTSP HLAQRVASTVYQNCEHA DNYTAYCLGISHMEPSF GLILHDGGTTLKFVDTP ESLSGLYVFVVYFNGHV EAVAYTVVSTVDHFVNA IEERGFPPTAGQPPATT KPKEITPVNPGTSPLLR YAAWTGGLAAVVLLCLV IFLICTAKRMRVKAYRV DKSPYNQSMYYAGLPVD DFEDSESTDTEEEFGNA IGGSHGGSSYTVYIDKT R | ATGGAGACTCCCGCTCA GCTACTGTTCCTCCTGC TCCTTTGGCTGCCTGAT ACTACAGGCTCTGTTTT GCGGTACGACGACTTTC ACATCGATGAGGACAAG CTCGACACTAATAGCGT GTATGAGCCCTACTACC ATTCAGATCACGCCGAG TCCTCTTGGGTGAACAG GGGTGAAAGTTCTAGGA AAGCCTATGATCACAAC AGCCCTTATATTTGGCC ACGGAATGATTACGACG GATTTCTCGAAAATGCC CACGAGCATCACGGAGT GTACAACCAGGGCCGTG GAATCGACTCTGGGGAG AGATTGATGCAACCTAC ACAGATGAGCGCCCAGG AAGATCTCGGGGATGAT ACAGGAATTCACGTTAT CCCTACATTAAACGGAG ATGACCGCCACAAAATC GTCAATGTCGATCAAAG ACAGTATGGAGATGTGT TCAAAGGCGATCTCAAC CCTAAGCCGCAGGGCCA GAGACTCATTGAGGTGT CTGTCGAAGAGAACCAC CCTTTCACTCTGCGCGC TCCCATTCAGAGAATCT ATGGAGTTCGCTATACG GAGACTTGGTCATTCCT TCCTTCCCTGACATGCA CCGGAGACGCCGCCCCT GCCATTCAGCACATATG CCTGAAACATACCACCT GTTTCCAGGATGTGGTG GTTGATGTTGATTGTGC TGAAAATACCAAGGAAG ACCAACTGGCCGAGATT AGTTACCGGTTCCAAGG GAAAAAGGAAGCCGACC AGCCATGGATTGTGGTT AATACAAGCACTCTGTT CGATGAGCTCGAGCTGG ATCCCCCCGAGATAGAA CCCGGAGTTCTGAAAGT GCTCCGGACAGAAAAAC AATATCTGGGAGTCTAC ATATGGAACATGCGCGG TTCCGATGGGACCTCCA CTTATGCAACCTTTCTC GTCACGTGGAAGGGAGA TGAGAAAACTAGGAATC CCACACCCGCTGTCACA CCACAGCCAAGAGGGGC TGAGTTCCATATGTGGA ACTATCATAGTCACGTG TTTAGTGTCGGAGATAC GTTTTCATTGGCTATGC ATCTCCAGTACAAGATT CATGAGGCTCCCTTCGA TCTGTTGCTTGAGTGGT TGTACGTCCCGATTGAC CCGACCTGCCAGCCCAT GCGACTGTACAGCACCT GTCTCTACCATCCAAAC GCTCCGCAATGTCTGAG CCACATGAACTCTGGGT GTACTTTCACCAGTCCC CACCTCGCCCAGCGGGT GGCCTCTACTGTTTACC AGAACTGTGAGCACGCC GACAACTACACCGCATA CTGCCTCGGTATTTCTC ACATGGAACCCTCCTTC | G*GGGAAATAAG AGAGAAAAGAAG AGTAAGAAGAAA TATAAGAGCCAC CATGGAGACTCC CGCTCAGCTACT GTTCCTCCTGCT CCTTTGGCTGCC TGATACTACAGG CTCTGTTTTGCG GTACGACGACTT TCACATCGATGA GGACAAGCTCGA CACTAATAGCGT GTATGAGCCCTA CTACCATTCAGA TCACGCCGAGTC CTCTTGGGTGAA CAGGGGTGAAAG TTCTAGGAAAGC CTATGATCACAA CAGCCCTTATAT TTGGCCACGGAA TGATTACGACGG ATTTCTCGAAAA TGCCCACGAGCA TCACGGAGTGTA CAACCAGGGCCG TGGAATCGACTC TGGGGAGAGATT GATGCAACCTAC ACAGATGAGCGC CCAGGAAGATCT CGGGGATGATAC AGGAATTCACGT TATCCCTACATT AAACGGAGATGA CCGCCACAAAAT CGTCAATGTCGA TCAAAGACAGTA TGGAGATGTGTT CAAAGGCGATCT CAACCCTAAGCC GCAGGGCCAGAG ACTCATTGAGGT GTCTGTCGAAGA GAACCACCCTTT CACTCTGCGCGC TCCCATTCAGAG AATCTATGGAGT TCGCTATACGGA GACTTGGTCATT CCTTCCTTCCCT GACATGCACCGG AGACGCCGCCCC TGCCATTCAGCA CATATGCCTGAA ACATACCACCTG TTTCCAGGATGT GGTGGTTGATGT TGATTGTGCTGA AAATACCAAGGA AGACCAACTGGC CGAGATTAGTTA CCGGTTCCAAGG GAAAAAGGAAGC CGACCAGCCATG GATTGTGGTTAA TACAAGCACTCT GTTCGATGAGCT CGAGCTGGATCC CCCCGAGATAGA ACCCGGAGTTCT GAAAGTGCTCCG GACAGAAAAACA ATATCTGGGAGT CTACATATGGAA CATGCGCGGTTC |

TABLE 2-continued

| | | |
|---|---|---|
| AAAAACAATATC | GGACTCATCCTGCACGA | CGATGGGACCTC |
| TGGGAGTCTACA | TGGGGGCACTACCCTGA | CACTTATGCAAC |
| TATGGAACATGC | AGTTCGTTGATACGCCA | CTTTCTCGTCAC |
| GCGGTTCCGATG | GAATCTCTGTCTGGGCT | GTGGAAGGGAGA |
| GGACCTCCACTT | CTATGTTTTCGTGGTCT | TGAGAAAACTAG |
| ATGCAACCTTTC | ACTTCAATGGCCATGTC | GAATCCCACACC |
| TCGTCACGTGGA | GAGGCCGTGGCCTATAC | CGCTGTCACACC |
| AGGGAGATGAGA | TGTCGTTTCTACCGTGG | ACAGCCAAGAGG |
| AAACTAGGAATC | ATCATTTTGTGAACGCC | GGCTGAGTTCCA |
| CCACACCCGCTG | ATCGAAGAACGGGGATT | TATGTGGAACTA |
| TCACACCACAGC | CCCCCCTACGGCAGGCC | TCATAGTCACGT |
| CAAGAGGGGCTG | AGCCGCCTGCAACCACC | GTTTAGTGTCGG |
| AGTTCCATATGT | AAGCCCAAGGAAATAAC | AGATACGTTTTC |
| GGAACTATCATA | ACCAGTGAACCCTGGCA | ATTGGCTATGCA |
| GTCACGTGTTTA | CCTCACCTCTCCTAAGA | TCTCCAGTACAA |
| GTGTCGGAGATA | TATGCCGCGTGGACAGG | GATTCATGAGGC |
| CGTTTTCATTGG | GGGACTGGCGGCAGTGG | TCCCTTCGATCT |
| CTATGCATCTCC | TGCTCCTCTGTCTCGTG | GTTGCTTGAGTG |
| AGTACAAGATTC | ATCTTTCTGATCTGTAC | GTTGTACGTCCC |
| ATGAGGCTCCCT | AGCCAAGAGGATGAGGG | GATTGACCCGAC |
| TCGATCTGTTGC | TCAAGGCTTATAGAGTG | CTGCCAGCCCAT |
| TTGAGTGGTTGT | GACAAGTCCCCCTACAA | GCGACTGTACAG |
| ACGTCCCGATTG | TCAGTCAATGTACTACG | CACCTGTCTCTA |
| ACCCGACCTGCC | CCGGCCTTCCCGTTGAT | CCATCCAAACGC |
| AGCCCATGCGAC | GATTTTGAGGATTCCGA | TCCGCAATGTCT |
| TGTACAGCACCT | GTCCACAGATACTGAGG | GAGCCACATGAA |
| GTCTCTACCATC | AAGAGTTCGGTAACGCT | CTCTGGGTGTAC |
| CAAACGCTCCGC | ATAGGCGGCTCTCACGG | TTTCACCAGTCC |
| AATGTCTGAGCC | GGGTTCAAGCTACACGG | CCACCTCGCCCA |
| ACATGAACTCTG | TTTACATTGACAAGACA | GCGGGTGGCCTC |
| GGTGTACTTTCA | CGC | TACTGTTTACCA |
| CCAGTCCCCACC | | GAACTGTGAGCA |
| TCGCCCAGCGGG | | CGCCGACAACTA |
| TGGCCTCTACTG | | CACCGCATACTG |
| TTTACCAGAACT | | CCTCGGTATTTC |
| GTGAGCACGCCG | | TCACATGGAACC |
| ACAACTACACCG | | CTCCTTCGGACT |
| CATACTGCCTCG | | CATCCTGCACGA |
| GTATTTCTCACA | | TGGGGGCACTAC |
| TGGAACCCTCCT | | CCTGAAGTTCGT |
| TCGGACTCATCC | | TGATACGCCAGA |
| TGCACGATGGGG | | ATCTCTGTCTGG |
| GCACTACCCTGA | | GCTCTATGTTTT |
| AGTTCGTTGATA | | CGTGGTCTACTT |
| CGCCAGAATCTC | | CAATGGCCATGT |
| TGTCTGGGCTCT | | CGAGGCCGTGGC |
| ATGTTTTCGTGG | | CTATACTGTCGT |
| TCTACTTCAATG | | TTCTACCGTGGA |
| GCCATGTCGAGG | | TCATTTTGTGAA |
| CCGTGGCCTATA | | CGCCATCGAAGA |
| CTGTCGTTTCTA | | ACGGGGATTCCC |
| CCGTGGATCATT | | CCCTACGGCAGG |
| TTGTGAACGCCA | | CCAGCCGCCTGC |
| TCGAAGAACGGG | | AACCACCAAGCC |
| GATTCCCCCCTA | | CAAGGAAATAAC |
| CGGCAGGCCAGC | | ACCAGTGAACCC |
| CGCCTGCAACCA | | TGGCACCTCACC |
| CCAAGCCCAAGG | | TCTCCTAAGATA |
| AAATAACACCAG | | TGCCGCGTGGAC |
| TGAACCCTGGCA | | AGGGGGACTGGC |
| CCTCACCTCTCC | | GGCAGTGGTGCT |
| TAAGATATGCCG | | CCTCTGTCTCGT |
| CGTGGACAGGGG | | GATCTTTCTGAT |
| GACTGGCGGCAG | | CTGTACAGCCAA |
| TGGTGCTCCTCT | | GAGGATGAGGGT |
| GTCTCGTGATCT | | CAAGGCTTATAG |
| TTCTGATCTGTA | | AGTGGACAAGTC |
| CAGCCAAGAGGA | | CCCCTACAATCA |
| TGAGGGTCAAGG | | GTCAATGTACTA |
| CTTATAGAGTGG | | CGCCGGCCTTCC |
| ACAAGTCCCCCT | | CGTTGATGATTT |
| ACAATCAGTCAA | | TGAGGATTCCGA |
| TGTACTACGCCG | | GTCCACAGATAC |
| GCCTTCCCGTTG | | TGAGGAAGAGTT |
| ATGATTTTGAGG | | CGGTAACGCTAT |
| ATTCCGAGTCCA | | AGGCGGCTCTCA |
| CAGATACTGAGG | | CGGGGGTTCAAG |
| AAGAGTTCGGTA | | CTACACGGTTTA |
| ACGCTATAGGCG | | CATTGACAAGAC |
| GCTCTCACGGGG | | ACGCTGATAATA |

TABLE 2-continued

| | | | | |
|---|---|---|---|---|
| | GTTCAAGCTACA | | | GGCTGGAGCCTC |
| | CGGTTTACATTG | | | GGTGGCCATGCT |
| | ACAAGACACGCT | | | TCTTGCCCCTTG |
| | GATAATAGGCTG | | | GGCCTCCCCCCA |
| | GAGCCTCGGTGG | | | GCCCCTCCTCCC |
| | CCATGCTTCTTG | | | CTTCCTGCACCC |
| | CCCCTTGGGCCT | | | GTACCCCCGTGG |
| | CCCCCCAGCCCC | | | TCTTTGAATAAA |
| | TCCTCCCCTTCC | | | GTCTGAGTGGGC |
| | TGCACCCGTACC | | | GGCAAAAAAAAA |
| | CCCGTGGTCTTT | | | AAAAAAAAAAAA |
| | GAATAAAGTCTG | | | AAAAAAAAAAAA |
| | AGTGGGCGGC | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAATCTAG |
| | SEQ ID NO: 17 | SEQ ID NO: 18 | SEQ ID NO: 19 | SEQ ID NO: 20 |
| VZV-GE- | TCAAGCTTTTGG | MGTVNKPVVGVLMGFGI | ATGGGGACAGTTAATAA | G*GGGAAATAAG |
| delete- | ACCCTCGTACAG | ITGTLRITNPVRASVLR | ACCTGTGGTGGGGGTAT | AGAGAAAAGAAG |
| 562 | AAGCTAATACGA | YDDFHIDEDKLDTNSVY | TGATGGGGTTCGGAATT | AGTAAGAAGAAA |
| | CTCACTATAGGG | EPYYHSDHAESSWVNRG | ATCACGGGAACGTTGCG | TATAAGAGCCAC |
| | AAATAAGAGAGA | ESSRKAYDHNSPYIWPR | TATAACGAATCCGGTCA | CATGGGGACAGT |
| | AAAGAAGAGTAA | NDYDGFLENAHEHHGVY | GAGCATCCGTCTTGCGA | TAATAAACCTGT |
| | GAAGAAATATAA | NQGRGIDSGERLMQPTQ | TACGATGATTTTCACAT | GGTGGGGGTATT |
| | GAGCCACCATGG | MSAQEDLGDDTGIHVIP | CGATGAAGACAAACTGG | GATGGGGTTCGG |
| | GGACAGTTAATA | TLNGDDRHKIVNVDQRQ | ATACAAACTCCGTATAT | AATTATCACGGG |
| | AACCTGTGGTGG | YGDVFKGDLNPKPQGQR | GAGCCTTACTACCATTC | AACGTTGCGTAT |
| | GGGTATTGATGG | LIEVSVEENHPFTLRAP | AGATCATGCGGAGTCTT | AACGAATCCGGT |
| | GGTTCGGAATTA | IQRIYGVRYTETWSFLP | CATGGGTAAATCGGGGA | CAGAGCATCCGT |
| | TCACGGGAACGT | SLTCTGDAAPAIQHICL | GAGTCTTCGCGAAAAGC | CTTGCGATACGA |
| | TGCGTATAACGA | KHTTCFQDVVVDVDCAE | GTACGATCATAACTCAC | TGATTTTCACAT |
| | ATCCGGTCAGAG | NTKEDQLAEISYRFQGK | CTTATATATGGCCACGT | CGATGAAGACAA |
| | CATCCGTCTTGC | KEADQPWIVVNTSTLFD | AATGATTATGATGGATT | ACTGGATACAAA |
| | GATACGATGATT | ELELDPPEIEPGVLKVL | TTTAGAGAACGCACACG | CTCCGTATATGA |
| | TTCACATCGATG | RTEKQYLGVYIWNMRGS | AACACCATGGGGTGTAT | GCCTTACTACCA |
| | AAGACAAACTGG | DGTSTYATFLVTWKGDE | AATCAGGGCCGTGGTAT | TTCAGATCATGC |
| | ATACAAACTCCG | KTRNPTPAVTPQPRGAE | CGATAGCGGGGAACGGT | GGAGTCTTCATG |
| | TATATGAGCCTT | FHMWNYHSHVFSVGDTF | TAATGCAACCCACACAA | GGTAAATCGGGG |
| | ACTACCATTCAG | SLAMHLQYKIHEAPFDL | ATGTCTGCACAGGAGGA | AGAGTCTTCGCG |
| | ATCATGCGGAGT | LLEWLYVPIDPTCQPMR | TCTTGGGGACGATACGG | AAAAGCGTACGA |
| | CTTCATGGGTAA | LYSTCLYHPNAPQCLSH | GCATCCACGTTATCCCT | TCATAACTCACC |
| | ATCGGGGAGAGT | MNSGCTFTSPHLAQRVA | ACGTTAAACGGCGATGA | TTATATATGGCC |
| | CTTCGCGAAAAG | STVYQNCEHADNYTAYC | CAGACATAAAATTGTAA | ACGTAATGATTA |
| | CGTACGATCATA | LGISHMEPSFGLILHDG | ATGTGGACCAACGTCAA | TGATGGATTTTT |
| | ACTCACCTTATA | GTTLKFVDTPESLSGLY | TACGGTGACGTGTTTAA | AGAGAACGCACA |
| | TATGGCCACGTA | VFVVYFNGHVEAVAYTV | AGGAGATCTTAATCCAA | CGAACACCATGG |
| | ATGATTATGATG | VSTVDHFVNAIEERGFP | AACCCCAAGGCCAAAGA | GGTGTATAATCA |
| | GATTTTTAGAGA | PTAGQPPATTKPKEITP | CTCATTGAGGTGTCAGT | GGGCCGTGGTAT |
| | ACGCACACGAAC | VNPGTSPLLRYAAWTGG | GGAAGAAAATCACCCGT | CGATAGCGGGGA |
| | ACCATGGGGTGT | LAAVVLLCLVIFLICTA | TTACTTTACGCGCACCG | ACGGTTAATGCA |
| | ATAATCAGGGCC | * | ATTCAGCGGATTTATGG | ACCCACACAAAT |
| | GTGGTATCGATA | | AGTCCGGTACACCGAGA | GTCTGCACAGGA |
| | GCGGGGAACGGT | | CTTGGAGCTTTTTGCCG | GGATCTTGGGGA |
| | TAATGCAACCCA | | TCATTAACCTGTACGGG | CGATACGGGCAT |
| | CACAAATGTCTG | | AGACGCAGCGCCCGCCA | CCACGTTATCCC |
| | CACAGGAGGATC | | TCCAGCATATATGTTTA | TACGTTAAACGG |
| | TTGGGGACGATA | | AAACATACAACATGCTT | CGATGACAGACA |
| | CGGGCATCCACG | | TCAAGACGTGGTGGTGG | TAAAATTGTAAA |
| | TTATCCCTACGT | | ATGTGGATTGCGCGGAA | TGTGGACCAACG |
| | TAAACGGCGATG | | AATACTAAAGAGGATCA | TCAATACGGTGA |
| | ACAGACATAAAA | | GTTGGCCGAAATCAGTT | CGTGTTTAAAGG |
| | TTGTAAATGTGG | | ACCGTTTTCAAGGTAAG | AGATCTTAATCC |
| | ACCAACGTCAAT | | AAGGAAGCGGACCAACC | AAAACCCCAAGG |
| | ACGGTGACGTGT | | GTGGATTGTTGTAAACA | CCAAAGACTCAT |
| | TTAAAGGAGATC | | CGAGCACACTGTTTGAT | TGAGGTGTCAGT |
| | TTAATCCAAAAC | | GAACTCGAATTAGACCC | GGAAGAAAATCA |
| | CCCAAGGCCAAA | | CCCCGAGATTGAACCGG | CCCGTTTACTTT |
| | GACTCATTGAGG | | GTGTCTTGAAAGTACTT | ACGCGCACCGAT |
| | TGTCAGTGGAAG | | CGGACAGAAAAACAATA | TCAGCGGATTTA |
| | AAAATCACCCGT | | CTTGGGTGTGTACATTT | TGGAGTCCGGTA |
| | TTACTTTACGCG | | GGAACATGCGCGGCTCC | CACCGAGACTTG |
| | CACCGATTCAGC | | GATGGTACGTCTACCTA | GAGCTTTTTGCC |
| | GGATTTATGGAG | | CGCCACGTTTTTGGTCA | GTCATTAACCTG |
| | TCCGGTACACCG | | CCTGGAAAGGGGATGAA | TACGGGAGACGC |
| | AGACTTGGAGCT | | AAAACAAGAAACCCTAC | AGCGCCCGCCAT |
| | TTTTGCCGTCAT | | GCCCGCAGTAACTCCTC | CCAGCATATATG |

TABLE 2-continued

| | | |
|---|---|---|
| TAACCTGTACGG | AACCAAGAGGGGCTGAG | TTTAAAACATAC |
| GAGACGCAGCGC | TTTCATATGTGGAATTA | AACATGCTTTCA |
| CCGCCATCCAGC | CCACTCGCATGTATTTT | AGACGTGGTGGT |
| ATATATGTTTAA | CAGTTGGTGATACGTTT | GGATGTGGATTG |
| AACATACAACAT | AGCTTGGCAATGCATCT | CGCGGAAAATAC |
| GCTTTCAAGACG | TCAGTATAAGATACATG | TAAAGAGGATCA |
| TGGTGGTGGATG | AAGCGCCATTTGATTTG | GTTGGCCGAAAT |
| TGGATTGCGCGG | CTGTTAGAGTGGTTGTA | CAGTTACCGTTT |
| AAAATACTAAAG | TGTCCCCATCGATCCTA | TCAAGGTAAGAA |
| AGGATCAGTTGG | CATGTCAACCAATGCGG | GGAAGCGGACCA |
| CCGAAATCAGTT | TTATATTCTACGTGTTT | ACCGTGGATTGT |
| ACCGTTTTCAAG | GTATCATCCCAACGCAC | TGTAAACACGAG |
| GTAAGAAGGAAG | CCCAATGCCTCTCTCAT | CACACTGTTTGA |
| CGGACCAACCGT | ATGAATTCCGGTTGTAC | TGAACTCGAATT |
| GGATTGTTGTAA | ATTTACCTCGCCACATT | AGACCCCCCCGA |
| ACACGAGCACAC | TAGCCCAGCGTGTTGCA | GATTGAACCGGG |
| TGTTTGATGAAC | AGCACAGTGTATCAAAA | TGTCTTGAAAGT |
| TCGAATTAGACC | TTGTGAACATGCAGATA | ACTTCGGACAGA |
| CCCCCGAGATTG | ACTACACCGCATATTGT | AAAACAATACTT |
| AACCGGGTGTCT | CTGGGAATATCTCATAT | GGGTGTGTACAT |
| TGAAAGTACTTC | GGAGCCTAGCTTTGGTC | TTGGAACATGCG |
| GGACAGAAAAAC | TAATCTTACACGACGGG | CGGCTCCGATGG |
| AATACTTGGGTG | GGCACCACGTTAAAGTT | TACGTCTACCTA |
| TGTACATTTGGA | TGTAGATACACCCGAGA | CGCCACGTTTTT |
| ACATGCGCGGCT | GTTTGTCGGGATTATAC | GGTCACCTGGAA |
| CCGATGGTACGT | GTTTTTGTGGTGTATTT | AGGGGATGAAAA |
| CTACCTACGCCA | TAACGGGCATGTTGAAG | AACAAGAAACCC |
| CGTTTTTGGTCA | CCGTAGCATACACTGTT | TACGCCCGCAGT |
| CCTGGAAAGGGG | GTATCCACAGTAGATCA | AACTCCTCAACC |
| ATGAAAAAACAA | TTTTGTAAACGCAATTG | AAGAGGGGCTGA |
| GAAACCCTACGC | AAGAGCGTGGATTTCCG | GTTTCATATGTG |
| CCGCAGTAACTC | CCAACGGCCGGTCAGCC | GAATTACCACTC |
| CTCAACCAAGAG | ACCGGCGACTACTAAAC | GCATGTATTTTC |
| GGGCTGAGTTTC | CCAAGGAAATTACCCCC | AGTTGGTGATAC |
| ATATGTGGAATT | GTAAACCCCGGAACGTC | GTTTAGCTTGGC |
| ACCACTCGCATG | ACCACTTCTACGATATG | AATGCATCTTCA |
| TATTTTCAGTTG | CCGCATGGACCGGAGGG | GTATAAGATACA |
| GTGATACGTTTA | CTTGCAGCAGTAGTACT | TGAAGCGCCATT |
| GCTTGGCAATGC | TTTATGTCTCGTAATAT | TGATTTGCTGTT |
| ATCTTCAGTATA | TTTTAATCTGTACGGCT | AGAGTGGTTGTA |
| AGATACATGAAG | TGA | TGTCCCCATCGA |
| CGCCATTTGATT | | TCCTACATGTCA |
| TGCTGTTAGAGT | | ACCAATGCGGTT |
| GGTTGTATGTCC | | ATATTCTACGTG |
| CCATCGATCCTA | | TTTGTATCATCC |
| CATGTCAACCAA | | CAACGCACCCCA |
| TGCGGTTATATT | | ATGCCTCTCTCA |
| CTACGTGTTTGT | | TATGAATTCCGG |
| ATCATCCCAACG | | TTGTACATTTAC |
| CACCCCAATGCC | | CTCGCCACATTT |
| TCTCTCATATGA | | AGCCCAGCGTGT |
| ATTCCGGTTGTA | | TGCAAGCACAGT |
| CATTTACCTCGC | | GTATCAAAATTG |
| CACATTTAGCCC | | TGAACATGCAGA |
| AGCGTGTTGCAA | | TAACTACACCGC |
| GCACAGTGTATC | | ATATTGTCTGGG |
| AAAATTGTGAAC | | AATATCTCATAT |
| ATGCAGATAACT | | GGAGCCTAGCTT |
| ACACCGCATATT | | TGGTCTAATCTT |
| GTCTGGGAATAT | | ACACGACGGGGG |
| CTCATATGGAGC | | CACCACGTTAAA |
| CTAGCTTTGGTC | | GTTTGTAGATAC |
| TAATCTTACACG | | ACCCGAGAGTTT |
| ACGGGGGCACCA | | GTCGGGATTATA |
| CGTTAAAGTTTG | | CGTTTTTGTGGT |
| TAGATACACCCG | | GTATTTTAACGG |
| AGAGTTTGTCGG | | GCATGTTGAAGC |
| GATTATACGTTT | | CGTAGCATACAC |
| TTGTGGTGTATT | | TGTTGTATCCAC |
| TTAACGGGCATG | | AGTAGATCATTT |
| TTGAAGCCGTAG | | TGTAAACGCAAT |
| CATACACTGTTG | | TGAAGAGCGTGG |
| TATCCACAGTAG | | ATTTCCGCCAAC |
| ATCATTTTGTAA | | GGCCGGTCAGCC |
| ACGCAATTGAAG | | ACCGGCGACTAC |
| AGCGTGGATTTC | | TAAACCCAAGGA |
| CGCCAACGGCCG | | AATTACCCCCGT |
| GTCAGCCACCGG | | AAACCCCGGAAC |
| CGACTACTAAAC | | GTCACCACTTCT |
| CCAAGGAAATTA | | ACGATATGCCGC |

TABLE 2-continued

| | | | | |
|---|---|---|---|---|
| | CCCCCGTAAACC | | | ATGGACCGGAGG |
| | CCGGAACGTCAC | | | GCTTGCAGCAGT |
| | CACTTCTACGAT | | | AGTACTTTTATG |
| | ATGCCGCATGGA | | | TCTCGTAATATT |
| | CCGGAGGGCTTG | | | TTTAATCTGTAC |
| | CAGCAGTAGTAC | | | GGCTTGATGATA |
| | TTTTATGTCTCG | | | ATAGGCTGGAGC |
| | TAATATTTTTAA | | | CTCGGTGGCCAT |
| | TCTGTACGGCTT | | | GCTTCTTGCCCC |
| | GATGATAATAGG | | | TTGGGCCTCCCC |
| | CTGGAGCCTCGG | | | CCAGCCCCTCCT |
| | TGGCCATGCTTC | | | CCCCTTCCTGCA |
| | TTGCCCCTTGGG | | | CCCGTACCCCCG |
| | CCTCCCCCCAGC | | | TGGTCTTTGAAT |
| | CCCTCCTCCCCT | | | AAAGTCTGAGTG |
| | TCCTGCACCCGT | | | GGCGGCAAAAAA |
| | ACCCCCGTGGTC | | | AAAAAAAAAAAA |
| | TTTGAATAAAGT | | | AAAAAAAAAAAA |
| | CTGAGTGGGCGG | | | AAAAAAAAAAAA |
| | C | | | AAAAAAAAAAAA |
| | | | | AAAAAAAAAAAA |
| | | | | AAAAAAAAAAAA |
| | | | | AAAAAAAAAAAA |
| | | | | AAAAAAAAAATC |
| | | | | TAG |
| | SEQ ID NO: 21 | SEQ ID NO: 22 | SEQ ID NO: 23 | SEQ ID NO: 24 |
| VZV-GE- | TCAAGCTTTTGG | METPAQLLFLLLLWLPD | ATGGAAACCCCGGCGCA | G*GGGAAATAAG |
| delete- | ACCCTCGTACAG | TTGSVLRYDDFHIDEDK | GCTGCTGTTTCTGCTGC | AGAGAAAAGAAG |
| 562- | AAGCTAATACGA | LDTNSVYEPYYHSDHAE | TGCTGTGGCTGCCGGAT | AGTAAGAAGAAA |
| replace | CTCACTATAGGG | SSWVNRGESSRKAYDHN | ACCACCGGCTCCGTCTT | TATAAGAGCCAC |
| dSP- | AAATAAGAGAGA | SPYIWPRNDYDGFLENA | GCGATACGATGATTTTC | CATGGAAACCCC |
| withIgKappa | AAAGAAGAGTAA | HEHHGVYNQGRGIDSGE | ACATCGATGAAGACAAA | GGCGCAGCTGCT |
| | GAAGAAATATAA | RLMQPTQMSAQEDLGDD | CTGGATACAAACTCCGT | GTTTCTGCTGCT |
| | GAGCCACCATGG | TGIHVIPTLNGDDRHKI | ATATGAGCCTTACTACC | GCTGTGGCTGCC |
| | AAACCCCGGCGC | VNVDQRQYGDVFKGDLN | ATTCAGATCATGCGGAG | GGATACCACCGG |
| | AGCTGCTGTTTC | PKPQGQRLIEVSVEENH | TCTTCATGGGTAAATCG | CTCCGTCTTGCG |
| | TGCTGCTGCTGT | PFTLRAPIQRIYGVRYT | GGGAGAGTCTTCGCGAA | ATACGATGATTT |
| | GGCTGCCGGATA | ETWSFLPSLTCTGDAAP | AAGCGTACGATCATAAC | TCACATCGATGA |
| | CCACCGGCTCCG | AIQHICLKHTTCFQDVV | TCACCTTATATATGGCC | AGACAAACTGGA |
| | TCTTGCGATACG | VDVDCAENTKEDQLAEI | ACGTAATGATTATGATG | TACAAACTCCGT |
| | ATGATTTTCACA | SYRFQGKKEADQPWIVV | GATTTTTAGAGAACGCA | ATATGAGCCTTA |
| | TCGATGAAGACA | NTSTLFDELELDPPEIE | CACGAACACCATGGGGT | CTACCATTCAGA |
| | AACTGGATACAA | PGVLKVLRTEKQYLGVY | GTATAATCAGGGCCGTG | TCATGCGGAGTC |
| | ACTCCGTATATG | IWNMRGSDGTSTYATFL | GTATCGATAGCGGGGAA | TTCATGGGTAAA |
| | AGCCTTACTACC | VTWKGDEKTRNPTPAVT | CGGTTAATGCAACCCAC | TCGGGGAGAGTC |
| | ATTCAGATCATG | PQPRGAEFHMWNYHSHV | ACAAATGTCTGCACAGG | TTCGCGAAAAGC |
| | CGGAGTCTTCAT | FSVGDTFSLAMHLQYKI | AGGATCTTGGGGACGAT | GTACGATCATAA |
| | GGGTAAATCGGG | HEAPFDLLLEWLYVPID | ACGGGCATCCACGTTAT | CTCACCTTATAT |
| | GAGAGTCTTCGC | PTCQPMRLYSTCLYHPN | CCCTACGTTAAACGGCG | ATGGCCACGTAA |
| | GAAAAGCGTACG | APQCLSHMNSGCTFTSP | ATGACAGACATAAAATT | TGATTATGATGG |
| | ATCATAACTCAC | HLAQRVASTVYQNCEHA | GTAAATGTGGACCAACG | ATTTTTAGAGAA |
| | CTTATATATGGC | DNYTAYCLGISHMEPSF | TCAATACGGTGACGTGT | CGCACACGAACA |
| | CACGTAATGATT | GLILHDGGTTLKFVDTP | TTAAAGGAGATCTTAAT | CCATGGGGTGTA |
| | ATGATGGATTTT | ESLSGLYVFVVYFNGHV | CCAAAACCCCAAGGCCA | TAATCAGGGCCG |
| | TAGAGAACGCAC | EAVAYTVVSTVDHFVNA | AAGACTCATTGAGGTGT | TGGTATCGATAG |
| | ACGAACACCATG | IEERGFPPTAGQPPATT | CAGTGGAAGAAAATCAC | CGGGGAACGGTT |
| | GGGTGTATAATC | KPKEITPVNPGTSPLLR | CCGTTTACTTTACGCGC | AATGCAACCCAC |
| | AGGGCCGTGGTA | YAAWTGGLAAVVLLCLV | ACCGATTCAGCGGATTT | ACAAATGTCTGC |
| | TCGATAGCGGGG | IFLICTA* | ATGGAGTCCGGTACACC | ACAGGAGGATCT |
| | AACGGTTAATGC | | GAGACTTGGAGCTTTTT | TGGGGACGATAC |
| | AACCCACACAAA | | GCCGTCATTAACCTGTA | GGGCATCCACGT |
| | TGTCTGCACAGG | | CGGGAGACGCAGCGCCC | TATCCCTACGTT |
| | AGGATCTTGGGG | | GCCATCCAGCATATATG | AAACGGCGATGA |
| | ACGATACGGGCA | | TTTAAAACATACAACAT | CAGACATAAAAT |
| | TCCACGTTATCC | | GCTTTCAAGACGTGGTG | TGTAAATGTGGA |
| | CTACGTTAAACG | | GTGGATGTGGATTGCGC | CCAACGTCAATA |
| | GCGATGACAGAC | | GGAAAATACTAAAGAGG | CGGTGACGTGTT |
| | ATAAAATTGTAA | | ATCAGTTGGCCGAAATC | TAAAGGAGATCT |
| | ATGTGGACCAAC | | AGTTACCGTTTTCAAGG | TAATCCAAAACC |
| | GTCAATACGGTG | | TAAGAAGGAAGCGGACC | CCAAGGCCAAAG |
| | ACGTGTTTAAAG | | AACCGTGGATTGTTGTA | ACTCATTGAGGT |
| | GAGATCTTAATC | | AACACGAGCACACTGTT | GTCAGTGGAAGA |
| | CAAAACCCCAAG | | TGATGAACTCGAATTAG | AAATCACCCGTT |
| | GCCAAAGACTCA | | ACCCCCCCGAGATTGAA | TACTTTACGCGC |
| | TTGAGGTGTCAG | | CCGGGTGTCTTGAAAGT | ACCGATTCAGCG |
| | TGGAAGAAAATC | | ACTTCGGACAGAAAAAC | GATTTATGGAGT |
| | ACCCGTTTACTT | | AATACTTGGGTGTGTAC | CCGGTACACCGA |
| | TACGCGCACCGA | | ATTTGGAACATGCGCGG | GACTTGGAGCTT |

TABLE 2-continued

| | | |
|---|---|---|
| TTCAGCGGATTT | CTCCGATGGTACGTCTA | TTTGCCGTCATT |
| ATGGAGTCCGGT | CCTACGCCACGTTTTTG | AACCTGTACGGG |
| ACACCGAGACTT | GTCACCTGGAAAGGGGA | AGACGCAGCGCC |
| GGAGCTTTTTGC | TGAAAAAACAAGAAACC | CGCCATCCAGCA |
| CGTCATTAACCT | CTACGCCCGCAGTAACT | TATATGTTTAAA |
| GTACGGGAGACG | CCTCAACCAAGAGGGGC | ACATACAACATG |
| CAGCGCCCGCCA | TGAGTTTCATATGTGGA | CTTTCAAGACGT |
| TCCAGCATATAT | ATTACCACTCGCATGTA | GGTGGTGGATGT |
| GTTTAAAACATA | TTTTCAGTTGGTGATAC | GGATTGCGCGGA |
| CAACATGCTTTC | GTTTAGCTTGGCAATGC | AAATACTAAAGA |
| AAGACGTGGTGG | ATCTTCAGTATAAGATA | GGATCAGTTGGC |
| TGGATGTGGATT | CATGAAGCGCCATTTGA | CGAAATCAGTTA |
| GCGCGGAAAATA | TTTGCTGTTAGAGTGGT | CCGTTTTCAAGG |
| CTAAAGAGGATC | TGTATGTCCCCATCGAT | TAAGAAGGAAGC |
| AGTTGGCCGAAA | CCTACATGTCAACCAAT | GGACCAACCGTG |
| TCAGTTACCGTT | GCGGTTATATTCTACGT | GATTGTTGTAAA |
| TTCAAGGTAAGA | GTTTGTATCATCCCAAC | CACGAGCACACT |
| AGGAAGCGGACC | GCACCCCAATGCCTCTC | GTTTGATGAACT |
| AACCGTGGATTG | TCATATGAATTCCGGTT | CGAATTAGACCC |
| TTGTAAACACGA | GTACATTTACCTCGCCA | CCCCGAGATTGA |
| GCACACTGTTTG | CATTTAGCCCAGCGTGT | ACCGGGTGTCTT |
| ATGAACTCGAAT | TGCAAGCACAGTGTATC | GAAAGTACTTCG |
| TAGACCCCCCCG | AAAATTGTGAACATGCA | GACAGAAAAACA |
| AGATTGAACCGG | GATAACTACACCGCATA | ATACTTGGGTGT |
| GTGTCTTGAAAG | TTGTCTGGGAATATCTC | GTACATTTGGAA |
| TACTTCGGACAG | ATATGGAGCCTAGCTTT | CATGCGCGGCTC |
| AAAAACAATACT | GGTCTAATCTTACACGA | CGATGGTACGTC |
| TGGGTGTGTACA | CGGGGGCACCACGTTAA | TACCTACGCCAC |
| TTTGGAACATGC | AGTTTGTAGATACACCC | GTTTTTGGTCAC |
| GCGGCTCCGATG | GAGAGTTTGTCGGGATT | CTGGAAAGGGGA |
| GTACGTCTACCT | ATACGTTTTTGTGGTGT | TGAAAAAACAAG |
| ACGCCACGTTTT | ATTTTAACGGGCATGTT | AAACCCTACGCC |
| TGGTCACCTGGA | GAAGCCGTAGCATACAC | CGCAGTAACTCC |
| AAGGGGATGAAA | TGTTGTATCCACAGTAG | TCAACCAAGAGG |
| AAACAAGAAACC | ATCATTTTGTAAACGCA | GGCTGAGTTTCA |
| CTACGCCCGCAG | ATTGAAGAGCGTGGATT | TATGTGGAATTA |
| TAACTCCTCAAC | TCCGCCAACGGCCGGTC | CCACTCGCATGT |
| CAAGAGGGGCTG | AGCCACCGGCGACTACT | ATTTTCAGTTGG |
| AGTTTCATATGT | AAACCCAAGGAAATTAC | TGATACGTTTAG |
| GGAATTACCACT | CCCCGTAAACCCCGGAA | CTTGGCAATGCA |
| CGCATGTATTTT | CGTCACCACTTCTACGA | TCTTCAGTATAA |
| CAGTTGGTGATA | TATGCCGCATGGACCGG | GATACATGAAGC |
| CGTTTAGCTTGG | AGGGCTTGCAGCAGTAG | GCCATTTGATTT |
| CAATGCATCTTC | TACTTTTATGTCTCGTA | GCTGTTAGAGTG |
| AGTATAAGATAC | ATATTTTTAATCTGTAC | GTTGTATGTCCC |
| ATGAAGCGCCAT | GGCTTGA | CATCGATCCTAC |
| TTGATTTGCTGT | | ATGTCAACCAAT |
| TAGAGTGGTTGT | | GCGGTTATATTC |
| ATGTCCCCATCG | | TACGTGTTTGTA |
| ATCCTACATGTC | | TCATCCCAACGC |
| AACCAATGCGGT | | ACCCCAATGCCT |
| TATATTCTACGT | | CTCTCATATGAA |
| GTTTGTATCATC | | TTCCGGTTGTAC |
| CCAACGCACCCC | | ATTTACCTCGCC |
| AATGCCTCTCTC | | ACATTTAGCCCA |
| ATATGAATTCCG | | GCGTGTTGCAAG |
| GTTGTACATTTA | | CACAGTGTATCA |
| CCTCGCCACATT | | AAATTGTGAACA |
| TAGCCCAGCGTG | | TGCAGATAACTA |
| TTGCAAGCACAG | | CACCGCATATTG |
| TGTATCAAAATT | | TCTGGGAATATC |
| GTGAACATGCAG | | TCATATGGAGCC |
| ATAACTACACCG | | TAGCTTTGGTCT |
| CATATTGTCTGG | | AATCTTACACGA |
| GAATATCTCATA | | CGGGGGCACCAC |
| TGGAGCCTAGCT | | GTTAAAGTTTGT |
| TTGGTCTAATCT | | AGATACACCCGA |
| TACACGACGGGG | | GAGTTTGTCGGG |
| GCACCACGTTAA | | ATTATACGTTTT |
| AGTTTGTAGATA | | TGTGGTGTATTT |
| CACCCGAGAGTT | | TAACGGGCATGT |
| TGTCGGGATTAT | | TGAAGCCGTAGC |
| ACGTTTTTGTGG | | ATACACTGTTGT |
| TGTATTTTAACG | | ATCCACAGTAGA |
| GGCATGTTGAAG | | TCATTTTGTAAA |
| CCGTAGCATACA | | CGCAATTGAAGA |
| CTGTTGTATCCA | | GCGTGGATTTCC |
| CAGTAGATCATT | | GCCAACGGCCGG |
| TTGTAAACGCAA | | TCAGCCACCGGC |
| TTGAAGAGCGTG | | GACTACTAAACC |

TABLE 2-continued

| | | | | |
|---|---|---|---|---|
| | GATTTCCGCCAA | | | CAAGGAAATTAC |
| | CGGCCGGTCAGC | | | CCCCGTAAACCC |
| | CACCGGCGACTA | | | CGGAACGTCACC |
| | CTAAACCCAAGG | | | ACTTCTACGATA |
| | AAATTACCCCCG | | | TGCCGCATGGAC |
| | TAAACCCCGGAA | | | CGGAGGGCTTGC |
| | CGTCACCACTTC | | | AGCAGTAGTACT |
| | TACGATATGCCG | | | TTTATGTCTCGT |
| | CATGGACCGGAG | | | AATATTTTTAAT |
| | GGCTTGCAGCAG | | | CTGTACGGCTTG |
| | TAGTACTTTTAT | | | ATGATAATAGGC |
| | GTCTCGTAATAT | | | TGGAGCCTCGGT |
| | TTTTAATCTGTA | | | GGCCATGCTTCT |
| | CGGCTTGATGAT | | | TGCCCCTTGGGC |
| | AATAGGCTGGAG | | | CTCCCCCCAGCC |
| | CCTCGGTGGCCA | | | CCTCCTCCCCTT |
| | TGCTTCTTGCCC | | | CCTGCACCCGTA |
| | CTTGGGCCTCCC | | | CCCCCGTGGTCT |
| | CCCAGCCCCTCC | | | TTGAATAAAGTC |
| | TCCCCTTCCTGC | | | TGAGTGGGCGGC |
| | ACCCGTACCCCC | | | AAAAAAAAAAAA |
| | GTGGTCTTTGAA | | | AAAAAAAAAAAA |
| | TAAAGTCTGAGT | | | AAAAAAAAAAAA |
| | GGGCGGC | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAATCTAG |

| | SEQ ID NO: 25 | SEQ ID NO: 26 | SEQ ID NO: 27 | SEQ ID NO: 28 |
|---|---|---|---|---|
| VZV-GE- | TCAAGCTTTTGG | MGTVNKPVVGVLMGFGI | ATGGGGACAGTTAATAA | G*GGGAAATAAG |
| full_with_ | ACCCTCGTACAG | ITGTLRITNPVRASVLR | ACCTGTGGTGGGGGTAT | AGAGAAAAGAAG |
| AEAADA | AAGCTAATACGA | YDDFHIDEDKLDTNSVY | TGATGGGGTTCGGAATT | AGTAAGAAGAAA |
| (SEQ | CTCACTATAGGG | EPYYHSDHAESSWVNRG | ATCACGGGAACGTTGCG | TATAAGAGCCAC |
| ID NO: | AAATAAGAGAGA | ESSRKAYDHNSPYIWPR | TATAACGAATCCGGTCA | CATGGGGACAGT |
| 58) | AAAGAAGAGTAA | NDYDGFLENAHEHHGVY | GAGCATCCGTCTTGCGA | TAATAAACCTGT |
| | GAAGAAATATAA | NQGRGIDSGERLMQPTQ | TACGATGATTTTCACAT | GGTGGGGGTATT |
| | GAGCCACCATGG | MSAQEDLGDDTGIHVIP | CGATGAAGACAAACTGG | GATGGGGTTCGG |
| | GGACAGTTAATA | TLNGDDRHKIVNVDQRQ | ATACAAACTCCGTATAT | AATTATCACGGG |
| | AACCTGTGGTGG | YGDVFKGDLNPKPQGQR | GAGCCTTACTACCATTC | AACGTTGCGTAT |
| | GGGTATTGATGG | LIEVSVEENHPFTLRAP | AGATCATGCGGAGTCTT | AACGAATCCGGT |
| | GGTTCGGAATTA | IQRIYGVRYTETWSFLP | CATGGGTAAATCGGGGA | CAGAGCATCCGT |
| | TCACGGGAACGT | SLTCTGDAAPAIQHICL | GAGTCTTCGCGAAAAGC | CTTGCGATACGA |
| | TGCGTATAACGA | KHTTCFQDVVVDVDCAE | GTACGATCATAACTCAC | TGATTTTCACAT |
| | ATCCGGTCAGAG | NTKEDQLAEISYRFQGK | CTTATATATGGCCACGT | CGATGAAGACAA |
| | CATCCGTCTTGC | KEADQPWIVVNTSTLFD | AATGATTATGATGGATT | ACTGGATACAAA |
| | GATACGATGATT | ELELDPPEIEPGVLKVL | TTTAGAGAACGCACACG | CTCCGTATATGA |
| | TTCACATCGATG | RTEKQYLGVYIWNMRGS | AACACCATGGGGTGTAT | GCCTTACTACCA |
| | AAGACAAACTGG | DGTSTYATFLVTWKGDE | AATCAGGGCCGTGGTAT | TTCAGATCATGC |
| | ATACAAACTCCG | KTRNPTPAVTPQPRGAE | CGATAGCGGGGAACGGT | GGAGTCTTCATG |
| | TATATGAGCCTT | FHMWNYHSHVFSVGDTF | TAATGCAACCCACACAA | GGTAAATCGGGG |
| | ACTACCATTCAG | SLAMHLQYKIHEAPFDL | ATGTCTGCACAGGAGGA | AGAGTCTTCGCG |
| | ATCATGCGGAGT | LLEWLYVPIDPTCQPMR | TCTTGGGGACGATACGG | AAAAGCGTACGA |
| | CTTCATGGGTAA | LYSTCLYHPNAPQCLSH | GCATCCACGTTATCCCT | TCATAACTCACC |
| | ATCGGGGAGAGT | MNSGCTFTSPHLAQRVA | ACGTTAAACGGCGATGA | TTATATATGGCC |
| | CTTCGCGAAAAG | STVYQNCEHADNYTAYC | CAGACATAAAATTGTAA | ACGTAATGATTA |
| | CGTACGATCATA | LGISHMEPSFGLILHDG | ATGTGGACCAACGTCAA | TGATGGATTTTT |
| | ACTCACCTTATA | GTTLKFVDTPESLSGLY | TACGGTGACGTGTTTAA | AGAGAACGCACA |
| | TATGGCCACGTA | VFVVYFNGHVEAVAYTV | AGGAGATCTTAATCCAA | CGAACACCATGG |
| | ATGATTATGATG | VSTVDHFVNAIEERGFP | AACCCCAAGGCCAAAGA | GGTGTATAATCA |
| | GATTTTTAGAGA | PTAGQPPATTKPKEITP | CTCATTGAGGTGTCAGT | GGGCCGTGGTAT |
| | ACGCACACGAAC | VNPGTSPLLRYAAWTGG | GGAAGAAAATCACCCGT | CGATAGCGGGGA |
| | ACCATGGGGTGT | LAAVVLLCLVIFLICTA | TTACTTTACGCGCACCG | ACGGTTAATGCA |
| | ATAATCAGGGCC | KRMRVKAYRVDKSPYNQ | ATTCAGCGGATTTATGG | ACCCACACAAAT |
| | GTGGTATCGATA | SMYYAGLPVDDFEDAEA | AGTCCGGTACACCGAGA | GTCTGCACAGGA |
| | GCGGGGAACGGT | ADAEEEFGNAIGGSHGG | CTTGGAGCTTTTTGCCG | GGATCTTGGGGA |
| | TAATGCAACCCA | SSYTVYIDKTR* | TCATTAACCTGTACGGG | CGATACGGGCAT |
| | CACAAATGTCTG | | AGACGCAGCGCCCGCCA | CCACGTTATCCC |
| | CACAGGAGGATC | | TCCAGCATATATGTTTA | TACGTTAAACGG |
| | TTGGGGACGATA | | AAACATACAACATGCTT | CGATGACAGACA |
| | CGGGCATCCACG | | TCAAGACGTGGTGGTGG | TAAAATTGTAAA |
| | TTATCCCTACGT | | ATGTGGATTGCGCGGAA | TGTGGACCAACG |
| | TAAACGGCGATG | | AATACTAAAGAGGATCA | TCAATACGGTGA |
| | ACAGACATAAAA | | GTTGGCCGAAATCAGTT | CGTGTTTAAAGG |
| | TTGTAAATGTGG | | ACCGTTTTCAAGGTAAG | AGATCTTAATCC |
| | ACCAACGTCAAT | | AAGGAAGCGGACCAACC | AAAACCCCAAGG |
| | ACGGTGACGTGT | | GTGGATTGTTGTAAACA | CCAAAGACTCAT |
| | TTAAAGGAGATC | | CGAGCACACTGTTTGAT | TGAGGTGTCAGT |

TABLE 2-continued

| | | |
|---|---|---|
| TTAATCCAAAAC | GAACTCGAATTAGACCC | GGAAGAAAATCA |
| CCCAAGGCCAAA | CCCCGAGATTGAACCGG | CCCGTTTACTTT |
| GACTCATTGAGG | GTGTCTTGAAAGTACTT | ACGCGCACCGAT |
| TGTCAGTGGAAG | CGGACAGAAAAACAATA | TCAGCGGATTTA |
| AAAATCACCCGT | CTTGGGTGTGTACATTT | TGGAGTCCGGTA |
| TTACTTTACGCG | GGAACATGCGCGGCTCC | CACCGAGACTTG |
| CACCGATTCAGC | GATGGTACGTCTACCTA | GAGCTTTTTGCC |
| GGATTTATGGAG | CGCCACGTTTTTGGTCA | GTCATTAACCTG |
| TCCGGTACACCG | CCTGGAAAGGGGATGAA | TACGGGAGACGC |
| AGACTTGGAGCT | AAAACAAGAAACCCTAC | AGCGCCCGCCAT |
| TTTTGCCGTCAT | GCCCGCAGTAACTCCTC | CCAGCATATATG |
| TAACCTGTACGG | AACCAAGAGGGGCTGAG | TTTAAAACATAC |
| GAGACGCAGCGC | TTTCATATGTGGAATTA | AACATGCTTTCA |
| CCGCCATCCAGC | CCACTCGCATGTATTTT | AGACGTGGTGGT |
| ATATATGTTTAA | CAGTTGGTGATACGTTT | GGATGTGGATTG |
| AACATACAACAT | AGCTTGGCAATGCATCT | CGCGGAAAATAC |
| GCTTTCAAGACG | TCAGTATAAGATACATG | TAAAGAGGATCA |
| TGGTGGTGGATG | AAGCGCCATTTGATTTG | GTTGGCCGAAAT |
| TGGATTGCGCGG | CTGTTAGAGTGGTTGTA | CAGTTACCGTTT |
| AAAATACTAAAG | TGTCCCCATCGATCCTA | TCAAGGTAAGAA |
| AGGATCAGTTGG | CATGTCAACCAATGCGG | GGAAGCGGACCA |
| CCGAAATCAGTT | TTATATTCTACGTGTTT | ACCGTGGATTGT |
| ACCGTTTTCAAG | GTATCATCCCAACGCAC | TGTAAACACGAG |
| GTAAGAAGGAAG | CCCAATGCCTCTCTCAT | CACACTGTTTGA |
| CGGACCAACCGT | ATGAATTCCGGTTGTAC | TGAACTCGAATT |
| GGATTGTTGTAA | ATTTACCTCGCCACATT | AGACCCCCCCGA |
| ACACGAGCACAC | TAGCCCAGCGTGTTGCA | GATTGAACCGGG |
| TGTTTGATGAAC | AGCACAGTGTATCAAAA | TGTCTTGAAAGT |
| TCGAATTAGACC | TTGTGAACATGCAGATA | ACTTCGGACAGA |
| CCCCCGAGATTG | ACTACACCGCATATTGT | AAAACAATACTT |
| AACCGGGTGTCT | CTGGGAATATCTCATAT | GGGTGTGTACAT |
| TGAAAGTACTTC | GGAGCCTAGCTTTGGTC | TTGGAACATGCG |
| GGACAGAAAAAC | TAATCTTACACGACGGG | CGGCTCCGATGG |
| AATACTTGGGTG | GGCACCACGTTAAAGTT | TACGTCTACCTA |
| TGTACATTTGGA | TGTAGATACACCCGAGA | CGCCACGTTTTT |
| ACATGCGCGGCT | GTTTGTCGGGATTATAC | GGTCACCTGGAA |
| CCGATGGTACGT | GTTTTTGTGGTGTATTT | AGGGGATGAAAA |
| CTACCTACGCCA | TAACGGGCATGTTGAAG | AACAAGAAACCC |
| CGTTTTTGGTCA | CCGTAGCATACACTGTT | TACGCCCGCAGT |
| CCTGGAAAGGGG | GTATCCACAGTAGATCA | AACTCCTCAACC |
| ATGAAAAAACAA | TTTTGTAAACGCAATTG | AAGAGGGGCTGA |
| GAAACCCTACGC | AAGAGCGTGGATTTCCG | GTTTCATATGTG |
| CCGCAGTAACTC | CCAACGGCCGGTCAGCC | GAATTACCACTC |
| CTCAACCAAGAG | ACCGGCGACTACTAAAC | GCATGTATTTTC |
| GGGCTGAGTTTC | CCAAGGAAATTACCCCC | AGTTGGTGATAC |
| ATATGTGGAATT | GTAAACCCCGGAACGTC | GTTTAGCTTGGC |
| ACCACTCGCATG | ACCACTTCTACGATATG | AATGCATCTTCA |
| TATTTTCAGTTG | CCGCATGGACCGGAGGG | GTATAAGATACA |
| GTGATACGTTTA | CTTGCAGCAGTAGTACT | TGAAGCGCCATT |
| GCTTGGCAATGC | TTTATGTCTCGTAATAT | TGATTTGCTGTT |
| ATCTTCAGTATA | TTTTAATCTGTACGGCT | AGAGTGGTTGTA |
| AGATACATGAAG | AAACGAATGAGGGTTAA | TGTCCCCATCGA |
| CGCCATTTGATT | AGCCTATAGGGTAGACA | TCCTACATGTCA |
| TGCTGTTAGAGT | AGTCCCCGTATAACCAA | ACCAATGCGGTT |
| GGTTGTATGTCC | AGCATGTATTACGCTGG | ATATTCTACGTG |
| CCATCGATCCTA | CCTTCCAGTGGACGATT | TTTGTATCATCC |
| CATGTCAACCAA | TCGAGGACGCCGAAGCC | CAACGCACCCCA |
| TGCGGTTATATT | GCCGATGCCGAAGAAGA | ATGCCTCTCTCA |
| CTACGTGTTTGT | GTTTGGTAACGCGATTG | TATGAATTCCGG |
| ATCATCCCAACG | GAGGGAGTCACGGGGGT | TTGTACATTTAC |
| CACCCCAATGCC | TCGAGTTACACGGTGTA | CTCGCCACATTT |
| TCTCTCATATGA | TATAGATAAGACCCGGT | AGCCCAGCGTGT |
| ATTCCGGTTGTA | GA | TGCAAGCACAGT |
| CATTTACCTCGC | | GTATCAAAATTG |
| CACATTTAGCCC | | TGAACATGCAGA |
| AGCGTGTTGCAA | | TAACTACACCGC |
| GCACAGTGTATC | | ATATTGTCTGGG |
| AAAATTGTGAAC | | AATATCTCATAT |
| ATGCAGATAACT | | GGAGCCTAGCTT |
| ACACCGCATATT | | TGGTCTAATCTT |
| GTCTGGGAATAT | | ACACGACGGGGG |
| CTCATATGGAGC | | CACCACGTTAAA |
| CTAGCTTTGGTC | | GTTTGTAGATAC |
| TAATCTTACACG | | ACCCGAGAGTTT |
| ACGGGGGCACCA | | GTCGGGATTATA |
| CGTTAAAGTTTG | | CGTTTTTGTGGT |
| TAGATACACCCG | | GTATTTTAACGG |
| AGAGTTTGTCGG | | GCATGTTGAAGC |
| GATTATACGTTT | | CGTAGCATACAC |
| TTGTGGTGTATT | | TGTTGTATCCAC |

TABLE 2-continued

| | | | | |
|---|---|---|---|---|
| | TTAACGGGCATG<br>TTGAAGCCGTAG<br>CATACACTGTTG<br>TATCCACAGTAG<br>ATCATTTTGTAA<br>ACGCAATTGAAG<br>AGCGTGGATTTC<br>CGCCAACGGCCG<br>GTCAGCCACCGG<br>CGACTACTAAAC<br>CCAAGGAAATTA<br>CCCCCGTAAACC<br>CCGGAACGTCAC<br>CACTTCTACGAT<br>ATGCCGCATGGA<br>CCGGAGGGCTTG<br>CAGCAGTAGTAC<br>TTTTATGTCTCG<br>TAATATTTTTAA<br>TCTGTACGGCTA<br>AACGAATGAGGG<br>TTAAAGCCTATA<br>GGGTAGACAAGT<br>CCCCGTATAACC<br>AAAGCATGTATT<br>ACGCTGGCCTTC<br>CAGTGGACGATT<br>TCGAGGACGCCG<br>AAGCCGCCGATG<br>CCGAAGAAGAGT<br>TTGGTAACGCGA<br>TTGGAGGGAGTC<br>ACGGGGGTTCGA<br>GTTACACGGTGT<br>ATATAGATAAGA<br>CCCGGTGATGAT<br>AATAGGCTGGAG<br>CCTCGGTGGCCA<br>TGCTTCTTGCCC<br>CTTGGGCCTCCC<br>CCCAGCCCCTCC<br>TCCCCTTCCTGC<br>ACCCGTACCCCC<br>GTGGTCTTTGAA<br>TAAAGTCTGAGT<br>GGGCGGC | | | AGTAGATCATTT<br>TGTAAACGCAAT<br>TGAAGAGCGTGG<br>ATTTCCGCCAAC<br>GGCCGGTCAGCC<br>ACCGGCGACTAC<br>TAAACCCAAGGA<br>AATTACCCCCGT<br>AAACCCCGGAAC<br>GTCACCACTTCT<br>ACGATATGCCGC<br>ATGGACCGGAGG<br>GCTTGCAGCAGT<br>AGTACTTTTATG<br>TCTCGTAATATT<br>TTTAATCTGTAC<br>GGCTAAACGAAT<br>GAGGGTTAAAGC<br>CTATAGGGTAGA<br>CAAGTCCCCGTA<br>TAACCAAAGCAT<br>GTATTACGCTGG<br>CCTTCCAGTGGA<br>CGATTTCGAGGA<br>CGCCGAAGCCGC<br>CGATGCCGAAGA<br>AGAGTTTGGTAA<br>CGCGATTGGAGG<br>GAGTCACGGGGG<br>TTCGAGTTACAC<br>GGTGTATATAGA<br>TAAGACCCGGTG<br>ATGATAATAGGC<br>TGGAGCCTCGGT<br>GGCCATGCTTCT<br>TGCCCCTTGGGC<br>CTCCCCCCAGCC<br>CCTCCTCCCCTT<br>CCTGCACCCGTA<br>CCCCCGTGGTCT<br>TTGAATAAAGTC<br>TGAGTGGGCGGC<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAATCTAG |
| | SEQ ID NO: 29 | SEQ ID NO: 30 | SEQ ID NO: 31 | SEQ ID NO: 32 |
| VZV-GE-full_with_AEAADA (SEQ ID NO: 58)_and_Y582G | TCAAGCTTTTGG<br>ACCCTCGTACAG<br>AAGCTAATACGA<br>CTCACTATAGGG<br>AAATAAGAGAGA<br>AAAGAAGAGTAA<br>GAAGAAATATAA<br>GAGCCACCATGG<br>GGACAGTTAATA<br>AACCTGTGGTGG<br>GGGTATTGATGG<br>GGTTCGGAATTA<br>TCACGGGAACGT<br>TGCGTATAACGA<br>ATCCGGTCAGAG<br>CATCCGTCTTGC<br>GATACGATGATT<br>TTCACATCGATG<br>AAGACAAACTGG<br>ATACAAACTCCG<br>TATATGAGCCTT<br>ACTACCATTCAG<br>ATCATGCGGAGT<br>CTTCATGGGTAA<br>ATCGGGGAGAGT<br>CTTCGCGAAAAG | MGTVNKPVVGVLMGFGI<br>ITGTLRITNPVRASVLR<br>YDDFHIDEDKLDTNSVY<br>EPYYHSDHAESSWVNRG<br>ESSRKAYDHNSPYIWPR<br>NDYDGFLENAHEHHGVY<br>NQGRGIDSGERLMQPTQ<br>MSAQEDLGDDTGIHVIP<br>TLNGDDRHKIVNVDQRQ<br>YGDVFKGDLNPKPQGQR<br>LIEVSVEENHPFTLRAP<br>IQRIYGVRYTETWSFLP<br>SLTCTGDAAPAIQHICL<br>KHTTCFQDVVVDVDCAE<br>NTKEDQLAEISYRFQGK<br>KEADQPWIVVNTSTLFD<br>ELELDPPEIEPGVLKVL<br>RTEKQYLGVYIWNMRGS<br>DGTSTYATFLVTWKGDE<br>KTRNPTPAVTPQPRGAE<br>FHMWNYHSHVFSVGDTF<br>SLAMHLQYKIHEAPFDL<br>LLEWLYVPIDPTCQPMR<br>LYSTCLYHPNAPQCLSH<br>MNSGCTFTSPHLAQRVA<br>STVYQNCEHADNYTAYC | ATGGGGACAGTTAATAA<br>ACCTGTGGTGGGGGTAT<br>TGATGGGGTTCGGAATT<br>ATCACGGGAACGTTGCG<br>TATAACGAATCCGGTCA<br>GAGCATCCGTCTTGCGA<br>TACGATGATTTTCACAT<br>CGATGAAGACAAACTGG<br>ATACAAACTCCGTATAT<br>GAGCCTTACTACCATTC<br>AGATCATGCGGAGTCTT<br>CATGGGTAAATCGGGGA<br>GAGTCTTCGCGAAAAGC<br>GTACGATCATAACTCAC<br>CTTATATATGGCCACGT<br>AATGATTATGATGGATT<br>TTTAGAGAACGCACACG<br>AACACCATGGGGTGTAT<br>AATCAGGGCCGTGGTAT<br>CGATAGCGGGGAACGGT<br>TAATGCAACCCACACAA<br>ATGTCTGCACAGGAGGA<br>TCTTGGGGACGATACGG<br>GCATCCACGTTATCCCT<br>ACGTTAAACGGCGATGA<br>CAGACATAAAATTGTAA | G*GGGAAATAAG<br>AGAGAAAAGAAG<br>AGTAAGAAGAAA<br>TATAAGAGCCAC<br>CATGGGGACAGT<br>TAATAAACCTGT<br>GGTGGGGGTATT<br>GATGGGGTTCGG<br>AATTATCACGGG<br>AACGTTGCGTAT<br>AACGAATCCGGT<br>CAGAGCATCCGT<br>CTTGCGATACGA<br>TGATTTTCACAT<br>CGATGAAGACAA<br>ACTGGATACAAA<br>CTCCGTATATGA<br>GCCTTACTACCA<br>TTCAGATCATGC<br>GGAGTCTTCATG<br>GGTAAATCGGGG<br>AGAGTCTTCGCG<br>AAAAGCGTACGA<br>TCATAACTCACC<br>TTATATATGGCC<br>ACGTAATGATTA |

TABLE 2-continued

| | | | |
|---|---|---|---|
| CGTACGATCATA | LGISHMEPSFGLILHDG | ATGTGGACCAACGTCAA | TGATGGATTTTT |
| ACTCACCTTATA | GTTLKFVDTPESLSGLY | TACGGTGACGTGTTTAA | AGAGAACGCACA |
| TATGGCCACGTA | VFVVYFNGHVEAVAYTV | AGGAGATCTTAATCCAA | CGAACACCATGG |
| ATGATTATGATG | VSTVDHFVNAIEERGFP | AACCCCAAGGCCAAAGA | GGTGTATAATCA |
| GATTTTTAGAGA | PTAGQPPATTKPKEITP | CTCATTGAGGTGTCAGT | GGGCCGTGGTAT |
| ACGCACACGAAC | VNPGTSPLLRYAAWTGG | GGAAGAAAATCACCCGT | CGATAGCGGGGA |
| ACCATGGGGTGT | LAAVVLLCLVIFLICTA | TTACTTTACGCGCACCG | ACGGTTAATGCA |
| ATAATCAGGGCC | KRMRVKAYRVDKSPYNQ | ATTCAGCGGATTTATGG | ACCCACACAAAT |
| GTGGTATCGATA | SMYGAGLPVDDFEDAEA | AGTCCGGTACACCGAGA | GTCTGCACAGGA |
| GCGGGGAACGGT | ADAEEEFGNAIGGSHGG | CTTGGAGCTTTTTGCCG | GGATCTTGGGGA |
| TAATGCAACCCA | SSYTVYIDKTR* | TCATTAACCTGTACGGG | CGATACGGGCAT |
| CACAAATGTCTG | | AGACGCAGCGCCCGCCA | CCACGTTATCCC |
| CACAGGAGGATC | | TCCAGCATATATGTTTA | TACGTTAAACGG |
| TTGGGGACGATA | | AAACATACAACATGCTT | CGATGACAGACA |
| CGGGCATCCACG | | TCAAGACGTGGTGGTGG | TAAAATTGTAAA |
| TTATCCCTACGT | | ATGTGGATTGCGCGGAA | TGTGGACCAACG |
| TAAACGGCGATG | | AATACTAAAGAGGATCA | TCAATACGGTGA |
| ACAGACATAAAA | | GTTGGCCGAAATCAGTT | CGTGTTTAAAGG |
| TTGTAAATGTGG | | ACCGTTTTCAAGGTAAG | AGATCTTAATCC |
| ACCAACGTCAAT | | AAGGAAGCGGACCAACC | AAAACCCCAAGG |
| ACGGTGACGTGT | | GTGGATTGTTGTAAACA | CCAAAGACTCAT |
| TTAAAGGAGATC | | CGAGCACACTGTTTGAT | TGAGGTGTCAGT |
| TTAATCCAAAAC | | GAACTCGAATTAGACCC | GGAAGAAAATCA |
| CCCAAGGCCAAA | | CCCCGAGATTGAACCGG | CCCGTTTACTTT |
| GACTCATTGAGG | | GTGTCTTGAAAGTACTT | ACGCGCACCGAT |
| TGTCAGTGGAAG | | CGGACAGAAAAACAATA | TCAGCGGATTTA |
| AAAATCACCCGT | | CTTGGGTGTGTACATTT | TGGAGTCCGGTA |
| TTACTTTACGCG | | GGAACATGCGCGGCTCC | CACCGAGACTTG |
| CACCGATTCAGC | | GATGGTACGTCTACCTA | GAGCTTTTTGCC |
| GGATTTATGGAG | | CGCCACGTTTTTGGTCA | GTCATTAACCTG |
| TCCGGTACACCG | | CCTGGAAAGGGGATGAA | TACGGGAGACGC |
| AGACTTGGAGCT | | AAAACAAGAAACCCTAC | AGCGCCCGCCAT |
| TTTTGCCGTCAT | | GCCCGCAGTAACTCCTC | CCAGCATATATG |
| TAACCTGTACGG | | AACCAAGAGGGGCTGAG | TTTAAAACATAC |
| GAGACGCAGCGC | | TTTCATATGTGGAATTA | AACATGCTTTCA |
| CCGCCATCCAGC | | CCACTCGCATGTATTTT | AGACGTGGTGGT |
| ATATATGTTTAA | | CAGTTGGTGATACGTTT | GGATGTGGATTG |
| AACATACAACAT | | AGCTTGGCAATGCATCT | CGCGGAAAATAC |
| GCTTTCAAGACG | | TCAGTATAAGATACATG | TAAAGAGGATCA |
| TGGTGGTGGATG | | AAGCGCCATTTGATTTG | GTTGGCCGAAAT |
| TGGATTGCGCGG | | CTGTTAGAGTGGTTGTA | CAGTTACCGTTT |
| AAAATACTAAAG | | TGTCCCCATCGATCCTA | TCAAGGTAAGAA |
| AGGATCAGTTGG | | CATGTCAACCAATGCGG | GGAAGCGGACCA |
| CCGAAATCAGTT | | TTATATTCTACGTGTTT | ACCGTGGATTGT |
| ACCGTTTTCAAG | | GTATCATCCCAACGCAC | TGTAAACACGAG |
| GTAAGAAGGAAG | | CCCAATGCCTCTCTCAT | CACACTGTTTGA |
| CGGACCAACCGT | | ATGAATTCCGGTTGTAC | TGAACTCGAATT |
| GGATTGTTGTAA | | ATTTACCTCGCCACATT | AGACCCCCCCGA |
| ACACGAGCACAC | | TAGCCCAGCGTGTTGCA | GATTGAACCGGG |
| TGTTTGATGAAC | | AGCACAGTGTATCAAAA | TGTCTTGAAAGT |
| TCGAATTAGACC | | TTGTGAACATGCAGATA | ACTTCGGACAGA |
| CCCCCGAGATTG | | ACTACACCGCATATTGT | AAAACAATACTT |
| AACCGGGTGTCT | | CTGGGAATATCTCATAT | GGGTGTGTACAT |
| TGAAAGTACTTC | | GGAGCCTAGCTTTGGTC | TTGGAACATGCG |
| GGACAGAAAAAC | | TAATCTTACACGACGGG | CGGCTCCGATGG |
| AATACTTGGGTG | | GGCACCACGTTAAAGTT | TACGTCTACCTA |
| TGTACATTTGGA | | TGTAGATACACCCGAGA | CGCCACGTTTTT |
| ACATGCGCGGCT | | GTTTGTCGGGATTATAC | GGTCACCTGGAA |
| CCGATGGTACGT | | GTTTTTGTGGTGTATTT | AGGGGATGAAAA |
| CTACCTACGCCA | | TAACGGGCATGTTGAAG | AACAAGAAACCC |
| CGTTTTTGGTCA | | CCGTAGCATACACTGTT | TACGCCCGCAGT |
| CCTGGAAAGGGG | | GTATCCACAGTAGATCA | AACTCCTCAACC |
| ATGAAAAAACAA | | TTTTGTAAACGCAATTG | AAGAGGGGCTGA |
| GAAACCCTACGC | | AAGAGCGTGGATTTCCG | GTTTCATATGTG |
| CCGCAGTAACTC | | CCAACGGCCGGTCAGCC | GAATTACCACTC |
| CTCAACCAAGAG | | ACCGGCGACTACTAAAC | GCATGTATTTTC |
| GGGCTGAGTTTC | | CCAAGGAAATTACCCCC | AGTTGGTGATAC |
| ATATGTGGAATT | | GTAAACCCCGGAACGTC | GTTTAGCTTGGC |
| ACCACTCGCATG | | ACCACTTCTACGATATG | AATGCATCTTCA |
| TATTTTCAGTTG | | CCGCATGGACCGGAGGG | GTATAAGATACA |
| GTGATACGTTTA | | CTTGCAGCAGTAGTACT | TGAAGCGCCATT |
| GCTTGGCAATGC | | TTTATGTCTCGTAATAT | TGATTTGCTGTT |
| ATCTTCAGTATA | | TTTTAATCTGTACGGCT | AGAGTGGTTGTA |
| AGATACATGAAG | | AAACGAATGAGGGTTAA | TGTCCCCATCGA |
| CGCCATTTGATT | | AGCCTATAGGGTAGACA | TCCTACATGTCA |
| TGCTGTTAGAGT | | AGTCCCCGTATAACCAA | ACCAATGCGGTT |
| GGTTGTATGTCC | | AGCATGTATGGCGCTGG | ATATTCTACGTG |
| CCATCGATCCTA | | CCTTCCAGTGGACGATT | TTTGTATCATCC |
| CATGTCAACCAA | | TCGAGGACGCCGAAGCC | CAACGCACCCCA |
| TGCGGTTATATT | | GCCGATGCCGAAGAAGA | ATGCCTCTCTCA |

TABLE 2-continued

| | | | | |
|---|---|---|---|---|
| | CTACGTGTTTGT<br>ATCATCCCAACG<br>CACCCCAATGCC<br>TCTCTCATATGA<br>ATTCCGGTTGTA<br>CATTTACCTCGC<br>CACATTTAGCCC<br>AGCGTGTTGCAA<br>GCACAGTGTATC<br>AAAATTGTGAAC<br>ATGCAGATAACT<br>ACACCGCATATT<br>GTCTGGGAATAT<br>CTCATATGGAGC<br>CTAGCTTTGGTC<br>TAATCTTACACG<br>ACGGGGGCACCA<br>CGTTAAAGTTTG<br>TAGATACACCCG<br>AGAGTTTGTCGG<br>GATTATACGTTT<br>TTGTGGTGTATT<br>TTAACGGGCATG<br>TTGAAGCCGTAG<br>CATACACTGTTG<br>TATCCACAGTAG<br>ATCATTTTGTAA<br>ACGCAATTGAAG<br>AGCGTGGATTTC<br>CGCCAACGGCCG<br>GTCAGCCACCGG<br>CGACTACTAAAC<br>CCAAGGAAATTA<br>CCCCCGTAAACC<br>CCGGAACGTCAC<br>CACTTCTACGAT<br>ATGCCGCATGGA<br>CCGGAGGGCTTG<br>CAGCAGTAGTAC<br>TTTTATGTCTCG<br>TAATATTTTTAA<br>TCTGTACGGCTA<br>AACGAATGAGGG<br>TTAAAGCCTATA<br>GGGTAGACAAGT<br>CCCCGTATAACC<br>AAAGCATGTATG<br>GCGCTGGCCTTC<br>CAGTGGACGATT<br>TCGAGGACGCCG<br>AAGCCGCCGATG<br>CCGAAGAAGAGT<br>TTGGTAACGCGA<br>TTGGAGGGAGTC<br>ACGGGGGTTCGA<br>GTTACACGGTGT<br>ATATAGATAAGA<br>CCCGGTGATGAT<br>AATAGGCTGGAG<br>CCTCGGTGGCCA<br>TGCTTCTTGCCC<br>CTTGGGCCTCCC<br>CCCAGCCCCTCC<br>TCCCCTTCCTGC<br>ACCCGTACCCCC<br>GTGGTCTTTGAA<br>TAAAGTCTGAGT<br>GGGCGGC | | GTTTGGTAACGCGATTG<br>GAGGGAGTCACGGGGGT<br>TCGAGTTACACGGTGTA<br>TATAGATAAGACCCGGT<br>GA | TATGAATTCCGG<br>TTGTACATTTAC<br>CTCGCCACATTT<br>AGCCCAGCGTGT<br>TGCAAGCACAGT<br>GTATCAAAATTG<br>TGAACATGCAGA<br>TAACTACACCGC<br>ATATTGTCTGGG<br>AATATCTCATAT<br>GGAGCCTAGCTT<br>TGGTCTAATCTT<br>ACACGACGGGGG<br>CACCACGTTAAA<br>GTTTGTAGATAC<br>ACCCGAGAGTTT<br>GTCGGGATTATA<br>CGTTTTTGTGGT<br>GTATTTTAACGG<br>GCATGTTGAAGC<br>CGTAGCATACAC<br>TGTTGTATCCAC<br>AGTAGATCATTT<br>TGTAAACGCAAT<br>TGAAGAGCGTGG<br>ATTTCCGCCAAC<br>GGCCGGTCAGCC<br>ACCGGCGACTAC<br>TAAACCCAAGGA<br>AATTACCCCCGT<br>AAACCCCGGAAC<br>GTCACCACTTCT<br>ACGATATGCCGC<br>ATGGACCGGAGG<br>GCTTGCAGCAGT<br>AGTACTTTTATG<br>TCTCGTAATATT<br>TTTAATCTGTAC<br>GGCTAAACGAAT<br>GAGGGTTAAAGC<br>CTATAGGGTAGA<br>CAAGTCCCCGTA<br>TAACCAAAGCAT<br>GTATGGCGCTGG<br>CCTTCCAGTGGA<br>CGATTTCGAGGA<br>CGCCGAAGCCGC<br>CGATGCCGAAGA<br>AGAGTTTGGTAA<br>CGCGATTGGAGG<br>GAGTCACGGGGG<br>TTCGAGTTACAC<br>GGTGTATATAGA<br>TAAGACCCGGTG<br>ATGATAATAGGC<br>TGGAGCCTCGGT<br>GGCCATGCTTCT<br>TGCCCCTTGGGC<br>CTCCCCCCAGCC<br>CCTCCTCCCCTT<br>CCTGCACCCGTA<br>CCCCCGTGGTCT<br>TTGAATAAAGTC<br>TGAGTGGGCGGC<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAATCTAG |
| | SEQ ID NO: 33 | SEQ ID NO: 34 | SEQ ID NO: 35 | SEQ ID NO: 36 |
| VZV-GE-<br>truncated-<br>delete_<br>from_574 | TCAAGCTTTTGG<br>ACCCTCGTACAG<br>AAGCTAATACGA<br>CTCACTATAGGG | MGTVNKPVVGVLMGFGI<br>ITGTLRITNPVRASVLR<br>YDDFHIDEDKLDTNSVY<br>EPYYHSDHAESSWVNRG | ATGGGGACAGTTAATAA<br>ACCTGTGGTGGGGTAT<br>TGATGGGGTTCGGAATT<br>ATCACGGGAACGTTGCG | G*GGGAAATAAG<br>AGAGAAAAGAAG<br>AGTAAGAAGAAA<br>TATAAGAGCCAC |

TABLE 2-continued

| | | | |
|---|---|---|---|
| AAATAAGAGAGA | ESSRKAYDHNSPYIWPR | TATAACGAATCCGGTCA | CATGGGGACAGT |
| AAAGAAGAGTAA | NDYDGFLENAHEHHGVY | GAGCATCCGTCTTGCGA | TAATAAACCTGT |
| GAAGAAATATAA | NQGRGIDSGERLMQPTQ | TACGATGATTTTCACAT | GGTGGGGGTATT |
| GAGCCACCATGG | MSAQEDLGDDTGIHVIP | CGATGAAGACAAACTGG | GATGGGGTTCGG |
| GGACAGTTAATA | TLNGDDRHKIVNVDQRQ | ATACAAACTCCGTATAT | AATTATCACGGG |
| AACCTGTGGTGG | YGDVFKGDLNPKPQGQR | GAGCCTTACTACCATTC | AACGTTGCGTAT |
| GGGTATTGATGG | LIEVSVEENHPFTLRAP | AGATCATGCGGAGTCTT | AACGAATCCGGT |
| GGTTCGGAATTA | IQRIYGVRYTETWSFLP | CATGGGTAAATCGGGGA | CAGAGCATCCGT |
| TCACGGGAACGT | SLTCTGDAAPAIQHICL | GAGTCTTCGCGAAAAGC | CTTGCGATACGA |
| TGCGTATAACGA | KHTTCFQDVVVDVDCAE | GTACGATCATAACTCAC | TGATTTTCACAT |
| ATCCGGTCAGAG | NTKEDQLAEISYRFQGK | CTTATATATGGCCACGT | CGATGAAGACAA |
| CATCCGTCTTGC | KEADQPWIVVNTSTLFD | AATGATTATGATGGATT | ACTGGATACAAA |
| GATACGATGATT | ELELDPPEIEPGVLKVL | TTTAGAGAACGCACACG | CTCCGTATATGA |
| TTCACATCGATG | RTEKQYLGVYIWNMRGS | AACACCATGGGGTGTAT | GCCTTACTACCA |
| AAGACAAACTGG | DGTSTYATFLVTWKGDE | AATCAGGGCCGTGGTAT | TTCAGATCATGC |
| ATACAAACTCCG | KTRNPTPAVTPQPRGAE | CGATAGCGGGGAACGGT | GGAGTCTTCATG |
| TATATGAGCCTT | FHMWNYHSHVFSVGDTF | TAATGCAACCCACACAA | GGTAAATCGGGG |
| ACTACCATTCAG | SLAMHLQYKIHEAPFDL | ATGTCTGCACAGGAGGA | AGAGTCTTCGCG |
| ATCATGCGGAGT | LLEWLYVPIDPTCQPMR | TCTTGGGGACGATACGG | AAAAGCGTACGA |
| CTTCATGGGTAA | LYSTCLYHPNAPQCLSH | GCATCCACGTTATCCCT | TCATAACTCACC |
| ATCGGGGAGAGT | MNSGCTFTSPHLAQRVA | ACGTTAAACGGCGATGA | TTATATATGGCC |
| CTTCGCGAAAAG | STVYQNCEHADNYTAYC | CAGACATAAAATTGTAA | ACGTAATGATTA |
| CGTACGATCATA | LGISHMEPSFGLILHDG | ATGTGGACCAACGTCAA | TGATGGATTTTT |
| ACTCACCTTATA | GTTLKFVDTPESLSGLY | TACGGTGACGTGTTTAA | AGAGAACGCACA |
| TATGGCCACGTA | VFVVYFNGHVEAVAYTV | AGGAGATCTTAATCCAA | CGAACACCATGG |
| ATGATTATGATG | VSTVDHFVNAIEERGFP | AACCCCAAGGCCAAAGA | GGTGTATAATCA |
| GATTTTTAGAGA | PTAGQPPATTKPKEITP | CTCATTGAGGTGTCAGT | GGGCCGTGGTAT |
| ACGCACACGAAC | VNPGTSPLLRYAAWTGG | GGAAGAAAATCACCCGT | CGATAGCGGGGA |
| ACCATGGGGTGT | LAAVVLLCLVIFLICTA | TTACTTTACGCGCACCG | ACGGTTAATGCA |
| ATAATCAGGGCC | KRMRVKAYRVDK* | ATTCAGCGGATTTATGG | ACCCACACAAAT |
| GTGGTATCGATA | | AGTCCGGTACACCGAGA | GTCTGCACAGGA |
| GCGGGGAACGGT | | CTTGGAGCTTTTTGCCG | GGATCTTGGGGA |
| TAATGCAACCCA | | TCATTAACCTGTACGGG | CGATACGGGCAT |
| CACAAATGTCTG | | AGACGCAGCGCCCGCCA | CCACGTTATCCC |
| CACAGGAGGATC | | TCCAGCATATATGTTTA | TACGTTAAACGG |
| TTGGGGACGATA | | AAACATACAACATGCTT | CGATGACAGACA |
| CGGGCATCCACG | | TCAAGACGTGGTGGTGG | TAAAATTGTAAA |
| TTATCCCTACGT | | ATGTGGATTGCGCGGAA | TGTGGACCAACG |
| TAAACGGCGATG | | AATACTAAAGAGGATCA | TCAATACGGTGA |
| ACAGACATAAAA | | GTTGGCCGAAATCAGTT | CGTGTTTAAAGG |
| TTGTAAATGTGG | | ACCGTTTTCAAGGTAAG | AGATCTTAATCC |
| ACCAACGTCAAT | | AAGGAAGCGGACCAACC | AAAACCCCAAGG |
| ACGGTGACGTGT | | GTGGATTGTTGTAAACA | CCAAAGACTCAT |
| TTAAAGGAGATC | | CGAGCACACTGTTTGAT | TGAGGTGTCAGT |
| TTAATCCAAAAC | | GAACTCGAATTAGACCC | GGAAGAAAATCA |
| CCCAAGGCCAAA | | CCCCGAGATTGAACCGG | CCCGTTTACTTT |
| GACTCATTGAGG | | GTGTCTTGAAAGTACTT | ACGCGCACCGAT |
| TGTCAGTGGAAG | | CGGACAGAAAAACAATA | TCAGCGGATTTA |
| AAAATCACCCGT | | CTTGGGTGTGTACATTT | TGGAGTCCGGTA |
| TTACTTTACGCG | | GGAACATGCGCGGCTCC | CACCGAGACTTG |
| CACCGATTCAGC | | GATGGTACGTCTACCTA | GAGCTTTTTGCC |
| GGATTTATGGAG | | CGCCACGTTTTTGGTCA | GTCATTAACCTG |
| TCCGGTACACCG | | CCTGGAAAGGGGATGAA | TACGGGAGACGC |
| AGACTTGGAGCT | | AAAACAAGAAACCCTAC | AGCGCCCGCCAT |
| TTTTGCCGTCAT | | GCCCGCAGTAACTCCTC | CCAGCATATATG |
| TAACCTGTACGG | | AACCAAGAGGGGCTGAG | TTTAAAACATAC |
| GAGACGCAGCGC | | TTTCATATGTGGAATTA | AACATGCTTTCA |
| CCGCCATCCAGC | | CCACTCGCATGTATTTT | AGACGTGGTGGT |
| ATATATGTTTAA | | CAGTTGGTGATACGTTT | GGATGTGGATTG |
| AACATACAACAT | | AGCTTGGCAATGCATCT | CGCGGAAAATAC |
| GCTTTCAAGACG | | TCAGTATAAGATACATG | TAAAGAGGATCA |
| TGGTGGTGGATG | | AAGCGCCATTTGATTTG | GTTGGCCGAAAT |
| TGGATTGCGCGG | | CTGTTAGAGTGGTTGTA | CAGTTACCGTTT |
| AAAATACTAAAG | | TGTCCCCATCGATCCTA | TCAAGGTAAGAA |
| AGGATCAGTTGG | | CATGTCAACCAATGCGG | GGAAGCGGACCA |
| CCGAAATCAGTT | | TTATATTCTACGTGTTT | ACCGTGGATTGT |
| ACCGTTTTCAAG | | GTATCATCCCAACGCAC | TGTAAACACGAG |
| GTAAGAAGGAAG | | CCCAATGCCTCTCTCAT | CACACTGTTTGA |
| CGGACCAACCGT | | ATGAATTCCGGTTGTAC | TGAACTCGAATT |
| GGATTGTTGTAA | | ATTTACCTCGCCACATT | AGACCCCCCCGA |
| ACACGAGCACAC | | TAGCCCAGCGTGTTGCA | GATTGAACCGGG |
| TGTTTGATGAAC | | AGCACAGTGTATCAAAA | TGTCTTGAAAGT |
| TCGAATTAGACC | | TTGTGAACATGCAGATA | ACTTCGGACAGA |
| CCCCCGAGATTG | | ACTACACCGCATATTGT | AAAACAATACTT |
| AACCGGGTGTCT | | CTGGGAATATCTCATAT | GGGTGTGTACAT |
| TGAAAGTACTTC | | GGAGCCTAGCTTTGGTC | TTGGAACATGCG |
| GGACAGAAAAAC | | TAATCTTACACGACGGG | CGGCTCCGATGG |
| AATACTTGGGTG | | GGCACCACGTTAAAGTT | TACGTCTACCTA |
| TGTACATTTGGA | | TGTAGATACACCCGAGA | CGCCACGTTTTT |
| ACATGCGCGGCT | | GTTTGTCGGGATTATAC | GGTCACCTGGAA |

TABLE 2-continued

CCGATGGTACGT
CTACCTACGCCA
CGTTTTTGGTCA
CCTGGAAAGGGG
ATGAAAAAACAA
GAAACCCTACGC
CCGCAGTAACTC
CTCAACCAAGAG
GGGCTGAGTTTC
ATATGTGGAATT
ACCACTCGCATG
TATTTTCAGTTG
GTGATACGTTTA
GCTTGGCAATGC
ATCTTCAGTATA
AGATACATGAAG
CGCCATTTGATT
TGCTGTTAGAGT
GGTTGTATGTCC
CCATCGATCCTA
CATGTCAACCAA
TGCGGTTATATT
CTACGTGTTTGT
ATCATCCCAACG
CACCCCAATGCC
TCTCTCATATGA
ATTCCGGTTGTA
CATTTACCTCGC
CACATTTAGCCC
AGCGTGTTGCAA
GCACAGTGTATC
AAAATTGTGAAC
ATGCAGATAACT
ACACCGCATATT
GTCTGGGAATAT
CTCATATGGAGC
CTAGCTTTGGTC
TAATCTTACACG
ACGGGGGCACCA
CGTTAAAGTTTG
TAGATACACCCG
AGAGTTTGTCGG
GATTATACGTTT
TTGTGGTGTATT
TTAACGGGCATG
TTGAAGCCGTAG
CATACACTGTTG
TATCCACAGTAG
ATCATTTTGTAA
ACGCAATTGAAG
AGCGTGGATTTC
CGCCAACGGCCG
GTCAGCCACCGG
CGACTACTAAAC
CCAAGGAAATTA
CCCCCGTAAACC
CCGGAACGTCAC
CACTTCTACGAT
ATGCCGCATGGA
CCGGAGGGCTTG
CAGCAGTAGTAC
TTTTATGTCTCG
TAATATTTTTAA
TCTGTACGGCTA
AACGAATGAGGG
TTAAAGCCTATA
GGGTAGACAAGT
GATGATAATAGG
CTGGAGCCTCGG
TGGCCATGCTTC
TTGCCCCTTGGG
CCTCCCCCCAGC
CCCTCCTCCCCT
TCCTGCACCCGT
ACCCCCGTGGTC
TTTGAATAAAGT
CTGAGTGGGCGG
C

GTTTTTGTGGTGTATTT
TAACGGGCATGTTGAAG
CCGTAGCATACACTGTT
GTATCCACAGTAGATCA
TTTTGTAAACGCAATTG
AAGAGCGTGGATTTCCG
CCAACGGCCGGTCAGCC
ACCGGCGACTACTAAAC
CCAAGGAAATTACCCCC
GTAAACCCCGGAACGTC
ACCACTTCTACGATATG
CCGCATGGACCGGAGGG
CTTGCAGCAGTAGTACT
TTTATGTCTCGTAATAT
TTTTAATCTGTACGGCT
AAACGAATGAGGGTTAA
AGCCTATAGGGTAGACA
AGTGA

AGGGGATGAAAA
AACAAGAAACCC
TACGCCCGCAGT
AACTCCTCAACC
AAGAGGGGCTGA
GTTTCATATGTG
GAATTACCACTC
GCATGTATTTTC
AGTTGGTGATAC
GTTTAGCTTGGC
AATGCATCTTCA
GTATAAGATACA
TGAAGCGCCATT
TGATTTGCTGTT
AGAGTGGTTGTA
TGTCCCCATCGA
TCCTACATGTCA
ACCAATGCGGTT
ATATTCTACGTG
TTTGTATCATCC
CAACGCACCCCA
ATGCCTCTCTCA
TATGAATTCCGG
TTGTACATTTAC
CTCGCCACATTT
AGCCCAGCGTGT
TGCAAGCACAGT
GTATCAAAATTG
TGAACATGCAGA
TAACTACACCGC
ATATTGTCTGGG
AATATCTCATAT
GGAGCCTAGCTT
TGGTCTAATCTT
ACACGACGGGGG
CACCACGTTAAA
GTTTGTAGATAC
ACCCGAGAGTTT
GTCGGGATTATA
CGTTTTTGTGGT
GTATTTTAACGG
GCATGTTGAAGC
CGTAGCATACAC
TGTTGTATCCAC
AGTAGATCATTT
TGTAAACGCAAT
TGAAGAGCGTGG
ATTTCCGCCAAC
GGCCGGTCAGCC
ACCGGCGACTAC
TAAACCCAAGGA
AATTACCCCCGT
AAACCCCGGAAC
GTCACCACTTCT
ACGATATGCCGC
ATGGACCGGAGG
GCTTGCAGCAGT
AGTACTTTTATG
TCTCGTAATATT
TTTAATCTGTAC
GGCTAAACGAAT
GAGGGTTAAAGC
CTATAGGGTAGA
CAAGTGATGATA
ATAGGCTGGAGC
CTCGGTGGCCAT
GCTTCTTGCCCC
TTGGGCCTCCCC
CCAGCCCCTCCT
CCCCTTCCTGCA
CCCGTACCCCCG
TGGTCTTTGAAT
AAAGTCTGAGTG
GGCGGCAAAAAA
AAAAAAAAAAAA
AAAAAAAAAAAA
AAAAAAAAAAAA
AAAAAAAAAAAA
AAAAAAAAAAAA
AAAAAAAAAAAA

TABLE 2-continued

| | | | | |
|---|---|---|---|---|
| | | | | AAAAAAAAAAAA |
| | | | | AAAAAAAAAATC |
| | | | | TAG |
| | SEQ ID NO: 37 | SEQ ID NO: 38 | SEQ ID NO: 39 | SEQ ID NO: 40 |
| VZV-GE- | TCAAGCTTTTGG | MGTVNKPVVGVLMGFGI | ATGGGGACAGTTAATAA | G*GGGAAATAAG |
| truncated- | ACCCTCGTACAG | ITGTLRITNPVRASVLR | ACCTGTGGTGGGGTAT | AGAGAAAAGAAG |
| delete_ | AAGCTAATACGA | YDDFHIDEDKLDTNSVY | TGATGGGGTTCGGAATT | AGTAAGAAGAAA |
| from_574_-_ | CTCACTATAGGG | EPYYHSDHAESSWVNRG | ATCACGGGAACGTTGCG | TATAAGAGCCAC |
| Y569A | AAATAAGAGAGA | ESSRKAYDHNSPYIWPR | TATAACGAATCCGGTCA | CATGGGGACAGT |
| | AAAGAAGAGTAA | NDYDGFLENAHEHHGVY | GAGCATCCGTCTTGCGA | TAATAAACCTGT |
| | GAAGAAATATAA | NQGRGIDSGERLMQPTQ | TACGATGATTTTCACAT | GGTGGGGTATT |
| | GAGCCACCATGG | MSAQEDLGDDTGIHVIP | CGATGAAGACAAACTGG | GATGGGGTTCGG |
| | GGACAGTTAATA | TLNGDDRHKIVNVDQRQ | ATACAAACTCCGTATAT | AATTATCACGGG |
| | AACCTGTGGTGG | YGDVFKGDLNPKPQGQR | GAGCCTTACTACCATTC | AACGTTGCGTAT |
| | GGGTATTGATGG | LIEVSVEENHPFTLRAP | AGATCATGCGGAGTCTT | AACGAATCCGGT |
| | GGTTCGGAATTA | IQRIYGVRYTETWSFLP | CATGGGTAAATCGGGGA | CAGAGCATCCGT |
| | TCACGGGAACGT | SLTCTGDAAPAIQHICL | GAGTCTTCGCGAAAAGC | CTTGCGATACGA |
| | TGCGTATAACGA | KHTTCFQDVVVDVDCAE | GTACGATCATAACTCAC | TGATTTTCACAT |
| | ATCCGGTCAGAG | NTKEDQLAEISYRFQGK | CTTATATATGGCCACGT | CGATGAAGACAA |
| | CATCCGTCTTGC | KEADQPWIVVNTSTLFD | AATGATTATGATGGATT | ACTGGATACAAA |
| | GATACGATGATT | ELELDPPEIEPGVLKVL | TTTAGAGAACGCACACG | CTCCGTATATGA |
| | TTCACATCGATG | RTEKQYLGVYIWNMRGS | AACACCATGGGGTGTAT | GCCTTACTACCA |
| | AAGACAAACTGG | DGTSTYATFLVTWKGDE | AATCAGGGCCGTGGTAT | TTCAGATCATGC |
| | ATACAAACTCCG | KTRNPTPAVTPQPRGAE | CGATAGCGGGGAACGGT | GGAGTCTTCATG |
| | TATATGAGCCTT | FHMWNYHSHVFSVGDTF | TAATGCAACCCACACAA | GGTAAATCGGGG |
| | ACTACCATTCAG | SLAMHLQYKIHEAPFDL | ATGTCTGCACAGGAGGA | AGAGTCTTCGCG |
| | ATCATGCGGAGT | LLEWLYVPIDPTCQPMR | TCTTGGGGACGATACGG | AAAAGCGTACGA |
| | CTTCATGGGTAA | LYSTCLYHPNAPQCLSH | GCATCCACGTTATCCCT | TCATAACTCACC |
| | ATCGGGGAGAGT | MNSGCTFTSPHLAQRVA | ACGTTAAACGGCGATGA | TTATATATGGCC |
| | CTTCGCGAAAAG | STVYQNCEHADNYTAYC | CAGACATAAAATTGTAA | ACGTAATGATTA |
| | CGTACGATCATA | LGISHMEPSFGLILHDG | ATGTGGACCAACGTCAA | TGATGGATTTTT |
| | ACTCACCTTATA | GTTLKFVDTPESLSGLY | TACGGTGACGTGTTTAA | AGAGAACGCACA |
| | TATGGCCACGTA | VFVVYFNGHVEAVAYTV | AGGAGATCTTAATCCAA | CGAACACCATGG |
| | ATGATTATGATG | VSTVDHFVNAIEERGFP | AACCCCAAGGCCAAAGA | GGTGTATAATCA |
| | GATTTTTAGAGA | PTAGQPPATTKPKEITP | CTCATTGAGGTGTCAGT | GGGCCGTGGTAT |
| | ACGCACACGAAC | VNPGTSPLLRYAAWTGG | GGAAGAAAATCACCCGT | CGATAGCGGGGA |
| | ACCATGGGGTGT | LAAVVLLCLVIFLICTA | TTACTTTACGCGCACCG | ACGGTTAATGCA |
| | ATAATCAGGGCC | KRMRVKAARVDK* | ATTCAGCGGATTTATGG | ACCCACACAAAT |
| | GTGGTATCGATA | | AGTCCGGTACACCGAGA | GTCTGCACAGGA |
| | GCGGGGAACGGT | | CTTGGAGCTTTTTGCCG | GGATCTTGGGGA |
| | TAATGCAACCCA | | TCATTAACCTGTACGGG | CGATACGGGCAT |
| | CACAAATGTCTG | | AGACGCAGCGCCCGCCA | CCACGTTATCCC |
| | CACAGGAGGATC | | TCCAGCATATATGTTTA | TACGTTAAACGG |
| | TTGGGGACGATA | | AAACATACAACATGCTT | CGATGACAGACA |
| | CGGGCATCCACG | | TCAAGACGTGGTGGTGG | TAAAATTGTAAA |
| | TTATCCCTACGT | | ATGTGGATTGCGCGGAA | TGTGGACCAACG |
| | TAAACGGCGATG | | AATACTAAAGAGGATCA | TCAATACGGTGA |
| | ACAGACATAAAA | | GTTGGCCGAAATCAGTT | CGTGTTTAAAGG |
| | TTGTAAATGTGG | | ACCGTTTTCAAGGTAAG | AGATCTTAATCC |
| | ACCAACGTCAAT | | AAGGAAGCGGACCAACC | AAAACCCCAAGG |
| | ACGGTGACGTGT | | GTGGATTGTTGTAAACA | CCAAAGACTCAT |
| | TTAAAGGAGATC | | CGAGCACACTGTTTGAT | TGAGGTGTCAGT |
| | TTAATCCAAAAC | | GAACTCGAATTAGACCC | GGAAGAAAATCA |
| | CCCAAGGCCAAA | | CCCCGAGATTGAACCGG | CCCGTTTACTTT |
| | GACTCATTGAGG | | GTGTCTTGAAAGTACTT | ACGCGCACCGAT |
| | TGTCAGTGGAAG | | CGGACAGAAAAACAATA | TCAGCGGATTTA |
| | AAAATCACCCGT | | CTTGGGTGTGTACATTT | TGGAGTCCGGTA |
| | TTACTTTACGCG | | GGAACATGCGCGGCTCC | CACCGAGACTTG |
| | CACCGATTCAGC | | GATGGTACGTCTACCTA | GAGCTTTTTGCC |
| | GGATTTATGGAG | | CGCCACGTTTTTGGTCA | GTCATTAACCTG |
| | TCCGGTACACCG | | CCTGGAAAGGGGATGAA | TACGGGAGACGC |
| | AGACTTGGAGCT | | AAAACAAGAAACCCTAC | AGCGCCCGCCAT |
| | TTTTGCCGTCAT | | GCCCGCAGTAACTCCTC | CCAGCATATATG |
| | TAACCTGTACGG | | AACCAAGAGGGGCTGAG | TTTAAAACATAC |
| | GAGACGCAGCGC | | TTTCATATGTGGAATTA | AACATGCTTTCA |
| | CCGCCATCCAGC | | CCACTCGCATGTATTTT | AGACGTGGTGGT |
| | ATATATGTTTAA | | CAGTTGGTGATACGTTT | GGATGTGGATTG |
| | AACATACAACAT | | AGCTTGGCAATGCATCT | CGCGGAAAATAC |
| | GCTTTCAAGACG | | TCAGTATAAGATACATG | TAAAGAGGATCA |
| | TGGTGGTGGATG | | AAGCGCCATTTGATTTG | GTTGGCCGAAAT |
| | TGGATTGCGCGG | | CTGTTAGAGTGGTTGTA | CAGTTACCGTTT |
| | AAAATACTAAAG | | TGTCCCCATCGATCCTA | TCAAGGTAAGAA |
| | AGGATCAGTTGG | | CATGTCAACCAATGCGG | GGAAGCGGACCA |
| | CCGAAATCAGTT | | TTATATTCTACGTGTTT | ACCGTGGATTGT |
| | ACCGTTTTCAAG | | GTATCATCCCAACGCAC | TGTAAACACGAG |
| | GTAAGAAGGAAG | | CCCAATGCCTCTCTCAT | CACACTGTTTGA |
| | CGGACCAACCGT | | ATGAATTCCGGTTGTAC | TGAACTCGAATT |
| | GGATTGTTGTAA | | ATTTACCTCGCCACATT | AGACCCCCCCGA |

TABLE 2-continued

| | | |
|---|---|---|
| ACACGAGCACAC | TAGCCCAGCGTGTTGCA | GATTGAACCGGG |
| TGTTTGATGAAC | AGCACAGTGTATCAAAA | TGTCTTGAAAGT |
| TCGAATTAGACC | TTGTGAACATGCAGATA | ACTTCGGACAGA |
| CCCCCGAGATTG | ACTACACCGCATATTGT | AAAACAATACTT |
| AACCGGGTGTCT | CTGGGAATATCTCATAT | GGGTGTGTACAT |
| TGAAAGTACTTC | GGAGCCTAGCTTTGGTC | TTGGAACATGCG |
| GGACAGAAAAAC | TAATCTTACACGACGGG | CGGCTCCGATGG |
| AATACTTGGGTG | GGCACCACGTTAAAGTT | TACGTCTACCTA |
| TGTACATTTGGA | TGTAGATACACCCGAGA | CGCCACGTTTTT |
| ACATGCGCGGCT | GTTTGTCGGGATTATAC | GGTCACCTGGAA |
| CCGATGGTACGT | GTTTTTGTGGTGTATTT | AGGGGATGAAAA |
| CTACCTACGCCA | TAACGGGCATGTTGAAG | AACAAGAAACCC |
| CGTTTTTGGTCA | CCGTAGCATACACTGTT | TACGCCCGCAGT |
| CCTGGAAAGGGG | GTATCCACAGTAGATCA | AACTCCTCAACC |
| ATGAAAAAACAA | TTTTGTAAACGCAATTG | AAGAGGGGCTGA |
| GAAACCCTACGC | AAGAGCGTGGATTTCCG | GTTTCATATGTG |
| CCGCAGTAACTC | CCAACGGCCGGTCAGCC | GAATTACCACTC |
| CTCAACCAAGAG | ACCGGCGACTACTAAAC | GCATGTATTTTC |
| GGGCTGAGTTTC | CCAAGGAAATTACCCCC | AGTTGGTGATAC |
| ATATGTGGAATT | GTAAACCCCGGAACGTC | GTTTAGCTTGGC |
| ACCACTCGCATG | ACCACTTCTACGATATG | AATGCATCTTCA |
| TATTTTCAGTTG | CCGCATGGACCGGAGGG | GTATAAGATACA |
| GTGATACGTTTA | CTTGCAGCAGTAGTACT | TGAAGCGCCATT |
| GCTTGGCAATGC | TTTATGTCTCGTAATAT | TGATTTGCTGTT |
| ATCTTCAGTATA | TTTTAATCTGTACGGCT | AGAGTGGTTGTA |
| AGATACATGAAG | AAACGAATGAGGGTTAA | TGTCCCCATCGA |
| CGCCATTTGATT | AGCCGCCAGGGTAGACA | TCCTACATGTCA |
| TGCTGTTAGAGT | AGTGA | ACCAATGCGGTT |
| GGTTGTATGTCC | | ATATTCTACGTG |
| CCATCGATCCTA | | TTTGTATCATCC |
| CATGTCAACCAA | | CAACGCACCCCA |
| TGCGGTTATATT | | ATGCCTCTCTCA |
| CTACGTGTTTGT | | TATGAATTCCGG |
| ATCATCCCAACG | | TTGTACATTTAC |
| CACCCCAATGCC | | CTCGCCACATTT |
| TCTCTCATATGA | | AGCCCAGCGTGT |
| ATTCCGGTTGTA | | TGCAAGCACAGT |
| CATTTACCTCGC | | GTATCAAAATTG |
| CACATTTAGCCC | | TGAACATGCAGA |
| AGCGTGTTGCAA | | TAACTACACCGC |
| GCACAGTGTATC | | ATATTGTCTGGG |
| AAAATTGTGAAC | | AATATCTCATAT |
| ATGCAGATAACT | | GGAGCCTAGCTT |
| ACACCGCATATT | | TGGTCTAATCTT |
| GTCTGGGAATAT | | ACACGACGGGGG |
| CTCATATGGAGC | | CACCACGTTAAA |
| CTAGCTTTGGTC | | GTTTGTAGATAC |
| TAATCTTACACG | | ACCCGAGAGTTT |
| ACGGGGGCACCA | | GTCGGGATTATA |
| CGTTAAAGTTTG | | CGTTTTTGTGGT |
| TAGATACACCCG | | GTATTTTAACGG |
| AGAGTTTGTCGG | | GCATGTTGAAGC |
| GATTATACGTTT | | CGTAGCATACAC |
| TTGTGGTGTATT | | TGTTGTATCCAC |
| TTAACGGGCATG | | AGTAGATCATTT |
| TTGAAGCCGTAG | | TGTAAACGCAAT |
| CATACACTGTTG | | TGAAGAGCGTGG |
| TATCCACAGTAG | | ATTTCCGCCAAC |
| ATCATTTTGTAA | | GGCCGGTCAGCC |
| ACGCAATTGAAG | | ACCGGCGACTAC |
| AGCGTGGATTTC | | TAAACCCAAGGA |
| CGCCAACGGCCG | | AATTACCCCCGT |
| GTCAGCCACCGG | | AAACCCCGGAAC |
| CGACTACTAAAC | | GTCACCACTTCT |
| CCAAGGAAATTA | | ACGATATGCCGC |
| CCCCCGTAAACC | | ATGGACCGGAGG |
| CCGGAACGTCAC | | GCTTGCAGCAGT |
| CACTTCTACGAT | | AGTACTTTTATG |
| ATGCCGCATGGA | | TCTCGTAATATT |
| CCGGAGGGCTTG | | TTTAATCTGTAC |
| CAGCAGTAGTAC | | GGCTAAACGAAT |
| TTTTATGTCTCG | | GAGGGTTAAAGC |
| TAATATTTTTAA | | CGCCAGGGTAGA |
| TCTGTACGGCTA | | CAAGTGATGATA |
| AACGAATGAGGG | | ATAGGCTGGAGC |
| TTAAAGCCGCCA | | CTCGGTGGCCAT |
| GGGTAGACAAGT | | GCTTCTTGCCCC |
| GATGATAATAGG | | TTGGGCCTCCCC |
| CTGGAGCCTCGG | | CCAGCCCCTCCT |
| TGGCCATGCTTC | | CCCCTTCCTGCA |

TABLE 2-continued

| | | | | |
|---|---|---|---|---|
| | TTGCCCCTTGGG<br>CCTCCCCCCAGC<br>CCCTCCTCCCCT<br>TCCTGCACCCGT<br>ACCCCCGTGGTC<br>TTTGAATAAAGT<br>CTGAGTGGGCGG<br>C | | | CCCGTACCCCCG<br>TGGTCTTTGAAT<br>AAAGTCTGAGTG<br>GGCGGCAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAATC<br>TAG |
| | SEQ ID NO: 2 | SEQ ID NO: 42 | SEQ ID NO: 43 | SEQ ID NO: 44 |
| VZV-GI-<br>full | TCAAGCTTTTGG<br>ACCCTCGTACAG<br>AAGCTAATACGA<br>CTCACTATAGGG<br>AAATAAGAGAGA<br>AAAGAAGAGTAA<br>GAAGAAATATAA<br>GAGCCACCATGT<br>TTTTAATCCAAT<br>GTTTGATATCGG<br>CCGTTATATTTT<br>ACATACAAGTGA<br>CCAACGCTTTGA<br>TCTTCAAGGGCG<br>ACCACGTGAGCT<br>TGCAAGTTAACA<br>GCAGTCTCACGT<br>CTATCCTTATTC<br>CCATGCAAAATG<br>ATAATTATACAG<br>AGATAAAAGGAC<br>AGCTTGTCTTTA<br>TTGGAGAGCAAC<br>TACCTACCGGGA<br>CAAACTATAGCG<br>GAACACTGGAAC<br>TGTTATACGCGG<br>ATACGGTGGCGT<br>TTTGTTTCCGGT<br>CAGTACAAGTAA<br>TAAGATACGACG<br>GATGTCCCCGGA<br>TTAGAACGAGCG<br>CTTTTATTTCGT<br>GTAGGTACAAAC<br>ATTCGTGGCATT<br>ATGGTAACTCAA<br>CGGATCGGATAT<br>CAACAGAGCCGG<br>ATGCTGGTGTAA<br>TGTTGAAAATTA<br>CCAAACCGGGAA<br>TAAATGATGCTG<br>GTGTGTATGTAC<br>TTCTTGTTCGGT<br>TAGACCATAGCA<br>GATCCACCGATG<br>GTTTCATTCTTG<br>GTGTAAATGTAT<br>ATACAGCGGGCT<br>CGCATCACAACA<br>TTCACGGGGTTA<br>TCTACACTTCTC<br>CATCTCTACAGA<br>ATGGATATTCTA<br>CAAGAGCCCTTT<br>TTCAACAAGCTC<br>GTTTGTGTGATT<br>TACCCGCGACAC<br>CCAAAGGGTCCG<br>GTACCTCCCTGT<br>TTCAACATATGC<br>TTGATCTTCGTG<br>CCGGTAAATCGT | MFLIQCLISAVIFYIQV<br>TNALIFKGDHVSLQVNS<br>SLTSILIPMQNDNYTEI<br>KGQLVFigEQLPTGTNY<br>SGTLELLYADTVAFCFR<br>SVQVIRYDGCPRIRTSA<br>FISCRYKHSWHYGNSTD<br>RISTEPDAGVMLKITKP<br>GINDAGVYVLLVRLDHS<br>RSTDGFILGVNVYTAGS<br>HHNIHGVIYTSPSLQNG<br>YSTRALFQQARLCDLPA<br>TPKGSGTSLFQHMLDLR<br>AGKSLEDNPWLHEDVVT<br>TETKSVVKEGIENHVYP<br>TDMSTLPEKSLNDPPEN<br>LLIIIPIVASVMILTAM<br>VIVIVISVKRRRIKKHP<br>IYRPNTKTRRGIQNATP<br>ESDVMLEAAIAQLATIR<br>EESPPHSVVNPFVK* | ATGTTTTTAATCCAATG<br>TTTGATATCGGCCGTTA<br>TATTTTACATACAAGTG<br>ACCAACGCTTTGATCTT<br>CAAGGGCGACCACGTGA<br>GCTTGCAAGTTAACAGC<br>AGTCTCACGTCTATCCT<br>TATTCCCATGCAAAATG<br>ATAATTATACAGAGATA<br>AAAGGACAGCTTGTCTT<br>TATTGGAGAGCAACTAC<br>CTACCGGGACAAACTAT<br>AGCGGAACACTGGAACT<br>GTTATACGCGGATACGG<br>TGGCGTTTTGTTTCCGG<br>TCAGTACAAGTAATAAG<br>ATACGACGGATGTCCCC<br>GGATTAGAACGAGCGCT<br>TTTATTTCGTGTAGGTA<br>CAAACATTCGTGGCATT<br>ATGGTAACTCAACGGAT<br>CGGATATCAACAGAGCC<br>GGATGCTGGTGTAATGT<br>TGAAAATTACCAAACCG<br>GGAATAAATGATGCTGG<br>TGTGTATGTACTTCTTG<br>TTCGGTTAGACCATAGC<br>AGATCCACCGATGGTTT<br>CATTCTTGGTGTAAATG<br>TATATACAGCGGGCTCG<br>CATCACAACATTCACGG<br>GGTTATCTACACTTCTC<br>CATCTCTACAGAATGGA<br>TATTCTACAAGAGCCCT<br>TTTTCAACAAGCTCGTT<br>TGTGTGATTTACCCGCG<br>ACACCCAAAGGGTCCGG<br>TACCTCCCTGTTTCAAC<br>ATATGCTTGATCTTCGT<br>GCCGGTAAATCGTTAGA<br>GGATAACCCTTGGTTAC<br>ATGAGGACGTTGTTACG<br>ACAGAAACTAAGTCCGT<br>TGTTAAGGAGGGGATAG<br>AAAATCACGTATATCCA<br>ACGGATATGTCCACGTT<br>ACCCGAAAAGTCCCTTA<br>ATGATCCTCCAGAAAAT<br>CTACTTATAATTATTCC<br>TATAGTAGCGTCTGTCA<br>TGATCCTCACCGCCATG<br>GTTATTGTTATTGTAAT<br>AAGCGTTAAGCGACGTA<br>GAATTAAAAAACATCCA<br>ATTTATCGCCCAAATAC<br>AAAAACAAGAAGGGGCA<br>TACAAAATGCGACACCA<br>GAATCCGATGTGATGTT<br>GGAGGCCGCCATTGCAC<br>AACTAGCAACGATTCGC<br>GAAGAATCCCCCCACA<br>TTCCGTTGTAAACCCGT<br>TTGTTAAATAG | G*GGGAAATAAG<br>AGAGAAAAGAAG<br>AGTAAGAAGAAA<br>TATAAGAGCCAC<br>CATGTTTTTAAT<br>CCAATGTTTGAT<br>ATCGGCCGTTAT<br>ATTTTACATACA<br>AGTGACCAACGC<br>TTTGATCTTCAA<br>GGGCGACCACGT<br>GAGCTTGCAAGT<br>TAACAGCAGTCT<br>CACGTCTATCCT<br>TATTCCCATGCA<br>AAATGATAATTA<br>TACAGAGATAAA<br>AGGACAGCTTGT<br>CTTTATTGGAGA<br>GCAACTACCTAC<br>CGGGACAAACTA<br>TAGCGGAACACT<br>GGAACTGTTATA<br>CGCGGATACGGT<br>GGCGTTTTGTTT<br>CCGGTCAGTACA<br>AGTAATAAGATA<br>CGACGGATGTCC<br>CCGGATTAGAAC<br>GAGCGCTTTTAT<br>TTCGTGTAGGTA<br>CAAACATTCGTG<br>GCATTATGGTAA<br>CTCAACGGATCG<br>GATATCAACAGA<br>GCCGGATGCTGG<br>TGTAATGTTGAA<br>AATTACCAAACC<br>GGGAATAAATGA<br>TGCTGGTGTGTA<br>TGTACTTCTTGT<br>TCGGTTAGACCA<br>TAGCAGATCCAC<br>CGATGGTTTCAT<br>TCTTGGTGTAAA<br>TGTATATACAGC<br>GGGCTCGCATCA<br>CAACATTCACGG<br>GGTTATCTACAC<br>TTCTCCATCTCT<br>ACAGAATGGATA<br>TTCTACAAGAGC<br>CCTTTTTCAACA<br>AGCTCGTTTGTG<br>TGATTTACCCGC<br>GACACCCAAAGG<br>GTCCGGTACCTC<br>CCTGTTTCAACA<br>TATGCTTGATCT<br>TCGTGCCGGTAA<br>ATCGTTAGAGGA<br>TAACCCTTGGTT<br>ACATGAGGACGT<br>TGTTACGACAGA |

TABLE 2-continued

| | | | | |
|---|---|---|---|---|
| | TAGAGGATAACC | | | AACTAAGTCCGT |
| | CTTGGTTACATG | | | TGTTAAGGAGGG |
| | AGGACGTTGTTA | | | GATAGAAAATCA |
| | CGACAGAAACTA | | | CGTATATCCAAC |
| | AGTCCGTTGTTA | | | GGATATGTCCAC |
| | AGGAGGGGATAG | | | GTTACCCGAAAA |
| | AAAATCACGTAT | | | GTCCCTTAATGA |
| | ATCCAACGGATA | | | TCCTCCAGAAAA |
| | TGTCCACGTTAC | | | TCTACTTATAAT |
| | CCGAAAAGTCCC | | | TATTCCTATAGT |
| | TTAATGATCCTC | | | AGCGTCTGTCAT |
| | CAGAAAATCTAC | | | GATCCTCACCGC |
| | TTATAATTATTC | | | CATGGTTATTGT |
| | CTATAGTAGCGT | | | TATTGTAATAAG |
| | CTGTCATGATCC | | | CGTTAAGCGACG |
| | TCACCGCCATGG | | | TAGAATTAAAAA |
| | TTATTGTTATTG | | | ACATCCAATTTA |
| | TAATAAGCGTTA | | | TCGCCCAAATAC |
| | AGCGACGTAGAA | | | AAAAACAAGAAG |
| | TTAAAAAACATC | | | GGGCATACAAAA |
| | CAATTTATCGCC | | | TGCGACACCAGA |
| | CAAATACAAAAA | | | ATCCGATGTGAT |
| | CAAGAAGGGGCA | | | GTTGGAGGCCGC |
| | TACAAAATGCGA | | | CATTGCACAACT |
| | CACCAGAATCCG | | | AGCAACGATTCG |
| | ATGTGATGTTGG | | | CGAAGAATCCCC |
| | AGGCCGCCATTG | | | CCCACATTCCGT |
| | CACAACTAGCAA | | | TGTAAACCCGTT |
| | CGATTCGCGAAG | | | TGTTAAATAGTG |
| | AATCCCCCCCAC | | | ATAATAGGCTGG |
| | ATTCCGTTGTAA | | | AGCCTCGGTGGC |
| | ACCCGTTTGTTA | | | CATGCTTCTTGC |
| | AATAGTGATAAT | | | CCCTTGGGCCTC |
| | AGGCTGGAGCCT | | | CCCCCAGCCCCT |
| | CGGTGGCCATGC | | | CCTCCCCTTCCT |
| | TTCTTGCCCCTT | | | GCACCCGTACCC |
| | GGGCCTCCCCCC | | | CCGTGGTCTTTG |
| | AGCCCCTCCTCC | | | AATAAAGTCTGA |
| | CCTTCCTGCACC | | | GTGGGCGGCAAA |
| | CGTACCCCCGTG | | | AAAAAAAAAAAA |
| | GTCTTTGAATAA | | | AAAAAAAAAAAA |
| | AGTCTGAGTGGG | | | AAAAAAAAAAAA |
| | CGGC | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | ATCTAG |

| | SEQ ID NO: 60 | SEQ ID NO: 61 | SEQ ID NO: 62 | SEQ ID NO: 63 |
|---|---|---|---|---|
| VZV-GE- | GGGAAATAAGAG | MGTVNKPVVGVLMGFGI | ATGGGCACCGTGAACAA | GGGAAATAAGAG |
| truncated- | AGAAAAGAAGAG | ITGTLRITNPVRASVLR | GCCCGTCGTGGGCGTGC | AGAAAAGAAGAG |
| delete_ | TAAGAAGAAATA | YDDFHIDEDKLDTNSVY | TGATGGGCTTCGGCATC | TAAGAAGAAATA |
| from_574_-_ | TAAGAGCCACCA | EPYYHSDHAESSWVNRG | ATCACCGGCACCCTGCG | TAAGAGCCACCA |
| Y569A | TGGGCACCGTGA | ESSRKAYDHNSPYIWPR | GATCACCAATCCTGTGC | TGGGCACCGTGA |
| Variant | ACAAGCCCGTCG | NDYDGFLENAHEHHGVY | GGGCCAGCGTGCTGAGA | ACAAGCCCGTCG |
| 1 | TGGGCGTGCTGA | NQGRGIDSGERLMQPTQ | TACGACGACTTCCACAT | TGGGCGTGCTGA |
| | TGGGCTTCGGCA | MSAQEDLGDDTGIHVIP | CGACGAGGACAAGCTGG | TGGGCTTCGGCA |
| | TCATCACCGGCA | TLNGDDRHKIVNVDQRQ | ACACCAACAGCGTGTAC | TCATCACCGGCA |
| | CCCTGCGGATCA | YGDVFKGDLNPKPQGQR | GAGCCCTACTACCACAG | CCCTGCGGATCA |
| | CCAATCCTGTGC | LIEVSVEENHPFTLRAP | CGACCACGCCGAGAGCA | CCAATCCTGTGC |
| | GGGCCAGCGTGC | IQRIYGVRYTETWSFLP | GCTGGGTCAACAGAGGC | GGGCCAGCGTGC |
| | TGAGATACGACG | SLTCTGDAAPAIQHICL | GAGTCCAGCCGGAAGGC | TGAGATACGACG |
| | ACTTCCACATCG | KHTTCFQDVVVDVDCAE | CTACGACCACAACAGCC | ACTTCCACATCG |
| | ACGAGGACAAGC | NTKEDQLAEISYRFQGK | CCTACATCTGGCCCCGG | ACGAGGACAAGC |
| | TGGACACCAACA | KEADQPWIVVNTSTLFD | AACGACTACGACGGCTT | TGGACACCAACA |
| | GCGTGTACGAGC | ELELDPPEIEPGVLKVL | CCTGGAAAATGCCCACG | GCGTGTACGAGC |
| | CCTACTACCACA | RTEKQYLGVYIWNMRGS | AGCACCACGGCGTGTAC | CCTACTACCACA |
| | GCGACCACGCCG | DGTSTYATFLVTWKGDE | AACCAGGGCAGAGGCAT | GCGACCACGCCG |
| | AGAGCAGCTGGG | KTRNPTPAVTPQPRGAE | CGACAGCGGCGAGAGAC | AGAGCAGCTGGG |
| | TCAACAGAGGCG | FHMWNYHSHVFSVGDTF | TGATGCAGCCCACCCAG | TCAACAGAGGCG |
| | AGTCCAGCCGGA | SLAMHLQYKIHEAPFDL | ATGAGCGCCCAGGAAGA | AGTCCAGCCGGA |
| | AGGCCTACGACC | LLEWLYVPIDPTCQPMR | TCTGGGCGACGACACCG | AGGCCTACGACC |
| | ACAACAGCCCCT | LYSTCLYHPNAPQCLSH | GCATCCACGTGATCCCT | ACAACAGCCCCT |
| | ACATCTGGCCCC | MNSGCTFTSPHLAQRVA | ACCCTGAACGGCGACGA | ACATCTGGCCCC |
| | GGAACGACTACG | STVYQNCEHADNYTAYC | CCGGCACAAGATCGTGA | GGAACGACTACG |
| | ACGGCTTCCTGG | LGISHMEPSFGLILHDG | ACGTGGACCAGCGGCAG | ACGGCTTCCTGG |
| | AAAATGCCCACG | GTTLKFVDTPESLSGLY | TACGGCGACGTGTTCAA | AAAATGCCCACG |
| | AGCACCACGGCG | VFVVYFNGHVEAVAYTV | GGGCGACCTGAACCCCA | AGCACCACGGCG |

TABLE 2-continued

| | | | |
|---|---|---|---|
| TGTACAACCAGG | VSTVDHFVNAIEERGFP | AGCCCCAGGGACAGCGG | TGTACAACCAGG |
| GCAGAGGCATCG | PTAGQPPATTKPKEITP | CTGATTGAGGTGTCCGT | GCAGAGGCATCG |
| ACAGCGGCGAGA | VNPGTSPLLRYAAWTGG | GGAAGAGAACCACCCCT | ACAGCGGCGAGA |
| GACTGATGCAGC | LAAVVLLCLVIFLICTA | TCACCCTGAGAGCCCCT | GACTGATGCAGC |
| CCACCCAGATGA | KRMRVKAARVDK | ATCCAGCGGATCTACGG | CCACCCAGATGA |
| GCGCCCAGGAAG | | CGTGCGCTATACCGAGA | GCGCCCAGGAAG |
| ATCTGGGCGACG | | CTTGGAGCTTCCTGCCC | ATCTGGGCGACG |
| ACACCGGCATCC | | AGCCTGACCTGTACTGG | ACACCGGCATCC |
| ACGTGATCCCTA | | CGACGCCGCTCCTGCCA | ACGTGATCCCTA |
| CCCTGAACGGCG | | TCCAGCACATCTGCCTG | CCCTGAACGGCG |
| ACGACCGGCACA | | AAGCACACCACCTGTTT | ACGACCGGCACA |
| AGATCGTGAACG | | CCAGGACGTGGTGGTGG | AGATCGTGAACG |
| TGGACCAGCGGC | | ACGTGGACTGCGCCGAG | TGGACCAGCGGC |
| AGTACGGCGACG | | AACACCAAAGAGGACCA | AGTACGGCGACG |
| TGTTCAAGGGCG | | GCTGGCCGAGATCAGCT | TGTTCAAGGGCG |
| ACCTGAACCCCA | | ACCGGTTCCAGGGCAAG | ACCTGAACCCCA |
| AGCCCCAGGGAC | | AAAGAGGCCGACCAGCC | AGCCCCAGGGAC |
| AGCGGCTGATTG | | CTGGATCGTCGTGAACA | AGCGGCTGATTG |
| AGGTGTCCGTGG | | CCAGCACCCTGTTCGAC | AGGTGTCCGTGG |
| AAGAGAACCACC | | GAGCTGGAACTGGACCC | AAGAGAACCACC |
| CCTTCACCCTGA | | TCCCGAGATCGAACCCG | CCTTCACCCTGA |
| GAGCCCCTATCC | | GGGTGCTGAAGGTGCTG | GAGCCCCTATCC |
| AGCGGATCTACG | | CGGACCGAGAAGCAGTA | AGCGGATCTACG |
| GCGTGCGCTATA | | CCTGGGAGTGTACATCT | GCGTGCGCTATA |
| CCGAGACTTGGA | | GGAACATGCGGGGCAGC | CCGAGACTTGGA |
| GCTTCCTGCCCA | | GACGGCACCTCTACCTA | GCTTCCTGCCCA |
| GCCTGACCTGTA | | CGCCACCTTCCTCGTGA | GCCTGACCTGTA |
| CTGGCGACGCCG | | CCTGGAAGGGCGACGAG | CTGGCGACGCCG |
| CTCCTGCCATCC | | AAAACCCGGAACCCTAC | CTCCTGCCATCC |
| AGCACATCTGCC | | CCCTGCCGTGACCCCTC | AGCACATCTGCC |
| TGAAGCACACCA | | AGCCTAGAGGCGCCGAG | TGAAGCACACCA |
| CCTGTTTCCAGG | | TTTCACATGTGGAATTA | CCTGTTTCCAGG |
| ACGTGGTGGTGG | | CCACAGCCACGTGTTCA | ACGTGGTGGTGG |
| ACGTGGACTGCG | | GCGTGGGCGACACCTTC | ACGTGGACTGCG |
| CCGAGAACACCA | | TCCCTGGCCATGCATCT | CCGAGAACACCA |
| AAGAGGACCAGC | | GCAGTACAAGATCCACG | AAGAGGACCAGC |
| TGGCCGAGATCA | | AGGCCCCTTTCGACCTG | TGGCCGAGATCA |
| GCTACCGGTTCC | | CTGCTGGAATGGCTGTA | GCTACCGGTTCC |
| AGGGCAAGAAAG | | CGTGCCCATCGACCCTA | AGGGCAAGAAAG |
| AGGCCGACCAGC | | CCTGCCAGCCCATGCGG | AGGCCGACCAGC |
| CCTGGATCGTCG | | CTGTACTCCACCTGTCT | CCTGGATCGTCG |
| TGAACACCAGCA | | GTACCACCCCAACGCCC | TGAACACCAGCA |
| CCCTGTTCGACG | | CTCAGTGCCTGAGCCAC | CCCTGTTCGACG |
| AGCTGGAACTGG | | ATGAATAGCGGCTGCAC | AGCTGGAACTGG |
| ACCCTCCCGAGA | | CTTCACCAGCCCTCACC | ACCCTCCCGAGA |
| TCGAACCCGGGG | | TGGCTCAGAGGGTGGCC | TCGAACCCGGGG |
| TGCTGAAGGTGC | | AGCACCGTGTACCAGAA | TGCTGAAGGTGC |
| TGCGGACCGAGA | | TTGCGAGCACGCCGACA | TGCGGACCGAGA |
| AGCAGTACCTGG | | ACTACACCGCCTACTGC | AGCAGTACCTGG |
| GAGTGTACATCT | | CTGGGCATCAGCCACAT | GAGTGTACATCT |
| GGAACATGCGGG | | GGAACCCAGCTTCGGCC | GGAACATGCGGG |
| GCAGCGACGGCA | | TGATCCTGCACGATGGC | GCAGCGACGGCA |
| CCTCTACCTACG | | GGCACCACCCTGAAGTT | CCTCTACCTACG |
| CCACCTTCCTCG | | CGTGGACACCCCTGAGT | CCACCTTCCTCG |
| TGACCTGGAAGG | | CCCTGAGCGGCCTGTAC | TGACCTGGAAGG |
| GCGACGAGAAAA | | GTGTTCGTGGTGTACTT | GCGACGAGAAAA |
| CCCGGAACCCTA | | CAACGGCCACGTGGAAG | CCCGGAACCCTA |
| CCCCTGCCGTGA | | CCGTGGCCTACACCGTG | CCCCTGCCGTGA |
| CCCCTCAGCCTA | | GTGTCCACCGTGGACCA | CCCCTCAGCCTA |
| GAGGCGCCGAGT | | CTTCGTGAACGCCATCG | GAGGCGCCGAGT |
| TTCACATGTGGA | | AGGAACGGGGCTTCCCT | TTCACATGTGGA |
| ATTACCACAGCC | | CCAACTGCTGGACAGCC | ATTACCACAGCC |
| ACGTGTTCAGCG | | TCCTGCCACCACCAAGC | ACGTGTTCAGCG |
| TGGGCGACACCT | | CCAAAGAAATCACCCCT | TGGGCGACACCT |
| TCTCCCTGGCCA | | GTGAACCCCGGCACCAG | TCTCCCTGGCCA |
| TGCATCTGCAGT | | CCCACTGCTGCGCTATG | TGCATCTGCAGT |
| ACAAGATCCACG | | CTGCTTGGACAGGCGGA | ACAAGATCCACG |
| AGGCCCCTTTCG | | CTGGCTGCTGTGGTGCT | AGGCCCCTTTCG |
| ACCTGCTGCTGG | | GCTGTGCCTCGTGATTT | ACCTGCTGCTGG |
| AATGGCTGTACG | | TCCTGATCTGCACCGCC | AATGGCTGTACG |
| TGCCCATCGACC | | AAGCGGATGAGAGTGAA | TGCCCATCGACC |
| CTACCTGCCAGC | | GGCCGCCAGAGTGGACA | CTACCTGCCAGC |
| CCATGCGGCTGT | | AG | CCATGCGGCTGT |
| ACTCCACCTGTC | | | ACTCCACCTGTC |
| TGTACCACCCCA | | | TGTACCACCCCA |
| ACGCCCCTCAGT | | | ACGCCCCTCAGT |
| GCCTGAGCCACA | | | GCCTGAGCCACA |
| TGAATAGCGGCT | | | TGAATAGCGGCT |
| GCACCTTCACCA | | | GCACCTTCACCA |
| GCCCTCACCTGG | | | GCCCTCACCTGG |

TABLE 2-continued

| | | | | |
|---|---|---|---|---|
| | CTCAGAGGGTGG<br>CCAGCACCGTGT<br>ACCAGAATTGCG<br>AGCACGCCGACA<br>ACTACACCGCCT<br>ACTGCCTGGGCA<br>TCAGCCACATGG<br>AACCCAGCTTCG<br>GCCTGATCCTGC<br>ACGATGGCGGCA<br>CCACCCTGAAGT<br>TCGTGGACACCC<br>CTGAGTCCCTGA<br>GCGGCCTGTACG<br>TGTTCGTGGTGT<br>ACTTCAACGGCC<br>ACGTGGAAGCCG<br>TGGCCTACACCG<br>TGGTGTCCACCG<br>TGGACCACTTCG<br>TGAACGCCATCG<br>AGGAACGGGGCT<br>TCCCTCCAACTG<br>CTGGACAGCCTC<br>CTGCCACCACCA<br>AGCCCAAAGAAA<br>TCACCCCTGTGA<br>ACCCCGGCACCA<br>GCCCACTGCTGC<br>GCTATGCTGCTT<br>GGACAGGCGGAC<br>TGGCTGCTGTGG<br>TGCTGCTGTGCC<br>TCGTGATTTTCC<br>TGATCTGCACCG<br>CCAAGCGGATGA<br>GAGTGAAGGCCG<br>CCAGAGTGGACA<br>AGTGATAATAGG<br>CTGGAGCCTCGG<br>TGGCCATGCTTC<br>TTGCCCCTTGGG<br>CCTCCCCCCAGC<br>CCCTCCTCCCCT<br>TCCTGCACCCGT<br>ACCCCCGTGGTC<br>TTTGAATAAAGT<br>CTGAGTGGGCGG<br>C | | | CTCAGAGGGTGG<br>CCAGCACCGTGT<br>ACCAGAATTGCG<br>AGCACGCCGACA<br>ACTACACCGCCT<br>ACTGCCTGGGCA<br>TCAGCCACATGG<br>AACCCAGCTTCG<br>GCCTGATCCTGC<br>ACGATGGCGGCA<br>CCACCCTGAAGT<br>TCGTGGACACCC<br>CTGAGTCCCTGA<br>GCGGCCTGTACG<br>TGTTCGTGGTGT<br>ACTTCAACGGCC<br>ACGTGGAAGCCG<br>TGGCCTACACCG<br>TGGTGTCCACCG<br>TGGACCACTTCG<br>TGAACGCCATCG<br>AGGAACGGGGCT<br>TCCCTCCAACTG<br>CTGGACAGCCTC<br>CTGCCACCACCA<br>AGCCCAAAGAAA<br>TCACCCCTGTGA<br>ACCCCGGCACCA<br>GCCCACTGCTGC<br>GCTATGCTGCTT<br>GGACAGGCGGAC<br>TGGCTGCTGTGG<br>TGCTGCTGTGCC<br>TCGTGATTTTCC<br>TGATCTGCACCG<br>CCAAGCGGATGA<br>GAGTGAAGGCCG<br>CCAGAGTGGACA<br>AGTGATAATAGG<br>CTGGAGCCTCGG<br>TGGCCATGCTTC<br>TTGCCCCTTGGG<br>CCTCCCCCCAGC<br>CCCTCCTCCCCT<br>TCCTGCACCCGT<br>ACCCCCGTGGTC<br>TTTGAATAAAGT<br>CTGAGTGGGCGG<br>CAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAATCTAG |
| | SEQ ID NO: 64 | SEQ ID NO: 65 | SEQ ID NO: 66 | SEQ ID NO: 67 |
| VZV-GE-<br>truncated-<br>delete_<br>from_574_-_<br>Y569A<br>Variant<br>2 | GGGAAATAAGAG<br>AGAAAAGAAGAG<br>TAAGAAGAAATA<br>TAAGAGCCACCA<br>TGGGGACAGTTA<br>ATAAACCTGTGG<br>TGGGGGTATTGA<br>TGGGGTTCGGAA<br>TTATCACGGGAA<br>CGTTGCGTATAA<br>CGAATCCGGTCA<br>GAGCATCCGTCT<br>TGCGATACGATG<br>ATTTTCACATCG<br>ATGAAGACAAAC<br>TGGATACAAACT<br>CCGTATATGAGC<br>CTTACTACCATT<br>CAGATCATGCGG<br>AGTCTTCATGGG | MGTVNKPVVGVLMGFGI<br>ITGTLRITNPVRASVLR<br>YDDFHIDEDKLDTNSVY<br>EPYYHSDHAESSWVNRG<br>ESSRKAYDHNSPYIWPR<br>NDYDGFLENAHEHHGVY<br>NQGRGIDSGERLMQPTQ<br>MSAQEDLGDDTGIHVIP<br>TLNGDDRHKIVNVDQRQ<br>YGDVFKGDLNPKPQGQR<br>LIEVSVEENHPFTLRAP<br>IQRIYGVRYTETWSFLP<br>SLTCTGDAAPAIQHICL<br>KHTTCFQDVVVDVDCAE<br>NTKEDQLAEISYRFQGK<br>KEADQPWIVVNTSTLFD<br>ELELDPPEIEPGVLKVL<br>RTEKQYLGVYIWNMRGS<br>DGTSTYATFLVTWKGDE<br>KTRNPTPAVTPQPRGAE | ATGGGGACAGTTAATAA<br>ACCTGTGGTGGGGGTAT<br>TGATGGGGTTCGGAATT<br>ATCACGGGAACGTTGCG<br>TATAACGAATCCGGTCA<br>GAGCATCCGTCTTGCGA<br>TACGATGATTTTCACAT<br>CGATGAAGACAAACTGG<br>ATACAAACTCCGTATAT<br>GAGCCTTACTACCATTC<br>AGATCATGCGGAGTCTT<br>CATGGGTAAATCGGGGA<br>GAGTCTTCGCGAAAAGC<br>GTACGATCATAACTCAC<br>CTTATATATGGCCACGT<br>AATGATTATGATGGATT<br>TTTAGAGAACGCACACG<br>AACACCATGGGGTGTAT<br>AATCAGGGCCGTGGTAT<br>CGATAGCGGGGAACGGT | GGGAAATAAGAG<br>AGAAAAGAAGAG<br>TAAGAAGAAATA<br>TAAGAGCCACCA<br>TGGGGACAGTTA<br>ATAAACCTGTGG<br>TGGGGGTATTGA<br>TGGGGTTCGGAA<br>TTATCACGGGAA<br>CGTTGCGTATAA<br>CGAATCCGGTCA<br>GAGCATCCGTCT<br>TGCGATACGATG<br>ATTTTCACATCG<br>ATGAAGACAAAC<br>TGGATACAAACT<br>CCGTATATGAGC<br>CTTACTACCATT<br>CAGATCATGCGG<br>AGTCTTCATGGG |

TABLE 2-continued

| | | | |
|---|---|---|---|
| TAAATCGGGGAG | FHMWNYHSHVFSVGDTF | TAATGCAACCCACACAA | TAAATCGGGGAG |
| AGTCTTCGCGAA | SLAMHLQYKIHEAPFDL | ATGTCTGCACAGGAGGA | AGTCTTCGCGAA |
| AAGCGTACGATC | LLEWLYVPIDPTCQPMR | TCTTGGGGACGATACGG | AAGCGTACGATC |
| ATAACTCACCTT | LYSTCLYHPNAPQCLSH | GCATCCACGTTATCCCT | ATAACTCACCTT |
| ATATATGGCCAC | MNSGCTFTSPHLAQRVA | ACGTTAAACGGCGATGA | ATATATGGCCAC |
| GTAATGATTATG | STVYQNCEHADNYTAYC | CAGACATAAAATTGTAA | GTAATGATTATG |
| ATGGATTTTTAG | LGISHMEPSFGLILHDG | ATGTGGACCAACGTCAA | ATGGATTTTTAG |
| AGAACGCACACG | GTTLKFVDTPESLSGLY | TACGGTGACGTGTTTAA | AGAACGCACACG |
| AACACCATGGGG | VFVVYFNGHVEAVAYTV | AGGAGATCTTAATCCAA | AACACCATGGGG |
| TGTATAATCAGG | VSTVDHFVNAIEERGFP | AACCCCAAGGCCAAAGA | TGTATAATCAGG |
| GCCGTGGTATCG | PTAGQPPATTKPKEITP | CTCATTGAGGTGTCAGT | GCCGTGGTATCG |
| ATAGCGGGGAAC | VNPGTSPLLRYAAWTGG | GGAAGAAAATCACCCGT | ATAGCGGGGAAC |
| GGTTAATGCAAC | LAAVVLLCLVIFLICTA | TTACTTTACGCGCACCG | GGTTAATGCAAC |
| CCACACAAATGT | KRMRVKAARVDK | ATTCAGCGGATTTATGG | CCACACAAATGT |
| CTGCACAGGAGG | | AGTCCGGTACACCGAGA | CTGCACAGGAGG |
| ATCTTGGGGACG | | CTTGGAGCTTTTTGCCG | ATCTTGGGGACG |
| ATACGGGCATCC | | TCATTAACCTGTACGGG | ATACGGGCATCC |
| ACGTTATCCCTA | | AGACGCAGCGCCCGCCA | ACGTTATCCCTA |
| CGTTAAACGGCG | | TCCAGCATATATGTTTA | CGTTAAACGGCG |
| ATGACAGACATA | | AAACATACAACATGCTT | ATGACAGACATA |
| AAATTGTAAATG | | TCAAGACGTGGTGGTGG | AAATTGTAAATG |
| TGGACCAACGTC | | ATGTGGATTGCGCGGAA | TGGACCAACGTC |
| AATACGGTGACG | | AATACTAAAGAGGATCA | AATACGGTGACG |
| TGTTTAAAGGAG | | GTTGGCCGAAATCAGTT | TGTTTAAAGGAG |
| ATCTTAATCCAA | | ACCGTTTTCAAGGTAAG | ATCTTAATCCAA |
| AACCCCAAGGCC | | AAGGAAGCGGACCAACC | AACCCCAAGGCC |
| AAAGACTCATTG | | GTGGATTGTTGTAAACA | AAAGACTCATTG |
| AGGTGTCAGTGG | | CGAGCACACTGTTTGAT | AGGTGTCAGTGG |
| AAGAAAATCACC | | GAACTCGAATTAGACCC | AAGAAAATCACC |
| CGTTTACTTTAC | | CCCCGAGATTGAACCGG | CGTTTACTTTAC |
| GCGCACCGATTC | | GTGTCTTGAAAGTACTT | GCGCACCGATTC |
| AGCGGATTTATG | | CGGACAGAGAAACAATA | AGCGGATTTATG |
| GAGTCCGGTACA | | CTTGGGTGTGTACATTT | GAGTCCGGTACA |
| CCGAGACTTGGA | | GGAACATGCGCGGCTCC | CCGAGACTTGGA |
| GCTTTTTGCCGT | | GATGGTACGTCTACCTA | GCTTTTTGCCGT |
| CATTAACCTGTA | | CGCCACGTTTTTGGTCA | CATTAACCTGTA |
| CGGGAGACGCAG | | CCTGGAAAGGGGATGAG | CGGGAGACGCAG |
| CGCCCGCCATCC | | AAGACAAGAAACCCTAC | CGCCCGCCATCC |
| AGCATATATGTT | | GCCCGCAGTAACTCCTC | AGCATATATGTT |
| TAAAACATACAA | | AACCAAGAGGGGCTGAG | TAAAACATACAA |
| CATGCTTTCAAG | | TTTCATATGTGGAATTA | CATGCTTTCAAG |
| ACGTGGTGGTGG | | CCACTCGCATGTATTTT | ACGTGGTGGTGG |
| ATGTGGATTGCG | | CAGTTGGTGATACGTTT | ATGTGGATTGCG |
| CGGAAAATACTA | | AGCTTGGCAATGCATCT | CGGAAAATACTA |
| AAGAGGATCAGT | | TCAGTATAAGATACATG | AAGAGGATCAGT |
| TGGCCGAAATCA | | AAGCGCCATTTGATTTG | TGGCCGAAATCA |
| GTTACCGTTTTC | | CTGTTAGAGTGGTTGTA | GTTACCGTTTTC |
| AAGGTAAGAAGG | | TGTCCCCATCGATCCTA | AAGGTAAGAAGG |
| AAGCGGACCAAC | | CATGTCAACCAATGCGG | AAGCGGACCAAC |
| CGTGGATTGTTG | | TTATATTCTACGTGTTT | CGTGGATTGTTG |
| TAAACACGAGCA | | GTATCATCCCAACGCAC | TAAACACGAGCA |
| CACTGTTTGATG | | CCCAATGCCTCTCTCAT | CACTGTTTGATG |
| AACTCGAATTAG | | ATGAATTCCGGTTGTAC | AACTCGAATTAG |
| ACCCCCCCGAGA | | ATTTACCTCGCCACATT | ACCCCCCCGAGA |
| TTGAACCGGGTG | | TAGCCCAGCGTGTTGCA | TTGAACCGGGTG |
| TCTTGAAAGTAC | | AGCACAGTGTATCAAAA | TCTTGAAAGTAC |
| TTCGGACAGAGA | | TTGTGAACATGCAGATA | TTCGGACAGAGA |
| AACAATACTTGG | | ACTACACCGCATATTGT | AACAATACTTGG |
| GTGTGTACATTT | | CTGGGAATATCTCATAT | GTGTGTACATTT |
| GGAACATGCGCG | | GGAGCCTAGCTTTGGTC | GGAACATGCGCG |
| GCTCCGATGGTA | | TAATCTTACACGACGGG | GCTCCGATGGTA |
| CGTCTACCTACG | | GGCACCACGTTAAAGTT | CGTCTACCTACG |
| CCACGTTTTTGG | | TGTAGATACACCCGAGA | CCACGTTTTTGG |
| TCACCTGGAAAG | | GTTTGTCGGGATTATAC | TCACCTGGAAAG |
| GGGATGAGAAGA | | GTTTTTGTGGTGTATTT | GGGATGAGAAGA |
| CAAGAAACCCTA | | TAACGGGCATGTTGAAG | CAAGAAACCCTA |
| CGCCCGCAGTAA | | CCGTAGCATACACTGTT | CGCCCGCAGTAA |
| CTCCTCAACCAA | | GTATCCACAGTAGATCA | CTCCTCAACCAA |
| GAGGGGCTGAGT | | TTTTGTAAACGCAATTG | GAGGGGCTGAGT |
| TTCATATGTGGA | | AAGAGCGTGGATTTCCG | TTCATATGTGGA |
| ATTACCACTCGC | | CCAACGGCCGGTCAGCC | ATTACCACTCGC |
| ATGTATTTTCAG | | ACCGGCGACTACTAAAC | ATGTATTTTCAG |
| TTGGTGATACGT | | CCAAGGAAATTACCCCC | TTGGTGATACGT |
| TTAGCTTGGCAA | | GTAAACCCCGGAACGTC | TTAGCTTGGCAA |
| TGCATCTTCAGT | | ACCACTTCTACGATATG | TGCATCTTCAGT |
| ATAAGATACATG | | CCGCATGGACCGGAGGG | ATAAGATACATG |
| AAGCGCCATTTG | | CTTGCAGCAGTAGTACT | AAGCGCCATTTG |
| ATTTGCTGTTAG | | TTTATGTCTCGTAATAT | ATTTGCTGTTAG |
| AGTGGTTGTATG | | TTTTAATCTGTACGGCT | AGTGGTTGTATG |
| TCCCCATCGATC | | AAACGAATGAGGGTTAA | TCCCCATCGATC |

TABLE 2-continued

| | | | | |
|---|---|---|---|---|
| | CTACATGTCAAC<br>CAATGCGGTTAT<br>ATTCTACGTGTT<br>TGTATCATCCCA<br>ACGCACCCCAAT<br>GCCTCTCTCATA<br>TGAATTCCGGTT<br>GTACATTTACCT<br>CGCCACATTTAG<br>CCCAGCGTGTTG<br>CAAGCACAGTGT<br>ATCAAAATTGTG<br>AACATGCAGATA<br>ACTACACCGCAT<br>ATTGTCTGGGAA<br>TATCTCATATGG<br>AGCCTAGCTTTG<br>GTCTAATCTTAC<br>ACGACGGGGGCA<br>CCACGTTAAAGT<br>TTGTAGATACAC<br>CCGAGAGTTTGT<br>CGGGATTATACG<br>TTTTTGTGGTGT<br>ATTTTAACGGGC<br>ATGTTGAAGCCG<br>TAGCATACACTG<br>TTGTATCCACAG<br>TAGATCATTTTG<br>TAAACGCAATTG<br>AAGAGCGTGGAT<br>TTCCGCCAACGG<br>CCGGTCAGCCAC<br>CGGCGACTACTA<br>AACCCAAGGAAA<br>TTACCCCCGTAA<br>ACCCCGGAACGT<br>CACCACTTCTAC<br>GATATGCCGCAT<br>GGACCGGAGGGC<br>TTGCAGCAGTAG<br>TACTTTTATGTC<br>TCGTAATATTTT<br>TAATCTGTACGG<br>CTAAACGAATGA<br>GGGTTAAAGCCG<br>CCAGGGTAGACA<br>AGTGATAATAGG<br>CTGGAGCCTCGG<br>TGGCCATGCTTC<br>TTGCCCCTTGGG<br>CCTCCCCCCAGC<br>CCCTCCTCCCCT<br>TCCTGCACCCGT<br>ACCCCCGTGGTC<br>TTTGAATAAAGT<br>CTGAGTGGGCGG<br>C | | AGCCGCCAGGGTAGACA<br>AG | CTACATGTCAAC<br>CAATGCGGTTAT<br>ATTCTACGTGTT<br>TGTATCATCCCA<br>ACGCACCCCAAT<br>GCCTCTCTCATA<br>TGAATTCCGGTT<br>GTACATTTACCT<br>CGCCACATTTAG<br>CCCAGCGTGTTG<br>CAAGCACAGTGT<br>ATCAAAATTGTG<br>AACATGCAGATA<br>ACTACACCGCAT<br>ATTGTCTGGGAA<br>TATCTCATATGG<br>AGCCTAGCTTTG<br>GTCTAATCTTAC<br>ACGACGGGGGCA<br>CCACGTTAAAGT<br>TTGTAGATACAC<br>CCGAGAGTTTGT<br>CGGGATTATACG<br>TTTTTGTGGTGT<br>ATTTTAACGGGC<br>ATGTTGAAGCCG<br>TAGCATACACTG<br>TTGTATCCACAG<br>TAGATCATTTTG<br>TAAACGCAATTG<br>AAGAGCGTGGAT<br>TTCCGCCAACGG<br>CCGGTCAGCCAC<br>CGGCGACTACTA<br>AACCCAAGGAAA<br>TTACCCCCGTAA<br>ACCCCGGAACGT<br>CACCACTTCTAC<br>GATATGCCGCAT<br>GGACCGGAGGGC<br>TTGCAGCAGTAG<br>TACTTTTATGTC<br>TCGTAATATTTT<br>TAATCTGTACGG<br>CTAAACGAATGA<br>GGGTTAAAGCCG<br>CCAGGGTAGACA<br>AGTGATAATAGG<br>CTGGAGCCTCGG<br>TGGCCATGCTTC<br>TTGCCCCTTGGG<br>CCTCCCCCCAGC<br>CCCTCCTCCCCT<br>TCCTGCACCCGT<br>ACCCCCGTGGTC<br>TTTGAATAAAGT<br>CTGAGTGGGCGG<br>CAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAAAAAAAAA<br>AAAAATCTAG |
| | SEQ ID NO: 68 | SEQ ID NO: 69 | SEQ ID NO: 70 | SEQ ID NO: 71 |
| VZV-GE-<br>truncated-<br>delete_<br>from_574_-_<br>Y569A<br>Variant<br>3 | GGGAAATAAGAG<br>AGAAAAGAAGAG<br>TAAGAAGAAATA<br>TAAGAGCCACCA<br>TGGGGACAGTTA<br>ATAAACCTGTGG<br>TGGGGGTATTGA<br>TGGGGTTCGGAA<br>TTATCACGGGAA<br>CGTTGCGTATAA<br>CGAATCCGGTCA | MGTVNKPVVGVLMGFGI<br>ITGTLRITNPVRASVLR<br>YDDFHIDEDKLDTNSVY<br>EPYYHSDHAESSWVNRG<br>ESSRKAYDHNSPYIWPR<br>NDYDGFLENAHEHHGVY<br>NQGRGIDSGERLMQPTQ<br>MSAQEDLGDDTGIHVIP<br>TLNGDDRHKIVNVDQRQ<br>YGDVFKGDLNPKPQGQR<br>LIEVSVEENHPFTLRAP | ATGGGGACAGTTAATAA<br>ACCTGTGGTGGGGGTAT<br>TGATGGGGTTCGGAATT<br>ATCACGGGAACGTTGCG<br>TATAACGAATCCGGTCA<br>GAGCATCCGTCTTGCGA<br>TACGATGATTTTCACAT<br>CGATGAAGACAAACTGG<br>ATACAAACTCCGTATAT<br>GAGCCTTACTACCATTC<br>AGATCATGCGGAGTCTT | GGGAAATAAGAG<br>AGAAAAGAAGAG<br>TAAGAAGAAATA<br>TAAGAGCCACCA<br>TGGGGACAGTTA<br>ATAAACCTGTGG<br>TGGGGGTATTGA<br>TGGGGTTCGGAA<br>TTATCACGGGAA<br>CGTTGCGTATAA<br>CGAATCCGGTCA |

TABLE 2-continued

| | | | |
|---|---|---|---|
| GAGCATCCGTCT | IQRIYGVRYTETWSFLP | CATGGGTAAATCGGGGA | GAGCATCCGTCT |
| TGCGATACGATG | SLTCTGDAAPAIQHICL | GAGTCTTCGCGAAAAGC | TGCGATACGATG |
| ATTTTCACATCG | KHTTCFQDVVVDVDCAE | GTACGATCATAACTCAC | ATTTTCACATCG |
| ATGAAGACAAAC | NTKEDQLAEISYRFQGK | CTTATATATGGCCACGT | ATGAAGACAAAC |
| TGGATACAAACT | KEADQPWIVVNTSTLFD | AATGATTATGATGGATT | TGGATACAAACT |
| CCGTATATGAGC | ELELDPPEIEPGVLKVL | TTTAGAGAACGCACACG | CCGTATATGAGC |
| CTTACTACCATT | RTEKQYLGVYIWNMRGS | AACACCATGGGGTGTAT | CTTACTACCATT |
| CAGATCATGCGG | DGTSTYATFLVTWKGDE | AATCAGGGCCGTGGTAT | CAGATCATGCGG |
| AGTCTTCATGGG | KTRNPTPAVTPQPRGAE | CGATAGCGGGGAACGGT | AGTCTTCATGGG |
| TAAATCGGGGAG | FHMWNYHSHVFSVGDTF | TAATGCAACCCACACAA | TAAATCGGGGAG |
| AGTCTTCGCGAA | SLAMHLQYKIHEAPFDL | ATGTCTGCACAGGAGGA | AGTCTTCGCGAA |
| AAGCGTACGATC | LLEWLYVPIDPTCQPMR | TCTTGGGGACGATACGG | AAGCGTACGATC |
| ATAACTCACCTT | LYSTCLYHPNAPQCLSH | GCATCCACGTTATCCCT | ATAACTCACCTT |
| ATATATGGCCAC | MNSGCTFTSPHLAQRVA | ACGTTAAACGGCGATGA | ATATATGGCCAC |
| GTAATGATTATG | STVYQNCEHADNYTAYC | CAGACATAAAATTGTAA | GTAATGATTATG |
| ATGGATTTTTAG | LGISHMEPSFGLILHDG | ATGTGGACCAACGTCAA | ATGGATTTTTAG |
| AGAACGCACACG | GTTLKFVDTPESLSGLY | TACGGTGACGTGTTTAA | AGAACGCACACG |
| AACACCATGGGG | VFVVYFNGHVEAVAYTV | AGGAGATCTTAATCCAA | AACACCATGGGG |
| TGTATAATCAGG | VSTVDHFVNAIEERGFP | AACCCCAAGGCCAAAGA | TGTATAATCAGG |
| GCCGTGGTATCG | PTAGQPPATTKPKEITP | CTCATTGAGGTGTCAGT | GCCGTGGTATCG |
| ATAGCGGGGAAC | VNPGTSPLLRYAAWTGG | GGAAGAAAATCACCCGT | ATAGCGGGGAAC |
| GGTTAATGCAAC | LAAVVLLCLVIFLICTA | TTACTTTACGCGCACCG | GGTTAATGCAAC |
| CCACACAAATGT | KRMRVKAARVDK | ATTCAGCGGATTTATGG | CCACACAAATGT |
| CTGCACAGGAGG | | AGTCCGGTACACCGAGA | CTGCACAGGAGG |
| ATCTTGGGGACG | | CTTGGAGCTTTTTGCCG | ATCTTGGGGACG |
| ATACGGGCATCC | | TCATTAACCTGTACGGG | ATACGGGCATCC |
| ACGTTATCCCTA | | AGACGCAGCGCCCGCCA | ACGTTATCCCTA |
| CGTTAAACGGCG | | TCCAGCATATATGTTTA | CGTTAAACGGCG |
| ATGACAGACATA | | AAACATACAACATGCTT | ATGACAGACATA |
| AAATTGTAAATG | | TCAAGACGTGGTGGTGG | AAATTGHAAATG |
| TGGACCAACGTC | | ATGTGGATTGCGCGGAA | TGGACCAACGTC |
| AATACGGTGACG | | AATACTAAAGAGGATCA | AATACGGTGACG |
| TGTTTAAAGGAG | | GTTGGCCGAAATCAGTT | TGTTTAAAGGAG |
| ATCTTAATCCAA | | ACCGTTTTCAAGGTAAG | ATCTTAATCCAA |
| AACCCCAAGGCC | | AAGGAAGCGGACCAACC | AACCCCAAGGCC |
| AAAGACTCATTG | | GTGGATTGTTGTAAACA | AAAGACTCATTG |
| AGGTGTCAGTGG | | CGAGCACACTGTTTGAT | AGGTGTCAGTGG |
| AAGAAAATCACC | | GAACTCGAATTAGACCC | AAGAAAATCACC |
| CGTTTACTTTAC | | ACCCGAGATTGAACCGG | CGTTTACTTTAC |
| GCGCACCGATTC | | GTGTCTTGAAAGTACTT | GCGCACCGATTC |
| AGCGGATTTATG | | CGGACAGAGAAACAATA | AGCGGATTTATG |
| GAGTCCGGTACA | | CTTGGGTGTGTACATTT | GAGTCCGGTACA |
| CCGAGACTTGGA | | GGAACATGCGCGGCTCC | CCGAGACTTGGA |
| GCTTTTTGCCGT | | GATGGTACGTCTACCTA | GCTTTTTGCCGT |
| CATTAACCTGTA | | CGCCACGTTTTTGGTCA | CATTAACCTGTA |
| CGGGAGACGCAG | | CCTGGAAAGGGGATGAG | CGGGAGACGCAG |
| CGCCCGCCATCC | | AAGACAAGAAACCCTAC | CGCCCGCCATCC |
| AGCATATATGTT | | GCCCGCAGTAACTCCTC | AGCATATATGTT |
| TAAAACATACAA | | AACCAAGAGGGGCTGAG | TAAAACATACAA |
| CATGCTTTCAAG | | TTTCATATGTGGAATTA | CATGCTTTCAAG |
| ACGTGGTGGTGG | | CCACTCGCATGTATTTT | ACGTGGTGGTGG |
| ATGTGGATTGCG | | CAGTTGGTGATACGTTT | ATGTGGATTGCG |
| CGGAAAATACTA | | AGCTTGGCAATGCATCT | CGGAAAATACTA |
| AAGAGGATCAGT | | TCAGTATAAGATACATG | AAGAGGATCAGT |
| TGGCCGAAATCA | | AAGCGCCATTTGATTTG | TGGCCGAAATCA |
| GTTACCGTTTTC | | CTGTTAGAGTGGTTGTA | GTTACCGTTTTC |
| AAGGTAAGAAGG | | TGTCCCCATCGATCCTA | AAGGTAAGAAGG |
| AAGCGGACCAAC | | CATGTCAACCAATGCGG | AAGCGGACCAAC |
| CGTGGATTGTTG | | TTATATTCTACGTGTTT | CGTGGATTGTTG |
| TAAACACGAGCA | | GTATCATCCCAACGCAC | TAAACACGAGCA |
| CACTGTTTGATG | | CCCAATGCCTCTCTCAT | CACTGTTTGATG |
| AACTCGAATTAG | | ATGAATTCCGGTTGTAC | AACTCGAATTAG |
| ACCCACCCGAGA | | ATTTACCTCGCCACATT | ACCCACCCGAGA |
| TTGAACCGGGTG | | TAGCCCAGCGTGTTGCA | TTGAACCGGGTG |
| TCTTGAAAGTAC | | AGCACAGTGTATCAAAA | TCTTGAAAGTAC |
| TTCGGACAGAGA | | TTGTGAACATGCAGATA | TTCGGACAGAGA |
| AACAATACTTGG | | ACTACACCGCATATTGT | AACAATACTTGG |
| GTGTGTACATTT | | CTGGGAATATCTCATAT | GTGTGTACATTT |
| GGAACATGCGCG | | GGAGCCTAGCTTTGGTC | GGAACATGCGCG |
| GCTCCGATGGTA | | TAATCTTACACGACGGG | GCTCCGATGGTA |
| CGTCTACCTACG | | GGCACCACGTTAAAGTT | CGTCTACCTACG |
| CCACGTTTTTGG | | TGTAGATACACCCGAGA | CCACGTTTTTGG |
| TCACCTGGAAAG | | GTTTGTCGGGATTATAC | TCACCTGGAAAG |
| GGGATGAGAAGA | | GTTTTTGTGGTGTATTT | GGGATGAGAAGA |
| CAAGAAACCCTA | | TAACGGGCATGTTGAAG | CAAGAAACCCTA |
| CGCCCGCAGTAA | | CCGTAGCATACACTGTT | CGCCCGCAGTAA |
| CTCCTCAACCAA | | GTATCCACAGTAGATCA | CTCCTCAACCAA |
| GAGGGGCTGAGT | | TTTTGTAAACGCAATTG | GAGGGGCTGAGT |
| TTCATATGTGGA | | AAGAGCGTGGATTTCCG | TTCATATGTGGA |
| ATTACCACTCGC | | CCAACGGCCGGTCAGCC | ATTACCACTCGC |

TABLE 2-continued

| | | | | |
|---|---|---|---|---|
| | ATGTATTTTCAG | | ACCGGCGACTACTAAAC | ATGTATTTTCAG |
| | TTGGTGATACGT | | CCAAGGAAATTACCCCC | TTGGTGATACGT |
| | TTAGCTTGGCAA | | GTAAACCCCGGAACGTC | TTAGCTTGGCAA |
| | TGCATCTTCAGT | | ACCACTTCTACGATATG | TGCATCTTCAGT |
| | ATAAGATACATG | | CCGCATGGACCGGAGGG | ATAAGATACATG |
| | AAGCGCCATTTG | | CTTGCAGCAGTAGTACT | AAGCGCCATTTG |
| | ATTTGCTGTTAG | | TTTATGTCTCGTAATAT | ATTTGCTGTTAG |
| | AGTGGTTGTATG | | TTTTAATCTGTACGGCT | AGTGGTTGTATG |
| | TCCCCATCGATC | | AAACGAATGAGGGTTAA | TCCCCATCGATC |
| | CTACATGTCAAC | | AGCCGCCAGGGTAGACA | CTACATGTCAAC |
| | CAATGCGGTTAT | | AG | CAATGCGGTTAT |
| | ATTCTACGTGTT | | | ATTCTACGTGTT |
| | TGTATCATCCCA | | | TGTATCATCCCA |
| | ACGCACCCCAAT | | | ACGCACCCCAAT |
| | GCCTCTCTCATA | | | GCCTCTCTCATA |
| | TGAATTCCGGTT | | | TGAATTCCGGTT |
| | GTACATTTACCT | | | GTACATTTACCT |
| | CGCCACATTTAG | | | CGCCACATTTAG |
| | CCCAGCGTGTTG | | | CCCAGCGTGTTG |
| | CAAGCACAGTGT | | | CAAGCACAGTGT |
| | ATCAAAATTGTG | | | ATCAAAATTGTG |
| | AACATGCAGATA | | | AACATGCAGATA |
| | ACTACACCGCAT | | | ACTACACCGCAT |
| | ATTGTCTGGGAA | | | ATTGTCTGGGAA |
| | TATCTCATATGG | | | TATCTCATATGG |
| | AGCCTAGCTTTG | | | AGCCTAGCTTTG |
| | GTCTAATCTTAC | | | GTCTAATCTTAC |
| | ACGACGGGGGCA | | | ACGACGGGGGCA |
| | CCACGTTAAAGT | | | CCACGTTAAAGT |
| | TTGTAGATACAC | | | TTGTAGATACAC |
| | CCGAGAGTTTGT | | | CCGAGAGTTTGT |
| | CGGGATTATACG | | | CGGGATTATACG |
| | TTTTTGTGGTGT | | | TTTTTGTGGTGT |
| | ATTTTAACGGGC | | | ATTTTAACGGGC |
| | ATGTTGAAGCCG | | | ATGTTGAAGCCG |
| | TAGCATACACTG | | | TAGCATACACTG |
| | TTGTATCCACAG | | | TTGTATCCACAG |
| | TAGATCATTTTG | | | TAGATCATTTTG |
| | TAAACGCAATTG | | | TAAACGCAATTG |
| | AAGAGCGTGGAT | | | AAGAGCGTGGAT |
| | TTCCGCCAACGG | | | TTCCGCCAACGG |
| | CCGGTCAGCCAC | | | CCGGTCAGCCAC |
| | CGGCGACTACTA | | | CGGCGACTACTA |
| | AACCCAAGGAAA | | | AACCCAAGGAAA |
| | TTACCCCCGTAA | | | TTACCCCCGTAA |
| | ACCCCGGAACGT | | | ACCCCGGAACGT |
| | CACCACTTCTAC | | | CACCACTTCTAC |
| | GATATGCCGCAT | | | GATATGCCGCAT |
| | GGACCGGAGGGC | | | GGACCGGAGGGC |
| | TTGCAGCAGTAG | | | TTGCAGCAGTAG |
| | TACTTTTATGTC | | | TACTTTTATGTC |
| | TCGTAATATTTT | | | TCGTAATATTTT |
| | TAATCTGTACGG | | | TAATCTGTACGG |
| | CTAAACGAATGA | | | CTAAACGAATGA |
| | GGGTTAAAGCCG | | | GGGTTAAAGCCG |
| | CCAGGGTAGACA | | | CCAGGGTAGACA |
| | AGTGATAATAGG | | | AGTGATAATAGG |
| | CTGGAGCCTCGG | | | CTGGAGCCTCGG |
| | TGGCCATGCTTC | | | TGGCCATGCTTC |
| | TTGCCCCTTGGG | | | TTGCCCCTTGGG |
| | CCTCCCCCCAGC | | | CCTCCCCCCAGC |
| | CCCTCCTCCCCT | | | CCCTCCTCCCCT |
| | TCCTGCACCCGT | | | TCCTGCACCCGT |
| | ACCCCCGTGGTC | | | ACCCCCGTGGTC |
| | TTTGAATAAAGT | | | TTTGAATAAAGT |
| | CTGAGTGGGCGG | | | CTGAGTGGGCGG |
| | C | | | CAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAATCTAG |
| | SEQ ID NO: 72 | SEQ ID NO: 73 | SEQ ID NO: 74 | SEQ ID NO: 75 |
| VZV-GE- | GGGAAATAAGAG | MGTVNKPVVGVLMGFGI | ATGGGGACAGTTAATAA | GGGAAATAAGAG |
| truncated- | AGAAAAGAAGAG | ITGTLRITNPVRASVLR | ACCTGTGGTGGGGTAT | AGAAAAGAAGAG |

TABLE 2-continued

| | | | | |
|---|---|---|---|---|
| delete_ | TAAGAAGAAATA | YDDFHIDEDKLDTNSVY | TGATGGGGTTCGGAATT | TAAGAAGAAATA |
| from_574_-_ | TAAGAGCCACCA | EPYYHSDHAESSWVNRG | ATCACGGGAACGTTGCG | TAAGAGCCACCA |
| Y569A | TGGGGACAGTTA | ESSRKAYDHNSPYIWPR | TATAACGAATCCGGTCA | TGGGGACAGTTA |
| Variant | ATAAACCTGTGG | NDYDGFLENAHEHHGVY | GAGCATCCGTCTTGCGA | ATAAACCTGTGG |
| 4 | TGGGGGTATTGA | NQGRGIDSGERLMQPTQ | TACGATGATTTTCACAT | TGGGGGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAGGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | TTTAGAGAACGCACACG | CCGTATATGAGC |
| | CTTACTACCATT | RTEKQYLGVYIWNMRGS | AACACCATGGGGTGTAT | CTTACTACCATT |
| | CAGATCATGCGG | DGTSTYATFLVTWKGDE | AATCAGGGCCGTGGTAT | CAGATCATGCGG |
| | AGTCTTCATGGG | KTRNPTPAVTPQPRGAE | CGATAGCGGGGAACGGT | AGTCTTCATGGG |
| | TAAATCGGGGAG | FHMWNYHSHVFSVGDTF | TAATGCAACCCACACAA | TAAATCGGGGAG |
| | AGTCTTCGCGAA | SLAMHLQYKIHEAPFDL | ATGTCTGCACAGGAGGA | AGTCTTCGCGAA |
| | AGGCGTACGATC | LLEWLYVPIDPTCQPMR | TCTTGGGGACGATACGG | AGGCGTACGATC |
| | ATAACTCACCTT | LYSTCLYHPNAPQCLSH | GCATCCACGTTATCCCT | ATAACTCACCTT |
| | ATATATGGCCAC | MNSGCTFTSPHLAQRVA | ACGTTAAACGGCGATGA | ATATATGGCCAC |
| | GTAATGATTATG | STVYQNCEHADNYTAYC | CAGACATAAGATTGTAA | GTAATGATTATG |
| | ATGGATTTTTAG | LGISHMEPSFGLILHDG | ATGTGGACCAACGTCAA | ATGGATTTTTAG |
| | AGAACGCACACG | GTTLKFVDTPESLSGLY | TACGGTGACGTGTTTAA | AGAACGCACACG |
| | AACACCATGGGG | VFVVYFNGHVEAVAYTV | AGGAGATCTTAATCCAA | AACACCATGGGG |
| | TGTATAATCAGG | VSTVDHFVNAIEERGFP | AGCCCCAAGGCCAAAGA | TGTATAATCAGG |
| | GCCGTGGTATCG | PTAGQPPATTKPKEITP | CTCATTGAGGTGTCAGT | GCCGTGGTATCG |
| | ATAGCGGGGAAC | VNPGTSPLLRYAAWTGG | GGAAGAGAATCACCCGT | ATAGCGGGGAAC |
| | GGTTAATGCAAC | LAAVVLLCLVIFLICTA | TTACTTTACGCGCACCG | GGTTAATGCAAC |
| | CCACACAAATGT | KRMRVKAARVDK | ATTCAGCGGATTTATGG | CCACACAAATGT |
| | CTGCACAGGAGG | | AGTCCGGTACACCGAGA | CTGCACAGGAGG |
| | ATCTTGGGGACG | | CTTGGAGCTTTTTGCCG | ATCTTGGGGACG |
| | ATACGGGCATCC | | TCATTAACCTGTACGGG | ATACGGGCATCC |
| | ACGTTATCCCTA | | AGACGCAGCGCCCGCCA | ACGTTATCCCTA |
| | CGTTAAACGGCG | | TCCAGCATATATGTTTA | CGTTAAACGGCG |
| | ATGACAGACATA | | AAGCATACAACATGCTT | ATGACAGACATA |
| | AGATTGTAAATG | | TCAAGACGTGGTGGTGG | AGATTGTAAATG |
| | TGGACCAACGTC | | ATGTGGATTGCGCGGAG | TGGACCAACGTC |
| | AATACGGTGACG | | AATACTAAAGAGGATCA | AATACGGTGACG |
| | TGTTTAAAGGAG | | GTTGGCCGAAATCAGTT | TGTTTAAAGGAG |
| | ATCTTAATCCAA | | ACCGTTTTCAAGGTAAG | ATCTTAATCCAA |
| | AGCCCCAAGGCC | | AAGGAAGCGGACCAACC | AGCCCCAAGGCC |
| | AAAGACTCATTG | | GTGGATTGTTGTAAACA | AAAGACTCATTG |
| | AGGTGTCAGTGG | | CGAGCACACTGTTTGAT | AGGTGTCAGTGG |
| | AAGAGAATCACC | | GAACTCGAATTAGACCC | AAGAGAATCACC |
| | CGTTTACTTTAC | | CCCCGAGATTGAACCGG | CGTTTACTTTAC |
| | GCGCACCGATTC | | GTGTCTTGAAAGTACTT | GCGCACCGATTC |
| | AGCGGATTTATG | | CGGACAGAGAAACAATA | AGCGGATTTATG |
| | GAGTCCGGTACA | | CTTGGGTGTGTACATTT | GAGTCCGGTACA |
| | CCGAGACTTGGA | | GGAACATGCGCGGCTCC | CCGAGACTTGGA |
| | GCTTTTTGCCGT | | GATGGTACGTCTACCTA | GCTTTTTGCCGT |
| | CATTAACCTGTA | | CGCCACGTTTTTGGTCA | CATTAACCTGTA |
| | CGGGAGACGCAG | | CCTGGAAAGGGGATGAG | CGGGAGACGCAG |
| | CGCCCGCCATCC | | AAGACAAGAAACCCTAC | CGCCCGCCATCC |
| | AGCATATATGTT | | GCCCGCAGTAACTCCTC | AGCATATATGTT |
| | TAAAGCATACAA | | AACCAAGAGGGGCTGAG | TAAAGCATACAA |
| | CATGCTTTCAAG | | TTTCATATGTGGAATTA | CATGCTTTCAAG |
| | ACGTGGTGGTGG | | CCACTCGCATGTATTTT | ACGTGGTGGTGG |
| | ATGTGGATTGCG | | CAGTTGGTGATACGTTT | ATGTGGATTGCG |
| | CGGAGAATACTA | | AGCTTGGCAATGCATCT | CGGAGAATACTA |
| | AAGAGGATCAGT | | TCAGTATAAGATACATG | AAGAGGATCAGT |
| | TGGCCGAAATCA | | AAGCGCCATTTGATTTG | TGGCCGAAATCA |
| | GTTACCGTTTTC | | CTGTTAGAGTGGTTGTA | GTTACCGTTTTC |
| | AAGGTAAGAAGG | | TGTCCCCATCGATCCTA | AAGGTAAGAAGG |
| | AAGCGGACCAAC | | CATGTCAACCAATGCGG | AAGCGGACCAAC |
| | CGTGGATTGTTG | | TTATATTCTACGTGTTT | CGTGGATTGTTG |
| | TAAACACGAGCA | | GTATCATCCCAACGCAC | TAAACACGAGCA |
| | CACTGTTTGATG | | CCCAATGCCTCTCTCAT | CACTGTTTGATG |
| | AACTCGAATTAG | | ATGAATTCCGGTTGTAC | AACTCGAATTAG |
| | ACCCCCCCGAGA | | ATTTACCTCGCCACATT | ACCCCCCCGAGA |
| | TTGAACCGGGTG | | TAGCCCAGCGTGTTGCA | TTGAACCGGGTG |
| | TCTTGAAAGTAC | | AGCACAGTGTATCAGAA | TCTTGAAAGTAC |
| | TTCGGACAGAGA | | TTGTGAACATGCAGATA | TTCGGACAGAGA |
| | AACAATACTTGG | | ACTACACCGCATATTGT | AACAATACTTGG |
| | GTGTGTACATTT | | CTGGGAATATCTCATAT | GTGTGTACATTT |
| | GGAACATGCGCG | | GGAGCCTAGCTTTGGTC | GGAACATGCGCG |
| | GCTCCGATGGTA | | TAATCTTACACGACGGG | GCTCCGATGGTA |
| | CGTCTACCTACG | | GGCACCACGTTAAAGTT | CGTCTACCTACG |

TABLE 2-continued

CCACGTTTTTGG
TCACCTGGAAAG
GGGATGAGAAGA
CAAGAAACCCTA
CGCCCGCAGTAA
CTCCTCAACCAA
GAGGGGCTGAGT
TTCATATGTGGA
ATTACCACTCGC
ATGTATTTTCAG
TTGGTGATACGT
TTAGCTTGGCAA
TGCATCTTCAGT
ATAAGATACATG
AAGCGCCATTTG
ATTTGCTGTTAG
AGTGGTTGTATG
TCCCCATCGATC
CTACATGTCAAC
CAATGCGGTTAT
ATTCTACGTGTT
TGTATCATCCCA
ACGCACCCCAAT
GCCTCTCTCATA
TGAATTCCGGTT
GTACATTTACCT
CGCCACATTTAG
CCCAGCGTGTTG
CAAGCACAGTGT
ATCAGAATTGTG
AACATGCAGATA
ACTACACCGCAT
ATTGTCTGGGAA
TATCTCATATGG
AGCCTAGCTTTG
GTCTAATCTTAC
ACGACGGGGGCA
CCACGTTAAAGT
TTGTAGATACAC
CCGAGAGTTTGT
CGGGATTATACG
TTTTTGTGGTGT
ATTTTAACGGGC
ATGTTGAAGCCG
TAGCATACACTG
TTGTATCCACAG
TAGATCATTTTG
TAAACGCAATTG
AAGAGCGTGGAT
TTCCGCCAACGG
CCGGTCAGCCAC
CGGCGACTACTA
AACCCAAGGAAA
TTACCCCCGTAA
ACCCCGGAACGT
CACCACTTCTAC
GATATGCCGCAT
GGACCGGAGGGC
TTGCAGCAGTAG
TACTTTTATGTC
TCGTAATATTTT
TAATCTGTACGG
CTAAACGAATGA
GGGTTAAAGCCG
CCAGGGTAGACA
AGTGATAATAGG
CTGGAGCCTCGG
TGGCCATGCTTC
TTGCCCCTTGGG
CCTCCCCCCAGC
CCCTCCTCCCCT
TCCTGCACCCGT
ACCCCCGTGGTC
TTTGAATAAAGT
CTGAGTGGGCGG
C

TGTAGATACACCCGAGA
GTTTGTCGGGATTATAC
GTTTTTGTGGTGTATTT
TAACGGGCATGTTGAAG
CCGTAGCATACACTGTT
GTATCCACAGTAGATCA
TTTTGTAAACGCAATTG
AAGAGCGTGGATTTCCG
CCAACGGCCGGTCAGCC
ACCGGCGACTACTAAAC
CCAAGGAAATTACCCCC
GTAAACCCCGGAACGTC
ACCACTTCTACGATATG
CCGCATGGACCGGAGGG
CTTGCAGCAGTAGTACT
TTTATGTCTCGTAATAT
TTTTAATCTGTACGGCT
AAACGAATGAGGGTTAA
AGCCGCCAGGGTAGACA
AG

CCACGTTTTTGG
TCACCTGGAAAG
GGGATGAGAAGA
CAAGAAACCCTA
CGCCCGCAGTAA
CTCCTCAACCAA
GAGGGGCTGAGT
TTCATATGTGGA
ATTACCACTCGC
ATGTATTTTCAG
TTGGTGATACGT
TTAGCTTGGCAA
TGCATCTTCAGT
ATAAGATACATG
AAGCGCCATTTG
ATTTGCTGTTAG
AGTGGTTGTATG
TCCCCATCGATC
CTACATGTCAAC
CAATGCGGTTAT
ATTCTACGTGTT
TGTATCATCCCA
ACGCACCCCAAT
GCCTCTCTCATA
TGAATTCCGGTT
GTACATTTACCT
CGCCACATTTAG
CCCAGCGTGTTG
CAAGCACAGTGT
ATCAGAATTGTG
AACATGCAGATA
ACTACACCGCAT
ATTGTCTGGGAA
TATCTCATATGG
AGCCTAGCTTTG
GTCTAATCTTAC
ACGACGGGGGCA
CCACGTTAAAGT
TTGTAGATACAC
CCGAGAGTTTGT
CGGGATTATACG
TTTTTGTGGTGT
ATTTTAACGGGC
ATGTTGAAGCCG
TAGCATACACTG
TTGTATCCACAG
TAGATCATTTTG
TAAACGCAATTG
AAGAGCGTGGAT
TTCCGCCAACGG
CCGGTCAGCCAC
CGGCGACTACTA
AACCCAAGGAAA
TTACCCCCGTAA
ACCCCGGAACGT
CACCACTTCTAC
GATATGCCGCAT
GGACCGGAGGGC
TTGCAGCAGTAG
TACTTTTATGTC
TCGTAATATTTT
TAATCTGTACGG
CTAAACGAATGA
GGGTTAAAGCCG
CCAGGGTAGACA
AGTGATAATAGG
CTGGAGCCTCGG
TGGCCATGCTTC
TTGCCCCTTGGG
CCTCCCCCCAGC
CCCTCCTCCCCT
TCCTGCACCCGT
ACCCCCGTGGTC
TTTGAATAAAGT
CTGAGTGGGCGG
CAAAAAAAAAAA
AAAAAAAAAAAA
AAAAAAAAAAAA
AAAAAAAAAAAA
AAAAAAAAAAAA

TABLE 2-continued

| | | | | |
|---|---|---|---|---|
| | | | | AAAAAAAAAAAA AAAAAAAAAAAA AAAAAAAAAAAA AAAAATCTAG |
| | SEQ ID NO: 76 | SEQ ID NO: 77 | SEQ ID NO: 78 | SEQ ID NO: 79 |
| VZV-GE-truncated-delete_from_574_-_Y569A Variant 5 | GGGAAATAAGAG AGAAAAGAAGAG TAAGAAGAAATA TAAGAGCCACCA TGGGGACAGTTA ATAAACCTGTGG TGGGGGTATTGA TGGGGTTCGGAA TTATCACGGGAA CGTTGCGTATAA CGAATCCGGTCA GAGCATCCGTCT TGCGATACGATG ATTTTCACATCG ATGAAGACAAAC TGGATACAAACT CCGTATATGAGC CTTACTACCATT CAGATCATGCGG AGTCTTCATGGG TAAATCGGGGAG AGTCTTCGCGAA AGGCGTACGATC ATAACTCACCTT ATATATGGCCAC GTAATGATTATG ATGGATTTTTAG AGAACGCACACG AACACCATGGGG TGTATAATCAGG GCCGTGGTATCG ATAGCGGGGAAC GGTTAATGCAAC CCACACAAATGT CTGCACAGGAGG ATCTTGGGGACG ATACGGGCATCC ACGTTATCCCTA CGTTAAACGGCG ATGACAGACATA AGATTGTAAATG TGGACCAACGTC AATACGGTGACG TGTTTAAAGGAG ATCTTAATCCAA AGCCCCAAGGCC AAAGACTCATTG AGGTGTCAGTGG AAGAGAATCACC CGTTTACTTTAC GCGCACCGATTC AGCGGATTTATG GAGTCCGGTACA CCGAGACTTGGA GCTTTTTGCCGT CATTAACCTGTA CGGGAGACGCAG CGCCCGCCATCC AGCATATATGTT TAAAGCATACAA CATGCTTTCAAG ACGTGGTGGTGG ATGTGGATTGCG CGGAGAATACTA AAGAGGATCAGT TGGCCGAAATCA GTTACCGTTTTC AAGGTAAGAAGG AAGCGGACCAAC CGTGGATTGTTG TAAACACGAGCA CACTGTTTGATG AACTCGAATTAG | MGTVNKPVVGVLMGFGI ITGTLRITNPVRASVLR YDDFHIDEDKLDTNSVY EPYYHSDHAESSWVNRG ESSRKAYDHNSPYIWPR NDYDGFLENAHEHHGVY NQGRGIDSGERLMQPTQ MSAQEDLGDDTGIHVIP TLNGDDRHKIVNVDQRQ YGDVFKGDLNPKPQGQR LIEVSVEENHPFTLRAP IQRIYGVRYTETWSFLP SLTCTGDAAPAIQHICL KHTTCFQDVVVDVDCAE NTKEDQLAEISYRFQGK KEADQPWIVVNTSTLFD ELELDPPEIEPGVLKVL RTEKQYLGVYIWNMRGS DGTSTYATFLVTWKGDE KTRNPTPAVTPQPRGAE FHMWNYHSHVFSVGDTF SLAMHLQYKIHEAPFDL LLEWLYVPIDPTCQPMR LYSTCLYHPNAPQCLSH MNSGCTFTSPHLAQRVA STVYQNCEHADNYTAYC LGISHMEPSFGLILHDG GTTLKFVDTPESLSGLY VFVVYFNGHVEAVAYTV VSTVDHFVNAIEERGFP PTAGQPPATTKPKEITP VNPGTSPLLRYAAWTGG LAAVVLLCLVIFLICTA KRMRVKAARVDK | ATGGGGACAGTTAATAA ACCTGTGGTGGGGGTAT TGATGGGGTTCGGAATT ATCACGGGAACGTTGCG TATAACGAATCCGGTCA GAGCATCCGTCTTGCGA TACGATGATTTTCACAT CGATGAAGACAAACTGG ATACAAACTCCGTATAT GAGCCTTACTACCATTC AGATCATGCGGAGTCTT CATGGGTAAATCGGGGA GAGTCTTCGCGAAAGGC GTACGATCATAACTCAC CTTATATATGGCCACGT AATGATTATGATGGATT TTTAGAGAACGCACACG AACACCATGGGGTGTAT AATCAGGGCCGTGGTAT CGATAGCGGGGAACGGT TAATGCAACCCACACAA ATGTCTGCACAGGAGGA TCTTGGGGACGATACGG GCATCCACGTTATCCCT ACGTTAAACGGCGATGA CAGACATAAGATTGTAA ATGTGGACCAACGTCAA TACGGTGACGTGTTTAA AGGAGATCTTAATCCAA AGCCCCAAGGCCAAAGA CTCATTGAGGTGTCAGT GGAAGAGAATCACCCGT TTACTTTACGCGCACCG ATTCAGCGGATTTATGG AGTCCGGTACACCGAGA CTTGGAGCTTTTTGCCG TCATTAACCTGTACGGG AGACGCAGCGCCCGCCA TCCAGCATATATGTTTA AAGCATACAACATGCTT TCAAGACGTGGTGGTGG ATGTGGATTGCGCGGAG AATACTAAAGAGGATCA GTTGGCCGAAATCAGTT ACCGTTTTCAAGGTAAG AAGGAAGCGGACCAACC GTGGATTGTTGTAAACA CGAGCACACTGTTTGAT GAACTCGAATTAGACCC ACCCGAGATTGAACCGG GTGTCTTGAAAGTACTT CGGACAGAGAAACAATA CTTGGGTGTGTACATTT GGAACATGCGCGGCTCC GATGGTACGTCTACCTA CGCCACGTTTTTGGTCA CCTGGAAAGGGGATGAG AAGACAAGAAACCCTAC GCCCGCAGTAACTCCTC AACCAAGAGGGGCTGAG TTTCATATGTGGAATTA CCACTCGCATGTATTTT CAGTTGGTGATACGTTT AGCTTGGCAATGCATCT TCAGTATAAGATACATG AAGCGCCATTTGATTTG CTGTTAGAGTGGTTGTA TGTCCCCATCGATCCTA CATGTCAACCAATGCGG TTATATTCTACGTGTTT GTATCATCCCAACGCAC CCCAATGCCTCTCTCAT ATGAATTCCGGTTGTAC | GGGAAATAAGAG AGAAAAGAAGAG TAAGAAGAAATA TAAGAGCCACCA TGGGGACAGTTA ATAAACCTGTGG TGGGGGTATTGA TGGGGTTCGGAA TTATCACGGGAA CGTTGCGTATAA CGAATCCGGTCA GAGCATCCGTCT TGCGATACGATG ATTTTCACATCG ATGAAGACAAAC TGGATACAAACT CCGTATATGAGC CTTACTACCATT CAGATCATGCGG AGTCTTCATGGG TAAATCGGGGAG AGTCTTCGCGAA AGGCGTACGATC ATAACTCACCTT ATATATGGCCAC GTAATGATTATG ATGGATTTTTAG AGAACGCACACG AACACCATGGGG TGTATAATCAGG GCCGTGGTATCG ATAGCGGGGAAC GGTTAATGCAAC CCACACAAATGT CTGCACAGGAGG ATCTTGGGGACG ATACGGGCATCC ACGTTATCCCTA CGTTAAACGGCG ATGACAGACATA AGATTGTAAATG TGGACCAACGTC AATACGGTGACG TGTTTAAAGGAG ATCTTAATCCAA AGCCCCAAGGCC AAAGACTCATTG AGGTGTCAGTGG AAGAGAATCACC CGTTTACTTTAC GCGCACCGATTC AGCGGATTTATG GAGTCCGGTACA CCGAGACTTGGA GCTTTTTGCCGT CATTAACCTGTA CGGGAGACGCAG CGCCCGCCATCC AGCATATATGTT TAAAGCATACAA CATGCTTTCAAG ACGTGGTGGTGG ATGTGGATTGCG CGGAGAATACTA AAGAGGATCAGT TGGCCGAAATCA GTTACCGTTTTC AAGGTAAGAAGG AAGCGGACCAAC CGTGGATTGTTG TAAACACGAGCA CACTGTTTGATG AACTCGAATTAG |

TABLE 2-continued

| | | |
|---|---|---|
| ACCCACCCGAGA | ATTTACCTCGCCACATT | ACCCACCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGG | GCTCCGATGGTA |
| CGTCTACCTACG | GGCACCACGTTAAAGTT | CGTCTACCTACG |
| CCACGTTTTTGG | TGTAGATACACCCGAGA | CCACGTTTTTGG |
| TCACCTGGAAAG | GTTTGTCGGGATTATAC | TCACCTGGAAAG |
| GGGATGAGAAGA | GTTTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACCCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TTTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGGGGCA | | ACGACGGGGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TTTTTGTGGTGT | | TTTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |
| TTGTATCCACAG | | TTGTATCCACAG |
| TAGATCATTTTG | | TAGATCATTTTG |
| TAAACGCAATTG | | TAAACGCAATTG |
| AAGAGCGTGGAT | | AAGAGCGTGGAT |
| TTCCGCCAACGG | | TTCCGCCAACGG |
| CCGGTCAGCCAC | | CCGGTCAGCCAC |
| CGGCGACTACTA | | CGGCGACTACTA |
| AACCCAAGGAAA | | AACCCAAGGAAA |
| TTACCCCCGTAA | | TTACCCCCGTAA |
| ACCCCGGAACGT | | ACCCCGGAACGT |
| CACCACTTCTAC | | CACCACTTCTAC |
| GATATGCCGCAT | | GATATGCCGCAT |
| GGACCGGAGGGC | | GGACCGGAGGGC |
| TTGCAGCAGTAG | | TTGCAGCAGTAG |
| TACTTTTATGTC | | TACTTTTATGTC |
| TCGTAATATTTT | | TCGTAATATTTT |
| TAATCTGTACGG | | TAATCTGTACGG |
| CTAAACGAATGA | | CTAAACGAATGA |
| GGGTTAAAGCCG | | GGGTTAAAGCCG |
| CCAGGGTAGACA | | CCAGGGTAGACA |
| AGTGATAATAGG | | AGTGATAATAGG |
| CTGGAGCCTCGG | | CTGGAGCCTCGG |
| TGGCCATGCTTC | | TGGCCATGCTTC |
| TTGCCCCTTGGG | | TTGCCCCTTGGG |
| CCTCCCCCCAGC | | CCTCCCCCCAGC |
| CCCTCCTCCCCT | | CCCTCCTCCCCT |

TABLE 2-continued

| | | | | |
|---|---|---|---|---|
| | TCCTGCACCCGT | | | TCCTGCACCCGT |
| | ACCCCCGTGGTC | | | ACCCCCGTGGTC |
| | TTTGAATAAAGT | | | TTTGAATAAAGT |
| | CTGAGTGGGCGG | | | CTGAGTGGGCGG |
| | C | | | CAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAATCTAG |

| | SEQ ID NO: 80 | SEQ ID NO: 81 | SEQ ID NO: 82 | SEQ ID NO: 83 |
|---|---|---|---|---|
| VZV-GE- | GGGAAATAAGAG | MGTVNKPVVGVLMGFGI | ATGGGGACAGTTAATAA | GGGAAATAAGAG |
| truncated- | AGAAAAGAAGAG | ITGTLRITNPVRASVLR | ACCTGTGGTGGGGGTAT | AGAAAAGAAGAG |
| delete_ | TAAGAAGAAATA | YDDFHIDEDKLDTNSVY | TGATGGGGTTCGGAATT | TAAGAAGAAATA |
| from_574_-_ | TAAGAGCCACCA | EPYYHSDHAESSWVNRG | ATCACGGGAACGTTGCG | TAAGAGCCACCA |
| Y569A | TGGGGACAGTTA | ESSRKAYDHNSPYIWPR | TATAACGAATCCGGTCA | TGGGGACAGTTA |
| Variant | ATAAACCTGTGG | NDYDGFLENAHEHHGVY | GAGCATCCGTCTTGCGA | ATAAACCTGTGG |
| 6 | TGGGGGTATTGA | NQGRGIDSGERLMQPTQ | TACGATGATTTTCACAT | TGGGGGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAAGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | TTTAGAGAACGCACACG | CCGTATATGAGC |
| | CTTACTACCATT | RTEKQYLGVYIWNMRGS | AACACCATGGGGTGTAT | CTTACTACCATT |
| | CAGATCATGCGG | DGTSTYATFLVTWKGDE | AATCAGGGCCGTGGTAT | CAGATCATGCGG |
| | AGTCTTCATGGG | KTRNPTPAVTPQPRGAE | CGATAGCGGGGAACGGT | AGTCTTCATGGG |
| | TAAATCGGGGAG | FHMWNYHSHVFSVGDTF | TAATGCAACCCACACAA | TAAATCGGGGAG |
| | AGTCTTCGCGAA | SLAMHLQYKIHEAPFDL | ATGTCTGCACAGGAGGA | AGTCTTCGCGAA |
| | AAGCGTACGATC | LLEWLYVPIDPTCQPMR | TCTTGGGGACGATACGG | AAGCGTACGATC |
| | ATAACTCACCTT | LYSTCLYHPNAPQCLSH | GCATCCACGTTATCCCT | ATAACTCACCTT |
| | ATATATGGCCAC | MNSGCTFTSPHLAQRVA | ACGTTAAACGGCGATGA | ATATATGGCCAC |
| | GTAATGATTATG | STVYQNCEHADNYTAYC | CAGACATAAAATTGTAA | GTAATGATTATG |
| | ATGGATTTTTAG | LGISHMEPSFGLILHDG | ATGTGGACCAACGTCAA | ATGGATTTTTAG |
| | AGAACGCACACG | GTTLKFVDTPESLSGLY | TACGGTGACGTGTTTAA | AGAACGCACACG |
| | AACACCATGGGG | VFVVYFNGHVEAVAYTV | AGGAGATCTTAATCCAA | AACACCATGGGG |
| | TGTATAATCAGG | VSTVDHFVNAIEERGFP | AACCCCAAGGCCAAAGA | TGTATAATCAGG |
| | GCCGTGGTATCG | PTAGQPPATTKPKEITP | CTCATTGAGGTGTCAGT | GCCGTGGTATCG |
| | ATAGCGGGGAAC | VNPGTSPLLRYAAWTGG | GGAAGAAAATCACCCGT | ATAGCGGGGAAC |
| | GGTTAATGCAAC | LAAVVLLCLVIFLICTA | TTACTTTACGCGCACCG | GGTTAATGCAAC |
| | CCACACAAATGT | KRMRVKAARVDK | ATTCAGCGGATTTATGG | CCACACAAATGT |
| | CTGCACAGGAGG | | AGTCCGGTACACCGAGA | CTGCACAGGAGG |
| | ATCTTGGGGACG | | CTTGGAGCTTTTTGCCG | ATCTTGGGGACG |
| | ATACGGGCATCC | | TCATTAACCTGTACGGG | ATACGGGCATCC |
| | ACGTTATCCCTA | | AGACGCAGCGCCCGCCA | ACGTTATCCCTA |
| | CGTTAAACGGCG | | TCCAGCATATATGTTTA | CGTTAAACGGCG |
| | ATGACAGACATA | | AAGCATACAACATGCTT | ATGACAGACATA |
| | AAATTGTAAATG | | TCAAGACGTGGTGGTGG | AAATTGTAAATG |
| | TGGACCAACGTC | | ATGTGGATTGCGCGGAA | TGGACCAACGTC |
| | AATACGGTGACG | | AATACTAAAGAGGATCA | AATACGGTGACG |
| | TGTTTAAAGGAG | | GTTGGCCGAAATCAGTT | TGTTTAAAGGAG |
| | ATCTTAATCCAA | | ACCGTTTTCAAGGTAAG | ATCTTAATCCAA |
| | AACCCCAAGGCC | | AAGGAAGCGGACCAACC | AACCCCAAGGCC |
| | AAAGACTCATTG | | GTGGATTGTTGTAAACA | AAAGACTCATTG |
| | AGGTGTCAGTGG | | CGAGCACACTGTTTGAT | AGGTGTCAGTGG |
| | AAGAAAATCACC | | GAACTCGAATTAGACCC | AAGAAAATCACC |
| | CGTTTACTTTAC | | CCCCGAGATTGAACCGG | CGTTTACTTTAC |
| | GCGCACCGATTC | | GTGTCTTGAAAGTACTT | GCGCACCGATTC |
| | AGCGGATTTATG | | CGGACAGAGAAACAATA | AGCGGATTTATG |
| | GAGTCCGGTACA | | CTTGGGTGTGTACATTT | GAGTCCGGTACA |
| | CCGAGACTTGGA | | GGAACATGCGCGGCTCC | CCGAGACTTGGA |
| | GCTTTTTGCCGT | | GATGGTACGTCTACCTA | GCTTTTTGCCGT |
| | CATTAACCTGTA | | CGCCACGTTTTTGGTCA | CATTAACCTGTA |
| | CGGGAGACGCAG | | CCTGGAAAGGGGATGAG | CGGGAGACGCAG |
| | CGCCCGCCATCC | | AAGACAAGAAACCCTAC | CGCCCGCCATCC |
| | AGCATATATGTT | | GCCCGCAGTAACTCCTC | AGCATATATGTT |
| | TAAAGCATACAA | | AACCAAGAGGGGCTGAG | TAAAGCATACAA |
| | CATGCTTTCAAG | | TTTCATATGTGGAATTA | CATGCTTTCAAG |
| | ACGTGGTGGTGG | | CCACTCGCATGTATTTT | ACGTGGTGGTGG |
| | ATGTGGATTGCG | | CAGTTGGTGATACGTTT | ATGTGGATTGCG |
| | CGGAAAATACTA | | AGCTTGGCAATGCATCT | CGGAAAATACTA |

TABLE 2-continued

| | | |
|---|---|---|
| AAGAGGATCAGT | TCAGTATAAGATACATG | AAGAGGATCAGT |
| TGGCCGAAATCA | AAGCGCCATTTGATTTG | TGGCCGAAATCA |
| GTTACCGTTTTC | CTGTTAGAGTGGTTGTA | GTTACCGTTTTC |
| AAGGTAAGAAGG | TGTCCCCATCGATCCTA | AAGGTAAGAAGG |
| AAGCGGACCAAC | CATGTCAACCAATGCGG | AAGCGGACCAAC |
| CGTGGATTGTTG | TTATATTCTACGTGTTT | CGTGGATTGTTG |
| TAAACACGAGCA | GTATCATCCCAACGCAC | TAAACACGAGCA |
| CACTGTTTGATG | CCCAATGCCTCTCTCAT | CACTGTTTGATG |
| AACTCGAATTAG | ATGAATTCCGGTTGTAC | AACTCGAATTAG |
| ACCCCCCCGAGA | ATTTACCTCGCCACATT | ACCCCCCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGG | GCTCCGATGGTA |
| CGTCTACCTACG | GGCACCACGTTAAAGTT | CGTCTACCTACG |
| CCACGTTTTTGG | TGTAGATACACCCGAGA | CCACGTTTTTGG |
| TCACCTGGAAAG | GTTTGTCGGGATTATAC | TCACCTGGAAAG |
| GGGATGAGAAGA | GTTTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACCCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TTTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGGGGCA | | ACGACGGGGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TTTTTGTGGTGT | | TTTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |
| TTGTATCCACAG | | TTGTATCCACAG |
| TAGATCATTTTG | | TAGATCATTTTG |
| TAAACGCAATTG | | TAAACGCAATTG |
| AAGAGCGTGGAT | | AAGAGCGTGGAT |
| TTCCGCCAACGG | | TTCCGCCAACGG |
| CCGGTCAGCCAC | | CCGGTCAGCCAC |
| CGGCGACTACTA | | CGGCGACTACTA |
| AACCCAAGGAAA | | AACCCAAGGAAA |
| TTACCCCCGTAA | | TTACCCCCGTAA |
| ACCCCGGAACGT | | ACCCCGGAACGT |
| CACCACTTCTAC | | CACCACTTCTAC |
| GATATGCCGCAT | | GATATGCCGCAT |
| GGACCGGAGGGC | | GGACCGGAGGGC |
| TTGCAGCAGTAG | | TTGCAGCAGTAG |
| TACTTTTATGTC | | TACTTTTATGTC |
| TCGTAATATTTT | | TCGTAATATTTT |
| TAATCTGTACGG | | TAATCTGTACGG |

TABLE 2-continued

| | | | | |
|---|---|---|---|---|
| | CTAAACGAATGA GGGTTAAAGCCG CCAGGGTAGACA AGTGATAATAGG CTGGAGCCTCGG TGGCCATGCTTC TTGCCCCTTGGG CCTCCCCCCAGC CCCTCCTCCCCT TCCTGCACCCGT ACCCCCGTGGTC TTTGAATAAAGT CTGAGTGGGCGG C | | | CTAAACGAATGA GGGTTAAAGCCG CCAGGGTAGACA AGTGATAATAGG CTGGAGCCTCGG TGGCCATGCTTC TTGCCCCTTGGG CCTCCCCCCAGC CCCTCCTCCCCT TCCTGCACCCGT ACCCCCGTGGTC TTTGAATAAAGT CTGAGTGGGCGG CAAAAAAAAAAA AAAAAAAAAAAA AAAAAAAAAAAA AAAAAAAAAAAA AAAAAAAAAAAA AAAAAAAAAAAA AAAAAAAAAAAA AAAAAAAAAAAA AAAAATCTAG |
| | SEQ ID NO: 84 | SEQ ID NO: 85 | SEQ ID NO: 86 | SEQ ID NO: 87 |
| VZV-GE-truncated-delete_from_574_-_Y569A 7 | GGGAAATAAGAG AGAAAAGAAGAG TAAGAAGAAATA TAAGAGCCACCA TGGGGACAGTTA ATAAACCTGTGG TGGGGGTATTGA TGGGGTTCGGAA TTATCACGGGAA CGTTGCGTATAA CGAATCCGGTCA GAGCATCCGTCT TGCGATACGATG ATTTTCACATCG ATGAAGACAAAC TGGATACAAACT CCGTATATGAGC CTTACTACCATT CAGATCATGCGG AGTCTTCATGGG TAAATCGGGGAG AGTCTTCGCGAA AAGCGTACGATC ATAACTCACCTT ATATATGGCCAC GTAATGATTATG ATGGATTTTTAG AGAACGCACACG AACACCATGGGG TGTATAATCAGG GCCGTGGTATCG ATAGCGGGGAAC GGTTAATGCAAC CCACACAAATGT CTGCACAGGAGG ATCTTGGGGACG ATACGGGCATCC ACGTTATCCCTA CGTTAAACGGCG ATGACAGACATA AAATTGTAAATG TGGACCAACGTC AATACGGTGACG TGTTTAAAGGAG ATCTTAATCCAA AACCCCAAGGCC AAAGACTCATTG AGGTGTCAGTGG AAGAAAATCACC CGTTTACTTTAC GCGCACCGATTC AGCGGATTTATG GAGTCCGGTACA CCGAGACTTGGA GCTTTTTGCCGT | MGTVNKPVVGVLMGFGI ITGTLRITNPVRASVLR YDDFHIDEDKLDTNSVY EPYYHSDHAESSWVNRG ESSRKAYDHNSPYIWPR NDYDGFLENAHEHHGVY NQGRGIDSGERLMQPTQ MSAQEDLGDDTGIHVIP TLNGDDRHKIVNVDQRQ YGDVFKGDLNPKPQGQR LIEVSVEENHPFTLRAP IQRIYGVRYTETWSFLP SLTCTGDAAPAIQHICL KHTTCFQDVVVDVDCAE NTKEDQLAEISYRFQGK KEADQPWIVVNTSTLFD ELELDPPEIEPGVLKVL RTEKQYLGVYIWNMRGS DGTSTYATFLVTWKGDE KTRNPTPAVTPQPRGAE FHMWNYHSHVFSVGDTF SLAMHLQYKIHEAPFDL LLEWLYVPIDPTCQPMR LYSTCLYHPNAPQCLSH MNSGCTFTSPHLAQRVA STVYQNCEHADNYTAYC LGISHMEPSFGLILHDG GTTLKFVDTPESLSGLY VFVVYFNGHVEAVAYTV VSTVDHFVNAIEERGFP PTAGQPPATTKPKEITP VNPGTSPLLRYAAWTGG LAAVVLLCLVIFLICTA KRMRVKAARVDK | ATGGGGACAGTTAATAA ACCTGTGGTGGGGGTAT TGATGGGGTTCGGAATT ATCACGGGAACGTTGCG TATAACGAATCCGGTCA GAGCATCCGTCTTGCGA TACGATGATTTTCACAT CGATGAAGACAAACTGG ATACAAACTCCGTATAT GAGCCTTACTACCATTC AGATCATGCGGAGTCTT CATGGGTAAATCGGGGA GAGTCTTCGCGAAAAGC GTACGATCATAACTCAC CTTATATATGGCCACGT AATGATTATGATGGATT TTTAGAGAACGCACACG AACACCATGGGGTGTAT AATCAGGGCCGTGGTAT CGATAGCGGGGAACGGT TAATGCAACCCACACAA ATGTCTGCACAGGAGGA TCTTGGGGACGATACGG GCATCCACGTTATCCCT ACGTTAAACGGCGATGA CAGACATAAAATTGTAA ATGTGGACCAACGTCAA TACGGTGACGTGTTTAA AGGAGATCTTAATCCAA AACCCCAAGGCCAAAGA CTCATTGAGGTGTCAGT GGAAGAAAATCACCCGT TTACTTTACGCGCACCG ATTCAGCGGATTTATGG AGTCCGGTACACCGAGA CTTGGAGCTTTTTGCCG TCATTAACCTGTACGGG AGACGCAGCGCCCGCCA TCCAGCATATATGTTTA AAGCATACAACATGCTT TCAAGACGTGGTGGTGG ATGTGGATTGCGCGGAA AATACTAAAGAGGATCA GTTGGCCGAAATCAGTT ACCGTTTTCAAGGTAAG AAGGAAGCGGACCAACC GTGGATTGTTGTAAACA CGAGCACACTGTTTGAT GAACTCGAATTAGACCC ACCCGAGATTGAACCGG GTGTCTTGAAAGTACTT CGGACAGAGAAACAATA CTTGGGTGTGTACATTT GGAACATGCGCGGCTCC GATGGTACGTCTACCTA | GGGAAATAAGAG AGAAAAGAAGAG TAAGAAGAAATA TAAGAGCCACCA TGGGGACAGTTA ATAAACCTGTGG TGGGGGTATTGA TGGGGTTCGGAA TTATCACGGGAA CGTTGCGTATAA CGAATCCGGTCA GAGCATCCGTCT TGCGATACGATG ATTTTCACATCG ATGAAGACAAAC TGGATACAAACT CCGTATATGAGC CTTACTACCATT CAGATCATGCGG AGTCTTCATGGG TAAATCGGGGAG AGTCTTCGCGAA AAGCGTACGATC ATAACTCACCTT ATATATGGCCAC GTAATGATTATG ATGGATTTTTAG AGAACGCACACG AACACCATGGGG TGTATAATCAGG GCCGTGGTATCG ATAGCGGGGAAC GGTTAATGCAAC CCACACAAATGT CTGCACAGGAGG ATCTTGGGGACG ATACGGGCATCC ACGTTATCCCTA CGTTAAACGGCG ATGACAGACATA AAATTGTAAATG TGGACCAACGTC AATACGGTGACG TGTTTAAAGGAG ATCTTAATCCAA AACCCCAAGGCC AAAGACTCATTG AGGTGTCAGTGG AAGAAAATCACC CGTTTACTTTAC GCGCACCGATTC AGCGGATTTATG GAGTCCGGTACA CCGAGACTTGGA GCTTTTTGCCGT |

TABLE 2-continued

| | | |
|---|---|---|
| CATTAACCTGTA | CGCCACGTTTTTGGTCA | CATTAACCTGTA |
| CGGGAGACGCAG | CCTGGAAAGGGGATGAG | CGGGAGACGCAG |
| CGCCCGCCATCC | AAGACAAGAAACCCTAC | CGCCCGCCATCC |
| AGCATATATGTT | GCCCGCAGTAACTCCTC | AGCATATATGTT |
| TAAAGCATACAA | AACCAAGAGGGGCTGAG | TAAAGCATACAA |
| CATGCTTTCAAG | TTTCATATGTGGAATTA | CATGCTTTCAAG |
| ACGTGGTGGTGG | CCACTCGCATGTATTTT | ACGTGGTGGTGG |
| ATGTGGATTGCG | CAGTTGGTGATACGTTT | ATGTGGATTGCG |
| CGGAAAATACTA | AGCTTGGCAATGCATCT | CGGAAAATACTA |
| AAGAGGATCAGT | TCAGTATAAGATACATG | AAGAGGATCAGT |
| TGGCCGAAATCA | AAGCGCCATTTGATTTG | TGGCCGAAATCA |
| GTTACCGTTTTC | CTGTTAGAGTGGTTGTA | GTTACCGTTTTC |
| AAGGTAAGAAGG | TGTCCCCATCGATCCTA | AAGGTAAGAAGG |
| AAGCGGACCAAC | CATGTCAACCAATGCGG | AAGCGGACCAAC |
| CGTGGATTGTTG | TTATATTCTACGTGTTT | CGTGGATTGTTG |
| TAAACACGAGCA | GTATCATCCCAACGCAC | TAAACACGAGCA |
| CACTGTTTGATG | CCCAATGCCTCTCTCAT | CACTGTTTGATG |
| AACTCGAATTAG | ATGAATTCCGGTTGTAC | AACTCGAATTAG |
| ACCCACCCGAGA | ATTTACCTCGCCACATT | ACCCACCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGG | GCTCCGATGGTA |
| CGTCTACCTACG | GGCACCACGTTAAAGTT | CGTCTACCTACG |
| CCACGTTTTTGG | TGTAGATACACCCGAGA | CCACGTTTTTGG |
| TCACCTGGAAAG | GTTTGTCGGGATTATAC | TCACCTGGAAAG |
| GGGATGAGAAGA | GTTTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACCCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TTTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGGGGCA | | ACGACGGGGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TTTTTGTGGTGT | | TTTTTGTGGTGT |
| ATTTTAACGGGC | | ATTTTAACGGGC |
| ATGTTGAAGCCG | | ATGTTGAAGCCG |
| TAGCATACACTG | | TAGCATACACTG |
| TTGTATCCACAG | | TTGTATCCACAG |
| TAGATCATTTTG | | TAGATCATTTTG |
| TAAACGCAATTG | | TAAACGCAATTG |
| AAGAGCGTGGAT | | AAGAGCGTGGAT |
| TTCCGCCAACGG | | TTCCGCCAACGG |
| CCGGTCAGCCAC | | CCGGTCAGCCAC |
| CGGCGACTACTA | | CGGCGACTACTA |
| AACCCAAGGAAA | | AACCCAAGGAAA |

TABLE 2-continued

| | | | | |
|---|---|---|---|---|
| | TTACCCCCGTAA | | | TTACCCCCGTAA |
| | ACCCCGGAACGT | | | ACCCCGGAACGT |
| | CACCACTTCTAC | | | CACCACTTCTAC |
| | GATATGCCGCAT | | | GATATGCCGCAT |
| | GGACCGGAGGGC | | | GGACCGGAGGGC |
| | TTGCAGCAGTAG | | | TTGCAGCAGTAG |
| | TACTTTTATGTC | | | TACTTTTATGTC |
| | TCGTAATATTTT | | | TCGTAATATTTT |
| | TAATCTGTACGG | | | TAATCTGTACGG |
| | CTAAACGAATGA | | | CTAAACGAATGA |
| | GGGTTAAAGCCG | | | GGGTTAAAGCCG |
| | CCAGGGTAGACA | | | CCAGGGTAGACA |
| | AGTGATAATAGG | | | AGTGATAATAGG |
| | CTGGAGCCTCGG | | | CTGGAGCCTCGG |
| | TGGCCATGCTTC | | | TGGCCATGCTTC |
| | TTGCCCCTTGGG | | | TTGCCCCTTGGG |
| | CCTCCCCCCAGC | | | CCTCCCCCCAGC |
| | CCCTCCTCCCCT | | | CCCTCCTCCCCT |
| | TCCTGCACCCGT | | | TCCTGCACCCGT |
| | ACCCCCGTGGTC | | | ACCCCCGTGGTC |
| | TTTGAATAAAGT | | | TTTGAATAAAGT |
| | CTGAGTGGGCGG | | | CTGAGTGGGCGG |
| | C | | | CAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAAAAAAAAA |
| | | | | AAAAATCTAG |

| | SEQ ID NO: 88 | SEQ ID NO: 89 | SEQ ID NO: 90 | SEQ ID NO: 91 |
|---|---|---|---|---|
| VZV-GE- | GGGAAATAAGAG | MGTVNKPVVGVLMGFGI | ATGGGGACAGTTAATAA | GGGAAATAAGAG |
| truncated- | AGAAAAGAAGAG | ITGTLRITNPVRASVLR | ACCTGTGGTGGGCGTAT | AGAAAAGAAGAG |
| delete_ | TAAGAAGAAATA | YDDFHIDEDKLDTNSVY | TGATGGGGTTCGGAATT | TAAGAAGAAATA |
| from_574_-_ | TAAGAGCCACCA | EPYYHSDHAESSWVNRG | ATCACGGGAACGTTGCG | TAAGAGCCACCA |
| Y569A | TGGGGACAGTTA | ESSRKAYDHNSPYIWPR | TATAACGAATCCGGTCA | TGGGGACAGTTA |
| Variant | ATAAACCTGTGG | NDYDGFLENAHEHHGVY | GAGCATCCGTCTTGCGA | ATAAACCTGTGG |
| 8 | TGGGCGTATTGA | NQGRGIDSGERLMQPTQ | TACGATGATTTTCACAT | TGGGCGTATTGA |
| | TGGGGTTCGGAA | MSAQEDLGDDTGIHVIP | CGATGAAGACAAACTGG | TGGGGTTCGGAA |
| | TTATCACGGGAA | TLNGDDRHKIVNVDQRQ | ATACAAACTCCGTATAT | TTATCACGGGAA |
| | CGTTGCGTATAA | YGDVFKGDLNPKPQGQR | GAGCCTTACTACCATTC | CGTTGCGTATAA |
| | CGAATCCGGTCA | LIEVSVEENHPFTLRAP | AGATCATGCGGAGTCTT | CGAATCCGGTCA |
| | GAGCATCCGTCT | IQRIYGVRYTETWSFLP | CATGGGTAAATCGGGGA | GAGCATCCGTCT |
| | TGCGATACGATG | SLTCTGDAAPAIQHICL | GAGTCTTCGCGAAAGGC | TGCGATACGATG |
| | ATTTTCACATCG | KHTTCFQDVVVDVDCAE | GTACGATCATAACTCAC | ATTTTCACATCG |
| | ATGAAGACAAAC | NTKEDQLAEISYRFQGK | CTTATATATGGCCACGT | ATGAAGACAAAC |
| | TGGATACAAACT | KEADQPWIVVNTSTLFD | AATGATTATGATGGATT | TGGATACAAACT |
| | CCGTATATGAGC | ELELDPPEIEPGVLKVL | CTTAGAGAACGCACACG | CCGTATATGAGC |
| | CTTACTACCATT | RTEKQYLGVYIWNMRGS | AACACCATGGGGTGTAT | CTTACTACCATT |
| | CAGATCATGCGG | DGTSTYATFLVTWKGDE | AATCAGGGCCGTGGTAT | CAGATCATGCGG |
| | AGTCTTCATGGG | KTRNPTPAVTPQPRGAE | CGATAGCGGGGAACGGT | AGTCTTCATGGG |
| | TAAATCGGGGAG | FHMWNYHSHVFSVGDTF | TAATGCAACCCACACAA | TAAATCGGGGAG |
| | AGTCTTCGCGAA | SLAMHLQYKIHEAPFDL | ATGTCTGCACAGGAGGA | AGTCTTCGCGAA |
| | AGGCGTACGATC | LLEWLYVPIDPTCQPMR | TCTTGGGGACGATACGG | AGGCGTACGATC |
| | ATAACTCACCTT | LYSTCLYHPNAPQCLSH | GCATCCACGTTATCCCT | ATAACTCACCTT |
| | ATATATGGCCAC | MNSGCTFTSPHLAQRVA | ACGTTAAACGGCGATGA | ATATATGGCCAC |
| | GTAATGATTATG | STVYQNCEHADNYTAYC | CAGACATAAGATTGTAA | GTAATGATTATG |
| | ATGGATTCTTAG | LGISHMEPSFGLILHDG | ATGTGGACCAACGTCAA | ATGGATTCTTAG |
| | AGAACGCACACG | GTTLKFVDTPESLSGLY | TACGGTGACGTGTTTAA | AGAACGCACACG |
| | AACACCATGGGG | VFVVYFNGHVEAVAYTV | AGGAGATCTTAATCCAA | AACACCATGGGG |
| | TGTATAATCAGG | VSTVDHFVNAIEERGFP | AGCCCCAAGGCCAAAGA | TGTATAATCAGG |
| | GCCGTGGTATCG | PTAGQPPATTKPKEITP | CTCATTGAGGTGTCAGT | GCCGTGGTATCG |
| | ATAGCGGGGAAC | VNPGTSPLLRYAAWTGG | GGAAGAGAATCACCCGT | ATAGCGGGGAAC |
| | GGTTAATGCAAC | LAAVVLLCLVIFLICTA | TTACTTTACGCGCACCG | GGTTAATGCAAC |
| | CCACACAAATGT | KRMRVKAARVDK | ATTCAGCGGATTTATGG | CCACACAAATGT |
| | CTGCACAGGAGG | | AGTCCGGTACACCGAGA | CTGCACAGGAGG |
| | ATCTTGGGGACG | | CTTGGAGCTTCTTGCCG | ATCTTGGGGACG |
| | ATACGGGCATCC | | TCATTAACCTGTACGGG | ATACGGGCATCC |
| | ACGTTATCCCTA | | AGACGCAGCGCCCGCCA | ACGTTATCCCTA |
| | CGTTAAACGGCG | | TCCAGCATATATGTTTA | CGTTAAACGGCG |
| | ATGACAGACATA | | AAGCATACAACATGCTT | ATGACAGACATA |
| | AGATTGTAAATG | | TCAAGACGTGGTGGTGG | AGATTGTAAATG |
| | TGGACCAACGTC | | ATGTGGATTGCGCGGAG | TGGACCAACGTC |
| | AATACGGTGACG | | AATACTAAAGAGGATCA | AATACGGTGACG |
| | TGTTTAAAGGAG | | GTTGGCCGAAATCAGTT | TGTTTAAAGGAG |
| | ATCTTAATCCAA | | ACCGTTTTCAAGGTAAG | ATCTTAATCCAA |
| | AGCCCCAAGGCC | | AAGGAAGCGGACCAACC | AGCCCCAAGGCC |

TABLE 2-continued

| | | |
|---|---|---|
| AAAGACTCATTG | GTGGATTGTTGTAAACA | AAAGACTCATTG |
| AGGTGTCAGTGG | CGAGCACACTGTTTGAT | AGGTGTCAGTGG |
| AAGAGAATCACC | GAACTCGAATTAGACCC | AAGAGAATCACC |
| CGTTTACTTTAC | ACCCGAGATTGAACCGG | CGTTTACTTTAC |
| GCGCACCGATTC | GTGTCTTGAAAGTACTT | GCGCACCGATTC |
| AGCGGATTTATG | CGGACAGAGAAACAATA | AGCGGATTTATG |
| GAGTCCGGTACA | CTTGGGTGTGTACATTT | GAGTCCGGTACA |
| CCGAGACTTGGA | GGAACATGCGCGGCTCC | CCGAGACTTGGA |
| GCTTCTTGCCGT | GATGGTACGTCTACCTA | GCTTCTTGCCGT |
| CATTAACCTGTA | CGCCACGTTCTTGGTCA | CATTAACCTGTA |
| CGGGAGACGCAG | CCTGGAAAGGGGATGAG | CGGGAGACGCAG |
| CGCCCGCCATCC | AAGACAAGAAACCCTAC | CGCCCGCCATCC |
| AGCATATATGTT | GCCCGCAGTAACTCCTC | AGCATATATGTT |
| TAAAGCATACAA | AACCAAGAGGGGCTGAG | TAAAGCATACAA |
| CATGCTTTCAAG | TTTCATATGTGGAATTA | CATGCTTTCAAG |
| ACGTGGTGGTGG | CCACTCGCATGTATTTT | ACGTGGTGGTGG |
| ATGTGGATTGCG | CAGTTGGTGATACGTTT | ATGTGGATTGCG |
| CGGAGAATACTA | AGCTTGGCAATGCATCT | CGGAGAATACTA |
| AAGAGGATCAGT | TCAGTATAAGATACATG | AAGAGGATCAGT |
| TGGCCGAAATCA | AAGCGCCATTTGATTTG | TGGCCGAAATCA |
| GTTACCGTTTTC | CTGTTAGAGTGGTTGTA | GTTACCGTTTTC |
| AAGGTAAGAAGG | TGTCCCCATCGATCCTA | AAGGTAAGAAGG |
| AAGCGGACCAAC | CATGTCAACCAATGCGG | AAGCGGACCAAC |
| CGTGGATTGTTG | TTATATTCTACGTGTTT | CGTGGATTGTTG |
| TAAACACGAGCA | GTATCATCCCAACGCAC | TAAACACGAGCA |
| CACTGTTTGATG | CCCAATGCCTCTCTCAT | CACTGTTTGATG |
| AACTCGAATTAG | ATGAATTCCGGTTGTAC | AACTCGAATTAG |
| ACCCACCCGAGA | ATTTACCTCGCCACATT | ACCCACCCGAGA |
| TTGAACCGGGTG | TAGCCCAGCGTGTTGCA | TTGAACCGGGTG |
| TCTTGAAAGTAC | AGCACAGTGTATCAGAA | TCTTGAAAGTAC |
| TTCGGACAGAGA | TTGTGAACATGCAGATA | TTCGGACAGAGA |
| AACAATACTTGG | ACTACACCGCATATTGT | AACAATACTTGG |
| GTGTGTACATTT | CTGGGAATATCTCATAT | GTGTGTACATTT |
| GGAACATGCGCG | GGAGCCTAGCTTTGGTC | GGAACATGCGCG |
| GCTCCGATGGTA | TAATCTTACACGACGGA | GCTCCGATGGTA |
| CGTCTACCTACG | GGCACCACGTTAAAGTT | CGTCTACCTACG |
| CCACGTTCTTGG | TGTAGATACACCCGAGA | CCACGTTCTTGG |
| TCACCTGGAAAG | GTTTGTCGGGATTATAC | TCACCTGGAAAG |
| GGGATGAGAAGA | GTCTTTGTGGTGTATTT | GGGATGAGAAGA |
| CAAGAAACCCTA | TAACGGGCATGTTGAAG | CAAGAAACCCTA |
| CGCCCGCAGTAA | CCGTAGCATACACTGTT | CGCCCGCAGTAA |
| CTCCTCAACCAA | GTATCCACAGTAGATCA | CTCCTCAACCAA |
| GAGGGGCTGAGT | TTTTGTAAACGCAATTG | GAGGGGCTGAGT |
| TTCATATGTGGA | AAGAGCGTGGATTTCCG | TTCATATGTGGA |
| ATTACCACTCGC | CCAACGGCCGGTCAGCC | ATTACCACTCGC |
| ATGTATTTTCAG | ACCGGCGACTACTAAAC | ATGTATTTTCAG |
| TTGGTGATACGT | CCAAGGAAATTACGCCC | TTGGTGATACGT |
| TTAGCTTGGCAA | GTAAACCCCGGAACGTC | TTAGCTTGGCAA |
| TGCATCTTCAGT | ACCACTTCTACGATATG | TGCATCTTCAGT |
| ATAAGATACATG | CCGCATGGACCGGAGGG | ATAAGATACATG |
| AAGCGCCATTTG | CTTGCAGCAGTAGTACT | AAGCGCCATTTG |
| ATTTGCTGTTAG | TTTATGTCTCGTAATAT | ATTTGCTGTTAG |
| AGTGGTTGTATG | TCTTAATCTGTACGGCT | AGTGGTTGTATG |
| TCCCCATCGATC | AAACGAATGAGGGTTAA | TCCCCATCGATC |
| CTACATGTCAAC | AGCCGCCAGGGTAGACA | CTACATGTCAAC |
| CAATGCGGTTAT | AG | CAATGCGGTTAT |
| ATTCTACGTGTT | | ATTCTACGTGTT |
| TGTATCATCCCA | | TGTATCATCCCA |
| ACGCACCCCAAT | | ACGCACCCCAAT |
| GCCTCTCTCATA | | GCCTCTCTCATA |
| TGAATTCCGGTT | | TGAATTCCGGTT |
| GTACATTTACCT | | GTACATTTACCT |
| CGCCACATTTAG | | CGCCACATTTAG |
| CCCAGCGTGTTG | | CCCAGCGTGTTG |
| CAAGCACAGTGT | | CAAGCACAGTGT |
| ATCAGAATTGTG | | ATCAGAATTGTG |
| AACATGCAGATA | | AACATGCAGATA |
| ACTACACCGCAT | | ACTACACCGCAT |
| ATTGTCTGGGAA | | ATTGTCTGGGAA |
| TATCTCATATGG | | TATCTCATATGG |
| AGCCTAGCTTTG | | AGCCTAGCTTTG |
| GTCTAATCTTAC | | GTCTAATCTTAC |
| ACGACGGAGGCA | | ACGACGGAGGCA |
| CCACGTTAAAGT | | CCACGTTAAAGT |
| TTGTAGATACAC | | TTGTAGATACAC |
| CCGAGAGTTTGT | | CCGAGAGTTTGT |
| CGGGATTATACG | | CGGGATTATACG |
| TCTTTGTGGTGT | | TCTTTGTGGTGT |
| ATTTTAACGGGC | | ATTTTAACGGGC |
| ATGTTGAAGCCG | | ATGTTGAAGCCG |

TABLE 2-continued

| | | |
|---|---|---|
| | TAGCATACACTG | TAGCATACACTG |
| | TTGTATCCACAG | TTGTATCCACAG |
| | TAGATCATTTTG | TAGATCATTTTG |
| | TAAACGCAATTG | TAAACGCAATTG |
| | AAGAGCGTGGAT | AAGAGCGTGGAT |
| | TTCCGCCAACGG | TTCCGCCAACGG |
| | CCGGTCAGCCAC | CCGGTCAGCCAC |
| | CGGCGACTACTA | CGGCGACTACTA |
| | AACCCAAGGAAA | AACCCAAGGAAA |
| | TTACGCCCGTAA | TTACGCCCGTAA |
| | ACCCCGGAACGT | ACCCCGGAACGT |
| | CACCACTTCTAC | CACCACTTCTAC |
| | GATATGCCGCAT | GATATGCCGCAT |
| | GGACCGGAGGGC | GGACCGGAGGGC |
| | TTGCAGCAGTAG | TTGCAGCAGTAG |
| | TACTTTTATGTC | TACTTTTATGTC |
| | TCGTAATATTCT | TCGTAATATTCT |
| | TAATCTGTACGG | TAATCTGTACGG |
| | CTAAACGAATGA | CTAAACGAATGA |
| | GGGTTAAAGCCG | GGGTTAAAGCCG |
| | CCAGGGTAGACA | CCAGGGTAGACA |
| | AGTGATAATAGG | AGTGATAATAGG |
| | CTGGAGCCTCGG | CTGGAGCCTCGG |
| | TGGCCATGCTTC | TGGCCATGCTTC |
| | TTGCCCCTTGGG | TTGCCCCTTGGG |
| | CCTCCCCCCAGC | CCTCCCCCCAGC |
| | CCCTCCTCCCCT | CCCTCCTCCCCT |
| | TCCTGCACCCGT | TCCTGCACCCGT |
| | ACCCCCGTGGTC | ACCCCCGTGGTC |
| | TTTGAATAAAGT | TTTGAATAAAGT |
| | CTGAGTGGGCGG | CTGAGTGGGCGG |
| | C | CAAAAAAAAAAA |
| | | AAAAAAAAAAAA |
| | | AAAAAAAAAAAA |
| | | AAAAAAAAAAAA |
| | | AAAAAAAAAAAA |
| | | AAAAAAAAAAAA |
| | | AAAAAAAAAAAA |
| | | AAAAAAAAAAAA |
| | | AAAAATCTAG |

VZV mRNA Sequences

| mRNA Name(s) | mRNA Sequence (assumes T100 tail) | SEQ ID NO |
|---|---|---|
| VZV_gE_ Oka | G*GGGAAAUAAGAGAGAAAAGAAGAGUAAGAAGAAAUAUAAGA<br>GCCACCAUGGGGACAGUGAAUAAGCCGGUUGUGGGCGUGCUUAU<br>GGGCUUUGGGAUUAUUACCGGUACAUUACGAAUUACCAAUCCAG<br>UGCGCGCCAGUGUGCUGCGUUACGACGACUUUCACAUUGACGAG<br>GAUAAGCUGGAUACUAACAGCGUGUACGAACCUUAUUACCACUC<br>AGAUCAUGCCGAAUCAAGCUGGGUUAAUAGAGGAGAAAGCAGC<br>CGAAAAGCCUACGACCACAACUCACCUUAUAUUUGGCCCAGAAA<br>CGAUUAUGACGGUUUCCUGGAAAACGCACAUGAACACCAUGGAG<br>UCUACAACCAAGGCAGGGGAAUCGACAGUGGCGAGCGUCUUAUG<br>CAGCCAACACAGAUGUCGGCACAGGAGGAUCUCGGUGAUGACAC<br>CGGCAUACACGUGAUUCCCACAUUAAACGGCGACGACAGACAUA<br>AGAUCGUCAAUGUGGAUCAGCGUCAGUAUGGGGAUGUCUUUAA<br>AGGCGAUUUGAAUCCAAAGCCCCAAGGACAGAGACUGAUCGAGG<br>UCUCUGUAGAAGAAAAUCACCCCUUCACUUUGCGCGCUCCAAUC<br>CAGAGGAUUUACGGGGUGCGUUAUACCGAAACUUGGAGUUUCU<br>UGCCGUCACUGACGUGUACGGGGGAUGCCGCCCCCGCAAUCCAG<br>CACAUCUGUCUGAAACACACCACAUGCUUUCAGGACGUGGUUGU<br>GGAUGUGGAUUGCGCGGAAAACACAAAAGAAGACCAACUCGCCG<br>AAAUCAGCUAUCGUUUUCAGGGUAAAAAGAGGCCGACCAACCG<br>UGGAUUGUUGUGAAUACGAGCACGCUCUUCGAUGAGCUUGAAC<br>UCGAUCCCCCGGAAAUCGAGCCUGGGGUUCUAAAAGUGUUGAGG<br>ACCGAGAAGCAGUACCUCGGGGUUUAUAUCUGGAAUAUGAGAG<br>GCUCCGAUGGCACCUCUACCUACGCAACGUUUCUGGUUACCUGG<br>AAGGGAGACGAGAAGACACGGAAUCCAACGCCCGCUGUGACCCC<br>UCAGCCUAGGGGAGCCGAAUUCCACAUGUGGAACUAUCACUCCC<br>AUGUAUUCAGUGUGGGUGACACUUUCAGCCUGGCCAUGCACCUG<br>CAGUAUAAGAUUCACGAGGCACCCUUCGACCUCCUGCUGGAGUG<br>GUUGUACGUACCUAUUGAUCCCACUUGUCAGCCCAUGCGCCUGU<br>ACUCCACUUGCUUGUACCACCCCAAUGCACCACAGUGUCUAUCA<br>CACAUGAACUCCGGGUGUACCUUUACUUCACCCCAUCUUGCCCA<br>GCGGGUCGCCAGCACAGUGUAUCAGAACUGUGAGCAUGCUGACA<br>ACUAUACUGCUUAUUGCCUCGGAAUAUCCCAUAUGGAGCCAAGC<br>UUCGGGCUCAUACUGCACGAUGGUGGUACGACACUCAAGUUCGU<br>GGACACCCCCGAAAGCCUUUCUGGCUUGUACGUGUUCGUGGUCU | 92 |

TABLE 2-continued

| | | |
|---|---|---|
| | ACUUCAAUGGACAUGUGGAGGCAGUGGCUUACACAGUGGUUUC<br>GACAGUUGAUCACUUUGUAAAUGCCAUUGAGGAACGCGGCUUCC<br>CGCCUACAGCGGGCCAGCCCCCUGCGACAACAAAACCAAAAGAG<br>AUUACGCCCGUUAAUCCUGGGACUAGUCCAUUGCUGAGGUAUGC<br>CGCCUGGACUGGCGGUCUGGCGGCCGUGGUACUUCUGUGUUUAG<br>UCAUAUUUCUGAUCUGUACCGCUAAACGUAUGCGGGUCAAGGCU<br>UACCGUGUUGACAAGUCUCCUUACAAUCAGUCAAUGUACUAUGC<br>AGGACUCCCUGUUGACGAUUUCGAAGACUCAGAGAGUACAGACA<br>CAGAAGAAGAAUUCGGAAACGCUAUAGGUGGCUCUCACGGAGG<br>UAGCUCGUAUACAGUGUACAUCGAUAAAACCAGAUGAUAAUAG<br>GCUGGAGCCUCGGUGGCCAUGCUUCUUGCCCCUUGGGCCUCCCC<br>CCAGCCCCUCCUCCCCUUCCUGCACCCGUACCCCCGUGGUCUUUG<br>AAUAAAGUCUGAGUGGGCGGCAAAAAAAAAAAAAAAAAAAAA<br>AAAAAAAAAAAAAAAAAAAAAAAAAAAAAAAAAAAAAAAAAA<br>AAAAAAAAAAAAAAAAAAAAAAAAAAAAAAAAAAAAAUCUAG | |
| VZV_gE_<br>full_indel_<br>fixed | G*GGGAAAUAAGAGAGAAAAGAAGAGUAAGAAGAAAUAUAAGA<br>GCCACCAUGGGGACAGUUAAUAAACCUGUGGUGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAGCAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCACCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAGAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCUACAGGGUAGACAAGUCUCCUUACAAUCAGUCAAU<br>GUACUAUGCAGGACUCCCUGUUGACGAUUUCGAAGACUCAGAGA<br>GUACAGACACAGAAGAAGAAUUCGGAAACGCUAUAGGUGGCUC<br>UCACGGAGGUAGCUCGUAUACAGUGUACAUCGAUAAAACCAGA<br>UGAUAAUAGGCUGGAGCCUCGGUGGCCAUGCUUCUUGCCCCUUG<br>GGCCUCCCCCCAGCCCCUCCUCCCCUUCCUGCACCCGUACCCCCG<br>UGGUCUUUGAAUAAAGUCUGAGUGGGCGGC | 135 |
| VZV_gE_<br>Oka_hIgkappa | G*GGGAAAUAAGAGAGAAAAGAAGAGUAAGAAGAAAUAUAAGA<br>GCCACCAUGGAGACUCCCGCUCAGCUACUGUUCCUCCUGCUCCU<br>UUGGCUGCCUGAUACUACAGGCUCUGUUUUGCGGUACGACGACU<br>UUCACAUCGAUGAGGACAAGCUCGACACUAAUAGCGUGUAUGAG<br>CCCUACUACCAUUCAGAUCACGCCGAGUCCUCUUGGGUGAACAG<br>GGGUGAAAGUUCUAGGAAAGCCUAUGAUCACAACAGCCCUUAUA<br>UUUGGCCACGGAAUGAUUACGACGGAUUUCUCGAAAAUGCCCAC<br>GAGCAUCACGGAGUGUACAACCAGGGCCGUGGAAUCGACUCUGG<br>GGAGAGAUUGAUGCAACCUACACAGAUGAGCGCCCAGGAAGAUC<br>UCGGGGAUGAUACAGGAAUUCACGUUAUCCCUACAUUAAACGGA<br>GAUGACCGCCACAAAAUCGUCAAUGUCGAUCAAAGACAGUAUGG<br>AGAUGUGUUCAAAGGCGAUCUCAACCCUAAGCCGCAGGGCCAGA<br>GACUCAUUGAGGUGUCUGUCGAAGAGAACCACCCUUUCACUCUG<br>CGCGCUCCCAUUCAGAGAAUCUAUGGAGUUCGCUAUACGGAGAC<br>UUGGUCAUUCCUUCCUUCCCUGACAUGCACCGGAGACGCCGCCC<br>CUGCCAUUCAGCACAUAUGCCUGAAACAUACCACCUGUUUCCAG | 93 |

TABLE 2-continued

| | | |
|---|---|---|
| | GAUGUGGUGGUUGAUGUUGAUUGUGCUGAAAAUACCAAGGAAG<br>ACCAACUGGCCGAGAUUAGUUACCGGUUCCAAGGGAAAAAGGAA<br>GCCGACCAGCCAUGGAUUGUGGUUAAUACAAGCACUCUGUUCGA<br>UGAGCUCGAGCUGGAUCCCCCCGAGAUAGAACCCGGAGUUCUGA<br>AAGUGCUCCGGACAGAAAAACAAUAUCUGGGAGUCUACAUAUG<br>GAACAUGCGCGGUUCCGAUGGGACCUCCACUUAUGCAACCUUUC<br>UCGUCACGUGGAAGGGAGAUGAGAAAACUAGGAAUCCCACACCC<br>GCUGUCACACCACAGCCAAGAGGGGCUGAGUUCCAUAUGUGGAA<br>CUAUCAUAGUCACGUGUUUAGUGUCGGAGAUACGUUUUCAUUG<br>GCUAUGCAUCUCCAGUACAAGAUUCAUGAGGCUCCCUUCGAUCU<br>GUUGCUUGAGUGGUUGUACGUCCCGAUUGACCCGACCUGCCAGC<br>CCAUGCGACUGUACAGCACCUGUCUCUACCAUCCAAACGCUCCG<br>CAAUGUCUGAGCCACAUGAACUCUGGGUGUACUUUCACCAGUCC<br>CCACCUCGCCCAGCGGGUGGCCUCUACUGUUUACCAGAACUGUG<br>AGCACGCCGACAACUACACCGCAUACUGCCUCGGUAUUUCUCAC<br>AUGGAACCCUCCUUCGGACUCAUCCUGCACGAUGGGGGCACUAC<br>CCUGAAGUUCGUUGAUACGCCAGAAUCUCUGUCUGGGCUCUAUG<br>UUUUCGUGGUCUACUUCAAUGGCCAUGUCGAGGCCGUGGCCUAU<br>ACUGUCGUUUCUACCGUGGAUCAUUUUGUGAACGCCAUCGAAGA<br>ACGGGGAUUCCCCCCUACGGCAGGCCAGCCGCCUGCAACCACCA<br>AGCCCAAGGAAAUAACACCAGUGAACCCUGGCACCUCACCUCUC<br>CUAAGAUAUGCCGCGUGGACAGGGGGACUGGCGGCAGUGGUGCU<br>CCUCUGUCUCGUGAUCUUUCUGAUCUGUACAGCCAAGAGGAUGA<br>GGGUCAAGGCUUAUAGAGUGGACAAGUCCCCCUACAAUCAGUCA<br>AUGUACUACGCCGGCCUUCCCGUUGAUGAUUUUGAGGAUUCCGA<br>GUCCACAGAUACUGAGGAAGAGUUCGGUAACGCUAUAGGCGGCU<br>CUCACGGGGGUUCAAGCUACACGGUUUACAUUGACAAGACACGC<br>UGAUAAUAGGCUGGAGCCUCGGUGGCCAUGCUUCUUGCCCCUUG<br>GGCCUCCCCCCAGCCCCUCCUCCCCUUCCUGCACCCGUACCCCCG<br>UGGUCUUUGAAUAAAGUCUGAGUGGGCGGCAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AUCUAG | |
| VZV-GE-<br>delete-562 | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAACAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAAAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAAAAAACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAAAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUUGAUGAUAAUAG<br>GCUGGAGCCUCGGUGGCCAUGCUUCUUGCCCCUUGGGCCUCCCC<br>CCAGCCCCUCCUCCCCUUCCUGCACCCGUACCCCCGUGGUCUUUG<br>AAUAAAGUCUGAGUGGGCGGCAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAUCUA | 94 |

TABLE 2-continued

| | | |
|---|---|---|
| VZV-GE-<br>delete-<br>562-<br>replacedSP-<br>withIgKappa | G*GGGAAAUAAGAGAGAAAAGAAGAGUAAGAAGAAAUAUAAGA<br>GCCACCAUGGAAACCCCGGCGCAGCUGCUGUUUCUGCUGCUGCU<br>GUGGCUGCCGGAUACCACCGGCUCCGUCUUGCGAUACGAUGAUU<br>UUCACAUCGAUGAAGACAAACUGGAUACAAACUCCGUAUAUGAG<br>CCUUACUACCAUUCAGAUCAUGCGGAGUCUUCAUGGGUAAAUCG<br>GGGAGAGUCUUCGCGAAAAGCGUACGAUCAUAACUCACCUUAUA<br>UAUGGCCACGUAAUGAUUAUGAUGGAUUUUUAGAGAACGCACA<br>CGAACACCAUGGGGUGUAUAAUCAGGGCCGUGGUAUCGAUAGCG<br>GGGAACGGUUAAUGCAACCCACACAAAUGUCUGCACAGGAGGAU<br>CUUGGGGACGAUACGGGCAUCCACGUUAUCCCUACGUUAAACGG<br>CGAUGACAGACAUAAAAUUGUAAAUGUGGACCAACGUCAAUAC<br>GGUGACGUGUUUAAAGGAGAUCUUAAUCCAAAACCCCAAGGCCA<br>AAGACUCAUUGAGGUGUCAGUGGAAGAAAAUCACCCGUUUACU<br>UUACGCGCACCGAUUCAGCGGAUUUAUGGAGUCCGGUACACCGA<br>GACUUGGAGCUUUUUGCCGUCAUUAACCUGUACGGGAGACGCAG<br>CGCCCGCCAUCCAGCAUAUAUGUUUAAAACAUACAACAUGCUUU<br>CAAGACGUGGUGGUGGAUGUGGAUUGCGCGGAAAAUACUAAAG<br>AGGAUCAGUUGGCCGAAAUCAGUUACCGUUUUCAAGGUAAGAA<br>GGAAGCGGACCAACCGUGGAUUGUUGUAAACACGAGCACACUGU<br>UUGAUGAACUCGAAUUAGACCCCCCCGAGAUUGAACCGGGUGUC<br>UUGAAAGUACUUCGGACAGAAAAACAAUACUUGGGUGUGUACA<br>UUUGGAACAUGCGCGGCUCCGAUGGUACGUCUACCUACGCCACG<br>UUUUUGGUCACCUGGAAAGGGGAUGAAAAACAAGAAACCCUA<br>CGCCCGCAGUAACUCCUCAACCAAGAGGGGCUGAGUUUCAUAUG<br>UGGAAUUACCACUCGCAUGUAUUUUCAGUUGGUGAUACGUUUA<br>GCUUGGCAAUGCAUCUUCAGUAUAAGAUACAUGAAGCGCCAUUU<br>GAUUUGCUGUUAGAGUGGUUGUAUGUCCCCAUCGAUCCUACAUG<br>UCAACCAAUGCGGUUAUAUUCUACGUGUUUGUAUCAUCCCAACG<br>CACCCCAAUGCCUCUCUCAUAUGAAUUCCGGUUGUACAUUUACC<br>UCGCCACAUUUAGCCCAGCGUGUUGCAAGCACAGUGUAUCAAAA<br>UUGUGAACAUGCAGAUAACUACACCGCAUAUUGUCUGGGAAUA<br>UCUCAUAUGGAGCCUAGCUUUGGUCUAAUCUUACACGACGGGGG<br>CACCACGUUAAAGUUUGUAGAUACACCCGAGAGUUUGUCGGGAU<br>UAUACGUUUUUGUGGUGUAUUUUAACGGGCAUGUUGAAGCCGU<br>AGCAUACACUGUUGUAUCCACAGUAGAUCAUUUUGUAAACGCAA<br>UUGAAGAGCGUGGAUUUCCGCCAACGGCCGGUCAGCCACCGGCG<br>ACUACUAAACCCAAGGAAAUUACCCCCGUAAACCCCGGAACGUC<br>ACCACUUCUACGAUAUGCCGCAUGGACCGGAGGGCUUGCAGCAG<br>UAGUACUUUUAUGUCUCGUAAUAUUUUUAAUCUGUACGGCUUG<br>AUGAUAAUAGGCUGGAGCCUCGGUGGCCAUGCUUCUUGCCCCUU<br>GGGCCUCCCCCCAGCCCCUCCUCCCCUUCCUGCACCCGUACCCCC<br>GUGGUCUUUGAAUAAAGUCUGAGUGGGCGGCAAAAAAAAAAA<br>AAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA<br>AAUCUAG | 95 |
| VZV-GE-<br>full_with_<br>AEAADA<br>(SEQ ID<br>NO: 58) | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAACAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAAAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAAAAACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAAAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU | 96 |

TABLE 2-continued

| | | |
|---|---|---|
| | GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCUAUAGGGUAGACAAGUCCCCGUAUAACCAAAGCAU<br>GUAUUACGCUGGCCUUCCAGUGGACGAUUUCGAGGACGCCGAAG<br>CCGCCGAUGCCGAAGAAGAGUUUGGUAACGCGAUUGGAGGGAG<br>UCACGGGGGUUCGAGUUACACGGUGUAUAUAGAUAAGACCCGG<br>UGAUGAUAAUAGGCUGGAGCCUCGGUGGCCAUGCUUCUUGCCCC<br>UUGGGCCUCCCCCCAGCCCCUCCUCCCCUUCCUGCACCCGUACCC<br>CCGUGGUCUUUGAAUAAAGUCUGAGUGGGCGGCAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAUCUAG | |
| VZV-GE-full_with_AEAADA (SEQ ID NO: 58)_and_Y582G | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAACAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAAAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAAAAACAAGAAACCCUACGCCCGCAGUAA<br>CUCCUCAACCAAGAGGGGCUGAGUUUCAUAUGUGGAAUUACCAC<br>UCGCAUGUAUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAAAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCUAUAGGGUAGACAAGUCCCCGUAUAACCAAAGCAU<br>GUAUGGCGCUGGCCUUCCAGUGGACGAUUUCGAGGACGCCGAAG<br>CCGCCGAUGCCGAAGAAGAGUUUGGUAACGCGAUUGGAGGGAG<br>UCACGGGGGUUCGAGUUACACGGUGUAUAUAGAUAAGACCCGG<br>UGAUGAUAAUAGGCUGGAGCCUCGGUGGCCAUGCUUCUUGCCCC<br>UUGGGCCUCCCCCCAGCCCCUCCUCCCCUUCCUGCACCCGUACCC<br>CCGUGGUCUUUGAAUAAAGUCUGAGUGGGCGGCAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAAAAAAA<br>AAAAUCUAG | 97 |
| VZV-GE-Truncated-delete_from_574 | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU | 98 |

TABLE 2-continued

| | | |
|---|---|---|
| | UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAACAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAAAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAAAAAACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAAAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCUAUAGGGUAGACAAGUGAUGAUAAUAGGCUGGAG<br>CCUCGGUGGCCAUGCUUCUUGCCCCUUGGGCCUCCCCCCAGCCCC<br>UCCUCCCCUUCCUGCACCCGUACCCCCGUGGUCUUUGAAUAAAG<br>UCUGAGUGGGCGGCAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAUCUAG | |
| VZV-GE-<br>Truncated-<br>delete_from_<br>574_-_<br>Y569A | G*GGGAAAUAAGAGAGAAAAGAAGAGUAAGAAGAAAUAUAAGA<br>GCCACCAUGGGGACAGUUAAUAAACCUGUGGUGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAACAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAAAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAAAAAACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAAAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUGAUAAUAGGCUGGAG<br>CCUCGGUGGCCAUGCUUCUUGCCCCUUGGGCCUCCCCCCAGCCCC<br>UCCUCCCCUUCCUGCACCCGUACCCCCGUGGUCUUUGAAUAAAG | 99 |

TABLE 2-continued

| | | |
|---|---|---|
| | UCUGAGUGGGCGGCAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAAAAAAAAAAAAAAAAAAAAUCUAG | |
| VZV-GE-<br>Truncated-<br>delete_from_<br>574_-_<br>Y569A<br>(ORF) | AUGGGGACAGUUAAUAAACCUGUGGUGGGGGUAUUGAUGGGGU<br>UCGGAAUUAUCACGGGAACGUUGCGUAUAACGAAUCCGGUCAGA<br>GCAUCCGUCUUGCGAUACGAUGAUUUUCACAUCGAUGAAGACAA<br>ACUGGAUACAAACUCCGUAUAUGAGCCUUACUACCAUUCAGAUC<br>AUGCGGAGUCUUCAUGGGUAAAUCGGGGAGAGUCUUCGCGAAA<br>AGCGUACGAUAAUCAUAACUCACCUUAUAUAUGGCCACGUAAUG<br>AUUAUGAUGGAUUUUUAGAGAACGCACACGAACACCAUGGGGU<br>GUAUAAUCAGGGCCGUGGUAUCGAUAGCGGGGAACGGUUAAUG<br>CAACCCACACAAAUGUCUGCACAGGAGGAUCUUGGGGACGAUAC<br>GGGCAUCCACGUUAUCCCUACGUUAAACGGCGAUGACAGACAUA<br>AAAUUGUAAAUGUGGACCAACGUCAAUACGGUGACGUGUUUAA<br>AGGAGAUCUUAAUCCAAAACCCCAAGGCCAAAGACUCAUUGAGG<br>UGUCAGUGGAAGAAAAUCACCCGUUUACUUUACGCGCACCGAUU<br>CAGCGGAUUUAUGGAGUCCGGUACACCGAGACUUGGAGCUUUUU<br>GCCGUCAUUAACCUGUACGGGAGACGCAGCGCCCGCCAUCCAGC<br>AUAUAUGUUUAAAACAUACAACAUGCUUUCAAGACGUGGUGGU<br>GGAUGUGGAUUGCGCGGAAAAUACUAAAGAGGAUCAGUUGGCC<br>GAAAUCAGUUACCGUUUUCAAGGUAAGAAGGAAGCGGACCAACC<br>GUGGAUUGUUGUAAACACGAGCACACUGUUUGAUGAACUCGAA<br>UUAGACCCCCCCGAGAUUGAACCGGGUGUCUUGAAAGUACUUCG<br>GACAGAAAAACAAUACUUGGGUGUGUACAUUUGGAACAUGCGC<br>GGCUCCGAUGGUACGUCUACCUACGCCACGUUUUUGGUCACCUG<br>GAAAGGGGAUGAAAAACAAGAAACCCUACGCCCGCAGUAACUC<br>CUCAACCAAGAGGGGCUGAGUUUCAUAUGUGGAAUUACCACUCG<br>CAUGUAUUUUCAGUUGGUGAUACGUUUAGCUUGGCAAUGCAUC<br>UUCAGUAUAAGAUACAUGAAGCGCCAUUUGAUUUGCUGUUAGA<br>GUGGUUGUAUGUCCCCAUCGAUCCUACAUGUCAACCAAUGCGGU<br>UAUAUUCUACGUGUUUGUAUCAUCCCAACGCACCCCAAUGCCUC<br>UCUCAUAUGAAUUCCGGUUGUACAUUUACCUCGCCACAUUUAGC<br>CCAGCGUGUUGCAAGCACAGUGUAUCAAAAUUGUGAACAUGCAG<br>AUAACUACACCGCAUAUUGUCUGGGAAUAUCUCAUAUGGAGCCU<br>AGCUUUGGUCUAAUCUUACACGACGGGGGCACCACGUUAAAGUU<br>UGUAGAUACACCCGAGAGUUUGUCGGGAUUAUACGUUUUUGUG<br>GUGUAUUUUAACGGGCAUGUUGAAGCCGUAGCAUACACUGUUG<br>UAUCCACAGUAGAUCAUUUUGUAAACGCAAUUGAAGAGCGUGG<br>AUUUCCGCCAACGGCCGGUCAGCCACCGGCGACUACUAAACCCA<br>AGGAAAUUACCCCCGUAAACCCCGGAACGUCACCACUUCUACGA<br>UAUGCCGCAUGGACCGGAGGGCUUGCAGCAGUAGUACUUUUAUG<br>UCUCGUAAUAUUUUUAAUCUGUACGGCUAAACGAAUGAGGGUU<br>AAAGCCGCCAGGGUAGACAAGUGAUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGC | 133 |
| VZV-GI-<br>full | G*GGGAAAUAAGAGAGAAAAGAAGAGUAAGAAGAAAUAUAAGA<br>GCCACCAUGUUUUUAAUCCAAUGUUUGAUAUCGGCCGUUAUAUU<br>UUACAUACAAGUGACCAACGCUUUGAUCUUCAAGGGCGACCACG<br>UGAGCUUGCAAGUUAACAGCAGUCUCACGUCUAUCCUUAUUCCC<br>AUGCAAAAUGAUAAUUAUACAGAGAUAAAAGGACAGCUUGUCU<br>UUAUUGGAGAGCAACUACCUACCGGGACAAACUAUAGCGGAACA<br>CUGGAACUGUUAUACGCGGAUACGGUGGCGUUUUGUUUCCGGUC<br>AGUACAAGUAAUAAGAUACGACGGAUGUCCCCGGAUUAGAACG<br>AGCGCUUUUAUUUCGUGUAGGUACAAACAUUCGUGGCAUUAUG<br>GUAACUCAACGGAUCGGAUAUCAACAGAGCCGGAUGCUGGUGUA<br>AUGUUGAAAAUUACCAAACCGGGAAUAAAUGAUGCUGGUGUGU<br>AUGUACUUCUUGUUCGGUUAGACCAUAGCAGAUCCACCGAUGGU<br>UUCAUUCUUGGUGUAAAUGUAUAUACAGCGGGCUCGCAUCACAA<br>CAUUCACGGGGUUAUCUACACUUCUCCAUCUCUACAGAAUGGAU<br>AUUCUACAAGAGCCCUUUUUCAACAAGCUCGUUUGUGUGAUUUA<br>CCCGCGACACCCAAAGGGUCCGGUACCUCCCUGUUUCAACAUAU<br>GCUUGAUCUUCGUGCCGGUAAAUCGUUAGAGGAUAACCCUUGGU<br>UACAUGAGGACGUUGUUACGACAGAAACUAAGUCCGUUGUUAA<br>GGAGGGGAUAGAAAAUCACGUAUAUCCAACGGAUAUGUCCACG<br>UUACCCGAAAAGUCCCUUAAUGAUCCUCCAGAAAAUCUACUUAU<br>AAUUAUUCCUAUAGUAGCGUCUGUCAUGAUCCUCACCGCCAUGG<br>UUAUUGUUAUUGUAAUAAGCGUUAAGCGACGUAGAAUUAAAAA<br>ACAUCCAAUUUAUCGCCCAAAUACAAAAACAAGAAGGGGCAUAC<br>AAAAUGCGACACCAGAAUCCGAUGUGAUGUUGGAGGCCGCCAUU<br>GCACAACUAGCAACGAUUCGCGAAGAAUCCCCCCCACAUUCCGU<br>UGUAAACCCGUUUGUUAAAUAGUGAUAAUAGGCUGGAGCCUCG<br>GUGGCCAUGCUUCUUGCCCCUUGGGCCUCCCCCCAGCCCCUCCUC<br>CCCUUCCUGCACCCGUACCCCCGUGGUCUUUGAAUAAAGUCUGA<br>GUGGGCGGCAAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAAAAAAAAAAAAAUCUAG | 100 |

TABLE 2-continued

| | | |
|---|---|---|
| VZV-GE-<br>Truncated-<br>delete_from_<br>574_-_<br>Y569A<br>Variant 1 | G*GGGAAAUAAGAGAGAAAAGAAGAGUAAGAAGAAAUAUAAGA<br>GCCACCAUGGGCACCGUGAACAAGCCCGUCGUGGGCGUGCUGAU<br>GGGCUUCGGCAUCAUCACCGGCACCCUGCGGAUCACCAAUCCUG<br>UGCGGGCCAGCGUGCUGAGAUACGACGACUUCCACAUCGACGAG<br>GACAAGCUGGACACCAACAGCGUGUACGAGCCCUACUACCACAG<br>CGACCACGCCGAGAGCAGCUGGGUCAACAGAGGCGAGUCCAGCC<br>GGAAGGCCUACGACCACAACAGCCCCUACAUCUGGCCCCGGAAC<br>GACUACGACGGCUUCCUGGAAAAUGCCCACGAGCACCACGGCGU<br>GUACAACCAGGGCAGAGGCAUCGACAGCGGCGAGAGACUGAUGC<br>AGCCCACCCAGAUGAGCGCCCAGGAAGAUCUGGGCGACGACACC<br>GGCAUCCACGUGAUCCCUACCCUGAACGGCGACGACCGGCACAA<br>GAUCGUGAACGUGGACCAGCGGCAGUACGGCGACGUGUUCAAGG<br>GCGACCUGAACCCCAAGCCCCAGGGACAGCGGCUGAUUGAGGUG<br>UCCGUGGAAGAGAACCACCCCUUCACCCUGAGAGCCCCUAUCCA<br>GCGGAUCUACGGCGUGCGCUAUACCGAGACUUGGAGCUUCCUGC<br>CCAGCCUGACCUGUACUGGCGACGCCGCUCCUGCCAUCCAGCAC<br>AUCUGCCUGAAGCACACCACCUGUUUCCAGGACGUGGUGGUGGA<br>CGUGGACUGCGCCGAGAACACCAAAGAGGACCAGCUGGCCGAGA<br>UCAGCUACCGGUUCCAGGGCAAGAAAGAGGCCGACCAGCCCUGG<br>AUCGUCGUGAACACCAGCACCCUGUUCGACGAGCUGGAACUGGA<br>CCCUCCCGAGAUCGAACCCGGGGUGCUGAAGGUGCUGCGGACCG<br>AGAAGCAGUACCUGGGAGUGUACAUCUGGAACAUGCGGGGCAGC<br>GACGGCACCUCUACCUACGCCACCUUCCUCGUGACCUGGAAGGG<br>CGACGAGAAAACCCGGAACCCUACCCCUGCCGUGACCCCUCAGC<br>CUAGAGGCGCCGAGUUUCACAUGUGGAAUUACCACAGCCACGUG<br>UUCAGCGUGGGCGACACCUUCUCCCUGGCCAUGCAUCUGCAGUA<br>CAAGAUCCACGAGGCCCCUUUCGACCUGCUGCUGGAAUGGCUGU<br>ACGUGCCCAUCGACCCUACCUGCCAGCCCAUGCGGCUGUACUCC<br>ACCUGUCUGUACCACCCCAACGCCCCUCAGUGCCUGAGCCACAU<br>GAAUAGCGGCUGCACCUUCACCAGCCCUCACCUGGCUCAGAGGG<br>UGGCCAGCACCGUGUACCAGAAUUGCGAGCACGCCGACAACUAC<br>ACCGCCUACUGCCUGGGCAUCAGCCACAUGGAACCCAGCUUCGG<br>CCUGAUCCUGCACGAUGGCGGCACCACCCUGAAGUUCGUGGACA<br>CCCCUGAGUCCCUGAGCGGCCUGUACGUGUUCGUGGUGUACUUC<br>AACGGCCACGUGGAAGCCGUGGCCUACACCGUGGUGUCCACCGU<br>GGACCACUUCGUGAACGCCAUCGAGGAACGGGGCUUCCCUCCAA<br>CUGCUGGACAGCCUCCUGCCACCACCAAGCCCAAAGAAAUCACC<br>CCUGUGAACCCCGGCACCAGCCCACUGCUGCGCUAUGCUGCUUG<br>GACAGGCGGACUGGCUGCUGUGGUGCUGCUGUGCCUCGUGAUUU<br>UCCUGAUCUGCACCGCCAAGCGGAUGAGAGUGAAGGCCGCCAGA<br>GUGGACAAGUGAUAAUAGGCUGGAGCCUCGGUGGCCAUGCUUCU<br>UGCCCCUUGGGCCUCCCCCCAGCCCCUCCUCCCCUUCCUGCACCC<br>GUACCCCCGUGGUCUUUGAAUAAAGUCUGAGUGGGCGGCAAAAA<br>AAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAUCUAG | 101 |
| VZV-GE-<br>Truncated-<br>delete_from_<br>574_-_<br>Y569A<br>Variant 2 | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAACAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAAAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA | 102 |

TABLE 2-continued

| | | |
|---|---|---|
| | GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAAAAAAAAAAAAAAAUCUAG | |
| VZV-GE-Truncated-delete_from_574_-_Y569A Variant 3 | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAACAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCACCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAAAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAAAAAAAAAAAAAAAUCUAG | 103 |
| VZV-GE-Truncated-delete_from_574_-_Y569A Variant 4 | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAGGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAGAUUGUAAAUGUGGACCAACGUCAAUACGGUGACGUGU<br>UUAAAGGAGAUCUUAAUCCAAAGCCCCAAGGCCAAAGACUCAUU<br>GAGGUGUCAGUGGAAGAGAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAGCAUACAACAUGCUUUCAAGACGUGG<br>UGGUGGAUGUGGAUUGCGCGGAGAAUACUAAAGAGGAUCAGUU<br>GGCCGAAAUCAGUUACCGUUUUCAAGGUAAGAAGGAAGCGGACC | 104 |

TABLE 2-continued

| | | |
|---|---|---|
| | AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAGAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAUCUAG | |
| VZV-GE-<br>Truncated-<br>delete_from_<br>574_-_<br>Y569A<br>Variant 5 | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAGGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAGAUUGUAAAUGUGGACCAACGUCAAUACGGUGACGUGU<br>UUAAAGGAGAUCUUAAUCCAAAGCCCCAAGGCCAAAGACUCAUU<br>GAGGUGUCAGUGGAAGAGAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAGCAUACAACAUGCUUUCAAGACGUGG<br>UGGUGGAUGUGGAUUGCGCGGAGAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCACCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAGAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAUCUAG | 105 |
| VZV-GE-<br>Truncated-<br>delete_from_<br>574_-_<br>Y569A | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU | 106 |

TABLE 2-continued

| | | |
|---|---|---|
| Variant 6 | UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAGCAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAGAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAAAAAAAAAAAAAAUCUAG | |
| VZV-GE-Truncated-delete_from_574_-_Y569A Variant 6 (version 2) | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAGCAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCCCCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAGAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA | 136 |

TABLE 2-continued

| | | |
|---|---|---|
| | CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAUCUAG | |
| VZV-GE-<br>Truncated-<br>delete_from_<br>574_-_<br>Y569A<br>Variant 7 | G*GGGAAAUAAGAGAGAAAAGAAGAGUAAGAAGAAAUAUAAGA<br>GCCACCAUGGGGACAGUUAAUAAACCUGUGGUGGGGGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAAGCGUACGAUCAUAACUCACCUUAUAUAUGGCCACGU<br>AAUGAUUAUGAUGGAUUUUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAAAUUGUAAAUGUGGACCAACGUCAAUACGGUGACGUGU<br>UUAAAGGAGAUCUUAAUCCAAAACCCCAAGGCCAAAGACUCAUU<br>GAGGUGUCAGUGGAAGAAAAUCACCCGUUUACUUUACGCGCACC<br>GAUUCAGCGGAUUUAUGGAGUCCGGUACACCGAGACUUGGAGCU<br>UUUUGCCGUCAUUAACCUGUACGGGAGACGCAGCGCCCGCCAUC<br>CAGCAUAUAUGUUUAAAGCAUACAACAUGCUUUCAAGACGUGG<br>UGGUGGAUGUGGAUUGCGCGGAAAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCACCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUUUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAGAAUUGUGAACAUG<br>CAGAUAACUACACCGCAUAUUGUCUGGGAAUAUCUCAUAUGGAG<br>CCUAGCUUUGGUCUAAUCUUACACGACGGGGGCACCACGUUAAA<br>GUUUGUAGAUACACCCGAGAGUUUGUCGGGAUUAUACGUUUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACCCCCGUAAACCCCGGAACGUCACCACUUCUA<br>CGAUAUGCCGCAUGGACCGGAGGGCUUGCAGCAGUAGUACUUUU<br>AUGUCUCGUAAUAUUUUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAUCUAG | 107 |
| VZV-GE-<br>Truncated-<br>delete_from_<br>574_-_<br>Y569A<br>Variant 7 | AUGGGGACAGUUAAUAAACCUGUGGUGGGGGUAUUGAUGGGGU<br>UCGGAAUUAUCACGGGAACGUUGCGUAUAACGAAUCCGGUCAGA<br>GCAUCCGUCUUGCGAUACGAUGAUUUUCACAUCGAUGAAGACAA<br>ACUGGAUACAAACUCCGUAUAUGAGCCUUACUACCAUUCAGAUC<br>AUGCGGAGUCUUCAUGGGUAAAUCGGGGAGAGUCUUCGCGAAA<br>AGCGUACGAUCAUAACUCACCUUAUAUAUGGCCACGUAAUGAUU<br>AUGAUGGAUUUUUAGAGAACGCACACGAACACCAUGGGGGUGUA<br>UAAUCAGGGCCGUGGUAUCGAUAGCGGGGAACGGUUAAUGCAA<br>CCCACACAAAUGUCUGCACAGGAGGAUCUUGGGGACGAUACGGG<br>CAUCCACGUUAUCCCUACGUUAAACGGCGAUGACAGACAUAAAA<br>UUGUAAAUGUGGACCAACGUCAAUACGGUGACGUGUUUAAAGG<br>AGAUCUUAAUCCAAAACCCCAAGGCCAAAGACUCAUUGAGGUGU<br>CAGUGGAAGAAAAUCACCCGUUUACUUUACGCGCACCGAUUCAG<br>CGGAUUUAUGGAGUCCGGUACACCGAGACUUGGAGCUUUUUGCC<br>GUCAUUAACCUGUACGGGAGACGCAGCGCCCGCCAUCCAGCAUA<br>UAUGUUUAAAGCAUACAACAUGCUUUCAAGACGUGGUGGUGGA<br>UGUGGAUUGCGCGGAAAAUACUAAAGAGGAUCAGUUGGCCGAA<br>AUCAGUUACCGUUUUCAAGGUAAGAAGGAAGCGGACCAACCGUG<br>GAUUGUUGUAAACACGAGCACACUGUUUGAUGAACUCGAAUUA<br>GACCCACCCGAGAUUGAACCGGGUGUCUUGAAAGUACUUCGGAC<br>AGAGAAACAAUACUUGGGUGUGUACAUUUGGAACAUGCGCGGC<br>UCCGAUGGUACGUCUACCUACGCCACGUUUUUGGUCACCUGGAA<br>AGGGGAUGAGAAGACAAGAAACCCUACGCCCGCAGUAACUCCUC<br>AACCAAGAGGGGCUGAGUUUCAUAUGUGGAAUUACCACUCGCAU | 134 |

TABLE 2-continued

| | | |
|---|---|---|
| | GUAUUUUCAGUUGGUGAUACGUUUAGCUUGGCAAUGCAUCUUC<br>AGUAUAAGAUACAUGAAGCGCCAUUUGAUUUGCUGUUAGAGUG<br>GUUGUAUGUCCCCAUCGAUCCUACAUGUCAACCAAUGCGGUUAU<br>AUUCUACGUGUUUGUAUCAUCCCAACGCACCCCAAUGCCUCUCU<br>CAUAUGAAUUCCGGUUGUACAUUUACCUCGCCACAUUUAGCCCA<br>GCGUGUUGCAAGCACAGUGUAUCAGAAUUGUGAACAUGCAGAU<br>AACUACACCGCAUAUUGUCUGGGAAUAUCUCAUAUGGAGCCUAG<br>CUUUGGUCUAAUCUUACACGACGGGGGCACCACGUUAAAGUUUG<br>UAGAUACACCCGAGAGUUUGUCGGGAUUAUACGUUUUUGUGGU<br>GUAUUUUAACGGGCAUGUUGAAGCCGUAGCAUACACUGUUGUA<br>UCCACAGUAGAUCAUUUUGUAAACGCAAUUGAAGAGCGUGGAU<br>UUCCGCCAACGGCCGGUCAGCCACCGGCGACUACUAAACCCAAG<br>GAAAUUACCCCCGUAAACCCCGGAACGUCACCACUUCUACGAUA<br>UGCCGCAUGGACCGGAGGGCUUGCAGCAGUAGUACUUUUAUGUC<br>UCGUAAUAUUUUUAAUCUGUACGGCUAAACGAAUGAGGGUUAA<br>AGCCGCCAGGGUAGACAAGUGAUAAUAGGCUGGAGCCUCGGUGG<br>CCAUGCUUCUUGCCCCUUGGGCCUCCCCCCAGCCCCUCCUCCCCU<br>UCCUGCACCCGUACCCCCGUGGUCUUUGAAUAAAGUCUGAGUGG<br>GCGGC | |
| VZV-GE-<br>Truncated-<br>delete_from_<br>574_-_<br>Y569A<br>Variant 8 | G*AGAAGAAAUAUAAGAGCCACCAUGGGGACAGUUAAUAAACCU<br>GUGGUGGGCGUAUUGAUGGGGUUCGGAAUUAUCACGGGAACGU<br>UGCGUAUAACGAAUCCGGUCAGAGCAUCCGUCUUGCGAUACGAU<br>GAUUUUCACAUCGAUGAAGACAAACUGGAUACAAACUCCGUAUA<br>UGAGCCUUACUACCAUUCAGAUCAUGCGGAGUCUUCAUGGGUAA<br>AUCGGGGAGAGUCUUCGCGAAAGGCGUACGAUCAUAACUCACCU<br>UAUAUAUGGCCACGUAAUGAUUAUGAUGGAUUCUUAGAGAACG<br>CACACGAACACCAUGGGGUGUAUAAUCAGGGCCGUGGUAUCGAU<br>AGCGGGGAACGGUUAAUGCAACCCACACAAAUGUCUGCACAGGA<br>GGAUCUUGGGGACGAUACGGGCAUCCACGUUAUCCCUACGUUAA<br>ACGGCGAUGACAGACAUAAGAUUGUAAAUGUGGACCAACGUCA<br>AUACGGUGACGUGUUUAAAGGAGAUCUUAAUCCAAAGCCCCAAG<br>GCCAAAGACUCAUUGAGGUGUCAGUGGAAGAGAAUCACCCGUUU<br>ACUUUACGCGCACCGAUUCAGCGGAUUUAUGGAGUCCGGUACAC<br>CGAGACUUGGAGCUUCUUGCCGUCAUUAACCUGUACGGGAGACG<br>CAGCGCCCGCCAUCCAGCAUAUAUGUUUAAAGCAUACAACAUGC<br>UUUCAAGACGUGGUGGUGGAUGUGGAUUGCGCGGAGAAUACUA<br>AAGAGGAUCAGUUGGCCGAAAUCAGUUACCGUUUUCAAGGUAA<br>GAAGGAAGCGGACCAACCGUGGAUUGUUGUAAACACGAGCACAC<br>UGUUUGAUGAACUCGAAUUAGACCCACCCGAGAUUGAACCGGGU<br>GUCUUGAAAGUACUUCGGACAGAGAAACAAUACUUGGGUGUGU<br>ACAUUUGGAACAUGCGCGGCUCCGAUGGUACGUCUACCUACGCC<br>ACGUUCUUGGUCACCUGGAAAGGGGAUGAGAAGACAAGAAACCC<br>UACGCCCGCAGUAACUCCUCAACCAAGAGGGGCUGAGUUUCAUA<br>UGUGGAAUUACCACUCGCAUGUAUUUUCAGUUGGUGAUACGUU<br>UAGCUUGGCAAUGCAUCUUCAGUAUAAGAUACAUGAAGCGCCAU<br>UUGAUUUGCUGUUAGAGUGGUUGUAUGUCCCCAUCGAUCCUACA<br>UGUCAACCAAUGCGGUUAUAUUCUACGUGUUUGUAUCAUCCCAA<br>CGCACCCCAAUGCCUCUCUCAUAUGAAUUCCGGUUGUACAUUUA<br>CCUCGCCACAUUUAGCCCAGCGUGUUGCAAGCACAGUGUAUCAG<br>AAUUGUGAACAUGCAGAUAACUACACCGCAUAUUGUCUGGGAA<br>UAUCUCAUAUGGAGCCUAGCUUUGGUCUAAUCUUACACGACGGA<br>GGCACCACGUUAAAGUUUGUAGAUACACCCGAGAGUUUGUCGGG<br>AUUAUACGUCUUUGUGGUGUAUUUUAACGGGCAUGUUGAAGCC<br>GUAGCAUACACUGUUGUAUCCACAGUAGAUCAUUUUGUAAACGC<br>AAUUGAAGAGCGUGGAUUUCCGCCAACGGCCGGUCAGCCACCGG<br>CGACUACUAAACCCAAGGAAAUUACGCCCGUAAACCCCGGAACG<br>UCACCACUUCUACGAUAUGCCGCAUGGACCGGAGGGCUUGCAGC<br>AGUAGUACUUUUAUGUCUCGUAAUAUUCUUAAUCUGUACGGCU<br>AAACGAAUGAGGGUUAAAGCCGCCAGGGUAGACAAGUGAUAAU<br>AGGCUGGAGCCUCGGUGGCCAUGCUUCUUGCCCCUUGGGCCUCC<br>CCCCAGCCCCUCCUCCCCUUCCUGCACCCGUACCCCCGUGGUCUU<br>UGAAUAAAGUCUGAGUGGGCGGCAAAAAAAAAAAAAAAAAAAA<br>AAAAAAAAAAAAAAAAAAAAAAAAAAAAAAAAAAAAAAAAAAA<br>AAAAAAAAAAAAAAAAAAAAAAAAAAAAAAAAAAAAAUCUAG | 108 |
| VZV-GE-<br>Truncated-<br>delete_from_<br>574_-_<br>Y569A<br>Variant 8<br>(5'UTR<br>includes<br>promoter<br>region) | G*GGGAAAUAAGAGAGAAAAGAAGAGUAAGAAGAAAUAUAAGA<br>GCCACCAUGGGGACAGUUAAUAAACCUGUGGUGGGCGUAUUGA<br>UGGGGUUCGGAAUUAUCACGGGAACGUUGCGUAUAACGAAUCC<br>GGUCAGAGCAUCCGUCUUGCGAUACGAUGAUUUUCACAUCGAUG<br>AAGACAAACUGGAUACAAACUCCGUAUAUGAGCCUUACUACCAU<br>UCAGAUCAUGCGGAGUCUUCAUGGGUAAAUCGGGGAGAGUCUU<br>CGCGAAAGGCGUACGAUCAUAACUCACCUUAUAUAUGGCCACGU<br>AAUGAUUAUGAUGGAUUCUUAGAGAACGCACACGAACACCAUG<br>GGGUGUAUAAUCAGGGCCGUGGUAUCGAUAGCGGGGAACGGUU<br>AAUGCAACCCACACAAAUGUCUGCACAGGAGGAUCUUGGGGACG<br>AUACGGGCAUCCACGUUAUCCCUACGUUAAACGGCGAUGACAGA<br>CAUAAGAUUGUAAAUGUGGACCAACGUCAAUACGGUGACGUGU<br>UUAAAGGAGAUCUUAAUCCAAAGCCCCAAGGCCAAAGACUCAUU<br>GAGGUGUCAGUGGAAGAGAAUCACCCGUUUACUUUACGCGCACC | 141 |

TABLE 2-continued

| | | |
|---|---|---|
| | GAUUCAGCGGAUUUAUGGAGUCCGGUACACCGAGACUUGGAGCU<br>UCUUGCCGUCAUUAACCUGUACGGGAGACGCAGCGCCCGCCAUC<br>CAGCAUAUAUGUUUAAAGCAUACAACAUGCUUUCAAGACGUGG<br>UGGUGGAUGUGGAUUGCGCGGAGAAUACUAAAGAGGAUCAGUU<br>GGCCGAAAUCAGUUACCGUUUUCAAGGUAAGAAGGAAGCGGACC<br>AACCGUGGAUUGUUGUAAACACGAGCACACUGUUUGAUGAACUC<br>GAAUUAGACCCACCCGAGAUUGAACCGGGUGUCUUGAAAGUACU<br>UCGGACAGAGAAACAAUACUUGGGUGUGUACAUUUGGAACAUG<br>CGCGGCUCCGAUGGUACGUCUACCUACGCCACGUUCUUGGUCAC<br>CUGGAAAGGGGAUGAGAAGACAAGAAACCCUACGCCCGCAGUAA<br>CUCCUCAACCAAGAGGGGCUGAGUUUCAUAUGUGGAAUUACCAC<br>UCGCAUGUAUUUUCAGUUGGUGAUACGUUUAGCUUGGCAAUGC<br>AUCUUCAGUAUAAGAUACAUGAAGCGCCAUUUGAUUUGCUGUU<br>AGAGUGGUUGUAUGUCCCCAUCGAUCCUACAUGUCAACCAAUGC<br>GGUUAUAUUCUACGUGUUUGUAUCAUCCCAACGCACCCCAAUGC<br>CUCUCUCAUAUGAAUUCCGGUUGUACAUUUACCUCGCCACAUUU<br>AGCCCAGCGUGUUGCAAGCACAGUGUAUCAGAAUUGUGAACAUG<br>CAGAUAACUACACCGCAUAUUGUCUGGGAAUAUCUCAUAUGGAG<br>CCUAGCUUUGGUCUAAUCUUACACGACGGAGGCACCACGUUAAA<br>GUUUGUAGAUACACCCGAGAGUUUGUCGGGAUUAUACGUCUUU<br>GUGGUGUAUUUUAACGGGCAUGUUGAAGCCGUAGCAUACACUG<br>UUGUAUCCACAGUAGAUCAUUUUGUAAACGCAAUUGAAGAGCG<br>UGGAUUUCCGCCAACGGCCGGUCAGCCACCGGCGACUACUAAAC<br>CCAAGGAAAUUACGCCCGUAAACCCCGGAACGUCACCACUUCUA<br>CGAUAUGCCGCAUGGACCGGAGGGCUUGCAGCAGUAGUACUUUU<br>AUGUCUCGUAAUAUUCUUAAUCUGUACGGCUAAACGAAUGAGG<br>GUUAAAGCCGCCAGGGUAGACAAGUGAUAAUAGGCUGGAGCCUC<br>GGUGGCCAUGCUUCUUGCCCCUUGGGCCUCCCCCCAGCCCCUCCU<br>CCCCUUCCUGCACCCGUACCCCCGUGGUCUUUGAAUAAAGUCUG<br>AGUGGGCGGCAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAAAAAAAAAAAAAAUCUAG | |
| VZV-GE-<br>Truncated-<br>delete_from_<br>574_-_<br>Y569A<br>Variant 9 | G*GGGAAAUAAGAGAGAAAAGAAGAGUAAGAAGAAAUAUAAGA<br>GCCACCAUGGGCACCGUGAACAAGCCUGUUGUGGGCGUGCUGAU<br>GGGCUUCGGCAUCAUCACAGGCACCCUGCGGAUCACCAAUCCUG<br>UGCGGGCUAGCGUGCUGAGAUACGACGACUUCCACAUCGACGAG<br>GACAAGCUGGACACCAACAGCGUGUACGAGCCCUACUACCACAG<br>CGAUCACGCCGAGUCUAGCUGGGUCAACAGAGGCGAGAGCAGCA<br>GAAAGGCCUACGACCACAACAGCCCUUACAUCUGGCCCAGAAAC<br>GACUACGACGGCUUCCUCGAGAAUGCCCACGAACACCACGGCGU<br>GUACAAUCAAGGCAGAGGCAUCGACAGCGGCGAGAGACUGAUGC<br>AGCCUACACAGAUGAGCGCCCAAGAGGACCUGGGAGAUGAUACC<br>GGCAUCCACGUGAUCCCUACACUGAACGGCGACGACCGGCACAA<br>GAUCGUGAACGUGGACCAGAGACAGUACGGCGACGUGUUCAAGG<br>GCGACCUGAAUCCUAAGCCUCAGGGCCAGCGCCUGAUCGAGGUU<br>UCCGUGGAAGAGAAUCACCCUUUCACACUGCGGGCUCCCAUCCA<br>GAGAAUCUACGGCGUGCGCUAUACCGAGACAUGGUCCUUUCUGC<br>CCAGCCUGACAUGUACCGGCGACGCCGCUCCUGCCAUCCAGCAC<br>AUUUGUCUGAAGCACACCACCUGUUUCCAGGACGUGGUGGUGGA<br>UGUGGACUGCGCCGAGAACACCAAAGAGGAUCAGCUGGCCGAGA<br>UCAGCUACCGGUUCCAGGGAAAGAAAGAGGCCGACCAGCCUUGG<br>AUCGUGGUCAACACCAGCACACUGUUCGACGAGCUGGAACUGGA<br>CCCUCCUGAGAUUGAACCCGGCGUCCUGAAGGUGCUGAGAACCG<br>AGAAGCAGUACCUGGGAGUGUACAUCUGGAACAUGAGAGGCAG<br>CGACGGCACCUCUACCUACGCCACCUUUCUGGUCACAUGGAAGG<br>GCGACGAGAAGACCAGAAAUCCCACACCAGCCGUGACACCUCAG<br>CCUAGAGGCGCCGAAUUUCACAUGUGGAACUACCACUCUCACGU<br>GUUCAGCGUGGGCGAUACCUUCAGCCUGGCCAUGCAUCUGCAGU<br>ACAAGAUCCACGAGGCUCCCUUCGACCUGCUGCUGGAAUGGCUG<br>UACGUGCCCAUCGAUCCUACCUGCCAGCCUAUGCGGCUGUACUC<br>CACCUGUCUGUAUCACCCUAACGCUCCUCAGUGCCUGAGCCACA<br>UGAAUAGCGGCUGCACCUUCACAAGCCCUCACCUGGCUCAGCGA<br>GUGGCCAGCACAGUGUACCAGAAUUGCGAGCACGCCGACAAUUA<br>CACCGCCUACUGUCUGGGCAUCAGCCACAUGGAACCUAGCUUCG<br>GCCUGAUCCUGCACGAUGGCGGCACCACACUGAAGUUCGUGGAC<br>ACACCUGAGAGCCUGAGCGGCCUGUAUGUGUUUGUGGUGUACUU<br>CAACGGCCACGUGGAAGCCGUGGCCUACACCGUGGUGUCUACCG<br>UGGACCACUUCGUGAACGCCAUCGAGGAAAGAGGCUUCCCUCCA<br>ACUGCUGGACAGCCUCCUGCCACCACCAAGCCUAAAGAAAUCAC<br>ACCCGUGAAUCCCGGCACUAGCCCUCUGCUUAGAUACGCCGCUU<br>GGACAGGCGGACUGGCUGCUGUUGUUCUGCUGUGCCUGGUCAUC<br>UUCCUGAUCUGCACCGCCAAGCGGAUGAGAGUGAAAGCCGCCAG<br>AGUGGACAAGUGAUAAUAGGCUGGAGCCUCGGUGGCCAUGCUUC<br>UUGCCCCUUGGGCCUCCCCCCAGCCCCUCCUCCCCUUCCUGCACC<br>CGUACCCCCGUGGUCUUUGAAUAAAGUCUGAGUGGGCGGCAAAA | 137 |

TABLE 2-continued

| |
|---|
| AAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAUCUAG |

G* represents a 5' terminal cap, e.g., 7mG(5')ppp(5')NlmpNp
All mRNAs contains a 5'-UTR, a 3'UTR, and a polyA tail.
5'-UTR: GGGAAAUAAGAGAGAAAAGAAGAGUAAGAAGAAAUAUAAGAGCCACC (SEQ ID NO: 138)
3'-UTR: UGAUAAUAGGCUGGAGCCUCGGUGGCCAUGCUUCUUGCCCCUUGGGCCUCCCCCCAGCCCCUCCUCCCCUU CCUGCACCCGUACCCCCGUGGUCUUUGAAUAAAGUCUGAGUGGGCGGC (SEQ ID NO: 139)
polyA tail: AAAAAAAAAAAAAAAAAAAAAAAAAAAAAAAAAAAAAAAAAAAAAAAAAAAAAAAAAAAAAAAAAAA AAAAAAAAAAAAAAAAAAAAAAAAAAAAAAAAAAUCUAG (SEQ ID NO: 140)

It should also be understood that the 5' and/or 3' UTR for each construct may be omitted, modified or substituted for a different UTR sequences in any one of the vaccines as provided herein.

Example 14: Variant gE Antigen Distribution in Vero and Mewo Cells

The expression and trafficking of VZV gE antigens having different C terminal variants was investigated in Vero cells and Mewo cells.

Vero cells are lineages of cells used in cell cultures. The 'Vero' lineage was isolated from kidney epithelial cells extracted from an African green monkey. MeWo cells are human malignant melanoma cells that are susceptible to VZV infection. Vero cells or Mewo cells were transfected with the constructs indicated below in Table 3. The transfected cells were stained with antibodies for gE and for golgi markers GM 130 and golgin. Confocal microscopy was used to visualize the stained cells. The results for the constructs are described in Table 3 ("Cellular localization" column). FIG. 9 provides an exemplary experiment, which shows the results of the following transfected constructs: (1) VZV gE mRNA encoding a VZV gE polypeptide having a 62 amino acid deletion at the C-terminus (encoded by SEQ ID NO: 3); (2) full-length VZV gE mRNA encoding a VZV gE polypeptide having the AEAADA sequence (SEQ ID NO: 58) (encoded by SEQ ID NO: 7); or (3) PBS (as negative control). Using an anti-gE antibody, FIG. 9 shows that the truncated VZV gE polypeptide (having the 62 amino acid C-terminal deletion) localizes to a perinuclear location and organelles. The full-length VZV gE polypeptide having AEAADA sequence (SEQ ID NO: 58) was localized to the golgi and a perinuclear location. Importantly, several of the constructs, e.g., gE-truncated-delete_from_574_Y569A, gE full length with AEAADA (SEQ ID NO: 58), gE full length with AEAADA (SEQ ID NO: 58) and Y582C mutation, gE-truncated-delete_from_574, and gE-truncated-delete_from_574 with Y569A mutation each encoded polypeptides that localized to the cell membrane, indicating that these polypeptides may have enhanced antigenicity.

TABLE 3

Summary of Results for Cellular Trafficking of Variant VZV gE Polypeptides

| Construct | Experimental conditions | Expression | Cellular localization |
|---|---|---|---|
| Full length gE | Vero cells- 500 ng/well, transfected 24 h transfection (C8) Construct = Full length GE | + | shows Golgi localization |
| GE-full with AEAADA (SEQ ID NO: 58) | Vero cells- 500 ng/well, transfected 24 h transfection (C1)- Construct = VZV-GE-full with AEAADA (SEQ ID NO: 58) | +++ | shows Golgi localization and diffuse perinuclear |
| GE-full with AEAADA (SEQ ID NO: 58) and Y582C | Vero cells- 500 ng/well, transfected 24 h transfection (C6) Construct = VZV-GE full_with_AEAADA (SEQ ID NO: 58)_and_Y582G | low | shows organelles and cytoplasmic localization |
| GE-delete-562 | Vero cells- 500 ng/well, transfected 24 h transfection (C2)-Construct = C2 VZV-GE-delete-562 | + | shows perinuclear and organelles |
| GE-delete-562-replaced SP-with IgKappa | Vero cells- 500 ng/well, transfected 24 h transfection (C5) VZV-GE-delete-562-replacedSignal Peptide-with IgKappa | +++ | shows golgi localization and cytoplasmic |
| GE-truncated-delete_from_574 | Vero cells- 500 ng/well, transfected 24 h transfection (C4) - Construct = VZV-GE-truncated-delete_from_574 | ++ | shows Golgi and cytoplasmic localization |
| GE-truncated-delete_from_574_Y569A | Vero cells- 500 ng/well, transfected 24 h transfection (C3)- Construct = VZV-GE-truncated-delete_from_574_Y569A | +++ | shows Golgi and cell membrane localization |
| Full length gE | MeWo cells- 500 ng/well, transfected 24 h transfection (C8) Construct = Full length GE | +++ | shows Golgi localization |
| GE-full with AEAADA (SEQ ID NO: 58) | MeWo cells- 500 ng/well, transfected 24 h transfection (C1)- Construct = VZV-GE-full with AEAADA (SEQ ID NO: 58) | +++ | shows Golgi and Membrane localization |
| GE-full with AEAADA (SEQ ID NO: 58) and Y582C | MeWo cells- 500 ng/well, transfected 24 h transfection (C6) Construct = SE-VZV-GE full_with_AEADA (SEQ ID NO: 58)_and_Y582G | ++ | shows golgi and cell membrane localization |
| GE-delete-562 | MeWo cells- 500 ng/well, transfected 24 h transfection (C2)- Construct = C2 VZV-GE-delete-562 | +++ | shows perinuclear and cytoplasmic localization |

TABLE 3-continued

| Summary of Results for Cellular Trafficking of Variant VZV gE Polypeptides | | | |
|---|---|---|---|
| Construct | Experimental conditions | Expression | Cellular localization |
| GE-delete-562-replaced SP-with Ig Kappa | MeWo cells- 500 ng/well, transfected 24 h transfection (C5) VZV-GE-delete-562-replacedSignal Peptide with IgKappa | +++ | shows golgi localization and cytoplasmic |
| GE-truncated-delete_from_574 | MeWo cells- 500 ng/well, transfected 24 h transfection (C4) - Construct = -VZV-GE-truncated-delete_from_574 | +++ | shows Golgi and cell membrane localization |
| GE-truncated-delete_from_574_Y569A | MeWo cells- 500 ng/well, transfected 24 h transfection (C3)- Construct = VZV-GE-truncated-delete_from_574_Y569A | +++ | shows Golgi and cell membrane localization |

Example 15: Immunization of BALB/C Mice with MC3 Formulated mRNA Encoded VZV gE Antigens An immunization study was conducted as an initial evaluation of the effect of MC3-formulated mRNAs encoding VZV antigens as vaccine candidates to achieve immunization in BALB/C mice post intramuscular or intradermal administration.

The candidate vaccines were as follows:

(1) MC3 formulated VZVgE-hIg kappa mRNA having 5' cap: m7G(5')ppp(5')G-2'-O-methyl, N1-methylpseudouridine chemical modification, and the additional hlg Kappa sequence.

(2) MC3 formulated VZV gE mRNA having 5' cap: m7G(5')ppp(5')G-2'-O-methyl and N1-methylpseudouridine chemical modification.

(3) MC3 formulated VZVgE mRNA having 5' cap: m7G (5')ppp(5')G-2'-O-methyl and no chemical modification.

All of the VZV gE mRNAs were strain Oka.

BALB/C mice were given a single 10 μg dose or two 10 μg doses (at day 28) of MC3 formulated VZV gE mRNA (either vaccine (1), (2), or (3) described above) either intramuscularly or intradermally. G5 refers mRNA having N1-methylpseudouridine chemical modification. GO refers to unmodified mRNA. Cap 1 refers to 5' cap: m7G(5')ppp (5')G-2'-O-methyl. Each treatment group contained eight mice. The positive control was VARIVAX® vaccine and the negative control was PBS.

Figure 2:
FIG. 2 is a schematic of the constructs encoding VZV gE (strain Oka).

Blood samples were taken to determine the presence/level of serum protein and antibodies. Western blots were performed to detect VZV-gE protein expression at six hours and ELISAs were performed to detect mouse IgGs. Schematics of the constructs encoding VZV gE (strain Oka) are shown in FIG. 2. Schematics of the study's design and schedule of injection are shown in FIG. 3 and Table 3. Table 4 shows the various time points for collection of different samples. Blood was collected for serum protein and antibody determination, while VZV protein expression was surveyed 6 hours post-dosing on day 0 for groups 1-4, 13, and 14, and 6 hours post-dosing on day 28 for groups 2, 4, and 14. Antibody detection assays were performed on day −3, day 14, day 27, day 42, and day 56.

TABLE 4

| Injection Schedule | | | | | | | | | | |
|---|---|---|---|---|---|---|---|---|---|---|
| G# | Antigen | Route | N = | Dose (μg) | Dose Vol (μl) | $1^{st}$ dose | $2^{nd}$ dose | LNP | mRNA Conc. (mg/ml) | Volume + Overage |
| 1 | VZV-gE-oka-hIgkappa (G5; cap 1) (SEQ ID NO: 93) | IM | 8 | 10 | 50 | Day 0 | | MC3 | 0.2 | 1 × 600 μl |
| 2 | VZV-gE-oka-hIgkappa (G5; cap 1) | IM | 8 | 10 | 50 | Day 0 | Day 28 | MC3 | 0.2 | 2 × 600 μl |
| 3 | VZV-gE-oka-hIgkappa (G5; cap 1) | ID | 8 | 10 | 50 | Day 0 | | MC3 | 0.2 | 1 × 600 μl |
| 4 | VZV-gE-oka-hIgkappa (G5; cap 1) | ID | 8 | 10 | 50 | Day 0 | Day 28 | MC3 | 0.2 | 2 × 600 μl |
| 5 | VZV-gE-oka (G0; cap 1) (SEQ ID NO: 92) | IM | 8 | 10 | 50 | Day 0 | | MC3 | 0.2 | 1 × 600 μl |
| 6 | VZV-gE-oka (G0; cap1) | IM | 8 | 10 | 50 | Day 0 | Day 28 | MC3 | 0.2 | 2 × 600 μl |
| 7 | VZV-gE-oka (G0; cap1) | ID | 8 | 10 | 50 | Day 0 | | MC3 | 0.2 | 1 × 600 μl |
| 8 | VZV-gE-oka (G0; cap1) | ID | 8 | 10 | 50 | Day 0 | Day 28 | MC3 | 0.2 | 2 × 600 μl |
| 9 | VZV-gE-oka (G5; cap1) | IM | 8 | 10 | 50 | Day 0 | | MC3 | 0.2 | 1 × 600 μl |
| 10 | VZV-gE-oka (G5; cap 1) | IM | 8 | 10 | 50 | Day 0 | Day 28 | MC3 | 0.2 | 2 × 600 μl |
| 11 | VZV-gE-oka (G5; cap1) | ID | 8 | 10 | 50 | Day 0 | | MC3 | 0.2 | 1 × 600 μl |
| 12 | VZV-gE-oka (G5; cap1) | ID | 8 | 10 | 50 | Day 0 | Day 28 | MC3 | 0.2 | 2 × 600 μl |

TABLE 4-continued

| Injection Schedule | | | | | | | | | | |
|---|---|---|---|---|---|---|---|---|---|---|
| G# | Antigen | Route | N = | Dose (μg) | Dose Vol (μl) | $1^{st}$ dose | $2^{nd}$ dose | LNP | mRNA Conc. (mg/ml) | Volume + Overage |
| 13 | Negative control (PBS) | IM | 6 | / | 50 | Day 0 | | PBS | / | 1 × 600 μl |
| 14 | Negative control (PBS) | IM | 6 | / | 50 | Day 0 | Day 28 | PBS | / | 2 × 600 μl |
| 15 | Positive control (VARIVAX ®) | SC | 6 | 54 (pfu) | 50 | Day 0 | | | / | 1 × 1250 μl |
| 16 | Positive control (VARIVAX ®) | SC | 6 | 54 (pfu) | 50 | Day 0 | Day 28 | | / | |
| 17 | Positive control (VARIVAX ®) | SC | 4 | 675 (pfu) | 100 | Day 0 | | | / | 4 × 220 μl |
| 18 | Positive control (VARIVAX ®) | SC | 4 | 675 (pfu) | 100 | Day 0 | Day 28 | | / | |

TABLE 5

| Schedule of Sample Collection | | | | | | | | |
|---|---|---|---|---|---|---|---|---|
| G# | Antigen | Pre-bleed | Day0 + 6 h | Day 14 | Day27 | Day28 + 6 h | Day 42 | Day 56 |
| 1 | VZV-gE-oka-hIgkappa (G5; cap1) | √ | √ | √ | √ | | √ | √ |
| 2 | VZV-gE-oka-hIgkappa (G5; cap1) | √ | √ | √ | √ | √ | √ | √ |
| 3 | VZV-gE-oka-hIgkappa (G5; cap1) | √ | √ | √ | √ | | √ | √ |
| 4 | VZV-gE-oka-hIgkappa (G5; cap1) | √ | √ | √ | √ | √ | √ | √ |
| 5 | VZV-gE-oka (G0; cap1) | √ | | √ | √ | | √ | √ |
| 6 | VZV-gE-oka (G0; cap1) | √ | | √ | √ | | √ | √ |
| 7 | VZV-gE-oka (G0; cap1) | √ | | √ | √ | | √ | √ |
| 8 | VZV-gE-oka (G0; cap1) | √ | | √ | √ | | √ | √ |
| 9 | VZV-gE-oka (G5; cap1) | √ | | √ | √ | | √ | √ |
| 10 | VZV-gE-oka (G5; cap1) | √ | | √ | √ | | √ | √ |
| 11 | VZV-gE-oka (G5; cap1) | √ | | √ | √ | | √ | √ |
| 12 | VZV-gE-oka (G5; cap1) | √ | | √ | √ | | √ | √ |
| 13 | PBS | √ | √ | √ | √ | | √ | √ |
| 14 | PBS | √ | √ | √ | √ | √ | √ | √ |
| 15 | Positive control | √ | | √ | √ | | √ | √ |
| 16 | Positive control | √ | | √ | √ | | √ | √ |
| 17 | Positive control | √ | | √ | √ | | √ | √ |
| 18 | Positive control | √ | | √ | √ | | √ | √ |

Example 16: Immunogenicity Study—ELISA

The instant studies were designed to test the immunogenicity in BALB/C mice of candidate VZV vaccines comprising a mRNA polynucleotide encoding glycoprotein gE from VZV. Mice were immunized with various VZV mRNA vaccine formulations at set intervals, and sera were collected after each immunization. The immunization schedule is provided in Table 2 of Example 15. The sera collection schedule is set forth in Table 4 of Example 15.

Enzyme-Linked Immunosorbent Assay (ELISA)

Serum antibody titers against VZV glycoprotein E were determined by Enzyme-linked immunosorbent assay (ELISA) using standard methods. In one study, the amount of anti-VZV gE mouse IgG was measured in the pre-bleed and in serum collected at day 14 and day 42 post vaccination in mice vaccinated intramuscularly with two 10 μg doses of either: (1) VZV-gE-hlgkappa (SEQ ID NO: 93) having 5' cap: m7G(5')ppp(5')G-2'-O-methyl and N1-methylpseudouridine chemical modification (#1 in Tables 2 and 3); (2) VZV-gE (SEQ ID NO: 135) having 5' cap: m7G(5')ppp(5')G-2'-O-methyl, and no chemical modification (#6 in Tables 2 and 3) (SEQ ID NO: 135); (3) VZV-gE having 5' cap: m7G(5')ppp(5')G-2'-O-methyl and N1-methylpseudouridine chemical modification (#10 in Tables 2 and 3); (4) VARIVAX® vaccine (positive control); or (5) PBS (negative control).

Figure 5:
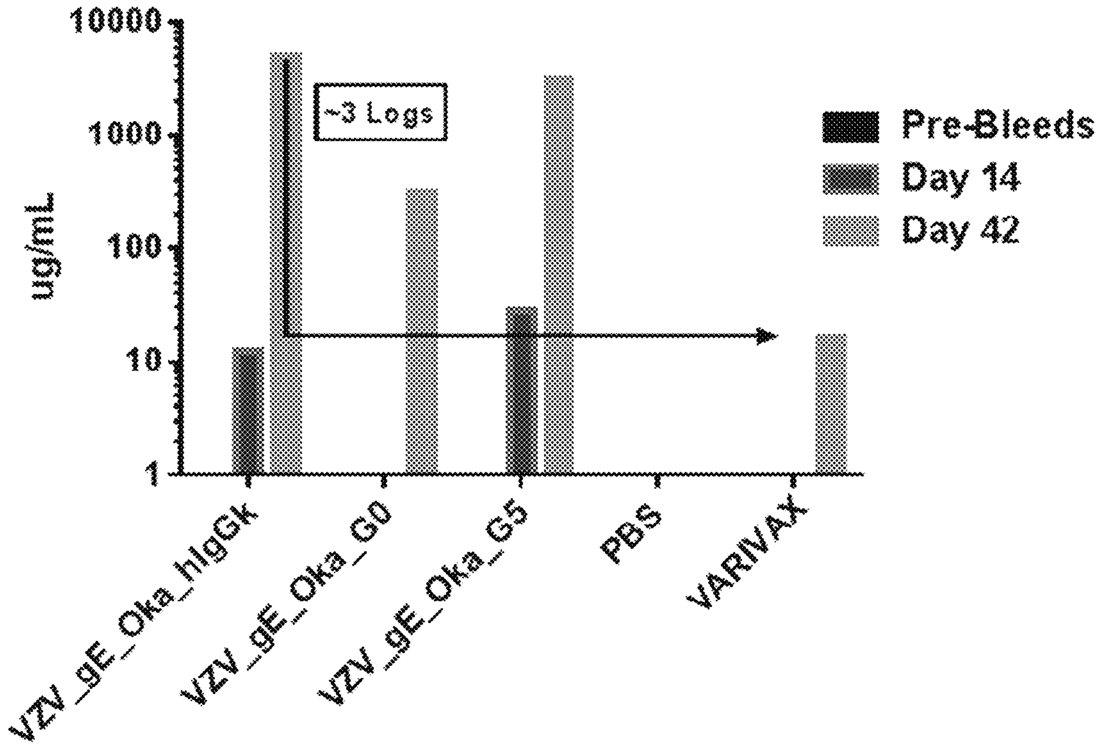
FIG. 5 is a graph showing the results of an ELISA assay that shows the levels of anti-VZV gE IgG in the serum of mice vaccinated with various VZV gE mRNAs in comparison with VARIVAX® vaccine.
Figure 6:
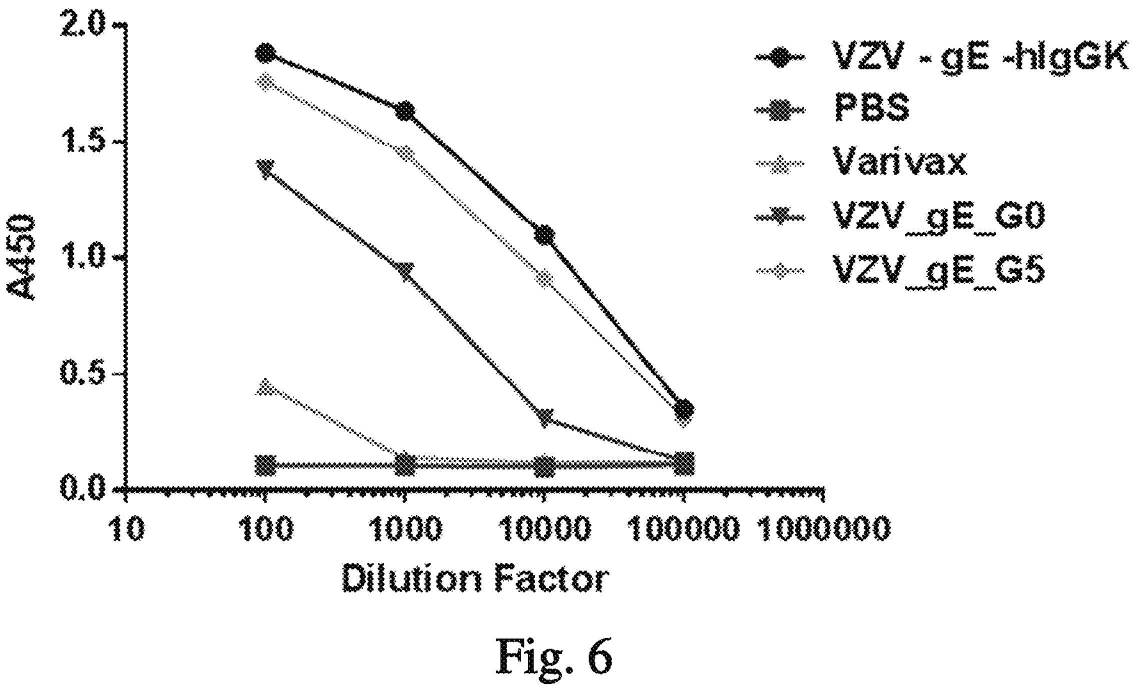
FIG. 6 is a graph showing the results of an ELISA assay indicating the levels of anti-VZV gE IgG in the serum of mice vaccinated with various VZV gE mRNAs in comparison with VARIVAX® vaccine.
Figure 7:
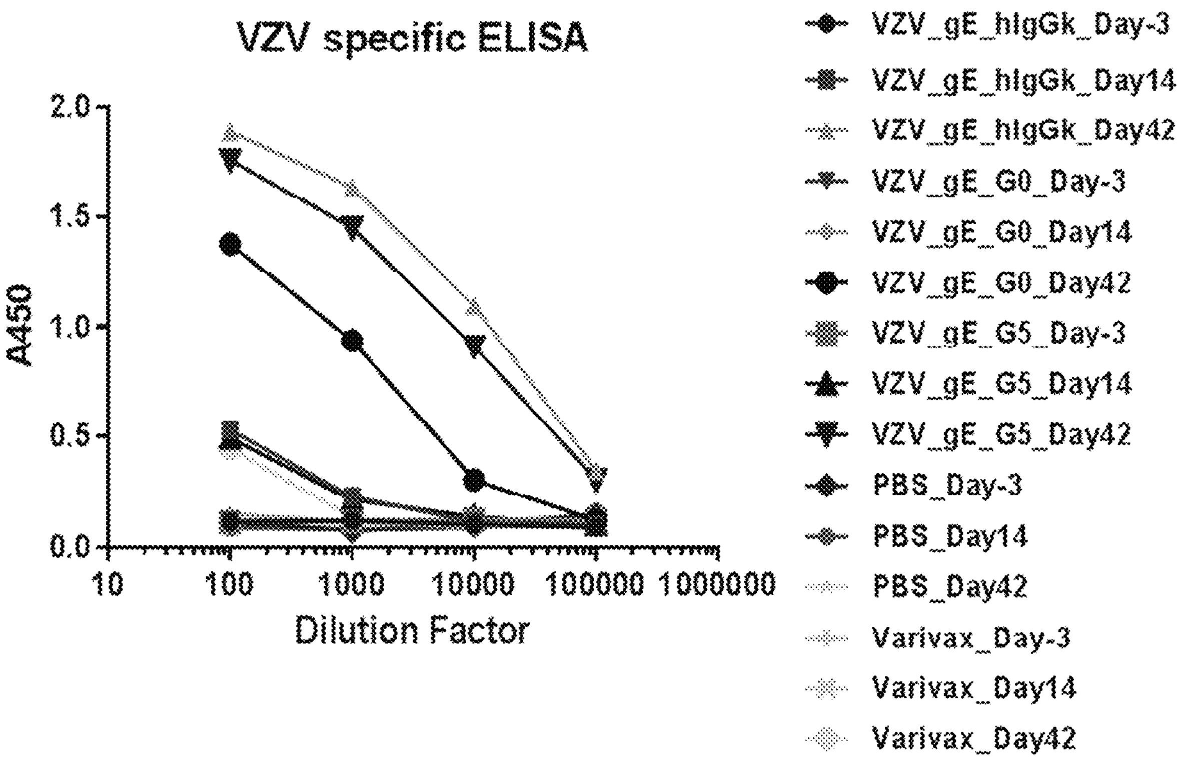
FIG. 7 is a graph showing the results of an ELISA assay indicating the levels of anti-VZV gE IgG in the serum of mice vaccinated with various VZV gE mRNAs in comparison with VARIVAX® vaccine.
Figure 10A:
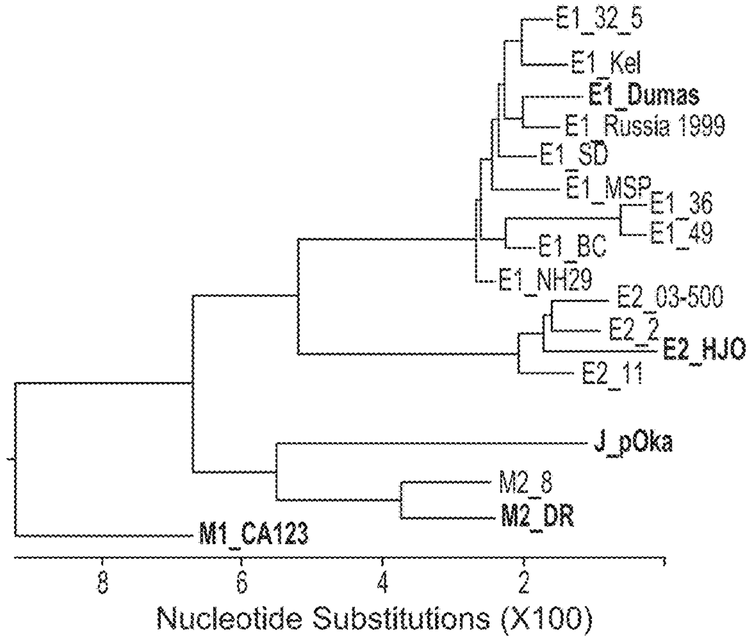
FIGS. 10A and 10B are schematics depicting various VZV wildtype genotypes.
Figure 10B:
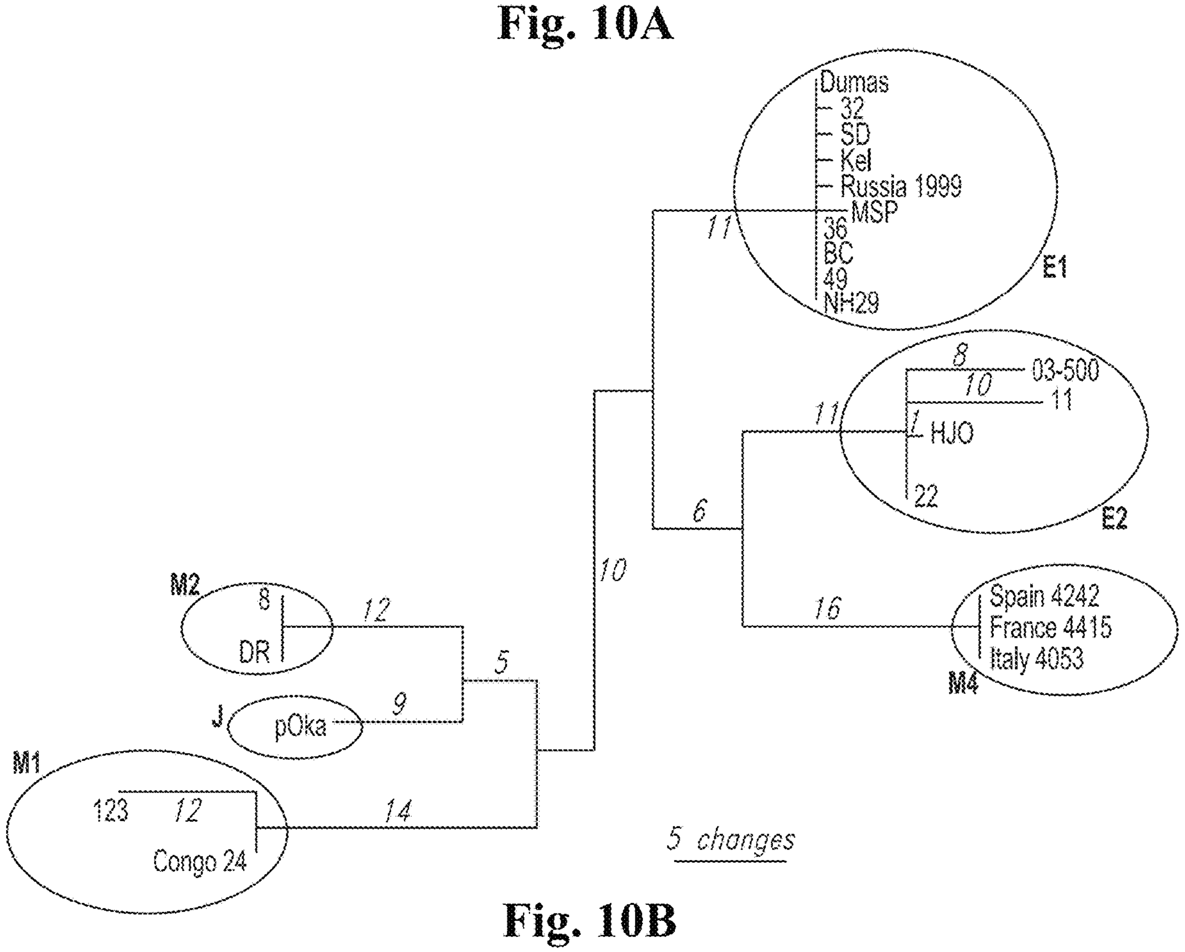

FIGS. 5-7 show that there was a very strong immune response with all mRNA encoded VZV-gE vaccines tested relative to the current VARIVAX® vaccine. FIG. 5 shows that at day 14, the titer for anti-VZV-gE IgG was about 10p g/mL in the serum of mice vaccinated with vaccine candidate (1) VZV-gE-hIgkappa having 5' cap: m7G(5')ppp(5')G-2'-O-methyl and N1-methylpseudouridine chemical modification and about 50 μg/mL in the serum of mice vaccinated with vaccine candidate (3) VZV-gE having 5' cap: m7G(5')ppp(5')G-2'-O-methyl and N1-methylpseudouridine chemical modification. The level of anti-VZV-gE IgG in the serum of mice vaccinated with VARIVAX® was not detectable at day 14. At day 42, the amount of anti-VZV-gE IgG present in the serum of mice vaccinated with vaccine candidate (1) VZV-gE-hlgkappa having 5' cap: m7G(5')ppp(5')G-2'-O-methyl and N1-methylpseudouridine chemical modification or vaccine candidate (3) VZV-gE having 5' cap: m7G(5')ppp(5')G-2'-O-methyl and N1-methylpseudouridine chemical modification was almost 1000-fold greater than the amount of anti-VZV-gE IgG present in the serum of mice vaccinated with VARIVAX®. The amount of anti-VZV gE IgG present in the serum of mice vaccinated with vaccine candidate (2) VZV-gE having 5' cap: m7G(5')ppp(5')G-2'-O-methyl and no chemical modification was almost 100-fold greater than the amount of anti-VZV-gE IgG present in the serum of mice vaccinated with VARIVAX®. This study indicates that each of the VZV gE mRNA vaccines tested is a more immunogenic vaccine that the current VARIVAX® VZV vaccine.

Example 17: Immunogenicity Study— ELISA

The instant studies were designed to test the immunogenicity in BALB/C mice of candidate VZV vaccines comprising a mRNA polynucleotide encoding glycoprotein gE from VZV. Mice were immunized with various VZV mRNA vaccine formulations at set intervals, and sera were collected after each immunization. The immunization schedule is provided in Table 4 of Example 15. The sera collection schedule is set forth in Table 5 of Example 15.

Serum antibody titers against VZV glycoprotein E was determined by Enzyme-linked immunosorbent assay (ELISA) using standard methods. In a second expanded study, the serum samples were serially diluted to bring the signal within the scope of detectability using ELISA. The amount of anti-VZV gE mouse IgG was measured in serum collected at day 42 post vaccination in mice vaccinated intramuscularly with two 10 μg doses of either: (1) VZV-gE-hIgkappa having 5' cap: m7G(5')ppp(5')G-2'-O-methyl and N1-methylpseudouridine chemical modification (#1 in Tables 2 and 3); (2) VZV-gE having 5' cap: m7G(5')ppp(5')G-2'-O-methyl and no chemical modification (#6 in Tables 2 and 3); (3) VZV-gE having 5' cap: m7G(5')ppp(5')G-2'-O-methyl and N1-methylpseudouridine chemical modification (#10 in Tables 2 and 3); (4) VARIVAX® vaccine (positive control); or (5) PBS (negative control). The concentration of anti-VZV-gE mouse IgG was measured in 10-fold serial dilutions.

FIG. 6 shows that the strongest immune response was found in mice vaccinated with vaccine candidate (1) VZV-gE-hlgkappa having 5' cap: m7G(5')ppp(5')G-2'-O-methyl and N1-methylpseudouridine chemical modification. The second strongest response was found in mice vaccinated with vaccine candidate (3) VZV-gE having 5' cap: m7G(5')ppp(5')G-2'-O-methyl and N1-methylpseudouridine chemical modification. The third strongest response was found in mice vaccinated with vaccine candidate (2) VZV-gE having 5' cap: m7G(5')ppp(5')G-2'-O-methyl and no chemical modification. All three VZV gE mRNA vaccines generated a significantly greater immune response than VARIVAX® vaccine.

FIG. 7 shows the amount of anti-VZV-gE mouse IgG present in mice vaccinated with vaccines (1)-(4) and (5) negative control at day 3, day 14, and day 42 post-vaccination.

Example 18: Immunogenicity Study

The instant studies are designed to test the immunogenicity in BALB/C mice of candidate VZV vaccines comprising a mRNA polynucleotide encoding variant glycoprotein gE from VZV. Mice were immunized with various VZV mRNA vaccine formulations at set intervals, and sera were collected after each immunization at indicated time points. The immunization schedule is provided in Table 6 below. The sera collection schedule is set forth in Table 7 below.

The amount of anti-VZV gE mouse IgG is measured in serum collected at the times indicated in Table 7 post vaccination in mice vaccinated intramuscularly with two 10 μg or 2 μg doses of the indicated constructs. All mRNAs used have the 5' cap: m7G(5')ppp(5')G-2'-O-methyl and N1-methylpseudouridine chemical modification. ZOSTAVAX® was used as a positive control and was injected into mice intramuscularly with twice clinical dose of 19400 pfu SC. PBS was used as negative control.

Antibody titers against the VZV gE variant polypeptides in the sera of mice immunized with VZV gE variant mRNA vaccines indicated in Table 6 were determined by enzyme-linked immunosorbent assay (ELISA). To perform the ELISA, wells of a plate were coated with VZV gE antigen (Abcam: ab43050) in PBS. 100 μl of the VZV gE antigen at a concentration of 1, 2, or 4 μg/ml were used for coating overnight at 4° C. The wells were then washed with 300 μl of PBST (PBS with 0.05% tween) 3 times. The VZV gE-coated wells were blocked with 200 μl of blocking butter containing 1% Blotto in PBS for 30 minutes at room temperature. Mice sera containing anti-VZV gE antibodies were diluted 1:2000 and then subject to 1:3 serial dilutions using PBST. The diluted sera were added to the VZV gE-coated wells and incubated for 1 hour at room temperature. A secondary antibody, rabbit anti-mouse conjugated to horseradish peroxidase (HRP, Abcam: ab6728) was diluted 1:1000 in PBST and 100 μl of the secondary antibody containing solution was added to the wells and incubated for 45 minutes at room temperature. 100 μl of HRP substrates, KPL TMB, were added the wells and incubated for 3 minutes at room temperature before 100 μl of a stop solution (2M $H_2SO_4$) was added to stop the HRP reaction. Signals generated from the HRP substrates were measured at A450. The results were shown in FIGS. 11A, 11B, 12A, 12B, 13 and Tables 8 and 9.

Figure 11A:
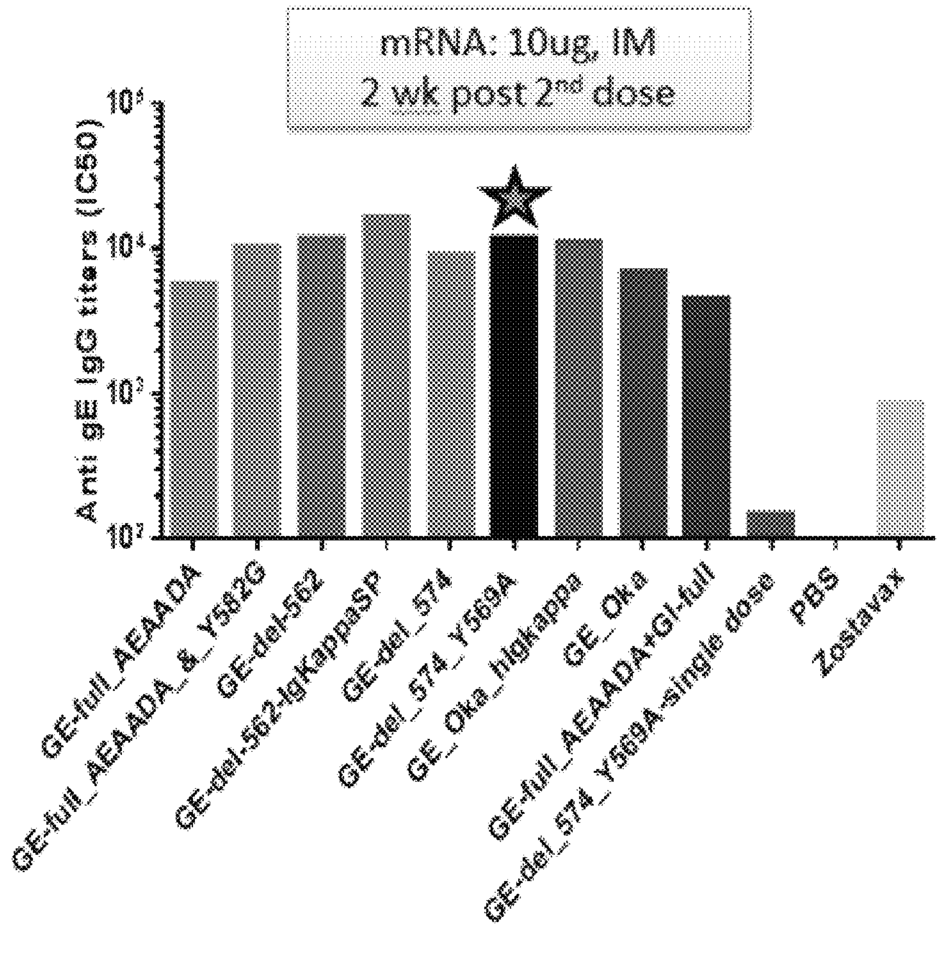
FIGS. 11A and 11B are graphs showing the results of an ELISA assay, which shows the levels of anti-VZV gE IgG in the serum of mice vaccinated with VZV gE variant mRNAs in comparison with ZOSTAVAX® vaccine. The sequence AEAADA depicted throughout
Figure 11B:
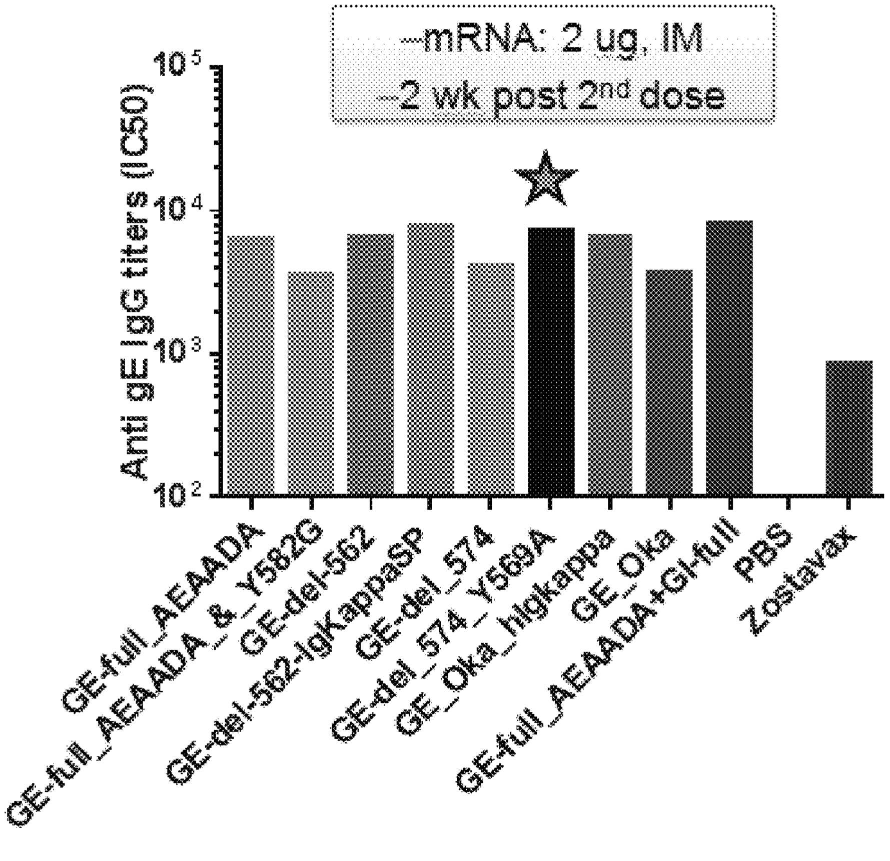

FIG. 11A shows that all gE variants induced much stronger immune response than ZOSTAVAX® after the two 10 μg doses. FIG. 11B show that all gE variants induced much stronger immune response than ZOSTAVAX® after the two 2 μg doses. With both dosages, the gE variants GE-del_574_Y569A and GE-del-562-IgKappaSP induced the strongest immune response and the antibody titer measured in the sera of mice immunized with this gE variant is over 10 times more than the antibody titer measured in the sera of mice immunized with ZOSTAVAX®, indicating that the GE-del_574_Y569A and GE-del_562-IgKappaSP mRNAs are superior vaccine candidates against VZV.

Figure 12A:
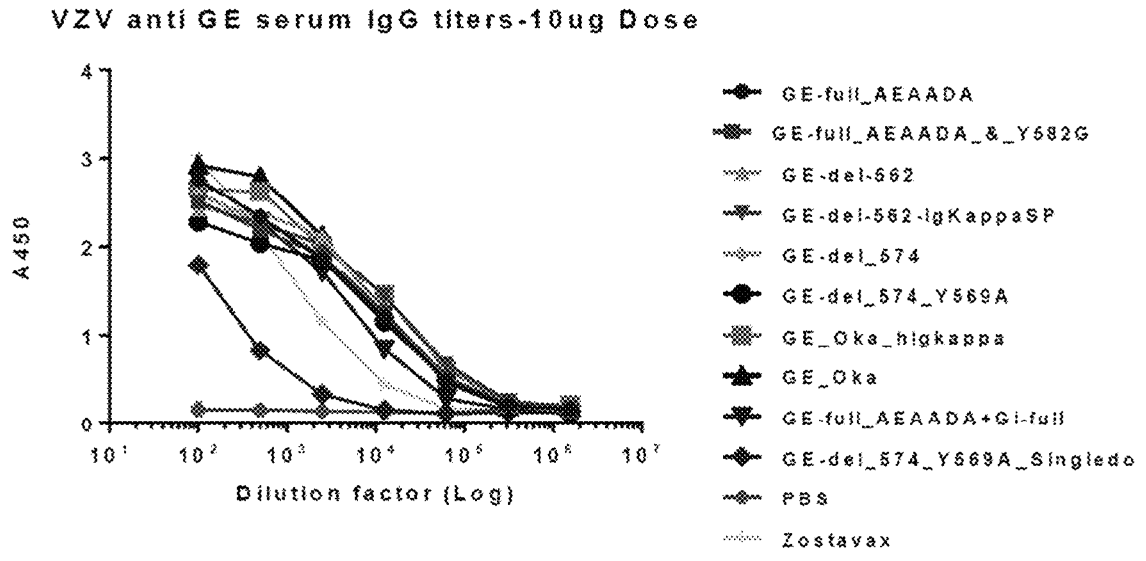
FIGS. 12A and 12B are graphs showing the results of an ELISA assay, which shows the levels of anti-VZV gE IgG in the serum of mice vaccinated with VZV gE variant mRNAs in comparison with ZOSTAVAX® vaccine. The sequence AEAADA depicted throughout
Figure 12B:
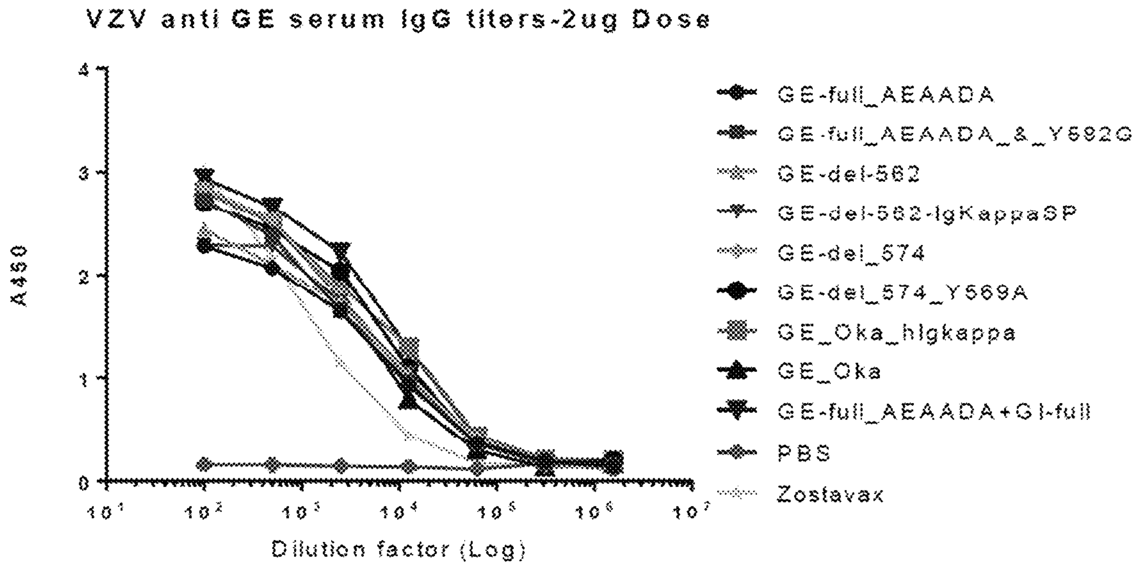

FIG. 12A shows the amount of antibodies in titrated sera collected from mice immunized twice with 10 μg of VZV gE mRNA variants described in Table 6. FIG. 12B shows the amount of antibodies in titrated sera collected from mice immunized twice with 2 μg of VZV gE mRNA variants described in Table 6. When the sera were diluted more than 100 fold, the antibody titer is higher in VZV gE variants vaccinated mice sera than in ZOSTAVAX® vaccinated mice sera, suggesting that the VZV gE mRNA variants induced much stronger immune response than ZOSTAVAX® in mice. All the VZV gE mRNA variants tested showed comparable ability in inducing immune response in mice.

Figure 13:
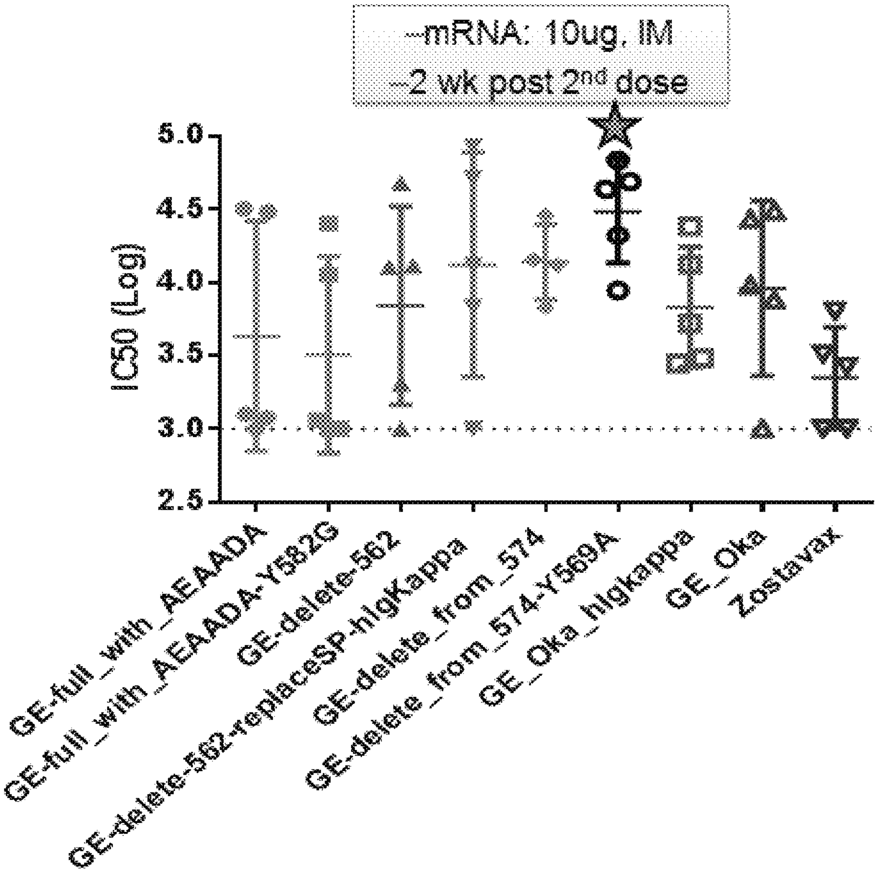
FIG. 13 is a graph showing the results of an ELISA assay measuring the antibody titer in the sera of mice immunized with VZV gE variant mRNA vaccines. Anti-VZV gE response induced by VZV gE variants mRNAs in mice are greater than that of ZOSTAVAX®. The gE variant mRNA for GE-delete_from_574-Y569A induced an immune response that is 1 log greater than ZOSTAVAX®. The sequence AEAADA depicted throughout

FIG. 13 is a graph showing the anti-VZV gE immune response induced by the VZV gE variant mRNA vaccines compared to ZOSTAVAX®. The VZV gE variant GE-delete_from_574-Y569A induced immune response in mice that is about 1 log greater than ZOSTAVAX®.

Table 9 summarizes the reciprocal IgG titer (IC50) in the sera collected from mice immunized with 10 μg or 2 μg of the respective VZV gE mRNAs twice. GE-delete_from_574-Y569A induced strong immune response with either 10 μg or 2 μg dosages. The Geometric Mean Titer (GMT) was used to indicate the immunogenic potential of the VZV gE variant mRNA vaccines. GE-delete_from_574-Y569A showed the highest GMT value, indicating that it is the most efficacious in inducing immune response against VZV gE.

TABLE 6

| Injection Schedule | | | | | | | | | |
|---|---|---|---|---|---|---|---|---|---|
| G# | Antigen | Route | N | Dosage (μg) | Vol (μl) | $1^{st}$ dose | $2^{nd}$ dose | MC3/ conc | |
| 1 | SE-VZV-GE-full_with_AEAADA (SEQ ID NO: 58) | IM | 5 | 10 | 50 | Day 0 | Day 28 | 0.2 mg/ml | 2 x 500 |
| 2 | SE-VZV-GE-full_with_AEAADA (SEQ ID NO: 58) | IM | 5 | 2 | 50 | Day 0 | Day 28 | 0.04 mg/ml | 2 x0 500 |
| 3 | SE-VZV-GE-full with AEAADA (SEQ ID NO: 58)_and_Y582G | IM | 5 | 10 | 50 | Day 0 | Day 28 | 0.2 mg/ml | 2 x 500 |
| 4 | SE-VZV--GE-full with AEAADA (SEQ ID NO: 58)_and_Y582G | IM | 5 | 2 | 50 | Day 0 | Day 28 | 0.04 mg/ml | 2 x 500 |
| 5 | SE-VZV-GE-delete-562 | IM | 5 | 10 | 50 | Day 0 | Day 28 | 0.2 mg/ml | 2 x 500 |
| 6 | SE-VZV-GE-delete-562 | IM | 5 | 2 | 50 | Day 0 | Day 28 | 0.04 mg/ml | 2 x 500 |
| 7 | SE-VZV-GE-delete-562-replacedSP-withIgKappa | IM | 5 | 10 | 50 | Day 0 | Day 28 | 0.2 mg/ml | 2 x 500 |
| 8 | SE-VZV-GE-delete-562-replacedSP-withIgKappa | IM | 5 | 2 | 50 | Day 0 | Day 28 | 0.04 mg/ml | 2 x 500 |
| 9 | SE-VZV-GE-truncated-delete from_574 | 1M | 5 | 10 | 50 | Day 0 | Day 28 | 0.2 mg/ml | 2 x 500 |
| 10 | SE-VZV--GE-truncated-delete_from_574 | IM | 5 | 2 | 50 | Day 0 | Day 28 | 0.04 mg/ml | 2 x 500 |
| 11 | SE-VZV-GE-truncated-delete_from_574_-_Y569A | IM | 5 | 10 | 50 | Day 0 | Day 28 | 0.2 mg/ml | 2 x 500 |
| 12 | SE-VZV-GE-truncated-delete_from_574_-_Y569A | IM | 5 | 2 | 50 | Day 0 | Day 28 | 0.04 mg/ml | 2 x 500 |
| 13 | KB_VZV_gE_Oka_hIgkappa | IM | 5 | 10 | 50 | Day 0 | Day 28 | 0.2 mg/ml | 2 x 500 |
| 14 | KB_VZV_gE_Oka_hIgkappa | IM | 5 | 2 | 50 | Day 0 | Day 28 | 0.04 mg/ml | 2 x 500 |
| 15 | KB_VZV_gE_Oka | IM | 5 | 10 | 50 | Day 0 | Day 28 | 0.2 mg/ml | 2 x 500 |
| 16 | KB_VZV_gE_Oka | IM | 5 | 2 | 50 | Day 0 | Day 28 | 0.04 mg/ml | 2 x 500 |
| 17 | SE-VZV-GI-full | IM | 5 | 10 | 50 | Day 0 | Day 28 | 0.2 mg/ml | 2 x 500 |
| 18 | SE-VZV-GI-full | IM | 5 | 2 | 50 | Day 0 | Day 28 | 0.04 mg/ml | 2 x 500 |
| 19 | SE-VZV-GE-full with AEAADA (SEQ ID NO: 58)+SE-VZV-GI-full | IM | 5 | 10 | 50 | Day 0 | Day 28 | 0.2 mg/ml | 2 x 500 |
| 20 | SE-VZV-GE-full with AEAADA (SEQ ID NO: 58)+SE-VZV-GI-full | IM | 5 | 2 | 50 | Day 0 | Day 28 | 0.04 mg/ml | 2 x 500 |
| 21 | SE-VZV-GE-truncated-delete_from_574_-_Y569A | IM | 5 | 10 | 50 | Day 0 | No dosing | 0.2 mg/ml | 500 |
| 22 | PBS | IM | 5 | — | 50 | Day 0 | Day 28 | | 2 x 500 |
| 23 | Positive control | SC | 5 | 19400 PFUs | 100 | Day 0 | Day 28 | | 2x 500 |

TABLE 7

| Schedule of Sample Collection | | | | | | |
|---|---|---|---|---|---|---|
| G# | Antigen | Pre-bleed | Day 14 | Day 27 | Day 42 | Day 56 |
| 1 | SE-VZV-GE-full_with_AEAADA (SEQ ID NO: 58) | ✓ | ✓ | ✓ | ✓ | ✓ |
| 2 | SE-VZV-GE-full_with_AEAADA (SEQ ID NO: 58) | ✓ | ✓ | ✓ | ✓ | ✓ |
| 3 | SE-VZV-GE-full with_AEAADA (SEQ ID NO: 58)_and_Y5-82G | ✓ | ✓ | ✓ | ✓ | ✓ |
| 4 | SE-VZV-GE-full with_AEAADA (SEQ ID NO: 58)_and_Y5-82G | ✓ | ✓ | ✓ | ✓ | ✓ |
| 5 | SE-VZV-GE-delete-562 | ✓ | ✓ | ✓ | ✓ | ✓ |
| 6 | SE-VZV-GE-delete-562 | ✓ | ✓ | ✓ | ✓ | ✓ |

TABLE 7-continued

| Schedule of Sample Collection | | | | | | |
|---|---|---|---|---|---|---|
| G# | Antigen | Pre-bleed | Day 14 | Day 27 | Day 42 | Day 56 |
| 7 | SE-VZV-GE-delete-562-replacedSP-withIgKappa | ✓ | ✓ | ✓ | ✓ | ✓ |
| 8 | SE-VZV-GE-delete-562-replacedSP-withIgKappa | ✓ | ✓ | ✓ | ✓ | ✓ |
| 9 | SE-VZV-GE-truncated-delete_from_574 | ✓ | ✓ | ✓ | ✓ | ✓ |
| 10 | SE-VZV-GE-truncated-delete_fr0m_574 | ✓ | ✓ | ✓ | ✓ | ✓ |
| 11 | SE-VZV-GE-truncated-deletefrom574_-_Y569A | ✓ | ✓ | ✓ | ✓ | ✓ |
| 12 | SE-VZV-GE-truncated-deletefrom574_-_Y569A | ✓ | ✓ | ✓ | ✓ | ✓ |
| 13 | KB_VZV_gE_Oka_hIgkappa | ✓ | ✓ | ✓ | ✓ | ✓ |
| 14 | KB_VZV_gE_Oka_hIgkappa | ✓ | ✓ | ✓ | ✓ | ✓ |
| 15 | KB_VZV_gE_Oka | ✓ | ✓ | ✓ | ✓ | ✓ |
| 16 | KB_VZV_gE_Oka | ✓ | ✓ | ✓ | ✓ | ✓ |
| 17 | SE-VZV-GI-full | ✓ | ✓ | ✓ | ✓ | ✓ |
| 18 | SE-VZV-GI-full | ✓ | ✓ | ✓ | ✓ | ✓ |
| 19 | SE-VZV-GE-full_with_AEAADA (SEQ ID NO: 58)+SE-VZV-GI-full | ✓ | ✓ | ✓ | ✓ | ✓ |
| 20 | SE-VZV-GE-full_with_AEAADA (SEQ ID NO: 58)+SE-VZV-GI-Full | ✓ | ✓ | ✓ | ✓ | ✓ |
| 21 | SE-VZV-GE-truncated-delete_from_574_-_Y569A | ✓ | ✓ | ✓ | ✓ | ✓ |
| 22 | PBS | ✓ | ✓ | ✓ | ✓ | ✓ |
| 23 | Positive control | ✓ | ✓ | ✓ | ✓ | ✓ |

TABLE 8

| Summary of $IC_{50}$ of the different VZV constructs Reciprocal IgG titer (IC50) | | |
|---|---|---|
| Name | 10 ug | 2 ug |
| GE-FULL_AEAADA | 5741 | 6378 |
| GE-FULL_AEAADA_&_Y582G | 10306 | 3556 |
| GE-del-562 | 11672 | 6445 |
| GE-del-562-laKappaSP | 16490 | 7939 |
| GE-del_574 | 9031 | 4082 |
| GE-del_574_Y569A | 11704 | 7291 |
| GE_Oka_hIgkappa | 11708 | 6448 |
| GE_Oka_hIgkappa | 7045 | 3672 |
| GE-full_AEAADA_GI-full | 4457 | 8242 |
| GE-del_574_Y569A | NA | |
| PBS | NA | NA |
| Zostavax | 860 | 860 |

| | Assay controls | | | | | |
|---|---|---|---|---|---|---|
| | plate 1 | plate 2 | % CV | std | mean | CV |
| VZV_gE_Oka_hIgkappa | 12808 | 11078 | 7.22 | 862.5 | 11940.5 | 0.07 |

TABLE 9

| Reciprocal anti-gE IgG titer (IC50) measured by ELISA | | |
|---|---|---|
| Name | IC50 | GMT |
| GE-full_AEAADA | 1188.5 | 4291.4 |
| | 31915.4 | |
| | 1261.8 | |
| | 30408.9 | |
| | 1000 | |
| GE-full_AEAADA_&_Y582G | 1150.8 | 3181.3 |
| | 25351.3 | |
| | 1000 | |
| | 1000 | |
| | 11168.6 | |

TABLE 9-continued

| Reciprocal anti-gE IgG titer (IC50) measured by ELISA | | |
|---|---|---|
| Name | IC50 | GMT |
| GE-del-562 | 1000 | 6921.5 |
| | 47752.9 | |
| | 12676.5 | |
| | 12912.2 | |
| | 2032.4 | |
| GE-del-562-IgKappaSP | 1000 | 13140.1 |
| | 13122 | |
| | 51760.7 | |
| | 84918.1 | |
| | 6792 | |
| GE-del_574 | 13091.8 | 13795.9 |
| | 6760.8 | |
| | 14223.3 | |
| | 28774 | |
| GE-del_574_Y569A | 20941.1 | |
| | 48865.2 | |
| | 8810.5 | |
| | 43351.1 | |
| | 68076.9 | |
| GE_Oka_hIgkappa | 24266.1 | 6763.9 |
| | 3026.9 | |
| | 13213 | |
| | 5236 | |
| | 2786.1 | |
| GE_Oka | 27227 | 9078.2 |
| | 30903 | |
| | 7638.4 | |
| | 1000 | |
| | 9594 | |
| Zostavax | 6397.3 | 2228.4 |
| | 1000 | |
| | 1000 | |
| | 2660.7 | |
| | 3228.5 | |

Example 19: VZV In Vitro Neutralization Assay

A VZV in vitro neutralization assay was performed to evaluate the anti-VZV gE antibodies in neutralizing VZV. The anti-VZV gE antibodies were obtained by collecting the sera of mice vaccinated with VZV gE variant mRNA vaccines. Mice were vaccinated with VZV gE variant mRNA vaccines at dosages or 10 μg or 2 μg as described in Table 6 and sera were collected 2 weeks post 2' immunization.

To perform the assay, mice sera were diluted 1:5 and then subjected to 1:2 serial dilutions. VZV virus were added to the sera and neutralization was allowed to continue for 1 hour at room temperature. ARPE-19 cells were seeded in 96-wells one day before and the virus/serum mixtures were added to ARPE-19 cells at 50-100 pfu per well. The ARPE-19 cells were fixed on the next day and VZV-specific staining was performed. The plates were scanned and analyzed. Results of the VZV in vitro neutralization assay were summarized in Table 10. Values in Table 10 are serum dilutions showing 50% reduction in well-area coverage by VZV virus plaques. No reduction in plaque number was observed. As shown in Table 10, one replicate of serum from mice immunized with GE-delete_from_574-Y569A variant mRNA vaccine was able to reduce well-area coverage by VZV virus plaques at 1:80 dilution.

all age group of adults 50+. However, this vaccine demonstrated grade 3 severe AE's in 10% of the vaccinated subjects. Shingrix demonstrated about a log fold better T and B cell response after two doses to ZOSTAVAX®. In the present studies mRNA immunization with a gE construct was investigated for immunogenicity in mice and NHP.

Figure 14A:
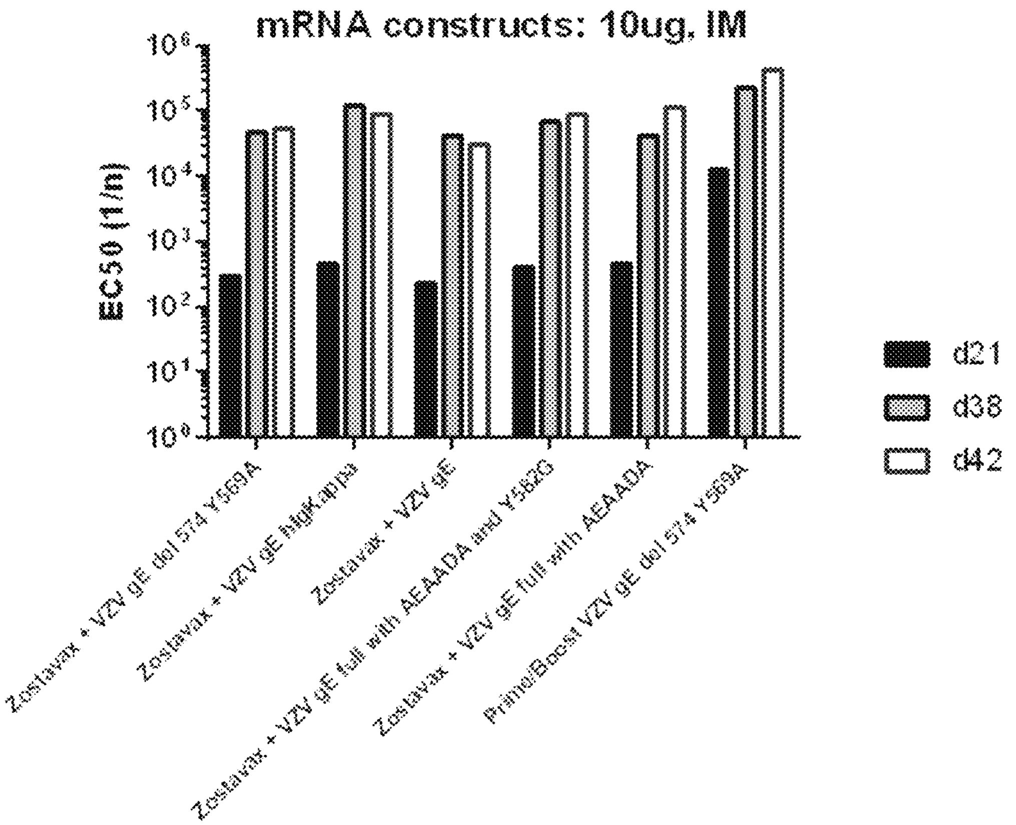
FIG. 14A is a graph showing the results of an ELISA assay, which shows the levels of anti-VZV gE IgG in the serum of mice vaccinated with VZV gE variant mRNAs after primary exposure with ZOSTAVAX® vaccine (groups 1-5) or VZV-gE-del_574_Y569A (group 6). The sequence AEAADA depicted throughout
Figure 14B:
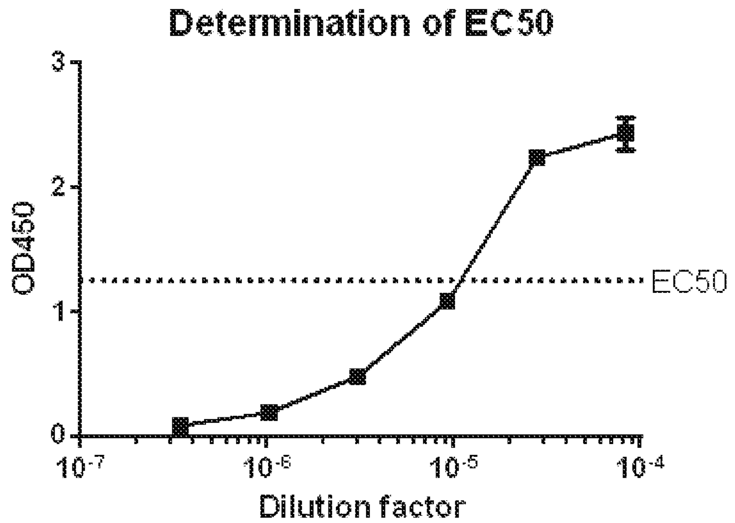
FIG. 14B is a graph showing the determination of EC50.
Figure 15A:
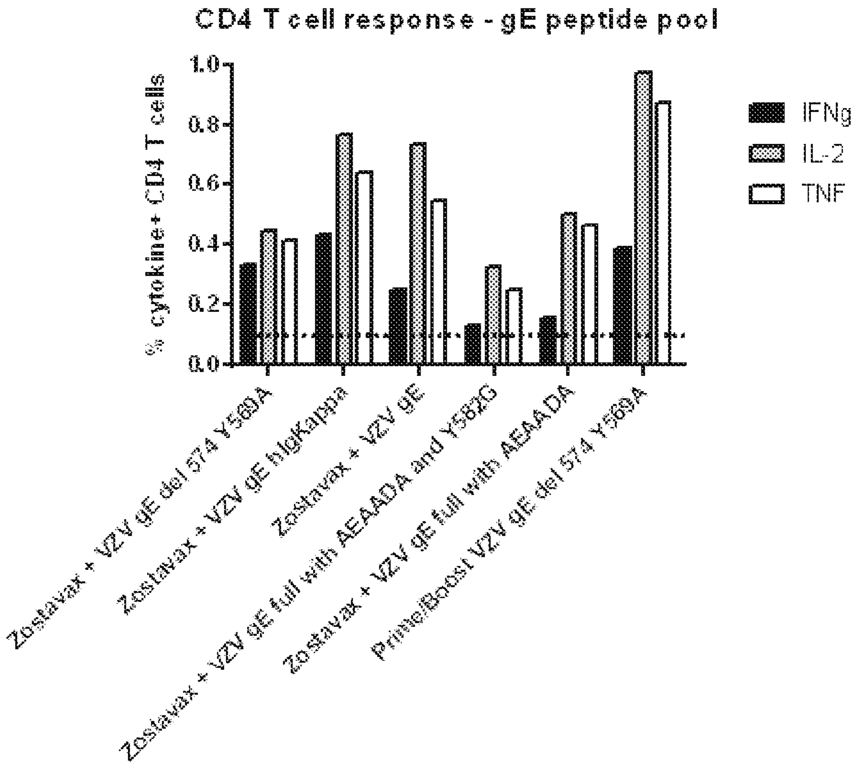
FIGS. 15A and 15B are graphs showing the results of the T cell analysis of mice vaccinated with VZV gE variant mRNAs after primary exposure with ZOSTAVAX® vaccine (groups 1-5) or VZV-gE-del_574_Y569A (group 6). The sequence AEAADA depicted throughout
Figure 15B:
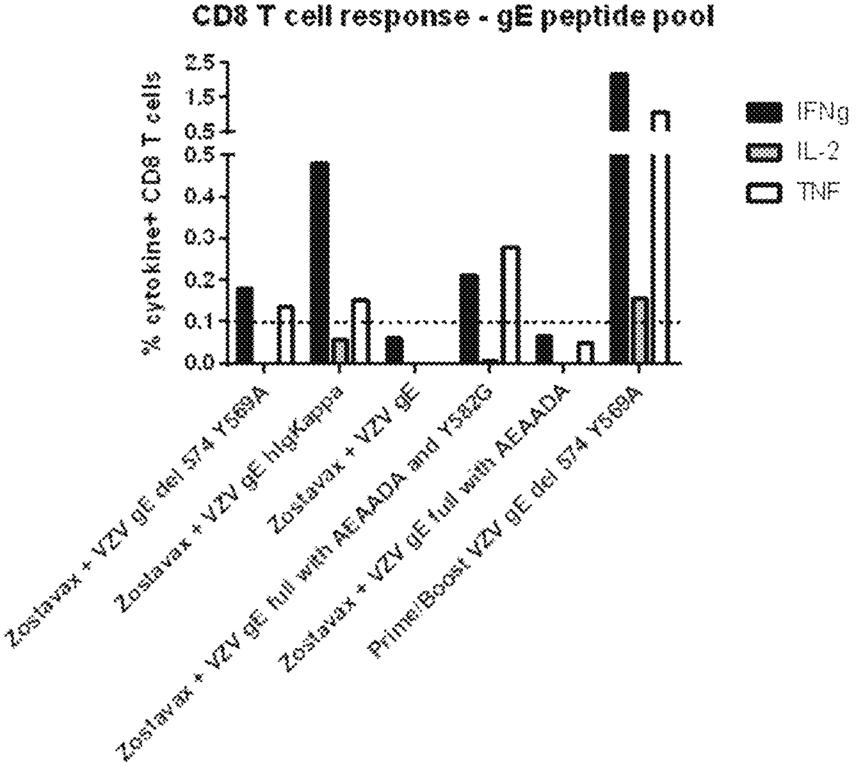

The instant study was defined to test the immunogenicity in BALB/C mice of candidate VZV vaccines comprising a mRNA polynucleotide encoding glycoprotein gE from VZV. Mice were immunized with various VZV mRNA vaccine formulations as set forth below in Table 11. Groups 1 to 5 were primed with ZOSTAVAX® to mimic a primary Varicella exposure and group 6 was primed with mRNA construct VZV-gE-del_574_Y569A. All groups (groups 1-6) were boosted on day 28, as shown in Table 11. The animals were bled on days −3, 21, 38 and 42. Blood and spleens were collected for serological and T cell analysis on days 38 and 42. As shown in FIG. 14A, all groups gave comparable anti-gE antibody responses to mRNA vaccination with the animal receiving mRNA for prime and boost (group 6) trending higher. As shown in FIG. 15A, all groups demonstrated CD4 T-cell responses with mRNA prime and boost (group 6) trending towards a higher response. As shown in FIG. 15B, variable CD8 T-cell responses were noted with the mRNA prime and boost (group 6) demonstrating highest CD8 T-cell frequencies.

TABLE 10

In vitro neutralization assay

| Antigen | 10 ug Replicate1 | 10 ug Replicate2 | 20 ug Replicate1 | 20 ug Replicate2 |
|---|---|---|---|---|
| SE-VZV-GE-full_with_AEAADA | 20 | 10 | 10 | 10 |
| SE-VZV-GE-full_with_AEAADA_and_Y582G | 40 | 20 | | 10 |
| SE-VZV-GE-delete-562 | 40 | 20 | 20 | 10 |
| SE-VZV-GE-delete-562-replacedSP-withIgKappa | 40 | 40 | 20 | 40 |
| SE-VZV-GE_truncated-delete_from_574 | 80 | 40 | 40 | 20 |
| SE-VZV-GE-truncated-delete_from_574_-_Y569A | 20 | 80 | 10 | 10 |
| KB_VZV_gE_Oka_hIgkappa | 40 | <20 | 20 | 10 |
| KB_VZV_gE_Oka | 160 | 10 | 10 | 10 |
| SE-VZV-GI-full | <10 | <10 | <20 | <20 |
| SE-VZV-GE-full_with_AEAADA + SE-VZV-GI-full | 20 | 10 | — | — |
| SE-VZV-GE-truncated-delete from_574_ -_Y569A | <10 | <10 | — | — |
| PBS | <20 | <20 | | |
| Positive control | 20 | 20 | | |

Example 20: Immunogenicity in Mice

Herpes zoster (HZ) or shingles is a debilitating disease characterized by a vesicular rash, with the most common complication being post-herpetic neuralgia (PHN). PHN is a constant and severe pain that develops after clearance of the cutaneous outbreak, and can last for several years, thereby contributing to the high morbidity of affected individuals. HZ is caused by reactivation of latent varicella-zoster virus (VZV) from the sensory ganglia. Immune responses generated during primary VZV infection (chickenpox) have been shown to prevent the reactivation of latent VZV. However, the incidence of HZ is strongly associated with advancing age. Several investigations have shown that T cell-mediated immune responses decline with increasing age and during immunosuppression, resulting in reactivation of VZV. Nonetheless, the levels of anti-VZV antibodies remain relatively stable with increasing age, demonstrating that the humoral immune response may not be sufficient for the prevention of HZ. Several studies have reported the induction of VZV-specific $CD4^+$ and $CD8^+$ T cells, with $CD4^+$ T cells dominating the memory response.

The approved vaccine ZOSTAVAX® demonstrates around 60-70% efficacy in 50-60 years adults and declines with age. Recently a subunit adjuvanted vaccine (Shingrix: gE protein +ASO1B) was shown to have ~90% efficacy in

TABLE 11

Injection Schedule

| G# | Primary Immunization (Day 0) 10 μg | Boost (Day 28) 10 μg | Localization (VERO/MeWo) of Boost Construct | Number mice per group |
|---|---|---|---|---|
| 1 | ZOSTAVAX ® | VZV-gE-del_ 574_Y569A | Golgi (high) & cell membrane (high) | 10 |
| 2 | ZOSTAVAX ® | VZV-gE-Oka-hIgKappa | Golgi (low) & cytoplasmic | 10 |
| 3 | ZOSTAVAX ® | VZV-gE-Oka | Golgi/Golgi | 10 |
| 4 | ZOSTAVAX ® | VZV-gE full_ with_AEAADA (SEQ ID NO: 58)_ and_Y582G | Organelles & cytoplasmic/cell membrane | 10 |
| 5 | ZOSTAVAX ® | VZV-gE-full with AEAADA (SEQ ID NO: 58) | Golgi & diffuse perinuclear/cell membrane | 10 |

TABLE 11-continued

| Injection Schedule | | | | |
|---|---|---|---|---|
| G# | Primary Immunization (Day 0) 10 μg | Boost (Day 28) 10 μg | Localization (VERO/MeWo) of Boost Construct | Number mice per group |
| 6 | VZV-gE-del_574_Y569A | VZV-gE-del_574_Y569A | Golgi (high) & cell membrane (high) | 10 |

Example 21: Immunogenicity in Non-Human Primates

Figure 16A:
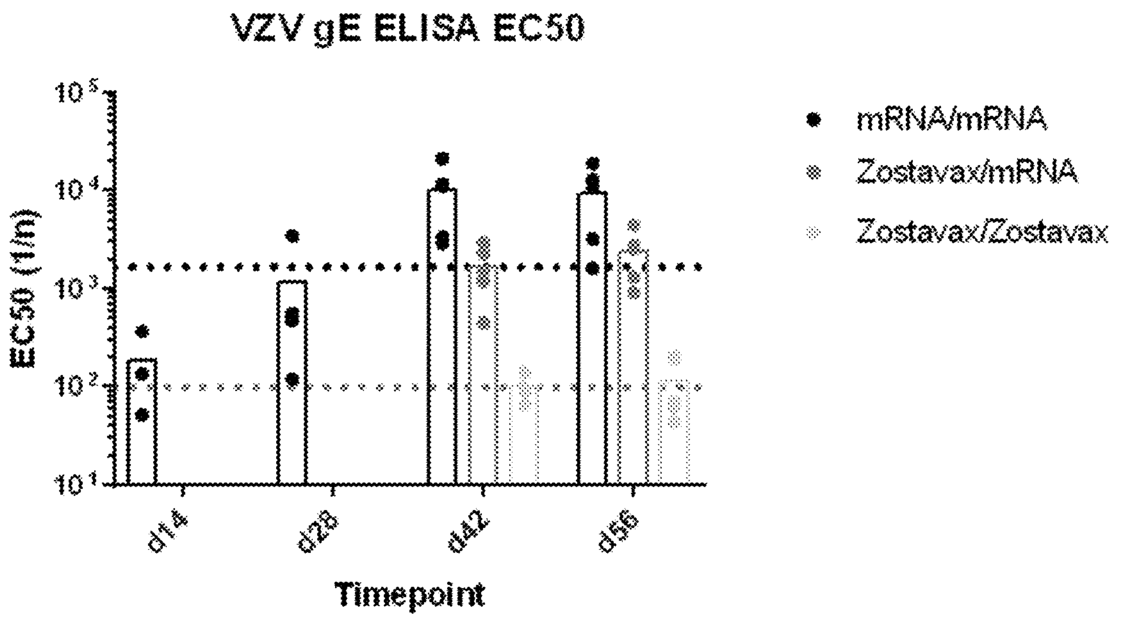
FIGS. 16A and 16B are graphs showing the results of an ELISA assay, which shows the levels of anti-VZV gE IgG in serum of rhesus monkeys vaccinated with either VZV-gE-del_574_Y569A or ZOSTAVAX® after primary exposure with VZV-gE-de1_574_Y569A or ZOSTAVAX.
Figure 16B:
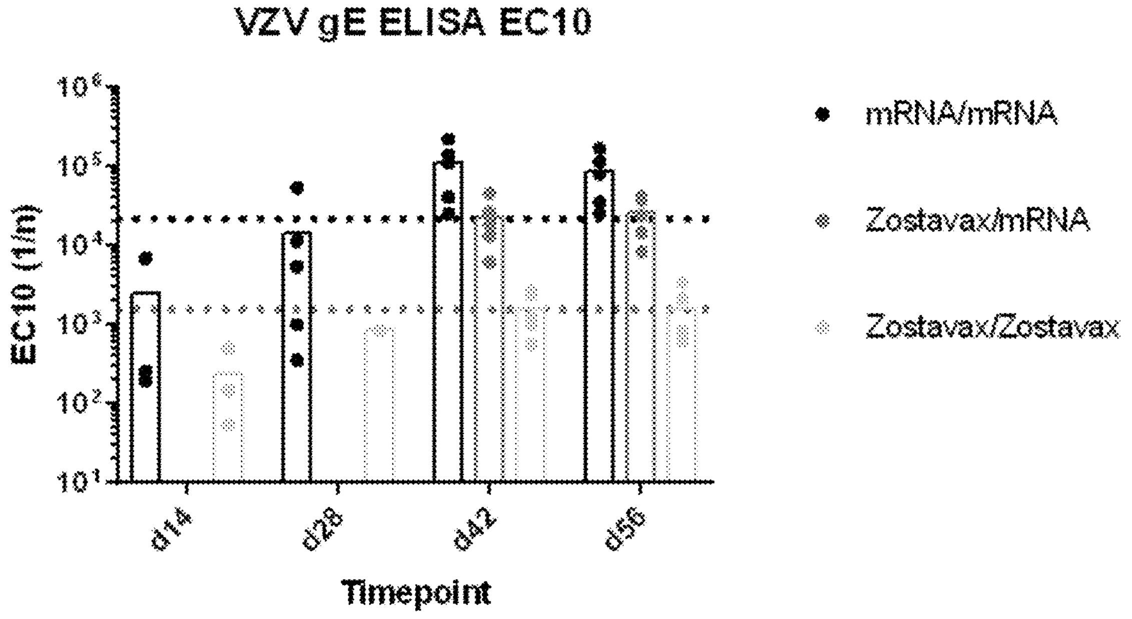
Figure 16C:
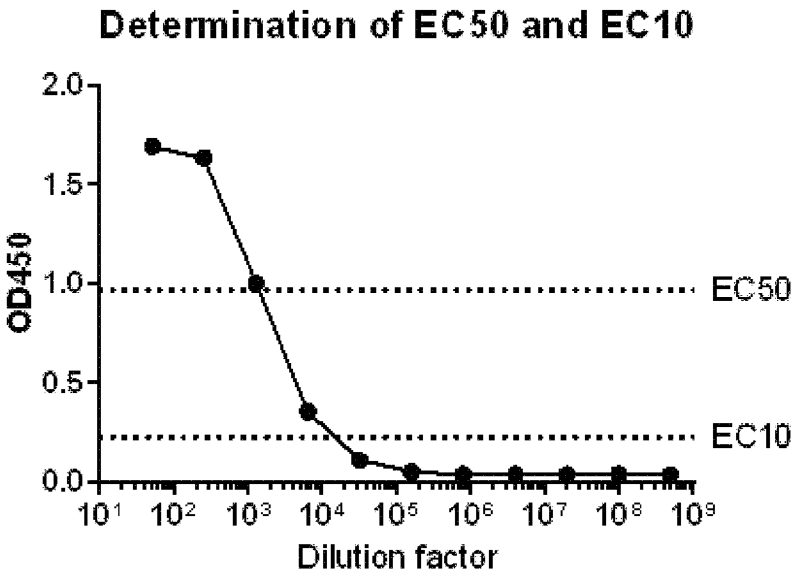
FIG. 16C is a graph showing the determination of EC50 and EC10.
Figure 16D:
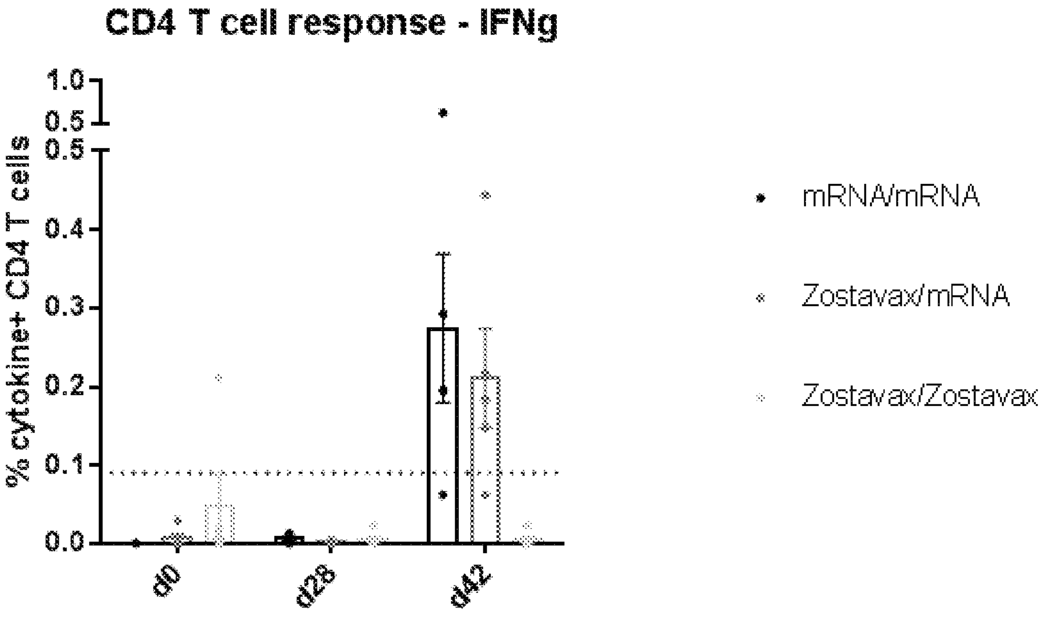
FIGS. 16D, 16E, and 16F are graphs showing the results of the T cell analysis of rhesus monkeys vaccinated with either VZV-gE-del_574_Y569A or ZOSTAVAX® after primary exposure with VZV-gE-del_574_Y569A or ZOSTAVAX®.
Figure 16E:
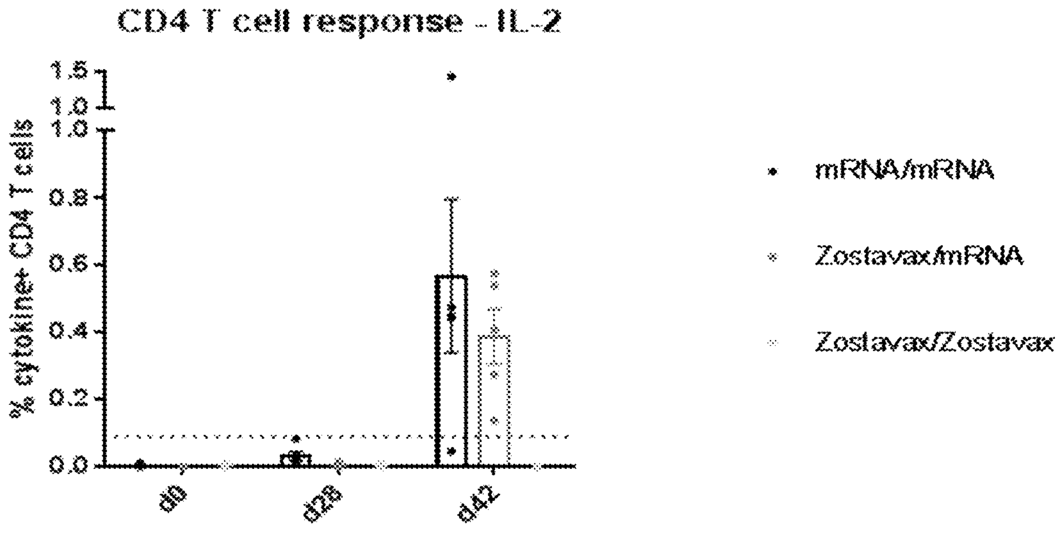
Figure 16F:
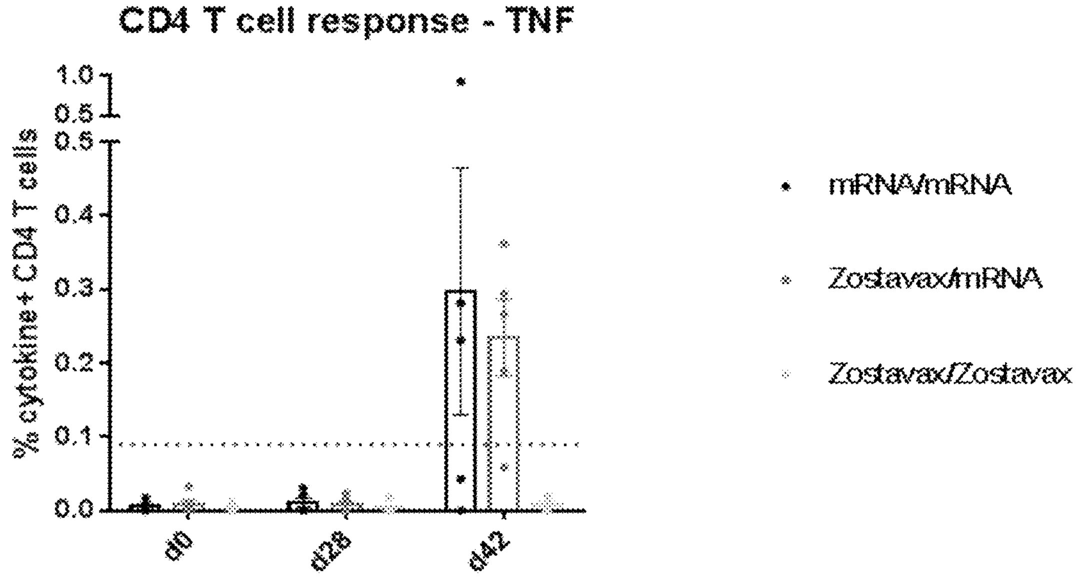

Based on the data in Example 20, the mRNA construct VZV-gE-del_574_Y569A was further evaluated for immunogenicity in non-human primates. Three groups of Rhesus monkeys were primed with mRNA (VZV-gE-del_574_Y569A) or ZOSTAVAX® and boosted as set forth below in Table 12. The animals were bled at days 0, 14, 28, and 42 for serological and T-cell analysis. T-cell analysis was performed on days 0, 28, and 42. As shown in FIGS. 16A and 16B, the mRNA prime and boost (group 1) gave the highest anti-gE titers which were followed by ZOSTAVAX® prime, mRNA boost (group 2). The latter group (group 2) anti-gE titers were approximately 10× better than the ZOSTAVAX® prime, ZOSTAVAX® boost (group 3). As shown in FIGS. 16C and 16D, no CD4-T cells producing IFNγ, IL-2 or TNFα were detected in the ZOSTAVAX® prime, ZOSTAVAX® boost group (group 3). In contrast, as shown in FIGS. 16C and 16D, reasonable frequency of CD4 T-cells producing IFNγ, IL-2 or TNFα were detected in the mRNA prime, mRNA boost group (group 1) and the ZOSTAVAX® prime, mRNA boost group (group 2) and were statistically undifferentiated. These data indicate that one dose of mRNA vaccination after ZOSTAVAX® exposure was equivalent to two doses of mRNA vaccination in inducing comparable T-cell responses.

TABLE 12

| Injection Schedule | | | |
|---|---|---|---|
| G# | Primary Immunization (Day 0) 10 μg | Boost (Day 28) 10 μg | Number Rhesus macaques (male and female) per group |
| 1 | VZV-gE-del_574_Y569A | VZV-gE-del_574_Y569A | 5 |
| 2 | ZOSTAVAX ® | VZV-gE-del_574_Y569A | 5 |
| 3 | ZOSTAVAX ® | ZOSTAVAX ® | 5 |

Figure 17:
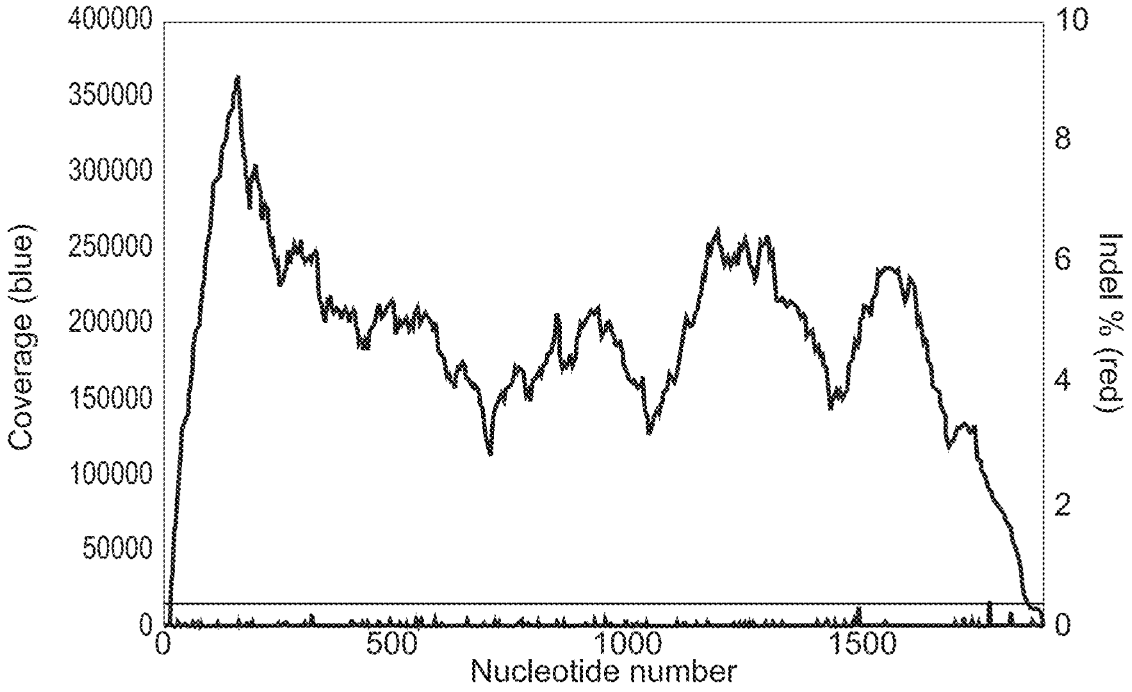
FIG. 17 shows next generation sequencing (NGS) data of VZV mRNA vaccine construct encoding a modified VZV-gE-del_574_Y569A antigen (VZV-gE-del_574_Y569A-v7). Compared to the VZV-gE-del_574_Y569A mRNA vaccine construct, which encodes the gE antigen (e.g., described in FIGS. 13-16), VZV-gE-del_574_Y569A-v7 was modified (6 nucleotide changes were introduced) to reduce the occurrence of indel-causing homopolymeric stretches (stretches of 6 As, 5 As, or 4 As). The data shows that VZV-gE-del_574_Y569A-v7 does not contain significant indels.

Example 22: Expression and In Vivo Localization of VZV-gE-Del_574_Y569A Variants Variants of mRNAs encoding the VZV-gE-del_574_Y569A (variant 7, SEQ ID NO: 107, ORF sequence: SEQ ID NO: 86) or VZV-gE-full length (SEQ ID NO: 135) were constructed, where the nucleotide sequence of the homopolymeric stretches (e.g., 6, 5, or 4 consecutive As) were altered (without altering the amino acid sequence) to reduce the frequency of potential indel formation. Next generation sequencing showed the absence of significant indels in VZV-gE-del_574_Y569A variant 7 (VZV-gE-del_574_Y569A-v7) (FIG. 17). Mass spectrometry detected very low levels of indels in a 4A stretch in nucleotides 760-771 of the ORF.

Figure 18A:
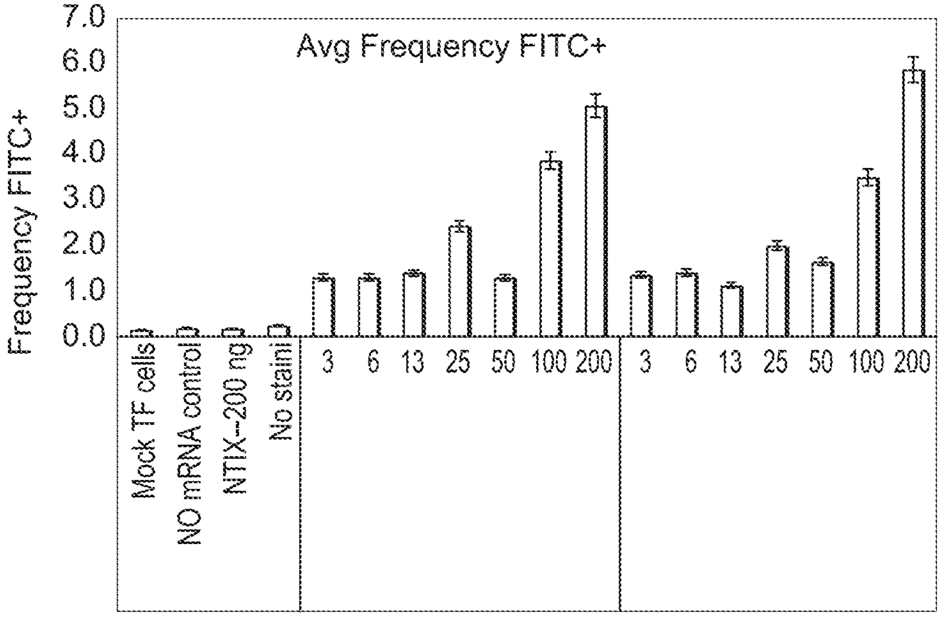
FIG. 18A shows the average frequency of $FITC^+$ MeWo cells six hours post transfection with VZV-gE-del_574_Y569A or VZV-gE-del_574_Y569A-v7, measured by fluorescence-activated cell sorting (FACS).
Figure 18B:
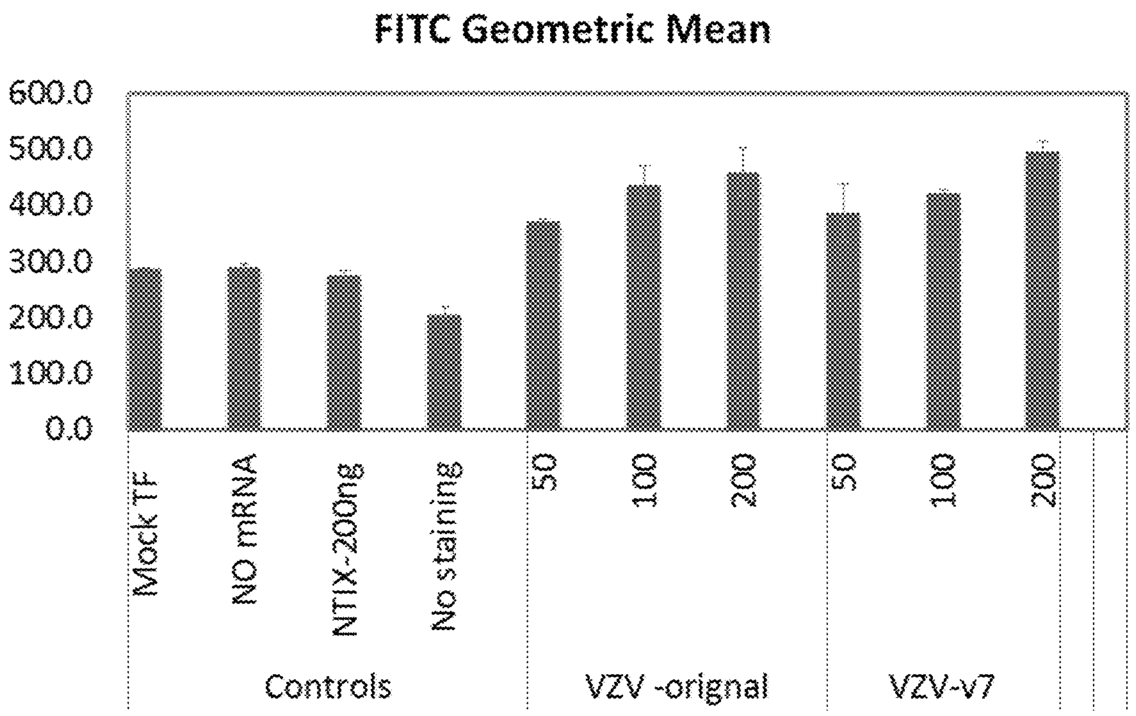
FIG. 18B shows the FITC geometric mean.

Next, the expression levels of VZV-gE-del_574_Y569A-v7 were tested in Mewo and HeLa cells and compared to the VZV-gE-del_574_Y569A mRNA construct. The mRNA constructs (200 ng) were transfected into Mewo or HeLa cells, using the Mirus TF transfection reagent in 96-well plates. NTIX control mRNA and PBS control were used in 30 K of MeWo cells. All cells were serially diluted (2 fold) 6 hours post transfection, permeabilized, stained, and analyzed by flow cytometry for FITC+ cells (cells with antigen expression). Results show that the VZV-gE-del_574_Y569A-v7 mRNA construct was expressed at a level comparable to the VZV-gE-del_574_Y569A mRNA construct in both Mewo cells (FIG. 18A) and HeLa cells (FIG. 18B).

Figure 19A:
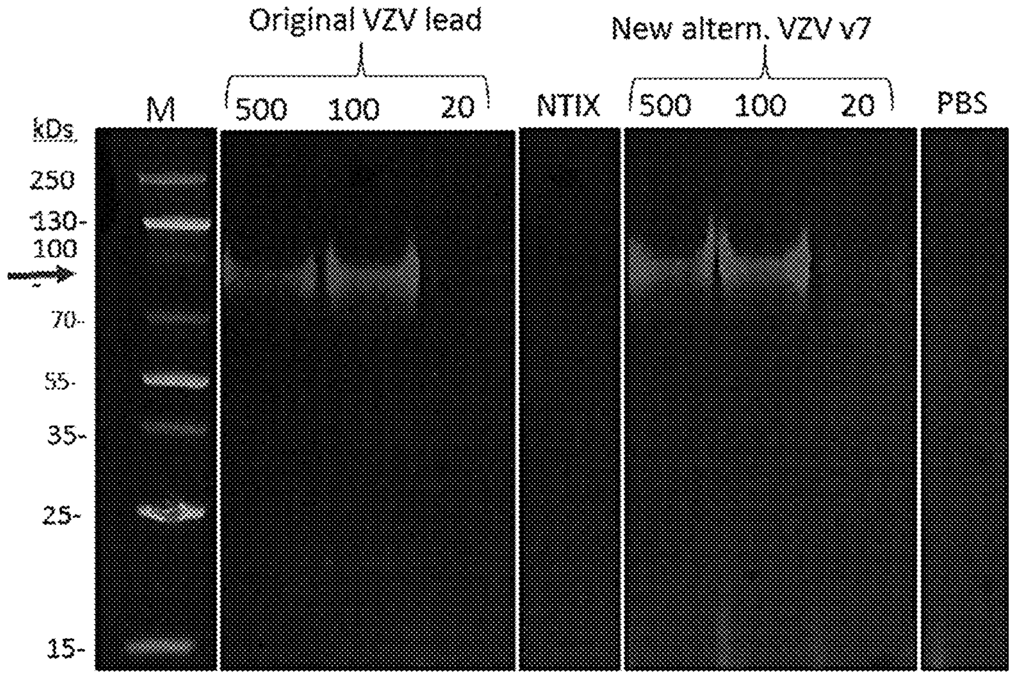
FIGS. 19A-19B are Western blots showing detection of VZV-gE-del_574_Y569A antigens in the lysates of HeLa cells 16 hours post transfection. Expression of the VZV-gE-del_574_Y569A antigen was detected in HeLa cells transfected with the VZV-gE_574_Y569A mRNA construct and in HeLa cells transfected with the VZV-gE-del_574_Y569A-v7 mRNA construct.
Figure 19B:
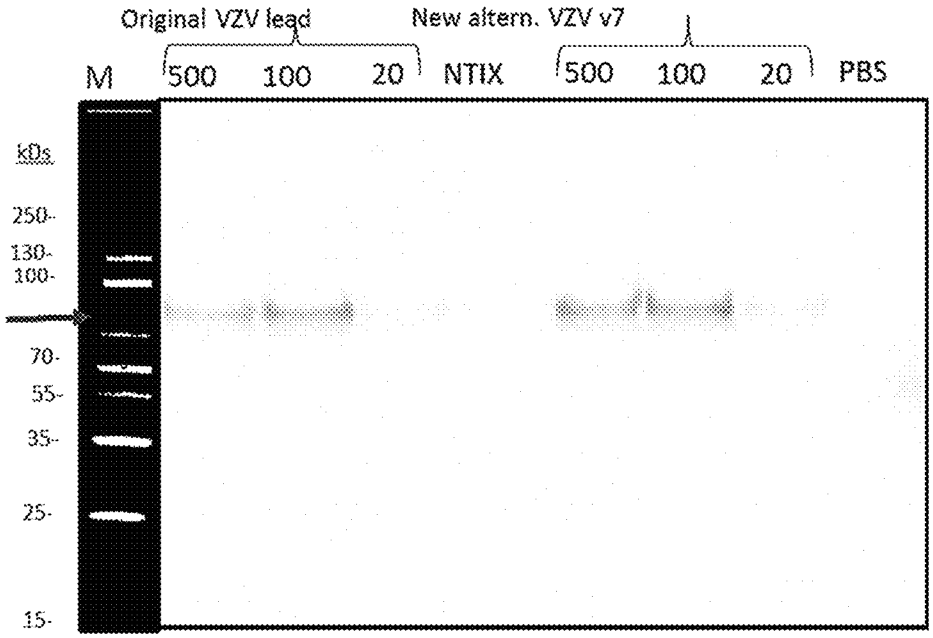

Protein was then detected in cell lysates of HeLa cells transfected (IIpoplexed with 3 μl LF2000 per well in a 24-well plate) with either the VZV-gE-del_574_Y569A mRNA construct (500 ng) or the VZV-gE-del_574_Y569A-v7 mRNA construct (500 ng), serially diluted to 100 μg or 20 μg. Western blots for the VZV-gE antigen 16 hours post transfection showed that the VZV-gE-del_574_Y569A-v7 mRNA construct was expressed at a level comparable to the VZV-gE-del_574_Y569A mRNA construct in HeLa cells (FIGS. 19A and 19B).

Next, the in vivo trafficking and localization of different VZV gE antigens were assessed. HeLa or MeWo cells were plated on 96 well plates and transfected with mRNA constructs encoding NTFIX control, full length VZV-gE, VZV-gE-del_574_Y569A, or VZV-gE-del_574_Y569A-v7 with Lipofectamine 2000 (100 ng mRNA/0.4 μl LF per well). Twenty-four hours after transfection, the cells were fixed in 4% PFA, permeabilized with 0.5% TX-100, and co-stained with rabbit anti-GM130 (CST D6B1-Golgi marker) and mouse anti-gE (Abcam 52549) antibodies at room temperature for 1 h in blocking buffer (1% BSA in PBS). The samples were then washed to remove the primary antibody and were incubated with anti-rabbit Alexa 647 and anti-mouse Alexa 488 conjugated antibodies for 30 minutes at room temperature, followed by counterstaining with DAPI for nuclear localization and HCS blue mask for cell segmentation. Cells were imaged with the Opera Phenix high throughput spinning disk confocal.

Figure 20A:
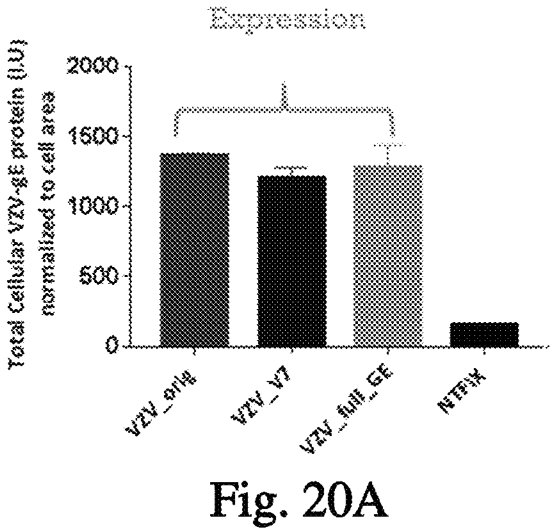
FIGS. 20A-20B are graphs showing the expression (FIG. 20A) and localization (FIG. 20B) of the VZV-gE-del_574_Y569A antigen expressed in HeLa cells transfected with either the VZV-gE-del_574_Y569A mRNA construct or the VZV-gE-del_574_Y569A-v7 mRNA construct.
Figure 20B:
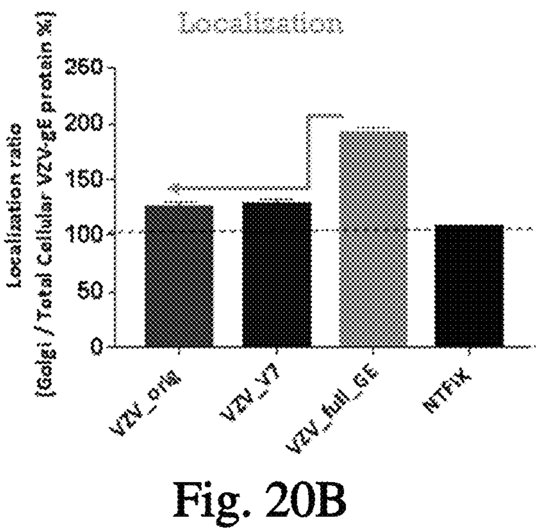
Figure 21A:
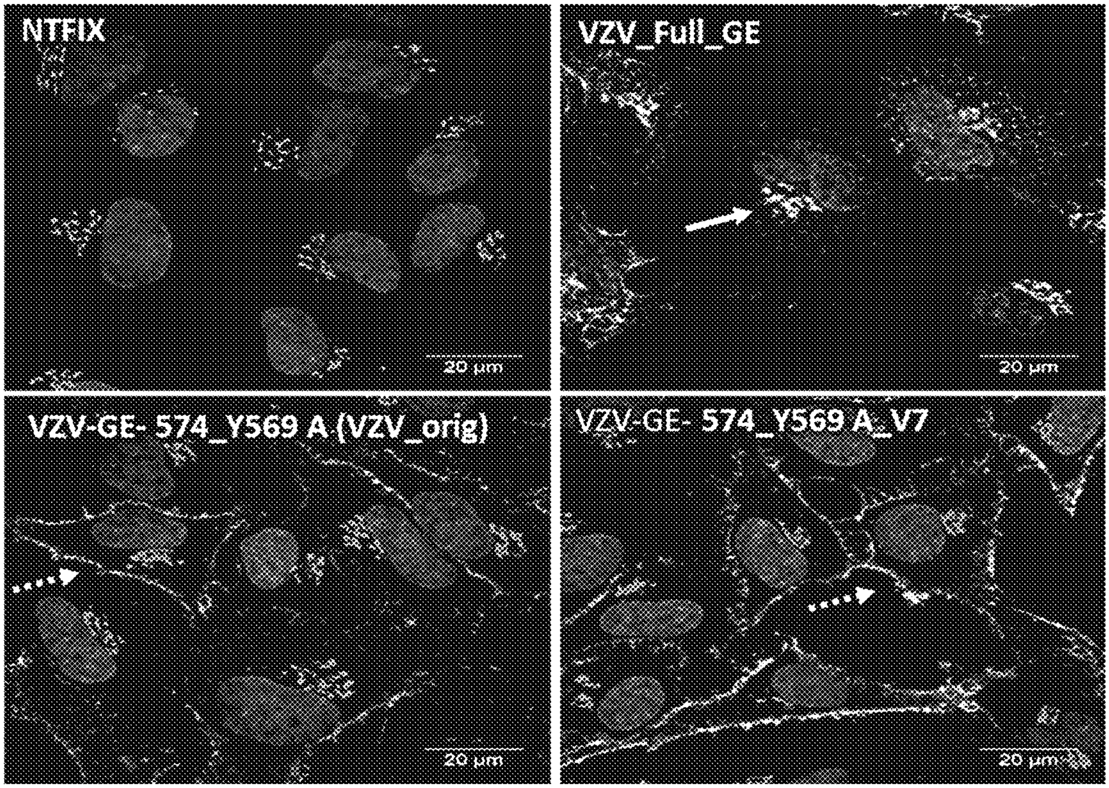
FIGS. 21A-21C are microscopy images showing the localization in HeLa cells (FIG. 21) or MeWo cells (FIGS. 21B and 21C) of full length VZV-gE and VZV-gE-del_574_Y569A antigens encoded by the VZV-gE-del_574_Y569A mRNA construct or the VZV-gE-del_574_Y569A-v7 mRNA construct. The full length VZV gE antigen localized to the golgi, and VZV-gE-del_574_Y569A antigen localized to the cell membrane.
Figure 21B:
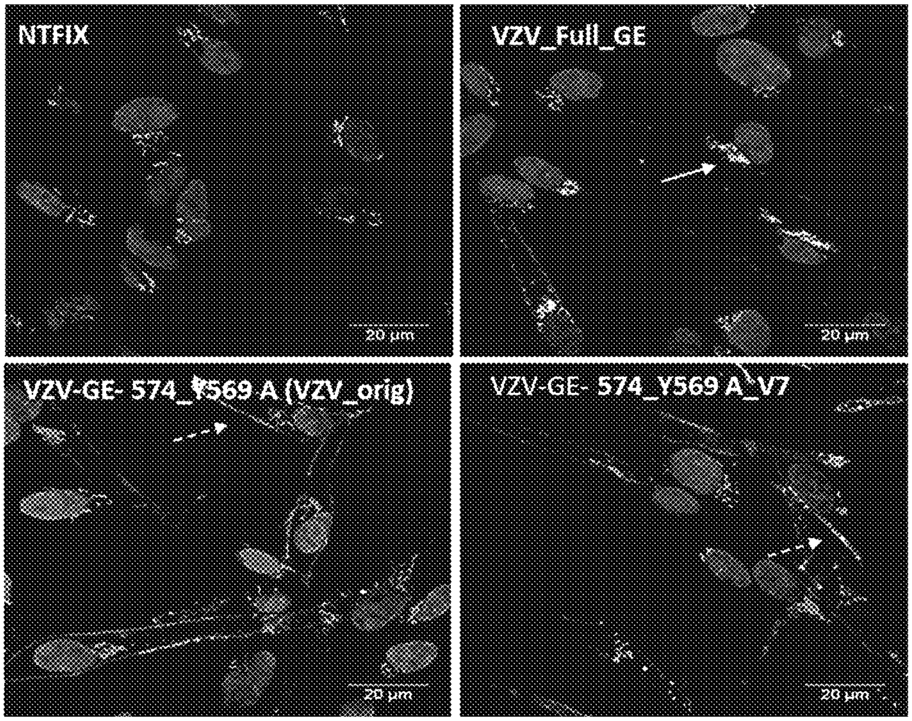
Figure 21C:
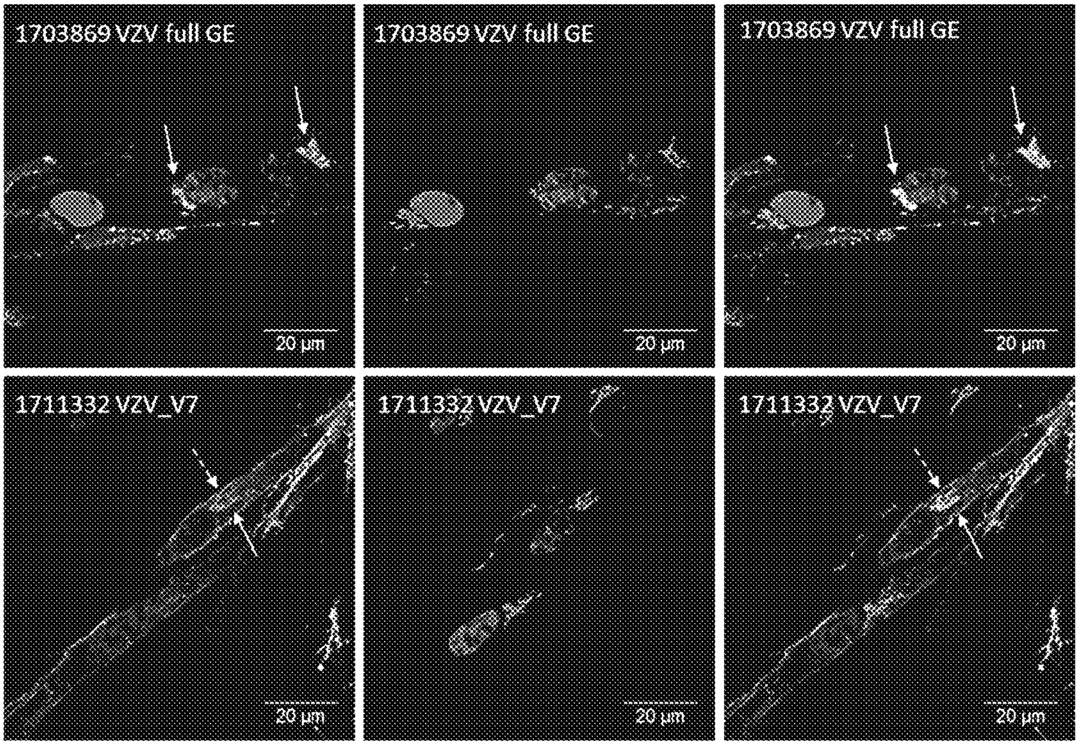
Figure 22A:
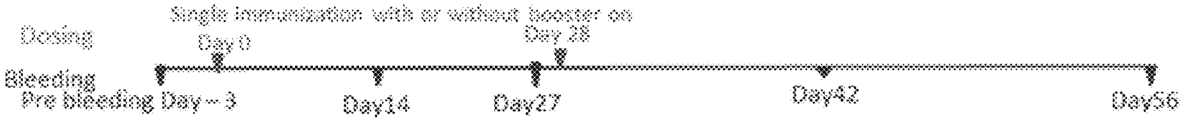
FIGS. 22A-22B show injection schedules.
Figure 22B:
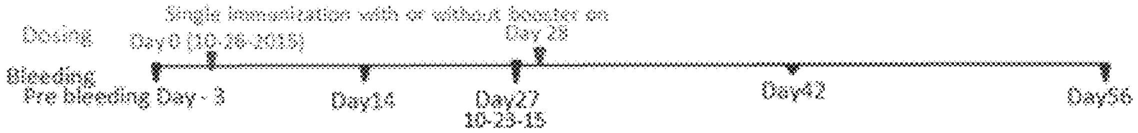

The expression level and the localization of each antigen were quantified. The antigens expressed at comparable levels (FIG. 20A) but VZV-gE-del_574_Y569A encoded by the VZV-gE-del_574_Y569A mRNA construct or the VZV-gE-del_574_Y569A-v7 mRNA construct showed lower golgi localization compared to the full-length VZV-gE (FIG. 20B). A shift in the localization of VZV-gE-del_574_Y569A (encoded by either the VZV-gE-del_574_Y569A mRNA construct or the VZV-gE-del_574_Y569A-v7 mRNA construct) from golgi to the cell membrane, compared to the full-length VZV gE, was observed in HeLA cells (FIG. 21A) and in MeWo cells (FIGS. 21B and 21C).

TABLE 13

Exemplary VZV gE mRNA constructs

| mRNA Construct | ORF of mRNA Construct (excluding the stop codon) |
| --- | --- |
| SE_VZV_gE_full_indel_fixed | AUGGGGACAGUUAAUAAACCUGUGGUGGGGGUAUUGAUGGGGUU<br>CGGAAUUAUCACGGGAACGUUGCGUAUAACGAAUCCGGUCAGAG<br>CAUCCGUCUUGCGAUACGAUGAUUUUCACAUCGAUGAAGACAAA<br>CUGGAUACAAACUCCGUAUAUGAGCCUUACUACCAUUCAGAUCA<br>UGCGGAGUCUUCAUGGGUAAAUCGGGGAGAGUCUUCGCGAAAAG<br>CGUACGAUCAUAACUCACCUUAUAUAUGGCCACGUAAUGAUUAU<br>GAUGGAUUUUUAGAGAACGCACACGAACACCAUGGGGUGUAUAA<br>UCAGGGCCGUGGUAUCGAUAGCGGGGAACGGUUAAUGCAACCCA<br>CACAAAUGUCUGCACAGGAGGAUCUUGGGGACGAUACGGGCAUC<br>CACGUUAUCCCUACGUUAAACGGCGAUGACAGACAUAAAAUUGU<br>AAAUGUGGACCAACGUCAAUACGGUGACGUGUUUAAAGGAGAUC<br>UUAAUCCAAAACCCCAAGGCCAAAGACUCAUUGAGGUGUCAGUG<br>GAAGAAAAUCACCCGUUUACUUUACGCGCACCGAUUCAGCGGAU<br>UUAUGGAGUCCGGUACACCGAGACUUGGAGCUUUUUGCCGUCAU<br>UAACCUGUACGGGAGACGCAGCGCCCGCCAUCCAGCAUAUAUGUU<br>UAAAGCAUACAACAUGCUUUCAAGACGUGGUGGUGGAUGUGGAU<br>UGCGCGGAAAAUACUAAAGAGGAUCAGUUGGCCGAAAUCAGUUA<br>CCGUUUUCAAGGUAAGAAGGAAGCGGACCAACCGUGGAUUGUUG<br>UAAACACGAGCACACUGUUUGAUGAACUCGAAUUAGACCCACCC<br>GAGAUUGAACCGGGUGUCUUGAAAGUACUUCGGACAGAGAAACA<br>AUACUUGGGUGUGUACAUUUGGAACAUGCGCGGCUCCGAUGGUA<br>CGUCUACCUACGCCACGUUUUUGGUCACCUGGAAAGGGGAUGAG<br>AAGACAAGAAACCCUACGCCCGCAGUAACUCCUCAACCAAGAGGG<br>GCUGAGUUUCAUAUGUGGAAUUACCACUCGCAUGUAUUUUCAGU<br>UGGUGAUACGUUUAGCUUGGCAAUGCAUCUUCAGUAUAAGAUAC<br>AUGAAGCGCCAUUUGAUUUGCUGUUAGAGUGGUUGUAUGUCCCC<br>AUCGAUCCUACAUGUCAACCAAUGCGGUUAUAUUCUACGUGUUU<br>GUAUCAUCCCAACGCACCCCAAUGCCUCUCUCAUAUGAAUUCCGG<br>UUGUACAUUUACCUCGCCACAUUUAGCCCAGCGUGUUGCAAGCAC<br>AGUGUAUCAGAAUUGUGAACAUGCAGAUAACUACACCGCAUAUU<br>GUCUGGGAAUAUCUCAUAUGGAGCCUAGCUUUGGUCUAAUCUUA<br>CACGACGGGGGCACCACGUUAAAGUUUGUAGAUACACCCGAGAG<br>UUUGUCGGGAUUAUACGUUUUUGUGGUGUAUUUUAACGGGCAUG<br>UUGAAGCCGUAGCAUACACUGUUGUAUCCACAGUAGAUCAUUUU<br>GUAAACGCAAUUGAAGAGCGUGGAUUUCCGCCAACGGCCGGUCA<br>GCCACCGGCGACUACUAAACCCAAGGAAAUUACCCCCGUAAACCC<br>CGGAACGUCACCACUUCUACGAUAUGCCGCAUGGACCGGAGGGCU<br>UGCAGCAGUAGUACUUUUAUGUCUCGUAAUAUUUUUAAUCUGUA<br>CGGCUAAACGAAUGAGGGUUAAAGCCUACAGGGUAGACAAGUCU<br>CCUUACAAUCAGUCAAUGUACUAUGCAGGACUCCCUGUUGACGA<br>UUUCGAAGACUCAGAGAGUACAGACACAGAAGAAGAAUUCGGAA<br>ACGCUAUAGGUGGCUCUCACGGAGGUAGCUCGUAUACAGUGUAC<br>AUCGAUAAAACCAGA (SEQ ID NO: 142) |
| SE-VZV-GE-574-Y569A-v2 | AUGGGGACAGUUAAUAAACCUGUGGUGGGGGUAUUGAUGGGGUU<br>CGGAAUUAUCACGGGAACGUUGCGUAUAACGAAUCCGGUCAGAG<br>CAUCCGUCUUGCGAUACGAUGAUUUUCACAUCGAUGAAGACAAA<br>CUGGAUACAAACUCCGUAUAUGAGCCUUACUACCAUUCAGAUCA<br>UGCGGAGUCUUCAUGGGUAAAUCGGGGAGAGUCUUCGCGAAAAG<br>CGUACGAUCAUAACUCACCUUAUAUAUGGCCACGUAAUGAUUAU<br>GAUGGAUUUUUAGAGAACGCACACGAACACCAUGGGGUGUAUAA<br>UCAGGGCCGUGGUAUCGAUAGCGGGGAACGGUUAAUGCAACCCA<br>CACAAAUGUCUGCACAGGAGGAUCUUGGGGACGAUACGGGCAUC<br>CACGUUAUCCCUACGUUAAACGGCGAUGACAGACAUAAAAUUGU<br>AAAUGUGGACCAACGUCAAUACGGUGACGUGUUUAAAGGAGAUC<br>UUAAUCCAAAACCCCAAGGCCAAAGACUCAUUGAGGUGUCAGUG<br>GAAGAAAAUCACCCGUUUACUUUACGCGCACCGAUUCAGCGGAU<br>UUAUGGAGUCCGGUACACCGAGACUUGGAGCUUUUUGCCGUCAU<br>UAACCUGUACGGGAGACGCAGCGCCCGCCAUCCAGCAUAUAUGUU<br>UAAAACAUACAACAUGCUUUCAAGACGUGGUGGUGGAUGUGGAU<br>UGCGCGGAAAAUACUAAAGAGGAUCAGUUGGCCGAAAUCAGUUA<br>CCGUUUUCAAGGUAAGAAGGAAGCGGACCAACCGUGGAUUGUUG<br>UAAACACGAGCACACUGUUUGAUGAACUCGAAUUAGACCCCCCCG<br>AGAUUGAACCGGGUGUCUUGAAAGUACUUCGGACAGAGAAACAA<br>UACUUGGGUGUGUACAUUUGGAACAUGCGCGGCUCCGAUGGUAC<br>GUCUACCUACGCCACGUUUUUGGUCACCUGGAAAGGGGAUGAGA<br>AGACAAGAAACCCUACGCCCGCAGUAACUCCUCAACCAAGAGGGG<br>CUGAGUUUCAUAUGUGGAAUUACCACUCGCAUGUAUUUUCAGUU<br>GGUGAUACGUUUAGCUUGGCAAUGCAUCUUCAGUAUAAGAUACA<br>UGAAGCGCCAUUUGAUUUGCUGUUAGAGUGGUUGUAUGUCCCCA<br>UCGAUCCUACAUGUCAACCAAUGCGGUUAUAUUCUACGUGUUUG<br>UAUCAUCCCAACGCACCCCAAUGCCUCUCUCAUAUGAAUUCCGGU<br>UGUACAUUUACCUCGCCACAUUUAGCCCAGCGUGUUGCAAGCACA<br>GUGUAUCAAAAUUGUGAACAUGCAGAUAACUACACCGCAUAUUG<br>UCUGGGAAUAUCUCAUAUGGAGCCUAGCUUUGGUCUAAUCUUAC<br>ACGACGGGGGCACCACGUUAAAGUUUGUAGAUACACCCGAGAGU |

TABLE 13-continued

| Exemplary VZV gE mRNA constructs | |
|---|---|
| mRNA Construct | ORF of mRNA Construct (excluding the stop codon) |
| | UUGUCGGGAUUAUACGUUUUUGUGGUGUAUUUUAACGGGCAUGU UGAAGCCGUAGCAUACACUGUUGUAUCCACAGUAGAUCAUUUUG UAAACGCAAUUGAAGAGCGUGGAUUUCCGCCAACGGCCGGUCAG CCACCGGCGACUACUAAACCCAAGGAAAUUACCCCCGUAAACCCC GGAACGUCACCACUUCUACGAUAUGCCGCAUGGACCGGAGGGCU UGCAGCAGUAGUACUUUUAUGUCUCGUAAUAUUUUUAAUCUGUA CGGCUAAACGAAUGAGGGUUAAAGCCGCCAGGGUAGACAAG (SEQ ID NO: 143) |
| SE-VZV-GE-574-Y569A-v3 | AUGGGGACAGUUAAUAAACCUGUGGUGGGGGUAUUGAUGGGGUU CGGAAUUAUCACGGGAACGUUGCGUAUAACGAAUCCGGUCAGAG CAUCCGUCUUGCGAUACGAUGAUUUUCACAUCGAUGAAGACAAA CUGGAUACAAACUCCGUAUAUGAGCCUUACUACCAUUCAGAUCA UGCGGAGUCUUCAUGGGUAAAUCGGGGAGAGUCUUCGCGAAAAG CGUACGAUCAUAACUCACCUUAUAUAUGGCCACGUAAUGAUUAU GAUGGAUUUUUAGAGAACGCACACGAACACCAUGGGGUGUAUAA UCAGGGCCGUGGUAUCGAUAGCGGGGAACGGUUAAUGCAACCCA CACAAAUGUCUGCACAGGAGGAUCUUGGGGACGAUACGGGCAUC CACGUUAUCCCUACGUUAAACGGCGAUGACAGACAUAAAAUUGU AAAUGUGGACCAACGUCAAUACGGUGACGUGUUUAAAGGAGAUC UUAAUCCAAAACCCCAAGGCCAAAGACUCAUUGAGGUGUCAGUG GAAGAAAAUCACCCGUUUACUUUACGCGCACCGAUUCAGCGGAU UUAUGGAGUCCGGUACACCGAGACUUGGAGCUUUUUGCCGUCAU UAACCUGUACGGGAGACGCAGCGCCCGCCAUCCAGCAUAUAUGUU UAAAACAUACAACAUGCUUUCAAGACGUGGUGGUGGAUGUGGAU UGCGCGGAAAAUACUAAAGAGGAUCAGUUGGCCGAAAUCAGUUA CCGUUUUCAAGGUAAGAAGGAAGCGGACCAACCGUGGAUUGUUG UAAACACGAGCACACUGUUUGAUGAACUCGAAUUAGACCCACCC GAGAUUGAACCGGGUGUCUUGAAAGUACUUCGGACAGAGAAACA AUACUUGGGUGUGUACAUUUGGAACAUGCGCGGCUCCGAUGGUA CGUCUACCUACGCCACGUUUUUGGUCACCUGGAAAGGGGAUGAG AAGACAAGAAACCCUACGCCCGCAGUAACUCCUCAACCAAGAGGG GCUGAGUUUCAUAUGUGGAAUUACCACUCGCAUGUAUUUUCAGU UGGUGAUACGUUUAGCUUGGCAAUGCAUCUUCAGUAUAAGAUAC AUGAAGCGCCAUUUGAUUUGCUGUUAGAGUGGUUGUAUGUCCCC AUCGAUCCUACAUGUCAACCAAUGCGGUUAUAUUCUACGUGUUU GUAUCAUCCCAACGCACCCCAAUGCCUCUCUCAUAUGAAUUCCGG UUGUACAUUUACCUCGCCACAUUUAGCCCAGCGUGUUGCAAGCAC AGUGUAUCAAAAUUGUGAACAUGCAGAUAACUACACCGCAUAUU GUCUGGGAAUAUCUCAUAUGGAGCCUAGCUUUGGUCUAAUCUUA CACGACGGGGGCACCACGUUAAAGUUUGUAGAUACACCCGAGAG UUUGUCGGGAUUAUACGUUUUUGUGGUGUAUUUUAACGGGCAUG UUGAAGCCGUAGCAUACACUGUUGUAUCCACAGUAGAUCAUUUU GUAAACGCAAUUGAAGAGCGUGGAUUUCCGCCAACGGCCGGUCA GCCACCGGCGACUACUAAACCCAAGGAAAUUACCCCCGUAAACCC CGGAACGUCACCACUUCUACGAUAUGCCGCAUGGACCGGAGGGCU UGCAGCAGUAGUACUUUUAUGUCUCGUAAUAUUUUUAAUCUGUA CGGCUAAACGAAUGAGGGUUAAAGCCGCCAGGGUAGACAAG (SEQ ID NO: 144) |
| SE-VZV-GE-574-Y569A-v4 | AUGGGGACAGUUAAUAAACCUGUGGUGGGGGUAUUGAUGGGGUU CGGAAUUAUCACGGGAACGUUGCGUAUAACGAAUCCGGUCAGAG CAUCCGUCUUGCGAUACGAUGAUUUUCACAUCGAUGAAGACAAA CUGGAUACAAACUCCGUAUAUGAGCCUUACUACCAUUCAGAUCA UGCGGAGUCUUCAUGGGUAAAUCGGGGAGAGUCUUCGCGAAAGG CGUACGAUCAUAACUCACCUUAUAUAUGGCCACGUAAUGAUUAU GAUGGAUUUUUAGAGAACGCACACGAACACCAUGGGGUGUAUAA UCAGGGCCGUGGUAUCGAUAGCGGGGAACGGUUAAUGCAACCCA CACAAAUGUCUGCACAGGAGGAUCUUGGGGACGAUACGGGCAUC CACGUUAUCCCUACGUUAAACGGCGAUGACAGACAUAAGAUUGU AAAUGUGGACCAACGUCAAUACGGUGACGUGUUUAAAGGAGAUC UUAAUCCAAAGCCCCAAGGCCAAAGACUCAUUGAGGUGUCAGUG GAAGAGAAUCACCCGUUUACUUUACGCGCACCGAUUCAGCGGAU UUAUGGAGUCCGGUACACCGAGACUUGGAGCUUUUUGCCGUCAU UAACCUGUACGGGAGACGCAGCGCCCGCCAUCCAGCAUAUAUGUU UAAAGCAUACAACAUGCUUUCAAGACGUGGUGGUGGAUGUGGAU UGCGCGGAGAAUACUAAAGAGGAUCAGUUGGCCGAAAUCAGUUA CCGUUUUCAAGGUAAGAAGGAAGCGGACCAACCGUGGAUUGUUG UAAACACGAGCACACUGUUUGAUGAACUCGAAUUAGACCCCCCCG AGAUUGAACCGGGUGUCUUGAAAGUACUUCGGACAGAGAAACAA UACUUGGGUGUGUACAUUUGGAACAUGCGCGGCUCCGAUGGUAC GUCUACCUACGCCACGUUUUUGGUCACCUGGAAAGGGGAUGAGA AGACAAGAAACCCUACGCCCGCAGUAACUCCUCAACCAAGAGGGG CUGAGUUUCAUAUGUGGAAUUACCACUCGCAUGUAUUUUCAGUU GGUGAUACGUUUAGCUUGGCAAUGCAUCUUCAGUAUAAGAUACA UGAAGCGCCAUUUGAUUUGCUGUUAGAGUGGUUGUAUGUCCCCA |

TABLE 13-continued

| Exemplary VZV gE mRNA constructs | |
|---|---|
| mRNA Construct | ORF of mRNA Construct (excluding the stop codon) |
| | UCGAUCCUACAUGUCAACCAAUGCGGUUAUAUUCUACGUGUUUG UAUCAUCCCAACGCACCCCAAUGCCUCUCUCAUAUGAAUUCCGGU UGUACAUUUACCUCGCCACAUUUAGCCCAGCGUGUUGCAAGCACA GUGUAUCAGAAUUGUGAACAUGCAGAUAACUACACCGCAUAUUG UCUGGGAAUAUCUCAUAUGGAGCCUAGCUUUGGUCUAAUCUUAC ACGACGGGGGCACCACGUUAAAGUUUGUAGAUACACCCGAGAGU UUGUCGGGAUUAUACGUUUUUGUGGUGUAUUUUAACGGGCAUGU UGAAGCCGUAGCAUACACUGUUGUAUCCACAGUAGAUCAUUUUG UAAACGCAAUUGAAGAGCGUGGAUUUCCGCCAACGGCCGGUCAG CCACCGGCGACUACUAAACCCAAGGAAAUUACCCCCGUAAACCCC GGAACGUCACCACUUCUACGAUAUGCCGCAUGGACCGGAGGGCU UGCAGCAGUAGUACUUUUAUGUCUCGUAAUAUUUUUAAUCUGUA CGGCUAAACGAAUGAGGGUUAAAGCCGCCAGGGUAGACAA (SEQ ID NO: 145) |
| SE-VZV-GE-574-Y569A-v5 | AUGGGGACAGUUAAUAAACCUGUGGUGGGGGUAUUGAUGGGGUU CGGAAUUAUCACGGGAACGUUGCGUAUAACGAAUCCGGUCAGAG CAUCCGUCUUGCGAUACGAUGAUUUUCACAUCGAUGAAGACAAA CUGGAUACAAACUCCGUAUAUGAGCCUUACUACCAUUCAGAUCA UGCGGAGUCUUCAUGGGUAAAUCGGGGAGAGUCUUCGCGAAAGG CGUACGAUCAUAACUCACCUUAUAUAUGGCCACGUAAUGAUUAU GAUGGAUUUUUAGAGAACGCACACGAACACCAUGGGGUGUAUAA UCAGGGCCGUGGUAUCGAUAGCGGGGAACGGUUAAUGCAACCCA CACAAAUGUCUGCACAGGAGGAUCUUGGGGACGAUACGGGCAUC CACGUUAUCCCUACGUUAAACGGCGAUGACAGACAUAAGAUUGU AAAUGUGGACCAACGUCAAUACGGUGACGUGUUUAAAGGAGAUC UUAAUCCAAAGCCCCAAGGCCAAAGACUCAUUGAGGUGUCAGUG GAAGAGAAUCACCCGUUUACUUUACGCGCACCGAUUCAGCGGAU UUAUGGAGUCCGGUACACCGAGACUUGGAGCUUUUUGCCGUCAU UAACCUGUACGGGAGACGCAGCGCCCGCCAUCCAGCAUAUAUGUU UAAAGCAUACAACAUGCUUUCAAGACGUGGUGGUGGAUGUGGAU UGCGCGGAGAAUACUAAAGAGGAUCAGUUGGCCGAAAUCAGUUA CCGUUUUCAAGGUAAGAAGGAAGCGGACCAACCGUGGAUUGUUG UAAACACGAGCACACUGUUUGAUGAACUCGAAUUAGACCCACCC GAGAUUGAACCGGGUGUCUUGAAAGUACUUCGGACAGAGAAACA AUACUUGGGUGUGUACAUUUGGAACAUGCGCGGCUCCGAUGGUA CGUCUACCUACGCCACGUUUUUGGUCACCUGGAAAGGGGAUGAG AAGACAAGAAACCCUACGCCCGCAGUAACUCCUCAACCAAGAGGG GCUGAGUUUCAUAUGUGGAAUUACCACUCGCAUGUAUUUUCAGU UGGUGAUACGUUUAGCUUGGCAAUGCAUCUUCAGUAUAAGAUAC AUGAAGCGCCAUUUGAUUUGCUGUUAGAGUGGUUGUAUGUCCCC AUCGAUCCUACAUGUCAACCAAUGCGGUUAUAUUCUACGUGUUU GUAUCAUCCCAACGCACCCCAAUGCCUCUCUCAUAUGAAUUCCGG UUGUACAUUUACCUCGCCACAUUUAGCCCAGCGUGUUGCAAGCAC AGUGUAUCAGAAUUGUGAACAUGCAGAUAACUACACCGCAUAUU GUCUGGGAAUAUCUCAUAUGGAGCCUAGCUUUGGUCUAAUCUUA CACGACGGGGGCACCACGUUAAAGUUUGUAGAUACACCCGAGAG UUUGUCGGGAUUAUACGUUUUUGUGGUGUAUUUUAACGGGCAUG UUGAAGCCGUAGCAUACACUGUUGUAUCCACAGUAGAUCAUUUU GUAAACGCAAUUGAAGAGCGUGGAUUUCCGCCAACGGCCGGUCA GCCACCGGCGACUACUAAACCCAAGGAAAUUACCCCCGUAAACCC CGGAACGUCACCACUUCUACGAUAUGCCGCAUGGACCGGAGGGCU UGCAGCAGUAGUACUUUUAUGUCUCGUAAUAUUUUUAAUCUGUA CGGCUAAACGAAUGAGGGUUAAAGCCGCCAGGGUAGACAAG (SEQ ID NO: 146) |
| SE-VZV-GE-574-Y569A-v6 | AUGGGGACAGUUAAUAAACCUGUGGUGGGGGUAUUGAUGGGGUU CGGAAUUAUCACGGGAACGUUGCGUAUAACGAAUCCGGUCAGAG CAUCCGUCUUGCGAUACGAUGAUUUUCACAUCGAUGAAGACAAA CUGGAUACAAACUCCGUAUAUGAGCCUUACUACCAUUCAGAUCA UGCGGAGUCUUCAUGGGUAAAUCGGGGAGAGUCUUCGCGAAAAG CGUACGAUCAUAACUCACCUUAUAUAUGGCCACGUAAUGAUUAU GAUGGAUUUUUAGAGAACGCACACGAACACCAUGGGGUGUAUAA UCAGGGCCGUGGUAUCGAUAGCGGGGAACGGUUAAUGCAACCCA CACAAAUGUCUGCACAGGAGGAUCUUGGGGACGAUACGGGCAUC CACGUUAUCCCUACGUUAAACGGCGAUGACAGACAUAAAAUUGU AAAUGUGGACCAACGUCAAUACGGUGACGUGUUUAAAGGAGAUC UUAAUCCAAAACCCCAAGGCCAAAGACUCAUUGAGGUGUCAGUG GAAGAAAAUCACCCGUUUACUUUACGCGCACCGAUUCAGCGGAU UUAUGGAGUCCGGUACACCGAGACUUGGAGCUUUUUGCCGUCAU UAACCUGUACGGGAGACGCAGCGCCCGCCAUCCAGCAUAUAUGUU UAAAGCAUACAACAUGCUUUCAAGACGUGGUGGUGGAUGUGGAU UGCGCGGAAAAUACUAAAGAGGAUCAGUUGGCCGAAAUCAGUUA CCGUUUUCAAGGUAAGAAGGAAGCGGACCAACCGUGGAUUGUUG UAAACACGAGCACACUGUUUGAUGAACUCGAAUUAGACCCCCCCG AGAUUGAACCGGGUGUCUUGAAAGUACUUCGGACAGAGAAACAA |

TABLE 13-continued

| Exemplary VZV gE mRNA constructs | |
|---|---|
| mRNA Construct | ORF of mRNA Construct (excluding the stop codon) |
| | UACUUGGGUGUGUACAUUUGGAACAUGCGCGGCUCCGAUGGUAC<br>GUCUACCUACGCCACGUUUUUGGUCACCUGGAAAGGGGAUGAGA<br>AGACAAGAAACCCUACGCCCGCAGUAACUCCUCAACCAAGAGGGG<br>CUGAGUUUCAUAUGUGGAAUUACCACUCGCAUGUAUUUUCAGUU<br>GGUGAUACGUUUAGCUUGGCAAUGCAUCUUCAGUAUAAGAUACA<br>UGAAGCGCCAUUUGAUUUGCUGUUAGAGUGGUUGUAUGUCCCCA<br>UCGAUCCUACAUGUCAACCAAUGCGGUUAUAUUCUACGUGUUUG<br>UAUCAUCCCAACGCACCCCAAUGCCUCUCUCAUAUGAAUUCCGGU<br>UGUACAUUUACCUCGCCACAUUUAGCCCAGCGUGUUGCAAGCACA<br>GUGUAUCAGAAUUGUGAACAUGCAGAUAACUACACCGCAUAUUG<br>UCUGGGAAUAUCUCAUAUGGAGCCUAGCUUUGGUCUAAUCUUAC<br>ACGACGGGGGCACCACGUUAAAGUUUGUAGAUACACCCGAGAGU<br>UUGUCGGGAUUAUACGUUUUUGUGGUGUAUUUUAACGGGCAUGU<br>UGAAGCCGUAGCAUACACUGUUGUAUCCACAGUAGAUCAUUUUG<br>UAAACGCAAUUGAAGAGCGUGGAUUUCCGCCAACGGCCGGUCAG<br>CCACCGGCGACUACUAAACCCAAGGAAAUUACCCCCGUAAACCCC<br>GGAACGUCACCACUUCUACGAUAUGCCGCAUGGACCGGAGGGCU<br>UGCAGCAGUAGUACUUUUAUGUCUCGUAAUAUUUUUAAUCUGUA<br>CGGCUAAACGAAUGAGGGUUAAAGCCGCCAGGGUAGACAAG (SEQ<br>ID NO: 147) |
| SE-VZV-GE-574-Y569A-v7 | AUGGGGACAGUUAAUAAACCUGUGGUGGGGGUAUUGAUGGGGUU<br>CGGAAUUAUCACGGGAACGUUGCGUAUAACGAAUCCGGUCAGAG<br>CAUCCGUCUUGCGAUACGAUGAUUUUCACAUCGAUGAAGACAAA<br>CUGGAUACAAACUCCGUAUAUGAGCCUUACUACCAUUCAGAUCA<br>UGCGGAGUCUUCAUGGGUAAAUCGGGGAGAGUCUUCGCGAAAAG<br>CGUACGAUCAUAACUCACCUUAUAUAUGGCCACGUAAUGAUUAU<br>GAUGGAUUUUUAGAGAACGCACACGAACACCAUGGGGUGUAUAA<br>UCAGGGCCGUGGUAUCGAUAGCGGGGAACGGUUAAUGCAACCCA<br>CACAAAUGUCUGCACAGGAGGAUCUUGGGGACGAUACGGGCAUC<br>CACGUUAUCCCUACGUUAAACGGCGAUGACAGACAUAAAAUUGU<br>AAAUGUGGACCAACGUCAAUACGGUGACGUGUUUAAAGGAGAUC<br>UUAAUCCAAAACCCCAAGGCCAAAGACUCAUUGAGGUGUCAGUG<br>GAAGAAAAUCACCCGUUUACUUUACGCGCACCGAUUCAGCGGAU<br>UUAUGGAGUCCGGUACACCGAGACUUGGAGCUUUUUGCCGUCAU<br>UAACCUGUACGGGAGACGCAGCGCCCGCCAUCCAGCAUAUAUGUU<br>UAAAGCAUACAACAUGCUUUCAAGACGUGGUGGUGGAUGUGGAU<br>UGCGCGGAAAAUACUAAAGAGGAUCAGUUGGCCGAAAUCAGUUA<br>CCGUUUUCAAGGUAAGAAGGAAGCGGACCAACCGUGGAUUGUUG<br>UAAACACGAGCACACUGUUUGAUGAACUCGAAUUAGACCCACCC<br>GAGAUUGAACCGGGUGUCUUGAAAGUACUUCGGACAGAGAAACA<br>AUACUUGGGUGUGUACAUUUGGAACAUGCGCGGCUCCGAUGGUA<br>CGUCUACCUACGCCACGUUUUUGGUCACCUGGAAAGGGGAUGAG<br>AAGACAAGAAACCCUACGCCCGCAGUAACUCCUCAACCAAGAGGG<br>GCUGAGUUUCAUAUGUGGAAUUACCACUCGCAUGUAUUUUCAGU<br>UGGUGAUACGUUUAGCUUGGCAAUGCAUCUUCAGUAUAAGAUAC<br>AUGAAGCGCCAUUUGAUUUGCUGUUAGAGUGGUUGUAUGUCCCC<br>AUCGAUCCUACAUGUCAACCAAUGCGGUUAUAUUCUACGUGUUU<br>GUAUCAUCCCAACGCACCCCAAUGCCUCUCUCAUAUGAAUUCCGG<br>UUGUACAUUUACCUCGCCACAUUUAGCCCAGCGUGUUGCAAGCAC<br>AGUGUAUCAGAAUUGUGAACAUGCAGAUAACUACACCGCAUAUU<br>GUCUGGGAAUAUCUCAUAUGGAGCCUAGCUUUGGUCUAAUCUUA<br>CACGACGGGGGCACCACGUUAAAGUUUGUAGAUACACCCGAGAG<br>UUUGUCGGGAUUAUACGUUUUUGUGGUGUAUUUUAACGGGCAUG<br>UUGAAGCCGUAGCAUACACUGUUGUAUCCACAGUAGAUCAUUUU<br>GUAAACGCAAUUGAAGAGCGUGGAUUUCCGCCAACGGCCGGUCA<br>GCCACCGGCGACUACUAAACCCAAGGAAAUUACCCCCGUAAACCC<br>CGGAACGUCACCACUUCUACGAUAUGCCGCAUGGACCGGAGGGCU<br>UGCAGCAGUAGUACUUUUAUGUCUCGUAAUAUUUUUAAUCUGUA<br>CGGCUAAACGAAUGAGGGUUAAAGCCGCCAGGGUAGACAAG (SEQ<br>ID NO: 148) |
| SE-VZV-GE-574-Y569A-v8 | AUGGGGACAGUUAAUAAACCUGUGGUGGGCGUAUUGAUGGGGUU<br>CGGAAUUAUCACGGGAACGUUGCGUAUAACGAAUCCGGUCAGAG<br>CAUCCGUCUUGCGAUACGAUGAUUUUCACAUCGAUGAAGACAAA<br>CUGGAUACAAACUCCGUAUAUGAGCCUUACUACCAUUCAGAUCA<br>UGCGGAGUCUUCAUGGGUAAAUCGGGGAGAGUCUUCGCGAAAGG<br>CGUACGAUCAUAACUCACCUUAUAUAUGGCCACGUAAUGAUUAU<br>GAUGGAUUCUUAGAGAACGCACACGAACACCAUGGGGUGUAUAA<br>UCAGGGCCGUGGUAUCGAUAGCGGGGAACGGUUAAUGCAACCCA<br>CACAAAUGUCUGCACAGGAGGAUCUUGGGGACGAUACGGGCAUC<br>CACGUUAUCCCUACGUUAAACGGCGAUGACAGACAUAAGAUUGU<br>AAAUGUGGACCAACGUCAAUACGGUGACGUGUUUAAAGGAGAUC<br>UUAAUCCAAAGCCCCAAGGCCAAAGACUCAUUGAGGUGUCAGUG<br>GAAGAGAAUCACCCGUUUACUUUACGCGCACCGAUUCAGCGGAU<br>UUAUGGAGUCCGGUACACCGAGACUUGGAGCUUCUUGCCGUCAU |

TABLE 13-continued

| Exemplary VZV gE mRNA constructs | |
|---|---|
| mRNA Construct | ORF of mRNA Construct (excluding the stop codon) |
| | UAACCUGUACGGGAGACGCAGCGCCCGCCAUCCAGCAUAUAUGUU UAAAGCAUACAACAUGCUUUCAAGACGUGGUGGUGGAUGUGGAU UGCGCGGAGAAUACUAAAGAGGAUCAGUUGGCCGAAAUCAGUUA CCGUUUUCAAGGUAAGAAGGAAGCGGACCAACCGUGGAUUGUUG UAAACACGAGCACACUGUUUGAUGAACUCGAAUUAGACCCACCC GAGAUUGAACCGGGUGUCUUGAAAGUACUUCGGACAGAGAAACA AUACUUGGGUGUGUACAUUUGGAACAUGCGCGGCUCCGAUGGUA CGUCUACCUACGCCACGUUCUUGGUCACCUGGAAAGGGGAUGAG AAGACAAGAAACCCUACGCCCGCAGUAACUCCUCAACCAAGAGGG GCUGAGUUUCAUAUGUGGAAUUACCACUCGCAUGUAUUUUCAGU UGGUGAUACGUUUAGCUUGGCAAUGCAUCUUCAGUAUAAGAUAC AUGAAGCGCCAUUUGAUUUGCUGUUAGAGUGGUUGUAUGUCCCC AUCGAUCCUACAUGUCAACCAAUGCGGUUAUAUUCUACGUGUUU GUAUCAUCCCAACGCACCCCAAUGCCUCUCUCAUAUGAAUUCCGG UUGUACAUUUACCUCGCCACAUUUAGCCCAGCGUGUUGCAAGCAC AGUGUAUCAGAAUUGUGAACAUGCAGAUAACUACACCGCAUAUU GUCUGGGAAUAUCUCAUAUGGAGCCUAGCUUUGGUCUAAUCUUA CACGACGGAGGCACCACGUUAAAGUUUGUAGAUACACCCGAGAG UUUGUCGGGAUUAUACGUCUUUGUGGUGUAUUUUAACGGGCAUG UUGAAGCCGUAGCAUACACUGUUGUAUCCACAGUAGAUCAUUUU GUAAACGCAAUUGAAGAGCGUGGAUUUCCGCCAACGGCCGGUCA GCCACCGGCGACUACUAAACCCAAGGAAAUUACGCCCGUAAACCC CGGAACGUCACCACUUCUACGAUAUGCCGCAUGGACCGGAGGGCU UGCAGCAGUAGUACUUUUAUGUCUCGUAAUAUUCUUAAUCUGUA CGGCUAAACGAAUGAGGGUUAAAGCCGCCAGGGUAGACAAG (SEQ ID NO: 149) |
| VZV-GE-Truncated-modified-V9 | AUGGGCACCGUGAACAAGCCUGUUGUGGGCGUGCUGAUGGGCUU CGGCAUCAUCACAGGCACCCUGCGGAUCACCAAUCCUGUGCGGGC UAGCGUGCUGAGAUACGACGACUUCCACAUCGACGAGGACAAGC UGGACACCAACAGCGUGUACGAGCCCUACUACCACAGCGAUCACG CCGAGUCUAGCUGGGUCAACAGAGGCGAGAGCAGCAGAAAGGCC UACGACCACAACAGCCCUUACAUCUGGCCCAGAAACGACUACGAC GGCUUCCUCGAGAAUGCCCACGAACACCACGGCGUGUACAAUCAA GGCAGAGGCAUCGACAGCGGCGAGAGACUGAUGCAGCCUACACA GAUGAGCGCCCAAGAGGACCUGGGAGAUGAUACCGGCAUCCACG UGAUCCCUACACUGAACGGCGACGACCGGCACAAGAUCGUGAACG UGGACCAGAGACAGUACGGCGACGUGUUCAAGGGCGACCUGAAU CCUAAGCCUCAGGGCCAGCGCCUGAUCGAGGUUUCCGUGGAAGA GAAUCACCCUUUCACACUGCGGGCUCCCAUCCAGAGAAUCUACGG CGUGCGCUAUACCGAGACAUGGUCCUUUCUGCCCAGCCUGACAUG UACCGGCGACGCCGCUCCUGCCAUCCAGCACAUUUGUCUGAAGCA CACCACCUGUUUCCAGGACGUGGUGGUGGAUGUGGACUGCGCCG AGAACACCAAAGAGGAUCAGCUGGCCGAGAUCAGCUACCGGUUC CAGGGAAAGAAAGAGGCCGACCAGCCUUGGAUCGUGGUCAACAC CAGCACACUGUUCGACGAGCUGGAACUGGACCCUCCUGAGAUUG AACCCGGCGUCCUGAAGGUGCUGAGAACCGAGAAGCAGUACCUG GGAGUGUACAUCUGGAACAUGAGAGGCAGCGACGGCACCUCUAC CUACGCCACCUUUCUGGUCACAUGGAAGGGCGACGAGAAGACCA GAAAUCCCACACCAGCCGUGACACCUCAGCCUAGAGGCGCCGAAU UUCACAUGUGGAACUACCACUCUCACGUGUUCAGCGUGGGCGAU ACCUUCAGCCUGGCCAUGCAUCUGCAGUACAAGAUCCACGAGGCU CCCUUCGACCUGCUGCUGGAAUGGCUGUACGUGCCCAUCGAUCCU ACCUGCCAGCCUAUGCGGCUGUACUCCACCUGUCUGUAUCACCCU AACGCUCCUCAGUGCCUGAGCCACAUGAAUAGCGGCUGCACCUUC ACAAGCCCUCACCUGGCUCAGCGAGUGGCCAGCACAGUGUACCAG AAUUGCGAGCACGCCGACAAUUACACCGCCUACUGUCUGGGCAUC AGCCACAUGGAACCUAGCUUCGGCCUGAUCCUGCACGAUGGCGGC ACCACACUGAAGUUCGUGGACACACCUGAGAGCCUGAGCGGCCUG UAUGUGUUUGUGGUGUACUUCAACGGCCACGUGGAAGCCGUGGC CUACACCGUGGUGUCUACCGUGGACCACUUCGUGAACGCCAUCGA GGAAAGAGGCUUCCCUCCAACUGCUGGACAGCCUCCUGCCACCAC CAAGCCUAAAGAAAUCACACCCGUGAAUCCCGGCACUAGCCCUCU GCUUAGAUACGCCGCUUGGACAGGCGGACUGGCUGCUGUUGUUC UGCUGUGCCUGGUCAUCUUCCUGAUCUGCACCGCCAAGCGGAUGA GAGUGAAAGCCGCCAGAGUGGACAAG (SEQ ID NO: 150) |
| Corresponding amino acid sequence | MGTVNKPVVGVLMGFGIITGTLRITNPVRASVLRYDDFHIDEDKLDTN SVYEPYYHSDHAESSWVNRGESSRKAYDHNSPYIWPRNDYDGFLENA HEHHGVYNQGRGIDSGERLMQPTQMSAQEDLGDDTGIHVIPTLNGDD RHKIVNVDQRQYGDVFKGDLNPKPQGQRLIEVSVEENHPFTLRAPIQRI YGVRYTETWSFLPSLTCTGDAAPAIQHICLKHTTCFQDVVVDVDCAEN TKEDQLAEISYRFQGKKEADQPWIVVNTSTLFDELELDPPEIEPGVLKV LRTEKQYLGVYIWNMRGSDGTSTYATFLVTWKGDEKTRNPTPAVTPQ PRGAEFHMWNYHSHVFSVGDTFSLAMHLQYKIHEAPFDLLLEWLYVP IDPTCQPMRLYSTCLYHPNAPQCLSHMNSGCTFTSPHLAQRVASTVYQ |

TABLE 13-continued

| Exemplary VZV gE mRNA constructs | |
|---|---|
| mRNA Construct | ORF of mRNA Construct (excluding the stop codon) |
| | NCEHADNYTAYCLGISHMEPSFGLILHDGGTTLKFVDTPESLSGLYVFV VYFNGHVEAVAYTVVSTVDHFVNAIEERGFPPTAGQPPATTKPKEITP VNPGTSPLLRYAAWTGGLAAVVLLCLVIFLICTAKRMRVKAARVDK (SEQ ID NO: 38) |
| 5' UTR | GGGAAAUAAGAGAGAAAAGAAGAGUAAGAAGAAAUAUAAGAGCC ACC (SEQ ID NO: 138) |
| 3' UTR | UGAUAAUAGGCUGGAGCCUCGGUGGCCAUGCUUCUUGCCCCUUG GGCCUCCCCCCAGCCCCUCCUCCCCUUCCUGCACCCGUACCCCCGU GGUCUUUGAAUAAAGUCUGAGUGGGCGGC (SEQ ID NO: 139) |
| PolyA Tail | 100 nt (SEQ ID NO: 140) |

TABLE 14

Varicella zoster virus Amino Acid Sequences

| Protein | Name | GenBank Accession |
|---|---|---|
| glycoprotein B | envelope glycoprotein B [Human herpesvirus 3] | NP_040154.2 |
| glycoprotein B | ORF31 [Human herpesvirus 3] | AKG57704.1 |
| glycoprotein B | ORF 31 [Human herpesvirus 3] | AIT52967.1 |
| glycoprotein B | envelope glycoprotein B [Human herpesvirus 3] | AFJ68532.1 |
| glycoprotein B | ORF31 [Human herpesvirus 3] | AKG57414.1 |
| glycoprotein B | ORF31 [Human herpesvirus 3] | AKG58507.1 |
| glycoprotein B | RecName: Full = Envelope glycoprotein B; Short = gB; AltName: Full = Glycoprotein II; Flags: Precursor [Human herpesvirus 3 strain Oka vaccine] | Q4JR05.2 |
| glycoprotein B | ORF31 [Human herpesvirus 3] | AEL30845.1 |
| glycoprotein B | glycoprotein B [Human herpesvirus 3] | AAK01041.1 |
| glycoprotein B | glycoprotein B [Human herpesvirus 3] | AEW89232.1 |
| glycoprotein B | glycoprotein B [Human herpesvirus 3] | AEW88728.1 |
| glycoprotein B | ORF31 [Human herpesvirus 3] | AAK19938.1 |
| glycoprotein B | glycoprotein B [Human herpesvirus 3] | AAP32845.1 |
| glycoprotein B | ORF 31 [Human herpesvirus 3] | AHJ08729.1 |
| glycoprotein B | ORF31 [Human herpesvirus 3] | AAY57715.1 |
| glycoprotein B | ORF31 [Human herpesvirus 3] | AGY33726.1 |
| glycoprotein B | ORF 31 [Human herpesvirus 3] | AHJ09321.1 |
| glycoprotein B | ORF31 [Human herpesvirus 3] | AAY57644.1 |
| glycoprotein B | ORF 31 [Human herpesvirus 3] | AHJ09025.1 |
| glycoprotein B | glycoprotein B [Human herpesvirus 3] | AEW88584.1 |
| glycoprotein B | ORF 31 [Human herpesvirus 3] | AHJ09099.1 |
| glycoprotein B | ORF31 [Human herpesvirus 3] | AGY33060.1 |
| glycoprotein B | ORF 31 [Human herpesvirus 3] | AHJ09395.1 |
| glycoprotein C | RecName: Full = Envelope glycoprotein C; Short = gC; AltName: Full = Glycoprotein V; Short = gpV | P09256.2 |
| glycoprotein C | envelope glycoprotein gC [Human herpesvirus 3] | ABH08453.1 |
| glycoprotein C | ORF14 [Human herpesvirus 3] | AIH07125.1 |
| glycoprotein C | unknown protein [Human herpesvirus 3] | AAA69563.1 |
| glycoprotein C | ORF14 [Human herpesvirus 3] | AIH07051.1 |
| glycoprotein C | ORF14 [Human herpesvirus 3] | AIJ28607.1 |
| glycoprotein C | ORF14 [Human herpesvirus 3] | AEL30828.1 |
| glycoprotein C | envelope glycoprotein gC [Human herpesvirus 3] | ABE03032.1 |
| glycoprotein C | envelope glycoprotein gC [Human herpesvirus 3] | ABE67122.1 |
| glycoprotein C | envelope glycoprotein C [Human herpesvirus 3] | NP_040137.1 |
| glycoprotein C | membrane glycoprotein C [Human herpesvirus 3] | AEW88351.1 |
| glycoprotein C | envelope glycoprotein C [Human herpesvirus 3] | AFJ68515.1 |
| glycoprotein C | membrane glycoprotein C [Human herpesvirus 3] | AAT07696.1 |
| glycoprotein C | envelope glycoprotein gC [Human herpesvirus 3] | ABF22098.1 |
| glycoprotein C | membrane glycoprotein C [Human herpesvirus 3] | AEW89287.1 |
| glycoprotein C | glycoprotein C [Human herpesvirus 3] | AGC94505.1 |
| glycoprotein C | envelope glycoprotein gC [Human herpesvirus 3] | ABF21514.1 |
| glycoprotein C | envelope glycoprotein gC [Human herpesvirus 3] | ABF21879.1 |
| glycoprotein C | envelope glycoprotein gC [Human herpesvirus 3] | ABF21587.1 |
| glycoprotein C | ORF 14 [Human herpesvirus 3] | AIT53315.1 |
| glycoprotein C | membrane glycoprotein C [Human herpesvirus 3] | AEW89215.1 |
| glycoprotein C | envelope glycoprotein gC [Human herpesvirus 3] | ABF21660.1 |
| glycoprotein C | membrane glycoprotein C [Human herpesvirus 3] | AEW88567.1 |
| glycoprotein C | envelope glycoprotein gC [Human herpesvirus 3] | CAI44857.1 |
| glycoprotein C | envelope glycoprotein C [Human herpesvirus 3] | AHB80244.1 |
| glycoprotein C | ORF14 [Human herpesvirus 3] | AAY57702.1 |

TABLE 14-continued

Varicella zoster virus Amino Acid Sequences

| Protein | Name | GenBank Accession |
|---|---|---|
| glycoprotein C | glycoprotein c [Human herpesvirus 3] | AGS32072.1 |
| glycoprotein C | envelope glycoprotein gC [Human herpesvirus 3] | AGL50971.1 |
| glycoprotein C | membrane glycoprotein C [Human herpesvirus 3] | AAT07772.1 |
| glycoprotein C | membrane glycoprotein C [Human herpesvirus 3] | AEW88495.1 |
| glycoprotein C | ORF 14 [Human herpesvirus 3] | AIT53461.1 |
| glycoprotein C | ORF 14 [Human herpesvirus 3] | AIT52950.1 |
| glycoprotein C | ORF14 [Human herpesvirus 3] | AAY57631.1 |
| glycoprotein C | envelope glycoprotein gC [Human herpesvirus 3] | ABF21952.1 |
| glycoprotein C | membrane glycoprotein C [Human herpesvirus 3] | AEW89143.1 |
| glycoprotein C | membrane glycoprotein C [Human herpesvirus 3] | AEW88783.1 |
| glycoprotein C | membrane glycoprotein C [Human herpesvirus 3] | AEW88999.1 |
| glycoprotein C | membrane glycoprotein C [Human herpesvirus 3] | AEW88063.1 |
| glycoprotein C | membrane glycoprotein C [Human herpesvirus 3] | AEW89071.1 |
| glycoprotein C | membrane glycoprotein C [Human herpesvirus 3] | AEW88639.1 |
| glycoprotein C | membrane glycoprotein C [Human herpesvirus 3] | AEW87991.1 |
| glycoprotein C | ORF 14 [Human herpesvirus 3] | AIT53753.1 |
| glycoprotein C | ORF 14 [Human herpesvirus 3] | AIT53096.1 |
| glycoprotein C | envelope glycoprotein gC [Human herpesvirus 3] | ABF22025.1 |
| glycoprotein C | envelope glycoprotein gC [Human herpesvirus 3] | AFO85518.1 |
| glycoprotein C | envelope glycoprotein gC [Human herpesvirus 3] | ABF21733.1 |
| glycoprotein C | envelope glycoprotein gC [Human herpesvirus 3] | ABF21806.1 |
| glycoprotein C | membrane glycoprotein C [Human herpesvirus 3] | AEW89359.1 |
| glycoprotein C | membrane glycoprotein C [Human herpesvirus 3] | AEW88855.1 |
| glycoprotein C | envelope glycoprotein gC [Human herpesvirus 3] | AFO85591.1 |
| glycoprotein C | membrane glycoprotein C [Human herpesvirus 3] | AEW89431.1 |
| glycoprotein C | membrane glycoprotein C [Human herpesvirus 3] | AEW88711.1 |
| glycoprotein C | membrane glycoprotein C [Human herpesvirus 3] | AEW88135.1 |
| glycoprotein C | membrane glycoprotein C [Human herpesvirus 3] | AEW88927.1 |
| glycoprotein C | ORF14 [Human herpesvirus 3] | AKG56156.1 |
| glycoprotein C | ORF14 [Human herpesvirus 3] | AKG57178.1 |
| glycoprotein C | ORF14 [Human herpesvirus 3] | AKG58125.1 |
| glycoprotein C | ORF14 [Human herpesvirus 3] | AGY32970.1 |
| glycoprotein C | ORF14 [Human herpesvirus 3] | AKG56229.1 |
| glycoprotein C | ORF14 [Human herpesvirus 3] | AGY32896.1 |
| glycoprotein C | ORF14 [Human herpesvirus 3] | AKG56521.1 |
| glycoprotein C | ORF 14 [Human herpesvirus 3] | AHJ08712.1 |
| glycoprotein E | unknown [Human herpesvirus 3] | ABE03086.1 |
| glycoprotein E | glycoprotein E [Human herpesvirus 3] | AAK01047.1 |
| glycoprotein E | RecName: Full = Envelope glycoprotein E; Short = gE; Flags: Precursor | Q9J3M8.1 |
| glycoprotein E | membrane glycoprotein E [Human herpesvirus 3] | AEW88548.1 |
| glycoprotein E | ORF68 [Human herpesvirus 3] | AGY33616.1 |
| glycoprotein E | membrane glycoprotein E [Human herpesvirus 3] | AEW89124.1 |
| glycoprotein E | ORF 68 [Human herpesvirus 3] | AIT53150.1 |
| glycoprotein E | unnamed protein product [Human herpesvirus 3] | CAA25033.1 |
| glycoprotein E | envelope glycoprotein E [Human herpesvirus 3] | NP_040190.1 |
| glycoprotein E | ORF68 [Human herpesvirus 3] | AKG56356.1 |
| glycoprotein E | membrane glycoprotein E [Human herpesvirus 3] | AEW89412.1 |
| glycoprotein E | membrane glycoprotein gE [Human herpesvirus 3] | ABF21714.1 |
| glycoprotein E | membrane glycoprotein E [Human herpesvirus 3] | AAT07749.1 |
| glycoprotein E | membrane glycoprotein E [Human herpesvirus 3] | AEW88764.1 |
| glycoprotein E | glycoprotein E [Human herpesvirus 3] | AAG48520.1 |
| glycoprotein E | membrane glycoprotein E [Human herpesvirus 3] | AEW88980.1 |
| glycoprotein H | envelope glycoprotein H [Human herpesvirus 3] | NP_040160.1 |
| glycoprotein H | glycoprotein H [Human herpesvirus 3] | AEW89454.1 |
| glycoprotein H | ORF37 [Human herpesvirus 3 VZV-32] | AAK19252.1 |
| glycoprotein H | RecName: Full = Envelope glycoprotein H; Short = gH; AltName: Full = Glycoprotein III; Short = GPIII; Flags:Precursor | Q775J3.1 |
| glycoprotein H | glycoprotein H [Human herpesvirus 3] | AAK01042.1 |
| glycoprotein H | ORF37 [Human herpesvirus 3] | AKG58587.1 |
| glycoprotein H | ORF37 [Human herpesvirus 3] | AGY33215.1 |
| glycoprotein H | glycoprotein H [Human herpesvirus 3] | AAP32857.1 |
| glycoprotein H | envelope glycoprotein gH [Human herpesvirus 3] | ABE03056.1 |
| glycoprotein H | ORF 37 [Human herpesvirus 3] | AHJ09328.1 |
| glycoprotein H | glycoprotein H [Human herpesvirus 3] | AAP32862.1 |
| glycoprotein H | ORF37 [Human herpesvirus 3] | AKG57421.1 |
| glycoprotein H | ORF37 [Human herpesvirus 3] | AKG56618.1 |
| glycoprotein H | ORF37 [Human herpesvirus 3] | AKG56545.1 |
| glycoprotein H | glycoprotein H [Human herpesvirus 3] | AEW89382.1 |
| glycoprotein H | glycoprotein H [Human herpesvirus 3] | AGC94548.1 |
| glycoprotein I | envelope glycoprotein I [Human herpesvirus 3] | NP_040189.1 |
| glycoprotein I | membrane glycoprotein I [Human herpesvirus 3] | AEW89195.1 |
| glycoprotein I | ORF67 [Human herpesvirus 3] | AKG58616.1 |
| glycoprotein I | ORF67 [Human herpesvirus 3] | AGY34059.1 |
| glycoprotein I | membrane glycoprotein I [Human herpesvirus 3] | AEW89051.1 |

TABLE 14-continued

| Varicella zoster virus Amino Acid Sequences | | |
|---|---|---|
| Protein | Name | GenBank Accession |
| glycoprotein I | ORF67 [Human herpesvirus 3 VZV-32] | AAK19249.1 |
| glycoprotein I | membrane glycoprotein I [Human herpesvirus 3] | AEW89483.1 |
| glycoprotein K | envelope glycoprotein K [Human herpesvirus 3] | NP_040128.1 |
| glycoprotein K | glycoprotein K [Human herpesvirus 3] | AEW88773.1 |
| glycoprotein K | ORF 5 [Human herpesvirus 3] | AHJ09368.1 |
| glycoprotein K | ORF5 [Human herpesvirus 3] | AKG58699.1 |
| glycoprotein K | glycoprotein K [Human herpesvirus 3] | AEW88701.1 |
| glycoprotein K | ORF5 [Human herpesvirus 3] | AKG56803.1 |
| glycoprotein K | glycoprotein K [Human herpesvirus 3] | AEW88053.1 |
| glycoprotein L | RecName: Full = Envelope glycoprotein L; Short = gL; Flags: Precursor | Q9J3N1.1 |
| glycoprotein L | virion glycoprotein gL [Human herpesvirus 3] | ABE03078.1 |
| glycoprotein L | glycoprotein L [Human herpesvirus 3] | AGM33094.1 |
| glycoprotein L | ORF60 [Human herpesvirus 3] | AKG56786.1 |
| glycoprotein L | envelope glycoprotein L [Human herpesvirus 3] | NP_040182.1 |
| glycoprotein L | virion glycoprotein gL [Human herpesvirus 3] | ABF21706.1 |
| glycoprotein M | envelope glycoprotein M [Human herpesvirus 3] | NP_040172.1 |
| glycoprotein M | ORF 50 [Human herpesvirus 3] | AIT53351.1 |
| glycoprotein M | ORF50 [Human herpesvirus 3] | AKG56119.1 |
| glycoprotein M | ORF50 [Human herpesvirus 3] | AGY33080.1 |
| glycoprotein M | envelope glycoprotein gM [Human herpesvirus 3] | ABE03068.1 |
| glycoprotein M | virion membmne glycoprotein M [Human herpesvirus 3] | AEW88530.1 |
| glycoprotein M | virion membmne glycoprotein M [Human herpesvirus 3] | AEW88674.1 |
| glycoprotein N | envelope glycoprotein N [Human herpesvirus 3] | YP_068406.1 |
| glycoprotein N | ORF9a [Human herpesvirus 3] | AGY33038.1 |
| glycoprotein N | membrane protein [Human herpesvirus 3] | AAT07690.1 |
| glycoprotein N | membrane protein [Human herpesvirus 3] | AEW88273.1 |
| glycoprotein N | membrane protein [Human herpesvirus 3] | AEW88489.1 |

TABLE 15

| VZV Polypeptide Sequences | | |
|---|---|---|
| Name | Sequence | SEQ ID NO: |
| gi\|443500676\|gb\|AGC94542.1\| glycoprotein E [Human herpesvirus 3] | MGTVNKPVVGVLMGFGIITGTLRITNPVRASVLRYDDFH<br>IDEDKLDTNSVYEPYYHSDHAESSWVNRGESSRKAYDH<br>NSPYIWPRNDYDGFLENAHEHHGVYNQGRGIDSGERLM<br>QPTQMSAQEDLGDDTGIHVIPTLNGDDRHKIVNVDQRQ<br>YGDVFKGDLNPKPQGQRLIEVSVEENHPFTLRAPIQRIYG<br>VRYTETWSFLPSLTCTGDAAPAIQHICLKHTTCFQDVVV<br>DVDCAENTKEDQLAEISYRFQGKKEADQPWIVVNTSTLF<br>DELELDPPEIEPGVLKVLRTEKQYLGVYIWNMRGSDGTS<br>TYATFLVTWKGDEKTRNPTPAVTPQPRGAEFHMWNYH<br>SHVFSVGDTFSLAMHLQYKIHEAPFDLLLEWLYVPIDPT<br>CQPMRLYSTCLYHPNAPQCLSHMNSGCTFTSPHLAQRV<br>ASTVYQNCEHADNYTAYCLGISHMEPSFGLILHDGGTTL<br>KFVDTPESLSGLYVFVVYFNGHVEAVAYTVVSTVDHFV<br>NAIEERGFPPTAGQPPATTKPKEITPVNPGTSPLLRYAAW<br>TGGLAAVVLLCLVIFLICTAKRMRVKAYRVDKSPYNQS<br>MYYAGLPVDDFEDSESTDTEEEFGNAIGGSHGGSSYTVY<br>IDKTR | 45 |
| gi\|443500675\|gb\|AGC94541.1\| glycoprotein I [Human herpesvirus 3] | MFLIQCLISAVIFYIQVTNALIFKGDHVSLQVNSSLTSILIP<br>MQNDNYTEIKGQLVFigEQLPTGTNYSGTLELLYADTVA<br>FCFRSVQVIRYDGCPRIRTSAFISCRYKHSWHYGNSTDRI<br>STEPDAGVMLKITKPGINDAGVYVLLVRLDHSRSTDGFI<br>LGVNVYTAGSHHNIHGVIYTSPSLQNGYSTRALFQQARL<br>CDLPATPKGSGTSLFQHMLDLRAGKSLEDNPWLHEDVV<br>TTETKSVVKEGIENHVYPTDMSTLPEKSLNDPPENLLIIIPI<br>VASVMILTAMVIVIVISVKRRRIKKHPIYRPNTKTRRGIQ<br>NATPESDVMLEAAIAQLATIREESPPHSVVNPFVK | 46 |
| VZV-GE-delete-562 | MGTVNKPVVGVLMGFGIITGTLRITNPVRASVLRYDDFH<br>IDEDKLDTNSVYEPYYHSDHAESSWVNRGESSRKAYDH<br>NSPYIWPRNDYDGFLENAHEHHGVYNQGRGIDSGERLM<br>QPTQMSAQEDLGDDTGVIPTLNGDDRHKIVNVDQRQYG<br>DVFKGDLNPKPQGQRLIEVSVEENHPFTLRAPIQRIYGVR<br>YTETWSFLPSLTCTGDAAPAIQHICLKHTTCFQDVVVDV<br>DCAENTKEDQLAEISYRFQGKKEADQPWIVVNTTLFDEL<br>ELDPPEIEPGVLKVLRTEKQYLGVYIWNMRGSDGTSTYA<br>TFLVTWKGDEKTRNPTPAVTPQPRGAEFHMWNYHSHVF | 47 |

TABLE 15-continued

VZV Polypeptide Sequences

| Name | Sequence | SEQ ID NO: |
|---|---|---|
| | SVGDTFSLAMHLQYKIHEAPFDLLLEWLYVPIDPTCQPM RLYSTCLYHPNAQCLSHMNSGCTFTSPHLAQRVASTVY QNCEHADNYTAYCLGISHMEPSFGLILHDGGTTLKFVDT PESLSGLYVFVVYFNGHVEAVAYTVVSTVDHFVNAIEER GFPPTAGQPPATTKPKEITPVNPGTSPLLRYAWTGGLAA VVLLCLVIFLICTA | |
| gi\|46981496\|gb\|AAT07772.1\| membrane glycoprotein C [Human herpesvirus 3] | MKRIQINLILTIACIQLSTESQPTPVSITELYTSAATRKPDP AVAPTSAATRKPDPAVAPTSAATRKPDPAVAPTSAATRK PDPAVAPTSAATRKPDPAVAPTSAATRKPDPAVAPTSAA SRKPDPAVAPTSAASRKPDPAVAPTSAASRKPDPAANTQ HSQPPFLYENIQCVHGGIQSIPYFHTFIMPCYMRLTTGQQ AAFKQQQKTYEQYSLDPEGSNITRWKSLIRPDLHIEVWF TRHLIDPHRQLGNALIRMPDLPVMLYSNSADLNLINNPEI FTHAKENYVIPDVKTTSDFSVTILSMDATTEGTYIWRVV NTKTKNVISEHSITVTTYYRPNITVVGDPVLTGQTYAAY CNVSKYYPPHSVRVRWTSRFGNIGKNFITDAIQEYANGL FSYVSAVRIPQQKQMDYPPPAIQCNVLWIRDGVSNMKY SAVVTPDVYPFPNVSIGIIDGHIVCTAKCVPRGVVHFVW WVNDSPINHENSEITGVCDQNKRFVNMQSSCPTSELDGP ITYSCHLDGYPKKFPPFSAVYTYDASTYATTFSVVAVIIG VISILGTLGLIAVIATLCIRCCS | 48 |
| gi\|9625934\|ref\|NP_040182.1\| envelope glycoprotein L [Human herpesvirus 3] | MASHKWLLQIVFLKTITIAYCLHLQDDTPLFFGAKPLSD VSLIITEPCVSSVYEAWDYAAPPVSNLSEALSGIVVKTKC PVPEVILWFKDKQMAYWTNPYVTLKGLAQSVGEEHKS GDIRDALLDALSGVWVDSTPSSTNIPENGCVWGADRLFQ RVCQ | 49 |
| gi\|9625925\|ref\|NP_040172.1\| envelope glycoprotein M [Human herpesvirus 3] | MGTQKKGPRSEKVSPYDTTTPEVEALDHQMDTLNWRI WIIQVMMFTLGAVMLLATLIAASSEYTGIPCFYAAVVDY ELFNATLDGGVWSGNRGGYSAPVLFLEPHSVVAFTYYT ALTAMAMAVYTLITAAIIHRETKNQRVRQSSGVAWLVV DPTTLFWGLLSLWLLNAVVLLLAYKQIGVAATLYLGHF ATSVIFTTYFCGRGKLDETNIKAVANLRQQSVFLYRLAG PTRAVFVNLMAALMAICILFVSLMLELVVANHLHTGLW SSVSVAMSTFSTLSVVYLIVSELILAHYIHVLIGPSLGTLV ACATLGTAAHSYMDRLYDPISVQSPRLIPTTRGTLACLA VFSVVMLLLRLMRAYVYHRQKRSRFYGAVRRVPERVR GYIRKVKPAHRNSRRTNYPSQGYGYVYENDSTYETDRE DELLYERSNSGWE | 50 |
| gi\|9625912\|ref\|NP_040160.1\| envelope glycoprotein H [Human herpesvirus 3] | MFALVLAVVILPLWTTANKSYVTPTPATRSIGHMSALLR EYSDRNMSLKLEAFYPTGFDEELIKSLHWGNDRKHVFL VIVKVNPTTHEGDVGLVIFPKYLLSPYHFKAEHRAPFPA GRFGFLSHPVTPDVSFFDSSFAPYLTTQHLVAFTTFPPNPL VWHLERAETAATAERPFGVSLLPARPTVPKNTILEHKAH FATWDALARHTFFSAEAIITNSTLRIHVPLFGSVWPIRYW ATGSVLLTSDSGRVEVNIGVGFMSSLISLSSGPPIELIVVP HTVKLNAVTSDTTWFQLNPPGPDPGPSYRVYLLGRGLD MNFSKHATVDICAYPEESLDYRYHLSMAHTEALRMTTK ADQHDINEESYYHIAARIATSIFALSEMGRTTEYFLLDEIV DVQYQLKFLNYILMRIGAGAHPNTISGTSDLIFADPSQLH DELSLLFGQVKPANVDYFISYDEARDQLKTAYALSRGQ DHVNALSLARRVIMSIYKGLLVKQNLNATERQALFFAS MILLNFREGLENSSRVLDGRTTLLLMTSMCTAAHATQA ALNIQEGLAYLNPSKHMFTIPNVYSPCMGSLRTDLTEEIH VMNLLSAIPTRPGLNEVLHTQLDESEIFDAAFKTMMIFTT WTAKDLHILHTHVPEVFTCQDAAARNGEYVLILPAVQG HSYVITRNKPQRGLVYSLADVDVYNPISVVYLSRDTCVS EHGVIETVALPHPDNLKECLYCGSVFLRYLTTGAIMDIIII DSKDTERQLAAMGNSTIPPFNPDMHGDDSKAVLLFPNG TVVTLLGFERRQAIRMSGQYLGASLGGAFLAVVGFGIIG WMLCGNSRLREYNKIPLT | 51 |
| gi\|584403829\|gb\|AHB80298.1\| envelope glycoprotein E [Human herpesvirus 3] | MFYEALKAELVYTRAVHGFRPRANCVVLSDYIPRVACN MGTVNKPVVGVLMGFGIITGTLRITNPVRASVLRYDDFH IDEDKLDTNSVYEPYYHSDHAESSWVNRGESSRKAYDH NSPYIWPRNDYDGFLENAHEHHGVYNQGRGIDSGERLM QPTQMSAQEDLGDDTGIHVIPTLNGDDRHKIVNVDQRQ YGDVFKGDLNPKPQGQRLIEVSVEENHPFTLRAPIQRIYG VRYTETWSFLPSLTCTGDAAPAIQHICLKHTTCFQDVVV DVDCAENTKEDQLAEISYRFQGKKEADQPWIVVNTSTLF DELELDPPEIEPGVLKVLRTEKQYLGVYIWNMRGSDGTS TYATFLVTWKGDEKTRNPTPAVTPQPRGAEFHMWNYH | 52 |

TABLE 15-continued

| VZV Polypeptide Sequences | | |
|---|---|---|
| Name | Sequence | SEQ ID NO: |
| | SHVFSVGDTFSLAMHLQYKIHEAPFDLLLEWLYVPIDPT CQPMRLYSTCLYHPNAPQCLSHMNSGCTFTSPHLAQRV ASTVYQNCEHADNYTAYCLGISHMEPSFGLILHDGGTTL KFVDTPESLSGLYVFVVYFNGHVEAVAYTVVSTVDHFV NAIEERGFPPTAGQPPATTKPKEITPVNPGTSPLLRYAAW TGGLAAVVLLCLVIFLICTAKRMRVKAYRVDKSPYNQS MYYAGLPVDDFEDSESTDTEEEFGNAIGGSHGGSSYTVY IDKTR | |
| gi\|46981513\|gb\| AAT07789.11 glycoprotein B [Human herpesvirus 3] | MFVTAVVSVSPSSFYESLQVEPTQSEDITRSAHLGDGDEI REAIHKSQDAETKPTFYVCPPPTGSTIVRLEPTRTCPDYH LGKNFTEGIAVVYKENIAAYKFKATVYYKDVIVSTAWA GSSYTQITNRYADRVPIPVSEITDTIDKFGKCSSKATYVR NNHKVEAFNEDKNPQDMPLIASKYNSVGSKAWHTTND TYMVAGTPGTYRTGTSVNCIIEEVEARSIFPYDSFGLSTG DIIYMSPFFGLRDGAYREHSNYAMDRFHQFEGYRQRDL DTRALLEPAARNFLVTPHLTVGWNWKPKRTEVCSLVK WREVEDVVRDEYAHNFRFTMKTLSTTFISETNEFNLNQI HLSQCVKEEARAIINRIYTTRYNSSHVRTGDIQTYLARGG FVVVFQPLLSNSLARLYLQELVRENTNHSPQKHPTRNTR SRRSVPVELRANRTITTTSSVEFAMLQFTYDHIQEHVNE MLARISSSWCQLQNRERALWSGLFPINPSALASTILDQRV KARILGDVISVSNCPELGSDTRIILQNSMRVSGSTTRCYSR PLISIVSLNGSGTVEGQLGTDNELIMSRDLLEPCVANHKR YFLFGHHYVYYEDYRYVREIAVHDVGMISTYVDLNLTL LKDREFMPLQVYTRDELRDTGLLDYSEIQRRNQMHSLRF YDIDKVVQYDSGTAIMQGMAQFFQGLGTAGQAVGHVV LGATGALLSTVHGFTTFLSNPFGALAVGLLVLAGLVAAF FAYRYVLKLKTSPMKALYPLTTKGLKQLPEGMDPFAEK PNATDTPIEEIGDSQNTEPSVNSGFDPDKFREAQEMIKYM TLVSAAERQESKARKKNKTSALLTSRLTGLALRNRRGYS RVRTENVTGV | 53 |
| gi\|46981487\|gb\| AAT07763.1\| glycoprotein K [Human herpesvirus 3] | MQALGIKTEHFIIMCLLSGHAVFTLWYTARVKFEHECVY ATTVINGGPVVWGSYNNSLIYVTFVNHSTFLDGLSGYDY SCRENLLSGDTMVKTAISTPLHDKIRIVLGTRNCHAYFW CVQLKMIFFAWFVYGMYLQFRRIRRMFGPFRSSCELISPT SYSLNYVTRVISNILLGYPYTKLARLLCDVSMRRDGMSK VFNADPISFLYMHKGVTLLMLLEVIAHISSGCIVLLTLGV AYTPCALLYPTYIRILAWVVVCTLAIVELISYVRPKPTKD NHLNHINTGGIRGICTTCCATVMSGLAIKCFYIVIFAIAVV IFMHYEQRVQVSLFGESENSQKH | 54 |
| gi\|443500633\|gb\| AGC94499.1\| glycoprotein N [Human herpesvirus 3] | MGSITASFILITMQILFFCEDSSGEPNFAERNFWHASCSAR GVYIDGSMITTLFFYASLLGVCVALISLAYHACFRLFTRS VLRSTW | 55 |
| Ig heavy chain epsilon-1 signal peptide (IgE HC SP) | MDWTWILFLVAAATRVHS | 56 |
| IgGk chain V-III region HAH signal peptide (IgGk SP) | METPAQLLFLLLLWLPDTTG | 57 |
| Japanese encephalitis PRM signal sequence | MLGSNSGQRVVFTILLLLVAPAYS | 109 |
| VSVg protein signal sequence | MKCLLYLAFLFIGVNCA | 110 |
| Japanese encephalitis JEV signal sequence | MWLVSLAIVTACAGA | 111 |

TABLE 16

| Flagellin Nucleic Acid Sequences | | |
|---|---|---|
| Name | Sequence | SEQ ID NO: |
| NT (5' UTR, ORF, 3' UTR) | TCAAGCTTTTGGACCCTCGTACAGAAGCTAATACGACTCACTAT<br>AGGGAAATAAGAGAGAAAAGAAGAGTAAGAAGAAATATAAG<br>AGCCACCATGGCACAAGTCATTAATACAAACAGCCTGTCGCTG<br>TTGACCCAGAATAACCTGAACAAATCCCAGTCCGCACTGGGCA<br>CTGCTATCGAGCGTTTGTCTTCCGGTCTGCGTATCAACAGCGCG<br>AAAGACGATGCGGCAGGACAGGCGATTGCTAACCGTTTTACCG<br>CGAACATCAAAGGTCTGACTCAGGCTTCCCGTAACGCTAACGA<br>CGGTATCTCCATTGCGCAGACCACTGAAGGCGCGCTGAACGAA<br>ATCAACAACAACCTGCAGCGTGTGCGTGAACTGGCGGTTCAGT<br>CTGCGAATGGTACTAACTCCCAGTCTGACCTCGACTCCATCCAG<br>GCTGAAATCACCCAGCGCCTGAACGAAATCGACCGTGTATCCG<br>GCCAGACTCAGTTCAACGGCGTGAAAGTCCTGGCGCAGGACAA<br>CACCCTGACCATCCAGGTTGGTGCCAACGACGGTGAAACTATC<br>GATATTGATTTAAAAGAAATCAGCTCTAAAACACTGGGACTTG<br>ATAAGCTTAATGTCCAAGATGCCTACACCCCGAAAGAAACTGC<br>TGTAACCGTTGATAAAACTACCTATAAAAATGGTACAGATCCT<br>ATTACAGCCCAGAGCAATACTGATATCCAAACTGCAATTGGCG<br>GTGGTGCAACGGGGGTTACTGGGGCTGATATCAAATTTAAAGA<br>TGGTCAATACTATTTAGATGTTAAAGGCGGTGCTTCTGCTGGTG<br>TTTATAAAGCCACTTATGATGAAACTACAAAGAAAGTTAATAT<br>TGATACGACTGATAAAACTCCGTTGGCAACTGCGGAAGCTACA<br>GCTATTCGGGGAACGGCCACTATAACCCACAACCAAATTGCTG<br>AAGTAACAAAAGAGGGTGTTGATACGACCACAGTTGCGGCTCA<br>ACTTGCTGCAGCAGGGGTTACTGGCGCCGATAAGGACAATACT<br>AGCCTTGTAAAACTATCGTTTGAGGATAAAAACGGTAAGGTTA<br>TTGATGGTGGCTATGCAGTGAAAATGGGCGACGATTTCTATGC<br>CGCTACATATGATGAGAAAACAGGTGCAATTACTGCTAAAACC<br>ACTACTTATACAGATGGTACTGGCGTTGCTCAAACTGGAGCTGT<br>GAAATTTGGTGGCGCAAATGGTAAATCTGAAGTTGTTACTGCT<br>ACCGATGGTAAGACTTACTTAGCAAGCGACCTTGACAAACATA<br>ACTTCAGAACAGGCGGTGAGCTTAAAGAGGTTAATACAGATAA<br>GACTGAAAACCCACTGCAGAAAATTGATGCTGCCTTGGCACAG<br>GTTGATACACTTCGTTCTGACCTGGGTGCGGTTCAGAACCGTTT<br>CAACTCCGCTATCACCAACCTGGGCAATACCGTAAATAACCTG<br>TCTTCTGCCCGTAGCCGTATCGAAGATTCCGACTACGCAACCGA<br>AGTCTCCAACATGTCTCGCGCGCAGATTCTGCAGCAGGCCGGT<br>ACCTCCGTTCTGGCGCAGGCGAACCAGGTTCCGCAAAACGTCC<br>TCTCTTTACTGCGTTGATAATAGGCTGGAGCCTCGGTGGCCATG<br>CTTCTTGCCCCTTGGGCCTCCCCCCAGCCCCTCCTCCCCTTCCTG<br>CACCCGTACCCCCGTGGTCTTTGAATAAAGTCTGAGTGGGCGG<br>C | 112 |
| ORF Sequence, NT | ATGGCACAAGTCATTAATACAAACAGCCTGTCGCTGTTGACCC<br>AGAATAACCTGAACAAATCCCAGTCCGCACTGGGCACTGCTAT<br>CGAGCGTTTGTCTTCCGGTCTGCGTATCAACAGCGCGAAAGAC<br>GATGCGGCAGGACAGGCGATTGCTAACCGTTTTACCGCGAACA<br>TCAAAGGTCTGACTCAGGCTTCCCGTAACGCTAACGACGGTAT<br>CTCCATTGCGCAGACCACTGAAGGCGCGCTGAACGAAATCAAC<br>AACAACCTGCAGCGTGTGCGTGAACTGGCGGTTCAGTCTGCGA<br>ATGGTACTAACTCCCAGTCTGACCTCGACTCCATCCAGGCTGAA<br>ATCACCCAGCGCCTGAACGAAATCGACCGTGTATCCGGCCAGA<br>CTCAGTTCAACGGCGTGAAAGTCCTGGCGCAGGACAACACCCT<br>GACCATCCAGGTTGGTGCCAACGACGGTGAAACTATCGATATT<br>GATTTAAAAGAAATCAGCTCTAAAACACTGGGACTTGATAAGC<br>TTAATGTCCAAGATGCCTACACCCCGAAAGAAACTGCTGTAAC<br>CGTTGATAAAACTACCTATAAAAATGGTACAGATCCTATTACA<br>GCCCAGAGCAATACTGATATCCAAACTGCAATTGGCGGTGGTG<br>CAACGGGGGTTACTGGGGCTGATATCAAATTTAAAGATGGTCA<br>ATACTATTTAGATGTTAAAGGCGGTGCTTCTGCTGGTGTTTATA<br>AAGCCACTTATGATGAAACTACAAAGAAAGTTAATATTGATAC<br>GACTGATAAAACTCCGTTGGCAACTGCGGAAGCTACAGCTATT<br>CGGGGAACGGCCACTATAACCCACAACCAAATTGCTGAAGTAA<br>CAAAAGAGGGTGTTGATACGACCACAGTTGCGGCTCAACTTGC<br>TGCAGCAGGGGTTACTGGCGCCGATAAGGACAATACTAGCCTT<br>GTAAAACTATCGTTTGAGGATAAAAACGGTAAGGTTATTGATG<br>GTGGCTATGCAGTGAAAATGGGCGACGATTTCTATGCCGCTAC<br>ATATGATGAGAAAACAGGTGCAATTACTGCTAAAACCACTACT<br>TATACAGATGGTACTGGCGTTGCTCAAACTGGAGCTGTGAAAT<br>TTGGTGGCGCAAATGGTAAATCTGAAGTTGTTACTGCTACCGAT<br>GGTAAGACTTACTTAGCAAGCGACCTTGACAAACATAACTTCA<br>GAACAGGCGGTGAGCTTAAAGAGGTTAATACAGATAAGACTG<br>AAAACCCACTGCAGAAAATTGATGCTGCCTTGGCACAGGTTGA<br>TACACTTCGTTCTGACCTGGGTGCGGTTCAGAACCGTTTCAACT<br>CCGCTATCACCAACCTGGGCAATACCGTAAATAACCTGTCTTCT<br>GCCCGTAGCCGTATCGAAGATTCCGACTACGCAACCGAAGTCT | 113 |

TABLE 16-continued

| Flagellin Nucleic Acid Sequences | | |
|---|---|---|
| Name | Sequence | SEQ ID NO: |
| | CCAACATGTCTCGCGCGCAGATTCTGCAGCAGGCCGGTACCTC<br>CGTTCTGGCGCAGGCGAACCAGGTTCCGCAAAACGTCCTCTCTT<br>TACTGCGT | |
| mRNA Sequence (assumes T100 tail) | G*GGGAAAUAAGAGAGAAAAGAAGAGUAAGAAGAAAUAUAA<br>GAGCCACCAUGGCACAAGUCAUUAAUACAAACAGCCUGUCGC<br>UGUUGACCCAGAAUAACCUGAACAAAUCCCAGUCCGCACUGG<br>GCACUGCUAUCGAGCGUUUGUCUUCCGGUCUGCGUAUCAACA<br>GCGCGAAAGACGAUGCGGCAGGACAGGCGAUUGCUAACCGUU<br>UUACCGCGAACAUCAAAGGUCUGACUCAGGCUUCCCGUAACG<br>CUAACGACGGUAUCUCCAUUGCGCAGACCACUGAAGGCGCGC<br>UGAACGAAAUCAACAACAACCUGCAGCGUGUGCGUGAACUGG<br>CGGUUCAGUCUGCGAAUGGUACUAACUCCCAGUCUGACCUCG<br>ACUCCAUCCAGGCUGAAAUCACCCAGCGCCUGAACGAAAUCG<br>ACCGUGUAUCCGGCCAGACUCAGUUCAACGGCGUGAAAGUCC<br>UGGCGCAGGACAACACCCUGACCAUCCAGGUUGGUGCCAACG<br>ACGGUGAAACUAUCGAUAUUGAUUUAAAAGAAAUCAGCUCU<br>AAAACACUGGGACUUGAUAAGCUUAAUGUCCAAGAUGCCUAC<br>ACCCCGAAAGAAACUGCUGUAACCGUUGAUAAAACUACCUAU<br>AAAAAUGGUACAGAUCCUAUUACAGCCCAGAGCAAUACUGAU<br>AUCCAAACUGCAAUUGGCGGUGGUGCAACGGGGGUUACUGG<br>GGCUGAUAUCAAAUUUAAAGAUGGUCAAUACUAUUUAGAUG<br>UUAAAGGCGGUGCUUCUGCUGGUGUUUAUAAAGCCACUUAU<br>GAUGAAACUACAAAGAAAGUUAAUAUUGAUACGACUGAUAA<br>AACUCCGUUGGCAACUGCGGAAGCUACAGCUAUUCGGGGAAC<br>GGCCACUAUAACCCACAACCAAAUUGCUGAAGUAACAAAAGA<br>GGGUGUUGAUACGACCACAGUUGCGGCUCAACUUGCUGCAGC<br>AGGGGUUACUGGCGCCGAUAAGGACAAUACUAGCCUUGUAA<br>AACUAUCGUUUGAGGAUAAAAACGGUAAGGUUAUUGAUGGU<br>GGCUAUGCAGUGAAAAUGGGCGACGAUUUCUAUGCCGCUACA<br>UAUGAUGAGAAAACAGGUGCAAUUACUGCUAAAACCACUAC<br>UUAUACAGAUGGUACUGGCGUUGCUCAAACUGGAGCUGUGA<br>AAUUUGGUGGCGCAAAUGGUAAAUCUGAAGUUGUUACUGCU<br>ACCGAUGGUAAGACUUACUUAGCAAGCGACCUUGACAAACAU<br>AACUUCAGAACAGGCGGUGAGCUUAAAGAGGUUAAUACAGA<br>UAAGACUGAAAACCCACUGCAGAAAAUUGAUGCUGCCUUGGC<br>ACAGGUUGAUACACUUCGUUCUGACCUGGGUGCGGUUCAGAA<br>CCGUUUCAACUCCGCUAUCACCAACCUGGGCAAUACCGUAAA<br>UAACCUGUCUUCUGCCCGUAGCCGUAUCGAAGAUUCCGACUA<br>CGCAACCGAAGUCUCCAACAUGUCUCGCGCGCAGAUUCUGCA<br>GCAGGCCGGUACCUCCGUUCUGGCGCAGGCGAACCAGGUUCC<br>GCAAAACGUCCUCUCUUUACUGCGUUGAUAAUAGGCUGGAGC<br>CUCGGUGGCCAUGCUUCUUGCCCCUUGGGCCUCCCCCCAGCC<br>CCUCCUCCCCUUCCUGCACCCGUACCCCCGUGGUCUUUGAAU<br>AAAGUCUGAGUGGGCGGCAAAAAAAAAAAAAAAAAAAAAAA<br>AAAAAAAAAAAAAAAAAAAAAAAAAAAAAAAAAAAAAAAAA<br>AAAAAAAAAAAAAAAAAAAAAAAAAAAAAAAAAAAAUCUAG | 114 |

It should be understood that each of the ORF sequences provided herein may be combined with a 5' and/or 3' UTR, such as those described herein. It should also be understood that the 5' and/or 3' UTR for each construct may be omitted, modified or substituted for a different UTR sequences in any one of the vaccines as provided herein.

TABLE 17

| Flagellin Amino Acid Sequences | | |
|---|---|---|
| Name | Sequence | SEQ ID NO: |
| ORF Sequence, AA | MAQVINTNSLSLLTQNNLNKSQSALGTAIERLSSGLRINSAKDDAA<br>GQAIANRFTANIKGLTQASRNANDGISIAQTTEGALNEINNNLQRV<br>RELAVQSANGTNSQSDLDSIQAEITQRLNEIDRVSGQTQFNGVKVL<br>AQDNTLTIQVGANDGETIDIDLKEISSKTLGLDKLNVQDAYTPKET<br>AVTVDKTTYKNGTDPITAQSNTDIQTAIGGGATGVTGADIKFKDG<br>QYYLDVKGGASAGVYKATYDETTKKVNIDTTDKTPLATAEATAI<br>RGTATITHNQIAEVTKEGVDTTTVAAQLAAAGVTGADKDNTSLV<br>KLSFEDKNGKVIDGGYAVKMGDDFYAATYDEKTGAITAKTTTYT<br>DGTGVAQTGAVKFGGANGKSEVVTATDGKTYLASDLDKHNFRT<br>GGELKEVNTDKTENPLQKIDAALAQVDTLRSDLGAVQNRFNSAIT | 115 |

TABLE 17-continued

Flagellin Amino Acid Sequences

| Name | Sequence | SEQ ID NO: |
|---|---|---|
| | NLGNTVNNLSSARSRIEDSDYATEVSNMSRAQILQQAGTSVLAQA<br>NQVPQNVLSLLR | |
| Flagellin-GS linker-circumsporozoite protein | MAQVINTNSLSLLTQNNLNKSQSALGTAIERLSSGLRINSAKDDAA<br>GQAIANRFTANIKGLTQASRNANDGISIAQTTEGALNEINNNLQRV<br>RELAVQSANSTNSQSDLDSIQAEITQRLNEIDRVSGQTQFNGVKVL<br>AQDNTLTIQVGANDGETIDIDLKQINSQTLGLDTLNVQQKYKVSD<br>TAATVTGYADTTIALDNSTFKASATGLGGTDQKIDGDLKFDDTTG<br>KYYAKVTVTGGTGKDGYYEVSVDKTNGEVTLAGGATSPLTGGLP<br>ATATEDVKNVQVANADLTEAKAALTAAGVTGTASVVKMSYTDN<br>NGKTIDGGLAVKVGDDYYSATQNKDGSISINTTKYTADDGTSKTA<br>LNKLGGADGKTEVVSIGGKTYAASKAEGHNFKAQPDLAEAAATT<br>TENPLQKIDAALAQVDTLRSDLGAVQNRFNSAITNLGNTVNNLTS<br>ARSRIEDSDYATEVSNMSRAQILQQAGTSVLAQANQVPQNVLSLL<br>RGGGGSGGGGSMMAPDPNANPNANPNANPNANPNANPNANPNA<br>NPNANPNANPNANPNANPNANPNANPNANPNANPNANPNANPN<br>ANPNANPNKNNQGNGQGHNMPNDPNRNVDENANANNAVKNNN<br>NEEPSDKHIEQYLKKIKNSISTEWSPCSVTCGNGIQVRIKPGSANKP<br>KDELDYENDIEKKICKMEKCSSVFNVVNS | 116 |
| Flagellin-RPVT linker-circumsporozoite protein | MMAPDPNANPNANPNANPNANPNANPNANPNANPNANPNANPN<br>ANPNANPNANPNANPNANPNANPNANPNANPNANPNANPNKNN<br>QGNGQGHNMPNDPNRNVDENANANNAVKNNNNEEPSDKHIEQY<br>LKKIKNSISTEWSPCSVTCGNGIQVRIKPGSANKPKDELDYENDIEK<br>KICKMEKCSSVFNVVNSRPVTMAQVINTNSLSLLTQNNLNKSQSA<br>LGTAIERLSSGLRINSAKDDAAGQAIANRFTANIKGLTQASRNAND<br>GISIAQTTEGALNEINNNLQRVRELAVQSANSTNSQSDLDSIQAEIT<br>QRLNEIDRVSGQTQFNGVKVLAQDNTLTIQVGANDGETIDIDLKQI<br>NSQTLGLDTLNVQQKYKVSDTAATVTGYADTTIALDNSTFKASAT<br>GLGGTDQKIDGDLKFDDTTGKYYAKVTVTGGTGKDGYYEVSVD<br>KTNGEVTLAGGATSPLTGGLPATATEDVKNVQVANADLTEAKAA<br>LTAAGVTGTASVVKMSYTDNNGKTIDGGLAVKVGDDYYSATQN<br>KDGSISINTTKYTADDGTSKTALNKLGGADGKTEVVSIGGKTYAA<br>SKAEGHNFKAQPDLAEAAATTTENPLQKIDAALAQVDTLRSDLG<br>AVQNRFNSAITNLGNTVNNLTSARSRIEDSDYATEVSNMSRAQILQ<br>QAGTSVLAQANQVPQNVLSLLR | 117 |

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A composition comprising an RNA polynucleotide having an open reading frame encoding a varicella zoster virus (VZV) polypeptide, wherein the VZV polypeptide comprises VZV gE or gI, formulated in a lipid nanoparticle comprising 20-60 mol % cationic lipid, 5-25 mol % neutral lipid, 25-55 mol % cholesterol, and 0.5-15 mol % polyethylene glycol (PEG)-modified lipid, wherein the ionizable cationic lipid comprises Compound 25:

(Compound 25)

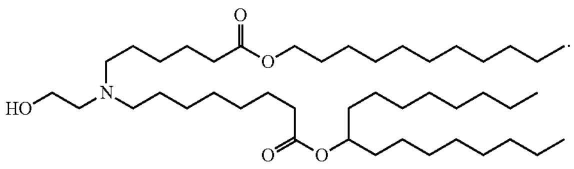

2. The composition of claim 1, wherein the RNA polynucleotide has an open reading frame encoding two or more VZV polypeptides.

3. The composition of claim 1, wherein the VZV polypeptide is VZV gE.

4. The composition of claim 1, wherein the VZV polypeptide is VZV gI.

5. The composition of claim 1, wherein the open reading frame is codon-optimized.

6. The composition of claim 1, wherein the composition is multivalent.

7. The composition of claim 1, wherein the RNA polynucleotide comprises a chemical modification.

8. The composition of claim 7, wherein the chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

9. The composition of claim 8, wherein the chemical modification is in the carbon 5-position of the uracil.

10. The composition of claim 8, wherein the chemical modification is N1-methylpseudouridine.

11. The composition of claim 1, wherein the lipid nanoparticle has a polydispersity value of less than 0.4.

12. The composition of claim 1, wherein the lipid nanoparticle has a net neutral charge at a neutral pH.

13. The composition of claim 1, wherein the nanoparticle has a mean diameter of 50-200 nanometers (nm).

14. A method of inducing an antigen-specific immune response in a subject, the method comprising administering to the subject the composition of claim 1 in an amount effective to produce an antigen-specific immune response to VZV.

15. The composition of claim 1, wherein the lipid nanoparticle comprises 40-50 mol % cationic lipid, 5-15 mol % neutral lipid, 20-40 mol % cholesterol, and 0.2-4.5 mol % PEG-modified lipid.

16. The composition of claim 15, wherein the lipid nanoparticle comprises 50 mol % cationic lipid, 10 mol % neutral lipid, 38.5 mol % cholesterol, and 1.5 mol % PEG-modified lipid.

17. The composition of claim 3, wherein the lipid nanoparticle comprises 40-50 mol % cationic lipid, 5-15 mol % neutral lipid, 20-40 mol % cholesterol, and 0.2-4.5 mol % PEG-modified lipid.

18. The composition of claim 17, wherein the lipid nanoparticle comprises 50 mol % cationic lipid, 10 mol % neutral lipid, 38.5 mol % cholesterol, and 1.5 mol % PEG-modified lipid.

19. The composition of claim 4, wherein the lipid nanoparticle comprises 40-50 mol % cationic lipid, 5-15 mol % neutral lipid, 20-40 mol % cholesterol, and 0.2-4.5 mol % PEG-modified lipid.

20. The composition of claim 19, wherein the lipid nanoparticle comprises 50 mol % cationic lipid, 10 mol % neutral lipid, 38.5 mol % cholesterol, and 1.5 mol % PEG-modified lipid.

* * * * *

SEQUENCE LISTING

<160> NUMBER OF SEQ ID NOS: 150

<210> SEQ ID NO 1
<211> LENGTH: 2080
<212> TYPE: DNA
<213> ORGANISM: Varicella Zoster Virus

<400> SEQUENCE: 1

```
tcaagctttt ggaccctcgt acagaagcta atacgactca ctatagggaa ataagagaga     60

aaagaagagt aagaagaaat ataagagcca ccatggggac agtgaataag ccggttgtgg    120

gcgtgcttat gggctttggg attattaccg gtacattacg aattaccaat ccagtgcgcg    180

ccagtgtgct gcgttacgac gactttcaca ttgacgagga taagctggat actaacagcg    240

tgtacgaacc ttattaccac tcagatcatg ccgaatcaag ctgggttaat agaggagaaa    300

gcagccgaaa agcctacgac cacaactcac cttatatttg gcccagaaac gattatgacg    360
```

```
gtttcctgga aaacgcacat gaacaccatg gagtctacaa ccaaggcagg ggaatcgaca    420
gtggcgagcg tcttatgcag ccaacacaga tgtcggcaca ggaggatctc ggtgatgaca    480
ccggcataca cgtgattccc acattaaacg gcgacgacag acataagatc gtcaatgtgg    540
atcagcgtca gtatggggat gtctttaaag gcgatttgaa tccaaagccc caaggacaga    600
gactgatcga ggtctctgta gaagaaaatc accccttcac tttgcgcgct ccaatccaga    660
ggatttacgg ggtgcgttat accgaaactt ggagtttctt gccgtcactg acgtgtacgg    720
gggatgccgc ccccgcaatc cagcacatct gtctgaaaca caccacatgc tttcaggacg    780
tggttgtgga tgtggattgc gcggaaaaca caaaagaaga ccaactcgcc gaaatcagct    840
atcgttttca gggtaaaaaa gaggccgacc aaccgtggat tgttgtgaat acgagcacgc    900
tcttcgatga gcttgaactc gatccccgg aaatcgagcc tggggttcta aaagtgttga    960
ggaccgagaa gcagtacctc ggggtttata tctggaatat gagaggctcc gatggcacct   1020
ctacctacgc aacgtttctg gttacctgga agggagacga gaagacacgg aatccaacgc   1080
ccgctgtgac ccctcagcct aggggagccg aattccacat gtggaactat cactcccatg   1140
tattcagtgt gggtgacact ttcagcctgg ccatgcacct gcagtataag attcacgagg   1200
caccccttcga cctcctgctg gagtggttgt acgtacctat tgatcccact tgtcagccca   1260
tgcgcctgta ctccacttgc ttgtaccacc ccaatgcacc acagtgtcta tcacacatga   1320
actccgggtg tacctttact tcaccccatc ttgcccagcg ggtcgccagc acagtgtatc   1380
agaactgtga gcatgctgac aactatactg cttattgcct cggaatatcc catatggagc   1440
caagcttcgg gctcatactg cacgatggtg gtacgacact caagttcgtg gacaccccccg   1500
aaagcctttc tggcttgtac gtgttcgtgg tctacttcaa tggacatgtg gaggcagtgg   1560
cttacacagt ggtttcgaca gttgatcact ttgtaaatgc cattgaggaa cgcggcttcc   1620
cgcctacagc gggccagccc cctgcgacaa caaaaccaaa agagattacg cccgttaatc   1680
ctgggactag tccattgctg aggtatgccg cctggactgg cggtctggcg gccgtggtac   1740
ttctgtgttt agtcatattt ctgatctgta ccgctaaacg tatgcgggtc aaggcttacc   1800
gtgttgacaa gtctccttac aatcagtcaa tgtactatgc aggactccct gttgacgatt   1860
tcgaagactc agagagtaca gacacagaag aagaattcgg aaacgctata ggtggctctc   1920
acggaggtag ctcgtataca gtgtacatcg ataaaaccag atgataatag gctggagcct   1980
cggtggccat gcttcttgcc ccttgggcct ccccccagcc cctcctcccc ttcctgcacc   2040
cgtacccccg tggtctttga ataaagtctg agtgggcggc                        2080
```

<210> SEQ ID NO 2
<211> LENGTH: 1276
<212> TYPE: DNA
<213> ORGANISM: Varicella Zoster Virus

<400> SEQUENCE: 2

```
tcaagctttt ggaccctcgt acagaagcta atacgactca ctatagggaa ataagagaga     60
aaagaagagt aagaagaaat ataagagcca ccatgttttt aatccaatgt ttgatatcgg    120
ccgttatatt ttacatacaa gtgaccaacg ctttgatctt caagggcgac cacgtgagct    180
tgcaagttaa cagcagtctc acgtctatcc ttattcccat gcaaaatgat aattatacag    240
agataaaagg acagcttgtc tttattggag agcaactacc taccgggaca aactatagcg    300
gaacactgga actgttatac gcggatacgg tggcgttttg tttccggtca gtacaagtaa    360
```

taagatacga cggatgtccc cggattagaa cgagcgcttt tatttcgtgt aggtacaaac 420
attcgtggca ttatggtaac tcaacggatc ggatatcaac agagccggat gctggtgtaa 480
tgttgaaaat taccaaaccg ggaataaatg atgctggtgt gtatgtactt cttgttcggt 540
tagaccatag cagatccacc gatggtttca ttcttggtgt aaatgtatat acagcgggct 600
cgcatcacaa cattcacggg gttatctaca cttctccatc tctacagaat ggatattcta 660
caagagccct ttttcaacaa gctcgtttgt gtgatttacc cgcgacaccc aaagggtccg 720
gtacctccct gtttcaacat atgcttgatc ttcgtgccgg taaatcgtta gaggataacc 780
cttggttaca tgaggacgtt gttacgacag aaactaagtc cgttgttaag gaggggatag 840
aaaatcacgt atatccaacg gatatgtcca cgttacccga aaagtccctt aatgatcctc 900
cagaaaatct acttataatt attcctatag tagcgtctgt catgatcctc accgccatgg 960
ttattgttat tgtaataagc gttaagcgac gtagaattaa aaaacatcca atttatcgcc 1020
caaatacaaa aacaagaagg ggcatacaaa atgcgacacc agaatccgat gtgatgttgg 1080
aggccgccat tgcacaacta gcaacgattc gcgaagaatc ccccccacat tccgttgtaa 1140
acccgtttgt taaatagtga taataggctg gagcctcggt ggccatgctt cttgcccctt 1200
gggcctcccc ccagcccctc ctccccttcc tgcacccgta cccccgtggt ctttgaataa 1260
agtctgagtg ggcggc 1276

<210> SEQ ID NO 3
<211> LENGTH: 1897
<212> TYPE: DNA
<213> ORGANISM: Artificial Sequence
<220> FEATURE:
<223> OTHER INFORMATION: Synthetic Polynucleotide

<400> SEQUENCE: 3
tcaagctttt ggaccctcgt acagaagcta atacgactca ctatagggaa ataagagaga 60
aaagaagagt aagaagaaat ataagagcca ccatggggac agttaataaa cctgtggtgg 120
gggtattgat ggggttcgga attatcacgg gaacgttgcg tataacgaat ccggtcagag 180
catccgtctt gcgatacgat gattttcaca tcgatgaaga caaactggat acaaactccg 240
tatatgagcc ttactaccat tcagatcatg cggagtcttc atgggtaaat cggggagagt 300
cttcgcgaaa agcgtacgat cataactcac cttatatatg gccacgtaat gattatgatg 360
gatttttaga gaacgcacac gaacaccatg ggtgtataa tcagggccgt ggtatcgata 420
gcggggaacg gttaatgcaa cccacacaaa tgtctgcaca ggaggatctt ggggacgata 480
cgggcatcca cgttatccct acgttaaacg gcgatgacag acataaaatt gtaaatgtgg 540
accaacgtca atacggtgac gtgtttaaag gagatcttaa tccaaaaccc caaggccaaa 600
gactcattga ggtgtcagtg gaagaaaatc acccgtttac tttacgcgca ccgattcagc 660
ggatttatgg agtccggtac accgagactt ggagcttttt gccgtcatta acctgtacgg 720
gagacgcagc gcccgccatc cagcatatat gtttaaaaca tacaacatgc tttcaagacg 780
tggtggtgga tgtggattgc gcggaaaata ctaaagagga tcagttggcc gaaatcagtt 840
accgttttca aggtaagaag gaagcggacc aaccgtggat tgttgtaaac acgagcacac 900
tgtttgatga actcgaatta gacccccccg agattgaacc gggtgtcttg aaagtacttc 960
ggacagaaaa acaatacttg ggtgtgtaca tttggaacat gcgcggctcc gatggtacgt 1020
ctacctacgc cacgtttttg gtcacctgga aaggggatga aaaaacaaga aaccctacgc 1080
ccgcagtaac tcctcaacca agaggggctg agtttcatat gtggaattac cactcgcatg 1140

```
tattttcagt tggtgatacg tttagcttgg caatgcatct tcagtataag atacatgaag   1200

cgccatttga tttgctgtta gagtggttgt atgtccccat cgatcctaca tgtcaaccaa   1260

tgcggttata ttctacgtgt ttgtatcatc ccaacgcacc ccaatgcctc tctcatatga   1320

attccggttg tacatttacc tcgccacatt tagcccagcg tgttgcaagc acagtgtatc   1380

aaaattgtga acatgcagat aactacaccg catattgtct gggaatatct catatggagc   1440

ctagctttgg tctaatctta cacgacgggg gcaccacgtt aaagtttgta gatacacccg   1500

agagtttgtc gggattatac gtttttgtgg tgtattttaa cgggcatgtt gaagccgtag   1560

catacactgt tgtatccaca gtagatcatt ttgtaaacgc aattgaagag cgtggatttc   1620

cgccaacggc cggtcagcca ccggcgacta ctaaacccaa ggaaattacc cccgtaaacc   1680

ccggaacgtc accacttcta cgatatgccg catggaccgg agggcttgca gcagtagtac   1740

ttttatgtct cgtaatattt ttaatctgta cggcttgatg ataataggct ggagcctcgg   1800

tggccatgct tcttgcccct tgggcctccc cccagcccct cctccccttc ctgcacccgt   1860

acccccgtgg tctttgaata aagtctgagt gggcggc                            1897
```

<210> SEQ ID NO 4
<211> LENGTH: 1867
<212> TYPE: DNA
<213> ORGANISM: Artificial Sequence
<220> FEATURE:
<223> OTHER INFORMATION: Synthetic Polynucleotide

<400> SEQUENCE: 4

```
tcaagctttt ggaccctcgt acagaagcta atacgactca ctatagggaa ataagagaga     60

aaagaagagt aagaagaaat ataagagcca ccatggaaac ccccggcgcag ctgctgtttc   120

tgctgctgct gtggctgccg gataccaccg gctccgtctt gcgatacgat gattttcaca    180

tcgatgaaga caaactggat acaaactccg tatatgagcc ttactaccat tcagatcatg    240

cggagtcttc atgggtaaat cggggagagt cttcgcgaaa agcgtacgat cataactcac    300

cttatatatg gccacgtaat gattatgatg gatttttaga gaacgcacac gaacaccatg    360

gggtgtataa tcagggccgt ggtatcgata gcggggaacg gttaatgcaa cccacacaaa    420

tgtctgcaca ggaggatctt ggggacgata cgggcatcca cgttatccct acgttaaacg    480

gcgatgacag acataaaatt gtaaatgtgg accaacgtca atacggtgac gtgtttaaag    540

gagatcttaa tccaaaaccc caaggccaaa gactcattga ggtgtcagtg gaagaaaatc    600

acccgtttac tttacgcgca ccgattcagc ggatttatgg agtccggtac accgagactt    660

ggagcttttt gccgtcatta acctgtacgg gagacgcagc gcccgccatc cagcatatat    720

gtttaaaaca tacaacatgc tttcaagacg tggtggtgga tgtggattgc gcggaaaata    780

ctaaagagga tcagttggcc gaaatcagtt accgttttca aggtaagaag gaagcggacc    840

aaccgtggat tgttgtaaac acgagcacac tgtttgatga actcgaatta gacccccccg    900

agattgaacc gggtgtcttg aaagtacttc ggacagaaaa acaatacttg ggtgtgtaca    960

tttggaacat gcgcggctcc gatggtacgt ctacctacgc cacgtttttg gtcacctgga   1020

aaggggatga aaaaacaaga aaccctacgc ccgcagtaac tcctcaacca agaggggctg   1080

agtttcatat gtggaattac cactcgcatg tattttcagt tggtgatacg tttagcttgg   1140

caatgcatct tcagtataag atacatgaag cgccatttga tttgctgtta gagtggttgt   1200

atgtccccat cgatcctaca tgtcaaccaa tgcggttata ttctacgtgt ttgtatcatc   1260
```

```
ccaacgcacc ccaatgcctc tctcatatga attccggttg tacatttacc tcgccacatt   1320

tagcccagcg tgttgcaagc acagtgtatc aaaattgtga acatgcagat aactacaccg   1380

catattgtct gggaatatct catatggagc ctagctttgg tctaatctta cacgacgggg   1440

gcaccacgtt aaagtttgta gatacacccg agagtttgtc gggattatac gtttttgtgg   1500

tgtattttaa cgggcatgtt gaagccgtag catacactgt tgtatccaca gtagatcatt   1560

ttgtaaacgc aattgaagag cgtggatttc cgccaacggc cggtcagcca ccggcgacta   1620

ctaaacccaa ggaaattacc cccgtaaacc ccggaacgtc accacttcta cgatatgccg   1680

catggaccgg agggcttgca gcagtagtac ttttatgtct cgtaatattt ttaatctgta   1740

cggcttgatg ataataggct ggagcctcgg tggccatgct tcttgcccct tgggcctccc   1800

cccagcccct cctccccttc ctgcacccgt acccccgtgg tctttgaata aagtctgagt   1860

gggcggc                                                             1867
```

<210> SEQ ID NO 5
<211> LENGTH: 1933
<212> TYPE: DNA
<213> ORGANISM: Artificial Sequence
<220> FEATURE:
<223> OTHER INFORMATION: Synthetic Polynucleotide

<400> SEQUENCE: 5

```
tcaagctttt ggaccctcgt acagaagcta atacgactca ctatagggaa ataagagaga     60

aaagaagagt aagaagaaat ataagagcca ccatggggac agttaataaa cctgtggtgg    120

gggtattgat ggggttcgga attatcacgg gaacgttgcg tataacgaat ccggtcagag    180

catccgtctt gcgatacgat gattttcaca tcgatgaaga caaactggat acaaactccg    240

tatatgagcc ttactaccat tcagatcatg cggagtcttc atgggtaaat cggggagagt    300

cttcgcgaaa agcgtacgat cataactcac cttatatatg gccacgtaat gattatgatg    360

gatttttaga gaacgcacac gaacaccatg gggtgtataa tcagggccgt ggtatcgata    420

gcggggaacg gttaatgcaa cccacacaaa tgtctgcaca ggaggatctt ggggacgata    480

cgggcatcca cgttatccct acgttaaacg gcgatgacag acataaaatt gtaaatgtgg    540

accaacgtca atacggtgac gtgtttaaag gagatcttaa tccaaaaccc caaggccaaa    600

gactcattga ggtgtcagtg gaagaaaatc acccgtttac tttacgcgca ccgattcagc    660

ggatttatgg agtccggtac accgagactt ggagcttttt gccgtcatta acctgtacgg    720

gagacgcagc gcccgccatc cagcatatat gtttaaaaca tacaacatgc tttcaagacg    780

tggtggtgga tgtggattgc gcggaaaata ctaaagagga tcagttggcc gaaatcagtt    840

accgttttca aggtaagaag gaagcggacc aaccgtggat tgttgtaaac acgagcacac    900

tgtttgatga actcgaatta gaccccccg agattgaacc gggtgtcttg aaagtacttc     960

ggacagaaaa acaatacttg ggtgtgtaca tttggaacat gcgcggctcc gatggtacgt   1020

ctacctacgc cacgtttttg gtcacctgga aaggggatga aaaaacaaga aaccctacgc   1080

ccgcagtaac tcctcaacca agaggggctg agtttcatat gtggaattac cactcgcatg   1140

tattttcagt tggtgatacg tttagcttgg caatgcatct tcagtataag atacatgaag   1200

cgccatttga tttgctgtta gagtggttgt atgtccccat cgatcctaca tgtcaaccaa   1260

tgcggttata ttctacgtgt ttgtatcatc ccaacgcacc ccaatgcctc tctcatatga   1320

attccggttg tacatttacc tcgccacatt tagcccagcg tgttgcaagc acagtgtatc   1380

aaaattgtga acatgcagat aactacaccg catattgtct gggaatatct catatggagc   1440
```

ctagctttgg tctaatctta cacgacgggg gcaccacgtt aaagtttgta gatacacccg 1500
agagtttgtc gggattatac gtttttgtgg tgtattttaa cgggcatgtt gaagccgtag 1560
catacactgt tgtatccaca gtagatcatt ttgtaaacgc aattgaagag cgtggatttc 1620
cgccaacggc cggtcagcca ccggcgacta ctaaacccaa ggaaattacc cccgtaaacc 1680
ccggaacgtc accacttcta cgatatgccg catggaccgg agggcttgca gcagtagtac 1740
ttttatgtct cgtaatattt ttaatctgta cggctaaacg aatgagggtt aaagcctata 1800
gggtagacaa gtgatgataa taggctggag cctcggtggc catgcttctt gccccttggg 1860
cctcccccca gcccctcctc cccttcctgc acccgtaccc ccgtggtctt tgaataaagt 1920
ctgagtgggc ggc 1933

<210> SEQ ID NO 6
<211> LENGTH: 1933
<212> TYPE: DNA
<213> ORGANISM: Artificial Sequence
<220> FEATURE:
<223> OTHER INFORMATION: Synthetic Polynucleotide

<400> SEQUENCE: 6
tcaagctttt ggaccctcgt acagaagcta atacgactca ctatagggaa ataagagaga 60
aaagaagagt aagaagaaat ataagagcca ccatggggac agttaataaa cctgtggtgg 120
gggtattgat ggggttcgga attatcacgg gaacgttgcg tataacgaat ccggtcagag 180
catccgtctt gcgatacgat gattttcaca tcgatgaaga caaactggat acaaactccg 240
tatatgagcc ttactaccat tcagatcatg cggagtcttc atgggtaaat cggggagagt 300
cttcgcgaaa agcgtacgat cataactcac cttatatatg gccacgtaat gattatgatg 360
gatttttaga gaacgcacac gaacaccatg gggtgtataa tcagggccgt ggtatcgata 420
gcggggaacg gttaatgcaa cccacacaaa tgtctgcaca ggaggatctt ggggacgata 480
cgggcatcca cgttatccct acgttaaacg gcgatgacag acataaaatt gtaaatgtgg 540
accaacgtca atacggtgac gtgtttaaag gagatcttaa tccaaaaccc caaggccaaa 600
gactcattga ggtgtcagtg gaagaaaatc acccgtttac tttacgcgca ccgattcagc 660
ggatttatgg agtccggtac accgagactt ggagcttttt gccgtcatta acctgtacgg 720
gagacgcagc gcccgccatc cagcatatat gtttaaaaca tacaacatgc tttcaagacg 780
tggtggtgga tgtggattgc gcggaaaata ctaaagagga tcagttggcc gaaatcagtt 840
accgttttca aggtaagaag gaagcggacc aaccgtggat tgttgtaaac acgagcacac 900
tgtttgatga actcgaatta gacccccccg agattgaacc gggtgtcttg aaagtacttc 960
ggacagaaaa acaatacttg ggtgtgtaca tttggaacat gcgcggctcc gatggtacgt 1020
ctacctacgc cacgtttttg gtcacctgga aaggggatga aaaaacaaga aaccctacgc 1080
ccgcagtaac tcctcaacca agaggggctg agtttcatat gtggaattac cactcgcatg 1140
tattttcagt tggtgatacg tttagcttgg caatgcatct tcagtataag atacatgaag 1200
cgccatttga tttgctgtta gagtggttgt atgtccccat cgatcctaca tgtcaaccaa 1260
tgcggttata ttctacgtgt ttgtatcatc ccaacgcacc ccaatgcctc tctcatatga 1320
attccggttg tacatttacc tcgccacatt tagcccagcg tgttgcaagc acagtgtatc 1380
aaaattgtga acatgcagat aactacaccg catattgtct gggaatatct catatggagc 1440
ctagctttgg tctaatctta cacgacgggg gcaccacgtt aaagtttgta gatacacccg 1500
agagtttgtc gggattatac gtttttgtgg tgtattttaa cgggcatgtt gaagccgtag 1560
catacactgt tgtatccaca gtagatcatt ttgtaaacgc aattgaagag cgtggatttc 1620
cgccaacggc cggtcagcca ccggcgacta ctaaacccaa ggaaattacc cccgtaaacc 1680
ccggaacgtc accacttcta cgatatgccg catggaccgg agggcttgca gcagtagtac 1740
ttttatgtct cgtaatattt ttaatctgta cggctaaacg aatgagggtt aaagccgcca 1800
gggtagacaa gtgatgataa taggctggag cctcggtggc catgcttctt gccccttggg 1860
cctcccccca gcccctcctc cccttcctgc acccgtaccc ccgtggtctt tgaataaagt 1920
ctgagtgggc ggc 1933

<210> SEQ ID NO 7
<211> LENGTH: 2083
<212> TYPE: DNA
<213> ORGANISM: Artificial Sequence
<220> FEATURE:
<223> OTHER INFORMATION: Synthetic Polynucleotide

<400> SEQUENCE: 7
tcaagctttt ggaccctcgt acagaagcta atacgactca ctatagggaa ataagagaga 60
aaagaagagt aagaagaaat ataagagcca ccatggggac agttaataaa cctgtggtgg 120
gggtattgat ggggttcgga attatcacgg gaacgttgcg tataacgaat ccggtcagag 180
catccgtctt gcgatacgat gattttcaca tcgatgaaga caaactggat acaaactccg 240
tatatgagcc ttactaccat tcagatcatg cggagtcttc atgggtaaat cggggagagt 300
cttcgcgaaa agcgtacgat cataactcac cttatatatg gccacgtaat gattatgatg 360
gatttttaga gaacgcacac gaacaccatg ggtgtataa tcagggccgt ggtatcgata 420
gcggggaacg gttaatgcaa cccacacaaa tgtctgcaca ggaggatctt ggggacgata 480
cgggcatcca cgttatccct acgttaaacg gcgatgacag acataaaatt gtaaatgtgg 540
accaacgtca atacggtgac gtgtttaaag gagatcttaa tccaaaaccc caaggccaaa 600
gactcattga ggtgtcagtg gaagaaaatc acccgtttac tttacgcgca ccgattcagc 660
ggatttatgg agtccggtac accgagactt ggagcttttt gccgtcatta acctgtacgg 720
gagacgcagc gcccgccatc cagcatatat gtttaaaaca tacaacatgc tttcaagacg 780
tggtggtgga tgtggattgc gcggaaaata ctaaagagga tcagttggcc gaaatcagtt 840
accgttttca aggtaagaag gaagcggacc aaccgtggat tgttgtaaac acgagcacac 900
tgtttgatga actcgaatta gacccccccg agattgaacc gggtgtcttg aaagtacttc 960
ggacagaaaa acaatacttg ggtgtgtaca tttggaacat gcgcggctcc gatggtacgt 1020
ctacctacgc cacgtttttg gtcacctgga aaggggatga aaaaacaaga aaccctacgc 1080
ccgcagtaac tcctcaacca agaggggctg agtttcatat gtggaattac cactcgcatg 1140
tattttcagt tggtgatacg tttagcttgg caatgcatct tcagtataag atacatgaag 1200
cgccatttga tttgctgtta gagtggttgt atgtccccat cgatcctaca tgtcaaccaa 1260
tgcggttata ttctacgtgt ttgtatcatc ccaacgcacc ccaatgcctc tctcatatga 1320
attccggttg tacatttacc tcgccacatt tagcccagcg tgttgcaagc acagtgtatc 1380
aaaattgtga acatgcagat aactacaccg catattgtct gggaatatct catatggagc 1440
ctagctttgg tctaatctta cacgacgggg gcaccacgtt aaagtttgta gatacacccg 1500
agagtttgtc gggattatac gtttttgtgg tgtattttaa cgggcatgtt gaagccgtag 1560
catacactgt tgtatccaca gtagatcatt ttgtaaacgc aattgaagag cgtggatttc 1620
cgccaacggc cggtcagcca ccggcgacta ctaaacccaa ggaaattacc cccgtaaacc 1680
ccggaacgtc accacttcta cgatatgccg catggaccgg agggcttgca gcagtagtac 1740
ttttatgtct cgtaatattt ttaatctgta cggctaaacg aatgagggtt aaagcctata 1800
gggtagacaa gtccccgtat aaccaaagca tgtattacgc tggccttcca gtggacgatt 1860
tcgaggacgc cgaagccgcc gatgccgaag aagagtttgg taacgcgatt ggagggagtc 1920
acgggggttc gagttacacg gtgtatatag ataagacccg gtgatgataa taggctggag 1980
cctcggtggc catgcttctt gccccttggg cctcccccca gcccctcctc cccttcctgc 2040
acccgtaccc ccgtggtctt tgaataaagt ctgagtgggc ggc 2083

<210> SEQ ID NO 8
<211> LENGTH: 2083
<212> TYPE: DNA
<213> ORGANISM: Artificial Sequence
<220> FEATURE:
<223> OTHER INFORMATION: Synthetic Polynucleotide

<400> SEQUENCE: 8
tcaagctttt ggaccctcgt acagaagcta atacgactca ctatagggaa ataagagaga 60
aaagaagagt aagaagaaat ataagagcca ccatggggac agttaataaa cctgtggtgg 120
gggtattgat ggggttcgga attatcacgg gaacgttgcg tataacgaat ccggtcagag 180
catccgtctt gcgatacgat gattttcaca tcgatgaaga caaactggat acaaactccg 240
tatatgagcc ttactaccat tcagatcatg cggagtcttc atgggtaaat cggggagagt 300
cttcgcgaaa agcgtacgat cataactcac cttatatatg gccacgtaat gattatgatg 360
gatttttaga gaacgcacac gaacaccatg ggtgtataa tcagggccgt ggtatcgata 420
gcggggaacg gttaatgcaa cccacacaaa tgtctgcaca ggaggatctt ggggacgata 480
cgggcatcca cgttatccct acgttaaacg gcgatgacag acataaaatt gtaaatgtgg 540
accaacgtca atacggtgac gtgtttaaag gagatcttaa tccaaaaccc caaggccaaa 600
gactcattga ggtgtcagtg gaagaaaatc acccgtttac tttacgcgca ccgattcagc 660
ggatttatgg agtccggtac accgagactt ggagcttttt gccgtcatta acctgtacgg 720
gagacgcagc gcccgccatc cagcatatat gtttaaaaca tacaacatgc tttcaagacg 780
tggtggtgga tgtggattgc gcggaaaata ctaaagagga tcagttggcc gaaatcagtt 840
accgttttca aggtaagaag gaagcggacc aaccgtggat tgttgtaaac acgagcacac 900
tgtttgatga actcgaatta gacccccccg agattgaacc gggtgtcttg aaagtacttc 960
ggacagaaaa acaatacttg ggtgtgtaca tttggaacat gcgcggctcc gatggtacgt 1020
ctacctacgc cacgtttttg gtcacctgga aaggggatga aaaaacaaga aaccctacgc 1080
ccgcagtaac tcctcaacca agaggggctg agtttcatat gtggaattac cactcgcatg 1140
tattttcagt tggtgatacg tttagcttgg caatgcatct tcagtataag atacatgaag 1200
cgccatttga tttgctgtta gagtggttgt atgtccccat cgatcctaca tgtcaaccaa 1260
tgcggttata ttctacgtgt ttgtatcatc ccaacgcacc ccaatgcctc tctcatatga 1320
attccggttg tacatttacc tcgccacatt tagcccagcg tgttgcaagc acagtgtatc 1380
aaaattgtga acatgcagat aactacaccg catattgtct gggaatatct catatggagc 1440
ctagctttgg tctaatctta cacgacgggg gcaccacgtt aaagtttgta gatacacccg 1500
agagtttgtc gggattatac gtttttgtgg tgtattttaa cgggcatgtt gaagccgtag 1560

-continued catacactgt tgtatccaca gtagatcatt ttgtaaacgc aattgaagag cgtggatttc 1620
cgccaacggc cggtcagcca ccggcgacta ctaaacccaa ggaaattacc cccgtaaacc 1680
ccggaacgtc accacttcta cgatatgccg catggaccgg agggcttgca gcagtagtac 1740
ttttatgtct cgtaatattt ttaatctgta cggctaaacg aatgagggtt aaagcctata 1800
gggtagacaa gtccccgtat aaccaaagca tgtatggcgc tggccttcca gtggacgatt 1860
tcgaggacgc cgaagccgcc gatgccgaag aagagtttgg taacgcgatt ggagggagtc 1920
acgggggttc gagttacacg gtgtatatag ataagacccg gtgatgataa taggctggag 1980
cctcggtggc catgcttctt gccccttggg cctcccccca gcccctcctc cccttcctgc 2040
acccgtaccc ccgtggtctt tgaataaagt ctgagtgggc ggc 2083

<210> SEQ ID NO 9
<211> LENGTH: 2080
<212> TYPE: DNA
<213> ORGANISM: Artificial Sequence
<220> FEATURE:
<223> OTHER INFORMATION: Synthetic Polynucleotide

<400> SEQUENCE: 9
tcaagctttt ggaccctcgt acagaagcta atacgactca ctatagggaa ataagagaga 60
aaagaagagt aagaagaaat ataagagcca ccatggggac agtgaataag ccggttgtgg 120
gcgtgcttat gggctttggg attattaccg gtacattacg aattaccaat ccagtgcgcg 180
ccagtgtgct gcgttacgac gactttcaca ttgacgagga taagctggat actaacagcg 240
tgtacgaacc ttattaccac tcagatcatg ccgaatcaag ctgggttaat agaggagaaa 300
gcagccgaaa agcctacgac cacaactcac cttatatttg gcccagaaac gattatgacg 360
gtttcctgga aaacgcacat gaacaccatg gagtctacaa ccaaggcagg ggaatcgaca 420
gtggcgagcg tcttatgcag ccaacacaga tgtcggcaca ggaggatctc ggtgatgaca 480
ccggcataca cgtgattccc acattaaacg gcgacgacag acataagatc gtcaatgtgg 540
atcagcgtca gtatggggat gtctttaaag gcgatttgaa tccaaagccc caaggacaga 600
gactgatcga ggtctctgta gaagaaaatc accccttcac tttgcgcgct ccaatccaga 660
ggatttacgg ggtgcgttat accgaaactt ggagtttctt gccgtcactg acgtgtacgg 720
gggatgccgc ccccgcaatc cagcacatct gtctgaaaca caccacatgc tttcaggacg 780
tggttgtgga tgtggattgc gcggaaaaca caaaagaaga ccaactcgcc gaaatcagct 840
atcgttttca gggtaaaaaa gaggccgacc aaccgtggat tgttgtgaat acgagcacgc 900
tcttcgatga gcttgaactc gatcccccgg aaatcgagcc tggggttcta aaagtgttga 960
ggaccgagaa gcagtacctc ggggtttata tctggaatat gagaggctcc gatggcacct 1020
ctacctacgc aacgtttctg gttacctgga agggagacga gaagacacgg aatccaacgc 1080
ccgctgtgac ccctcagcct aggggagccg aattccacat gtggaactat cactcccatg 1140
tattcagtgt gggtgacact ttcagcctgg ccatgcacct gcagtataag attcacgagg 1200
cacccttcga cctcctgctg gagtggttgt acgtacctat tgatcccact tgtcagccca 1260
tgcgcctgta ctccacttgc ttgtaccacc ccaatgcacc acagtgtcta tcacacatga 1320
actccgggtg tacctttact tcaccccatc ttgcccagcg ggtcgccagc acagtgtatc 1380
agaactgtga gcatgctgac aactatactg cttattgcct cggaatatcc catatggagc 1440
caagcttcgg gctcatactg cacgatggtg gtacgacact caagttcgtg gacaccccccg 1500 aaagcctttc tggcttgtac gtgttcgtgg tctacttcaa tggacatgtg gaggcagtgg 1560

```
cttacacagt ggtttcgaca gttgatcact ttgtaaatgc cattgaggaa cgcggcttcc   1620

cgcctacagc gggccagccc cctgcgacaa caaaaccaaa agagattacg cccgttaatc   1680

ctgggactag tccattgctg aggtatgccg cctggactgg cggtctggcg gccgtggtac   1740

ttctgtgttt agtcatattt ctgatctgta ccgctaaacg tatgcgggtc aaggcttacc   1800

gtgttgacaa gtctccttac aatcagtcaa tgtactatgc aggactccct gttgacgatt   1860

tcgaagactc agagagtaca gacacagaag aagaattcgg aaacgctata ggtggctctc   1920

acggaggtag ctcgtataca gtgtacatcg ataaaaccag atgataatag gctggagcct   1980

cggtggccat gcttcttgcc ccttgggcct ccccccagcc cctcctcccc ttcctgcacc   2040

cgtacccccg tggtctttga ataaagtctg agtgggcggc                         2080
```

<210> SEQ ID NO 10
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 10

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270
```

```
Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620
```

<210> SEQ ID NO 11
<211> LENGTH: 1869
<212> TYPE: DNA
<213> ORGANISM: Artificial Sequence
<220> FEATURE:
<223> OTHER INFORMATION: Synthetic Polynucleotide

<400> SEQUENCE: 11
atggggacag tgaataagcc ggttgtgggc gtgcttatgg gctttgggat tattaccggt     60

```
acattacgaa ttaccaatcc agtgcgcgcc agtgtgctgc gttacgacga ctttcacatt    120
gacgaggata agctggatac taacagcgtg tacgaacctt attaccactc agatcatgcc    180
gaatcaagct gggttaatag aggagaaagc agccgaaaag cctacgacca caactcacct    240
tatatttggc ccagaaacga ttatgacggt ttcctggaaa acgcacatga acaccatgga    300
gtctacaacc aaggcagggg aatcgacagt ggcgagcgtc ttatgcagcc aacacagatg    360
tcggcacagg aggatctcgg tgatgacacc ggcatacacg tgattcccac attaaacggc    420
gacgacagac ataagatcgt caatgtggat cagcgtcagt atggggatgt ctttaaaggc    480
gatttgaatc caaagcccca aggacagaga ctgatcgagg tctctgtaga agaaaatcac    540
cccttcactt tgcgcgctcc aatccagagg atttacgggg tgcgttatac cgaaacttgg    600
agtttcttgc cgtcactgac gtgtacgggg gatgccgccc ccgcaatcca gcacatctgt    660
ctgaaacaca ccacatgctt tcaggacgtg gttgtggatg tggattgcgc ggaaaacaca    720
aaagaagacc aactcgccga aatcagctat cgttttcagg gtaaaaaaga ggccgaccaa    780
ccgtggattg ttgtgaatac gagcacgctc ttcgatgagc ttgaactcga tcccccggaa    840
atcgagcctg gggttctaaa agtgttgagg accgagaagc agtacctcgg ggtttatatc    900
tggaatatga gaggctccga tggcacctct acctacgcaa cgtttctggt tacctggaag    960
ggagacgaga agacacggaa tccaacgccc gctgtgaccc ctcagcctag gggagccgaa   1020
ttccacatgt ggaactatca ctcccatgta ttcagtgtgg gtgacacttt cagcctggcc   1080
atgcacctgc agtataagat tcacgaggca cccttcgacc tcctgctgga gtggttgtac   1140
gtacctattg atcccacttg tcagcccatg cgcctgtact ccacttgctt gtaccacccc   1200
aatgcaccac agtgtctatc acacatgaac tccgggtgta cctttacttc accccatctt   1260
gcccagcggg tcgccagcac agtgtatcag aactgtgagc atgctgacaa ctatactgct   1320
tattgcctcg gaatatccca tatggagcca agcttcgggc tcatactgca cgatggtggt   1380
acgacactca agttcgtgga cacccccgaa agcctttctg gcttgtacgt gttcgtggtc   1440
tacttcaatg gacatgtgga ggcagtggct tacacagtgg tttcgacagt tgatcacttt   1500
gtaaatgcca ttgaggaacg cggcttcccg cctacagcgg gccagccccc tgcgacaaca   1560
aaaccaaaag agattacgcc cgttaatcct gggactagtc cattgctgag gtatgccgcc   1620
tggactggcg gtctggcggc cgtggtactt ctgtgtttag tcatatttct gatctgtacc   1680
gctaaacgta tgcgggtcaa ggcttaccgt gttgacaagt ctccttacaa tcagtcaatg   1740
tactatgcag gactccctgt tgacgatttc gaagactcag agagtacaga cacagaagaa   1800
gaattcggaa acgctatagg tggctctcac ggaggtagct cgtatacagt gtacatcgat   1860
aaaaccaga                                                           1869
```

<210> SEQ ID NO 12
<211> LENGTH: 2141
<212> TYPE: DNA
<213> ORGANISM: Artificial Sequence
<220> FEATURE:
<223> OTHER INFORMATION: Synthetic Polynucleotide

<400> SEQUENCE: 12

```
ggggaaataa gagagaaaag aagagtaaga agaaatataa gagccaccat ggggacagtg     60
aataagccgg ttgtgggcgt gcttatgggc tttgggatta ttaccggtac attacgaatt    120
accaatccag tgcgcgccag tgtgctgcgt tacgacgact ttcacattga cgaggataag    180
ctggatacta acagcgtgta cgaaccttat taccactcag atcatgccga atcaagctgg    240
```

```
gttaatagag gagaaagcag ccgaaaagcc tacgaccaca actcacctta tatttggccc    300
agaaacgatt atgacggttt cctggaaaac gcacatgaac accatggagt ctacaaccaa    360
ggcaggggaa tcgacagtgg cgagcgtctt atgcagccaa cacagatgtc ggcacaggag    420
gatctcggtg atgacaccgg catacacgtg attcccacat taaacggcga cgacagacat    480
aagatcgtca atgtggatca gcgtcagtat ggggatgtct ttaaaggcga tttgaatcca    540
aagccccaag gacagagact gatcgaggtc tctgtagaag aaaatcaccc cttcactttg    600
cgcgctccaa tccagaggat ttacggggtg cgttataccg aaacttggag tttcttgccg    660
tcactgacgt gtacgggga tgccgccccc gcaatccagc acatctgtct gaaacacacc    720
acatgctttc aggacgtggt tgtggatgtg gattgcgcgg aaaacacaaa agaagaccaa    780
ctcgccgaaa tcagctatcg ttttcagggt aaaaaagagg ccgaccaacc gtggattgtt    840
gtgaatacga gcacgctctt cgatgagctt gaactcgatc cccggaaat cgagcctggg    900
gttctaaaag tgttgaggac cgagaagcag tacctcgggg tttatatctg gaatatgaga    960
ggctccgatg gcacctctac ctacgcaacg tttctggtta cctggaaggg agacgagaag   1020
acacggaatc caacgcccgc tgtgacccct cagcctaggg gagccgaatt ccacatgtgg   1080
aactatcact cccatgtatt cagtgtgggt gacactttca gcctggccat gcacctgcag   1140
tataagattc acgaggcacc cttcgacctc ctgctggagt ggttgtacgt acctattgat   1200
cccacttgtc agcccatgcg cctgtactcc acttgcttgt accaccccaa tgcaccacag   1260
tgtctatcac acatgaactc cgggtgtacc tttacttcac cccatcttgc ccagcgggtc   1320
gccagcacag tgtatcagaa ctgtgagcat gctgacaact atactgctta ttgcctcgga   1380
atatcccata tggagccaag cttcgggctc atactgcacg atggtggtac gacactcaag   1440
ttcgtggaca cccccgaaag cctttctggc ttgtacgtgt tcgtggtcta cttcaatgga   1500
catgtggagg cagtggctta cacagtggtt tcgacagttg atcactttgt aaatgccatt   1560
gaggaacgcg gcttcccgcc tacagcgggc cagccccctg cgacaacaaa accaaaagag   1620
attacgcccg ttaatcctgg gactagtcca ttgctgaggt atgccgcctg gactggcggt   1680
ctggcggccg tggtacttct gtgtttagtc atatttctga tctgtaccgc taaacgtatg   1740
cgggtcaagg cttaccgtgt tgacaagtct ccttacaatc agtcaatgta ctatgcagga   1800
ctccctgttg acgatttcga agactcagag agtacagaca cagaagaaga attcggaaac   1860
gctataggtg gctctcacgg aggtagctcg tatacagtgt acatcgataa aaccagatga   1920
taataggctg gagcctcggt ggccatgctt cttgcccctt gggcctcccc ccagcccctc   1980
ctccccttcc tgcacccgta cccccgtggt ctttgaataa agtctgagtg ggcggcaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaatcta g                       2141
```

<210> SEQ ID NO 13
<211> LENGTH: 2050
<212> TYPE: DNA
<213> ORGANISM: Artificial Sequence
<220> FEATURE:
<223> OTHER INFORMATION: Synthetic Polynucleotide

<400> SEQUENCE: 13

```
tcaagctttt ggaccctcgt acagaagcta atacgactca ctatagggaa ataagagaga     60
aaagaagagt aagaagaaat ataagagcca ccatggagac tcccgctcag ctactgttcc    120
```

```
tcctgctcct ttggctgcct gatactacag gctctgtttt gcggtacgac gactttcaca    180

tcgatgagga caagctcgac actaatagcg tgtatgagcc ctactaccat tcagatcacg    240

ccgagtcctc ttgggtgaac aggggtgaaa gttctaggaa agcctatgat cacaacagcc    300

cttatatttg gccacggaat gattacgacg gatttctcga aaatgcccac gagcatcacg    360

gagtgtacaa ccagggccgt ggaatcgact ctggggagag attgatgcaa cctacacaga    420

tgagcgccca ggaagatctc ggggatgata caggaattca cgttatccct acattaaacg    480

gagatgaccg ccacaaaatc gtcaatgtcg atcaaagaca gtatggagat gtgttcaaag    540

gcgatctcaa ccctaagccg cagggccaga gactcattga ggtgtctgtc gaagagaacc    600

accctttcac tctgcgcgct cccattcaga gaatctatgg agttcgctat acggagactt    660

ggtcattcct tccttccctg acatgcaccg gagacgccgc ccctgccatt cagcacatat    720

gcctgaaaca taccacctgt ttccaggatg tggtggttga tgttgattgt gctgaaaata    780

ccaaggaaga ccaactggcc gagattagtt accggttcca agggaaaaag gaagccgacc    840

agccatggat tgtggttaat acaagcactc tgttcgatga gctcgagctg gatccccccg    900

agatagaacc cggagttctg aaagtgctcc ggacagaaaa acaatatctg ggagtctaca    960

tatggaacat gcgcggttcc gatgggacct ccacttatgc aacctttctc gtcacgtgga   1020

agggagatga gaaaactagg aatcccacac ccgctgtcac accacagcca agaggggctg   1080

agttccatat gtggaactat catagtcacg tgtttagtgt cggagatacg ttttcattgg   1140

ctatgcatct ccagtacaag attcatgagg ctcccttcga tctgttgctt gagtggttgt   1200

acgtcccgat tgacccgacc tgccagccca tgcgactgta cagcacctgt ctctaccatc   1260

caaacgctcc gcaatgtctg agccacatga actctgggtg tactttcacc agtccccacc   1320

tcgcccagcg ggtggcctct actgtttacc agaactgtga gcacgccgac aactacaccg   1380

catactgcct cggtatttct cacatggaac cctccttcgg actcatcctg cacgatgggg   1440

gcactaccct gaagttcgtt gatacgccag aatctctgtc tgggctctat gttttcgtgg   1500

tctacttcaa tggccatgtc gaggccgtgg cctatactgt cgtttctacc gtggatcatt   1560

ttgtgaacgc catcgaagaa cggggattcc cccctacggc aggccagccg cctgcaacca   1620

ccaagcccaa ggaaataaca ccagtgaacc ctggcacctc acctctccta agatatgccg   1680

cgtggacagg gggactggcg gcagtggtgc tcctctgtct cgtgatcttt ctgatctgta   1740

cagccaagag gatgagggtc aaggcttata gagtggacaa gtccccctac aatcagtcaa   1800

tgtactacgc cggccttccc gttgatgatt ttgaggattc cgagtccaca gatactgagg   1860

aagagttcgg taacgctata ggcggctctc acgggggttc aagctacacg gtttacattg   1920

acaagacacg ctgataatag gctggagcct cggtggccat gcttcttgcc ccttgggcct   1980

ccccccagcc cctcctcccc ttcctgcacc cgtacccccg tggtctttga ataaagtctg   2040

agtgggcggc                                                          2050
```

<210> SEQ ID NO 14
<211> LENGTH: 613
<212> TYPE: PRT
<213> ORGANISM: Artificial Sequence
<220> FEATURE:
<223> OTHER INFORMATION: Synthetic Polypeptide

<400> SEQUENCE: 14

```
Met Glu Thr Pro Ala Gln Leu Leu Phe Leu Leu Leu Leu Trp Leu Pro
1               5                   10                  15
```

-continued

```
Asp Thr Thr Gly Ser Val Leu Arg Tyr Asp Asp Phe His Ile Asp Glu
            20                  25                  30

Asp Lys Leu Asp Thr Asn Ser Val Tyr Glu Pro Tyr Tyr His Ser Asp
        35                  40                  45

His Ala Glu Ser Ser Trp Val Asn Arg Gly Glu Ser Ser Arg Lys Ala
    50                  55                  60

Tyr Asp His Asn Ser Pro Tyr Ile Trp Pro Arg Asn Asp Tyr Asp Gly
65                  70                  75                  80

Phe Leu Glu Asn Ala His Glu His His Gly Val Tyr Asn Gln Gly Arg
                85                  90                  95

Gly Ile Asp Ser Gly Glu Arg Leu Met Gln Pro Thr Gln Met Ser Ala
            100                 105                 110

Gln Glu Asp Leu Gly Asp Asp Thr Gly Ile His Val Ile Pro Thr Leu
        115                 120                 125

Asn Gly Asp Asp Arg His Lys Ile Val Asn Val Asp Gln Arg Gln Tyr
    130                 135                 140

Gly Asp Val Phe Lys Gly Asp Leu Asn Pro Lys Pro Gln Gly Gln Arg
145                 150                 155                 160

Leu Ile Glu Val Ser Val Glu Glu Asn His Pro Phe Thr Leu Arg Ala
                165                 170                 175

Pro Ile Gln Arg Ile Tyr Gly Val Arg Tyr Thr Glu Thr Trp Ser Phe
            180                 185                 190

Leu Pro Ser Leu Thr Cys Thr Gly Asp Ala Ala Pro Ala Ile Gln His
        195                 200                 205

Ile Cys Leu Lys His Thr Thr Cys Phe Gln Asp Val Val Val Asp Val
    210                 215                 220

Asp Cys Ala Glu Asn Thr Lys Glu Asp Gln Leu Ala Glu Ile Ser Tyr
225                 230                 235                 240

Arg Phe Gln Gly Lys Lys Glu Ala Asp Gln Pro Trp Ile Val Val Asn
                245                 250                 255

Thr Ser Thr Leu Phe Asp Glu Leu Glu Leu Asp Pro Pro Glu Ile Glu
            260                 265                 270

Pro Gly Val Leu Lys Val Leu Arg Thr Glu Lys Gln Tyr Leu Gly Val
        275                 280                 285

Tyr Ile Trp Asn Met Arg Gly Ser Asp Gly Thr Ser Thr Tyr Ala Thr
    290                 295                 300

Phe Leu Val Thr Trp Lys Gly Asp Glu Lys Thr Arg Asn Pro Thr Pro
305                 310                 315                 320

Ala Val Thr Pro Gln Pro Arg Gly Ala Glu Phe His Met Trp Asn Tyr
                325                 330                 335

His Ser His Val Phe Ser Val Gly Asp Thr Phe Ser Leu Ala Met His
            340                 345                 350

Leu Gln Tyr Lys Ile His Glu Ala Pro Phe Asp Leu Leu Leu Glu Trp
        355                 360                 365

Leu Tyr Val Pro Ile Asp Pro Thr Cys Gln Pro Met Arg Leu Tyr Ser
    370                 375                 380

Thr Cys Leu Tyr His Pro Asn Ala Pro Gln Cys Leu Ser His Met Asn
385                 390                 395                 400

Ser Gly Cys Thr Phe Thr Ser Pro His Leu Ala Gln Arg Val Ala Ser
                405                 410                 415

Thr Val Tyr Gln Asn Cys Glu His Ala Asp Asn Tyr Thr Ala Tyr Cys
            420                 425                 430

Leu Gly Ile Ser His Met Glu Pro Ser Phe Gly Leu Ile Leu His Asp
```

```
        435                 440                 445

Gly Gly Thr Thr Leu Lys Phe Val Asp Thr Pro Glu Ser Leu Ser Gly
    450                 455                 460

Leu Tyr Val Phe Val Val Tyr Phe Asn Gly His Val Glu Ala Val Ala
465                 470                 475                 480

Tyr Thr Val Val Ser Thr Val Asp His Phe Val Asn Ala Ile Glu Glu
                485                 490                 495

Arg Gly Phe Pro Pro Thr Ala Gly Gln Pro Pro Ala Thr Thr Lys Pro
            500                 505                 510

Lys Glu Ile Thr Pro Val Asn Pro Gly Thr Ser Pro Leu Leu Arg Tyr
        515                 520                 525

Ala Ala Trp Thr Gly Gly Leu Ala Ala Val Val Leu Leu Cys Leu Val
    530                 535                 540

Ile Phe Leu Ile Cys Thr Ala Lys Arg Met Arg Val Lys Ala Tyr Arg
545                 550                 555                 560

Val Asp Lys Ser Pro Tyr Asn Gln Ser Met Tyr Tyr Ala Gly Leu Pro
                565                 570                 575

Val Asp Asp Phe Glu Asp Ser Glu Ser Thr Asp Thr Glu Glu Glu Phe
            580                 585                 590

Gly Asn Ala Ile Gly Gly Ser His Gly Gly Ser Ser Tyr Thr Val Tyr
        595                 600                 605

Ile Asp Lys Thr Arg
    610
```

<210> SEQ ID NO 15
<211> LENGTH: 1839
<212> TYPE: DNA
<213> ORGANISM: Artificial Sequence
<220> FEATURE:
<223> OTHER INFORMATION: Synthetic Polynucleotide

<400> SEQUENCE: 15

```
atggagactc ccgctcagct actgttcctc ctgctccttt ggctgcctga tactacaggc     60

tctgttttgc ggtacgacga ctttcacatc gatgaggaca agctcgacac taatagcgtg    120

tatgagccct actaccattc agatcacgcc gagtcctctt gggtgaacag gggtgaaagt    180

tctaggaaag cctatgatca caacagccct tatatttggc cacggaatga ttacgacgga    240

tttctcgaaa atgcccacga gcatcacgga gtgtacaacc agggccgtgg aatcgactct    300

ggggagagat tgatgcaacc tacacagatg agcgcccagg aagatctcgg ggatgataca    360

ggaattcacg ttatccctac attaaacgga gatgaccgcc acaaaatcgt caatgtcgat    420

caaagacagt atggagatgt gttcaaaggc gatctcaacc ctaagccgca gggccagaga    480

ctcattgagg tgtctgtcga agagaaccac cctttcactc tgcgcgctcc cattcagaga    540

atctatggag ttcgctatac ggagacttgg tcattccttc cttccctgac atgcaccgga    600

gacgccgccc ctgccattca gcacatatgc ctgaaacata ccacctgttt ccaggatgtg    660

gtggttgatg ttgattgtgc tgaaaatacc aaggaagacc aactggccga gattagttac    720

cggttccaag ggaaaaagga agccgaccag ccatggattg tggttaatac aagcactctg    780

ttcgatgagc tcgagctgga tccccccgag atagaacccg gagttctgaa agtgctccgg    840

acagaaaaac aatatctggg agtctacata tggaacatgc gcggttccga tgggacctcc    900

acttatgcaa cctttctcgt cacgtggaag ggagatgaga aaactaggaa tcccacaccc    960

gctgtcacac cacagccaag aggggctgag ttccatatgt ggaactatca tagtcacgtg   1020
```

tttagtgtcg gagatacgtt ttcattggct atgcatctcc agtacaagat tcatgaggct 1080
cccttcgatc tgttgcttga gtggttgtac gtcccgattg acccgacctg ccagcccatg 1140
cgactgtaca gcacctgtct ctaccatcca aacgctccgc aatgtctgag ccacatgaac 1200
tctgggtgta ctttcaccag tccccacctc gcccagcggg tggcctctac tgtttaccag 1260
aactgtgagc acgccgacaa ctacaccgca tactgcctcg gtatttctca catggaaccc 1320
tccttcggac tcatcctgca cgatgggggc actaccctga agttcgttga tacgccagaa 1380
tctctgtctg ggctctatgt tttcgtggtc tacttcaatg gccatgtcga ggccgtggcc 1440
tatactgtcg tttctaccgt ggatcatttt gtgaacgcca tcgaagaacg ggattcccc 1500 cctacggcag gccagccgcc tgcaaccacc aagcccaagg aaataacacc agtgaaccct 1560
ggcacctcac ctctcctaag atatgccgcg tggacagggg gactggcggc agtggtgctc 1620
ctctgtctcg tgatctttct gatctgtaca gccaagagga tgagggtcaa ggcttataga 1680
gtggacaagt ccccctacaa tcagtcaatg tactacgccg gccttcccgt tgatgatttt 1740
gaggattccg agtccacaga tactgaggaa gagttcggta acgctatagg cggctctcac 1800
gggggttcaa gctacacggt ttacattgac aagacacgc 1839

<210> SEQ ID NO 16
<211> LENGTH: 2111
<212> TYPE: DNA
<213> ORGANISM: Artificial Sequence
<220> FEATURE:
<223> OTHER INFORMATION: Synthetic Polynucleotide

<400> SEQUENCE: 16
ggggaaataa gagagaaaag aagagtaaga agaaatataa gagccaccat ggagactccc 60
gctcagctac tgttcctcct gctcctttgg ctgcctgata ctacaggctc tgttttgcgg 120
tacgacgact ttcacatcga tgaggacaag ctcgacacta atagcgtgta tgagccctac 180
taccattcag atcacgccga gtcctcttgg gtgaacaggg gtgaaagttc taggaaagcc 240
tatgatcaca acagccctta tatttggcca cggaatgatt acgacggatt tctcgaaaat 300
gcccacgagc atcacggagt gtacaaccag ggccgtggaa tcgactctgg ggagagattg 360
atgcaaccta cacagatgag cgcccaggaa gatctcgggg atgatacagg aattcacgtt 420
atccctacat taaacggaga tgaccgccac aaaatcgtca atgtcgatca aagacagtat 480
ggagatgtgt tcaaaggcga tctcaaccct aagccgcagg gccagagact cattgaggtg 540
tctgtcgaag agaaccaccc tttcactctg cgcgctccca ttcagagaat ctatggagtt 600
cgctatacgg agacttggtc attccttcct tccctgacat gcaccggaga cgccgcccct 660
gccattcagc acatatgcct gaaacatacc acctgtttcc aggatgtggt ggttgatgtt 720
gattgtgctg aaaataccaa ggaagaccaa ctggccgaga ttagttaccg gttccaaggg 780
aaaaaggaag ccgaccagcc atggattgtg gttaatacaa gcactctgtt cgatgagctc 840
gagctggatc cccccgagat agaacccgga gttctgaaag tgctccggac agaaaaacaa 900
tatctgggag tctacatatg gaacatgcgc ggttccgatg ggacctccac ttatgcaacc 960
tttctcgtca cgtggaaggg agatgagaaa actaggaatc ccacacccgc tgtcacacca 1020
cagccaagag gggctgagtt ccatatgtgg aactatcata gtcacgtgtt tagtgtcgga 1080
gatacgtttt cattggctat gcatctccag tacaagattc atgaggctcc cttcgatctg 1140
ttgcttgagt ggttgtacgt cccgattgac ccgacctgcc agcccatgcg actgtacagc 1200
acctgtctct accatccaaa cgctccgcaa tgtctgagcc acatgaactc tgggtgtact 1260
ttcaccagtc cccacctcgc ccagcgggtg gcctctactg tttaccagaa ctgtgagcac 1320
gccgacaact acaccgcata ctgcctcggt atttctcaca tggaaccctc cttcggactc 1380
atcctgcacg atgggggcac taccctgaag ttcgttgata cgccagaatc tctgtctggg 1440
ctctatgttt tcgtggtcta cttcaatggc catgtcgagg ccgtggccta tactgtcgtt 1500
tctaccgtgg atcattttgt gaacgccatc gaagaacggg gattcccccc tacggcaggc 1560
cagccgcctg caaccaccaa gcccaaggaa ataacaccag tgaaccctgg cacctcacct 1620
ctcctaagat atgccgcgtg gacaggggga ctggcggcag tggtgctcct ctgtctcgtg 1680
atctttctga tctgtacagc caagaggatg agggtcaagg cttatagagt ggacaagtcc 1740
ccctacaatc agtcaatgta ctacgccggc cttcccgttg atgattttga ggattccgag 1800
tccacagata ctgaggaaga gttcggtaac gctataggcg gctctcacgg gggttcaagc 1860
tacacggttt acattgacaa gacacgctga taataggctg gagcctcggt ggccatgctt 1920
cttgcccctt gggcctcccc ccagcccctc ctccccttcc tgcacccgta cccccgtggt 1980
ctttgaataa agtctgagtg ggcggcaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaatcta g 2111

<210> SEQ ID NO 17
<211> LENGTH: 1897
<212> TYPE: DNA
<213> ORGANISM: Artificial Sequence
<220> FEATURE:
<223> OTHER INFORMATION: Synthetic Polynucleotide

<400> SEQUENCE: 17
tcaagctttt ggaccctcgt acagaagcta atacgactca ctatagggaa ataagagaga 60
aaagaagagt aagaagaaat ataagagcca ccatggggac agttaataaa cctgtggtgg 120
gggtattgat ggggttcgga attatcacgg gaacgttgcg tataacgaat ccggtcagag 180
catccgtctt gcgatacgat gattttcaca tcgatgaaga caaactggat acaaactccg 240
tatatgagcc ttactaccat tcagatcatg cggagtcttc atgggtaaat cggggagagt 300
cttcgcgaaa agcgtacgat cataactcac cttatatatg gccacgtaat gattatgatg 360
gatttttaga gaacgcacac gaacaccatg ggtgtataa tcagggccgt ggtatcgata 420
gcggggaacg gttaatgcaa cccacacaaa tgtctgcaca ggaggatctt ggggacgata 480
cgggcatcca cgttatccct acgttaaacg gcgatgacag acataaaatt gtaaatgtgg 540
accaacgtca atacggtgac gtgtttaaag gagatcttaa tccaaaaccc caaggccaaa 600
gactcattga ggtgtcagtg gaagaaaatc acccgtttac tttacgcgca ccgattcagc 660
ggatttatgg agtccggtac accgagactt ggagcttttt gccgtcatta acctgtacgg 720
gagacgcagc gcccgccatc cagcatatat gtttaaaaca tacaacatgc tttcaagacg 780
tggtggtgga tgtggattgc gcggaaaata ctaaagagga tcagttggcc gaaatcagtt 840
accgttttca aggtaagaag gaagcggacc aaccgtggat tgttgtaaac acgagcacac 900
tgtttgatga actcgaatta gacccccccg agattgaacc gggtgtcttg aaagtacttc 960
ggacagaaaa acaatacttg ggtgtgtaca tttggaacat gcgcggctcc gatggtacgt 1020
ctacctacgc cacgtttttg gtcacctgga aaggggatga aaaaacaaga aaccctacgc 1080
ccgcagtaac tcctcaacca agaggggctg agtttcatat gtggaattac cactcgcatg 1140

```
tattttcagt tggtgatacg tttagcttgg caatgcatct tcagtataag atacatgaag   1200

cgccatttga tttgctgtta gagtggttgt atgtccccat cgatcctaca tgtcaaccaa   1260

tgcggttata ttctacgtgt ttgtatcatc ccaacgcacc ccaatgcctc tctcatatga   1320

attccggttg tacatttacc tcgccacatt tagcccagcg tgttgcaagc acagtgtatc   1380

aaaattgtga acatgcagat aactacaccg catattgtct gggaatatct catatggagc   1440

ctagctttgg tctaatctta cacgacgggg gcaccacgtt aaagtttgta gatacacccg   1500

agagtttgtc gggattatac gtttttgtgg tgtattttaa cgggcatgtt gaagccgtag   1560

catacactgt tgtatccaca gtagatcatt ttgtaaacgc aattgaagag cgtggatttc   1620

cgccaacggc cggtcagcca ccggcgacta ctaaacccaa ggaaattacc cccgtaaacc   1680

ccggaacgtc accacttcta cgatatgccg catggaccgg agggcttgca gcagtagtac   1740

ttttatgtct cgtaatattt ttaatctgta cggcttgatg ataataggct ggagcctcgg   1800

tggccatgct tcttgcccct tggcctcccc cccagcccct cctccccttc ctgcacccgt   1860

acccccgtgg tctttgaata aagtctgagt gggcggc                            1897


<210> SEQ ID NO 18
<211> LENGTH: 561
<212> TYPE: PRT
<213> ORGANISM: Artificial Sequence
<220> FEATURE:
<223> OTHER INFORMATION: Synthetic Polypeptide

<400> SEQUENCE: 18

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
```

-continued

```
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala
```

<210> SEQ ID NO 19
<211> LENGTH: 1686
<212> TYPE: DNA
<213> ORGANISM: Artificial Sequence
<220> FEATURE:
<223> OTHER INFORMATION: Synthetic Polynucleotide

<400> SEQUENCE: 19

```
atggggacag ttaataaacc tgtggtgggg gtattgatgg ggttcggaat tatcacggga     60

acgttgcgta taacgaatcc ggtcagagca tccgtcttgc gatacgatga ttttcacatc    120

gatgaagaca aactggatac aaactccgta tatgagcctt actaccattc agatcatgcg    180
```

```
gagtcttcat gggtaaatcg gggagagtct tcgcgaaaag cgtacgatca taactcacct    240

tatatatggc cacgtaatga ttatgatgga tttttagaga acgcacacga acaccatggg    300

gtgtataatc agggccgtgg tatcgatagc ggggaacggt taatgcaacc cacacaaatg    360

tctgcacagg aggatcttgg ggacgatacg ggcatccacg ttatccctac gttaaacggc    420

gatgacagac ataaaattgt aaatgtggac caacgtcaat acggtgacgt gtttaaagga    480

gatcttaatc caaaacccca aggccaaaga ctcattgagg tgtcagtgga agaaaatcac    540

ccgtttactt tacgcgcacc gattcagcgg atttatggag tccggtacac cgagacttgg    600

agctttttgc cgtcattaac ctgtacggga gacgcagcgc ccgccatcca gcatatatgt    660

ttaaaacata caacatgctt tcaagacgtg gtggtggatg tggattgcgc ggaaaatact    720

aaagaggatc agttggccga aatcagttac cgttttcaag gtaagaagga agcggaccaa    780

ccgtggattg ttgtaaacac gagcacactg tttgatgaac tcgaattaga cccccccgag    840

attgaaccgg gtgtcttgaa agtacttcgg acagaaaaac aatacttggg tgtgtacatt    900

tggaacatgc gcggctccga tggtacgtct acctacgcca cgtttttggt cacctggaaa    960

ggggatgaaa aaacaagaaa ccctacgccc gcagtaactc ctcaaccaag aggggctgag   1020

tttcatatgt ggaattacca ctcgcatgta ttttcagttg gtgatacgtt tagcttggca   1080

atgcatcttc agtataagat acatgaagcg ccatttgatt tgctgttaga gtggttgtat   1140

gtccccatcg atcctacatg tcaaccaatg cggttatatt ctacgtgttt gtatcatccc   1200

aacgcacccc aatgcctctc tcatatgaat tccggttgta catttacctc gccacattta   1260

gcccagcgtg ttgcaagcac agtgtatcaa aattgtgaac atgcagataa ctacaccgca   1320

tattgtctgg gaatatctca tatggagcct agctttggtc taatcttaca cgacgggggc   1380

accacgttaa agtttgtaga tacacccgag agtttgtcgg gattatacgt tttgtggtg    1440

tattttaacg ggcatgttga agccgtagca tacactgttg tatccacagt agatcatttt   1500

gtaaacgcaa ttgaagagcg tggatttccg ccaacggccg gtcagccacc ggcgactact   1560

aaacccaagg aaattacccc cgtaaacccc ggaacgtcac cacttctacg atatgccgca   1620

tggaccggag ggcttgcagc agtagtactt ttatgtctcg taatattttt aatctgtacg   1680

gcttga                                                              1686
```

<210> SEQ ID NO 20
<211> LENGTH: 1958
<212> TYPE: DNA
<213> ORGANISM: Artificial Sequence
<220> FEATURE:
<223> OTHER INFORMATION: Synthetic Polynucleotide

<400> SEQUENCE: 20

```
ggggaaataa gagagaaaag aagagtaaga agaaatataa gagccaccat ggggacagtt     60

aataaacctg tggtgggggt attgatgggg ttcggaatta tcacgggaac gttgcgtata    120

acgaatccgg tcagagcatc cgtcttgcga tacgatgatt ttcacatcga tgaagacaaa    180

ctggatacaa actccgtata tgagccttac taccattcag atcatgcgga gtcttcatgg    240

gtaaatcggg gagagtcttc gcgaaaagcg tacgatcata actcacctta tatatggcca    300

cgtaatgatt atgatggatt tttagagaac gcacacgaac accatggggt gtataatcag    360

ggccgtggta tcgatagcgg ggaacggtta atgcaaccca cacaaatgtc tgcacaggag    420

gatcttgggg acgatacggg catccacgtt atccctacgt taaacggcga tgacagacat    480
```

aaaattgtaa atgtggacca acgtcaatac ggtgacgtgt ttaaaggaga tcttaatcca 540
aaaccccaag gccaaagact cattgaggtg tcagtggaag aaaatcaccc gtttacttta 600
cgcgcaccga ttcagcggat ttatggagtc cggtacaccg agacttggag ctttttgccg 660
tcattaacct gtacgggaga cgcagcgccc gccatccagc atatatgttt aaaacataca 720
acatgctttc aagacgtggt ggtggatgtg gattgcgcgg aaaatactaa agaggatcag 780
ttggccgaaa tcagttaccg ttttcaaggt aagaaggaag cggaccaacc gtggattgtt 840
gtaaacacga gcacactgtt tgatgaactc gaattagacc cccccgagat tgaaccgggt 900
gtcttgaaag tacttcggac agaaaaacaa tacttgggtg tgtacatttg gaacatgcgc 960
ggctccgatg gtacgtctac ctacgccacg tttttggtca cctggaaagg ggatgaaaaa 1020
acaagaaacc ctacgcccgc agtaactcct caaccaagag ggctgagtt tcatatgtgg 1080 aattaccact cgcatgtatt ttcagttggt gatacgttta gcttggcaat gcatcttcag 1140
tataagatac atgaagcgcc atttgatttg ctgttagagt ggttgtatgt ccccatcgat 1200
cctacatgtc aaccaatgcg gttatattct acgtgtttgt atcatcccaa cgcaccccaa 1260
tgcctctctc atatgaattc cggttgtaca tttacctcgc cacatttagc ccagcgtgtt 1320
gcaagcacag tgtatcaaaa ttgtgaacat gcagataact acaccgcata ttgtctggga 1380
atatctcata tggagcctag ctttggtcta atcttacacg acgggggcac cacgttaaag 1440
tttgtagata cacccgagag tttgtcggga ttatacgttt ttgtggtgta ttttaacggg 1500
catgttgaag ccgtagcata cactgttgta tccacagtag atcattttgt aaacgcaatt 1560
gaagagcgtg gatttccgcc aacggccggt cagccaccgg cgactactaa acccaaggaa 1620
attacccccg taaaccccgg aacgtcacca cttctacgat atgccgcatg gaccggaggg 1680
cttgcagcag tagtactttt atgtctcgta atatttttaa tctgtacggc ttgatgataa 1740
taggctggag cctcggtggc catgcttctt gccccttggg cctcccccca gcccctcctc 1800
cccttcctgc acccgtaccc ccgtggtctt tgaataaagt ctgagtgggc ggcaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaatctag 1958

<210> SEQ ID NO 21
<211> LENGTH: 1867
<212> TYPE: DNA
<213> ORGANISM: Artificial Sequence
<220> FEATURE:
<223> OTHER INFORMATION: Synthetic Polynucleotide

<400> SEQUENCE: 21
tcaagctttt ggaccctcgt acagaagcta atacgactca ctatagggaa ataagagaga 60
aaagaagagt aagaagaaat ataagagcca ccatggaaac cccggcgcag ctgctgtttc 120
tgctgctgct gtggctgccg gataccaccg gctccgtctt gcgatacgat gattttcaca 180
tcgatgaaga caaactggat acaaactccg tatatgagcc ttactaccat tcagatcatg 240
cggagtcttc atgggtaaat cggggagagt cttcgcgaaa agcgtacgat cataactcac 300
cttatatatg gccacgtaat gattatgatg gatttttaga gaacgcacac gaacaccatg 360
gggtgtataa tcagggccgt ggtatcgata gcggggaacg gttaatgcaa cccacacaaa 420
tgtctgcaca ggaggatctt ggggacgata cgggcatcca cgttatccct acgttaaacg 480
gcgatgacag acataaaatt gtaaatgtgg accaacgtca atacggtgac gtgtttaaag 540
gagatcttaa tccaaaaccc caaggccaaa gactcattga ggtgtcagtg gaagaaaatc 600
acccgtttac tttacgcgca ccgattcagc ggatttatgg agtccggtac accgagactt 660
ggagcttttt gccgtcatta acctgtacgg gagacgcagc gcccgccatc cagcatatat 720
gtttaaaaca tacaacatgc tttcaagacg tggtggtgga tgtggattgc gcggaaaata 780
ctaaagagga tcagttggcc gaaatcagtt accgttttca aggtaagaag gaagcggacc 840
aaccgtggat tgttgtaaac acgagcacac tgtttgatga actcgaatta gacccccccg 900
agattgaacc gggtgtcttg aaagtacttc ggacagaaaa acaatacttg ggtgtgtaca 960
tttggaacat gcgcggctcc gatggtacgt ctacctacgc cacgtttttg gtcacctgga 1020
aaggggatga aaaaacaaga aaccctacgc ccgcagtaac tcctcaacca agaggggctg 1080
agtttcatat gtggaattac cactcgcatg tattttcagt tggtgatacg tttagcttgg 1140
caatgcatct tcagtataag atacatgaag cgccatttga tttgctgtta gagtggttgt 1200
atgtccccat cgatcctaca tgtcaaccaa tgcggttata ttctacgtgt ttgtatcatc 1260
ccaacgcacc ccaatgcctc tctcatatga attccggttg tacatttacc tcgccacatt 1320
tagcccagcg tgttgcaagc acagtgtatc aaaattgtga acatgcagat aactacaccg 1380
catattgtct gggaatatct catatggagc ctagctttgg tctaatctta cacgacgggg 1440
gcaccacgtt aaagtttgta gatacacccg agagtttgtc gggattatac gtttttgtgg 1500
tgtattttaa cgggcatgtt gaagccgtag catacactgt tgtatccaca gtagatcatt 1560
ttgtaaacgc aattgaagag cgtggatttc cgccaacggc cggtcagcca ccggcgacta 1620
ctaaacccaa ggaaattacc cccgtaaacc ccggaacgtc accacttcta cgatatgccg 1680
catggaccgg agggcttgca gcagtagtac ttttatgtct cgtaatattt ttaatctgta 1740
cggcttgatg ataataggct ggagcctcgg tggccatgct tcttgcccct tgggcctccc 1800
cccagcccct cctccccttc ctgcacccgt acccccgtgg tctttgaata aagtctgagt 1860
gggcggc 1867

<210> SEQ ID NO 22
<211> LENGTH: 551
<212> TYPE: PRT
<213> ORGANISM: Artificial Sequence
<220> FEATURE:
<223> OTHER INFORMATION: Synthetic Polypeptide

<400> SEQUENCE: 22

Met Glu Thr Pro Ala Gln Leu Leu Phe Leu Leu Leu Leu Trp Leu Pro
1 5 10 15

Asp Thr Thr Gly Ser Val Leu Arg Tyr Asp Asp Phe His Ile Asp Glu
20 25 30

Asp Lys Leu Asp Thr Asn Ser Val Tyr Glu Pro Tyr Tyr His Ser Asp
35 40 45

His Ala Glu Ser Ser Trp Val Asn Arg Gly Glu Ser Ser Arg Lys Ala
50 55 60

Tyr Asp His Asn Ser Pro Tyr Ile Trp Pro Arg Asn Asp Tyr Asp Gly
65 70 75 80

Phe Leu Glu Asn Ala His Glu His His Gly Val Tyr Asn Gln Gly Arg
85 90 95

Gly Ile Asp Ser Gly Glu Arg Leu Met Gln Pro Thr Gln Met Ser Ala
100 105 110

Gln Glu Asp Leu Gly Asp Asp Thr Gly Ile His Val Ile Pro Thr Leu
115 120 125

```
Asn Gly Asp Asp Arg His Lys Ile Val Asn Val Asp Gln Arg Gln Tyr
    130                 135                 140

Gly Asp Val Phe Lys Gly Asp Leu Asn Pro Lys Pro Gln Gly Gln Arg
145                 150                 155                 160

Leu Ile Glu Val Ser Val Glu Glu Asn His Pro Phe Thr Leu Arg Ala
                165                 170                 175

Pro Ile Gln Arg Ile Tyr Gly Val Arg Tyr Thr Glu Thr Trp Ser Phe
            180                 185                 190

Leu Pro Ser Leu Thr Cys Thr Gly Asp Ala Ala Pro Ala Ile Gln His
        195                 200                 205

Ile Cys Leu Lys His Thr Thr Cys Phe Gln Asp Val Val Val Asp Val
    210                 215                 220

Asp Cys Ala Glu Asn Thr Lys Glu Asp Gln Leu Ala Glu Ile Ser Tyr
225                 230                 235                 240

Arg Phe Gln Gly Lys Lys Glu Ala Asp Gln Pro Trp Ile Val Val Asn
                245                 250                 255

Thr Ser Thr Leu Phe Asp Glu Leu Glu Leu Asp Pro Pro Glu Ile Glu
            260                 265                 270

Pro Gly Val Leu Lys Val Leu Arg Thr Glu Lys Gln Tyr Leu Gly Val
        275                 280                 285

Tyr Ile Trp Asn Met Arg Gly Ser Asp Gly Thr Ser Thr Tyr Ala Thr
    290                 295                 300

Phe Leu Val Thr Trp Lys Gly Asp Glu Lys Thr Arg Asn Pro Thr Pro
305                 310                 315                 320

Ala Val Thr Pro Gln Pro Arg Gly Ala Glu Phe His Met Trp Asn Tyr
                325                 330                 335

His Ser His Val Phe Ser Val Gly Asp Thr Phe Ser Leu Ala Met His
            340                 345                 350

Leu Gln Tyr Lys Ile His Glu Ala Pro Phe Asp Leu Leu Leu Glu Trp
        355                 360                 365

Leu Tyr Val Pro Ile Asp Pro Thr Cys Gln Pro Met Arg Leu Tyr Ser
    370                 375                 380

Thr Cys Leu Tyr His Pro Asn Ala Pro Gln Cys Leu Ser His Met Asn
385                 390                 395                 400

Ser Gly Cys Thr Phe Thr Ser Pro His Leu Ala Gln Arg Val Ala Ser
                405                 410                 415

Thr Val Tyr Gln Asn Cys Glu His Ala Asp Asn Tyr Thr Ala Tyr Cys
            420                 425                 430

Leu Gly Ile Ser His Met Glu Pro Ser Phe Gly Leu Ile Leu His Asp
        435                 440                 445

Gly Gly Thr Thr Leu Lys Phe Val Asp Thr Pro Glu Ser Leu Ser Gly
    450                 455                 460

Leu Tyr Val Phe Val Val Tyr Phe Asn Gly His Val Glu Ala Val Ala
465                 470                 475                 480

Tyr Thr Val Val Ser Thr Val Asp His Phe Val Asn Ala Ile Glu Glu
                485                 490                 495

Arg Gly Phe Pro Pro Thr Ala Gly Gln Pro Pro Ala Thr Thr Lys Pro
            500                 505                 510

Lys Glu Ile Thr Pro Val Asn Pro Gly Thr Ser Pro Leu Leu Arg Tyr
        515                 520                 525

Ala Ala Trp Thr Gly Gly Leu Ala Ala Val Val Leu Leu Cys Leu Val
    530                 535                 540

Ile Phe Leu Ile Cys Thr Ala
```

-continued 545 550

<210> SEQ ID NO 23
<211> LENGTH: 1656
<212> TYPE: DNA
<213> ORGANISM: Artificial Sequence
<220> FEATURE:
<223> OTHER INFORMATION: Synthetic Polynucleotide

<400> SEQUENCE: 23
atggaaaccc cggcgcagct gctgtttctg ctgctgctgt ggctgccgga taccaccggc 60
tccgtcttgc gatacgatga ttttcacatc gatgaagaca aactggatac aaactccgta 120
tatgagcctt actaccattc agatcatgcg gagtcttcat gggtaaatcg gggagagtct 180
tcgcgaaaag cgtacgatca taactcacct tatatatggc cacgtaatga ttatgatgga 240
tttttagaga acgcacacga acaccatggg gtgtataatc agggccgtgg tatcgatagc 300
ggggaacggt taatgcaacc cacacaaatg tctgcacagg aggatcttgg ggacgatacg 360
ggcatccacg ttatccctac gttaaacggc gatgacagac ataaaattgt aaatgtggac 420
caacgtcaat acggtgacgt gtttaaagga gatcttaatc caaaacccca aggccaaaga 480
ctcattgagg tgtcagtgga agaaaatcac ccgtttactt tacgcgcacc gattcagcgg 540
atttatggag tccggtacac cgagacttgg agctttttgc cgtcattaac ctgtacggga 600
gacgcagcgc ccgccatcca gcatatatgt ttaaaacata caacatgctt tcaagacgtg 660
gtggtggatg tggattgcgc ggaaaatact aaagaggatc agttggccga aatcagttac 720
cgttttcaag gtaagaagga agcggaccaa ccgtggattg ttgtaaacac gagcacactg 780
tttgatgaac tcgaattaga cccccccgag attgaaccgg gtgtcttgaa agtacttcgg 840
acagaaaaac aatacttggg tgtgtacatt tggaacatgc gcggctccga tggtacgtct 900
acctacgcca cgtttttggt cacctggaaa ggggatgaaa aaacaagaaa ccctacgccc 960
gcagtaactc ctcaaccaag aggggctgag tttcatatgt ggaattacca ctcgcatgta 1020
ttttcagttg gtgatacgtt tagcttggca atgcatcttc agtataagat acatgaagcg 1080
ccatttgatt tgctgttaga gtggttgtat gtccccatcg atcctacatg tcaaccaatg 1140
cggttatatt ctacgtgttt gtatcatccc aacgcacccc aatgcctctc tcatatgaat 1200
tccggttgta catttacctc gccacattta gcccagcgtg ttgcaagcac agtgtatcaa 1260
aattgtgaac atgcagataa ctacaccgca tattgtctgg gaatatctca tatggagcct 1320
agctttggtc taatcttaca cgacgggggc accacgttaa agtttgtaga tacacccgag 1380
agtttgtcgg gattatacgt tttgtggtg tattttaacg ggcatgttga agccgtagca 1440
tacactgttg tatccacagt agatcatttt gtaaacgcaa ttgaagagcg tggatttccg 1500
ccaacggccg gtcagccacc ggcgactact aaacccaagg aaattacccc cgtaaacccc 1560
ggaacgtcac cacttctacg atatgccgca tggaccggag ggcttgcagc agtagtactt 1620
ttatgtctcg taatattttt aatctgtacg gcttga 1656

<210> SEQ ID NO 24
<211> LENGTH: 1928
<212> TYPE: DNA
<213> ORGANISM: Artificial Sequence
<220> FEATURE:
<223> OTHER INFORMATION: Synthetic Polynucleotide

<400> SEQUENCE: 24
ggggaaataa gagagaaaag aagagtaaga agaaatataa gagccaccat ggaaaccccg 60

```
gcgcagctgc tgtttctgct gctgctgtgg ctgccggata ccaccggctc cgtcttgcga    120
tacgatgatt ttcacatcga tgaagacaaa ctggatacaa actccgtata tgagccttac    180
taccattcag atcatgcgga gtcttcatgg gtaaatcggg gagagtcttc gcgaaaagcg    240
tacgatcata actcacctta tatatggcca cgtaatgatt atgatggatt tttagagaac    300
gcacacgaac accatggggt gtataatcag ggccgtggta tcgatagcgg ggaacggtta    360
atgcaaccca cacaaatgtc tgcacaggag gatcttgggg acgatacggg catccacgtt    420
atccctacgt taaacggcga tgacagacat aaaattgtaa atgtggacca acgtcaatac    480
ggtgacgtgt ttaaaggaga tcttaatcca aaaccccaag gccaaagact cattgaggtg    540
tcagtggaag aaaatcaccc gtttacttta cgcgcaccga ttcagcggat ttatggagtc    600
cggtacaccg agacttggag ctttttgccg tcattaacct gtacgggaga cgcagcgccc    660
gccatccagc atatatgttt aaaacataca acatgctttc aagacgtggt ggtggatgtg    720
gattgcgcgg aaaatactaa agaggatcag ttggccgaaa tcagttaccg ttttcaaggt    780
aagaaggaag cggaccaacc gtggattgtt gtaaacacga gcacactgtt tgatgaactc    840
gaattagacc cccccgagat tgaaccgggt gtcttgaaag tacttcggac agaaaaacaa    900
tacttgggtg tgtacatttg gaacatgcgc ggctccgatg gtacgtctac ctacgccacg    960
tttttggtca cctggaaagg ggatgaaaaa acaagaaacc ctacgcccgc agtaactcct   1020
caaccaagag ggctgagtt tcatatgtgg aattaccact cgcatgtatt ttcagttggt   1080
gatacgttta gcttggcaat gcatcttcag tataagatac atgaagcgcc atttgatttg   1140
ctgttagagt ggttgtatgt ccccatcgat cctacatgtc aaccaatgcg gttatattct   1200
acgtgtttgt atcatcccaa cgcaccccaa tgcctctctc atatgaattc cggttgtaca   1260
tttacctcgc cacatttagc ccagcgtgtt gcaagcacag tgtatcaaaa ttgtgaacat   1320
gcagataact acaccgcata ttgtctggga atatctcata tggagcctag ctttggtcta   1380
atcttacacg acgggggcac cacgttaaag tttgtagata cacccgagag tttgtcggga   1440
ttatacgttt ttgtggtgta ttttaacggg catgttgaag ccgtagcata cactgttgta   1500
tccacagtag atcattttgt aaacgcaatt gaagagcgtg gatttccgcc aacggccggt   1560
cagccaccgg cgactactaa acccaaggaa attacccccg taaaccccgg aacgtcacca   1620
cttctacgat atgccgcatg gaccggaggg cttgcagcag tagtactttt atgtctcgta   1680
atatttttaa tctgtacggc ttgatgataa taggctggag cctcggtggc catgcttctt   1740
gccccttggg cctcccccca gcccctcctc cccttcctgc acccgtaccc ccgtggtctt   1800
tgaataaagt ctgagtgggc ggcaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaatctag                                                            1928
```

<210> SEQ ID NO 25
<211> LENGTH: 2083
<212> TYPE: DNA
<213> ORGANISM: Artificial Sequence
<220> FEATURE:
<223> OTHER INFORMATION: Synthetic Polynucleotide

<400> SEQUENCE: 25

```
tcaagctttt ggaccctcgt acagaagcta atacgactca ctatagggaa ataagagaga     60
aaagaagagt aagaagaaat ataagagcca ccatggggac agttaataaa cctgtggtgg    120
```

```
gggtattgat ggggttcgga attatcacgg gaacgttgcg tataacgaat ccggtcagag    180
catccgtctt gcgatacgat gattttcaca tcgatgaaga caaactggat acaaactccg    240
tatatgagcc ttactaccat tcagatcatg cggagtcttc atgggtaaat cggggagagt    300
cttcgcgaaa agcgtacgat cataactcac cttatatatg gccacgtaat gattatgatg    360
gatttttaga gaacgcacac gaacaccatg gggtgtataa tcagggccgt ggtatcgata    420
gcggggaacg gttaatgcaa cccacacaaa tgtctgcaca ggaggatctt ggggacgata    480
cgggcatcca cgttatccct acgttaaacg gcgatgacag acataaaatt gtaaatgtgg    540
accaacgtca atacggtgac gtgtttaaag gagatcttaa tccaaaaccc caaggccaaa    600
gactcattga ggtgtcagtg gaagaaaatc acccgtttac tttacgcgca ccgattcagc    660
ggatttatgg agtccggtac accgagactt ggagcttttt gccgtcatta acctgtacgg    720
gagacgcagc gcccgccatc cagcatatat gtttaaaaca tacaacatgc tttcaagacg    780
tggtggtgga tgtggattgc gcggaaaata ctaaagagga tcagttggcc gaaatcagtt    840
accgttttca aggtaagaag gaagcggacc aaccgtggat tgttgtaaac acgagcacac    900
tgtttgatga actcgaatta gaccccccg agattgaacc gggtgtcttg aaagtacttc    960
ggacagaaaa acaatacttg ggtgtgtaca tttggaacat gcgcggctcc gatggtacgt   1020
ctacctacgc cacgtttttg gtcacctgga aaggggatga aaaaacaaga aaccctacgc   1080
ccgcagtaac tcctcaacca agaggggctg agtttcatat gtggaattac cactcgcatg   1140
tattttcagt tggtgatacg tttagcttgg caatgcatct tcagtataag atacatgaag   1200
cgccatttga tttgctgtta gagtggttgt atgtccccat cgatcctaca tgtcaaccaa   1260
tgcggttata ttctacgtgt ttgtatcatc ccaacgcacc ccaatgcctc tctcatatga   1320
attccggttg tacatttacc tcgccacatt tagcccagcg tgttgcaagc acagtgtatc   1380
aaaattgtga acatgcagat aactacaccg catattgtct gggaatatct catatggagc   1440
ctagctttgg tctaatctta cacgacgggg gcaccacgtt aaagtttgta gatacacccg   1500
agagtttgtc gggattatac gtttttgtgg tgtattttaa cgggcatgtt gaagccgtag   1560
catacactgt tgtatccaca gtagatcatt ttgtaaacgc aattgaagag cgtggatttc   1620
cgccaacggc cggtcagcca ccggcgacta ctaaacccaa ggaaattacc cccgtaaacc   1680
ccggaacgtc accacttcta cgatatgccg catggaccgg agggcttgca gcagtagtac   1740
ttttatgtct cgtaatattt ttaatctgta cggctaaacg aatgagggtt aaagcctata   1800
gggtagacaa gtccccgtat aaccaaagca tgtattacgc tggccttcca gtggacgatt   1860
tcgaggacgc cgaagccgcc gatgccgaag aagagtttgg taacgcgatt ggagggagtc   1920
acgggggttc gagttacacg gtgtatatag ataagacccg gtgatgataa taggctggag   1980
cctcggtggc catgcttctt gccccttggg cctcccccca gcccctcctc cccttcctgc   2040
acccgtaccc ccgtggtctt tgaataaagt ctgagtgggc ggc                     2083
```

<210> SEQ ID NO 26
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 26

```
Met Gly Thr Val Asn Lys Pro Val Val Gly Val Leu Met Gly Phe Gly
1               5                   10                  15
```

-continued

```
Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
```

```
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ala Glu Ala Ala Asp Ala Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620
```

<210> SEQ ID NO 27
<211> LENGTH: 1872
<212> TYPE: DNA
<213> ORGANISM: Artificial Sequence
<220> FEATURE:
<223> OTHER INFORMATION: Synthetic Polynucleotide

<400> SEQUENCE: 27

```
atggggacag ttaataaacc tgtggtgggg gtattgatgg ggttcggaat tatcacggga     60

acgttgcgta taacgaatcc ggtcagagca tccgtcttgc gatacgatga ttttcacatc    120

gatgaagaca aactggatac aaactccgta tatgagcctt actaccattc agatcatgcg    180

gagtcttcat gggtaaatcg gggagagtct tcgcgaaaag cgtacgatca taactcacct    240

tatatatggc cacgtaatga ttatgatgga tttttagaga acgcacacga acaccatggg    300

gtgtataatc agggccgtgg tatcgatagc ggggaacggt taatgcaacc cacacaaatg    360

tctgcacagg aggatcttgg ggacgatacg ggcatccacg ttatccctac gttaaacggc    420

gatgacagac ataaaattgt aaatgtggac caacgtcaat acggtgacgt gtttaaagga    480

gatcttaatc caaaacccca aggccaaaga ctcattgagg tgtcagtgga agaaaatcac    540

ccgtttactt tacgcgcacc gattcagcgg atttatggag tccggtacac cgagacttgg    600

agctttttgc cgtcattaac ctgtacggga gacgcagcgc ccgccatcca gcatatatgt    660

ttaaaacata caacatgctt tcaagacgtg gtggtggatg tggattgcgc ggaaaatact    720

aaagaggatc agttggccga aatcagttac cgttttcaag gtaagaagga agcggaccaa    780

ccgtggattg ttgtaaacac gagcacactg tttgatgaac tcgaattaga cccccccgag    840

attgaaccgg gtgtcttgaa agtacttcgg acagaaaaac aatacttggg tgtgtacatt    900

tggaacatgc gcggctccga tggtacgtct acctacgcca cgtttttggt cacctggaaa    960

ggggatgaaa aaacaagaaa ccctacgccc gcagtaactc ctcaaccaag aggggctgag   1020
```

tttcatatgt ggaattacca ctcgcatgta ttttcagttg gtgatacgtt tagcttggca 1080
atgcatcttc agtataagat acatgaagcg ccatttgatt tgctgttaga gtggttgtat 1140
gtccccatcg atcctacatg tcaaccaatg cggttatatt ctacgtgttt gtatcatccc 1200
aacgcacccc aatgcctctc tcatatgaat tccggttgta catttacctc gccacattta 1260
gcccagcgtg ttgcaagcac agtgtatcaa aattgtgaac atgcagataa ctacaccgca 1320
tattgtctgg gaatatctca tatggagcct agctttggtc taatcttaca cgacgggggc 1380
accacgttaa agtttgtaga tacacccgag agtttgtcgg gattatacgt tttgtggtg 1440 tattttaacg ggcatgttga agccgtagca tacactgttg tatccacagt agatcatttt 1500
gtaaacgcaa ttgaagagcg tggatttccg ccaacggccg gtcagccacc ggcgactact 1560
aaacccaagg aaattacccc cgtaaacccc ggaacgtcac cacttctacg atatgccgca 1620
tggaccggag ggcttgcagc agtagtactt ttatgtctcg taatattttt aatctgtacg 1680
gctaaacgaa tgagggttaa agcctatagg gtagacaagt ccccgtataa ccaaagcatg 1740
tattacgctg gccttccagt ggacgatttc gaggacgccg aagccgccga tgccgaagaa 1800
gagtttggta acgcgattgg agggagtcac gggggttcga gttacacggt gtatatagat 1860
aagacccggt ga 1872

<210> SEQ ID NO 28
<211> LENGTH: 2144
<212> TYPE: DNA
<213> ORGANISM: Artificial Sequence
<220> FEATURE:
<223> OTHER INFORMATION: Synthetic Polynucleotide

<400> SEQUENCE: 28
ggggaaataa gagagaaaag aagagtaaga agaaatataa gagccaccat ggggacagtt 60
aataaacctg tggtgggggt attgatgggg ttcggaatta tcacgggaac gttgcgtata 120
acgaatccgg tcagagcatc cgtcttgcga tacgatgatt ttcacatcga tgaagacaaa 180
ctggatacaa actccgtata tgagccttac taccattcag atcatgcgga gtcttcatgg 240
gtaaatcggg gagagtcttc gcgaaaagcg tacgatcata actcacctta tatatggcca 300
cgtaatgatt atgatggatt tttagagaac gcacacgaac accatggggt gtataatcag 360
ggccgtggta tcgatagcgg ggaacggtta atgcaaccca cacaaatgtc tgcacaggag 420
gatcttgggg acgatacggg catccacgtt atccctacgt taaacggcga tgacagacat 480
aaaattgtaa atgtggacca acgtcaatac ggtgacgtgt ttaaaggaga tcttaatcca 540
aaaccccaag gccaaagact cattgaggtg tcagtggaag aaaatcaccc gtttacttta 600
cgcgcaccga ttcagcggat ttatggagtc cggtacaccg agacttggag ctttttgccg 660
tcattaacct gtacgggaga cgcagcgccc gccatccagc atatatgttt aaaacataca 720
acatgctttc aagacgtggt ggtggatgtg gattgcgcgg aaaatactaa agaggatcag 780
ttggccgaaa tcagttaccg ttttcaaggt aagaaggaag cggaccaacc gtggattgtt 840
gtaaacacga gcacactgtt tgatgaactc gaattagacc cccccgagat tgaaccgggt 900
gtcttgaaag tacttcggac agaaaaacaa tacttgggtg tgtacatttg gaacatgcgc 960
ggctccgatg gtacgtctac ctacgccacg tttttggtca cctggaaagg ggatgaaaaa 1020
acaagaaacc ctacgcccgc agtaactcct caaccaagag ggctgagtt tcatatgtgg 1080 aattaccact cgcatgtatt ttcagttggt gatacgttta gcttggcaat gcatcttcag 1140
tataagatac atgaagcgcc atttgatttg ctgttagagt ggttgtatgt ccccatcgat 1200

```
cctacatgtc aaccaatgcg gttatattct acgtgtttgt atcatcccaa cgcaccccaa   1260

tgcctctctc atatgaattc cggttgtaca tttacctcgc cacatttagc ccagcgtgtt   1320

gcaagcacag tgtatcaaaa ttgtgaacat gcagataact acaccgcata ttgtctggga   1380

atatctcata tggagcctag ctttggtcta atcttacacg acgggggcac cacgttaaag   1440

tttgtagata cacccgagag tttgtcggga ttatacgttt ttgtggtgta ttttaacggg   1500

catgttgaag ccgtagcata cactgttgta tccacagtag atcattttgt aaacgcaatt   1560

gaagagcgtg gatttccgcc aacggccggt cagccaccgg cgactactaa acccaaggaa   1620

attacccccg taaaccccgg aacgtcacca cttctacgat atgccgcatg gaccggaggg   1680

cttgcagcag tagtactttt atgtctcgta atatttttaa tctgtacggc taaacgaatg   1740

agggttaaag cctatagggt agacaagtcc ccgtataacc aaagcatgta ttacgctggc   1800

cttccagtgg acgatttcga ggacgccgaa gccgccgatg ccgaagaaga gtttggtaac   1860

gcgattggag ggagtcacgg gggttcgagt tacacggtgt atatagataa gacccggtga   1920

tgataatagg ctggagcctc ggtggccatg cttcttgccc cttgggcctc cccccagccc   1980

ctcctcccct tcctgcaccc gtacccccgt ggtctttgaa taaagtctga gtgggcggca   2040

aaaaaaaaaa aaaaaaaaaa aaaaaaaaaa aaaaaaaaaa aaaaaaaaaa aaaaaaaaaa   2100

aaaaaaaaaa aaaaaaaaaa aaaaaaaaaa aaaaaaaaat ctag                    2144
```

```
<210> SEQ ID NO 29
<211> LENGTH: 2083
<212> TYPE: DNA
<213> ORGANISM: Artificial Sequence
<220> FEATURE:
<223> OTHER INFORMATION: Synthetic Polynucleotide

<400> SEQUENCE: 29

tcaagctttt ggaccctcgt acagaagcta atacgactca ctatagggaa ataagagaga     60

aaagaagagt aagaagaaat ataagagcca ccatggggac agttaataaa cctgtggtgg    120

gggtattgat ggggttcgga attatcacgg gaacgttgcg tataacgaat ccggtcagag    180

catccgtctt gcgatacgat gattttcaca tcgatgaaga caaactggat acaaactccg    240

tatatgagcc ttactaccat tcagatcatg cggagtcttc atgggtaaat cggggagagt    300

cttcgcgaaa agcgtacgat cataactcac cttatatatg gccacgtaat gattatgatg    360

gatttttaga gaacgcacac gaacaccatg gggtgtataa tcagggccgt ggtatcgata    420

gcggggaacg gttaatgcaa cccacacaaa tgtctgcaca ggaggatctt ggggacgata    480

cgggcatcca cgttatccct acgttaaacg gcgatgacag acataaaatt gtaaatgtgg    540

accaacgtca atacggtgac gtgtttaaag gagatcttaa tccaaaaccc caaggccaaa    600

gactcattga ggtgtcagtg gaagaaaatc acccgtttac tttacgcgca ccgattcagc    660

ggatttatgg agtccggtac accgagactt ggagcttttt gccgtcatta acctgtacgg    720

gagacgcagc gcccgccatc cagcatatat gtttaaaaca tacaacatgc tttcaagacg    780

tggtggtgga tgtggattgc gcggaaaata ctaaagagga tcagttggcc gaaatcagtt    840

accgttttca aggtaagaag gaagcggacc aaccgtggat tgttgtaaac acgagcacac    900

tgtttgatga actcgaatta gacccccccg agattgaacc gggtgtcttg aaagtacttc    960

ggacagaaaa acaatacttg ggtgtgtaca tttggaacat gcgcggctcc gatggtacgt   1020

ctacctacgc cacgtttttg gtcacctgga aaggggatga aaaaacaaga aaccctacgc   1080
```

```
ccgcagtaac tcctcaacca agaggggctg agtttcatat gtggaattac cactcgcatg   1140

tattttcagt tggtgatacg tttagcttgg caatgcatct tcagtataag atacatgaag   1200

cgccatttga tttgctgtta gagtggttgt atgtccccat cgatcctaca tgtcaaccaa   1260

tgcggttata ttctacgtgt ttgtatcatc ccaacgcacc ccaatgcctc tctcatatga   1320

attccggttg tacatttacc tcgccacatt tagcccagcg tgttgcaagc acagtgtatc   1380

aaaattgtga acatgcagat aactacaccg catattgtct gggaatatct catatggagc   1440

ctagctttgg tctaatctta cacgacgggg gcaccacgtt aaagtttgta gatacacccg   1500

agagtttgtc gggattatac gtttttgtgg tgtattttaa cgggcatgtt gaagccgtag   1560

catacactgt tgtatccaca gtagatcatt ttgtaaacgc aattgaagag cgtggatttc   1620

cgccaacggc cggtcagcca ccggcgacta ctaaacccaa ggaaattacc cccgtaaacc   1680

ccggaacgtc accacttcta cgatatgccg catggaccgg agggcttgca gcagtagtac   1740

ttttatgtct cgtaatattt ttaatctgta cggctaaacg aatgagggtt aaagcctata   1800

gggtagacaa gtccccgtat aaccaaagca tgtatggcgc tggccttcca gtggacgatt   1860

tcgaggacgc cgaagccgcc gatgccgaag aagagtttgg taacgcgatt ggagggagtc   1920

acgggggttc gagttacacg gtgtatatag ataagacccg gtgatgataa taggctggag   1980

cctcggtggc catgcttctt gccccttggg cctcccccca gcccctcctc cccttcctgc   2040

acccgtaccc ccgtggtctt tgaataaagt ctgagtgggc ggc                     2083
```

<210> SEQ ID NO 30
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 30

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190
```

```
Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Gly Ala Gly Leu Pro Val Asp Asp Phe Glu Asp
            580                 585                 590

Ala Glu Ala Ala Asp Ala Glu Glu Glu Phe Gly Asn Ala Ile Gly Gly
        595                 600                 605
```

Ser His Gly Gly Ser Ser Tyr Thr Val Tyr Ile Asp Lys Thr Arg
    610                 615                 620

<210> SEQ ID NO 31
<211> LENGTH: 1872
<212> TYPE: DNA
<213> ORGANISM: Artificial Sequence
<220> FEATURE:
<223> OTHER INFORMATION: Synthetic Polynucleotide

<400> SEQUENCE: 31
atggggacag ttaataaacc tgtggtgggg gtattgatgg ggttcggaat tatcacggga 60
acgttgcgta taacgaatcc ggtcagagca tccgtcttgc gatacgatga ttttcacatc 120
gatgaagaca aactggatac aaactccgta tatgagcctt actaccattc agatcatgcg 180
gagtcttcat gggtaaatcg gggagagtct tcgcgaaaag cgtacgatca taactcacct 240
tatatatggc cacgtaatga ttatgatgga tttttagaga acgcacacga acaccatggg 300
gtgtataatc agggccgtgg tatcgatagc ggggaacggt taatgcaacc cacacaaatg 360
tctgcacagg aggatcttgg ggacgatacg ggcatccacg ttatccctac gttaaacggc 420
gatgacagac ataaaattgt aaatgtggac caacgtcaat acggtgacgt gtttaaagga 480
gatcttaatc caaaacccca aggccaaaga ctcattgagg tgtcagtgga agaaaatcac 540
ccgtttactt tacgcgcacc gattcagcgg atttatggag tccggtacac cgagacttgg 600
agctttttgc cgtcattaac ctgtacggga gacgcagcgc ccgccatcca gcatatatgt 660
ttaaaacata caacatgctt tcaagacgtg gtggtggatg tggattgcgc ggaaaatact 720
aaagaggatc agttggccga aatcagttac cgttttcaag gtaagaagga agcggaccaa 780
ccgtggattg ttgtaaacac gagcacactg tttgatgaac tcgaattaga cccccccgag 840
attgaaccgg gtgtcttgaa agtacttcgg acagaaaaac aatacttggg tgtgtacatt 900
tggaacatgc gcggctccga tggtacgtct acctacgcca cgtttttggt cacctggaaa 960
ggggatgaaa aaacaagaaa ccctacgccc gcagtaactc ctcaaccaag aggggctgag 1020
tttcatatgt ggaattacca ctcgcatgta ttttcagttg gtgatacgtt tagcttggca 1080
atgcatcttc agtataagat acatgaagcg ccatttgatt tgctgttaga gtggttgtat 1140
gtccccatcg atcctacatg tcaaccaatg cggttatatt ctacgtgttt gtatcatccc 1200
aacgcacccc aatgcctctc tcatatgaat tccggttgta catttacctc gccacattta 1260
gcccagcgtg ttgcaagcac agtgtatcaa aattgtgaac atgcagataa ctacaccgca 1320
tattgtctgg gaatatctca tatggagcct agctttggtc taatcttaca cgacgggggc 1380
accacgttaa agtttgtaga tacacccgag agtttgtcgg gattatacgt tttgtggtg 1440 tattttaacg ggcatgttga agccgtagca tacactgttg tatccacagt agatcatttt 1500
gtaaacgcaa ttgaagagcg tggatttccg ccaacggccg gtcagccacc ggcgactact 1560
aaacccaagg aaattacccc cgtaaacccc ggaacgtcac cacttctacg atatgccgca 1620
tggaccggag ggcttgcagc agtagtactt ttatgtctcg taatattttt aatctgtacg 1680
gctaaacgaa tgagggttaa agcctatagg gtagacaagt ccccgtataa ccaaagcatg 1740
tatggcgctg gccttccagt ggacgatttc gaggacgccg aagccgccga tgccgaagaa 1800
gagtttggta acgcgattgg agggagtcac gggggttcga gttacacggt gtatatagat 1860
aagacccggt ga 1872

<210> SEQ ID NO 32

<211> LENGTH: 2144
<212> TYPE: DNA
<213> ORGANISM: Artificial Sequence
<220> FEATURE:
<223> OTHER INFORMATION: Synthetic Polynucleotide

<400> SEQUENCE: 32
ggggaaataa gagagaaaag aagagtaaga agaaatataa gagccaccat ggggacagtt 60
aataaacctg tggtgggggt attgatgggg ttcggaatta tcacgggaac gttgcgtata 120
acgaatccgg tcagagcatc cgtcttgcga tacgatgatt ttcacatcga tgaagacaaa 180
ctggatacaa actccgtata tgagccttac taccattcag atcatgcgga gtcttcatgg 240
gtaaatcggg gagagtcttc gcgaaaagcg tacgatcata actcacctta tatatggcca 300
cgtaatgatt atgatggatt tttagagaac gcacacgaac accatggggt gtataatcag 360
ggccgtggta tcgatagcgg ggaacggtta atgcaaccca cacaaatgtc tgcacaggag 420
gatcttgggg acgatacggg catccacgtt atccctacgt taaacggcga tgacagacat 480
aaaattgtaa atgtggacca acgtcaatac ggtgacgtgt ttaaaggaga tcttaatcca 540
aaaccccaag gccaaagact cattgaggtg tcagtggaag aaaatcaccc gtttacttta 600
cgcgcaccga ttcagcggat ttatggagtc cggtacaccg agacttggag ctttttgccg 660
tcattaacct gtacgggaga cgcagcgccc gccatccagc atatatgttt aaaacataca 720
acatgctttc aagacgtggt ggtggatgtg gattgcgcgg aaaatactaa agaggatcag 780
ttggccgaaa tcagttaccg ttttcaaggt aagaaggaag cggaccaacc gtggattgtt 840
gtaaacacga gcacactgtt tgatgaactc gaattagacc cccccgagat tgaaccgggt 900
gtcttgaaag tacttcggac agaaaaacaa tacttgggtg tgtacatttg gaacatgcgc 960
ggctccgatg gtacgtctac ctacgccacg tttttggtca cctggaaagg ggatgaaaaa 1020
acaagaaacc ctacgcccgc agtaactcct caaccaagag ggctgagtt tcatatgtgg 1080 aattaccact cgcatgtatt ttcagttggt gatacgttta gcttggcaat gcatcttcag 1140
tataagatac atgaagcgcc atttgatttg ctgttagagt ggttgtatgt ccccatcgat 1200
cctacatgtc aaccaatgcg gttatattct acgtgtttgt atcatcccaa cgcaccccaa 1260
tgcctctctc atatgaattc cggttgtaca tttacctcgc cacatttagc ccagcgtgtt 1320
gcaagcacag tgtatcaaaa ttgtgaacat gcagataact acaccgcata ttgtctggga 1380
atatctcata tggagcctag ctttggtcta atcttacacg acgggggcac cacgttaaag 1440
tttgtagata cacccgagag tttgtcggga ttatacgttt ttgtggtgta ttttaacggg 1500
catgttgaag ccgtagcata cactgttgta tccacagtag atcattttgt aaacgcaatt 1560
gaagagcgtg gatttccgcc aacggccggt cagccaccgg cgactactaa acccaaggaa 1620
attacccccg taaaccccgg aacgtcacca cttctacgat atgccgcatg gaccggaggg 1680
cttgcagcag tagtactttt atgtctcgta atatttttaa tctgtacggc taaacgaatg 1740
agggttaaag cctatagggt agacaagtcc ccgtataacc aaagcatgta tggcgctggc 1800
cttccagtgg acgatttcga ggacgccgaa gccgccgatg ccgaagaaga gtttggtaac 1860
gcgattggag ggagtcacgg gggttcgagt tacacggtgt atatagataa gacccggtga 1920
tgataatagg ctggagcctc ggtggccatg cttcttgccc cttgggcctc cccccagccc 1980
ctcctcccct tcctgcaccc gtacccccgt ggtctttgaa taaagtctga gtgggcggca 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaat ctag 2144

<210> SEQ ID NO 33
<211> LENGTH: 1933
<212> TYPE: DNA
<213> ORGANISM: Artificial Sequence
<220> FEATURE:
<223> OTHER INFORMATION: Synthetic Polynucleotide

<400> SEQUENCE: 33
tcaagctttt ggaccctcgt acagaagcta atacgactca ctatagggaa ataagagaga 60
aaagaagagt aagaagaaat ataagagcca ccatggggac agttaataaa cctgtggtgg 120
gggtattgat ggggttcgga attatcacgg gaacgttgcg tataacgaat ccggtcagag 180
catccgtctt gcgatacgat gattttcaca tcgatgaaga caaactggat acaaactccg 240
tatatgagcc ttactaccat tcagatcatg cggagtcttc atgggtaaat cggggagagt 300
cttcgcgaaa agcgtacgat cataactcac cttatatatg gccacgtaat gattatgatg 360
gatttttaga gaacgcacac gaacaccatg gggtgtataa tcagggccgt ggtatcgata 420
gcggggaacg gttaatgcaa cccacacaaa tgtctgcaca ggaggatctt ggggacgata 480
cgggcatcca cgttatccct acgttaaacg gcgatgacag acataaaatt gtaaatgtgg 540
accaacgtca atacggtgac gtgtttaaag gagatcttaa tccaaaaccc caaggccaaa 600
gactcattga ggtgtcagtg gaagaaaatc acccgtttac tttacgcgca ccgattcagc 660
ggatttatgg agtccggtac accgagactt ggagcttttt gccgtcatta acctgtacgg 720
gagacgcagc gcccgccatc cagcatatat gtttaaaaca tacaacatgc tttcaagacg 780
tggtggtgga tgtggattgc gcggaaaata ctaaagagga tcagttggcc gaaatcagtt 840
accgttttca aggtaagaag gaagcggacc aaccgtggat tgttgtaaac acgagcacac 900
tgtttgatga actcgaatta gacccccccg agattgaacc gggtgtcttg aaagtacttc 960
ggacagaaaa acaatacttg ggtgtgtaca tttggaacat gcgcggctcc gatggtacgt 1020
ctacctacgc cacgtttttg gtcacctgga aaggggatga aaaaacaaga aaccctacgc 1080
ccgcagtaac tcctcaacca agaggggctg agtttcatat gtggaattac cactcgcatg 1140
tattttcagt tggtgatacg tttagcttgg caatgcatct tcagtataag atacatgaag 1200
cgccatttga tttgctgtta gagtggttgt atgtccccat cgatcctaca tgtcaaccaa 1260
tgcggttata ttctacgtgt ttgtatcatc ccaacgcacc ccaatgcctc tctcatatga 1320
attccggttg tacatttacc tcgccacatt tagcccagcg tgttgcaagc acagtgtatc 1380
aaaattgtga acatgcagat aactacaccg catattgtct gggaatatct catatggagc 1440
ctagctttgg tctaatctta cacgacgggg gcaccacgtt aaagtttgta gatacacccg 1500
agagtttgtc gggattatac gtttttgtgg tgtattttaa cgggcatgtt gaagccgtag 1560
catacactgt tgtatccaca gtagatcatt ttgtaaacgc aattgaagag cgtggatttc 1620
cgccaacggc cggtcagcca ccggcgacta ctaaacccaa ggaaattacc cccgtaaacc 1680
ccggaacgtc accacttcta cgatatgccg catggaccgg agggcttgca gcagtagtac 1740
ttttatgtct cgtaatattt ttaatctgta cggctaaacg aatgagggtt aaagcctata 1800
gggtagacaa gtgatgataa taggctggag cctcggtggc catgcttctt gccccttggg 1860
cctcccccca gcccctcctc cccttcctgc acccgtaccc ccgtggtctt tgaataaagt 1920
ctgagtgggc ggc 1933

<210> SEQ ID NO 34

<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 34

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Ile Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Ile His Val Ile Pro Thr Leu Asn Gly Asp Asp Arg His
130 135 140

Lys Ile Val Asn Val Asp Gln Arg Gln Tyr Gly Asp Val Phe Lys Gly
145 150 155 160

Asp Leu Asn Pro Lys Pro Gln Gly Gln Arg Leu Ile Glu Val Ser Val
165 170 175

Glu Glu Asn His Pro Phe Thr Leu Arg Ala Pro Ile Gln Arg Ile Tyr
180 185 190

Gly Val Arg Tyr Thr Glu Thr Trp Ser Phe Leu Pro Ser Leu Thr Cys
195 200 205

Thr Gly Asp Ala Ala Pro Ala Ile Gln His Ile Cys Leu Lys His Thr
210 215 220

Thr Cys Phe Gln Asp Val Val Val Asp Val Asp Cys Ala Glu Asn Thr
225 230 235 240

Lys Glu Asp Gln Leu Ala Glu Ile Ser Tyr Arg Phe Gln Gly Lys Lys
245 250 255

Glu Ala Asp Gln Pro Trp Ile Val Val Asn Thr Ser Thr Leu Phe Asp
260 265 270

Glu Leu Glu Leu Asp Pro Pro Glu Ile Glu Pro Gly Val Leu Lys Val
275 280 285

Leu Arg Thr Glu Lys Gln Tyr Leu Gly Val Tyr Ile Trp Asn Met Arg
290 295 300

Gly Ser Asp Gly Thr Ser Thr Tyr Ala Thr Phe Leu Val Thr Trp Lys
305 310 315 320

Gly Asp Glu Lys Thr Arg Asn Pro Thr Pro Ala Val Thr Pro Gln Pro
325 330 335

Arg Gly Ala Glu Phe His Met Trp Asn Tyr His Ser His Val Phe Ser
340 345 350

Val Gly Asp Thr Phe Ser Leu Ala Met His Leu Gln Tyr Lys Ile His
355 360 365

Glu Ala Pro Phe Asp Leu Leu Leu Glu Trp Leu Tyr Val Pro Ile Asp
370 375 380

```
Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys
                565                 570
```

<210> SEQ ID NO 35
<211> LENGTH: 1722
<212> TYPE: DNA
<213> ORGANISM: Artificial Sequence
<220> FEATURE:
<223> OTHER INFORMATION: Synthetic Polynucleotide

<400> SEQUENCE: 35

```
atggggacag ttaataaacc tgtggtgggg gtattgatgg ggttcggaat tatcacggga     60

acgttgcgta taacgaatcc ggtcagagca tccgtcttgc gatacgatga ttttcacatc    120

gatgaagaca aactggatac aaactccgta tatgagcctt actaccattc agatcatgcg    180

gagtcttcat gggtaaatcg gggagagtct tcgcgaaaag cgtacgatca taactcacct    240

tatatatggc cacgtaatga ttatgatgga tttttagaga acgcacacga acaccatggg    300

gtgtataatc agggccgtgg tatcgatagc ggggaacggt taatgcaacc cacacaaatg    360

tctgcacagg aggatcttgg ggacgatacg ggcatccacg ttatccctac gttaaacggc    420

gatgacagac ataaaattgt aaatgtggac caacgtcaat acggtgacgt gtttaaagga    480

gatcttaatc caaaacccca aggccaaaga ctcattgagg tgtcagtgga agaaaatcac    540

ccgtttactt tacgcgcacc gattcagcgg atttatggag tccggtacac cgagacttgg    600

agctttttgc cgtcattaac ctgtacggga gacgcagcgc ccgccatcca gcatatatgt    660

ttaaaacata caacatgctt tcaagacgtg gtggtggatg tggattgcgc ggaaaatact    720

aaagaggatc agttggccga aatcagttac cgttttcaag gtaagaagga agcggaccaa    780

ccgtggattg ttgtaaacac gagcacactg tttgatgaac tcgaattaga cccccccgag    840

attgaaccgg gtgtcttgaa agtacttcgg acagaaaaac aatacttggg tgtgtacatt    900

tggaacatgc gcggctccga tggtacgtct acctacgcca cgtttttggt cacctggaaa    960
```

```
ggggatgaaa aaacaagaaa ccctacgccc gcagtaactc ctcaaccaag aggggctgag   1020
tttcatatgt ggaattacca ctcgcatgta ttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt gtatcatccc   1200
aacgcacccc aatgcctctc tcatatgaat tccggttgta catttacctc gccacattta   1260
gcccagcgtg ttgcaagcac agtgtatcaa aattgtgaac atgcagataa ctacaccgca   1320
tattgtctgg gaatatctca tatggagcct agctttggtc taatcttaca cgacgggggc   1380
accacgttaa agtttgtaga tacacccgag agtttgtcgg gattatacgt tttgtggtg    1440
tattttaacg ggcatgttga agccgtagca tacactgttg tatccacagt agatcatttt   1500
gtaaacgcaa ttgaagagcg tggatttccg ccaacggccg gtcagccacc ggcgactact   1560
aaacccaagg aaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agcctatagg gtagacaagt ga                      1722
```

<210> SEQ ID NO 36
<211> LENGTH: 1994
<212> TYPE: DNA
<213> ORGANISM: Artificial Sequence
<220> FEATURE:
<223> OTHER INFORMATION: Synthetic Polynucleotide

<400> SEQUENCE: 36

```
ggggaaataa gagagaaaag aagagtaaga agaaatataa gagccaccat ggggacagtt     60
aataaacctg tggtgggggt attgatgggg ttcggaatta tcacgggaac gttgcgtata    120
acgaatccgg tcagagcatc cgtcttgcga tacgatgatt ttcacatcga tgaagacaaa    180
ctggatacaa actccgtata tgagccttac taccattcag atcatgcgga gtcttcatgg    240
gtaaatcggg gagagtcttc gcgaaaagcg tacgatcata actcacctta tatatggcca    300
cgtaatgatt atgatggatt tttagagaac gcacacgaac accatggggt gtataatcag    360
ggccgtggta tcgatagcgg ggaacggtta atgcaaccca cacaaatgtc tgcacaggag    420
gatcttgggg acgatacggg catccacgtt atccctacgt taaacggcga tgacagacat    480
aaaattgtaa atgtggacca acgtcaatac ggtgacgtgt ttaaaggaga tcttaatcca    540
aaaccccaag gccaaagact cattgaggtg tcagtggaag aaaatcaccc gtttacttta    600
cgcgcaccga ttcagcggat ttatggagtc cggtacaccg agacttggag ctttttgccg    660
tcattaacct gtacgggaga cgcagcgccc gccatccagc atatatgttt aaaacataca    720
acatgctttc aagacgtggt ggtggatgtg gattgcgcgg aaaatactaa agaggatcag    780
ttggccgaaa tcagttaccg ttttcaaggt aagaaggaag cggaccaacc gtggattgtt    840
gtaaacacga gcacactgtt tgatgaactc gaattagacc cccccgagat tgaaccgggt    900
gtcttgaaag tacttcggac agaaaaacaa tacttgggtg tgtacatttg gaacatgcgc    960
ggctccgatg gtacgtctac ctacgccacg tttttggtca cctggaaagg ggatgaaaaa   1020
acaagaaacc ctacgcccgc agtaactcct caaccaagag gggctgagtt tcatatgtgg   1080
aattaccact cgcatgtatt ttcagttggt gatacgttta gcttggcaat gcatcttcag   1140
tataagatac atgaagcgcc atttgatttg ctgttagagt ggttgtatgt ccccatcgat   1200
cctacatgtc aaccaatgcg gttatattct acgtgtttgt atcatcccaa cgcaccccaa   1260
tgcctctctc atatgaattc cggttgtaca tttacctcgc cacatttagc ccagcgtgtt   1320
```

gcaagcacag tgtatcaaaa ttgtgaacat gcagataact acaccgcata ttgtctggga 1380
atatctcata tggagcctag ctttggtcta atcttacacg acgggggcac cacgttaaag 1440
tttgtagata cacccgagag tttgtcggga ttatacgttt ttgtggtgta ttttaacggg 1500
catgttgaag ccgtagcata cactgttgta tccacagtag atcattttgt aaacgcaatt 1560
gaagagcgtg gatttccgcc aacggccggt cagccaccgg cgactactaa acccaaggaa 1620
attacccccg taaaccccgg aacgtcacca cttctacgat atgccgcatg gaccggaggg 1680
cttgcagcag tagtactttt atgtctcgta atatttttaa tctgtacggc taaacgaatg 1740
agggttaaag cctatagggt agacaagtga tgataatagg ctggagcctc ggtggccatg 1800
cttcttgccc cttgggcctc cccccagccc ctcctcccct tcctgcaccc gtacccccgt 1860
ggtctttgaa taaagtctga gtgggcggca aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaat ctag 1994

<210> SEQ ID NO 37
<211> LENGTH: 1933
<212> TYPE: DNA
<213> ORGANISM: Artificial Sequence
<220> FEATURE:
<223> OTHER INFORMATION: Synthetic Polynucleotide

<400> SEQUENCE: 37
tcaagctttt ggaccctcgt acagaagcta atacgactca ctatagggaa ataagagaga 60
aaagaagagt aagaagaaat ataagagcca ccatggggac agttaataaa cctgtggtgg 120
gggtattgat ggggttcgga attatcacgg gaacgttgcg tataacgaat ccggtcagag 180
catccgtctt gcgatacgat gattttcaca tcgatgaaga caaactggat acaaactccg 240
tatatgagcc ttactaccat tcagatcatg cggagtcttc atgggtaaat cggggagagt 300
cttcgcgaaa agcgtacgat cataactcac cttatatatg gccacgtaat gattatgatg 360
gatttttaga gaacgcacac gaacaccatg gggtgtataa tcagggccgt ggtatcgata 420
gcggggaacg gttaatgcaa ccccacacaaa tgtctgcaca ggaggatctt ggggacgata 480
cgggcatcca cgttatccct acgttaaacg gcgatgacag acataaaatt gtaaatgtgg 540
accaacgtca atacggtgac gtgtttaaag gagatcttaa tccaaaaccc caaggccaaa 600
gactcattga ggtgtcagtg gaagaaaatc acccgtttac tttacgcgca ccgattcagc 660
ggatttatgg agtccggtac accgagactt ggagcttttt gccgtcatta acctgtacgg 720
gagacgcagc gcccgccatc cagcatatat gtttaaaaca tacaacatgc tttcaagacg 780
tggtggtgga tgtggattgc gcggaaaata ctaaagagga tcagttggcc gaaatcagtt 840
accgttttca aggtaagaag gaagcggacc aaccgtggat tgttgtaaac acgagcacac 900
tgtttgatga actcgaatta gacccccccg agattgaacc gggtgtcttg aaagtacttc 960
ggacagaaaa acaatacttg ggtgtgtaca tttggaacat gcgcggctcc gatggtacgt 1020
ctacctacgc cacgtttttg gtcacctgga aaggggatga aaaaacaaga aaccctacgc 1080
ccgcagtaac tcctcaacca agaggggctg agtttcatat gtggaattac cactcgcatg 1140
tattttcagt tggtgatacg tttagcttgg caatgcatct tcagtataag atacatgaag 1200
cgccatttga tttgctgtta gagtggttgt atgtccccat cgatcctaca tgtcaaccaa 1260
tgcggttata ttctacgtgt ttgtatcatc ccaacgcacc ccaatgcctc tctcatatga 1320

-continued

```
attccggttg tacatttacc tcgccacatt tagcccagcg tgttgcaagc acagtgtatc   1380

aaaattgtga acatgcagat aactacaccg catattgtct gggaatatct catatggagc   1440

ctagctttgg tctaatctta cacgacgggg gcaccacgtt aaagtttgta gatacacccg   1500

agagtttgtc gggattatac gtttttgtgg tgtattttaa cgggcatgtt gaagccgtag   1560

catacactgt tgtatccaca gtagatcatt ttgtaaacgc aattgaagag cgtggatttc   1620

cgccaacggc cggtcagcca ccggcgacta ctaaacccaa ggaaattacc cccgtaaacc   1680

ccggaacgtc accacttcta cgatatgccg catggaccgg agggcttgca gcagtagtac   1740

ttttatgtct cgtaatattt ttaatctgta cggctaaacg aatgagggtt aaagccgcca   1800

gggtagacaa gtgatgataa taggctggag cctcggtggc catgcttctt gccccttggg   1860

cctcccccca gcccctcctc cccttcctgc acccgtaccc ccgtggtctt tgaataaagt   1920

ctgagtgggc ggc                                                       1933
```

<210> SEQ ID NO 38
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 38

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255
```

```
Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 39
<211> LENGTH: 1722
<212> TYPE: DNA
<213> ORGANISM: Artificial Sequence
<220> FEATURE:
<223> OTHER INFORMATION: Synthetic Polynucleotide

<400> SEQUENCE: 39

```
atggggacag ttaataaacc tgtggtgggg gtattgatgg ggttcggaat tatcacggga      60

acgttgcgta taacgaatcc ggtcagagca tccgtcttgc gatacgatga ttttcacatc     120

gatgaagaca aactggatac aaactccgta tatgagcctt actaccattc agatcatgcg     180

gagtcttcat gggtaaatcg gggagagtct tcgcgaaaag cgtacgatca taactcacct     240
```

```
tatatatggc cacgtaatga ttatgatgga tttttagaga acgcacacga acaccatggg    300

gtgtataatc agggccgtgg tatcgatagc ggggaacggt taatgcaacc cacacaaatg    360

tctgcacagg aggatcttgg ggacgatacg ggcatccacg ttatccctac gttaaacggc    420

gatgacagac ataaaattgt aaatgtggac caacgtcaat acggtgacgt gtttaaagga    480

gatcttaatc caaaacccca aggccaaaga ctcattgagg tgtcagtgga agaaaatcac    540

ccgtttactt tacgcgcacc gattcagcgg atttatggag tccggtacac cgagacttgg    600

agctttttgc cgtcattaac ctgtacggga gacgcagcgc ccgccatcca gcatatatgt    660

ttaaaacata caacatgctt tcaagacgtg gtggtggatg tggattgcgc ggaaaatact    720

aaagaggatc agttggccga aatcagttac cgttttcaag gtaagaagga agcggaccaa    780

ccgtggattg ttgtaaacac gagcacactg tttgatgaac tcgaattaga cccccccgag    840

attgaaccgg gtgtcttgaa agtacttcgg acagaaaaac aatacttggg tgtgtacatt    900

tggaacatgc gcggctccga tggtacgtct acctacgcca cgtttttggt cacctggaaa    960

ggggatgaaa aaacaagaaa ccctacgccc gcagtaactc ctcaaccaag aggggctgag   1020

tttcatatgt ggaattacca ctcgcatgta ttttcagttg gtgatacgtt tagcttggca   1080

atgcatcttc agtataagat acatgaagcg ccatttgatt tgctgttaga gtggttgtat   1140

gtccccatcg atcctacatg tcaaccaatg cggttatatt ctacgtgttt gtatcatccc   1200

aacgcacccc aatgcctctc tcatatgaat tccggttgta catttacctc gccacattta   1260

gcccagcgtg ttgcaagcac agtgtatcaa aattgtgaac atgcagataa ctacaccgca   1320

tattgtctgg gaatatctca tatggagcct agctttggtc taatcttaca cgacgggggc   1380

accacgttaa agtttgtaga tacacccgag agtttgtcgg gattatacgt tttgtggtg    1440

tattttaacg ggcatgttga agccgtagca tacactgttg tatccacagt agatcatttt   1500

gtaaacgcaa ttgaagagcg tggatttccg ccaacggccg gtcagccacc ggcgactact   1560

aaacccaagg aaattacccc cgtaaacccc ggaacgtcac cacttctacg atatgccgca   1620

tggaccggag ggcttgcagc agtagtactt ttatgtctcg taatattttt aatctgtacg   1680

gctaaacgaa tgagggttaa agccgccagg gtagacaagt ga                      1722
```

<210> SEQ ID NO 40
<211> LENGTH: 1994
<212> TYPE: DNA
<213> ORGANISM: Artificial Sequence
<220> FEATURE:
<223> OTHER INFORMATION: Synthetic Polynucleotide

<400> SEQUENCE: 40

```
ggggaaataa gagagaaaag aagagtaaga agaaatataa gagccaccat ggggacagtt     60

aataaacctg tggtgggggt attgatgggg ttcggaatta tcacgggaac gttgcgtata    120

acgaatccgg tcagagcatc cgtcttgcga tacgatgatt ttcacatcga tgaagacaaa    180

ctggatacaa actccgtata tgagccttac taccattcag atcatgcgga gtcttcatgg    240

gtaaatcggg gagagtcttc gcgaaaagcg tacgatcata actcacctta tatatggcca    300

cgtaatgatt atgatggatt tttagagaac gcacacgaac accatggggt gtataatcag    360

ggccgtggta tcgatagcgg ggaacggtta atgcaaccca cacaaatgtc tgcacaggag    420

gatcttgggg acgatacggg catccacgtt atccctacgt taaacggcga tgacagacat    480

aaaattgtaa atgtggacca acgtcaatac ggtgacgtgt ttaaaggaga tcttaatcca    540

aaaccccaag gccaaagact cattgaggtg tcagtggaag aaaatcaccc gtttacttta    600
```

```
cgcgcaccga ttcagcggat ttatggagtc cggtacaccg agacttggag ctttttgccg    660

tcattaacct gtacgggaga cgcagcgccc gccatccagc atatatgttt aaaacataca    720

acatgctttc aagacgtggt ggtggatgtg gattgcgcgg aaaatactaa agaggatcag    780

ttggccgaaa tcagttaccg ttttcaaggt aagaaggaag cggaccaacc gtggattgtt    840

gtaaacacga gcacactgtt tgatgaactc gaattagacc cccccgagat tgaaccgggt    900

gtcttgaaag tacttcggac agaaaaacaa tacttgggtg tgtacatttg gaacatgcgc    960

ggctccgatg gtacgtctac ctacgccacg tttttggtca cctggaaagg ggatgaaaaa   1020

acaagaaacc ctacgcccgc agtaactcct caaccaagag ggctgagtt tcatatgtgg   1080

aattaccact cgcatgtatt ttcagttggt gatacgttta gcttggcaat gcatcttcag   1140

tataagatac atgaagcgcc atttgatttg ctgttagagt ggttgtatgt ccccatcgat   1200

cctacatgtc aaccaatgcg gttatattct acgtgtttgt atcatcccaa cgcaccccaa   1260

tgcctctctc atatgaattc cggttgtaca tttacctcgc cacatttagc ccagcgtgtt   1320

gcaagcacag tgtatcaaaa ttgtgaacat gcagataact acaccgcata ttgtctggga   1380

atatctcata tggagcctag ctttggtcta atcttacacg acgggggcac cacgttaaag   1440

tttgtagata cacccgagag tttgtcggga ttatacgttt ttgtggtgta ttttaacggg   1500

catgttgaag ccgtagcata cactgttgta tccacagtag atcattttgt aaacgcaatt   1560

gaagagcgtg gatttccgcc aacggccggt cagccaccgg cgactactaa acccaaggaa   1620

attacccccg taaaccccgg aacgtcacca cttctacgat atgccgcatg gaccggaggg   1680

cttgcagcag tagtactttt atgtctcgta atatttttaa tctgtacggc taaacgaatg   1740

agggttaaag ccgccagggt agacaagtga tgataatagg ctggagcctc ggtggccatg   1800

cttcttgccc cttgggcctc cccccagccc ctcctcccct tcctgcaccc gtacccccgt   1860

ggtctttgaa taaagtctga gtgggcggca aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaaaat ctag                                                     1994
```

```
<210> SEQ ID NO 41
<211> LENGTH: 2050
<212> TYPE: DNA
<213> ORGANISM: Artificial Sequence
<220> FEATURE:
<223> OTHER INFORMATION: Synthetic Polynucleotide

<400> SEQUENCE: 41

tcaagctttt ggaccctcgt acagaagcta atacgactca ctatagggaa ataagagaga     60

aaagaagagt aagaagaaat ataagagcca ccatggagac tcccgctcag ctactgttcc    120

tcctgctcct ttggctgcct gatactacag gctctgtttt gcggtacgac gactttcaca    180

tcgatgagga caagctcgac actaatagcg tgtatgagcc ctactaccat tcagatcacg    240

ccgagtcctc ttgggtgaac aggggtgaaa gttctaggaa agcctatgat cacaacagcc    300

cttatatttg gccacggaat gattacgacg gatttctcga aaatgcccac gagcatcacg    360

gagtgtacaa ccagggccgt ggaatcgact ctggggagag attgatgcaa cctacacaga    420

tgagcgccca ggaagatctc ggggatgata caggaattca cgttatccct acattaaacg    480

gagatgaccg ccacaaaatc gtcaatgtcg atcaaagaca gtatggagat gtgttcaaag    540

gcgatctcaa ccctaagccg cagggccaga gactcattga ggtgtctgtc gaagagaacc    600
```

-continued

```
acccttttcac tctgcgcgct cccattcaga gaatctatgg agttcgctat acggagactt    660

ggtcattcct tccttccctg acatgcaccg gagacgccgc ccctgccatt cagcacatat    720

gcctgaaaca taccacctgt ttccaggatg tggtggttga tgttgattgt gctgaaaata    780

ccaaggaaga ccaactggcc gagattagtt accggttcca agggaaaaag gaagccgacc    840

agccatggat tgtggttaat acaagcactc tgttcgatga gctcgagctg gatccccccg    900

agatagaacc cggagttctg aaagtgctcc ggacagaaaa acaatatctg ggagtctaca    960

tatggaacat gcgcggttcc gatgggacct ccacttatgc aacctttctc gtcacgtgga   1020

agggagatga gaaaactagg aatcccacac ccgctgtcac accacagcca agaggggctg   1080

agttccatat gtggaactat catagtcacg tgtttagtgt cggagatacg ttttcattgg   1140

ctatgcatct ccagtacaag attcatgagg ctcccttcga tctgttgctt gagtggttgt   1200

acgtcccgat tgacccgacc tgccagccca tgcgactgta cagcacctgt ctctaccatc   1260

caaacgctcc gcaatgtctg agccacatga actctgggtg tactttcacc agtccccacc   1320

tcgcccagcg ggtggcctct actgtttacc agaactgtga gcacgccgac aactacaccg   1380

catactgcct cggtatttct cacatggaac cctccttcgg actcatcctg cacgatgggg   1440

gcactaccct gaagttcgtt gatacgccag aatctctgtc tgggctctat gttttcgtgg   1500

tctacttcaa tggccatgtc gaggccgtgg cctatactgt cgtttctacc gtggatcatt   1560

ttgtgaacgc catcgaagaa cggggattcc cccctacggc aggccagccg cctgcaacca   1620

ccaagcccaa ggaaataaca ccagtgaacc ctggcacctc acctctccta agatatgccg   1680

cgtggacagg gggactggcg gcagtggtgc tcctctgtct cgtgatcttt ctgatctgta   1740

cagccaagag gatgagggtc aaggcttata gagtggacaa gtccccctac aatcagtcaa   1800

tgtactacgc cggccttccc gttgatgatt ttgaggattc cgagtccaca gatactgagg   1860

aagagttcgg taacgctata ggcggctctc acgggggttc aagctacacg gtttacattg   1920

acaagacacg ctgataatag gctggagcct cggtggccat gcttcttgcc ccttgggcct   1980

ccccccagcc cctcctcccc ttcctgcacc cgtacccccg tggtctttga ataaagtctg   2040

agtgggcggc                                                          2050
```

<210> SEQ ID NO 42
<211> LENGTH: 354
<212> TYPE: PRT
<213> ORGANISM: Artificial Sequence
<220> FEATURE:
<223> OTHER INFORMATION: Synthetic Polypeptide

<400> SEQUENCE: 42

```
Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
            20                  25                  30

Asn Ser Ser Leu Thr Ser Ile Leu Ile Pro Met Gln Asn Asp Asn Tyr
        35                  40                  45

Thr Glu Ile Lys Gly Gln Leu Val Phe Ile Gly Glu Gln Leu Pro Thr
    50                  55                  60

Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
                85                  90                  95

Arg Ile Arg Thr Ser Ala Phe Ile Ser Cys Arg Tyr Lys His Ser Trp
```

```
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175

Val Ile Tyr Thr Ser Pro Ser Leu Gln Asn Gly Tyr Ser Thr Arg Ala
            180                 185                 190

Leu Phe Gln Gln Ala Arg Leu Cys Asp Leu Pro Ala Thr Pro Lys Gly
        195                 200                 205

Ser Gly Thr Ser Leu Phe Gln His Met Leu Asp Leu Arg Ala Gly Lys
    210                 215                 220

Ser Leu Glu Asp Asn Pro Trp Leu His Glu Asp Val Val Thr Thr Glu
225                 230                 235                 240

Thr Lys Ser Val Val Lys Glu Gly Ile Glu Asn His Val Tyr Pro Thr
                245                 250                 255

Asp Met Ser Thr Leu Pro Glu Lys Ser Leu Asn Asp Pro Pro Glu Asn
            260                 265                 270

Leu Leu Ile Ile Ile Pro Ile Val Ala Ser Val Met Ile Leu Thr Ala
        275                 280                 285

Met Val Ile Val Ile Val Ile Ser Val Lys Arg Arg Arg Ile Lys Lys
    290                 295                 300

His Pro Ile Tyr Arg Pro Asn Thr Lys Thr Arg Arg Gly Ile Gln Asn
305                 310                 315                 320

Ala Thr Pro Glu Ser Asp Val Met Leu Glu Ala Ala Ile Ala Gln Leu
                325                 330                 335

Ala Thr Ile Arg Glu Glu Ser Pro Pro His Ser Val Val Asn Pro Phe
            340                 345                 350

Val Lys
```

<210> SEQ ID NO 43
<211> LENGTH: 1065
<212> TYPE: DNA
<213> ORGANISM: Artificial Sequence
<220> FEATURE:
<223> OTHER INFORMATION: Synthetic Polynucleotide

<400> SEQUENCE: 43

```
atgtttttaa tccaatgttt gatatcggcc gttatatttt acatacaagt gaccaacgct      60

ttgatcttca agggcgacca cgtgagcttg caagttaaca gcagtctcac gtctatcctt     120

attcccatgc aaaatgataa ttatacagag ataaaaggac agcttgtctt tattggagag     180

caactaccta ccgggacaaa ctatagcgga acactggaac tgttatacgc ggatacggtg     240

gcgttttgtt tccggtcagt acaagtaata agatacgacg gatgtccccg gattagaacg     300

agcgctttta tttcgtgtag gtacaaacat tcgtggcatt atggtaactc aacggatcgg     360

atatcaacag agccggatgc tggtgtaatg ttgaaaatta ccaaaccggg aataaatgat     420

gctggtgtgt atgtacttct tgttcggtta gaccatagca gatccaccga tggtttcatt     480

cttggtgtaa atgtatatac agcgggctcg catcacaaca ttcacggggt tatctacact     540

tctccatctc tacagaatgg atattctaca agagcccttt ttcaacaagc tcgtttgtgt     600
```

gatttacccg cgacacccaa agggtccggt acctccctgt ttcaacatat gcttgatctt 660
cgtgccggta aatcgttaga ggataaccct tggttacatg aggacgttgt tacgacagaa 720
actaagtccg ttgttaagga ggggatagaa aatcacgtat atccaacgga tatgtccacg 780
ttacccgaaa agtcccttaa tgatcctcca gaaaatctac ttataattat tcctatagta 840
gcgtctgtca tgatcctcac cgccatggtt attgttattg taataagcgt taagcgacgt 900
agaattaaaa aacatccaat ttatcgccca aatacaaaaa caagaagggg catacaaaat 960
gcgacaccag aatccgatgt gatgttggag gccgccattg cacaactagc aacgattcgc 1020
gaagaatccc ccccacattc cgttgtaaac ccgtttgtta aatag 1065

<210> SEQ ID NO 44
<211> LENGTH: 1337
<212> TYPE: DNA
<213> ORGANISM: Artificial Sequence
<220> FEATURE:
<223> OTHER INFORMATION: Synthetic Polynucleotide

<400> SEQUENCE: 44
ggggaaataa gagagaaaag aagagtaaga agaaatataa gagccaccat gtttttaatc 60
caatgtttga tatcggccgt tatattttac atacaagtga ccaacgcttt gatcttcaag 120
ggcgaccacg tgagcttgca agttaacagc agtctcacgt ctatccttat tcccatgcaa 180
aatgataatt atacagagat aaaaggacag cttgtcttta ttggagagca actacctacc 240
gggacaaact atagcggaac actggaactg ttatacgcgg atacggtggc gttttgtttc 300
cggtcagtac aagtaataag atacgacgga tgtccccgga ttagaacgag cgcttttatt 360
tcgtgtaggt acaaacattc gtggcattat ggtaactcaa cggatcggat atcaacagag 420
ccggatgctg gtgtaatgtt gaaaattacc aaaccgggaa taaatgatgc tggtgtgtat 480
gtacttcttg ttcggttaga ccatagcaga tccaccgatg gtttcattct tggtgtaaat 540
gtatatacag cgggctcgca tcacaacatt cacggggtta tctacacttc tccatctcta 600
cagaatggat attctacaag agcccttttt caacaagctc gtttgtgtga tttacccgcg 660
acacccaaag ggtccggtac ctccctgttt caacatatgc ttgatcttcg tgccggtaaa 720
tcgttagagg ataacccttg gttacatgag gacgttgtta cgacagaaac taagtccgtt 780
gttaaggagg ggatagaaaa tcacgtatat ccaacggata tgtccacgtt acccgaaaag 840
tcccttaatg atcctccaga aaatctactt ataattattc ctatagtagc gtctgtcatg 900
atcctcaccg ccatggttat tgttattgta ataagcgtta agcgacgtag aattaaaaaa 960
catccaattt atcgcccaaa tacaaaaaca agaaggggca tacaaaatgc gacaccagaa 1020
tccgatgtga tgttggaggc cgccattgca caactagcaa cgattcgcga agaatccccc 1080
ccacattccg ttgtaaaccc gtttgttaaa tagtgataat aggctggagc ctcggtggcc 1140
atgcttcttg ccccttgggc ctccccccag cccctcctcc ccttcctgca cccgtacccc 1200
cgtggtcttt gaataaagtc tgagtgggcg gcaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aatctag 1337

<210> SEQ ID NO 45
<211> LENGTH: 623
<212> TYPE: PRT
<213> ORGANISM: Homo sapiens

<400> SEQUENCE: 45

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415
```

```
Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620


<210> SEQ ID NO 46
<211> LENGTH: 354
<212> TYPE: PRT
<213> ORGANISM: Homo sapiens

<400> SEQUENCE: 46

Met Phe Leu Ile Gln Cys Leu Ile Ser Ala Val Ile Phe Tyr Ile Gln
1               5                   10                  15

Val Thr Asn Ala Leu Ile Phe Lys Gly Asp His Val Ser Leu Gln Val
            20                  25                  30

Asn Ser Ser Leu Thr Ser Ile Leu Ile Pro Met Gln Asn Asp Asn Tyr
        35                  40                  45

Thr Glu Ile Lys Gly Gln Leu Val Phe Ile Gly Glu Gln Leu Pro Thr
    50                  55                  60

Gly Thr Asn Tyr Ser Gly Thr Leu Glu Leu Leu Tyr Ala Asp Thr Val
65                  70                  75                  80

Ala Phe Cys Phe Arg Ser Val Gln Val Ile Arg Tyr Asp Gly Cys Pro
                85                  90                  95

Arg Ile Arg Thr Ser Ala Phe Ile Ser Cys Arg Tyr Lys His Ser Trp
            100                 105                 110

His Tyr Gly Asn Ser Thr Asp Arg Ile Ser Thr Glu Pro Asp Ala Gly
        115                 120                 125

Val Met Leu Lys Ile Thr Lys Pro Gly Ile Asn Asp Ala Gly Val Tyr
    130                 135                 140

Val Leu Leu Val Arg Leu Asp His Ser Arg Ser Thr Asp Gly Phe Ile
145                 150                 155                 160

Leu Gly Val Asn Val Tyr Thr Ala Gly Ser His His Asn Ile His Gly
                165                 170                 175
```

Val Ile Tyr Thr Ser Pro Ser Leu Gln Asn Gly Tyr Ser Thr Arg Ala
180 185 190

Leu Phe Gln Gln Ala Arg Leu Cys Asp Leu Pro Ala Thr Pro Lys Gly
195 200 205

Ser Gly Thr Ser Leu Phe Gln His Met Leu Asp Leu Arg Ala Gly Lys
210 215 220

Ser Leu Glu Asp Asn Pro Trp Leu His Glu Asp Val Val Thr Thr Glu
225 230 235 240

Thr Lys Ser Val Val Lys Glu Gly Ile Glu Asn His Val Tyr Pro Thr
245 250 255

Asp Met Ser Thr Leu Pro Glu Lys Ser Leu Asn Asp Pro Pro Glu Asn
260 265 270

Leu Leu Ile Ile Ile Pro Ile Val Ala Ser Val Met Ile Leu Thr Ala
275 280 285

Met Val Ile Val Ile Val Ile Ser Val Lys Arg Arg Arg Ile Lys Lys
290 295 300

His Pro Ile Tyr Arg Pro Asn Thr Lys Thr Arg Arg Gly Ile Gln Asn
305 310 315 320

Ala Thr Pro Glu Ser Asp Val Met Leu Glu Ala Ala Ile Ala Gln Leu
325 330 335

Ala Thr Ile Arg Glu Glu Ser Pro Pro His Ser Val Val Asn Pro Phe
340 345 350

Val Lys

<210> SEQ ID NO 47
<211> LENGTH: 556
<212> TYPE: PRT
<213> ORGANISM: Artificial Sequence
<220> FEATURE:
<223> OTHER INFORMATION: Synthetic Polypeptide

<400> SEQUENCE: 47

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Ile Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Val Ile Pro Thr Leu Asn Gly Asp Asp Arg His Lys Ile
130 135 140

Val Asn Val Asp Gln Arg Gln Tyr Gly Asp Val Phe Lys Gly Asp Leu
145 150 155 160

Asn Pro Lys Pro Gln Gly Gln Arg Leu Ile Glu Val Ser Val Glu Glu
165 170 175

```
Asn His Pro Phe Thr Leu Arg Ala Pro Ile Gln Arg Ile Tyr Gly Val
            180                 185                 190

Arg Tyr Thr Glu Thr Trp Ser Phe Leu Pro Ser Leu Thr Cys Thr Gly
        195                 200                 205

Asp Ala Ala Pro Ala Ile Gln His Ile Cys Leu Lys His Thr Thr Cys
    210                 215                 220

Phe Gln Asp Val Val Val Asp Val Asp Cys Ala Glu Asn Thr Lys Glu
225                 230                 235                 240

Asp Gln Leu Ala Glu Ile Ser Tyr Arg Phe Gln Gly Lys Lys Glu Ala
                245                 250                 255

Asp Gln Pro Trp Ile Val Val Asn Thr Thr Leu Phe Asp Glu Leu Glu
            260                 265                 270

Leu Asp Pro Pro Glu Ile Glu Pro Gly Val Leu Lys Val Leu Arg Thr
        275                 280                 285

Glu Lys Gln Tyr Leu Gly Val Tyr Ile Trp Asn Met Arg Gly Ser Asp
    290                 295                 300

Gly Thr Ser Thr Tyr Ala Thr Phe Leu Val Thr Trp Lys Gly Asp Glu
305                 310                 315                 320

Lys Thr Arg Asn Pro Thr Pro Ala Val Thr Pro Gln Pro Arg Gly Ala
                325                 330                 335

Glu Phe His Met Trp Asn Tyr His Ser His Val Phe Ser Val Gly Asp
            340                 345                 350

Thr Phe Ser Leu Ala Met His Leu Gln Tyr Lys Ile His Glu Ala Pro
        355                 360                 365

Phe Asp Leu Leu Leu Glu Trp Leu Tyr Val Pro Ile Asp Pro Thr Cys
    370                 375                 380

Gln Pro Met Arg Leu Tyr Ser Thr Cys Leu Tyr His Pro Asn Ala Gln
385                 390                 395                 400

Cys Leu Ser His Met Asn Ser Gly Cys Thr Phe Thr Ser Pro His Leu
                405                 410                 415

Ala Gln Arg Val Ala Ser Thr Val Tyr Gln Asn Cys Glu His Ala Asp
            420                 425                 430

Asn Tyr Thr Ala Tyr Cys Leu Gly Ile Ser His Met Glu Pro Ser Phe
        435                 440                 445

Gly Leu Ile Leu His Asp Gly Gly Thr Thr Leu Lys Phe Val Asp Thr
    450                 455                 460

Pro Glu Ser Leu Ser Gly Leu Tyr Val Phe Val Val Tyr Phe Asn Gly
465                 470                 475                 480

His Val Glu Ala Val Ala Tyr Thr Val Val Ser Thr Val Asp His Phe
                485                 490                 495

Val Asn Ala Ile Glu Glu Arg Gly Phe Pro Pro Thr Ala Gly Gln Pro
            500                 505                 510

Pro Ala Thr Thr Lys Pro Lys Glu Ile Thr Pro Val Asn Pro Gly Thr
        515                 520                 525

Ser Pro Leu Leu Arg Tyr Ala Trp Thr Gly Gly Leu Ala Ala Val Val
    530                 535                 540

Leu Leu Cys Leu Val Ile Phe Leu Ile Cys Thr Ala
545                 550                 555
```

<210> SEQ ID NO 48
<211> LENGTH: 574
<212> TYPE: PRT
<213> ORGANISM: Homo sapiens

<400> SEQUENCE: 48

```
Met Lys Arg Ile Gln Ile Asn Leu Ile Leu Thr Ile Ala Cys Ile Gln
1               5                   10                  15

Leu Ser Thr Glu Ser Gln Pro Thr Pro Val Ser Ile Thr Glu Leu Tyr
            20                  25                  30

Thr Ser Ala Ala Thr Arg Lys Pro Asp Pro Ala Val Ala Pro Thr Ser
        35                  40                  45

Ala Ala Thr Arg Lys Pro Asp Pro Ala Val Ala Pro Thr Ser Ala Ala
    50                  55                  60

Thr Arg Lys Pro Asp Pro Ala Val Ala Pro Thr Ser Ala Ala Thr Arg
65                  70                  75                  80

Lys Pro Asp Pro Ala Val Ala Pro Thr Ser Ala Ala Thr Arg Lys Pro
                85                  90                  95

Asp Pro Ala Val Ala Pro Thr Ser Ala Ala Thr Arg Lys Pro Asp Pro
            100                 105                 110

Ala Val Ala Pro Thr Ser Ala Ala Ser Arg Lys Pro Asp Pro Ala Val
        115                 120                 125

Ala Pro Thr Ser Ala Ala Ser Arg Lys Pro Asp Pro Ala Val Ala Pro
    130                 135                 140

Thr Ser Ala Ala Ser Arg Lys Pro Asp Pro Ala Ala Asn Thr Gln His
145                 150                 155                 160

Ser Gln Pro Pro Phe Leu Tyr Glu Asn Ile Gln Cys Val His Gly Gly
                165                 170                 175

Ile Gln Ser Ile Pro Tyr Phe His Thr Phe Ile Met Pro Cys Tyr Met
            180                 185                 190

Arg Leu Thr Thr Gly Gln Gln Ala Ala Phe Lys Gln Gln Gln Lys Thr
        195                 200                 205

Tyr Glu Gln Tyr Ser Leu Asp Pro Glu Gly Ser Asn Ile Thr Arg Trp
    210                 215                 220

Lys Ser Leu Ile Arg Pro Asp Leu His Ile Glu Val Trp Phe Thr Arg
225                 230                 235                 240

His Leu Ile Asp Pro His Arg Gln Leu Gly Asn Ala Leu Ile Arg Met
                245                 250                 255

Pro Asp Leu Pro Val Met Leu Tyr Ser Asn Ser Ala Asp Leu Asn Leu
            260                 265                 270

Ile Asn Asn Pro Glu Ile Phe Thr His Ala Lys Glu Asn Tyr Val Ile
        275                 280                 285

Pro Asp Val Lys Thr Thr Ser Asp Phe Ser Val Thr Ile Leu Ser Met
    290                 295                 300

Asp Ala Thr Thr Glu Gly Thr Tyr Ile Trp Arg Val Val Asn Thr Lys
305                 310                 315                 320

Thr Lys Asn Val Ile Ser Glu His Ser Ile Thr Val Thr Thr Tyr Tyr
                325                 330                 335

Arg Pro Asn Ile Thr Val Val Gly Asp Pro Val Leu Thr Gly Gln Thr
            340                 345                 350

Tyr Ala Ala Tyr Cys Asn Val Ser Lys Tyr Tyr Pro Pro His Ser Val
        355                 360                 365

Arg Val Arg Trp Thr Ser Arg Phe Gly Asn Ile Gly Lys Asn Phe Ile
    370                 375                 380

Thr Asp Ala Ile Gln Glu Tyr Ala Asn Gly Leu Phe Ser Tyr Val Ser
385                 390                 395                 400

Ala Val Arg Ile Pro Gln Gln Lys Gln Met Asp Tyr Pro Pro Pro Ala
                405                 410                 415
```

```
Ile Gln Cys Asn Val Leu Trp Ile Arg Asp Gly Val Ser Asn Met Lys
            420                 425                 430

Tyr Ser Ala Val Val Thr Pro Asp Val Tyr Pro Phe Pro Asn Val Ser
        435                 440                 445

Ile Gly Ile Ile Asp Gly His Ile Val Cys Thr Ala Lys Cys Val Pro
    450                 455                 460

Arg Gly Val Val His Phe Val Trp Trp Val Asn Asp Ser Pro Ile Asn
465                 470                 475                 480

His Glu Asn Ser Glu Ile Thr Gly Val Cys Asp Gln Asn Lys Arg Phe
                485                 490                 495

Val Asn Met Gln Ser Ser Cys Pro Thr Ser Glu Leu Asp Gly Pro Ile
            500                 505                 510

Thr Tyr Ser Cys His Leu Asp Gly Tyr Pro Lys Lys Phe Pro Pro Phe
        515                 520                 525

Ser Ala Val Tyr Thr Tyr Asp Ala Ser Thr Tyr Ala Thr Thr Phe Ser
    530                 535                 540

Val Val Ala Val Ile Ile Gly Val Ile Ser Ile Leu Gly Thr Leu Gly
545                 550                 555                 560

Leu Ile Ala Val Ile Ala Thr Leu Cys Ile Arg Cys Cys Ser
                565                 570


<210> SEQ ID NO 49
<211> LENGTH: 159
<212> TYPE: PRT
<213> ORGANISM: Homo sapiens

<400> SEQUENCE: 49

Met Ala Ser His Lys Trp Leu Leu Gln Ile Val Phe Leu Lys Thr Ile
1               5                   10                  15

Thr Ile Ala Tyr Cys Leu His Leu Gln Asp Asp Thr Pro Leu Phe Phe
            20                  25                  30

Gly Ala Lys Pro Leu Ser Asp Val Ser Leu Ile Ile Thr Glu Pro Cys
        35                  40                  45

Val Ser Ser Val Tyr Glu Ala Trp Asp Tyr Ala Ala Pro Pro Val Ser
    50                  55                  60

Asn Leu Ser Glu Ala Leu Ser Gly Ile Val Val Lys Thr Lys Cys Pro
65                  70                  75                  80

Val Pro Glu Val Ile Leu Trp Phe Lys Asp Lys Gln Met Ala Tyr Trp
                85                  90                  95

Thr Asn Pro Tyr Val Thr Leu Lys Gly Leu Ala Gln Ser Val Gly Glu
            100                 105                 110

Glu His Lys Ser Gly Asp Ile Arg Asp Ala Leu Leu Asp Ala Leu Ser
        115                 120                 125

Gly Val Trp Val Asp Ser Thr Pro Ser Ser Thr Asn Ile Pro Glu Asn
    130                 135                 140

Gly Cys Val Trp Gly Ala Asp Arg Leu Phe Gln Arg Val Cys Gln
145                 150                 155


<210> SEQ ID NO 50
<211> LENGTH: 435
<212> TYPE: PRT
<213> ORGANISM: Homo sapiens

<400> SEQUENCE: 50

Met Gly Thr Gln Lys Lys Gly Pro Arg Ser Glu Lys Val Ser Pro Tyr
1               5                   10                  15
```

-continued

```
Asp Thr Thr Thr Pro Glu Val Glu Ala Leu Asp His Gln Met Asp Thr
            20                  25                  30

Leu Asn Trp Arg Ile Trp Ile Ile Gln Val Met Met Phe Thr Leu Gly
        35                  40                  45

Ala Val Met Leu Leu Ala Thr Leu Ile Ala Ala Ser Ser Glu Tyr Thr
    50                  55                  60

Gly Ile Pro Cys Phe Tyr Ala Ala Val Val Asp Tyr Glu Leu Phe Asn
65                  70                  75                  80

Ala Thr Leu Asp Gly Gly Val Trp Ser Gly Asn Arg Gly Gly Tyr Ser
                85                  90                  95

Ala Pro Val Leu Phe Leu Glu Pro His Ser Val Val Ala Phe Thr Tyr
            100                 105                 110

Tyr Thr Ala Leu Thr Ala Met Ala Met Ala Val Tyr Thr Leu Ile Thr
        115                 120                 125

Ala Ala Ile Ile His Arg Glu Thr Lys Asn Gln Arg Val Arg Gln Ser
    130                 135                 140

Ser Gly Val Ala Trp Leu Val Val Asp Pro Thr Thr Leu Phe Trp Gly
145                 150                 155                 160

Leu Leu Ser Leu Trp Leu Leu Asn Ala Val Val Leu Leu Leu Ala Tyr
                165                 170                 175

Lys Gln Ile Gly Val Ala Ala Thr Leu Tyr Leu Gly His Phe Ala Thr
            180                 185                 190

Ser Val Ile Phe Thr Thr Tyr Phe Cys Gly Arg Gly Lys Leu Asp Glu
        195                 200                 205

Thr Asn Ile Lys Ala Val Ala Asn Leu Arg Gln Gln Ser Val Phe Leu
    210                 215                 220

Tyr Arg Leu Ala Gly Pro Thr Arg Ala Val Phe Val Asn Leu Met Ala
225                 230                 235                 240

Ala Leu Met Ala Ile Cys Ile Leu Phe Val Ser Leu Met Leu Glu Leu
                245                 250                 255

Val Val Ala Asn His Leu His Thr Gly Leu Trp Ser Ser Val Ser Val
            260                 265                 270

Ala Met Ser Thr Phe Ser Thr Leu Ser Val Val Tyr Leu Ile Val Ser
        275                 280                 285

Glu Leu Ile Leu Ala His Tyr Ile His Val Leu Ile Gly Pro Ser Leu
    290                 295                 300

Gly Thr Leu Val Ala Cys Ala Thr Leu Gly Thr Ala Ala His Ser Tyr
305                 310                 315                 320

Met Asp Arg Leu Tyr Asp Pro Ile Ser Val Gln Ser Pro Arg Leu Ile
                325                 330                 335

Pro Thr Thr Arg Gly Thr Leu Ala Cys Leu Ala Val Phe Ser Val Val
            340                 345                 350

Met Leu Leu Leu Arg Leu Met Arg Ala Tyr Val Tyr His Arg Gln Lys
        355                 360                 365

Arg Ser Arg Phe Tyr Gly Ala Val Arg Arg Val Pro Glu Arg Val Arg
    370                 375                 380

Gly Tyr Ile Arg Lys Val Lys Pro Ala His Arg Asn Ser Arg Arg Thr
385                 390                 395                 400

Asn Tyr Pro Ser Gln Gly Tyr Gly Tyr Val Tyr Glu Asn Asp Ser Thr
                405                 410                 415

Tyr Glu Thr Asp Arg Glu Asp Glu Leu Leu Tyr Glu Arg Ser Asn Ser
            420                 425                 430

Gly Trp Glu
```

435

<210> SEQ ID NO 51
<211> LENGTH: 841
<212> TYPE: PRT
<213> ORGANISM: Homo sapiens

<400> SEQUENCE: 51

Met Phe Ala Leu Val Leu Ala Val Val Ile Leu Pro Leu Trp Thr Thr
1               5                   10                  15

Ala Asn Lys Ser Tyr Val Thr Pro Thr Pro Ala Thr Arg Ser Ile Gly
            20                  25                  30

His Met Ser Ala Leu Leu Arg Glu Tyr Ser Asp Arg Asn Met Ser Leu
        35                  40                  45

Lys Leu Glu Ala Phe Tyr Pro Thr Gly Phe Asp Glu Glu Leu Ile Lys
    50                  55                  60

Ser Leu His Trp Gly Asn Asp Arg Lys His Val Phe Leu Val Ile Val
65                  70                  75                  80

Lys Val Asn Pro Thr Thr His Glu Gly Asp Val Gly Leu Val Ile Phe
                85                  90                  95

Pro Lys Tyr Leu Leu Ser Pro Tyr His Phe Lys Ala Glu His Arg Ala
            100                 105                 110

Pro Phe Pro Ala Gly Arg Phe Gly Phe Leu Ser His Pro Val Thr Pro
        115                 120                 125

Asp Val Ser Phe Phe Asp Ser Ser Phe Ala Pro Tyr Leu Thr Thr Gln
    130                 135                 140

His Leu Val Ala Phe Thr Thr Phe Pro Pro Asn Pro Leu Val Trp His
145                 150                 155                 160

Leu Glu Arg Ala Glu Thr Ala Ala Thr Ala Glu Arg Pro Phe Gly Val
                165                 170                 175

Ser Leu Leu Pro Ala Arg Pro Thr Val Pro Lys Asn Thr Ile Leu Glu
            180                 185                 190

His Lys Ala His Phe Ala Thr Trp Asp Ala Leu Ala Arg His Thr Phe
        195                 200                 205

Phe Ser Ala Glu Ala Ile Ile Thr Asn Ser Thr Leu Arg Ile His Val
    210                 215                 220

Pro Leu Phe Gly Ser Val Trp Pro Ile Arg Tyr Trp Ala Thr Gly Ser
225                 230                 235                 240

Val Leu Leu Thr Ser Asp Ser Gly Arg Val Glu Val Asn Ile Gly Val
                245                 250                 255

Gly Phe Met Ser Ser Leu Ile Ser Leu Ser Ser Gly Pro Pro Ile Glu
            260                 265                 270

Leu Ile Val Val Pro His Thr Val Lys Leu Asn Ala Val Thr Ser Asp
        275                 280                 285

Thr Thr Trp Phe Gln Leu Asn Pro Pro Gly Pro Asp Pro Gly Pro Ser
    290                 295                 300

Tyr Arg Val Tyr Leu Leu Gly Arg Gly Leu Asp Met Asn Phe Ser Lys
305                 310                 315                 320

His Ala Thr Val Asp Ile Cys Ala Tyr Pro Glu Glu Ser Leu Asp Tyr
                325                 330                 335

Arg Tyr His Leu Ser Met Ala His Thr Glu Ala Leu Arg Met Thr Thr
            340                 345                 350

Lys Ala Asp Gln His Asp Ile Asn Glu Glu Ser Tyr Tyr His Ile Ala
        355                 360                 365

-continued

```
Ala Arg Ile Ala Thr Ser Ile Phe Ala Leu Ser Glu Met Gly Arg Thr
    370                 375                 380

Thr Glu Tyr Phe Leu Leu Asp Glu Ile Val Asp Val Gln Tyr Gln Leu
385                 390                 395                 400

Lys Phe Leu Asn Tyr Ile Leu Met Arg Ile Gly Ala Gly Ala His Pro
                405                 410                 415

Asn Thr Ile Ser Gly Thr Ser Asp Leu Ile Phe Ala Asp Pro Ser Gln
            420                 425                 430

Leu His Asp Glu Leu Ser Leu Leu Phe Gly Gln Val Lys Pro Ala Asn
        435                 440                 445

Val Asp Tyr Phe Ile Ser Tyr Asp Glu Ala Arg Asp Gln Leu Lys Thr
    450                 455                 460

Ala Tyr Ala Leu Ser Arg Gly Gln Asp His Val Asn Ala Leu Ser Leu
465                 470                 475                 480

Ala Arg Arg Val Ile Met Ser Ile Tyr Lys Gly Leu Leu Val Lys Gln
                485                 490                 495

Asn Leu Asn Ala Thr Glu Arg Gln Ala Leu Phe Phe Ala Ser Met Ile
            500                 505                 510

Leu Leu Asn Phe Arg Glu Gly Leu Glu Asn Ser Ser Arg Val Leu Asp
        515                 520                 525

Gly Arg Thr Thr Leu Leu Leu Met Thr Ser Met Cys Thr Ala Ala His
    530                 535                 540

Ala Thr Gln Ala Ala Leu Asn Ile Gln Glu Gly Leu Ala Tyr Leu Asn
545                 550                 555                 560

Pro Ser Lys His Met Phe Thr Ile Pro Asn Val Tyr Ser Pro Cys Met
                565                 570                 575

Gly Ser Leu Arg Thr Asp Leu Thr Glu Glu Ile His Val Met Asn Leu
            580                 585                 590

Leu Ser Ala Ile Pro Thr Arg Pro Gly Leu Asn Glu Val Leu His Thr
        595                 600                 605

Gln Leu Asp Glu Ser Glu Ile Phe Asp Ala Ala Phe Lys Thr Met Met
    610                 615                 620

Ile Phe Thr Thr Trp Thr Ala Lys Asp Leu His Ile Leu His Thr His
625                 630                 635                 640

Val Pro Glu Val Phe Thr Cys Gln Asp Ala Ala Ala Arg Asn Gly Glu
                645                 650                 655

Tyr Val Leu Ile Leu Pro Ala Val Gln Gly His Ser Tyr Val Ile Thr
            660                 665                 670

Arg Asn Lys Pro Gln Arg Gly Leu Val Tyr Ser Leu Ala Asp Val Asp
        675                 680                 685

Val Tyr Asn Pro Ile Ser Val Val Tyr Leu Ser Arg Asp Thr Cys Val
    690                 695                 700

Ser Glu His Gly Val Ile Glu Thr Val Ala Leu Pro His Pro Asp Asn
705                 710                 715                 720

Leu Lys Glu Cys Leu Tyr Cys Gly Ser Val Phe Leu Arg Tyr Leu Thr
                725                 730                 735

Thr Gly Ala Ile Met Asp Ile Ile Ile Ile Asp Ser Lys Asp Thr Glu
            740                 745                 750

Arg Gln Leu Ala Ala Met Gly Asn Ser Thr Ile Pro Pro Phe Asn Pro
        755                 760                 765

Asp Met His Gly Asp Asp Ser Lys Ala Val Leu Leu Phe Pro Asn Gly
    770                 775                 780

Thr Val Val Thr Leu Leu Gly Phe Glu Arg Arg Gln Ala Ile Arg Met
```

785 790 795 800

Ser Gly Gln Tyr Leu Gly Ala Ser Leu Gly Gly Ala Phe Leu Ala Val
805 810 815

Val Gly Phe Gly Ile Ile Gly Trp Met Leu Cys Gly Asn Ser Arg Leu
820 825 830

Arg Glu Tyr Asn Lys Ile Pro Leu Thr
835 840

<210> SEQ ID NO 52
<211> LENGTH: 661
<212> TYPE: PRT
<213> ORGANISM: Homo sapiens

<400> SEQUENCE: 52

Met Phe Tyr Glu Ala Leu Lys Ala Glu Leu Val Tyr Thr Arg Ala Val
1 5 10 15

His Gly Phe Arg Pro Arg Ala Asn Cys Val Val Leu Ser Asp Tyr Ile
20 25 30

Pro Arg Val Ala Cys Asn Met Gly Thr Val Asn Lys Pro Val Val Gly
35 40 45

Val Leu Met Gly Phe Gly Ile Ile Thr Gly Thr Leu Arg Ile Thr Asn
50 55 60

Pro Val Arg Ala Ser Val Leu Arg Tyr Asp Asp Phe His Ile Asp Glu
65 70 75 80

Asp Lys Leu Asp Thr Asn Ser Val Tyr Glu Pro Tyr Tyr His Ser Asp
85 90 95

His Ala Glu Ser Ser Trp Val Asn Arg Gly Glu Ser Ser Arg Lys Ala
100 105 110

Tyr Asp His Asn Ser Pro Tyr Ile Trp Pro Arg Asn Asp Tyr Asp Gly
115 120 125

Phe Leu Glu Asn Ala His Glu His His Gly Val Tyr Asn Gln Gly Arg
130 135 140

Gly Ile Asp Ser Gly Glu Arg Leu Met Gln Pro Thr Gln Met Ser Ala
145 150 155 160

Gln Glu Asp Leu Gly Asp Asp Thr Gly Ile His Val Ile Pro Thr Leu
165 170 175

Asn Gly Asp Asp Arg His Lys Ile Val Asn Val Asp Gln Arg Gln Tyr
180 185 190

Gly Asp Val Phe Lys Gly Asp Leu Asn Pro Lys Pro Gln Gly Gln Arg
195 200 205

Leu Ile Glu Val Ser Val Glu Glu Asn His Pro Phe Thr Leu Arg Ala
210 215 220

Pro Ile Gln Arg Ile Tyr Gly Val Arg Tyr Thr Glu Thr Trp Ser Phe
225 230 235 240

Leu Pro Ser Leu Thr Cys Thr Gly Asp Ala Ala Pro Ala Ile Gln His
245 250 255

Ile Cys Leu Lys His Thr Thr Cys Phe Gln Asp Val Val Val Asp Val
260 265 270

Asp Cys Ala Glu Asn Thr Lys Glu Asp Gln Leu Ala Glu Ile Ser Tyr
275 280 285

Arg Phe Gln Gly Lys Lys Glu Ala Asp Gln Pro Trp Ile Val Val Asn
290 295 300

Thr Ser Thr Leu Phe Asp Glu Leu Glu Leu Asp Pro Pro Glu Ile Glu
305 310 315 320

```
Pro Gly Val Leu Lys Val Leu Arg Thr Glu Lys Gln Tyr Leu Gly Val
                325                 330                 335

Tyr Ile Trp Asn Met Arg Gly Ser Asp Gly Thr Ser Thr Tyr Ala Thr
            340                 345                 350

Phe Leu Val Thr Trp Lys Gly Asp Glu Lys Thr Arg Asn Pro Thr Pro
        355                 360                 365

Ala Val Thr Pro Gln Pro Arg Gly Ala Glu Phe His Met Trp Asn Tyr
    370                 375                 380

His Ser His Val Phe Ser Val Gly Asp Thr Phe Ser Leu Ala Met His
385                 390                 395                 400

Leu Gln Tyr Lys Ile His Glu Ala Pro Phe Asp Leu Leu Leu Glu Trp
                405                 410                 415

Leu Tyr Val Pro Ile Asp Pro Thr Cys Gln Pro Met Arg Leu Tyr Ser
            420                 425                 430

Thr Cys Leu Tyr His Pro Asn Ala Pro Gln Cys Leu Ser His Met Asn
        435                 440                 445

Ser Gly Cys Thr Phe Thr Ser Pro His Leu Ala Gln Arg Val Ala Ser
    450                 455                 460

Thr Val Tyr Gln Asn Cys Glu His Ala Asp Asn Tyr Thr Ala Tyr Cys
465                 470                 475                 480

Leu Gly Ile Ser His Met Glu Pro Ser Phe Gly Leu Ile Leu His Asp
                485                 490                 495

Gly Gly Thr Thr Leu Lys Phe Val Asp Thr Pro Glu Ser Leu Ser Gly
            500                 505                 510

Leu Tyr Val Phe Val Val Tyr Phe Asn Gly His Val Glu Ala Val Ala
        515                 520                 525

Tyr Thr Val Val Ser Thr Val Asp His Phe Val Asn Ala Ile Glu Glu
    530                 535                 540

Arg Gly Phe Pro Pro Thr Ala Gly Gln Pro Pro Ala Thr Thr Lys Pro
545                 550                 555                 560

Lys Glu Ile Thr Pro Val Asn Pro Gly Thr Ser Pro Leu Leu Arg Tyr
                565                 570                 575

Ala Ala Trp Thr Gly Gly Leu Ala Ala Val Val Leu Leu Cys Leu Val
            580                 585                 590

Ile Phe Leu Ile Cys Thr Ala Lys Arg Met Arg Val Lys Ala Tyr Arg
        595                 600                 605

Val Asp Lys Ser Pro Tyr Asn Gln Ser Met Tyr Tyr Ala Gly Leu Pro
    610                 615                 620

Val Asp Asp Phe Glu Asp Ser Glu Ser Thr Asp Thr Glu Glu Glu Phe
625                 630                 635                 640

Gly Asn Ala Ile Gly Gly Ser His Gly Gly Ser Ser Tyr Thr Val Tyr
                645                 650                 655

Ile Asp Lys Thr Arg
            660


<210> SEQ ID NO 53
<211> LENGTH: 868
<212> TYPE: PRT
<213> ORGANISM: Homo sapiens

<400> SEQUENCE: 53

Met Phe Val Thr Ala Val Val Ser Val Ser Pro Ser Ser Phe Tyr Glu
1               5                   10                  15

Ser Leu Gln Val Glu Pro Thr Gln Ser Glu Asp Ile Thr Arg Ser Ala
            20                  25                  30
```

```
His Leu Gly Asp Gly Asp Glu Ile Arg Glu Ala Ile His Lys Ser Gln
        35                  40                  45

Asp Ala Glu Thr Lys Pro Thr Phe Tyr Val Cys Pro Pro Pro Thr Gly
    50                  55                  60

Ser Thr Ile Val Arg Leu Glu Pro Thr Arg Thr Cys Pro Asp Tyr His
65                  70                  75                  80

Leu Gly Lys Asn Phe Thr Glu Gly Ile Ala Val Val Tyr Lys Glu Asn
                85                  90                  95

Ile Ala Ala Tyr Lys Phe Lys Ala Thr Val Tyr Tyr Lys Asp Val Ile
            100                 105                 110

Val Ser Thr Ala Trp Ala Gly Ser Ser Tyr Thr Gln Ile Thr Asn Arg
        115                 120                 125

Tyr Ala Asp Arg Val Pro Ile Pro Val Ser Glu Ile Thr Asp Thr Ile
    130                 135                 140

Asp Lys Phe Gly Lys Cys Ser Ser Lys Ala Thr Tyr Val Arg Asn Asn
145                 150                 155                 160

His Lys Val Glu Ala Phe Asn Glu Asp Lys Asn Pro Gln Asp Met Pro
                165                 170                 175

Leu Ile Ala Ser Lys Tyr Asn Ser Val Gly Ser Lys Ala Trp His Thr
            180                 185                 190

Thr Asn Asp Thr Tyr Met Val Ala Gly Thr Pro Gly Thr Tyr Arg Thr
        195                 200                 205

Gly Thr Ser Val Asn Cys Ile Ile Glu Glu Val Glu Ala Arg Ser Ile
    210                 215                 220

Phe Pro Tyr Asp Ser Phe Gly Leu Ser Thr Gly Asp Ile Ile Tyr Met
225                 230                 235                 240

Ser Pro Phe Phe Gly Leu Arg Asp Gly Ala Tyr Arg Glu His Ser Asn
                245                 250                 255

Tyr Ala Met Asp Arg Phe His Gln Phe Glu Gly Tyr Arg Gln Arg Asp
            260                 265                 270

Leu Asp Thr Arg Ala Leu Leu Glu Pro Ala Ala Arg Asn Phe Leu Val
        275                 280                 285

Thr Pro His Leu Thr Val Gly Trp Asn Trp Lys Pro Lys Arg Thr Glu
    290                 295                 300

Val Cys Ser Leu Val Lys Trp Arg Glu Val Glu Asp Val Val Arg Asp
305                 310                 315                 320

Glu Tyr Ala His Asn Phe Arg Phe Thr Met Lys Thr Leu Ser Thr Thr
                325                 330                 335

Phe Ile Ser Glu Thr Asn Glu Phe Asn Leu Asn Gln Ile His Leu Ser
            340                 345                 350

Gln Cys Val Lys Glu Glu Ala Arg Ala Ile Ile Asn Arg Ile Tyr Thr
        355                 360                 365

Thr Arg Tyr Asn Ser Ser His Val Arg Thr Gly Asp Ile Gln Thr Tyr
    370                 375                 380

Leu Ala Arg Gly Gly Phe Val Val Val Phe Gln Pro Leu Leu Ser Asn
385                 390                 395                 400

Ser Leu Ala Arg Leu Tyr Leu Gln Glu Leu Val Arg Glu Asn Thr Asn
                405                 410                 415

His Ser Pro Gln Lys His Pro Thr Arg Asn Thr Arg Ser Arg Arg Ser
            420                 425                 430

Val Pro Val Glu Leu Arg Ala Asn Arg Thr Ile Thr Thr Thr Ser Ser
        435                 440                 445
```

```
Val Glu Phe Ala Met Leu Gln Phe Thr Tyr Asp His Ile Gln Glu His
    450                 455                 460

Val Asn Glu Met Leu Ala Arg Ile Ser Ser Ser Trp Cys Gln Leu Gln
465                 470                 475                 480

Asn Arg Glu Arg Ala Leu Trp Ser Gly Leu Phe Pro Ile Asn Pro Ser
                485                 490                 495

Ala Leu Ala Ser Thr Ile Leu Asp Gln Arg Val Lys Ala Arg Ile Leu
            500                 505                 510

Gly Asp Val Ile Ser Val Ser Asn Cys Pro Glu Leu Gly Ser Asp Thr
        515                 520                 525

Arg Ile Ile Leu Gln Asn Ser Met Arg Val Ser Gly Ser Thr Thr Arg
    530                 535                 540

Cys Tyr Ser Arg Pro Leu Ile Ser Ile Val Ser Leu Asn Gly Ser Gly
545                 550                 555                 560

Thr Val Glu Gly Gln Leu Gly Thr Asp Asn Glu Leu Ile Met Ser Arg
                565                 570                 575

Asp Leu Leu Glu Pro Cys Val Ala Asn His Lys Arg Tyr Phe Leu Phe
            580                 585                 590

Gly His His Tyr Val Tyr Tyr Glu Asp Tyr Arg Tyr Val Arg Glu Ile
        595                 600                 605

Ala Val His Asp Val Gly Met Ile Ser Thr Tyr Val Asp Leu Asn Leu
    610                 615                 620

Thr Leu Leu Lys Asp Arg Glu Phe Met Pro Leu Gln Val Tyr Thr Arg
625                 630                 635                 640

Asp Glu Leu Arg Asp Thr Gly Leu Leu Asp Tyr Ser Glu Ile Gln Arg
                645                 650                 655

Arg Asn Gln Met His Ser Leu Arg Phe Tyr Asp Ile Asp Lys Val Val
            660                 665                 670

Gln Tyr Asp Ser Gly Thr Ala Ile Met Gln Gly Met Ala Gln Phe Phe
        675                 680                 685

Gln Gly Leu Gly Thr Ala Gly Gln Ala Val Gly His Val Val Leu Gly
    690                 695                 700

Ala Thr Gly Ala Leu Leu Ser Thr Val His Gly Phe Thr Thr Phe Leu
705                 710                 715                 720

Ser Asn Pro Phe Gly Ala Leu Ala Val Gly Leu Leu Val Leu Ala Gly
                725                 730                 735

Leu Val Ala Ala Phe Phe Ala Tyr Arg Tyr Val Leu Lys Leu Lys Thr
            740                 745                 750

Ser Pro Met Lys Ala Leu Tyr Pro Leu Thr Thr Lys Gly Leu Lys Gln
        755                 760                 765

Leu Pro Glu Gly Met Asp Pro Phe Ala Glu Lys Pro Asn Ala Thr Asp
    770                 775                 780

Thr Pro Ile Glu Glu Ile Gly Asp Ser Gln Asn Thr Glu Pro Ser Val
785                 790                 795                 800

Asn Ser Gly Phe Asp Pro Asp Lys Phe Arg Glu Ala Gln Glu Met Ile
                805                 810                 815

Lys Tyr Met Thr Leu Val Ser Ala Ala Glu Arg Gln Glu Ser Lys Ala
            820                 825                 830

Arg Lys Lys Asn Lys Thr Ser Ala Leu Leu Thr Ser Arg Leu Thr Gly
        835                 840                 845

Leu Ala Leu Arg Asn Arg Arg Gly Tyr Ser Arg Val Arg Thr Glu Asn
    850                 855                 860

Val Thr Gly Val
```

865

<210> SEQ ID NO 54
<211> LENGTH: 340
<212> TYPE: PRT
<213> ORGANISM: Homo sapiens

<400> SEQUENCE: 54

Met Gln Ala Leu Gly Ile Lys Thr Glu His Phe Ile Ile Met Cys Leu
1               5                   10                  15

Leu Ser Gly His Ala Val Phe Thr Leu Trp Tyr Thr Ala Arg Val Lys
            20                  25                  30

Phe Glu His Glu Cys Val Tyr Ala Thr Thr Val Ile Asn Gly Gly Pro
        35                  40                  45

Val Val Trp Gly Ser Tyr Asn Asn Ser Leu Ile Tyr Val Thr Phe Val
    50                  55                  60

Asn His Ser Thr Phe Leu Asp Gly Leu Ser Gly Tyr Asp Tyr Ser Cys
65                  70                  75                  80

Arg Glu Asn Leu Leu Ser Gly Asp Thr Met Val Lys Thr Ala Ile Ser
                85                  90                  95

Thr Pro Leu His Asp Lys Ile Arg Ile Val Leu Gly Thr Arg Asn Cys
            100                 105                 110

His Ala Tyr Phe Trp Cys Val Gln Leu Lys Met Ile Phe Phe Ala Trp
        115                 120                 125

Phe Val Tyr Gly Met Tyr Leu Gln Phe Arg Arg Ile Arg Arg Met Phe
    130                 135                 140

Gly Pro Phe Arg Ser Ser Cys Glu Leu Ile Ser Pro Thr Ser Tyr Ser
145                 150                 155                 160

Leu Asn Tyr Val Thr Arg Val Ile Ser Asn Ile Leu Leu Gly Tyr Pro
                165                 170                 175

Tyr Thr Lys Leu Ala Arg Leu Leu Cys Asp Val Ser Met Arg Arg Asp
            180                 185                 190

Gly Met Ser Lys Val Phe Asn Ala Asp Pro Ile Ser Phe Leu Tyr Met
        195                 200                 205

His Lys Gly Val Thr Leu Leu Met Leu Leu Glu Val Ile Ala His Ile
    210                 215                 220

Ser Ser Gly Cys Ile Val Leu Leu Thr Leu Gly Val Ala Tyr Thr Pro
225                 230                 235                 240

Cys Ala Leu Leu Tyr Pro Thr Tyr Ile Arg Ile Leu Ala Trp Val Val
                245                 250                 255

Val Cys Thr Leu Ala Ile Val Glu Leu Ile Ser Tyr Val Arg Pro Lys
            260                 265                 270

Pro Thr Lys Asp Asn His Leu Asn His Ile Asn Thr Gly Gly Ile Arg
        275                 280                 285

Gly Ile Cys Thr Thr Cys Cys Ala Thr Val Met Ser Gly Leu Ala Ile
    290                 295                 300

Lys Cys Phe Tyr Ile Val Ile Phe Ala Ile Ala Val Val Ile Phe Met
305                 310                 315                 320

His Tyr Glu Gln Arg Val Gln Val Ser Leu Phe Gly Glu Ser Glu Asn
                325                 330                 335

Ser Gln Lys His
            340

<210> SEQ ID NO 55
<211> LENGTH: 87

<212> TYPE: PRT
<213> ORGANISM: Homo sapiens

<400> SEQUENCE: 55

Met Gly Ser Ile Thr Ala Ser Phe Ile Leu Ile Thr Met Gln Ile Leu
1 5 10 15

Phe Phe Cys Glu Asp Ser Ser Gly Glu Pro Asn Phe Ala Glu Arg Asn
20 25 30

Phe Trp His Ala Ser Cys Ser Ala Arg Gly Val Tyr Ile Asp Gly Ser
35 40 45

Met Ile Thr Thr Leu Phe Phe Tyr Ala Ser Leu Leu Gly Val Cys Val
50 55 60

Ala Leu Ile Ser Leu Ala Tyr His Ala Cys Phe Arg Leu Phe Thr Arg
65 70 75 80

Ser Val Leu Arg Ser Thr Trp
85

<210> SEQ ID NO 56
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 56

Met Asp Trp Thr Trp Ile Leu Phe Leu Val Ala Ala Ala Thr Arg Val
1 5 10 15

His Ser

<210> SEQ ID NO 57
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 57

Met Glu Thr Pro Ala Gln Leu Leu Phe Leu Leu Leu Leu Trp Leu Pro
1 5 10 15

Asp Thr Thr Gly
20

<210> SEQ ID NO 58
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 58

Ala Glu Ala Ala Asp Ala
1 5

<210> SEQ ID NO 59
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 59

Ser Glu Ser Thr Asp Thr
1 5

<210> SEQ ID NO 60
<211> LENGTH: 1885
<212> TYPE: DNA
<213> ORGANISM: Artificial Sequence
<220> FEATURE:
<223> OTHER INFORMATION: Synthetic Polynucleotide

<400> SEQUENCE: 60
gggaaataag agagaaaaga agagtaagaa gaaatataag agccaccatg ggcaccgtga 60
acaagcccgt cgtgggcgtg ctgatgggct tcggcatcat caccggcacc ctgcggatca 120
ccaatcctgt gcgggccagc gtgctgagat acgacgactt ccacatcgac gaggacaagc 180
tggacaccaa cagcgtgtac gagccctact accacagcga ccacgccgag agcagctggg 240
tcaacagagg cgagtccagc cggaaggcct acgaccacaa cagcccctac atctggcccc 300
ggaacgacta cgacggcttc ctggaaaatg cccacgagca ccacggcgtg tacaaccagg 360
gcagaggcat cgacagcggc gagagactga tgcagcccac ccagatgagc gcccaggaag 420
atctgggcga cgacaccggc atccacgtga tccctaccct gaacggcgac gaccggcaca 480
agatcgtgaa cgtggaccag cggcagtacg gcgacgtgtt caagggcgac ctgaacccca 540
agccccaggg acagcggctg attgaggtgt ccgtggaaga gaaccacccc ttcaccctga 600
gagcccctat ccagcggatc tacggcgtgc gctataccga gacttggagc ttcctgccca 660
gcctgacctg tactggcgac gccgctcctg ccatccagca catctgcctg aagcacacca 720
cctgtttcca ggacgtggtg gtggacgtgg actgcgccga gaacaccaaa gaggaccagc 780
tggccgagat cagctaccgg ttccagggca agaaagaggc cgaccagccc tggatcgtcg 840
tgaacaccag caccctgttc gacgagctgg aactggaccc tcccgagatc gaacccgggg 900
tgctgaaggt gctgcggacc gagaagcagt acctgggagt gtacatctgg aacatgcggg 960
gcagcgacgg cacctctacc tacgccacct tcctcgtgac ctggaagggc gacgagaaaa 1020
cccggaaccc tacccctgcc gtgacccctc agcctagagg cgccgagttt cacatgtgga 1080
attaccacag ccacgtgttc agcgtgggcg acaccttctc cctggccatg catctgcagt 1140
acaagatcca cgaggcccct ttcgacctgc tgctggaatg gctgtacgtg cccatcgacc 1200
ctacctgcca gcccatgcgg ctgtactcca cctgtctgta ccaccccaac gcccctcagt 1260
gcctgagcca catgaatagc ggctgcacct tcaccagccc tcacctggct cagagggtgg 1320
ccagcaccgt gtaccagaat tgcgagcacg ccgacaacta caccgcctac tgcctgggca 1380
tcagccacat ggaacccagc ttcggcctga tcctgcacga tggcggcacc accctgaagt 1440
tcgtggacac ccctgagtcc ctgagcggcc tgtacgtgtt cgtggtgtac ttcaacggcc 1500
acgtggaagc cgtggcctac accgtggtgt ccaccgtgga ccacttcgtg aacgccatcg 1560
aggaacgggg cttccctcca actgctggac agcctcctgc caccaccaag cccaaagaaa 1620
tcacccctgt gaaccccggc accagcccac tgctgcgcta tgctgcttgg acaggcggac 1680
tggctgctgt ggtgctgctg tgcctcgtga ttttcctgat ctgcaccgcc aagcggatga 1740
gagtgaaggc cgccagagtg gacaagtgat aataggctgg agcctcggtg gccatgcttc 1800
ttgccccttg ggcctccccc cagcccctcc tccccttcct gcacccgtac cccgtggtc 1860 tttgaataaa gtctgagtgg gcggc 1885

<210> SEQ ID NO 61
<211> LENGTH: 573
<212> TYPE: PRT

<213> ORGANISM: Artificial Sequence
<220> FEATURE:
<223> OTHER INFORMATION: Synthetic Polypeptide

<400> SEQUENCE: 61

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro

```
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570


<210> SEQ ID NO 62
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 62

atgggcaccg tgaacaagcc cgtcgtgggc gtgctgatgg gcttcggcat catcaccggc     60

accctgcgga tcaccaatcc tgtgcgggcc agcgtgctga gatacgacga cttccacatc    120

gacgaggaca agctggacac caacagcgtg tacgagccct actaccacag cgaccacgcc    180

gagagcagct gggtcaacag aggcgagtcc agccggaagg cctacgacca caacagcccc    240

tacatctggc cccggaacga ctacgacggc ttcctggaaa atgcccacga gcaccacggc    300

gtgtacaacc agggcagagg catcgacagc ggcgagagac tgatgcagcc cacccagatg    360

agcgcccagg aagatctggg cgacgacacc ggcatccacg tgatccctac cctgaacggc    420

gacgaccggc acaagatcgt gaacgtggac cagcggcagt acggcgacgt gttcaagggc    480

gacctgaacc ccaagcccca gggacagcgg ctgattgagg tgtccgtgga agagaaccac    540

cccttcaccc tgagagcccc tatccagcgg atctacggcg tgcgctatac cgagacttgg    600

agcttcctgc ccagcctgac ctgtactggc gacgccgctc ctgccatcca gcacatctgc    660

ctgaagcaca ccacctgttt ccaggacgtg gtggtggacg tggactgcgc cgagaacacc    720

aaagaggacc agctggccga gatcagctac cggttccagg gcaagaaaga ggccgaccag    780

ccctggatcg tcgtgaacac cagcaccctg ttcgacgagc tggaactgga ccctcccgag    840

atcgaacccg gggtgctgaa ggtgctgcgg accgagaagc agtacctggg agtgtacatc    900

tggaacatgc ggggcagcga cggcacctct acctacgcca ccttcctcgt gacctggaag    960

ggcgacgaga aaacccggaa ccctacccct gccgtgaccc ctcagcctag aggcgccgag   1020
```

```
tttcacatgt ggaattacca cagccacgtg ttcagcgtgg gcgacacctt ctccctggcc   1080
atgcatctgc agtacaagat ccacgaggcc cctttcgacc tgctgctgga atggctgtac   1140
gtgcccatcg accctacctg ccagcccatg cggctgtact ccacctgtct gtaccacccc   1200
aacgcccctc agtgcctgag ccacatgaat agcggctgca ccttcaccag ccctcacctg   1260
gctcagaggg tggccagcac cgtgtaccag aattgcgagc acgccgacaa ctacaccgcc   1320
tactgcctgg gcatcagcca catggaaccc agcttcggcc tgatcctgca cgatggcggc   1380
accaccctga agttcgtgga cacccctgag tccctgagcg gcctgtacgt gttcgtggtg   1440
tacttcaacg gccacgtgga agccgtggcc tacaccgtgg tgtccaccgt ggaccacttc   1500
gtgaacgcca tcgaggaacg gggcttccct ccaactgctg gacagcctcc tgccaccacc   1560
aagcccaaag aaatcacccc tgtgaacccc ggcaccagcc cactgctgcg ctatgctgct   1620
tggacaggcg gactggctgc tgtggtgctg ctgtgcctcg tgattttcct gatctgcacc   1680
gccaagcgga tgagagtgaa ggccgccaga gtggacaag                          1719
```

<210> SEQ ID NO 63
<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 63

```
gggaaataag agagaaaaga agagtaagaa gaaatataag agccaccatg ggcaccgtga     60
acaagcccgt cgtgggcgtg ctgatgggct tcggcatcat caccggcacc ctgcggatca    120
ccaatcctgt gcgggccagc gtgctgagat acgacgactt ccacatcgac gaggacaagc    180
tggacaccaa cagcgtgtac gagccctact accacagcga ccacgccgag agcagctggg    240
tcaacagagg cgagtccagc cggaaggcct acgaccacaa cagcccctac atctggcccc    300
ggaacgacta cgacggcttc ctggaaaatg cccacgagca ccacggcgtg tacaaccagg    360
gcagaggcat cgacagcggc gagagactga tgcagcccac ccagatgagc gcccaggaag    420
atctgggcga cgacaccggc atccacgtga tccctaccct gaacggcgac gaccggcaca    480
agatcgtgaa cgtggaccag cggcagtacg gcgacgtgtt caagggcgac ctgaacccca    540
agccccaggg acagcggctg attgaggtgt ccgtggaaga gaaccacccc ttcaccctga    600
gagcccctat ccagcggatc tacggcgtgc gctataccga gacttggagc ttcctgccca    660
gcctgacctg tactggcgac gccgctcctg ccatccagca catctgcctg aagcacacca    720
cctgtttcca ggacgtggtg gtggacgtgg actgcgccga gaacaccaaa gaggaccagc    780
tggccgagat cagctaccgg ttccagggca agaaagaggc cgaccagccc tggatcgtcg    840
tgaacaccag caccctgttc gacgagctgg aactggaccc tcccgagatc gaacccgggg    900
tgctgaaggt gctgcggacc gagaagcagt acctgggagt gtacatctgg aacatgcggg    960
gcagcgacgg cacctctacc tacgccacct tcctcgtgac ctggaagggc gacgagaaaa   1020
cccggaaccc taccccctgcc gtgacccctc agcctagagg cgccgagttt cacatgtgga   1080
attaccacag ccacgtgttc agcgtgggcg acaccttctc cctggccatg catctgcagt   1140
acaagatcca cgaggcccct ttcgacctgc tgctggaatg gctgtacgtg cccatcgacc   1200
ctacctgcca gcccatgcgg ctgtactcca cctgtctgta ccaccccaac gcccctcagt   1260
gcctgagcca catgaatagc ggctgcacct tcaccagccc tcacctggct cagagggtgg   1320
ccagcaccgt gtaccagaat tgcgagcacg ccgacaacta caccgcctac tgcctgggca   1380
```

```
tcagccacat ggaacccagc ttcggcctga tcctgcacga tggcggcacc accctgaagt   1440

tcgtggacac ccctgagtcc ctgagcggcc tgtacgtgtt cgtggtgtac ttcaacggcc   1500

acgtggaagc cgtggcctac accgtggtgt ccaccgtgga ccacttcgtg aacgccatcg   1560

aggaacgggg cttccctcca actgctggac agcctcctgc caccaccaag cccaaagaaa   1620

tcacccctgt gaaccccggc accagcccac tgctgcgcta tgctgcttgg acaggcggac   1680

tggctgctgt ggtgctgctg tgcctcgtga ttttcctgat ctgcaccgcc aagcggatga   1740

gagtgaaggc cgccagagtg gacaagtgat aataggctgg agcctcggtg gccatgcttc   1800

ttgccccttg ggcctccccc cagcccctcc tccccttcct gcacccgtac cccgtggtc   1860

tttgaataaa gtctgagtgg gcggcaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaatctag                                                          1990


<210> SEQ ID NO 64
<211> LENGTH: 1885
<212> TYPE: DNA
<213> ORGANISM: Artificial Sequence
<220> FEATURE:
<223> OTHER INFORMATION: Synthetic Polynucleotide

<400> SEQUENCE: 64

gggaaataag agagaaaaga agagtaagaa gaaatataag agccaccatg ggacagttta     60

ataaacctgt ggtgggggta ttgatggggt tcggaattat cacgggaacg ttgcgtataa    120

cgaatccggt cagagcatcc gtcttgcgat acgatgattt tcacatcgat gaagacaaac    180

tggatacaaa ctccgtatat gagccttact accattcaga tcatgcggag tcttcatggg    240

taaatcgggg agagtcttcg cgaaaagcgt acgatcataa ctcaccttat atatggccac    300

gtaatgatta tgatggattt ttagagaacg cacacgaaca ccatggggtg tataatcagg    360

gccgtggtat cgatagcggg gaacggttaa tgcaacccac acaaatgtct gcacaggagg    420

atcttgggga cgatacgggc atccacgtta tccctacgtt aaacggcgat gacagacata    480

aaattgtaaa tgtggaccaa cgtcaatacg gtgacgtgtt taaaggagat cttaatccaa    540

aaccccaagg ccaaagactc attgaggtgt cagtggaaga aaatcacccg tttactttac    600

gcgcaccgat tcagcggatt tatggagtcc ggtacaccga gacttggagc tttttgccgt    660

cattaacctg tacgggagac gcagcgcccg ccatccagca tatatgttta aaacatacaa    720

catgctttca agacgtggtg gtggatgtgg attgcgcgga aaatactaaa gaggatcagt    780

tggccgaaat cagttaccgt tttcaaggta agaaggaagc ggaccaaccg tggattgttg    840

taaacacgag cacactgttt gatgaactcg aattagaccc ccccgagatt gaaccgggtg    900

tcttgaaagt acttcggaca gagaaacaat acttgggtgt gtacatttgg aacatgcgcg    960

gctccgatgg tacgtctacc tacgccacgt tttggtcac ctggaaaggg gatgagaaga   1020

caagaaaccc tacgcccgca gtaactcctc aaccaagagg ggctgagttt catatgtgga   1080

attaccactc gcatgtattt tcagttggtg atacgtttag cttggcaatg catcttcagt   1140

ataagataca tgaagcgcca tttgatttgc tgttagagtg gttgtatgtc cccatcgatc   1200

ctacatgtca accaatgcgg ttatattcta cgtgtttgta tcatcccaac gcaccccaat   1260

gcctctctca tatgaattcc ggttgtacat ttacctcgcc acatttagcc cagcgtgttg   1320

caagcacagt gtatcaaaat tgtgaacatg cagataacta caccgcatat tgtctgggaa   1380
```

tatctcatat ggagcctagc tttggtctaa tcttacacga cgggggcacc acgttaaagt 1440
ttgtagatac acccgagagt ttgtcgggat tatacgtttt tgtggtgtat tttaacgggc 1500
atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttacccccgt aaaccccgga acgtcaccac ttctacgata tgccgcatgg accggagggc 1680
ttgcagcagt agtactttta tgtctcgtaa tatttttaat ctgtacggct aaacgaatga 1740
gggttaaagc cgccagggta gacaagtgat aataggctgg agcctcggtg gccatgcttc 1800
ttgccccttg ggcctccccc cagcccctcc tccccttcct gcacccgtac ccccgtggtc 1860
tttgaataaa gtctgagtgg gcggc 1885

<210> SEQ ID NO 65
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 65

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Ile Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Ile His Val Ile Pro Thr Leu Asn Gly Asp Asp Arg His
130 135 140

Lys Ile Val Asn Val Asp Gln Arg Gln Tyr Gly Asp Val Phe Lys Gly
145 150 155 160

Asp Leu Asn Pro Lys Pro Gln Gly Gln Arg Leu Ile Glu Val Ser Val
165 170 175

Glu Glu Asn His Pro Phe Thr Leu Arg Ala Pro Ile Gln Arg Ile Tyr
180 185 190

Gly Val Arg Tyr Thr Glu Thr Trp Ser Phe Leu Pro Ser Leu Thr Cys
195 200 205

Thr Gly Asp Ala Ala Pro Ala Ile Gln His Ile Cys Leu Lys His Thr
210 215 220

Thr Cys Phe Gln Asp Val Val Val Asp Val Asp Cys Ala Glu Asn Thr
225 230 235 240

Lys Glu Asp Gln Leu Ala Glu Ile Ser Tyr Arg Phe Gln Gly Lys Lys
245 250 255

Glu Ala Asp Gln Pro Trp Ile Val Val Asn Thr Ser Thr Leu Phe Asp
260 265 270

```
Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 66
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 66

```
atggggacag ttaataaacc tgtggtgggg gtattgatgg ggttcggaat tatcacggga     60

acgttgcgta taacgaatcc ggtcagagca tccgtcttgc gatacgatga ttttcacatc    120

gatgaagaca aactggatac aaactccgta tatgagcctt actaccattc agatcatgcg    180

gagtcttcat gggtaaatcg gggagagtct tcgcgaaaag cgtacgatca taactcacct    240

tatatatggc cacgtaatga ttatgatgga tttttagaga acgcacacga acaccatggg    300

gtgtataatc agggccgtgg tatcgatagc ggggaacggt taatgcaacc cacacaaatg    360
```

-continued

```
tctgcacagg aggatcttgg ggacgatacg ggcatccacg ttatccctac gttaaacggc    420

gatgacagac ataaaattgt aaatgtggac caacgtcaat acggtgacgt gtttaaagga    480

gatcttaatc caaaacccca aggccaaaga ctcattgagg tgtcagtgga agaaaatcac    540

ccgtttactt tacgcgcacc gattcagcgg atttatggag tccggtacac cgagacttgg    600

agctttttgc cgtcattaac ctgtacggga gacgcagcgc ccgccatcca gcatatatgt    660

ttaaaacata caacatgctt tcaagacgtg gtggtggatg tggattgcgc ggaaaatact    720

aaagaggatc agttggccga aatcagttac cgttttcaag gtaagaagga agcggaccaa    780

ccgtggattg ttgtaaacac gagcacactg tttgatgaac tcgaattaga cccccccgag    840

attgaaccgg gtgtcttgaa agtacttcgg acagagaaac aatacttggg tgtgtacatt    900

tggaacatgc gcggctccga tggtacgtct acctacgcca cgtttttggt cacctggaaa    960

ggggatgaga agacaagaaa ccctacgccc gcagtaactc ctcaaccaag aggggctgag   1020

tttcatatgt ggaattacca ctcgcatgta ttttcagttg gtgatacgtt tagcttggca   1080

atgcatcttc agtataagat acatgaagcg ccatttgatt tgctgttaga gtggttgtat   1140

gtccccatcg atcctacatg tcaaccaatg cggttatatt ctacgtgttt gtatcatccc   1200

aacgcacccc aatgcctctc tcatatgaat tccggttgta catttacctc gccacattta   1260

gcccagcgtg ttgcaagcac agtgtatcaa aattgtgaac atgcagataa ctacaccgca   1320

tattgtctgg gaatatctca tatggagcct agctttggtc taatcttaca cgacgggggc   1380

accacgttaa agtttgtaga tacacccgag agtttgtcgg gattatacgt tttgtggtg    1440

tattttaacg ggcatgttga agccgtagca tacactgttg tatccacagt agatcatttt   1500

gtaaacgcaa ttgaagagcg tggatttccg ccaacggccg gtcagccacc ggcgactact   1560

aaacccaagg aaattacccc cgtaaacccc ggaacgtcac cacttctacg atatgccgca   1620

tggaccggag ggcttgcagc agtagtactt ttatgtctcg taatattttt aatctgtacg   1680

gctaaacgaa tgagggttaa agccgccagg gtagacaag                          1719
```

<210> SEQ ID NO 67
<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 67

```
gggaaataag agagaaaaga agagtaagaa gaaatataag agccaccatg ggacagtta     60

ataaacctgt ggtgggggta ttgatggggt tcggaattat cacgggaacg ttgcgtataa    120

cgaatccggt cagagcatcc gtcttgcgat acgatgattt tcacatcgat gaagacaaac    180

tggatacaaa ctccgtatat gagccttact accattcaga tcatgcggag tcttcatggg    240

taaatcgggg agagtcttcg cgaaaagcgt acgatcataa ctcaccttat atatggccac    300

gtaatgatta tgatggattt ttagagaacg cacacgaaca ccatggggtg tataatcagg    360

gccgtggtat cgatagcggg gaacggttaa tgcaacccac acaaatgtct gcacaggagg    420

atcttgggga cgatacgggc atccacgtta tccctacgtt aaacggcgat gacagacata    480

aaattgtaaa tgtggaccaa cgtcaatacg gtgacgtgtt taaaggagat cttaatccaa    540

aaccccaagg ccaaagactc attgaggtgt cagtggaaga aaatcacccg tttactttac    600

gcgcaccgat tcagcggatt tatggagtcc ggtacaccga gacttggagc tttttgccgt    660

cattaacctg tacgggagac gcagcgcccg ccatccagca tatatgttta aaacatacaa    720
```

catgctttca agacgtggtg gtggatgtgg attgcgcgga aaatactaaa gaggatcagt 780
tggccgaaat cagttaccgt tttcaaggta agaaggaagc ggaccaaccg tggattgttg 840
taaacacgag cacactgttt gatgaactcg aattagaccc ccccgagatt gaaccgggtg 900
tcttgaaagt acttcggaca gagaaacaat acttgggtgt gtacatttgg aacatgcgcg 960
gctccgatgg tacgtctacc tacgccacgt ttttggtcac ctggaaaggg gatgagaaga 1020
caagaaaccc tacgcccgca gtaactcctc aaccaagagg ggctgagttt catatgtgga 1080
attaccactc gcatgtattt tcagttggtg atacgtttag cttggcaatg catcttcagt 1140
ataagataca tgaagcgcca tttgatttgc tgttagagtg gttgtatgtc cccatcgatc 1200
ctacatgtca accaatgcgg ttatattcta cgtgtttgta tcatcccaac gcaccccaat 1260
gcctctctca tatgaattcc ggttgtacat ttacctcgcc acatttagcc cagcgtgttg 1320
caagcacagt gtatcaaaat tgtgaacatg cagataacta caccgcatat tgtctgggaa 1380
tatctcatat ggagcctagc tttggtctaa tcttacacga cgggggcacc acgttaaagt 1440
ttgtagatac acccgagagt ttgtcgggat tatacgtttt tgtggtgtat tttaacgggc 1500
atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttacccccgt aaaccccgga acgtcaccac ttctacgata tgccgcatgg accggagggc 1680
ttgcagcagt agtactttta tgtctcgtaa tatttttaat ctgtacggct aaacgaatga 1740
gggttaaagc cgccagggta gacaagtgat aataggctgg agcctcggtg gccatgcttc 1800
ttgccccttg ggcctccccc cagcccctcc tccccttcct gcacccgtac ccccgtggtc 1860
tttgaataaa gtctgagtgg gcggcaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaatctag 1990

<210> SEQ ID NO 68
<211> LENGTH: 1885
<212> TYPE: DNA
<213> ORGANISM: Artificial Sequence
<220> FEATURE:
<223> OTHER INFORMATION: Synthetic Polynucleotide

<400> SEQUENCE: 68
gggaaataag agagaaaaga agagtaagaa gaaatataag agccaccatg gggacagtta 60
ataaacctgt ggtggggggta ttgatggggt tcggaattat cacgggaacg ttgcgtataa 120
cgaatccggt cagagcatcc gtcttgcgat acgatgattt tcacatcgat gaagacaaac 180
tggatacaaa ctccgtatat gagccttact accattcaga tcatgcggag tcttcatggg 240
taaatcgggg agagtcttcg cgaaaagcgt acgatcataa ctcaccttat atatggccac 300
gtaatgatta tgatggattt ttagagaacg cacacgaaca ccatggggtg tataatcagg 360
gccgtggtat cgatagcggg gaacggttaa tgcaacccac acaaatgtct gcacaggagg 420
atcttgggga cgatacgggc atccacgtta tccctacgtt aaacggcgat gacagacata 480
aaattgtaaa tgtggaccaa cgtcaatacg gtgacgtgtt taaaggagat cttaatccaa 540
aaccccaagg ccaaagactc attgaggtgt cagtggaaga aaatcacccg tttactttac 600
gcgcaccgat tcagcggatt tatggagtcc ggtacaccga gacttggagc tttttgccgt 660
cattaacctg tacgggagac gcagcgcccg ccatccagca tatatgttta aaacatacaa 720

```
catgctttca agacgtggtg gtggatgtgg attgcgcgga aaatactaaa gaggatcagt    780

tggccgaaat cagttaccgt tttcaaggta agaaggaagc ggaccaaccg tggattgttg    840

taaacacgag cacactgttt gatgaactcg aattagaccc acccgagatt gaaccgggtg    900

tcttgaaagt acttcggaca gagaaacaat acttgggtgt gtacatttgg aacatgcgcg    960

gctccgatgg tacgtctacc tacgccacgt ttttggtcac ctggaaaggg gatgagaaga   1020

caagaaaccc tacgcccgca gtaactcctc aaccaagagg ggctgagttt catatgtgga   1080

attaccactc gcatgtattt tcagttggtg atacgtttag cttggcaatg catcttcagt   1140

ataagataca tgaagcgcca tttgatttgc tgttagagtg gttgtatgtc cccatcgatc   1200

ctacatgtca accaatgcgg ttatattcta cgtgtttgta tcatcccaac gcaccccaat   1260

gcctctctca tatgaattcc ggttgtacat ttacctcgcc acatttagcc cagcgtgttg   1320

caagcacagt gtatcaaaat tgtgaacatg cagataacta caccgcatat tgtctgggaa   1380

tatctcatat ggagcctagc tttggtctaa tcttacacga cgggggcacc acgttaaagt   1440

ttgtagatac acccgagagt ttgtcgggat tatacgtttt tgtggtgtat tttaacgggc   1500

atgttgaagc cgtagcatac actgttgtat ccacagtaga tcattttgta aacgcaattg   1560

aagagcgtgg atttccgcca acggccggtc agccaccggc gactactaaa cccaaggaaa   1620

ttacccccgt aaaccccgga acgtcaccac ttctacgata tgccgcatgg accggagggc   1680

ttgcagcagt agtactttta tgtctcgtaa tatttttaat ctgtacggct aaacgaatga   1740

gggttaaagc cgccagggta gacaagtgat aataggctgg agcctcggtg gccatgcttc   1800

ttgccccttg ggcctccccc cagcccctcc tccccttcct gcacccgtac ccccgtggtc   1860

tttgaataaa gtctgagtgg gcggc                                         1885
```

<210> SEQ ID NO 69
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 69

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160
```

```
Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 70
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 70
atggggacag ttaataaacc tgtggtgggg gtattgatgg ggttcggaat tatcacggga 60
acgttgcgta taacgaatcc ggtcagagca tccgtcttgc gatacgatga ttttcacatc 120
gatgaagaca aactggatac aaactccgta tatgagcctt actaccattc agatcatgcg 180
gagtcttcat gggtaaatcg gggagagtct tcgcgaaaag cgtacgatca taactcacct 240
tatatatggc cacgtaatga ttatgatgga tttttagaga acgcacacga acaccatggg 300
gtgtataatc agggccgtgg tatcgatagc ggggaacggt taatgcaacc cacacaaatg 360
tctgcacagg aggatcttgg ggacgatacg ggcatccacg ttatccctac gttaaacggc 420
gatgacagac ataaaattgt aaatgtggac caacgtcaat acggtgacgt gtttaaagga 480
gatcttaatc caaaacccca aggccaaaga ctcattgagg tgtcagtgga agaaaatcac 540
ccgtttactt tacgcgcacc gattcagcgg atttatggag tccggtacac cgagacttgg 600
agctttttgc cgtcattaac ctgtacggga gacgcagcgc ccgccatcca gcatatatgt 660
ttaaaacata caacatgctt tcaagacgtg gtggtggatg tggattgcgc ggaaaatact 720
aaagaggatc agttggccga aatcagttac cgttttcaag gtaagaagga agcggaccaa 780
ccgtggattg ttgtaaacac gagcacactg tttgatgaac tcgaattaga cccacccgag 840
attgaaccgg gtgtcttgaa agtacttcgg acagagaaac aatacttggg tgtgtacatt 900
tggaacatgc gcggctccga tggtacgtct acctacgcca cgtttttggt cacctggaaa 960
ggggatgaga agacaagaaa ccctacgccc gcagtaactc ctcaaccaag aggggctgag 1020
tttcatatgt ggaattacca ctcgcatgta ttttcagttg gtgatacgtt tagcttggca 1080
atgcatcttc agtataagat acatgaagcg ccatttgatt tgctgttaga gtggttgtat 1140
gtccccatcg atcctacatg tcaaccaatg cggttatatt ctacgtgttt gtatcatccc 1200
aacgcacccc aatgcctctc tcatatgaat tccggttgta catttacctc gccacattta 1260
gcccagcgtg ttgcaagcac agtgtatcaa aattgtgaac atgcagataa ctacaccgca 1320
tattgtctgg gaatatctca tatggagcct agctttggtc taatcttaca cgacgggggc 1380
accacgttaa agtttgtaga tacacccgag agtttgtcgg gattatacgt tttgtggtg 1440 tattttaacg ggcatgttga agccgtagca tacactgttg tatccacagt agatcatttt 1500
gtaaacgcaa ttgaagagcg tggatttccg ccaacggccg gtcagccacc ggcgactact 1560
aaacccaagg aaattacccc cgtaaacccc ggaacgtcac cacttctacg atatgccgca 1620
tggaccggag ggcttgcagc agtagtactt ttatgtctcg taatattttt aatctgtacg 1680
gctaaacgaa tgagggttaa agccgccagg gtagacaag 1719

<210> SEQ ID NO 71
<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 71
gggaaataag agagaaaaga agagtaagaa gaaatataag agccaccatg gggacagtta 60

```
ataaacctgt ggtgggggta ttgatggggt tcggaattat cacgggaacg ttgcgtataa    120
cgaatccggt cagagcatcc gtcttgcgat acgatgattt tcacatcgat gaagacaaac    180
tggatacaaa ctccgtatat gagccttact accattcaga tcatgcggag tcttcatggg    240
taaatcgggg agagtcttcg cgaaaagcgt acgatcataa ctcaccttat atatggccac    300
gtaatgatta tgatggattt ttagagaacg cacacgaaca ccatggggtg tataatcagg    360
gccgtggtat cgatagcggg gaacggttaa tgcaacccac acaaatgtct gcacaggagg    420
atcttgggga cgatacgggc atccacgtta tccctacgtt aaacggcgat gacagacata    480
aaattgtaaa tgtggaccaa cgtcaatacg gtgacgtgtt taaaggagat cttaatccaa    540
aaccccaagg ccaaagactc attgaggtgt cagtggaaga aaatcacccg tttactttac    600
gcgcaccgat tcagcggatt tatggagtcc ggtacaccga gacttggagc tttttgccgt    660
cattaacctg tacgggagac gcagcgcccg ccatccagca tatatgttta aaacatacaa    720
catgctttca agacgtggtg gtggatgtgg attgcgcgga aaatactaaa gaggatcagt    780
tggccgaaat cagttaccgt tttcaaggta agaaggaagc ggaccaaccg tggattgttg    840
taaacacgag cacactgttt gatgaactcg aattagaccc acccgagatt gaaccgggtg    900
tcttgaaagt acttcggaca gagaaacaat acttgggtgt gtacatttgg aacatgcgcg    960
gctccgatgg tacgtctacc tacgccacgt tttggtcac ctggaaaggg gatgagaaga    1020
caagaaaccc tacgcccgca gtaactcctc aaccaagagg ggctgagttt catatgtgga    1080
attaccactc gcatgtattt tcagttggtg atacgtttag cttggcaatg catcttcagt    1140
ataagataca tgaagcgcca tttgatttgc tgttagagtg gttgtatgtc cccatcgatc    1200
ctacatgtca accaatgcgg ttatattcta cgtgtttgta tcatcccaac gcaccccaat    1260
gcctctctca tatgaattcc ggttgtacat ttacctcgcc acatttagcc cagcgtgttg    1320
caagcacagt gtatcaaaat tgtgaacatg cagataacta caccgcatat tgtctgggaa    1380
tatctcatat ggagcctagc tttggtctaa tcttacacga cgggggcacc acgttaaagt    1440
ttgtagatac acccgagagt ttgtcgggat tatacgtttt tgtggtgtat tttaacgggc    1500
atgttgaagc cgtagcatac actgttgtat ccacagtaga tcattttgta aacgcaattg    1560
aagagcgtgg atttccgcca acggccggtc agccaccggc gactactaaa cccaaggaaa    1620
ttacccccgt aaaccccgga acgtcaccac ttctacgata tgccgcatgg accggagggc    1680
ttgcagcagt agtactttta tgtctcgtaa tatttttaat ctgtacggct aaacgaatga    1740
gggttaaagc cgccagggta gacaagtgat aataggctgg agcctcggtg gccatgcttc    1800
ttgccccttg ggcctccccc cagcccctcc tccccttcct gcacccgtac ccccgtggtc    1860
tttgaataaa gtctgagtgg gcggcaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaatctag                                                           1990
```

<210> SEQ ID NO 72
<211> LENGTH: 1885
<212> TYPE: DNA
<213> ORGANISM: Artificial Sequence
<220> FEATURE:
<223> OTHER INFORMATION: Synthetic Polynucleotide

<400> SEQUENCE: 72

```
gggaaataag agagaaaaga agagtaagaa gaaatataag agccaccatg gggacagtta     60
```

```
ataaacctgt ggtgggggta ttgatggggt tcggaattat cacgggaacg ttgcgtataa    120

cgaatccggt cagagcatcc gtcttgcgat acgatgattt tcacatcgat gaagacaaac    180

tggatacaaa ctccgtatat gagccttact accattcaga tcatgcggag tcttcatggg    240

taaatcgggg agagtcttcg cgaaaggcgt acgatcataa ctcaccttat atatggccac    300

gtaatgatta tgatggattt ttagagaacg cacacgaaca ccatggggtg tataatcagg    360

gccgtggtat cgatagcggg gaacggttaa tgcaacccac acaaatgtct gcacaggagg    420

atcttgggga cgatacgggc atccacgtta tccctacgtt aaacggcgat gacagacata    480

agattgtaaa tgtggaccaa cgtcaatacg gtgacgtgtt taaaggagat cttaatccaa    540

agccccaagg ccaaagactc attgaggtgt cagtggaaga gaatcacccg tttactttac    600

gcgcaccgat tcagcggatt tatggagtcc ggtacaccga gacttggagc tttttgccgt    660

cattaacctg tacgggagac gcagcgcccg ccatccagca tatatgttta aagcatacaa    720

catgctttca agacgtggtg gtggatgtgg attgcgcgga gaatactaaa gaggatcagt    780

tggccgaaat cagttaccgt tttcaaggta agaaggaagc ggaccaaccg tggattgttg    840

taaacacgag cacactgttt gatgaactcg aattagaccc ccccgagatt gaaccgggtg    900

tcttgaaagt acttcggaca gagaaacaat acttgggtgt gtacatttgg aacatgcgcg    960

gctccgatgg tacgtctacc tacgccacgt tttggtcac ctggaaaggg gatgagaaga    1020

caagaaaccc tacgcccgca gtaactcctc aaccaagagg ggctgagttt catatgtgga    1080

attaccactc gcatgtattt tcagttggtg atacgtttag cttggcaatg catcttcagt    1140

ataagataca tgaagcgcca tttgatttgc tgttagagtg gttgtatgtc cccatcgatc    1200

ctacatgtca accaatgcgg ttatattcta cgtgtttgta tcatcccaac gcaccccaat    1260

gcctctctca tatgaattcc ggttgtacat ttacctcgcc acatttagcc cagcgtgttg    1320

caagcacagt gtatcagaat tgtgaacatg cagataacta caccgcatat tgtctgggaa    1380

tatctcatat ggagcctagc tttggtctaa tcttacacga cgggggcacc acgttaaagt    1440

ttgtagatac acccgagagt ttgtcgggat tatacgtttt tgtggtgtat tttaacgggc    1500

atgttgaagc cgtagcatac actgttgtat ccacagtaga tcattttgta aacgcaattg    1560

aagagcgtgg atttccgcca acggccggtc agccaccggc gactactaaa cccaaggaaa    1620

ttacccccgt aaaccccgga acgtcaccac ttctacgata tgccgcatgg accggagggc    1680

ttgcagcagt agtactttta tgtctcgtaa tatttttaat ctgtacggct aaacgaatga    1740

gggttaaagc cgccagggta gacaagtgat aataggctgg agcctcggtg gccatgcttc    1800

ttgccccttg ggcctccccc cagcccctcc tccccttcct gcacccgtac ccccgtggtc    1860

tttgaataaa gtctgagtgg gcggc                                          1885
```

<210> SEQ ID NO 73
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 73

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
```

```
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460
```

```
Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 74
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 74

```
atggggacag ttaataaacc tgtggtgggg gtattgatgg ggttcggaat tatcacggga     60

acgttgcgta taacgaatcc ggtcagagca tccgtcttgc gatacgatga ttttcacatc    120

gatgaagaca aactggatac aaactccgta tatgagcctt actaccattc agatcatgcg    180

gagtcttcat gggtaaatcg gggagagtct tcgcgaaagg cgtacgatca taactcacct    240

tatatatggc cacgtaatga ttatgatgga tttttagaga acgcacacga acaccatggg    300

gtgtataatc agggccgtgg tatcgatagc ggggaacggt taatgcaacc cacacaaatg    360

tctgcacagg aggatcttgg ggacgatacg ggcatccacg ttatccctac gttaaacggc    420

gatgacagac ataagattgt aaatgtggac caacgtcaat acggtgacgt gtttaaagga    480

gatcttaatc caaagcccca aggccaaaga ctcattgagg tgtcagtgga agagaatcac    540

ccgtttactt tacgcgcacc gattcagcgg atttatggag tccggtacac cgagacttgg    600

agctttttgc cgtcattaac ctgtacggga gacgcagcgc ccgccatcca gcatatatgt    660

ttaaagcata caacatgctt tcaagacgtg gtggtggatg tggattgcgc ggagaatact    720

aaagaggatc agttggccga aatcagttac cgttttcaag gtaagaagga agcggaccaa    780

ccgtggattg ttgtaaacac gagcacactg tttgatgaac tcgaattaga cccccccgag    840

attgaaccgg gtgtcttgaa agtacttcgg acagagaaac aatacttggg tgtgtacatt    900

tggaacatgc gcggctccga tggtacgtct acctacgcca cgtttttggt cacctggaaa    960

ggggatgaga agacaagaaa ccctacgccc gcagtaactc ctcaaccaag aggggctgag   1020

tttcatatgt ggaattacca ctcgcatgta ttttcagttg gtgatacgtt tagcttggca   1080

atgcatcttc agtataagat acatgaagcg ccatttgatt tgctgttaga gtggttgtat   1140

gtccccatcg atcctacatg tcaaccaatg cggttatatt ctacgtgttt gtatcatccc   1200

aacgcacccc aatgcctctc tcatatgaat tccggttgta catttacctc gccacattta   1260

gcccagcgtg ttgcaagcac agtgtatcag aattgtgaac atgcagataa ctacaccgca   1320

tattgtctgg gaatatctca tatggagcct agctttggtc taatcttaca cgacgggggc   1380

accacgttaa agtttgtaga tacacccgag agtttgtcgg gattatacgt tttgtggtg    1440
```

tattttaacg ggcatgttga agccgtagca tacactgttg tatccacagt agatcatttt 1500
gtaaacgcaa ttgaagagcg tggatttccg ccaacggccg gtcagccacc ggcgactact 1560
aaacccaagg aaattacccc cgtaaacccc ggaacgtcac cacttctacg atatgccgca 1620
tggaccggag ggcttgcagc agtagtactt ttatgtctcg taatattttt aatctgtacg 1680
gctaaacgaa tgagggttaa agccgccagg gtagacaag 1719

<210> SEQ ID NO 75
<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 75
gggaaataag agagaaaaga agagtaagaa gaaatataag agccaccatg gggacagtta 60
ataaacctgt ggtgggggta ttgatggggt tcggaattat cacgggaacg ttgcgtataa 120
cgaatccggt cagagcatcc gtcttgcgat acgatgattt tcacatcgat gaagacaaac 180
tggatacaaa ctccgtatat gagccttact accattcaga tcatgcggag tcttcatggg 240
taaatcgggg agagtcttcg cgaaaggcgt acgatcataa ctcaccttat atatggccac 300
gtaatgatta tgatggattt ttagagaacg cacacgaaca ccatggggtg tataatcagg 360
gccgtggtat cgatagcggg gaacggttaa tgcaacccac acaaatgtct gcacaggagg 420
atcttgggga cgatacgggc atccacgtta tccctacgtt aaacggcgat gacagacata 480
agattgtaaa tgtggaccaa cgtcaatacg gtgacgtgtt taaaggagat cttaatccaa 540
agccccaagg ccaaagactc attgaggtgt cagtggaaga gaatcacccg tttactttac 600
gcgcaccgat tcagcggatt tatggagtcc ggtacaccga gacttggagc tttttgccgt 660
cattaacctg tacgggagac gcagcgcccg ccatccagca tatatgttta aagcatacaa 720
catgctttca agacgtggtg gtggatgtgg attgcgcgga gaatactaaa gaggatcagt 780
tggccgaaat cagttaccgt tttcaaggta agaaggaagc ggaccaaccg tggattgttg 840
taaacacgag cacactgttt gatgaactcg aattagaccc ccccgagatt gaaccgggtg 900
tcttgaaagt acttcggaca gagaaacaat acttgggtgt gtacatttgg aacatgcgcg 960
gctccgatgg tacgtctacc tacgccacgt ttttggtcac ctggaaaggg gatgagaaga 1020
caagaaaccc tacgcccgca gtaactcctc aaccaagagg ggctgagttt catatgtgga 1080
attaccactc gcatgtattt tcagttggtg atacgtttag cttggcaatg catcttcagt 1140
ataagataca tgaagcgcca tttgatttgc tgttagagtg gttgtatgtc cccatcgatc 1200
ctacatgtca accaatgcgg ttatattcta cgtgtttgta tcatcccaac gcaccccaat 1260
gcctctctca tatgaattcc ggttgtacat ttacctcgcc acatttagcc cagcgtgttg 1320
caagcacagt gtatcagaat tgtgaacatg cagataacta caccgcatat tgtctgggaa 1380
tatctcatat ggagcctagc tttggtctaa tcttacacga cgggggcacc acgttaaagt 1440
ttgtagatac acccgagagt ttgtcgggat tatacgtttt tgtggtgtat tttaacgggc 1500
atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttacccccgt aaaccccgga acgtcaccac ttctacgata tgccgcatgg accggagggc 1680
ttgcagcagt agtactttta tgtctcgtaa tatttttaat ctgtacggct aaacgaatga 1740

```
gggttaaagc cgccagggta gacaagtgat aataggctgg agcctcggtg gccatgcttc   1800

ttgccccttg ggcctccccc cagcccctcc tccccttcct gcacccgtac ccccgtggtc   1860

tttgaataaa gtctgagtgg gcggcaaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaatctag                                                          1990
```

<210> SEQ ID NO 76
<211> LENGTH: 1885
<212> TYPE: DNA
<213> ORGANISM: Artificial Sequence
<220> FEATURE:
<223> OTHER INFORMATION: Synthetic Polynucleotide

<400> SEQUENCE: 76

```
gggaaataag agagaaaaga agagtaagaa gaaatataag agccaccatg ggacagttta     60

ataaacctgt ggtgggggta ttgatggggt tcggaattat cacgggaacg ttgcgtataa    120

cgaatccggt cagagcatcc gtcttgcgat acgatgattt tcacatcgat gaagacaaac    180

tggatacaaa ctccgtatat gagccttact accattcaga tcatgcggag tcttcatggg    240

taaatcgggg agagtcttcg cgaaaggcgt acgatcataa ctcaccttat atatggccac    300

gtaatgatta tgatggattt ttagagaacg cacacgaaca ccatggggtg tataatcagg    360

gccgtggtat cgatagcggg gaacggttaa tgcaacccac acaaatgtct gcacaggagg    420

atcttgggga cgatacgggc atccacgtta tccctacgtt aaacggcgat gacagacata    480

agattgtaaa tgtggaccaa cgtcaatacg gtgacgtgtt taaaggagat cttaatccaa    540

agccccaagg ccaaagactc attgaggtgt cagtggaaga gaatcacccg tttactttac    600

gcgcaccgat tcagcggatt tatggagtcc ggtacaccga gacttggagc tttttgccgt    660

cattaacctg tacgggagac gcagcgcccg ccatccagca tatatgttta aagcatacaa    720

catgctttca agacgtggtg gtggatgtgg attgcgcgga gaatactaaa gaggatcagt    780

tggccgaaat cagttaccgt tttcaaggta agaaggaagc ggaccaaccg tggattgttg    840

taaacacgag cacactgttt gatgaactcg aattagaccc acccgagatt gaaccgggtg    900

tcttgaaagt acttcggaca gagaaacaat acttgggtgt gtacatttgg aacatgcgcg    960

gctccgatgg tacgtctacc tacgccacgt ttttggtcac ctggaaaggg gatgagaaga   1020

caagaaaccc tacgcccgca gtaactcctc aaccaagagg ggctgagttt catatgtgga   1080

attaccactc gcatgtattt tcagttggtg atacgtttag cttggcaatg catcttcagt   1140

ataagataca tgaagcgcca tttgatttgc tgttagagtg gttgtatgtc cccatcgatc   1200

ctacatgtca accaatgcgg ttatattcta cgtgtttgta tcatcccaac gcaccccaat   1260

gcctctctca tatgaattcc ggttgtacat ttacctcgcc acatttagcc cagcgtgttg   1320

caagcacagt gtatcagaat tgtgaacatg cagataacta caccgcatat tgtctgggaa   1380

tatctcatat ggagcctagc tttggtctaa tcttacacga cgggggcacc acgttaaagt   1440

ttgtagatac acccgagagt ttgtcgggat tatacgtttt tgtggtgtat tttaacgggc   1500

atgttgaagc cgtagcatac actgttgtat ccacagtaga tcattttgta aacgcaattg   1560

aagagcgtgg atttccgcca acggccggtc agccaccggc gactactaaa cccaaggaaa   1620

ttacccccgt aaaccccgga acgtcaccac ttctacgata tgccgcatgg accggagggc   1680

ttgcagcagt agtactttta tgtctcgtaa tatttttaat ctgtacggct aaacgaatga   1740

gggttaaagc cgccagggta gacaagtgat aataggctgg agcctcggtg gccatgcttc   1800
```

ttgccccttg ggcctccccc cagcccctcc tccccttcct gcacccgtac ccccgtggtc 1860
tttgaataaa gtctgagtgg gcggc 1885

<210> SEQ ID NO 77
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 77

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Ile Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Ile His Val Ile Pro Thr Leu Asn Gly Asp Asp Arg His
130 135 140

Lys Ile Val Asn Val Asp Gln Arg Gln Tyr Gly Asp Val Phe Lys Gly
145 150 155 160

Asp Leu Asn Pro Lys Pro Gln Gly Gln Arg Leu Ile Glu Val Ser Val
165 170 175

Glu Glu Asn His Pro Phe Thr Leu Arg Ala Pro Ile Gln Arg Ile Tyr
180 185 190

Gly Val Arg Tyr Thr Glu Thr Trp Ser Phe Leu Pro Ser Leu Thr Cys
195 200 205

Thr Gly Asp Ala Ala Pro Ala Ile Gln His Ile Cys Leu Lys His Thr
210 215 220

Thr Cys Phe Gln Asp Val Val Val Asp Val Asp Cys Ala Glu Asn Thr
225 230 235 240

Lys Glu Asp Gln Leu Ala Glu Ile Ser Tyr Arg Phe Gln Gly Lys Lys
245 250 255

Glu Ala Asp Gln Pro Trp Ile Val Val Asn Thr Ser Thr Leu Phe Asp
260 265 270

Glu Leu Glu Leu Asp Pro Pro Glu Ile Glu Pro Gly Val Leu Lys Val
275 280 285

Leu Arg Thr Glu Lys Gln Tyr Leu Gly Val Tyr Ile Trp Asn Met Arg
290 295 300

Gly Ser Asp Gly Thr Ser Thr Tyr Ala Thr Phe Leu Val Thr Trp Lys
305 310 315 320

Gly Asp Glu Lys Thr Arg Asn Pro Thr Pro Ala Val Thr Pro Gln Pro
325 330 335

Arg Gly Ala Glu Phe His Met Trp Asn Tyr His Ser His Val Phe Ser

```
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 78
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 78

```
atggggacag ttaataaacc tgtggtgggg gtattgatgg ggttcggaat tatcacggga     60

acgttgcgta taacgaatcc ggtcagagca tccgtcttgc gatacgatga ttttcacatc    120

gatgaagaca aactggatac aaactccgta tatgagcctt actaccattc agatcatgcg    180

gagtcttcat gggtaaatcg gggagagtct tcgcgaaagg cgtacgatca taactcacct    240

tatatatggc cacgtaatga ttatgatgga tttttagaga acgcacacga acaccatggg    300

gtgtataatc agggccgtgg tatcgatagc ggggaacggt taatgcaacc cacacaaatg    360

tctgcacagg aggatcttgg ggacgatacg ggcatccacg ttatccctac gttaaacggc    420

gatgacagac ataagattgt aaatgtggac caacgtcaat acggtgacgt gtttaaagga    480

gatcttaatc caaagcccca aggccaaaga ctcattgagg tgtcagtgga agagaatcac    540

ccgtttactt tacgcgcacc gattcagcgg atttatggag tccggtacac cgagacttgg    600

agctttttgc cgtcattaac ctgtacggga gacgcagcgc ccgccatcca gcatatatgt    660

ttaaagcata caacatgctt tcaagacgtg gtggtggatg tggattgcgc ggagaatact    720

aaagaggatc agttggccga aatcagttac cgttttcaag gtaagaagga agcggaccaa    780
```

ccgtggattg ttgtaaacac gagcacactg tttgatgaac tcgaattaga cccacccgag 840
attgaaccgg gtgtcttgaa agtacttcgg acagagaaac aatacttggg tgtgtacatt 900
tggaacatgc gcggctccga tggtacgtct acctacgcca cgtttttggt cacctggaaa 960
ggggatgaga agacaagaaa ccctacgccc gcagtaactc ctcaaccaag aggggctgag 1020
tttcatatgt ggaattacca ctcgcatgta ttttcagttg gtgatacgtt tagcttggca 1080
atgcatcttc agtataagat acatgaagcg ccatttgatt tgctgttaga gtggttgtat 1140
gtccccatcg atcctacatg tcaaccaatg cggttatatt ctacgtgttt gtatcatccc 1200
aacgcacccc aatgcctctc tcatatgaat tccggttgta catttacctc gccacattta 1260
gcccagcgtg ttgcaagcac agtgtatcag aattgtgaac atgcagataa ctacaccgca 1320
tattgtctgg gaatatctca tatggagcct agctttggtc taatcttaca cgacgggggc 1380
accacgttaa agtttgtaga tacacccgag agtttgtcgg gattatacgt tttgtggtg 1440 tattttaacg ggcatgttga agccgtagca tacactgttg tatccacagt agatcatttt 1500
gtaaacgcaa ttgaagagcg tggatttccg ccaacggccg gtcagccacc ggcgactact 1560
aaacccaagg aaattacccc cgtaaacccc ggaacgtcac cacttctacg atatgccgca 1620
tggaccggag ggcttgcagc agtagtactt ttatgtctcg taatattttt aatctgtacg 1680
gctaaacgaa tgagggttaa agccgccagg gtagacaag 1719

<210> SEQ ID NO 79
<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 79
gggaaataag agagaaaaga agagtaagaa gaaatataag agccaccatg ggacagtta 60 ataaacctgt ggtgggggta ttgatggggt tcggaattat cacgggaacg ttgcgtataa 120
cgaatccggt cagagcatcc gtcttgcgat acgatgattt tcacatcgat gaagacaaac 180
tggatacaaa ctccgtatat gagccttact accattcaga tcatgcggag tcttcatggg 240
taaatcgggg agagtcttcg cgaaaggcgt acgatcataa ctcaccttat atatggccac 300
gtaatgatta tgatggattt ttagagaacg cacacgaaca ccatggggtg tataatcagg 360
gccgtggtat cgatagcggg gaacggttaa tgcaacccac acaaatgtct gcacaggagg 420
atcttgggga cgatacgggc atccacgtta tccctacgtt aaacggcgat gacagacata 480
agattgtaaa tgtggaccaa cgtcaatacg gtgacgtgtt taaaggagat cttaatccaa 540
agccccaagg ccaaagactc attgaggtgt cagtggaaga gaatcacccg tttactttac 600
gcgcaccgat tcagcggatt tatggagtcc ggtacaccga gacttggagc tttttgccgt 660
cattaacctg tacgggagac gcagcgcccg ccatccagca tatatgttta aagcatacaa 720
catgctttca agacgtggtg gtggatgtgg attgcgcgga gaatactaaa gaggatcagt 780
tggccgaaat cagttaccgt tttcaaggta agaaggaagc ggaccaaccg tggattgttg 840
taaacacgag cacactgttt gatgaactcg aattagaccc acccgagatt gaaccgggtg 900
tcttgaaagt acttcggaca gagaaacaat acttgggtgt gtacatttgg aacatgcgcg 960
gctccgatgg tacgtctacc tacgccacgt tttggtcac ctggaaaggg gatgagaaga 1020
caagaaaccc tacgcccgca gtaactcctc aaccaagagg ggctgagttt catatgtgga 1080
attaccactc gcatgtattt tcagttggtg atacgtttag cttggcaatg catcttcagt 1140
ataagataca tgaagcgcca tttgatttgc tgttagagtg gttgtatgtc cccatcgatc 1200
ctacatgtca accaatgcgg ttatattcta cgtgtttgta tcatcccaac gcaccccaat 1260
gcctctctca tatgaattcc ggttgtacat ttacctcgcc acatttagcc cagcgtgttg 1320
caagcacagt gtatcagaat tgtgaacatg cagataacta caccgcatat tgtctgggaa 1380
tatctcatat ggagcctagc tttggtctaa tcttacacga cgggggcacc acgttaaagt 1440
ttgtagatac acccgagagt ttgtcgggat tatacgtttt tgtggtgtat tttaacgggc 1500
atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttacccccgt aaaccccgga acgtcaccac ttctacgata tgccgcatgg accggagggc 1680
ttgcagcagt agtactttta tgtctcgtaa tatttttaat ctgtacggct aaacgaatga 1740
gggttaaagc cgccagggta gacaagtgat aataggctgg agcctcggtg gccatgcttc 1800
ttgccccttg ggcctccccc cagcccctcc tccccttcct gcacccgtac ccccgtggtc 1860
tttgaataaa gtctgagtgg gcggcaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaatctag 1990

<210> SEQ ID NO 80
<211> LENGTH: 1885
<212> TYPE: DNA
<213> ORGANISM: Artificial Sequence
<220> FEATURE:
<223> OTHER INFORMATION: Synthetic Polynucleotide

<400> SEQUENCE: 80
gggaaataag agagaaaaga agagtaagaa gaaatataag agccaccatg ggacagttta 60
ataaacctgt ggtgggggta ttgatggggt tcggaattat cacgggaacg ttgcgtataa 120
cgaatccggt cagagcatcc gtcttgcgat acgatgattt tcacatcgat gaagacaaac 180
tggatacaaa ctccgtatat gagccttact accattcaga tcatgcggag tcttcatggg 240
taaatcgggg agagtcttcg cgaaaagcgt acgatcataa ctcaccttat atatggccac 300
gtaatgatta tgatggattt ttagagaacg cacacgaaca ccatggggtg tataatcagg 360
gccgtggtat cgatagcggg gaacggttaa tgcaacccac acaaatgtct gcacaggagg 420
atcttgggga cgatacgggc atccacgtta tccctacgtt aaacggcgat gacagacata 480
aaattgtaaa tgtggaccaa cgtcaatacg gtgacgtgtt taaaggagat cttaatccaa 540
aaccccaagg ccaaagactc attgaggtgt cagtggaaga aaatcacccg tttactttac 600
gcgcaccgat tcagcggatt tatggagtcc ggtacaccga gacttggagc tttttgccgt 660
cattaacctg tacgggagac gcagcgcccg ccatccagca tatatgttta aagcatacaa 720
catgctttca agacgtggtg gtggatgtgg attgcgcgga aaatactaaa gaggatcagt 780
tggccgaaat cagttaccgt tttcaaggta agaaggaagc ggaccaaccg tggattgttg 840
taaacacgag cacactgttt gatgaactcg aattagaccc ccccgagatt gaaccgggtg 900
tcttgaaagt acttcggaca gagaaacaat acttgggtgt gtacatttgg aacatgcgcg 960
gctccgatgg tacgtctacc tacgccacgt tttggtcac ctggaaaggg gatgagaaga 1020
caagaaaccc tacgcccgca gtaactcctc aaccaagagg ggctgagttt catatgtgga 1080
attaccactc gcatgtattt tcagttggtg atacgtttag cttggcaatg catcttcagt 1140

```
ataagataca tgaagcgcca tttgatttgc tgttagagtg gttgtatgtc cccatcgatc   1200

ctacatgtca accaatgcgg ttatattcta cgtgtttgta tcatcccaac gcaccccaat   1260

gcctctctca tatgaattcc ggttgtacat ttacctcgcc acatttagcc cagcgtgttg   1320

caagcacagt gtatcagaat tgtgaacatg cagataacta caccgcatat tgtctgggaa   1380

tatctcatat ggagcctagc tttggtctaa tcttacacga cgggggcacc acgttaaagt   1440

ttgtagatac acccgagagt ttgtcgggat tatacgtttt tgtggtgtat tttaacgggc   1500

atgttgaagc cgtagcatac actgttgtat ccacagtaga tcattttgta aacgcaattg   1560

aagagcgtgg atttccgcca acggccggtc agccaccggc gactactaaa cccaaggaaa   1620

ttaccccgt aaaccccgga acgtcaccac ttctacgata tgccgcatgg accggagggc   1680

ttgcagcagt agtactttta tgtctcgtaa tatttttaat ctgtacggct aaacgaatga   1740

gggttaaagc cgccagggta gacaagtgat aataggctgg agcctcggtg gccatgcttc   1800

ttgccccttg ggcctccccc cagcccctcc tccccttcct gcacccgtac ccccgtggtc   1860

tttgaataaa gtctgagtgg gcggc                                         1885
```

<210> SEQ ID NO 81
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 81

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220
```

-continued

```
Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 82
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 82

```
atggggacag ttaataaacc tgtggtgggg gtattgatgg ggttcggaat tatcacggga      60

acgttgcgta taacgaatcc ggtcagagca tccgtcttgc gatacgatga ttttcacatc     120
```

gatgaagaca aactggatac aaactccgta tatgagcctt actaccattc agatcatgcg 180
gagtcttcat gggtaaatcg gggagagtct tcgcgaaaag cgtacgatca taactcacct 240
tatatatggc cacgtaatga ttatgatgga tttttagaga acgcacacga acaccatggg 300
gtgtataatc agggccgtgg tatcgatagc ggggaacggt taatgcaacc cacacaaatg 360
tctgcacagg aggatcttgg ggacgatacg ggcatccacg ttatccctac gttaaacggc 420
gatgacagac ataaaattgt aaatgtggac caacgtcaat acggtgacgt gtttaaagga 480
gatcttaatc caaaacccca aggccaaaga ctcattgagg tgtcagtgga agaaaatcac 540
ccgtttactt tacgcgcacc gattcagcgg atttatggag tccggtacac cgagacttgg 600
agctttttgc cgtcattaac ctgtacggga gacgcagcgc ccgccatcca gcatatatgt 660
ttaaagcata caacatgctt tcaagacgtg gtggtggatg tggattgcgc ggaaaatact 720
aaagaggatc agttggccga aatcagttac cgttttcaag gtaagaagga agcggaccaa 780
ccgtggattg ttgtaaacac gagcacactg tttgatgaac tcgaattaga cccccccgag 840
attgaaccgg gtgtcttgaa agtacttcgg acagagaaac aatacttggg tgtgtacatt 900
tggaacatgc gcggctccga tggtacgtct acctacgcca cgtttttggt cacctggaaa 960
ggggatgaga agacaagaaa ccctacgccc gcagtaactc ctcaaccaag aggggctgag 1020
tttcatatgt ggaattacca ctcgcatgta ttttcagttg gtgatacgtt tagcttggca 1080
atgcatcttc agtataagat acatgaagcg ccatttgatt tgctgttaga gtggttgtat 1140
gtccccatcg atcctacatg tcaaccaatg cggttatatt ctacgtgttt gtatcatccc 1200
aacgcacccc aatgcctctc tcatatgaat tccggttgta catttacctc gccacattta 1260
gcccagcgtg ttgcaagcac agtgtatcag aattgtgaac atgcagataa ctacaccgca 1320
tattgtctgg gaatatctca tatggagcct agctttggtc taatcttaca cgacgggggc 1380
accacgttaa agtttgtaga tacacccgag agtttgtcgg gattatacgt tttgtggtg 1440 tattttaacg ggcatgttga agccgtagca tacactgttg tatccacagt agatcatttt 1500
gtaaacgcaa ttgaagagcg tggatttccg ccaacggccg gtcagccacc ggcgactact 1560
aaacccaagg aaattacccc cgtaaacccc ggaacgtcac cacttctacg atatgccgca 1620
tggaccggag ggcttgcagc agtagtactt ttatgtctcg taatattttt aatctgtacg 1680
gctaaacgaa tgagggttaa agccgccagg gtagacaag 1719

<210> SEQ ID NO 83
<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 83
gggaaataag agagaaaaga agagtaagaa gaaatataag agccaccatg ggacagttta 60
ataaacctgt ggtgggggta ttgatggggt tcggaattat cacgggaacg ttgcgtataa 120
cgaatccggt cagagcatcc gtcttgcgat acgatgattt tcacatcgat gaagacaaac 180
tggatacaaa ctccgtatat gagccttact accattcaga tcatgcggag tcttcatggg 240
taaatcgggg agagtcttcg cgaaaagcgt acgatcataa ctcaccttat atatggccac 300
gtaatgatta tgatggattt ttagagaacg cacacgaaca ccatggggtg tataatcagg 360
gccgtggtat cgatagcggg gaacggttaa tgcaacccac acaaatgtct gcacaggagg 420
atcttgggga cgatacgggc atccacgtta tccctacgtt aaacggcgat gacagacata 480
aaattgtaaa tgtggaccaa cgtcaatacg gtgacgtgtt taaaggagat cttaatccaa 540
aaccccaagg ccaaagactc attgaggtgt cagtggaaga aaatcacccg tttactttac 600
gcgcaccgat tcagcggatt tatggagtcc ggtacaccga gacttggagc tttttgccgt 660
cattaacctg tacgggagac gcagcgcccg ccatccagca tatatgttta aagcatacaa 720
catgctttca agacgtggtg gtggatgtgg attgcgcgga aaatactaaa gaggatcagt 780
tggccgaaat cagttaccgt tttcaaggta agaaggaagc ggaccaaccg tggattgttg 840
taaacacgag cacactgttt gatgaactcg aattagaccc ccccgagatt gaaccgggtg 900
tcttgaaagt acttcggaca gagaaacaat acttgggtgt gtacatttgg aacatgcgcg 960
gctccgatgg tacgtctacc tacgccacgt ttttggtcac ctggaaaggg gatgagaaga 1020
caagaaaccc tacgcccgca gtaactcctc aaccaagagg ggctgagttt catatgtgga 1080
attaccactc gcatgtattt tcagttggtg atacgtttag cttggcaatg catcttcagt 1140
ataagataca tgaagcgcca tttgatttgc tgttagagtg gttgtatgtc cccatcgatc 1200
ctacatgtca accaatgcgg ttatattcta cgtgtttgta tcatcccaac gcaccccaat 1260
gcctctctca tatgaattcc ggttgtacat ttacctcgcc acatttagcc cagcgtgttg 1320
caagcacagt gtatcagaat tgtgaacatg cagataacta caccgcatat tgtctgggaa 1380
tatctcatat ggagcctagc tttggtctaa tcttacacga cgggggcacc acgttaaagt 1440
ttgtagatac acccgagagt ttgtcgggat tatacgtttt tgtggtgtat tttaacgggc 1500
atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttacccccgt aaaccccgga acgtcaccac ttctacgata tgccgcatgg accggagggc 1680
ttgcagcagt agtactttta tgtctcgtaa tatttttaat ctgtacggct aaacgaatga 1740
gggttaaagc cgccagggta gacaagtgat aataggctgg agcctcggtg gccatgcttc 1800
ttgccccttg ggcctccccc cagcccctcc tccccttcct gcacccgtac ccccgtggtc 1860
tttgaataaa gtctgagtgg gcggcaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaatctag 1990

<210> SEQ ID NO 84
<211> LENGTH: 1885
<212> TYPE: DNA
<213> ORGANISM: Artificial Sequence
<220> FEATURE:
<223> OTHER INFORMATION: Synthetic Polynucleotide

<400> SEQUENCE: 84
gggaaataag agagaaaaga agagtaagaa gaaatataag agccaccatg gggacagtta 60
ataaacctgt ggtgggggta ttgatggggt tcggaattat cacgggaacg ttgcgtataa 120
cgaatccggt cagagcatcc gtcttgcgat acgatgattt tcacatcgat gaagacaaac 180
tggatacaaa ctccgtatat gagccttact accattcaga tcatgcggag tcttcatggg 240
taaatcgggg agagtcttcg cgaaaagcgt acgatcataa ctcaccttat atatggccac 300
gtaatgatta tgatggattt ttagagaacg cacacgaaca ccatggggtg tataatcagg 360
gccgtggtat cgatagcggg gaacggttaa tgcaacccac acaaatgtct gcacaggagg 420
atcttgggga cgatacgggc atccacgtta tccctacgtt aaacggcgat gacagacata 480

-continued

```
aaattgtaaa tgtggaccaa cgtcaatacg gtgacgtgtt taaaggagat cttaatccaa    540

aaccccaagg ccaaagactc attgaggtgt cagtggaaga aaatcacccg tttactttac    600

gcgcaccgat tcagcggatt tatggagtcc ggtacaccga gacttggagc tttttgccgt    660

cattaacctg tacgggagac gcagcgcccg ccatccagca tatatgttta aagcatacaa    720

catgctttca agacgtggtg gtggatgtgg attgcgcgga aaatactaaa gaggatcagt    780

tggccgaaat cagttaccgt tttcaaggta agaaggaagc ggaccaaccg tggattgttg    840

taaacacgag cacactgttt gatgaactcg aattagaccc acccgagatt gaaccgggtg    900

tcttgaaagt acttcggaca gagaaacaat acttgggtgt gtacatttgg aacatgcgcg    960

gctccgatgg tacgtctacc tacgccacgt tttggtcac ctggaaaggg gatgagaaga    1020

caagaaaccc tacgcccgca gtaactcctc aaccaagagg ggctgagttt catatgtgga   1080

attaccactc gcatgtattt tcagttggtg atacgtttag cttggcaatg catcttcagt   1140

ataagataca tgaagcgcca tttgatttgc tgttagagtg gttgtatgtc cccatcgatc   1200

ctacatgtca accaatgcgg ttatattcta cgtgtttgta tcatcccaac gcaccccaat   1260

gcctctctca tatgaattcc ggttgtacat ttacctcgcc acatttagcc cagcgtgttg   1320

caagcacagt gtatcagaat tgtgaacatg cagataacta caccgcatat tgtctgggaa   1380

tatctcatat ggagcctagc tttggtctaa tcttacacga cgggggcacc acgttaaagt   1440

ttgtagatac acccgagagt ttgtcgggat tatacgtttt tgtggtgtat tttaacgggc   1500

atgttgaagc cgtagcatac actgttgtat ccacagtaga tcattttgta aacgcaattg   1560

aagagcgtgg atttccgcca acggccggtc agccaccggc gactactaaa cccaaggaaa   1620

ttacccccgt aaaccccgga acgtcaccac ttctacgata tgccgcatgg accggagggc   1680

ttgcagcagt agtactttta tgtctcgtaa tatttttaat ctgtacggct aaacgaatga   1740

gggttaaagc cgccagggta gacaagtgat aataggctgg agcctcggtg gccatgcttc   1800

ttgccccttg ggcctccccc cagcccctcc tccccttcct gcacccgtac cccgtggtc   1860

tttgaataaa gtctgagtgg gcggc                                          1885
```

<210> SEQ ID NO 85
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 85

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110
```

-continued

```
Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525
```

-continued

```
Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 86
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 86

```
atggggacag ttaataaacc tgtggtgggg gtattgatgg ggttcggaat tatcacggga     60
acgttgcgta taacgaatcc ggtcagagca tccgtcttgc gatacgatga ttttcacatc    120
gatgaagaca aactggatac aaactccgta tatgagcctt actaccattc agatcatgcg    180
gagtcttcat gggtaaatcg gggagagtct tcgcgaaaag cgtacgatca taactcacct    240
tatatatggc cacgtaatga ttatgatgga tttttagaga acgcacacga acaccatggg    300
gtgtataatc agggccgtgg tatcgatagc ggggaacggt taatgcaacc cacacaaatg    360
tctgcacagg aggatcttgg ggacgatacg ggcatccacg ttatccctac gttaaacggc    420
gatgacagac ataaaattgt aaatgtggac caacgtcaat acggtgacgt gtttaaagga    480
gatcttaatc caaaacccca aggccaaaga ctcattgagg tgtcagtgga agaaaatcac    540
ccgtttactt tacgcgcacc gattcagcgg atttatggag tccggtacac cgagacttgg    600
agctttttgc cgtcattaac ctgtacggga gacgcagcgc ccgccatcca gcatatatgt    660
ttaaagcata caacatgctt tcaagacgtg gtggtggatg tggattgcgc ggaaaatact    720
aaagaggatc agttggccga aatcagttac cgttttcaag gtaagaagga agcggaccaa    780
ccgtggattg ttgtaaacac gagcacactg tttgatgaac tcgaattaga cccacccgag    840
attgaaccgg gtgtcttgaa agtacttcgg acagagaaac aatacttggg tgtgtacatt    900
tggaacatgc gcggctccga tggtacgtct acctacgcca cgtttttggt cacctggaaa    960
ggggatgaga agacaagaaa ccctacgccc gcagtaactc ctcaaccaag aggggctgag   1020
tttcatatgt ggaattacca ctcgcatgta ttttcagttg gtgatacgtt tagcttggca   1080
atgcatcttc agtataagat acatgaagcg ccatttgatt tgctgttaga gtggttgtat   1140
gtccccatcg atcctacatg tcaaccaatg cggttatatt ctacgtgttt gtatcatccc   1200
aacgcacccc aatgcctctc tcatatgaat tccggttgta catttacctc gccacattta   1260
gcccagcgtg ttgcaagcac agtgtatcag aattgtgaac atgcagataa ctacaccgca   1320
tattgtctgg gaatatctca tatggagcct agctttggtc taatcttaca cgacgggggc   1380
accacgttaa agtttgtaga tacacccgag agtttgtcgg gattatacgt tttgtggtg   1440
tattttaacg ggcatgttga agccgtagca tacactgttg tatccacagt agatcatttt   1500
gtaaacgcaa ttgaagagcg tggatttccg ccaacggccg gtcagccacc ggcgactact   1560
aaacccaagg aaattacccc cgtaaacccc ggaacgtcac cacttctacg atatgccgca   1620
tggaccggag ggcttgcagc agtagtactt ttatgtctcg taatattttt aatctgtacg   1680
gctaaacgaa tgagggttaa agccgccagg gtagacaag                          1719
```

<210> SEQ ID NO 87

<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 87
gggaaataag agagaaaaga agagtaagaa gaaatataag agccaccatg ggacagtta 60 ataaacctgt ggtgggggta ttgatggggt tcggaattat cacgggaacg ttgcgtataa 120
cgaatccggt cagagcatcc gtcttgcgat acgatgattt tcacatcgat gaagacaaac 180
tggatacaaa ctccgtatat gagccttact accattcaga tcatgcggag tcttcatggg 240
taaatcgggg agagtcttcg cgaaaagcgt acgatcataa ctcaccttat atatggccac 300
gtaatgatta tgatggattt ttagagaacg cacacgaaca ccatggggtg tataatcagg 360
gccgtggtat cgatagcggg gaacggttaa tgcaacccac acaaatgtct gcacaggagg 420
atcttgggga cgatacgggc atccacgtta tccctacgtt aaacggcgat gacagacata 480
aaattgtaaa tgtggaccaa cgtcaatacg gtgacgtgtt taaaggagat cttaatccaa 540
aaccccaagg ccaaagactc attgaggtgt cagtggaaga aaatcacccg tttactttac 600
gcgcaccgat tcagcggatt tatggagtcc ggtacaccga gacttggagc tttttgccgt 660
cattaacctg tacgggagac gcagcgcccg ccatccagca tatatgttta aagcatacaa 720
catgctttca agacgtggtg gtggatgtgg attgcgcgga aaatactaaa gaggatcagt 780
tggccgaaat cagttaccgt tttcaaggta agaaggaagc ggaccaaccg tggattgttg 840
taaacacgag cacactgttt gatgaactcg aattagaccc acccgagatt gaaccgggtg 900
tcttgaaagt acttcggaca gagaaacaat acttgggtgt gtacatttgg aacatgcgcg 960
gctccgatgg tacgtctacc tacgccacgt ttttggtcac ctggaaaggg gatgagaaga 1020
caagaaaccc tacgcccgca gtaactcctc aaccaagagg ggctgagttt catatgtgga 1080
attaccactc gcatgtattt tcagttggtg atacgtttag cttggcaatg catcttcagt 1140
ataagataca tgaagcgcca tttgatttgc tgttagagtg gttgtatgtc cccatcgatc 1200
ctacatgtca accaatgcgg ttatattcta cgtgtttgta tcatcccaac gcaccccaat 1260
gcctctctca tatgaattcc ggttgtacat ttacctcgcc acatttagcc cagcgtgttg 1320
caagcacagt gtatcagaat tgtgaacatg cagataacta caccgcatat tgtctgggaa 1380
tatctcatat ggagcctagc tttggtctaa tcttacacga cgggggcacc acgttaaagt 1440
ttgtagatac acccgagagt ttgtcgggat tatacgtttt tgtggtgtat tttaacgggc 1500
atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttacccccgt aaaccccgga acgtcaccac ttctacgata tgccgcatgg accggagggc 1680
ttgcagcagt agtactttta tgtctcgtaa tatttttaat ctgtacggct aaacgaatga 1740
gggttaaagc cgccagggta gacaagtgat aataggctgg agcctcggtg gccatgcttc 1800
ttgccccttg ggcctccccc cagcccctcc tccccttcct gcacccgtac ccccgtggtc 1860
tttgaataaa gtctgagtgg gcggcaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaatctag 1990

<210> SEQ ID NO 88
<211> LENGTH: 1885

<212> TYPE: DNA
<213> ORGANISM: Artificial Sequence
<220> FEATURE:
<223> OTHER INFORMATION: Synthetic Polynucleotide

<400> SEQUENCE: 88

```
gggaaataag agagaaaaga agagtaagaa gaaatataag agccaccatg gggacagtta     60
ataaacctgt ggtgggcgta ttgatggggt tcggaattat cacgggaacg ttgcgtataa    120
cgaatccggt cagagcatcc gtcttgcgat acgatgattt tcacatcgat gaagacaaac    180
tggatacaaa ctccgtatat gagccttact accattcaga tcatgcggag tcttcatggg    240
taaatcgggg agagtcttcg cgaaaggcgt acgatcataa ctcaccttat atatggccac    300
gtaatgatta tgatggattc ttagagaacg cacacgaaca ccatggggtg tataatcagg    360
gccgtggtat cgatagcggg gaacggttaa tgcaacccac acaaatgtct gcacaggagg    420
atcttgggga cgatacgggc atccacgtta tccctacgtt aaacggcgat gacagacata    480
agattgtaaa tgtggaccaa cgtcaatacg gtgacgtgtt taaaggagat cttaatccaa    540
agccccaagg ccaaagactc attgaggtgt cagtggaaga gaatcacccg tttactttac    600
gcgcaccgat tcagcggatt tatggagtcc ggtacaccga gacttggagc ttcttgccgt    660
cattaacctg tacgggagac gcagcgcccg ccatccagca tatatgttta aagcatacaa    720
catgctttca agacgtggtg gtggatgtgg attgcgcgga gaatactaaa gaggatcagt    780
tggccgaaat cagttaccgt tttcaaggta agaaggaagc ggaccaaccg tggattgttg    840
taaacacgag cacactgttt gatgaactcg aattagaccc acccgagatt gaaccgggtg    900
tcttgaaagt acttcggaca gagaaacaat acttgggtgt gtacatttgg aacatgcgcg    960
gctccgatgg tacgtctacc tacgccacgt tcttggtcac ctggaaaggg gatgagaaga   1020
caagaaaccc tacgcccgca gtaactcctc aaccaagagg ggctgagttt catatgtgga   1080
attaccactc gcatgtattt tcagttggtg atacgtttag cttggcaatg catcttcagt   1140
ataagataca tgaagcgcca tttgatttgc tgttagagtg gttgtatgtc cccatcgatc   1200
ctacatgtca accaatgcgg ttatattcta cgtgtttgta tcatcccaac gcaccccaat   1260
gcctctctca tatgaattcc ggttgtacat ttacctcgcc acatttagcc cagcgtgttg   1320
caagcacagt gtatcagaat tgtgaacatg cagataacta caccgcatat tgtctgggaa   1380
tatctcatat ggagcctagc tttggtctaa tcttacacga cggaggcacc acgttaaagt   1440
ttgtagatac acccgagagt ttgtcgggat tatacgtctt tgtggtgtat tttaacgggc   1500
atgttgaagc cgtagcatac actgttgtat ccacagtaga tcattttgta aacgcaattg   1560
aagagcgtgg atttccgcca acggccggtc agccaccggc gactactaaa cccaaggaaa   1620
ttacgcccgt aaaccccgga acgtcaccac ttctacgata tgccgcatgg accggagggc   1680
ttgcagcagt agtactttta tgtctcgtaa tattcttaat ctgtacggct aaacgaatga   1740
gggttaaagc cgccagggta gacaagtgat aataggctgg agcctcggtg gccatgcttc   1800
ttgccccttg ggcctccccc cagcccctcc tccccttcct gcacccgtac ccccgtggtc   1860
tttgaataaa gtctgagtgg gcggc                                         1885
```

<210> SEQ ID NO 89
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 89

Met Gly Thr Val Asn Lys Pro Val Val Gly Val Leu Met Gly Phe Gly
1 5 10 15

Ile Ile Thr Gly Thr Leu Arg Ile Thr Asn Pro Val Arg Ala Ser Val
20 25 30

Leu Arg Tyr Asp Asp Phe His Ile Asp Glu Asp Lys Leu Asp Thr Asn
35 40 45

Ser Val Tyr Glu Pro Tyr Tyr His Ser Asp His Ala Glu Ser Ser Trp
50 55 60

Val Asn Arg Gly Glu Ser Ser Arg Lys Ala Tyr Asp His Asn Ser Pro
65 70 75 80

Tyr Ile Trp Pro Arg Asn Asp Tyr Asp Gly Phe Leu Glu Asn Ala His
85 90 95

Glu His His Gly Val Tyr Asn Gln Gly Arg Gly Ile Asp Ser Gly Glu
100 105 110

Arg Leu Met Gln Pro Thr Gln Met Ser Ala Gln Glu Asp Leu Gly Asp
115 120 125

Asp Thr Gly Ile His Val Ile Pro Thr Leu Asn Gly Asp Asp Arg His
130 135 140

Lys Ile Val Asn Val Asp Gln Arg Gln Tyr Gly Asp Val Phe Lys Gly
145 150 155 160

Asp Leu Asn Pro Lys Pro Gln Gly Gln Arg Leu Ile Glu Val Ser Val
165 170 175

Glu Glu Asn His Pro Phe Thr Leu Arg Ala Pro Ile Gln Arg Ile Tyr
180 185 190

Gly Val Arg Tyr Thr Glu Thr Trp Ser Phe Leu Pro Ser Leu Thr Cys
195 200 205

Thr Gly Asp Ala Ala Pro Ala Ile Gln His Ile Cys Leu Lys His Thr
210 215 220

Thr Cys Phe Gln Asp Val Val Val Asp Val Asp Cys Ala Glu Asn Thr
225 230 235 240

Lys Glu Asp Gln Leu Ala Glu Ile Ser Tyr Arg Phe Gln Gly Lys Lys
245 250 255

Glu Ala Asp Gln Pro Trp Ile Val Val Asn Thr Ser Thr Leu Phe Asp
260 265 270

Glu Leu Glu Leu Asp Pro Pro Glu Ile Glu Pro Gly Val Leu Lys Val
275 280 285

Leu Arg Thr Glu Lys Gln Tyr Leu Gly Val Tyr Ile Trp Asn Met Arg
290 295 300

Gly Ser Asp Gly Thr Ser Thr Tyr Ala Thr Phe Leu Val Thr Trp Lys
305 310 315 320

Gly Asp Glu Lys Thr Arg Asn Pro Thr Pro Ala Val Thr Pro Gln Pro
325 330 335

Arg Gly Ala Glu Phe His Met Trp Asn Tyr His Ser His Val Phe Ser
340 345 350

Val Gly Asp Thr Phe Ser Leu Ala Met His Leu Gln Tyr Lys Ile His
355 360 365

Glu Ala Pro Phe Asp Leu Leu Leu Glu Trp Leu Tyr Val Pro Ile Asp
370 375 380

Pro Thr Cys Gln Pro Met Arg Leu Tyr Ser Thr Cys Leu Tyr His Pro
385 390 395 400

Asn Ala Pro Gln Cys Leu Ser His Met Asn Ser Gly Cys Thr Phe Thr
405 410 415

```
Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Ala Arg Val Asp Lys
                565                 570
```

<210> SEQ ID NO 90
<211> LENGTH: 1719
<212> TYPE: DNA
<213> ORGANISM: Artificial Sequence
<220> FEATURE:
<223> OTHER INFORMATION: Synthetic Polynucleotide

<400> SEQUENCE: 90

```
atggggacag ttaataaacc tgtggtgggc gtattgatgg ggttcggaat tatcacggga     60

acgttgcgta taacgaatcc ggtcagagca tccgtcttgc gatacgatga ttttcacatc    120

gatgaagaca aactggatac aaactccgta tatgagcctt actaccattc agatcatgcg    180

gagtcttcat gggtaaatcg gggagagtct tcgcgaaagg cgtacgatca taactcacct    240

tatatatggc cacgtaatga ttatgatgga ttcttagaga acgcacacga acaccatggg    300

gtgtataatc agggccgtgg tatcgatagc ggggaacggt taatgcaacc cacacaaatg    360

tctgcacagg aggatcttgg ggacgatacg ggcatccacg ttatccctac gttaaacggc    420

gatgacagac ataagattgt aaatgtggac caacgtcaat acggtgacgt gtttaaagga    480

gatcttaatc caaagcccca aggccaaaga ctcattgagg tgtcagtgga agagaatcac    540

ccgtttactt tacgcgcacc gattcagcgg atttatggag tccggtacac cgagacttgg    600

agcttcttgc cgtcattaac ctgtacggga gacgcagcgc ccgccatcca gcatatatgt    660

ttaaagcata caacatgctt tcaagacgtg gtggtggatg tggattgcgc ggagaatact    720

aaagaggatc agttggccga aatcagttac cgttttcaag gtaagaagga agcggaccaa    780

ccgtggattg ttgtaaacac gagcacactg tttgatgaac tcgaattaga cccacccgag    840

attgaaccgg gtgtcttgaa agtacttcgg acagagaaac aatacttggg tgtgtacatt    900

tggaacatgc gcggctccga tggtacgtct acctacgcca cgttcttggt cacctggaaa    960

ggggatgaga agacaagaaa ccctacgccc gcagtaactc ctcaaccaag aggggctgag   1020

tttcatatgt ggaattacca ctcgcatgta ttttcagttg gtgatacgtt tagcttggca   1080

atgcatcttc agtataagat acatgaagcg ccatttgatt tgctgttaga gtggttgtat   1140
```

```
gtccccatcg atcctacatg tcaaccaatg cggttatatt ctacgtgttt gtatcatccc   1200

aacgcacccc aatgcctctc tcatatgaat tccggttgta catttacctc gccacattta   1260

gcccagcgtg ttgcaagcac agtgtatcag aattgtgaac atgcagataa ctacaccgca   1320

tattgtctgg gaatatctca tatggagcct agctttggtc taatcttaca cgacggaggc   1380

accacgttaa agtttgtaga tacacccgag agtttgtcgg gattatacgt ctttgtggtg   1440

tattttaacg ggcatgttga agccgtagca tacactgttg tatccacagt agatcatttt   1500

gtaaacgcaa ttgaagagcg tggatttccg ccaacggccg gtcagccacc ggcgactact   1560

aaacccaagg aaattacgcc cgtaaacccc ggaacgtcac cacttctacg atatgccgca   1620

tggaccggag ggcttgcagc agtagtactt ttatgtctcg taatattctt aatctgtacg   1680

gctaaacgaa tgagggttaa agccgccagg gtagacaag                          1719
```

```
<210> SEQ ID NO 91
<211> LENGTH: 1990
<212> TYPE: DNA
<213> ORGANISM: Artificial Sequence
<220> FEATURE:
<223> OTHER INFORMATION: Synthetic Polynucleotide

<400> SEQUENCE: 91

gggaaataag agagaaaaga agagtaagaa gaaatataag agccaccatg ggacagtta     60

ataaacctgt ggtgggcgta ttgatggggt tcggaattat cacgggaacg ttgcgtataa   120

cgaatccggt cagagcatcc gtcttgcgat acgatgattt tcacatcgat gaagacaaac   180

tggatacaaa ctccgtatat gagccttact accattcaga tcatgcggag tcttcatggg   240

taaatcgggg agagtcttcg cgaaaggcgt acgatcataa ctcaccttat atatggccac   300

gtaatgatta tgatggattc ttagagaacg cacacgaaca ccatggggtg tataatcagg   360

gccgtggtat cgatagcggg gaacggttaa tgcaacccac acaaatgtct gcacaggagg   420

atcttgggga cgatacgggc atccacgtta tccctacgtt aaacggcgat gacagacata   480

agattgtaaa tgtggaccaa cgtcaatacg gtgacgtgtt taaaggagat cttaatccaa   540

agccccaagg ccaaagactc attgaggtgt cagtggaaga gaatcacccg tttactttac   600

gcgcaccgat tcagcggatt tatggagtcc ggtacaccga gacttggagc ttcttgccgt   660

cattaacctg tacgggagac gcagcgcccg ccatccagca tatatgttta aagcatacaa   720

catgctttca agacgtggtg gtggatgtgg attgcgcgga gaatactaaa gaggatcagt   780

tggccgaaat cagttaccgt tttcaaggta agaaggaagc ggaccaaccg tggattgttg   840

taaacacgag cacactgttt gatgaactcg aattagaccc acccgagatt gaaccgggtg   900

tcttgaaagt acttcggaca gagaaacaat acttgggtgt gtacatttgg aacatgcgcg   960

gctccgatgg tacgtctacc tacgccacgt tcttggtcac ctggaaaggg gatgagaaga  1020

caagaaaccc tacgcccgca gtaactcctc aaccaagagg ggctgagttt catatgtgga  1080

attaccactc gcatgtattt tcagttggtg atacgtttag cttggcaatg catcttcagt  1140

ataagataca tgaagcgcca tttgatttgc tgttagagtg gttgtatgtc cccatcgatc  1200

ctacatgtca accaatgcgg ttatattcta cgtgtttgta tcatcccaac gcaccccaat  1260

gcctctctca tatgaattcc ggttgtacat ttacctcgcc acatttagcc cagcgtgttg  1320

caagcacagt gtatcagaat tgtgaacatg cagataacta caccgcatat tgtctgggaa  1380

tatctcatat ggagcctagc tttggtctaa tcttacacga cggaggcacc acgttaaagt  1440

ttgtagatac acccgagagt ttgtcgggat tatacgtctt tgtggtgtat tttaacgggc  1500
```

atgttgaagc cgtagcatac actgttgtat ccacagtaga tcattttgta aacgcaattg 1560
aagagcgtgg atttccgcca acggccggtc agccaccggc gactactaaa cccaaggaaa 1620
ttacgcccgt aaaccccgga acgtcaccac ttctacgata tgccgcatgg accggagggc 1680
ttgcagcagt agtactttta tgtctcgtaa tattcttaat ctgtacggct aaacgaatga 1740
gggttaaagc cgccagggta gacaagtgat aataggctgg agcctcggtg gccatgcttc 1800
ttgccccttg ggcctccccc cagcccctcc tccccttcct gcacccgtac ccccgtggtc 1860
tttgaataaa gtctgagtgg gcggcaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaatctag 1990

<210> SEQ ID NO 92
<211> LENGTH: 2141
<212> TYPE: RNA
<213> ORGANISM: Varicella Zoster Virus

<400> SEQUENCE: 92
ggggaaauaa gagagaaaag aagaguaaga agaaauauaa gagccaccau ggggacagug 60
aauaagccgg uugugggcgu gcuuaugggc uuugggauua uuaccgguac auuacgaauu 120
accaauccag ugcgcgccag ugugcugcgu uacgacgacu uucacauuga cgaggauaag 180
cuggauacua acagcgugua cgaaccuuau uaccacucag aucaugccga aucaagcugg 240
guuaauagag gagaaagcag ccgaaaagcc uacgaccaca acucaccuua uauuuggccc 300
agaaacgauu augacgguuu ccuggaaaac gcacaugaac accauggagu cuacaaccaa 360
ggcaggggaa ucgacagugg cgagcgucuu augcagccaa cacagauguc ggcacaggag 420
gaucucggug augacaccgg cauacacgug auucccacau uaaacggcga cgacagacau 480
aagaucguca auguggauca gcgucaguau ggggaugucu uuaaaggcga uuugaaucca 540
aagccccaag gacagagacu gaucgagguc ucuguagaag aaaaucaccc cuucacuuug 600
cgcgcuccaa uccagaggau uuacgggggug cguuauaccg aaacuuggag uuucuugccg 660
ucacugacgu guacggggga ugccgccccc gcaauccagc acaucugucu gaaacacacc 720
acaugcuuuc aggacguggu uguggaugug gauugcgcgg aaaacacaaa agaagaccaa 780
cucgccgaaa ucagcuaucg uuuucagggu aaaaaagagg ccgaccaacc guggauuguu 840
gugaauacga gcacgcucuu cgaugagcuu gaacucgauc ccccggaaau cgagccuggg 900
guucuaaaag uguugaggac cgagaagcag uaccucgggg uuuauaucug gaauaugaga 960
ggcuccgaug gcaccucuac cuacgcaacg uuucugguua ccuggaaggg agacgagaag 1020
acacggaauc caacgcccgc ugugaccccu cagccuaggg gagccgaauu ccacaugugg 1080
aacuaucacu cccauguauu caguguggguu gacacuuuca gccuggccau gcaccugcag 1140
uauaagauuc acgaggcacc cuucgaccuc cugcuggagu gguuguacgu accuauugau 1200
cccacuuguc agcccaugcg ccuguacucc acuugcuugu accaccccaa ugcaccacag 1260
ugucuaucac acaugaacuc cgggguguacc uuuacuucac cccaucuugc ccagcggguc 1320
gccagcacag uguaucagaa cugugagcau gcugacaacu auacugcuua uugccucgga 1380
auaucccaua uggagccaag cuucgggcuc auacugcacg augguggguac gacacucaag 1440 uucguggaca cccccgaaag ccuuucuggc uuguacgugu ucgugguucua cuucaaugga 1500 cauguggagg caguggcuua cacagugguu ucgacaguug aucacuuugu aaaugccauu 1560
gaggaacgcg gcuucccgcc uacagcgggc cagccccug cgacaacaaa accaaaagag 1620
auuacgcccg uuaauccugg gacuagucca uugcugaggu augccgccug gacuggcggu 1680
cuggcggccg ugguacuucu guguuuaguc auauuucuga ucuguaccgc uaaacguaug 1740
cgggucaagg cuuaccgugu ugacaagucu ccuuacaauc agucaaugua cuaugcagga 1800
cucccuguug acgauuucga agacucagag aguacagaca cagaagaaga auucggaaac 1860
gcuauaggug gcucucacgg agguagcucg uauacagugu acaucgauaa aaccagauga 1920
uaauaggcug gagccucggu ggccaugcuu cuugccccuu gggccucccc ccagccccuc 1980
cuccccuucc ugcacccgua cccccguggu cuuugaauaa agucugagug ggcggcaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaucua g 2141

<210> SEQ ID NO 93
<211> LENGTH: 2111
<212> TYPE: RNA
<213> ORGANISM: Artificial Sequence
<220> FEATURE:
<223> OTHER INFORMATION: Synthetic Polynucleotide

<400> SEQUENCE: 93
ggggaaauaa gagagaaaag aagaguaaga agaaauauaa gagccaccau ggagacuccc 60
gcucagcuac uguuccuccu gcuccuuugg cugccugaua cuacaggcuc uguuuugcgg 120
uacgacgacu uucacaucga ugaggacaag cucgacacua auagcgugua ugagcccuac 180
uaccauucag aucacgccga guccucuugg gugaacaggg gugaaaguuc uaggaaagcc 240
uaugaucaca acagcccuua uauuuggcca cggaaugauu acgacggauu ucucgaaaau 300
gcccacgagc aucacggagu guacaaccag ggccguggaa ucgacucugg ggagagauug 360
augcaaccua cacagaugag cgcccaggaa gaucucgggg augauacagg aauucacguu 420
aucccuacau uaaacggaga ugaccgccac aaaaucguca augucgauca aagacaguau 480
ggagaugugu ucaaaggcga ucucaacccu aagccgcagg gccagagacu cauugaggug 540
ucugucgaag agaaccaccc uuucacucug cgcgcuccca uucagagaau cuauggaguu 600
cgcuauacgg agacuugguc auuccuuccu ucccugacau gcaccggaga cgccgccccu 660
gccauucagc acauaugccu gaaacauacc accuguuucc aggaugugga gguugauguu 720
gauugugcug aaaauaccaa ggaagaccaa cuggccgaga uuaguuaccg guuccaaggg 780
aaaaaggaag ccgaccagcc auggauugug guuaauacaa gcacucuguu cgaugagcuc 840
gagcuggauc cccccgagau agaacccgga guucugaaag ugcuccggac agaaaaacaa 900
uaucugggag ucuacauaug gaacaugcgc gguuccgaug ggaccuccac uuaugcaacc 960
uuucucguca cguggaaggg agaugagaaa acuaggaauc ccacacccgc ugucacacca 1020
cagccaagag gggcugaguu ccauaugugg aacuaucaua gucacguguu uagugucgga 1080
gauacguuuu cauuggcuau gcaucuccag uacaagauuc augaggcucc cuucgaucug 1140
uugcuugagu gguuguacgu cccgauugac ccgaccugcc agcccaugcg acuguacagc 1200
accugucucu accauccaaa cgcuccgcaa ugucugagcc acaugaacuc ugggguguacu 1260 uucaccaguc cccaccucgc ccagcgggug gccucuacug uuuaccagaa cugugagcac 1320
gccgacaacu acaccgcaua cugccucggu auuucucaca uggaacccuc cuucggacuc 1380
auccugcacg augggggcac uacccugaag uucguugaua cgccagaauc ucugucuggg 1440
cucuauguuu ucguggucua cuucaauggc caugucgagg ccguggccua uacugucguu 1500
ucuaccgugg aucauuuugu gaacgccauc gaagaacggg gauuccccccc uacggcaggc 1560 cagccgccug caaccaccaa gcccaaggaa auaacaccag ugaacccugg caccucaccu 1620
cuccuaagau augccgcgug gacaggggga cuggcggcag uggugcuccu cugucucgug 1680
aucuuucuga ucuguacagc caagaggaug agggucaagg cuuauagagu ggacaagucc 1740
cccuacaauc agucaaugua cuacgccggc cuucccguug augauuuuga ggauuccgag 1800
uccacagaua cugaggaaga guucgguaac gcuauaggcg gcucucacgg ggguucaagc 1860
uacacgguuu acauugacaa gacacgcuga uaauaggcug gagccucggu ggccaugcuu 1920
cuugccccuu gggccucccc ccagccccuc cuccccuucc ugcacccgua cccccguggu 1980
cuuugaauaa agucugagug ggcggcaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaucua g 2111

<210> SEQ ID NO 94
<211> LENGTH: 1958
<212> TYPE: RNA
<213> ORGANISM: Artificial Sequence
<220> FEATURE:
<223> OTHER INFORMATION: Synthetic Polynucleotide

<400> SEQUENCE: 94
ggggaaauaa gagagaaaag aagaguaaga agaaauauaa gagccaccau ggggacaguu 60
aauaaaccug ugguggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accaugggu guauaaucag 360 ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaaacauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cccccgagau ugaaccgggu 900
gucuugaaag uacuucggac agaaaaacaa uacuugggug uguacauuug gaacaugcgc 960
ggcuccgaug guacgucuac cuacgccacg uuuuugguca ccuggaaagg ggaugaaaaa 1020
acaagaaacc cuacgcccgc aguaacuccu caaccaagag gggcugaguu ucauaugugg 1080
aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucaaaa uugugaacau gcagauaacu acaccgcaua uugucuggga 1380

-continued auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uugaugauaa 1740
uaggcuggag ccucgguggc caugcuucuu gccccuuggg ccucccccca gccccuccuc 1800
cccuuccugc acccguaccc ccguggucuu ugaauaaagu cugagugggc ggcaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaucuag 1958

<210> SEQ ID NO 95
<211> LENGTH: 1928
<212> TYPE: RNA
<213> ORGANISM: Artificial Sequence
<220> FEATURE:
<223> OTHER INFORMATION: Synthetic Polynucleotide

<400> SEQUENCE: 95
ggggaaauaa gagagaaaag aagaguaaga agaaauauaa gagccaccau ggaaaccccg 60
gcgcagcugc uguuucugcu gcugcugugg cugccggaua ccaccggcuc cgucuugcga 120
uacgaugauu uucacaucga ugaagacaaa cuggauacaa acuccguaua ugagccuuac 180
uaccauucag aucaugcgga gucuucaugg guaaaucggg gagagucuuc gcgaaaagcg 240
uacgaucaua acucaccuua uauauggcca cguaaugauu augauggauu uuuagagaac 300
gcacacgaac accauggggu guauaaucag ggccguggua ucgauagcgg ggaacgguua 360
augcaaccca cacaaauguc ugcacaggag gaucuugggg acgauacggg cauccacguu 420
aucccuacgu uaaacggcga ugacagacau aaaauuguaa auguggacca acgucaauac 480
ggugacgugu uuaaaggaga ucuuaaucca aaaccccaag gccaaagacu cauugaggug 540
ucaguggaag aaaaucaccc guuuacuuua cgcgcaccga uucagcggau uuauggaguc 600
cgguacaccg agacuuggag cuuuuugccg ucauuaaccu guacgggaga cgcagcgccc 660
gccauccagc auauauguuu aaaacauaca acaugcuuuc aagacguggu gguggaugug 720
gauugcgcgg aaaauacuaa agaggaucag uuggccgaaa ucaguuaccg uuuucaaggu 780
aagaaggaag cggaccaacc guggauuguu guaaacacga gcacacuguu ugaugaacuc 840
gaauuagacc cccccgagau ugaaccgggu gucuugaaag uacuucggac agaaaaacaa 900
uacuugggug uguacauuug gaacaugcgc ggcuccgaug guacgucuac cuacgccacg 960
uuuuugguca ccuggaaagg ggaugaaaaa acaagaaacc cuacgcccgc aguaacuccu 1020
caaccaagag ggcugaguu ucauaugugg aauuaccacu cgcauguauu uucaguuggu 1080
gauacguuua gcuuggcaau gcaucuucag uauaagauac augaagcgcc auuugauuug 1140
cuguuagagu gguuguaugu ccccaucgau ccuacauguc aaccaaugcg guuauauucu 1200
acguguuugu aucaucccaa cgcaccccaa ugccucucuc auaugaauuc cgguuguaca 1260
uuuaccucgc cacauuuagc ccagcguguu gcaagcacag uguaucaaaa uugugaacau 1320
gcagauaacu acaccgcaua uugucuggga auaucucaua uggagccuag cuuuggucua 1380
aucuuacacg acgggggcac cacguuaaag uuuguagaua cacccgagag uuugucggga 1440
uuauacguuu uuguggugua uuuuaacggg cauguugaag ccguagcaua cacuguugua 1500
uccacaguag aucauuuugu aaacgcaauu gaagagcgug gauuuccgcc aacggccggu 1560
cagccaccgg cgacuacuaa acccaaggaa auuacccccg uaaaccccgg aacgucacca 1620
cuucuacgau augccgcaug gaccggaggg cuugcagcag uaguacuuuu augucucgua 1680
auauuuuuaa ucuguacggc uugaugauaa uaggcuggag ccucggugge caugcuucuu 1740 gccccuuggg ccucccccca gccccuccuc cccuuccugc acccguaccc ccguggucuu 1800
ugaauaaagu cugagugggc ggcaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaucuag 1928

<210> SEQ ID NO 96
<211> LENGTH: 2144
<212> TYPE: RNA
<213> ORGANISM: Artificial Sequence
<220> FEATURE:
<223> OTHER INFORMATION: Synthetic Polynucleotide

<400> SEQUENCE: 96
ggggaaauaa gagagaaaag aagaguaaga agaaauauaa gagccaccau ggggacaguu 60
aauaaaccug ugguggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accaugggu guauaaucag 360 ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaaacauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cccccgagau ugaaccgggu 900
gucuugaaag uacuucggac agaaaaacaa uacuugggug uguacauuug gaacaugcgc 960
ggcuccgaug guacgucuac cuacgccacg uuuuugguca ccuggaaagg ggaugaaaaa 1020
acaagaaacc cuacgcccgc aguaacuccu caaccaagag ggcugaguu ucauaugugg 1080 aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucaaaa uugugaacau gcagauaacu acaccgcaua uugucuggga 1380
auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560

```
gaagagcgug gauuuccgcc aacggccggu cagccaccgg cgacuacuaa acccaaggaa   1620
auuacccccg uaaaccccgg aacgucacca cuucuacgau augccgcaug gaccggaggg   1680
cuugcagcag uaguacuuuu augucucgua auauuuuuaa ucuguacggc uaaacgaaug   1740
aggguuaaag ccuauagggu agacaagucc ccguauaacc aaagcaugua uuacgcuggc   1800
cuuccagugg acgauuucga ggacgccgaa gccgccgaug ccgaagaaga guuugguaac   1860
gcgauuggag ggagucacgg ggguucgagu uacacggugu auauagauaa gacccgguga   1920
ugauaauagg cuggagccuc gguggccaug cuucuugccc cuugggccuc cccccagccc   1980
cuccuccccu uccugcaccc guacccccgu ggucuuugaa uaaagucuga gugggcggca   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaau cuag                    2144
```

<210> SEQ ID NO 97
<211> LENGTH: 2144
<212> TYPE: RNA
<213> ORGANISM: Artificial Sequence
<220> FEATURE:
<223> OTHER INFORMATION: Synthetic Polynucleotide

<400> SEQUENCE: 97

```
ggggaaauaa gagagaaaag aagaguaaga agaaauauaa gagccaccau ggggacaguu     60
aauaaaccug uggugggggu auugaugggg uucggaauua ucacgggaac guugcguaua    120
acgaauccgg ucagagcauc cgucuugcga uacgaugauu uucacaucga ugaagacaaa    180
cuggauacaa acuccguaua ugagccuuac uaccauucag aucaugcgga gucuucaugg    240
guaaaucggg gagagucuuc gcgaaaagcg uacgaucaua acucaccuua uauauggcca    300
cguaaugauu augauggauu uuuagagaac gcacacgaac accauggggu guauaaucag    360
ggccguggua ucgauagcgg ggaacgguua augcaaccca cacaaauguc ugcacaggag    420
gaucuugggg acgauacggg cauccacguu aucccuacgu uaaacggcga ugacagacau    480
aaaauuguaa auguggacca acgucaauac ggugacgugu uuaaaggaga ucuuaaucca    540
aaaccccaag gccaaagacu cauugaggug ucaguggaag aaaaucaccc guuuacuuua    600
cgcgcaccga uucagcggau uuauggaguc cgguacaccg agacuuggag cuuuuugccg    660
ucauuaaccu guacgggaga cgcagcgccc gccauccagc auauauguuu aaaacauaca    720
acaugcuuuc aagacguggu gguggaugug gauugcgcgg aaaauacuaa agaggaucag    780
uuggccgaaa ucaguuaccg uuuucaaggu aagaaggaag cggaccaacc guggauuguu    840
guaaacacga gcacacuguu ugaugaacuc gaauuagacc cccccgagau ugaaccgggu    900
gucuugaaag uacuucggac agaaaaacaa uacuugggug uguacauuug gaacaugcgc    960
ggcuccgaug guacgucuac cuacgccacg uuuuugguca ccuggaaagg ggaugaaaaa   1020
acaagaaacc cuacgcccgc aguaacuccu caaccaagag ggcugaguu ucauaugugg   1080
aauuaccacu cgcauguauu uucaguuggu gauacguuua gcuuggcaau gcaucuucag   1140
uauaagauac augaagcgcc auuugauuug cuguuagagu gguuguaugu ccccaucgau   1200
ccuacauguc aaccaaugcg guuauauucu acguguuugu aucaucccaa cgcaccccaa   1260
ugccucucuc auaugaauuc cgguuguaca uuuaccucgc cacauuuagc ccagcguguu   1320
gcaagcacag uguaucaaaa uugugaacau gcagauaacu acaccgcaua uugucuggga   1380
auaucucaua uggagccuag cuuuggucua aucuuacacg acgggggcac cacguuaaag   1440
uuuguagaua cacccgagag uuugucggga uuauacguuu uuguggugua uuuuaacggg   1500
```

cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uaaacgaaug 1740
aggguuaaag ccuauagggu agacaagucc ccguauaacc aaagcaugua uggcgcuggc 1800
cuuccagugg acgauuucga ggacgccgaa gccgccgaug ccgaagaaga guuugguaac 1860
gcgauuggag ggagucacgg ggguucgagu uacacggugu auauagauaa gacccgguga 1920
ugauaauagg cuggagccuc gguggccaug cuucuugccc cuugggccuc cccccagccc 1980
cuccuccccu uccugcaccc guacccccgu ggucuuugaa uaaagucuga gugggcggca 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaau cuag 2144

<210> SEQ ID NO 98
<211> LENGTH: 1994
<212> TYPE: RNA
<213> ORGANISM: Artificial Sequence
<220> FEATURE:
<223> OTHER INFORMATION: Synthetic Polynucleotide

<400> SEQUENCE: 98
ggggaaauaa gagagaaaag aagaguaaga agaaauauaa gagccaccau ggggacaguu 60
aauaaaccug uggugggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaaacauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cccccgagau ugaaccgggu 900
gucuugaaag uacuucggac agaaaaacaa uacuugggug uguacauuug gaacaugcgc 960
ggcuccgaug guacgucuac cuacgccacg uuuuugguca ccuggaaagg ggaugaaaaa 1020
acaagaaacc cuacgcccgc aguaacuccu caaccaagag ggcugaguu ucauaugugg 1080 aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucaaaa uugugaacau gcagauaacu acaccgcaua uugucugga 1380 auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uaaacgaaug 1740
aggguuaaag ccuauagggu agacaaguga ugauaaauagg cuggagccuc gguggccaug 1800
cuucuugccc cuugggccuc cccccagccc cuccuccccu uccugcaccc guaccccgu 1860 ggucuuugaa uaaagucuga gugggcggca aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaau cuag 1994

<210> SEQ ID NO 99
<211> LENGTH: 1994
<212> TYPE: RNA
<213> ORGANISM: Artificial Sequence
<220> FEATURE:
<223> OTHER INFORMATION: Synthetic Polynucleotide

<400> SEQUENCE: 99
ggggaaauaa gagagaaaag aagaguaaga agaaauauaa gagccaccau ggggacaguu 60
aauaaaccug ugguggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accaugggu guauaaucag 360 ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaaacauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cccccgagau ugaaccgggu 900
gucuugaaag uacuucggac agaaaaacaa uacuugggug uguacauuug gaacaugcgc 960
ggcuccgaug guacgucuac cuacgccacg uuuuugguca ccuggaaagg ggaugaaaaa 1020
acaagaaacc cuacgcccgc aguaacuccu caaccaagag gggcugaguu ucauaugugg 1080
aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucaaaa uugugaacau gcagauaacu acaccgcaua uugucuggga 1380
auaucucaua uggagccuag cuuuggucua aucuuacacg acgggggcac cacguuaaag 1440

```
uuuguagaua cacccgagag uuugucggga uuauacguuu uuguggugua uuuuaacggg   1500
cauguugaag ccguagcaua cacuguugua uccacaguag aucauuuugu aaacgcaauu   1560
gaagagcgug gauuuccgcc aacggccggu cagccaccgg cgacuacuaa acccaaggaa   1620
auuacccccg uaaaccccgg aacgucacca cuucuacgau augccgcaug gaccggaggg   1680
cuugcagcag uaguacuuuu augucucgua auauuuuuaa ucuguacggc uaaacgaaug   1740
aggguuaaag ccgccagggu agacaaguga ugauaaauagg cuggagccuc gguggccaug   1800
cuucuugccc cuugggccuc cccccagccc cuccuccccu uccugcaccc guacccccgu   1860
ggucuuugaa uaaagucuga gugggcggca aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaau cuag                                                      1994
```

<210> SEQ ID NO 100
<211> LENGTH: 1337
<212> TYPE: RNA
<213> ORGANISM: Artificial Sequence
<220> FEATURE:
<223> OTHER INFORMATION: Synthetic Polynucleotide

<400> SEQUENCE: 100

```
ggggaaauaa gagagaaaag aagaguaaga agaaauauaa gagccaccau guuuuuaauc     60
caauguuuga uaucggccgu uauauuuuac auacaaguga ccaacgcuuu gaucuucaag    120
ggcgaccacg ugagcuugca aguuaacagc agucucacgu cuauccuuau ucccaugcaa    180
aaugauaauu auacagagau aaaaggacag cuugucuuua uuggagagca acuaccuacc    240
gggacaaacu auagcggaac acuggaacug uuauacgcgg auacggugc guuuuguuuc    300
cggucaguac aaguaauaag auacgacgga uguccccgga uuagaacgag cgcuuuuauu    360
ucguguaggu acaaacauuc guggcauuau gguaacucaa cggaucggau aucaacagag    420
ccggaugcug guguaauguu gaaaauuacc aaaccgggaa uaaaugaugc ugguguguau    480
guacuucuug uucgguuaga ccauagcaga uccaccgaug guuucauucu ugguguaaau    540
guauauacag cgggcucgca ucacaacauu cacgggguua ucuacacuuc uccaucucua    600
cagaauggau auucuacaag agcccuuuuu caacaagcuc guuuguguga uuuacccgcg    660
acacccaaag gguccgguac cucccuguuu caacauaugc uugaucuucg ugccgguaaa    720
ucguuagagg auaacccuug guuacaugag gacguuguua cgacagaaac uaaguccguu    780
guuaaggagg ggauagaaaa ucacguauau ccaacggaua uguccacguu acccgaaaag    840
ucccuuaaug auccuccaga aaaucuacuu auaauuauuc cuauaguagc gucugucaug    900
auccucaccg ccaugguuau uguuauugua auaagcguua agcgacguag aauuaaaaaa    960
cauccaauuu aucgcccaaa uacaaaaaca agaaggggca uacaaaaugc gacaccagaa   1020
uccgauguga uguuggaggc cgccauugca caacuagcaa cgauucgcga agaauccccc   1080
ccacauuccg uuguaaaccc guuuguuaaa uagugauaau aggcuggagc cucgguggcc   1140
augcuucuug ccccuugggc cuccccccag ccccuccucc ccuuccugca cccguacccc   1200
cguggucuuu gaauaaaguc ugagugggcg gcaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaucuag                                                  1337
```

<210> SEQ ID NO 101

<211> LENGTH: 1991
<212> TYPE: RNA
<213> ORGANISM: Artificial Sequence
<220> FEATURE:
<223> OTHER INFORMATION: Synthetic Polynucleotide

<400> SEQUENCE: 101
ggggaaauaa gagagaaaag aagaguaaga agaaauauaa gagccaccau gggcaccgug 60
aacaagcccg ucgugggcgu gcugaugggc uucggcauca ucaccggcac ccugcggauc 120
accaauccug ugcgggccag cgugcugaga uacgacgacu uccacaucga cgaggacaag 180
cuggacacca acagcgugua cgagcccuac uaccacagcg accacgccga gagcagcugg 240
gucaacagag gcgaguccag ccggaaggcc uacgaccaca acagccccua caucuggccc 300
cggaacgacu acgacggcuu ccuggaaaau gcccacgagc accacggcgu guacaaccag 360
ggcagaggca ucgacagcgg cgagagacug augcagccca cccagaugag cgcccaggaa 420
gaucugggcg acgacaccgg cauccacgug aucccuaccc ugaacggcga cgaccggcac 480
aagaucguga acguggacca gcggcaguac ggcgacgugu ucaagggcga ccugaacccc 540
aagccccagg gacagcggcu gauugaggug uccguggaag agaaccaccc cuucacccug 600
agagccccua uccagcggau cuacggcgug cgcuauaccg agacuuggag cuuccugccc 660
agccugaccu guacuggcga cgccgcuccu gccauccagc acaucugccu gaagcacacc 720
accuguuucc aggacguggu gguggacgug gacugcgccg agaacaccaa agaggaccag 780
cuggccgaga ucagcuaccg guuccagggc aagaaagagg ccgaccagcc cuggaucguc 840
gugaacacca gcacccuguu cgacgagcug gaacuggacc cucccgagau cgaacccggg 900
gugcugaagg ugcugcggac cgagaagcag uaccugggag uguacaucug gaacaugcgg 960
ggcagcgacg gcaccucuac cuacgccacc uuccucguga ccuggaaggg cgacgagaaa 1020
acccggaacc cuaccccugc cgugaccccu cagccuagag gcgccgaguu ucacaugugg 1080
aauuaccaca gccacguguu cagcgugggc gacaccuucu cccuggccau gcaucugcag 1140
uacaagaucc acgaggcccc uuucgaccug cugcuggaau ggcuguacgu gcccaucgac 1200
ccuaccugcc agcccaugcg gcuguacucc accugucugu accaccccaa cgccccucag 1260
ugccugagcc acaugaauag cggcugcacc uucaccagcc cucaccuggc ucagagggug 1320
gccagcaccg uguaccagaa uugcgagcac gccgacaacu acaccgccua cugccugggc 1380
aucagccaca uggaacccag cuucggccug auccugcacg auggcggcac cacccugaag 1440
uucguggaca ccccugaguc ccugagcggc cuguacgugu ucguggugua cuucaacggc 1500
cacguggaag ccguggccua caccguggug uccaccgugg accacuucgu gaacgccauc 1560
gaggaacggg gcuucccucc aacugcugga cagccuccug ccaccaccaa gcccaaagaa 1620
aucaccccug ugaaccccgg caccagccca cugcugcgcu augcugcuug gacaggcgga 1680
cuggcugcug uggugcugcu gugccucgug auuuuccuga ucugcaccgc caagcggaug 1740
agagugaagg ccgccagagu ggacaaguga uaauaggcug gagccucggu ggccaugcuu 1800
cuugccccuu gggccucccc ccagccccuc cuccccuucc ugcacccgua cccccguggu 1860
cuuugaauaa agucugagug ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaucua g 1991

<210> SEQ ID NO 102
<211> LENGTH: 1991

-continued

<212> TYPE: RNA
<213> ORGANISM: Artificial Sequence
<220> FEATURE:
<223> OTHER INFORMATION: Synthetic Polynucleotide

<400> SEQUENCE: 102

```
ggggaaauaa gagagaaaag aagaguaaga agaaauauaa gagccaccau ggggacaguu     60

aauaaaccug ugguggggu auugaugggg uucggaauua ucacgggaac guugcguaua    120

acgaauccgg ucagagcauc cgucuugcga uacgaugauu uucacaucga ugaagacaaa    180

cuggauacaa acuccguaua ugagccuuac uaccauucag aucaugcgga gucuucaugg    240

guaaaucggg gagagucuuc gcgaaaagcg uacgaucaua acucaccuua uauauggcca    300

cguaaugauu augauggauu uuuagagaac gcacacgaac accaugggggu guauaaucag    360

ggccguggua ucgauagcgg ggaacgguua augcaaccca cacaaauguc ugcacaggag    420

gaucuugggg acgauacggg cauccacguu aucccuacgu uaaacggcga ugacagacau    480

aaaauuguaa auguggacca acgucaauac ggugacgugu uuaaaggaga ucuuaaucca    540

aaaccccaag gccaaagacu cauugaggug ucaguggaag aaaaucaccc guuuacuuua    600

cgcgcaccga uucagcggau uuauggaguc cgguacaccg agacuuggag cuuuuugccg    660

ucauuaaccu guacgggaga cgcagcgccc gccauccagc auauauguuu aaaacauaca    720

acaugcuuuc aagacguggu gguggaugug gauugcgcgg aaaauacuaa agaggaucag    780

uuggccgaaa ucaguuaccg uuuucaaggu aagaaggaag cggaccaacc guggauuguu    840

guaaacacga gcacacuguu ugaugaacuc gaauuagacc cccccgagau ugaaccgggu    900

gucuugaaag uacuucggac agagaaacaa uacuugggug uguacauuug gaacaugcgc    960

ggcuccgaug guacgucuac cuacgccacg uuuuugguca ccuggaaagg ggaugagaag   1020

acaagaaacc cuacgcccgc aguaacuccu caaccaagag gggcugaguu ucauaugugg   1080

aauuaccacu cgcauguauu uucaguuggu gauacguuua gcuuggcaau gcaucuucag   1140

uauaagauac augaagcgcc auuugauuug cuguuagagu gguuguaugu ccccaucgau   1200

ccuacauguc aaccaaugcg guuauauucu acguguuugu aucaucccaa cgcaccccaa   1260

ugccucucuc auaugaauuc cgguuguaca uuuaccucgc cacauuuagc ccagcguguu   1320

gcaagcacag uguaucaaaa uugugaacau gcagauaacu acaccgcaua uugucuggga   1380

auaucucaua uggagccuag cuuuggucua aucuuacacg acgggggcac cacguuaaag   1440

uuuguagaua cacccgagag uuugucggga uuauacguuu uuguggugua uuuuaacggg   1500

cauguugaag ccguagcaua cacuguugua uccacaguag aucauuuugu aaacgcaauu   1560

gaagagcgug gauuuccgcc aacggccggu cagccaccgg cgacuacuaa acccaaggaa   1620

auuacccccg uaaaccccgg aacgucacca cuucuacgau augccgcaug gaccggaggg   1680

cuugcagcag uaguacuuuu augucucgua auauuuuuaa ucuguacggc uaaacgaaug   1740

aggguuaaag ccgccagggu agacaaguga uaauaggcug gagccucggu ggccaugcuu   1800

cuugccccuu gggccucccc ccagccccuc cuccccuucc ugcacccgua cccccguggu   1860

cuuugaauaa agucugagug ggcggcaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaucua g                                                        1991
```

<210> SEQ ID NO 103
<211> LENGTH: 1991
<212> TYPE: RNA

<213> ORGANISM: Artificial Sequence
<220> FEATURE:
<223> OTHER INFORMATION: Synthetic Polynucleotide

<400> SEQUENCE: 103
ggggaaauaa gagagaaaag aagaguaaga agaaauauaa gagccaccau ggggacaguu 60
aauaaaccug ugguggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaaacauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cacccgagau ugaaccgggu 900
gucuugaaag uacuucggac agagaaacaa uacuugggug uguacauuug gaacaugcgc 960
ggcuccgaug guacgucuac cuacgccacg uuuuugguca ccuggaaagg ggaugagaag 1020
acaagaaacc cuacgcccgc aguaacuccu caaccaagag gggcugaguu ucauaugugg 1080
aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucaaaa uugugaacau gcagauaacu acaccgcaua uugucuggga 1380
auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua ucccacagua g aucauuuugu aaacgcaauu 1560
gaagagcgug gauuuccgcc aacggccggu cagccaccgg cgacuacuaa acccaaggaa 1620
auuacccccg uaaacccegg aacgucacca cuucuacgau augccgcaug gaccggaggg 1680
cuugcagcag uaguacuuuu augucucgua auauuuuuaa ucuguacggc uaaacgaaug 1740
aggguuaaag ccgccagggu agacaaguga uaauaggcug gagccucggu ggccaugcuu 1800
cuugccccuu gggccucccc ccagccccuc cuccccuucc ugcacccgua cccccguggu 1860
cuuugaauaa agucugagug ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaucua g 1991

<210> SEQ ID NO 104
<211> LENGTH: 1991
<212> TYPE: RNA
<213> ORGANISM: Artificial Sequence
<220> FEATURE:
<223> OTHER INFORMATION: Synthetic Polynucleotide

<400> SEQUENCE: 104

```
ggggaaauaa gagagaaaag aagaguaaga agaaauauaa gagccaccau ggggacaguu     60
aauaaaccug uggugggggu auugaugggg uucggaauua ucacgggaac guugcguaua    120
acgaauccgg ucagagcauc cgucuugcga uacgaugauu uucacaucga ugaagacaaa    180
cuggauacaa acuccguaua ugagccuuac uaccauucag aucaugcgga gucuucaugg    240
guaaaucggg gagagucuuc gcgaaaggcg uacgaucaua acucaccuua uauauggcca    300
cguaaaugauu augauggauu uuuagagaac gcacacgaac accauggggu guauaaaucag   360
ggccguggua ucgauagcgg ggaacgguua augcaaccca cacaaauguc ugcacaggag    420
gaucuugggg acgauacggg cauccacguu aucccuacgu uaaacggcga ugacagacau    480
aagauuguaa auguggacca acgucaauac ggugacgugu uuaaaggaga ucuuaaucca    540
aagccccaag gccaaagacu cauugaggug ucaguggaag agaaucaccc guuuacuuua    600
cgcgcaccga uucagcggau uuauggaguc cgguacaccg agacuuggag cuuuuugccg    660
ucauuaaccu guacgggaga cgcagcgccc gccauccagc auauauguuu aaagcauaca    720
acaugcuuuc aagacguggu gguggaugug gauugcgcgg agaauacuaa agaggaucag    780
uuggccgaaa ucaguuaccg uuuucaaggu aagaaggaag cggaccaacc guggauuguu    840
guaaacacga gcacacuguu ugaugaacuc gaauuagacc cccccgagau ugaaccgggu    900
gucuugaaag uacuucggac agagaaacaa uacuugggug uguacauuug gaacaugcgc    960
ggcuccgaug guacgucuac cuacgccacg uuuuugguca ccuggaaagg ggaugagaag   1020
acaagaaacc cuacgcccgc aguaacuccu caaccaagag ggcugaguu ucauaugugg   1080
aauuaccacu cgcauguauu uucaguuggu gauacguuua gcuuggcaau gcaucuucag   1140
uauaagauac augaagcgcc auuugauuug cuguuagagu gguuguaugu ccccaucgau   1200
ccuacauguc aaccaaugcg guuauauucu acguguuugu aucaucccaa cgcaccccaa   1260
ugccucucuc auaugaauuc cgguuguaca uuuaccucgc cacauuuagc ccagcguguu   1320
gcaagcacag uguaucagaa uugugaacau gcagauaacu acaccgcaua uugucuggga   1380
auaucucaua uggagccuag cuuuggucua aucuuacacg acgggggcac cacguuaaag   1440
uuuguagaua cacccgagag uuugucggga uuauacguuu uuguggugua uuuuaacggg   1500
cauguugaag ccguagcaua cacuguugua uccacaguag aucauuuugu aaacgcaauu   1560
gaagagcgug gauuuccgcc aacggccggu cagccaccgg cgacuacuaa acccaaggaa   1620
auuacccccg uaaaccccgg aacgucacca cuucuacgau augccgcaug gaccggaggg   1680
cuugcagcag uaguacuuuu augucucgua auauuuuuaa ucuguacggc uaaacgaaug   1740
aggguuaaag ccgccagggu agacaaguga uaauaggcug gagccucggu ggccaugcuu   1800
cuugccccuu gggccucccc ccagccccuc cuccccuucc ugcacccgua cccccguggu   1860
cuuugaauaa agucugagug ggcggcaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaucua g                                                        1991
```

<210> SEQ ID NO 105
<211> LENGTH: 1991
<212> TYPE: RNA
<213> ORGANISM: Artificial Sequence
<220> FEATURE:

<223> OTHER INFORMATION: Synthetic Polynucleotide

<400> SEQUENCE: 105
ggggaaauaa gagagaaaag aagaguaaga agaaauauaa gagccaccau ggggacaguu 60
aauaaaccug uggugggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaggcg uacgaucaua acucaccuua uauauggcca 300
cguaaugauu augauggauu uuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aagauuguaa auguggacca acgucaauac ggugacgugu uuaaaggaga ucuuaaucca 540
aagccccaag gccaaagacu cauugaggug ucaguggaag agaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaagcauaca 720
acaugcuuuc aagacguggu gguggaugug gauugcgcgg agaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cacccgagau ugaaccgggu 900
gucuugaaag uacuucggac agagaaacaa uacuugggug uguacauuug gaacaugcgc 960
ggcuccgaug guacgucuac cuacgccacg uuuuugguca ccuggaaagg ggaugagaag 1020
acaagaaacc cuacgcccgc aguaacuccu caaccaagag gggcugaguu ucauaugugg 1080
aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucagaa uugugaacau gcagauaacu acaccgcaua uugucuggga 1380
auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uaaacgaaug 1740
aggguuaaag ccgccagggu agacaaguga uaauaggcug gagccucggu ggccaugcuu 1800
cuugccccuu gggccucccc ccagccccuc cuccccuucc ugcacccgua cccccguggu 1860
cuuugaauaa agucugagug ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaucua g 1991

<210> SEQ ID NO 106
<211> LENGTH: 1991
<212> TYPE: RNA
<213> ORGANISM: Artificial Sequence
<220> FEATURE:
<223> OTHER INFORMATION: Synthetic Polynucleotide

<400> SEQUENCE: 106
ggggaaauaa gagagaaaag aagaguaaga agaaauauaa gagccaccau ggggacaguu 60
aauaaaccug ugguggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaagcauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cccccgagau ugaaccgggu 900
gucuugaaag uacuucggac agagaaacaa uacuugggug uguacauuug gaacaugcgc 960
ggcuccgaug guacgucuac cuacgccacg uuuuugguca ccuggaaagg ggaugagaag 1020
acaagaaacc cuacgcccgc aguaacuccu caaccaagag ggcugaguu ucauaugugg 1080 aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucagaa uugugaacau gcagauaacu acaccgcaua uugucuggga 1380
auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uaaacgaaug 1740
aggguuaaag ccgccagggu agacaaguga uaauaggcug gagccucggu ggccaugcuu 1800
cuugccccuu gggccucccc ccagccccuc cuccccuucc ugcacccgua cccccguggu 1860
cuuugaauaa agucugagug ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaucua g 1991

<210> SEQ ID NO 107
<211> LENGTH: 1991
<212> TYPE: RNA
<213> ORGANISM: Artificial Sequence
<220> FEATURE:
<223> OTHER INFORMATION: Synthetic Polynucleotide

<400> SEQUENCE: 107
ggggaaauaa gagagaaaag aagaguaaga agaaauauaa gagccaccau ggggacaguu 60
aauaaaccug uggugggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaagcauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cacccgagau ugaaccgggu 900
gucuugaaag uacuucggac agagaaacaa uacuugggug uguacauuug gaacaugcgc 960
ggcuccgaug guacgucuac cuacgccacg uuuuugguca ccuggaaagg ggaugagaag 1020
acaagaaacc cuacgcccgc aguaacuccu caaccaagag ggcugaguu ucauaugugg 1080
aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucagaa uugugaacau gcagauaacu acaccgcaua uugucuggga 1380
auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uaaacgaaug 1740
aggguuaaag ccgccagggu agacaaguga uaauaggcug gagccucggu ggccaugcuu 1800
cuugccccuu gggccucccc ccagccccuc cuccccuucc ugcacccgua cccccguggu 1860
cuuugaauaa agucugagug ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaucua g 1991

<210> SEQ ID NO 108
<211> LENGTH: 1965
<212> TYPE: RNA
<213> ORGANISM: Artificial Sequence
<220> FEATURE:
<223> OTHER INFORMATION: Synthetic Polynucleotide

<400> SEQUENCE: 108

-continued

```
gagaagaaau auaagagcca ccauggggac aguuaauaaa ccuguggugg gcguauugau     60
gggguucgga auuaucacgg gaacguugcg uauaacgaau ccggucagag cauccgucuu    120
gcgauacgau gauuuucaca ucgaugaaga caaacuggau acaaacuccg uauaugagcc    180
uuacuaccau ucagaucaug cggagucuuc augguaaau cggggagagu cuucgcgaaa     240
ggcguacgau cauaacucac cuuauauaug gccacguaau gauuaugaug gauucuuaga    300
gaacgcacac gaacaccaug ggguguauaa ucagggccgu gguaucgaua gcggggaacg    360
guuaaugcaa cccacacaaa ugucugcaca ggaggaucuu ggggacgaua cgggcaucca    420
cguuaucccu acguuaaacg gcgaugacag acauaaagauu guaaaugugg accaacguca   480
auacggugac guguuuaaag gagaucuuaa uccaaagccc caaggccaaa gacucauuga    540
ggugucagug gaagagaauc acccguuuac uuuacgcgca ccgauucagc ggauuuaugg    600
aguccgguac accgagacuu ggagcuucuu gccgucauua accuguacgg gagacgcagc    660
gcccgccauc cagcauauau guuuaaagca uacaacaugc uuucaagacg ugguggugga    720
uguggauugc gcggagaaua cuaaagagga ucaguuggcc gaaaucaguu accguuuuca    780
agguaagaag gaagcggacc aaccguggau uguuguaaac acgagcacac uguuugauga    840
acucgaauua gacccacccg agauugaacc gggugucuug aaaguacuuc ggacagagaa    900
acaauacuug gguguguaca uuuggaacau gcgcggcucc gaugguacgu cuaccuacgc    960
cacguucuug gucaccugga aaggggauga gaagacaaga aacccuacgc ccgcaguaac   1020
uccucaacca agaggggcug aguuucauau guggaauuac cacucgcaug uauuuucagu   1080
uggugauacg uuuagcuugg caaugcaucu ucaguauaag auacaugaag cgccauuuga   1140
uuugcuguua gagugguugu auguccccau cgauccuaca ugucaaccaa ugcgguuaua   1200
uucuacgugu uuguaucauc ccaacgcacc ccaaugccuc ucucauauga auuccgguug   1260
uacauuuacc ucgccacauu uagcccagcg uguugcaagc acaguguauc agaauuguga   1320
acaugcagau aacuacaccg cauauugucu gggaauaucu cauauggagc cuagcuuugg   1380
ucuaaucuua cacgacggag gcaccacguu aaaguuugua gauacacccg agaguuuguc   1440
gggauuauac gucuuugugg uguauuuuaa cgggcauguu gaagccguag cauacacugu   1500
uguauccaca guagaucauu uuguaaacgc aauugaagag cguggauuuc cgccaacggc   1560
cggucagcca ccggcgacua cuaaacccaa ggaaauuacg cccguaaacc ccggaacguc   1620
accacuucua cgauaugccg cauggaccgg agggcuugca gcaguaguac uuuuaugucu   1680
cguaauauuc uuaaucugua cggcuaaacg aaugagggu aaagccgcca ggguagacaa    1740
gugauaauag gcuggagccu cgguggccau gcuucuugcc ccuugggccu ccccccagcc   1800
ccuccucccc uuccugcacc cguacccccg uggucuuuga auaaagucug agugggcggc   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa ucuag                   1965
```

```
<210> SEQ ID NO 109
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 109

Met Leu Gly Ser Asn Ser Gly Gln Arg Val Val Phe Thr Ile Leu Leu
1               5                   10                  15
```

Leu Leu Val Ala Pro Ala Tyr Ser
20

<210> SEQ ID NO 110
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 110

Met Lys Cys Leu Leu Tyr Leu Ala Phe Leu Phe Ile Gly Val Asn Cys
1 5 10 15

Ala

<210> SEQ ID NO 111
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 111

Met Trp Leu Val Ser Leu Ala Ile Val Thr Ala Cys Ala Gly Ala
1 5 10 15

<210> SEQ ID NO 112
<211> LENGTH: 1729
<212> TYPE: DNA
<213> ORGANISM: Artificial Sequence
<220> FEATURE:
<223> OTHER INFORMATION: Synthetic Polynucleotide

<400> SEQUENCE: 112
tcaagctttt ggaccctcgt acagaagcta atacgactca ctatagggaa ataagagaga 60
aaagaagagt aagaagaaat ataagagcca ccatggcaca agtcattaat acaaacagcc 120
tgtcgctgtt gacccagaat aacctgaaca aatcccagtc cgcactgggc actgctatcg 180
agcgtttgtc ttccggtctg cgtatcaaca gcgcgaaaga cgatgcggca ggacaggcga 240
ttgctaaccg ttttaccgcg aacatcaaag gtctgactca ggcttcccgt aacgctaacg 300
acggtatctc cattgcgcag accactgaag gcgcgctgaa cgaaatcaac aacaacctgc 360
agcgtgtgcg tgaactggcg gttcagtctg cgaatggtac taactcccag tctgacctcg 420
actccatcca ggctgaaatc acccagcgcc tgaacgaaat cgaccgtgta tccggccaga 480
ctcagttcaa cggcgtgaaa gtcctggcgc aggacaacac cctgaccatc caggttggtg 540
ccaacgacgg tgaaactatc gatattgatt taaaagaaat cagctctaaa acactgggac 600
ttgataagct taatgtccaa gatgcctaca ccccgaaaga aactgctgta accgttgata 660
aaactaccta taaaaatggt acagatccta ttacagccca gagcaatact gatatccaaa 720
ctgcaattgg cggtggtgca acgggggtta ctggggctga tatcaaattt aaagatggtc 780
aatactattt agatgttaaa ggcggtgctt ctgctggtgt ttataaagcc acttatgatg 840
aaactacaaa gaaagttaat attgatacga ctgataaaac tccgttggca actgcggaag 900
ctacagctat tcggggaacg gccactataa cccacaacca aattgctgaa gtaacaaaag 960
agggtgttga tacgaccaca gttgcggctc aacttgctgc agcaggggtt actggcgccg 1020
ataaggacaa tactagcctt gtaaaactat cgtttgagga taaaaacggt aaggttattg 1080
atggtggcta tgcagtgaaa atgggcgacg atttctatgc cgctacatat gatgagaaaa 1140
caggtgcaat tactgctaaa accactactt atacagatgg tactggcgtt gctcaaactg 1200
gagctgtgaa atttggtggc gcaaatggta aatctgaagt tgttactgct accgatggta 1260
agacttactt agcaagcgac cttgacaaac ataacttcag aacaggcggt gagcttaaag 1320
aggttaatac agataagact gaaaacccac tgcagaaaat tgatgctgcc ttggcacagg 1380
ttgatacact tcgttctgac ctgggtgcgg ttcagaaccg tttcaactcc gctatcacca 1440
acctgggcaa taccgtaaat aacctgtctt ctgcccgtag ccgtatcgaa gattccgact 1500
acgcaaccga agtctccaac atgtctcgcg cgcagattct gcagcaggcc ggtacctccg 1560
ttctggcgca ggcgaaccag gttccgcaaa acgtcctctc tttactgcgt tgataatagg 1620
ctggagcctc ggtggccatg cttcttgccc cttgggcctc cccccagccc ctcctcccct 1680
tcctgcaccc gtacccccgt ggtctttgaa taaagtctga gtgggcggc 1729

<210> SEQ ID NO 113
<211> LENGTH: 1518
<212> TYPE: DNA
<213> ORGANISM: Artificial Sequence
<220> FEATURE:
<223> OTHER INFORMATION: Synthetic Polynucleotide

<400> SEQUENCE: 113
atggcacaag tcattaatac aaacagcctg tcgctgttga cccagaataa cctgaacaaa 60
tcccagtccg cactgggcac tgctatcgag cgtttgtctt ccggtctgcg tatcaacagc 120
gcgaaagacg atgcggcagg acaggcgatt gctaaccgtt ttaccgcgaa catcaaaggt 180
ctgactcagg cttcccgtaa cgctaacgac ggtatctcca ttgcgcagac cactgaaggc 240
gcgctgaacg aaatcaacaa caacctgcag cgtgtgcgtg aactggcggt tcagtctgcg 300
aatggtacta actcccagtc tgacctcgac tccatccagg ctgaaatcac ccagcgcctg 360
aacgaaatcg accgtgtatc cggccagact cagttcaacg gcgtgaaagt cctggcgcag 420
gacaacaccc tgaccatcca ggttggtgcc aacgacggtg aaactatcga tattgattta 480
aaagaaatca gctctaaaac actgggactt gataagctta atgtccaaga tgcctacacc 540
ccgaaagaaa ctgctgtaac cgttgataaa actacctata aaaatggtac agatcctatt 600
acagcccaga gcaatactga tatccaaact gcaattggcg gtggtgcaac gggggttact 660
ggggctgata tcaaatttaa agatggtcaa tactatttag atgttaaagg cggtgcttct 720
gctggtgttt ataaagccac ttatgatgaa actacaaaga aagttaatat tgatacgact 780
gataaaactc cgttggcaac tgcggaagct acagctattc ggggaacggc cactataacc 840
cacaaccaaa ttgctgaagt aacaaaagag ggtgttgata cgaccacagt tgcggctcaa 900
cttgctgcag caggggttac tggcgccgat aaggacaata ctagccttgt aaaactatcg 960
tttgaggata aaaacggtaa ggttattgat ggtggctatg cagtgaaaat gggcgacgat 1020
ttctatgccg ctacatatga tgagaaaaca ggtgcaatta ctgctaaaac cactacttat 1080
acagatggta ctggcgttgc tcaaactgga gctgtgaaat ttggtggcgc aaatggtaaa 1140
tctgaagttg ttactgctac cgatggtaag acttacttag caagcgacct tgacaaacat 1200
aacttcagaa caggcggtga gcttaaagag gttaatacag ataagactga aaacccactg 1260
cagaaaattg atgctgcctt ggcacaggtt gatacacttc gttctgacct gggtgcggtt 1320
cagaaccgtt tcaactccgc tatcaccaac ctgggcaata ccgtaaataa cctgtcttct 1380
gcccgtagcc gtatcgaaga ttccgactac gcaaccgaag tctccaacat gtctcgcgcg 1440
cagattctgc agcaggccgg tacctccgtt ctggcgcagg cgaaccaggt tccgcaaaac 1500
gtcctctctt tactgcgt 1518

<210> SEQ ID NO 114
<211> LENGTH: 1790
<212> TYPE: RNA
<213> ORGANISM: Artificial Sequence
<220> FEATURE:
<223> OTHER INFORMATION: Synthetic Polynucleotide

<400> SEQUENCE: 114
ggggaaauaa gagagaaaag aagaguaaga agaaauauaa gagccaccau ggcacaaguc 60
auuaauacaa acagccuguc gcuguugacc cagaauaacc ugaacaaauc ccaguccgca 120
cugggcacug cuaucgagcg uuugucuucc ggucugcgua ucaacagcgc gaaagacgau 180
gcggcaggac aggcgauugc uaaccguuuu accgcgaaca ucaaaggucu gacucaggcu 240
ucccguaacg cuaacgacgg uaucuccauu gcgcagacca cugaaggcgc gcugaacgaa 300
aucaacaaca accugcagcg ugugcgugaa cuggcgguuc agucugcgaa ugguacuaac 360
ucccagucug accucgacuc cauccaggcu gaaaucaccc agcgccugaa cgaaaucgac 420
cguguauccg gccagacuca guucaacggc gugaaagucc uggcgcagga caacacccug 480
accauccagg uuggugccaa cgacggugaa acuaucgaua uugauuuaaa agaaaucagc 540
ucuaaaacac ugggacuuga uaagcuuaau guccaagaug ccuacacccc gaaagaaacu 600
gcuguaaccg uugauaaaac uaccuauaaa aaugguacag auccuauuac agcccagagc 660
aauacugaua uccaaacugc aauuggcggu ggugcaacgg ggguuacugg ggcugauauc 720
aaauuuaaag auggucaaua cuauuuagau guuaaaggcg gugcuucugc ugguguuuau 780
aaagccacuu augaugaaac uacaaagaaa guuaauauug auacgacuga uaaaacuccg 840
uuggcaacug cggaagcuac agcuauucgg ggaacggcca cuauaaccca caaccaaauu 900
gcugaaguaa caaaagaggg uguugauacg accacaguug cggcucaacu ugcugcagca 960
gggguuacug gcgccgauaa ggacaauacu agccuuguaa aacuaucguu ugaggauaaa 1020
aacgguaagg uuauugaugg uggcuaugca gugaaaaugg gcgacgauuu cuaugccgcu 1080
acauaugaug agaaaacagg ugcaauuacu gcuaaaacca cuacuuauac agaugguacu 1140
ggcguugcuc aaacuggagc ugugaaauuu gguggcgcaa augguaaauc ugaaguuguu 1200
acugcuaccg augguaagac uuacuuagca agcgaccuug acaaacauaa cuucagaaca 1260
ggcggugagc uuaaagaggu uaauacagau aagacugaaa acccacugca gaaaauugau 1320
gcugccuugg cacagguuga uacacuucgu ucugaccugg gugcgguuca gaaccguuuc 1380
aacuccgcua ucaccaaccu gggcaauacc guaaauaacc ugucuucugc ccguagccgu 1440
aucgaagauu ccgacuacgc aaccgaaguc uccaacaugu cucgcgcgca gauucugcag 1500
caggccggua ccuccguucu ggcgcaggcg aaccagguuc cgcaaaacgu ccucucuuua 1560
cugcguugau aauaggcugg agccucggug gccaugcuuc uugccccuug ggccuccccc 1620
cagccccucc uccccuuccu gcacccguac cccguggguc uuugaauaaa gucugagugg 1680
gcggcaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaucuag 1790

<210> SEQ ID NO 115
<211> LENGTH: 506
<212> TYPE: PRT
<213> ORGANISM: Artificial Sequence
<220> FEATURE:
<223> OTHER INFORMATION: Synthetic Polypeptide

<400> SEQUENCE: 115

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Gly Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Glu Ile Ser Ser Lys Thr Leu Gly Leu Asp Lys Leu Asn Val Gln
                165                 170                 175

Asp Ala Tyr Thr Pro Lys Glu Thr Ala Val Thr Val Asp Lys Thr Thr
            180                 185                 190

Tyr Lys Asn Gly Thr Asp Pro Ile Thr Ala Gln Ser Asn Thr Asp Ile
        195                 200                 205

Gln Thr Ala Ile Gly Gly Gly Ala Thr Gly Val Thr Gly Ala Asp Ile
    210                 215                 220

Lys Phe Lys Asp Gly Gln Tyr Tyr Leu Asp Val Lys Gly Gly Ala Ser
225                 230                 235                 240

Ala Gly Val Tyr Lys Ala Thr Tyr Asp Glu Thr Thr Lys Lys Val Asn
                245                 250                 255

Ile Asp Thr Thr Asp Lys Thr Pro Leu Ala Thr Ala Glu Ala Thr Ala
            260                 265                 270

Ile Arg Gly Thr Ala Thr Ile Thr His Asn Gln Ile Ala Glu Val Thr
        275                 280                 285

Lys Glu Gly Val Asp Thr Thr Thr Val Ala Ala Gln Leu Ala Ala Ala
    290                 295                 300

Gly Val Thr Gly Ala Asp Lys Asp Asn Thr Ser Leu Val Lys Leu Ser
305                 310                 315                 320

Phe Glu Asp Lys Asn Gly Lys Val Ile Asp Gly Gly Tyr Ala Val Lys
                325                 330                 335

Met Gly Asp Asp Phe Tyr Ala Ala Thr Tyr Asp Glu Lys Thr Gly Ala
            340                 345                 350

Ile Thr Ala Lys Thr Thr Thr Tyr Thr Asp Gly Thr Gly Val Ala Gln
        355                 360                 365

Thr Gly Ala Val Lys Phe Gly Gly Ala Asn Gly Lys Ser Glu Val Val
    370                 375                 380

Thr Ala Thr Asp Gly Lys Thr Tyr Leu Ala Ser Asp Leu Asp Lys His
385                 390                 395                 400
```

Asn Phe Arg Thr Gly Gly Glu Leu Lys Glu Val Asn Thr Asp Lys Thr
405 410 415

Glu Asn Pro Leu Gln Lys Ile Asp Ala Ala Leu Ala Gln Val Asp Thr
420 425 430

Leu Arg Ser Asp Leu Gly Ala Val Gln Asn Arg Phe Asn Ser Ala Ile
435 440 445

Thr Asn Leu Gly Asn Thr Val Asn Asn Leu Ser Ser Ala Arg Ser Arg
450 455 460

Ile Glu Asp Ser Asp Tyr Ala Thr Glu Val Ser Asn Met Ser Arg Ala
465 470 475 480

Gln Ile Leu Gln Gln Ala Gly Thr Ser Val Leu Ala Gln Ala Asn Gln
485 490 495

Val Pro Gln Asn Val Leu Ser Leu Leu Arg
500 505

<210> SEQ ID NO 116
<211> LENGTH: 698
<212> TYPE: PRT
<213> ORGANISM: Artificial Sequence
<220> FEATURE:
<223> OTHER INFORMATION: Synthetic Polypeptide

<400> SEQUENCE: 116

Met Ala Gln Val Ile Asn Thr Asn Ser Leu Ser Leu Leu Thr Gln Asn
1 5 10 15

Asn Leu Asn Lys Ser Gln Ser Ala Leu Gly Thr Ala Ile Glu Arg Leu
20 25 30

Ser Ser Gly Leu Arg Ile Asn Ser Ala Lys Asp Asp Ala Ala Gly Gln
35 40 45

Ala Ile Ala Asn Arg Phe Thr Ala Asn Ile Lys Gly Leu Thr Gln Ala
50 55 60

Ser Arg Asn Ala Asn Asp Gly Ile Ser Ile Ala Gln Thr Thr Glu Gly
65 70 75 80

Ala Leu Asn Glu Ile Asn Asn Asn Leu Gln Arg Val Arg Glu Leu Ala
85 90 95

Val Gln Ser Ala Asn Ser Thr Asn Ser Gln Ser Asp Leu Asp Ser Ile
100 105 110

Gln Ala Glu Ile Thr Gln Arg Leu Asn Glu Ile Asp Arg Val Ser Gly
115 120 125

Gln Thr Gln Phe Asn Gly Val Lys Val Leu Ala Gln Asp Asn Thr Leu
130 135 140

Thr Ile Gln Val Gly Ala Asn Asp Gly Glu Thr Ile Asp Ile Asp Leu
145 150 155 160

Lys Gln Ile Asn Ser Gln Thr Leu Gly Leu Asp Thr Leu Asn Val Gln
165 170 175

Gln Lys Tyr Lys Val Ser Asp Thr Ala Ala Thr Val Thr Gly Tyr Ala
180 185 190

Asp Thr Thr Ile Ala Leu Asp Asn Ser Thr Phe Lys Ala Ser Ala Thr
195 200 205

Gly Leu Gly Gly Thr Asp Gln Lys Ile Asp Gly Asp Leu Lys Phe Asp
210 215 220

Asp Thr Thr Gly Lys Tyr Tyr Ala Lys Val Thr Val Thr Gly Gly Thr
225 230 235 240

Gly Lys Asp Gly Tyr Tyr Glu Val Ser Val Asp Lys Thr Asn Gly Glu
245 250 255

```
Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg Gly
                485                 490                 495

Gly Gly Gly Ser Gly Gly Gly Gly Ser Met Met Ala Pro Asp Pro Asn
            500                 505                 510

Ala Asn Pro Asn Ala Asn Pro Asn Ala Asn Pro Asn Ala Asn Pro Asn
        515                 520                 525

Ala Asn Pro Asn Ala Asn Pro Asn Ala Asn Pro Asn Ala Asn Pro Asn
    530                 535                 540

Ala Asn Pro Asn Ala Asn Pro Asn Ala Asn Pro Asn Ala Asn Pro Asn
545                 550                 555                 560

Ala Asn Pro Asn Ala Asn Pro Asn Ala Asn Pro Asn Ala Asn Pro Asn
                565                 570                 575

Ala Asn Pro Asn Ala Asn Pro Asn Ala Asn Pro Asn Lys Asn Asn Gln
            580                 585                 590

Gly Asn Gly Gln Gly His Asn Met Pro Asn Asp Pro Asn Arg Asn Val
        595                 600                 605

Asp Glu Asn Ala Asn Ala Asn Asn Ala Val Lys Asn Asn Asn Asn Glu
    610                 615                 620

Glu Pro Ser Asp Lys His Ile Glu Gln Tyr Leu Lys Lys Ile Lys Asn
625                 630                 635                 640

Ser Ile Ser Thr Glu Trp Ser Pro Cys Ser Val Thr Cys Gly Asn Gly
                645                 650                 655

Ile Gln Val Arg Ile Lys Pro Gly Ser Ala Asn Lys Pro Lys Asp Glu
            660                 665                 670
```

```
Leu Asp Tyr Glu Asn Asp Ile Glu Lys Lys Ile Cys Lys Met Glu Lys
        675                 680                 685

Cys Ser Ser Val Phe Asn Val Val Asn Ser
    690                 695


<210> SEQ ID NO 117
<211> LENGTH: 692
<212> TYPE: PRT
<213> ORGANISM: Artificial Sequence
<220> FEATURE:
<223> OTHER INFORMATION: Synthetic Polypeptide

<400> SEQUENCE: 117

Met Met Ala Pro Asp Pro Asn Ala Asn Pro Asn Ala Asn Pro Asn Ala
1               5                   10                  15

Asn Pro Asn Ala Asn Pro Asn Ala Asn Pro Asn Ala Asn Pro Asn Ala
            20                  25                  30

Asn Pro Asn Ala Asn Pro Asn Ala Asn Pro Asn Ala Asn Pro Asn Ala
        35                  40                  45

Asn Pro Asn Ala Asn Pro Asn Ala Asn Pro Asn Ala Asn Pro Asn Ala
    50                  55                  60

Asn Pro Asn Ala Asn Pro Asn Ala Asn Pro Asn Ala Asn Pro Asn Ala
65                  70                  75                  80

Asn Pro Asn Lys Asn Asn Gln Gly Asn Gly Gln Gly His Asn Met Pro
                85                  90                  95

Asn Asp Pro Asn Arg Asn Val Asp Glu Asn Ala Asn Ala Asn Asn Ala
            100                 105                 110

Val Lys Asn Asn Asn Asn Glu Glu Pro Ser Asp Lys His Ile Glu Gln
        115                 120                 125

Tyr Leu Lys Lys Ile Lys Asn Ser Ile Ser Thr Glu Trp Ser Pro Cys
    130                 135                 140

Ser Val Thr Cys Gly Asn Gly Ile Gln Val Arg Ile Lys Pro Gly Ser
145                 150                 155                 160

Ala Asn Lys Pro Lys Asp Glu Leu Asp Tyr Glu Asn Asp Ile Glu Lys
                165                 170                 175

Lys Ile Cys Lys Met Glu Lys Cys Ser Ser Val Phe Asn Val Val Asn
            180                 185                 190

Ser Arg Pro Val Thr Met Ala Gln Val Ile Asn Thr Asn Ser Leu Ser
        195                 200                 205

Leu Leu Thr Gln Asn Asn Leu Asn Lys Ser Gln Ser Ala Leu Gly Thr
    210                 215                 220

Ala Ile Glu Arg Leu Ser Ser Gly Leu Arg Ile Asn Ser Ala Lys Asp
225                 230                 235                 240

Asp Ala Ala Gly Gln Ala Ile Ala Asn Arg Phe Thr Ala Asn Ile Lys
                245                 250                 255

Gly Leu Thr Gln Ala Ser Arg Asn Ala Asn Asp Gly Ile Ser Ile Ala
            260                 265                 270

Gln Thr Thr Glu Gly Ala Leu Asn Glu Ile Asn Asn Asn Leu Gln Arg
        275                 280                 285

Val Arg Glu Leu Ala Val Gln Ser Ala Asn Ser Thr Asn Ser Gln Ser
    290                 295                 300

Asp Leu Asp Ser Ile Gln Ala Glu Ile Thr Gln Arg Leu Asn Glu Ile
305                 310                 315                 320

Asp Arg Val Ser Gly Gln Thr Gln Phe Asn Gly Val Lys Val Leu Ala
                325                 330                 335
```

```
Gln Asp Asn Thr Leu Thr Ile Gln Val Gly Ala Asn Asp Gly Glu Thr
            340                 345                 350

Ile Asp Ile Asp Leu Lys Gln Ile Asn Ser Gln Thr Leu Gly Leu Asp
        355                 360                 365

Thr Leu Asn Val Gln Gln Lys Tyr Lys Val Ser Asp Thr Ala Ala Thr
    370                 375                 380

Val Thr Gly Tyr Ala Asp Thr Thr Ile Ala Leu Asp Asn Ser Thr Phe
385                 390                 395                 400

Lys Ala Ser Ala Thr Gly Leu Gly Gly Thr Asp Gln Lys Ile Asp Gly
                405                 410                 415

Asp Leu Lys Phe Asp Asp Thr Thr Gly Lys Tyr Tyr Ala Lys Val Thr
            420                 425                 430

Val Thr Gly Gly Thr Gly Lys Asp Gly Tyr Tyr Glu Val Ser Val Asp
        435                 440                 445

Lys Thr Asn Gly Glu Val Thr Leu Ala Gly Gly Ala Thr Ser Pro Leu
    450                 455                 460

Thr Gly Gly Leu Pro Ala Thr Ala Thr Glu Asp Val Lys Asn Val Gln
465                 470                 475                 480

Val Ala Asn Ala Asp Leu Thr Glu Ala Lys Ala Ala Leu Thr Ala Ala
                485                 490                 495

Gly Val Thr Gly Thr Ala Ser Val Val Lys Met Ser Tyr Thr Asp Asn
            500                 505                 510

Asn Gly Lys Thr Ile Asp Gly Gly Leu Ala Val Lys Val Gly Asp Asp
        515                 520                 525

Tyr Tyr Ser Ala Thr Gln Asn Lys Asp Gly Ser Ile Ser Ile Asn Thr
    530                 535                 540

Thr Lys Tyr Thr Ala Asp Asp Gly Thr Ser Lys Thr Ala Leu Asn Lys
545                 550                 555                 560

Leu Gly Gly Ala Asp Gly Lys Thr Glu Val Val Ser Ile Gly Gly Lys
                565                 570                 575

Thr Tyr Ala Ala Ser Lys Ala Glu Gly His Asn Phe Lys Ala Gln Pro
            580                 585                 590

Asp Leu Ala Glu Ala Ala Ala Thr Thr Thr Glu Asn Pro Leu Gln Lys
        595                 600                 605

Ile Asp Ala Ala Leu Ala Gln Val Asp Thr Leu Arg Ser Asp Leu Gly
    610                 615                 620

Ala Val Gln Asn Arg Phe Asn Ser Ala Ile Thr Asn Leu Gly Asn Thr
625                 630                 635                 640

Val Asn Asn Leu Thr Ser Ala Arg Ser Arg Ile Glu Asp Ser Asp Tyr
                645                 650                 655

Ala Thr Glu Val Ser Asn Met Ser Arg Ala Gln Ile Leu Gln Gln Ala
            660                 665                 670

Gly Thr Ser Val Leu Ala Gln Ala Asn Gln Val Pro Gln Asn Val Leu
        675                 680                 685

Ser Leu Leu Arg
    690


<210> SEQ ID NO 118
<211> LENGTH: 13
<212> TYPE: PRT
<213> ORGANISM: Salmonella typhimurium

<400> SEQUENCE: 118

Leu Gln Arg Val Arg Glu Leu Ala Val Gln Ser Ala Asn
1               5                   10
```

<210> SEQ ID NO 119
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 119

Ala Ala Arg Val
1

<210> SEQ ID NO 120
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 120

Ala Tyr Arg Val
1

<210> SEQ ID NO 121
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 121

Tyr Ala Gly Leu
1

<210> SEQ ID NO 122
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 122

Ser Ser Thr Thr
1

<210> SEQ ID NO 123
<211> LENGTH: 2080
<212> TYPE: RNA
<213> ORGANISM: Varicella Zoster Virus

<400> SEQUENCE: 123
ucaagcuuuu ggacccucgu acagaagcua auacgacuca cuauagggaa auaagagaga 60
aaagaagagu aagaagaaau auaagagcca ccauggggac agugaauaag ccgguugugg 120
gcgugcuuau gggcuuuggg auuauuaccg guacauuacg aauuaccaau ccagugcgcg 180
ccagugugcu gcguuacgac gacuuucaca uugacgagga uaagcuggau acuaacagcg 240
uguacgaacc uuauuaccac ucagaucaug ccgaaucaag cuggguuaau agaggagaaa 300
gcagccgaaa agccuacgac cacaacucac cuuauauuug gcccagaaac gauuaugacg 360
guuuccugga aaacgcacau gaacaccaug gagucuacaa ccaaggcagg ggaaucgaca 420
guggcgagcg ucuuaugcag ccaacacaga ugucggcaca ggaggaucuc ggugaugaca 480
ccggcauaca cgugauuccc acauuaaacg gcgacgacag acauaagauc gucaaugugg 540

-continued

```
aucagcguca guaugggau gucuuuaaag gcgauuugaa uccaaagccc caaggacaga    600

gacugaucga ggucucugua gaagaaaauc accccuucac uuugcgcgcu ccaauccaga    660

ggauuuacgg ggugcguuau accgaaacuu ggaguuucuu gccgucacug acguguacgg    720

gggaugccgc ccccgcaauc cagcacaucu gucugaaaca caccacaugc uuucaggacg    780

ugguugugga uguggauugc gcggaaaaca caaaagaaga ccaacucgcc gaaaucagcu    840

aucguuuuca ggguaaaaaa gaggccgacc aaccguggau uguugugaau acgagcacgc    900

ucuucgauga gcuugaacuc gaucccccgg aaaucgagcc uggggguucua aaaguguuga    960

ggaccgagaa gcaguaccuc ggggguuuaua ucuggaauau gagaggcucc gauggcaccu   1020

cuaccuacgc aacguuucug guuaccugga agggagacga gaagacacgg aauccaacgc   1080

ccgcugugac cccucagccu aggggagccg aauuccacau guggaacuau cacucccaug   1140

uauucagugu gggugacacu uucagccugg ccaugcaccu gcaguauaag auucacgagg   1200

cacccuucga ccuccugcug gagugguugu acguaccuau ugaucccacu ugucagccca   1260

ugcgccugua cuccacuugc uuguaccacc ccaaugcacc acagugucua ucacacauga   1320

acuccgggug uaccuuuacu ucaccccauc uugcccagcg ggucgccagc acaguguauc   1380

agaacuguga gcaugcugac aacuauacug cuuauugccu cggaauaucc cauauggagc   1440

caagcuucgg gcucauacug cacgauggug guacgacacu caaguucgug gacacccccg   1500

aaagccuuuc uggcuuguac guguucgugg ucuacuucaa uggacaugug gaggcagugg   1560

cuuacacagu gguuucgaca guugaucacu uuguaaaugc cauugaggaa cgcggcuucc   1620

cgccuacagc gggccagccc ccugcgacaa caaaaccaaa agagauuacg cccguuaaauc   1680

cugggacuag uccauugcug agguaugccg ccuggacugg cggucuggcg gccgugguac   1740

uucuguguuu agucauauuu cugaucugua ccgcuaaacg uaugcggguc aaggcuuacc   1800

guguugacaa gucuccuuac aaucagucaa uguacuaugc aggacucccu guugacgauu   1860

ucgaagacuc agagaguaca gacacagaag aagaauucgg aaacgcuaua gguggcucuc   1920

acggagguag cucguauaca guguacaucg auaaaaccag augauaaaug gcuggagccu   1980

cgguggccau gcuucuugcc ccuugggccu ccccccagcc ccuccucccc uuccugcacc   2040

cguacccccg uggucuuuga auaaagucug agugggcggc                          2080
```

```
<210> SEQ ID NO 124
<211> LENGTH: 1276
<212> TYPE: RNA
<213> ORGANISM: Varicella Zoster Virus

<400> SEQUENCE: 124

ucaagcuuuu ggacccucgu acagaagcua auacgacuca cuauagggaa auaagagaga     60

aaagaagagu aagaagaaau auaagagcca ccauguuuuu aauccaaugu uugauaucgg    120

ccguuauauu uuacauacaa gugaccaacg cuuugaucuu caagggcgac cacgugagcu    180

ugcaaguuaa cagcagucuc acgucuaucc uuauucccau gcaaaaugau aauuauacag    240

agauaaaagg acagcuuguc uuuauuggag agcaacuacc uaccgggaca aacuauagcg    300

gaacacugga acuguuauac gcggauacgg uggcguuuug uuuccgguca guacaaguaa    360

uaagauacga cggaugu ccc cggauuagaa cgagcgcuuu uauuucgugu agguacaaac    420

auucguggca uuaugguaac ucaacggauc ggauaucaac agagccggau gcuggugaa      480

uguugaaaau uaccaaaccg ggaauaaaug augcuggugu guauguacuu cuuguucggu    540

uagaccauag cagauccacc gaugguuuca uucuuggugu aaauguauau acagcgggcu    600
```

cgcaucacaa cauucacggg guuaucuaca cuucuccauc ucuacagaau ggauauucua 660
caagagcccu uuuucaacaa gcucguuugu gugauuuacc cgcgacaccc aaagggucccg 720 guaccucccu guuucaacau augcuugauc uucgugccgg uaaaucguua gaggauaacc 780
cuugguuaca ugaggacguu guuacgacag aaacuaaguc cguuguuaag gaggggauag 840
aaaaucacgu auauccaacg gauaugucca cguuacccga aaaguccuu aaugauccuc 900 cagaaaaucu acuuauaauu auuccuauag uagcgucugu caugauccuc accgccaugg 960
uuauuguuau uguaauaagc guuaagcgac guagaauuaa aaaacaucca auuuaucgcc 1020
caaauacaaa aacaagaagg ggcauacaaa augcgacacc agaauccgau gugauguugg 1080
aggccgccau ugcacaacua gcaacgauuc gcgaagaauc ccccccacau uccguuguaa 1140
acccguuugu uaaauaguga uaauaggcug gagccucggu ggccaugcuu cuugccccuu 1200
gggccucccc ccagccccuc cuccccuucc ugcacccgua cccccguggu cuuugaauaa 1260
agucugagug ggcggc 1276

<210> SEQ ID NO 125
<211> LENGTH: 1897
<212> TYPE: RNA
<213> ORGANISM: Artificial Sequence
<220> FEATURE:
<223> OTHER INFORMATION: Synthetic Polynucleotide

<400> SEQUENCE: 125
ucaagcuuuu ggacccucgu acagaagcua auacgacuca cuauagggaa auaagagaga 60
aaagaagagu aagaagaaau auaagagcca ccauggggac aguuaauaaa ccuguggugg 120
ggguauugau gggguucgga auuaucacgg gaacguugcg uauaacgaau ccggucagag 180
cauccgucuu gcgauacgau gauuuucaca ucgaugaaga caaacuggau acaaacuccg 240
uauaugagcc uuacuaccau ucagaucaug cggagucuuc augguaaau cggggagagu 300 cuucgcgaaa agcguacgau cauaacucac cuuauauaug gccacguaau gauuaugaug 360
gauuuuuaga gaacgcacac gaacaccaug ggguguauaa ucagggccgu gguaucgaua 420
gcggggaacg guuaaugcaa cccacacaaa ugucugcaca ggaggaucuu ggggacgaua 480
cgggcaucca cguuaucccu acguuaaacg gcgaugacag acauaaaaau guaaaugugg 540
accaacguca auacggugac guguuuaaag gagaucuuaa uccaaaaccc caaggccaaa 600
gacucauuga ggugucagug gaagaaaauc acccguuuac uuuacgcgca ccgauucagc 660
ggauuuaugg aguccgguac accgagacuu ggagcuuuuu gccgucauua accuguacgg 720
gagacgcagc gcccgccauc cagcauauau guuuaaaaca uacaacaugc uuucaagacg 780
ugguggugga uguggauugc gcggaaaaua cuaaagagga ucaguuggcc gaaaucaguu 840
accguuuuca agguaagaag gaagcggacc aaccguggau uguuguaaac acgagcacac 900
uguuugauga acucgaauua gacccccccg agauugaacc gggugucuug aaaguacuuc 960
ggacagaaaa acaauacuug ggugguguaca uuuggaacau gcgcggcucc gaugguacgu 1020
cuaccuacgc cacguuuuug gucaccugga aaggggauga aaaaacaaga aacccuacgc 1080
ccgcaguaac uccucaacca agaggggcug aguuucauau guggaauuac cacucgcaug 1140
uauuuucagu uggugauacg uuuagcuugg caaugcaucu ucaguauaag auacaugaag 1200
cgccauuuga uuugcuguua gagugguugu augucccau cgauccuaca ugucaaccaa 1260
ugcgguuaua uucuacgugu uuguaucauc ccaacgcacc ccaaugccuc ucucauauga 1320

-continued auuccgguug uacauuuacc ucgccacauu uagcccagcg uguugcaagc acaguguauc 1380
aaaauuguga acaugcagau aacuacaccg cauauugucu gggaauaucu cauauggagc 1440
cuagcuuugg ucuaaucuua cacgacgggg gcaccacguu aaaguuugua gauacacccg 1500
agaguuuguc gggauuauac guuuuugugg uguauuuuaa cgggcauguu gaagccguag 1560
cauacacugu uguauccaca guagaucauu uuguaaacgc aauugaagag cguggauuuc 1620
cgccaacggc cggucagcca ccggcgacua cuaaacccaa ggaaauuacc cccguaaacc 1680
ccggaacguc accacuucua cgauaugccg cauggaccgg agggcuugca gcaguaguac 1740
uuuuaugucu cguaaauauu uuaaucugua cggcuugaug auaauaggcu ggagccucgg 1800
uggccaugcu ucuugccccu ugggccuccc cccagccccu ccucccccuuc cugcacccgu 1860 acccccgugg ucuuugaaua aagucugagu gggcggc 1897

<210> SEQ ID NO 126
<211> LENGTH: 1867
<212> TYPE: RNA
<213> ORGANISM: Artificial Sequence
<220> FEATURE:
<223> OTHER INFORMATION: Synthetic Polynucleotide

<400> SEQUENCE: 126
ucaagcuuuu ggacccucgu acagaagcua auacgacuca cuauagggaa auaagagaga 60
aaagaagagu aagaagaaau auaagagcca ccauggaaac cccggcgcag cugcuguuuc 120
ugcugcugcu guggcugccg gauaccaccg gcuccgucuu gcgauacgau gauuuucaca 180
ucgaugaaga caaacuggau acaaacuccg uauaugagcc uuacuaccau ucagaucaug 240
cggagucuuc auggguaaau cggggagagu cuucgcgaaa agcguacgau cauaacucac 300
cuuauauaug gccacguaau gauuaugaug gauuuuuaga gaacgcacac gaacaccaug 360
gggguguaaa ucagggccgu gguaucgaua gcggggaacg guuaaugcaa cccacacaaa 420
ugucugcaca ggaggaucuu ggggacgaua cgggcaucca cguuaucccu acguuaaacg 480
gcgaugacag acauaaaauu guaaaugugg accaacguca auacggugac guguuuaaag 540
gagaucuuaa uccaaaaccc caaggccaaa gacucauuga ggugucagug gaagaaaauc 600
acccguuuac uuuacgcgca ccgauucagc ggauuuaugg aguccgguac accgagacuu 660
ggagcuuuuu gccgucauua accuguacgg gagacgcagc gcccgccauc cagcauauau 720
guuuaaaaca uacaacaugc uuucaagacg ugguggugga uguggauugc gcggaaaaua 780
cuaaagagga ucaguuggcc gaaaucaguu accguuuuca agguaagaag gaagcggacc 840
aaccguggau uguuguaaac acgagcacac uguuugauga acucgaauua gacccccccg 900
agauugaacc ggguguucuug aaaguacuuc ggacagaaaa acaauacuug ggugugauaca 960 uuuggaacau gcgcggcucc gaugguacgu cuaccuacgc cacguuuuug gucaccugga 1020
aaggggauga aaaaacaaga aacccuacgc ccgcaguaac ucucaacca agaggggcug 1080 aguuucauau guggaauuac cacucgcaug uauuuucagu uggugauacg uuuagcuugg 1140
caaugcaucu ucaguauaag auacaugaag cgccauuuga uuugcuguua gagugguugu 1200
auguccccau cgauccuaca ugucaaccaa ugcgguuaua uucuacgugu uuguaucauc 1260
ccaacgcacc ccaaugccuc ucucauauga auuccgguug uacauuuacc ucgccacauu 1320
uagcccagcg uguugcaagc acaguguauc aaaauuguga acaugcagau aacuacaccg 1380
cauauugucu gggaauaucu cauauggagc cuagcuuugg ucuaaucuua cacgacgggg 1440
gcaccacguu aaaguuugua gauacacccg agaguuuguc gggauuauac guuuuugugg 1500

```
uguauuuuaa cgggcauguu gaagccguag cauacacugu uguauccaca guagaucauu   1560

uuguaaacgc aauugaagag cguggauuuc cgccaacggc cggucagcca ccggcgacua   1620

cuaaacccaa ggaaauuacc cccguaaacc ccggaacguc accacuucua cgauaugccg   1680

cauggaccgg agggcuugca gcaguaguac uuuuaugucu cguaauauuu uuaaucugua   1740

cggcuugaug auaauaggcu ggagccucgg uggccaugcu ucuugccccu ugggccuccc   1800

cccagccccu ccuccccuuc cugcacccgu acccccgugg ucuuugaaua aagucugagu   1860

gggcggc                                                             1867
```

<210> SEQ ID NO 127
<211> LENGTH: 1933
<212> TYPE: RNA
<213> ORGANISM: Artificial Sequence
<220> FEATURE:
<223> OTHER INFORMATION: Synthetic Polynucleotide

<400> SEQUENCE: 127

```
ucaagcuuuu ggacccucgu acagaagcua auacgacuca cuauagggaa auaagagaga     60

aaagaagagu aagaagaaau auaagagcca ccauggggac aguuaauaaa ccuguggugg    120

ggguauugau gggguucgga auuaucacgg gaacguugcg uauaacgaau ccggucagag    180

cauccgucuu gcgauacgau gauuuucaca ucgaugaaga caaacuggau acaaacuccg    240

uauaugagcc uuacuaccau ucagaucaug cggagucuuc augguaaau cggggagagu    300

cuucgcgaaa agcguacgau cauaacucac cuuauauaug gccacguaau gauuaugaug    360

gauuuuuaga gaacgcacac gaacaccaug ggguguauaa ucagggccgu gguaucgaua    420

gcggggaacg guuaaugcaa cccacacaaa ugucugcaca ggaggaucuu ggggacgaua    480

cgggcaucca cguuaucccu acguuaaacg gcgaugacag acauaaaauu guaaaugugg    540

accaacguca auacggugac guguuuaaag gagaucuuaa uccaaaaccc caaggccaaa    600

gacucauuga ggugucagug gaagaaaauc acccguuuac uuuacgcgca ccgauucagc    660

ggauuuaugg aguccgguac accgagacuu ggagcuuuuu gccgucauua accuguacgg    720

gagacgcagc gcccgccauc cagcauauau guuuaaaaca uacaacaugc uuucaagacg    780

ugguggugga uguggauugc gcggaaaaua cuaaagagga ucaguuggcc gaaaucaguu    840

accguuuuca agguaagaag gaagcggacc aaccguggau uguuguaaac acgagcacac    900

uguuugauga acucgaauua gacccccccg agauugaacc ggguguguug aaaguacuuc    960

ggacagaaaa acaauacuug gguguguaca uuuggaacau gcgcggcucc gaugguacgu   1020

cuaccuacgc cacguuuuug gucaccugga aaggggauga aaaaacaaga aacccuacgc   1080

ccgcaguaac ucccucaacca agaggggcug aguuucauau guggaauuac cacucgcaug   1140

uauuuucagu uggugauacg uuuagcuugg caaugcaucu ucaguauaag auacaugaag   1200

cgccauuuga uuugcuguua gaguggguugu augucccau cgauccuaca ugucaaccaa   1260

ugcgguuaua uucuacgugu uuguaucauc ccaacgcacc ccaaugccuc ucucauauga   1320

auuccgguug uacauuuacc ucgccacauu uagcccagcg uguugcaagc acaguguauc   1380

aaaauuguga acaugcagau aacuacaccg cauauugucu gggaauaucu cauauggagc   1440

cuagcuuugg ucuaaucuua cacgacgggg gcaccacguu aaaguuugua gauacacccg   1500

agaguuuguc gggauuauac guuuuugugg uguauuuuaa cgggcauguu gaagccguag   1560

cauacacugu uguauccaca guagaucauu uuguaaacgc aauugaagag cguggauuuc   1620
```

cgccaacggc cggucagcca ccggcgacua cuaaacccaa ggaaauuacc cccguaaacc 1680
ccggaacguc accacuucua cgauaugccg cauggaccgg agggcuugca gcaguaguac 1740
uuuuaugucu cguaaauauu uuaaucugua cggcuaaacg aaugaggguu aaagccuaua 1800
ggguagacaa gugaugauaa uaggcuggag ccucgguggc caugcuucuu gccccuuggg 1860
ccucccccca gccccuccuc cccuuccugc acccguaccc ccgugggucuu ugaauaaagu 1920 cugagugggc ggc 1933

<210> SEQ ID NO 128
<211> LENGTH: 1933
<212> TYPE: RNA
<213> ORGANISM: Artificial Sequence
<220> FEATURE:
<223> OTHER INFORMATION: Synthetic Polynucleotide

<400> SEQUENCE: 128
ucaagcuuuu ggacccucgu acagaagcua auacgacuca cuauagggaa auaagagaga 60
aaagaagagu aagaagaaau auaagagcca ccaugggggac aguuaauaaa ccuguggugg 120
ggguauugau gggguucgga auuaucacgg gaacguugcg uauaacgaau ccggucagag 180
cauccgucuu gcgauacgau gauuuucaca ucgaugaaga caaacuggau acaaacuccg 240
uauaugagcc uuacuaccau ucagaucaug cggagucuuc augguaaau cggggagagu 300 cuucgcgaaa agcguacgau cauaacucac cuuauauaug gccacguaau gauuaugaug 360
gauuuuuaga gaacgcacac gaacaccaug ggguguauaa ucagggccgu gguaucgaua 420
gcggggaacg guuaaugcaa cccacacaaa ugucugcaca ggaggaucuu ggggacgaua 480
cgggcaucca cguuaucccu acguuaaacg gcgaugacag acauaaaauu guaaaugugg 540
accaacguca auacggugac guguuuaaag gagaucuuaa uccaaaaccc caaggccaaa 600
gacucauuga ggugucagug gaagaaaauc acccguuuac uuuacgcgca ccgauucagc 660
ggauuuaugg aguccgguac accgagacuu ggagcuuuuu gccgucauua accuguacgg 720
gagacgcagc gcccgccauc cagcauauau guuuaaaaca uacaacaugc uuucaagacg 780
ugguggugga uguggauugc gcggaaaaua cuaaagagga ucaguuggcc gaaaucaguu 840
accguuuuca agguaagaag gaagcggacc aaccguggau uguuguaaac acgagcacac 900
uguuugauga acucgaauua gacccccccg agauugaacc ggguguucuug aaaguacuuc 960 ggacagaaaa acaauacuug ggugugaca uuuggaacau gcgcggcucc gaugguacgu 1020
cuaccuacgc cacguuuuug gucaccugga aaggggauga aaaaacaaga aacccuacgc 1080
ccgcaguaac uccucaacca agaggggcug aguuucauau guggaauuac cacucgcaug 1140
uauuuucagu uggugauacg uuuagcuugg caaugcaucu ucaguauaag auacaugaag 1200
cgccauuuga uuugcuguua gagugguugu augucccau cgauccuaca ugucaaccaa 1260
ugcgguuaua uucuacgugu uuguaucauc ccaacgcacc ccaaugccuc ucucauauga 1320
auuccgguug uacauuuacc ucgccacauu uagcccagcg uguugcaagc acaguguauc 1380
aaaauuguga acaugcagau aacuacaccg cauauugucu gggaauaucu cauauggagc 1440
cuagcuuugg ucuaaucuua cacgacgggg gcaccacguu aaaguuugua gauacacccg 1500
agaguuuguc gggauuauac guuuuugugg uguauuuuaa cgggcauguu gaagccguag 1560
cauacacugu uguauccaca guagaucauu uuguaaacgc aauugaagag cguggauuuc 1620
cgccaacggc cggucagcca ccggcgacua cuaaacccaa ggaaauuacc cccguaaacc 1680
ccggaacguc accacuucua cgauaugccg cauggaccgg agggcuugca gcaguaguac 1740
uuuuaugucu cguaauauuu uuaaucugua cggcuaaacg aaugaggguu aaagccgcca 1800
ggguagacaa gugaugauaa uaggcuggag ccucgguggc caugcuucuu gccccuuggg 1860
ccucccccca gccccuccuc cccuuccugc acccguaccc ccguggucuu ugaauaaagu 1920
cugagugggc ggc 1933

<210> SEQ ID NO 129
<211> LENGTH: 2083
<212> TYPE: RNA
<213> ORGANISM: Artificial Sequence
<220> FEATURE:
<223> OTHER INFORMATION: Synthetic Polynucleotide

<400> SEQUENCE: 129
ucaagcuuuu ggacccucgu acagaagcua auacgacuca cuauagggaa auaagagaga 60
aaagaagagu aagaagaaau auaagagcca ccauggggac aguuaauaaa ccuguggugg 120
ggguauugau ggggguucgga auuaucacgg gaacguugcg uauaacgaau ccggucagag 180
cauccgucuu gcgauacgau gauuuucaca ucgaugaaga caaacuggau acaaacuccg 240
uauaugagcc uuacuaccau ucagaucaug cggagucuuc augguaaau cggggagagu 300 cuucgcgaaa agcguacgau cauaacucac cuuauauaug gccacguaau gauuaugaug 360
gauuuuuaga gaacgcacac gaacaccaug gggguguauaa ucagggccgu gguaucgaua 420
gcggggaacg guuaaugcaa cccacacaaa ugucugcaca ggaggaucuu ggggacgaua 480
cgggcaucca cguuaucccu acguuaaacg gcgaugacag acauaaaauu guaaaugugg 540
accaacguca auacggugac guguuuaaag gagaucuuaa uccaaaaccc caaggccaaa 600
gacucauuga ggugucagug gaagaaaauc acccguuuac uuuacgcgca ccgauucagc 660
ggauuuaugg aguccgguac accgagacuu ggagcuuuuu gccgucauua accuguacgg 720
gagacgcagc gcccgccauc cagcauauau guuuaaaaca uacaacaugc uuucaagacg 780
ugguggugga uguggauugc gcggaaaaua cuaaagagga ucaguuggcc gaaaucaguu 840
accguuuuca agguaagaag gaagcggacc aaccguggau uguuguaaac acgagcacac 900
uguuugauga acucgaauua gaccccccccg agauugaacc gggugucuug aaaguacuuc 960
ggacagaaaa acaauacuug ggugugauaca uuuggaacau gcgcggcucc gaugguacgu 1020
cuaccuacgc cacguuuuug gucaccugga aaggggauga aaaaacaaga aacccuacgc 1080
ccgcaguaac uccucaacca agaggggcug aguuucauau guggaauuac cacucgcaug 1140
uauuuucagu uggugauacg uuuagcuugg caaugcaucu ucaguauaag auacaugaag 1200
cgccauuuga uuugcuguua gagugguugu augucccau cgauccuaca ugucaaccaa 1260
ugcgguuaua uucuacgugu uuguaucauc ccaacgcacc ccaaugccuc ucucauauga 1320
auuccgguug uacauuuacc ucgccacauu uagcccagcg uguugcaagc acaguguauc 1380
aaaauuguga acaugcagau aacuacaccg cauauugucu gggaauaucu cauauggagc 1440
cuagcuuugg ucuaaucuua cacgacgggg gcaccacguu aaaguuugua gauacacccg 1500
agaguuuguc gggauuauac guuuuugugg uguauuuuaa cgggcauguu gaagccguag 1560
cauacacugu uguauccaca guagaucauu uuguaaacgc aauugaagag cguggauuuc 1620
cgccaacggc cggucagcca ccggcgacua cuaaacccaa ggaaauuacc cccguaaacc 1680
ccggaacguc accacuucua cgauaugccg cauggaccgg agggcuugca gcaguaguac 1740
uuuuaugucu cguaauauuu uuaaucugua cggcuaaacg aaugaggguu aaagccuaua 1800

```
ggguagacaa guccccguau aaccaaagca uguauuacgc uggccuucca guggacgauu   1860

ucgaggacgc cgaagccgcc gaugccgaag aagaguuugg uaacgcgauu ggagggaguc   1920

acgggggguuc gaguuacacg guguauauag auaagacccg gugaugauaa uaggcuggag   1980

ccucggugge caugcuucuu gccccuuggg ccucccccca gccccuccuc cccuuccugc   2040

acccguaccc ccguggucuu ugaauaaagu cugagugggc ggc                   2083
```

```
<210> SEQ ID NO 130
<211> LENGTH: 2083
<212> TYPE: RNA
<213> ORGANISM: Artificial Sequence
<220> FEATURE:
<223> OTHER INFORMATION: Synthetic Polynucleotide

<400> SEQUENCE: 130

ucaagcuuuu ggacccucgu acagaagcua auacgacuca cuauagggaa auaagagaga     60

aaagaagagu aagaagaaau auaagagcca ccaugggggac aguuaauaaa ccuguggugg    120

ggguauugau gggguucgga auuaucacgg gaacguugcg uauaacgaau ccggucagag    180

cauccgucuu gcgauacgau gauuuucaca ucgaugaaga caaacuggau acaaacuccg    240

uauaugagcc uuacuaccau ucagaucaug cggagucuuc augguaaau cggggagagu    300

cuucgcgaaa agcguacgau cauaacucac cuuauauaug gccacguaau gauuaugaug    360

gauuuuuaga gaacgcacac gaacaccaug ggguguauaa ucagggccgu gguaucgaua    420

gcggggaacg guuaaugcaa cccacacaaa ugucugcaca ggaggaucuu ggggacgaua    480

cgggcaucca cguuaucccu acguuaaacg gcgaugacag acauaaaauu guaaaugugg    540

accaacguca auacggugac guguuuaaag gagaucuuaa uccaaaaccc caaggccaaa    600

gacucauuga ggugucagug gaagaaaauc acccguuuac uuuacgcgca ccgauucagc    660

ggauuuaugg aguccgguac accgagacuu ggagcuuuuu gccgucauua accuguacgg    720

gagacgcagc gcccgccauc cagcauauau guuuaaaaca uacaacaugc uuucaagacg    780

ugguggugga uguggauugc gcggaaaaua cuaaagagga ucaguuggcc gaaaucaguu    840

accguuuuca agguaagaag gaagcggacc aaccguggau uguuguaaac acgagcacac    900

uguuugauga acucgaauua gacccccccg agauugaacc ggguguucuug aaaguacuuc    960

ggacagaaaa acaauacuug ggugugaca uuuggaacau gcgcggcucc gaugguacgu   1020

cuaccuacgc cacguuuuug gucaccugga aaggggauga aaaaacaaga aacccuacgc   1080

ccgcaguaac uccucaacca agaggggcug aguuucauau guggaauuac cacucgcaug   1140

uauuuucagu uggugauacg uuuagcuugg caaugcaucu ucaguauaag auacaugaag   1200

cgccauuuga uuugcuguua gaguggguugu augucccau cgauccuaca ugucaaccaa   1260

ugcgguuaua uucuacgugu uuguaucauc ccaacgcacc ccaaugccuc ucucauauga   1320

auuccgguug uacauuuacc ucgccacauu uagcccagcg uguugcaagc acaguguauc   1380

aaaauuguga acaugcagau aacuacaccg cauauugucu gggaauaucu cauauggagc   1440

cuagcuuugg ucuaaucuua cacgacgggg gcaccacguu aaaguuugua gauacacccg   1500

agaguuuguc gggauuauac guuuuugugg uguauuuuaa cgggcauguu gaagccguag   1560

cauacacugu uguauccaca guagaucauu uuguaaacgc aauugaagag cguggauuuc   1620

cgccaacggc cggucagcca ccggcgacua cuaaacccaa ggaaauuacc cccguaaacc   1680

ccggaacguc accacuucua cgauaugccg cauggaccgg agggcuugca gcaguaguac   1740

uuuuaugucu cguaauauuu uuaaucugua cggcuaaacg aaugaggguu aaagccuaua   1800
```

ggguagacaa guccccguau aaccaaagca uguauggcgc uggccuucca guggacgauu 1860
ucgaggacgc cgaagccgcc gaugccgaag aagaguuugg uaacgcgauu ggagggaguc 1920 acgggggguuc gaguuacacg guguauauag auaagacccg gugaugauaa uaggcuggag 1980
ccucgguggc caugcuucuu gccccuuggg ccucccccca gccccuccuc cccuuccugc 2040
acccguaccc ccguggucuu ugaauaaagu cugagugggc ggc 2083

<210> SEQ ID NO 131
<211> LENGTH: 2050
<212> TYPE: RNA
<213> ORGANISM: Artificial Sequence
<220> FEATURE:
<223> OTHER INFORMATION: Synthetic Polynucleotide

<400> SEQUENCE: 131
ucaagcuuuu ggacccucgu acagaagcua auacgacuca cuauagggaa auaagagaga 60
aaagaagagu aagaagaaau auaagagcca ccauggagac ucccgcucag cuacuguucc 120
uccugcuccu uuggcugccu gauacuacag gcucuguuuu gcgguacgac gacuuucaca 180
ucgaugagga caagcucgac acuaauagcg uguaugagcc cuacuaccau ucagaucacg 240
ccgaguccuc uugggugaac aggggugaaa guucuaggaa agccuaugau cacaacagcc 300
cuuauauuug gccacggaau gauuacgacg gauuucucga aaaugcccac gagcaucacg 360
gaguguacaa ccagggccgu ggaaucgacu cuggggagag auugaugcaa ccuacacaga 420
ugagcgccca ggaagaucuc ggggaugaua caggaauuca cguuaucccu acauuaaacg 480
gagaugaccg ccacaaaauc gucaaugucg aucaaagaca guauggagau guguucaaag 540
gcgaucucaa cccuaagccg cagggccaga gacucauuga ggugucuguc gaagagaacc 600
acccuuucac ucugcgcgcu cccauucaga gaaucuaugg aguucgcuau acggagacuu 660
ggucauuccu ucccucccug acaugcaccg gagacgccgc cccugccauu cagcacauau 720
gccugaaaca uaccaccugu uuccaggaug ugguugguuga uguugauugu gcugaaaaua 780
ccaaggaaga ccaacuggcc gagauuaguu accgguucca agggaaaaag gaagccgacc 840
agccauggau uguggguuaau acaagcacuc uguucgauga gcucgagcug gaucccccccg 900 agauagaacc cggaguucug aaagugcucc ggacagaaaa acaauaucug ggagucuaca 960
uauggaacau gcgcgguucc gaugggaccu ccacuuaugc aaccuuucuc gucacgugga 1020
agggagauga gaaaacuagg aaucccacac ccgcugucac accacagcca agaggggcug 1080
aguuccauau guggaacuau cauagucacg uguuuagugu cggagauacg uuuucauugg 1140
cuaugcaucu ccaguacaag auucaugagg cucccuucga ucuguugcuu gagugguugu 1200
acgucccgau ugacccgacc ugccagccca ugcgacugua cagcaccugu cucuaccauc 1260
caaacgcucc gcaaugucug agccacauga acucugggug uacuuucacc aguccccacc 1320
ucgcccagcg gguggccucu acuguuuacc agaacuguga gcacgccgac aacuacaccg 1380
cauacugccu cgguauuucu cacauggaac ccuccuucgg acucauccug cacgaugggg 1440
gcacuacccu gaaguucguu gauacgccag aaucucuguc ugggcucuau guuuucgugg 1500
ucuacuucaa uggccauguc gaggccgugg ccuauacugu cguuucuacc guggaucauu 1560
uugugaacgc caucgaagaa cggggauucc ccccuacggc aggccagccg ccugcaacca 1620
ccaagcccaa ggaaauaaca ccagugaacc cuggcaccuc accucuccua agauaugccg 1680
cguggacagg gggacuggcg gcaguggugc uccucugucu cgugaucuuu cugaucugua 1740
cagccaagag gaugaggguc aaggcuuaua gaguggacaa gucccccuac aaucagucaa 1800
uguacuacgc cggccuuccc guugaugauu uugaggauuc cgaguccaca gauacugagg 1860
aagaguucgg uaacgcuaua ggcggcucuc acggggguuc aagcuacacg guuuacauug 1920
acaagacacg cugauaauag gcuggagccu cgguggccau gcuucuugcc ccuugggccu 1980
ccccccagcc ccuccucccc uuccugcacc cguacccccg uggucuuuga auaaagucug 2040
agugggcggc 2050

<210> SEQ ID NO 132
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 132

Gly Ala Gly Leu
1

<210> SEQ ID NO 133
<211> LENGTH: 1844
<212> TYPE: RNA
<213> ORGANISM: Artificial Sequence
<220> FEATURE:
<223> OTHER INFORMATION: Synthetic Polynucleotide

<400> SEQUENCE: 133
auggggacag uuaauaaacc ugugguggggg guauugaugg gguucggaau uaucacggga 60
acguugcgua uaacgaaucc ggucagagca uccgucuugc gauacgauga uuuucacauc 120
gaugaagaca aacuggauac aaacuccgua uaugagccuu acuaccauuc agaucaugcg 180
gagucuucau ggguaaaucg gggagagucu ucgcgaaaag cguacgauaa ucauaacuca 240
ccuuauauau ggccacguaa ugauuaugau ggauuuuuag agaacgcaca cgaacaccau 300
gggguguaua aucagggccg ugguaucgau agcggggaac gguuaaugca acccacacaa 360
augucugcac aggaggaucu uggggacgau acgggcaucc acguuauccc uacguuaaac 420
ggcgaugaca gacauaaaau uguaaaugug gaccaacguc aauacgguga cguguuuaaa 480
ggagaucuua auccaaaacc ccaaggccaa agacucauug aggugucagu ggaagaaaau 540
cacccguuua cuuuacgcgc accgauucag cggauuuaug gaguccggua caccgagacu 600
uggagcuuuu ugccgucauu aaccuguacg ggagacgcag cgcccgccau ccagcauaua 660
uguuuaaaac auacaacaug cuuucaagac gugguggugg auguggauug cgcggaaaau 720
acuaaagagg aucaguuggc cgaaaucagu uaccguuuuc aagguaagaa ggaagcggac 780
caaccgugga uuguuguaaa cacgagcaca cuguuugaug aacucgaauu agacccccc 840 gagauugaac cgggugucuu gaaaguacuu cggacagaaa aacaauacuu gggugugugac 900 auuuggaaca ugcgcggcuc cgaugguacg ucuaccuacg ccacguuuuu ggucaccugg 960
aaaggggaug aaaaaacaag aaacccuacg cccgcaguaa cuccucaacc aagaggggcu 1020
gaguuucaua uguggaauua ccacucgcau guauuuucag uuggugauac guuuagcuug 1080
gcaaugcauc uucaguauaa gauacaugaa gcgccauuug auuugcuguu agagugguug 1140
uaugucccca ucgauccuac augucaacca augcgguuau auucuacgug uuuguaucau 1200
cccaacgcac cccaaugccu cucucauaug aauuccgguu guacauuuac cucgccacau 1260
uuagcccagc guguugcaag cacaguguau caaaauugug aacaugcaga uaacuacacc 1320

| | |
|---|---|
| gcauauuguc ugggaauauc ucauauggag ccuagcuuug gcuaaucuu acacgacggg | 1380 |
| ggcaccacgu uaaaguuugu agauacaccc gagaguuugu cgggauuaua cguuuuugug | 1440 |
| guguauuuua acgggcaugu ugaagccgua gcauacacug uuguauccac aguagaucau | 1500 |
| uuuguaaacg caauugaaga gcguggauuu ccgccaacgg ccggucagcc accggcgacu | 1560 |
| acuaaacccca aggaaauuac ccccguaaac cccggaacgu caccacuucu acgauaugcc | 1620 |
| gcauggaccg gagggcuugc agcaguagua cuuuuaugu ucguaauauu uuaaaucugu | 1680 |
| acggcuaaac gaaugagggu uaaagccgcc agggauagaca agugaugaua auaggcugga | 1740 |
| gccucggugg ccaugcuucu ugcccccuugg gccucccccc agcccuccu ccccuuccug | 1800 |
| cacccguacc cccguggucu ugaauaaag ucgaguggg cggc | 1844 |

<210> SEQ ID NO 134
<211> LENGTH: 1838
<212> TYPE: RNA
<213> ORGANISM: Artificial Sequence
<220> FEATURE:
<223> OTHER INFORMATION: Synthetic Polynucleotide

<400> SEQUENCE: 134

| | |
|---|---|
| augggggacag uuaauaaacc uguggugggg guauugaugg gguucggaau uaucacggga | 60 |
| acguugcgua uaacgaaucc ggucagagca uccgucuugc gauacgauga uuuucacauc | 120 |
| gaugaagaca aacuggauac aaacuccgua uaugagccuu acuaccauuc agaucaugcg | 180 |
| gagucuucau ggguaaaaucg gggagagucu cgcgaaaag cguacgauca uaacucaccu | 240 |
| uauauauggc cacguaauga uuaugaugga uuuuuagaga acgcacacga acaccauggg | 300 |
| guguauaauc agggccgugg uaucgauagc ggggaacggu uaaugcaacc cacacaaaug | 360 |
| ucugcacagg aggaucuugg ggacgauacg ggcauccacg uuauccuac guuaaacggc | 420 |
| gaugacagac auaaaauugu aaaugugggac caacgucaau acggugacgu guuuaaagga | 480 |
| gaucuuaauc caaaaccccca aggccaaaga cucauugagg ugucaggga gaaaaucac | 540 |
| ccguuuacuu uacgcgcacc gauucagcgg auuuaugag uccgguacac cgagacuugg | 600 |
| agcuuuuugc cgucauuaac cuguacggga gacgcagcgc ccgccaucca gcauauaugu | 660 |
| uuaaagcaua caacaugcuu ucaagacgug ugguggaug uggauugcgc ggaaaauacu | 720 |
| aaagaggauc aguggccgaa aaucaguuac cguuuucaag guaagaagga gcggaccaa | 780 |
| ccgguggauug uuguaaacac gagcacacug uuugauguaac ucgaauuaga cccacccgag | 840 |
| auugaaccggg ugucuugaa aguacuucgg acagagaaac aauacuuggg uguguacauu | 900 |
| uggaacaugc gcggcuccga ugguacgucu accuacgcca cguuuuuggu caccuggaaa | 960 |
| ggggaugaga agacaagaaa cccuacgccc gcaguaacuc ucaaccaag aggggcugag | 1020 |
| uuucauaugu ggaauuacca cucgcaugua uuuucaguug gugauacguu uagcuuggca | 1080 |
| augcaucuuc aguauaagau acaugaagcg ccauuugauu ugcuguuaga gugguugau | 1140 |
| gucccccaucg auccuacaug ucaaccaaug cgguuauauu cuacguguuu guaucauccc | 1200 |
| aacgcacccc aaugccucuc ucauaugaau uccgguugua cauuuaccuc gccacauuua | 1260 |
| gcccagcgug uugcaagcac aguguacag aauugugaac augcagauaa cuacaccgca | 1320 |
| uauugucugg gaauaucuca uaggagccu agcuugguc uaaucuuaca cgacgggggc | 1380 |
| accacguuaa aguuuguaga uacaccgag aguuugucgg gauuauacgu uuuguggug | 1440 |
| uauuuuaacg ggcauguuga agccuagca uacacguuug uauccacagu agaucauuuu | 1500 |
| guaaacgcaa uugaagagcg uggauuuccg ccaacggccg gucagccacc ggcgacuacu | 1560 |

aaacccaagg aaauuacccc cguaaacccc ggaacgucac cacuucuacg auaugccgca 1620
uggaccggag ggcuugcagc aguaguacuu uuaugucucg uaauauuuuu aaucuguacg 1680
gcuaaacgaa ugaggguuaa agccgccagg guagacaagu gauaauaggc uggagccucg 1740
guggccaugc uucuugcccc uugggccucc ccccagcccc uccuccccuu ccugcacccg 1800
uacccccgug gucuuugaau aaagucugag ugggcggc 1838

<210> SEQ ID NO 135
<211> LENGTH: 2036
<212> TYPE: RNA
<213> ORGANISM: Artificial Sequence
<220> FEATURE:
<223> OTHER INFORMATION: Synthetic Polynucleotide

<400> SEQUENCE: 135
ggggaaauaa gagagaaaag aagaguaaga agaaauauaa gagccaccau ggggacaguu 60
aauaaaccug ugguggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaagcauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cacccgagau ugaaccgggu 900
gucuugaaag uacuucggac agagaaacaa uacuugggug uguacauuug gaacaugcgc 960
ggcuccgaug guacgucuac cuacgccacg uuuuugguca ccuggaaagg ggaugagaag 1020
acaagaaacc cuacgcccgc aguaacuccu caaccaagag gggcugaguu ucauaugugg 1080
aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucagaa uugugaacau gcagauaacu acaccgcaua uugucuggga 1380
auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uaaacgaaug 1740
aggguuaaag ccuacagggu agacaagucu ccuuacaauc agucaaugua cuaugcagga 1800 cuccccuguug acgauuucga agacucagag aguacagaca cagaagaaga auucggaaac 1860
gcuauaggug gcucucacgg agguagcucg uauacagugu acaucgauaa aaccagauga 1920
uaauaggcug gagccucggu ggccaugcuu cuugccccuu gggccucccc ccagccccuc 1980
cuccccuucc ugcacccgua cccccguggu cuuugaauaa agucugagug ggcggc 2036

<210> SEQ ID NO 136
<211> LENGTH: 1991
<212> TYPE: RNA
<213> ORGANISM: Artificial Sequence
<220> FEATURE:
<223> OTHER INFORMATION: Synthetic Polynucleotide

<400> SEQUENCE: 136
ggggaaauaa gagagaaaag aagaguaaga agaaauauaa gagccaccau ggggacaguu 60
aauaaaccug uggugggggu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaagcg uacgaucaua acucaccuua uauauggcca 300
cguaaugauu augauggauu uuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aaaauuguaa auguggacca acgucaauac ggugacgugu uuaaaggaga ucuuaaucca 540
aaaccccaag gccaaagacu cauugaggug ucaguggaag aaaaucaccc guuuacuuua 600
cgcgcaccga uucagcggau uuauggaguc cgguacaccg agacuuggag cuuuuugccg 660
ucauuaaccu guacgggaga cgcagcgccc gccauccagc auauauguuu aaagcauaca 720
acaugcuuuc aagacguggu gguggaugug gauugcgcgg aaaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cccccgagau ugaaccgggu 900
gucuugaaag uacuucggac agagaaacaa uacuugggug uguacauuug gaacaugcgc 960
ggcuccgaug guacgucuac cuacgccacg uuuuugguca ccuggaaagg ggaugagaag 1020
acaagaaacc cuacgcccgc aguaacuccu caaccaagag ggcugaguu ucauaugugg 1080 aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucagaa uugugaacau gcagauaacu acaccgcaua uugucuggga 1380
auaucucaua uggagccuag cuuuggucua aucuuacacg acgggggcac cacguuaaag 1440
uuuguagaua cacccgagag uuugucggga uuauacguuu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacccccg uaaaccccgg aacgucacca cuucuacgau augccgcaug gaccggaggg 1680
cuugcagcag uaguacuuuu augucucgua auauuuuuaa ucuguacggc uaaacgaaug 1740
aggguuaaag ccgccagggu agacaaguga uaauaggcug gagccucggu ggccaugcuu 1800

```
cuugccccuu gggccucccc ccagccccuc cuccccuucc ugcacccgua cccccguggu   1860

cuuugaauaa agucugagug ggcggcaaaa aaaaaaaaaa aaaaaaaaaa aaaaaaaaaa   1920

aaaaaaaaaa aaaaaaaaaa aaaaaaaaaa aaaaaaaaaa aaaaaaaaaa aaaaaaaaaa   1980

aaaaaaucua g                                                        1991


<210> SEQ ID NO 137
<211> LENGTH: 1991
<212> TYPE: RNA
<213> ORGANISM: Artificial Sequence
<220> FEATURE:
<223> OTHER INFORMATION: Synthetic Polynucleotide

<400> SEQUENCE: 137

ggggaaauaa gagagaaaag aagaguaaga agaaauauaa gagccaccau gggcaccgug     60

aacaagccug uugugggcgu gcugaugggc uucggcauca ucacaggcac ccugcggauc    120

accaauccug ugcgggcuag cgugcugaga uacgacgacu uccacaucga cgaggacaag    180

cuggacacca acagcgugua cgagcccuac uaccacagcg aucacgccga gucuagcugg    240

gucaacagag gcgagagcag cagaaaggcc uacgaccaca acagcccuua caucuggccc    300

agaaacgacu acgacggcuu ccucgagaau gcccacgaac accacggcgu guacaaucaa    360

ggcagaggca ucgacagcgg cgagagacug augcagccua cacagaugag cgcccaagag    420

gaccugggag augauaccgg cauccacgug aucccuacac ugaacggcga cgaccggcac    480

aagaucguga acguggacca gagacaguac ggcgacgugu ucaagggcga ccugaauccu    540

aagccucagg gccagcgccu gaucgagguu uccguggaag agaaucaccc uuucacacug    600

cgggcuccca uccagagaau cuacggcgug cgcuauaccg agacaugguc cuuucugccc    660

agccugacau guaccggcga cgccgcuccu gccauccagc acauuugucu gaagcacacc    720

accuguuucc aggacguggu gguggaugug gacugcgccg agaacaccaa agaggaucag    780

cuggccgaga ucagcuaccg guuccaggga aagaaagagg ccgaccagcc uuggaucgug    840

gucaacacca gcacacuguu cgacgagcug gaacuggacc cuccugagau ugaacccggc    900

guccugaagg ugcugagaac cgagaagcag uaccugggag uguacaucug gaacaugaga    960

ggcagcgacg gcaccucuac cuacgccacc uuucugguca cauggaaggg cgacgagaag   1020

accagaaauc ccacaccagc cgugacaccu cagccuagag gcgccgaauu ucacaugugg   1080

aacuaccacu cucacguguu cagcgugggc gauaccuuca gccuggccau gcaucugcag   1140

uacaagaucc acgaggcucc cuucgaccug cugcuggaau ggcuguacgu gcccaucgau   1200

ccuaccugcc agccuaugcg gcuguacucc accugucugu aucacccuaa cgcuccucag   1260

ugccugagcc acaugaauag cggcugcacc uucacaagcc cucaccuggc ucagcgagug   1320

gccagcacag uguaccagaa uugcgagcac gccgacaauu acaccgccua cugucugggc   1380

aucagccaca uggaaccuag cuucggccug auccugcacg auggcggcac cacacugaag   1440

uucguggaca caccugagag ccugagcggc cuguaugugu uuguggugua cuucaacggc   1500

cacguggaag ccguggccua caccguggug ucuaccgugg accacuucgu gaacgccauc   1560

gaggaaagag gcuucccucc aacugcugga cagccuccug ccaccaccaa gccuaaagaa   1620

aucacacccg ugaaucccgg cacuagcccu cugcuuagau acgccgcuug gacaggcgga   1680

cuggcugcug uuguucugcu gugccugguc aucuuccuga ucugcaccgc caagcggaug   1740

agagugaaag ccgccagagu ggacaaguga uaauaggcug gagccucggu ggccaugcuu   1800
```

cuugccccuu gggccucccc ccagccccuc cuccccuucc ugcacccgua cccccguggu 1860
cuuugaauaa agucugagug ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaucua g 1991

<210> SEQ ID NO 138
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 138
gggaaauaag agagaaaaga agaguaagaa gaaauauaag agccacc 47

<210> SEQ ID NO 139
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 139
ugauaauagg cuggagccuc gguggccaug cuucuugccc cuugggccuc cccccagccc 60
cuccuccccu uccugcaccc guacccccgu ggucuuugaa uaaagucuga gugggcggc 119

<210> SEQ ID NO 140
<211> LENGTH: 105
<212> TYPE: RNA
<213> ORGANISM: Artificial Sequence
<220> FEATURE:
<223> OTHER INFORMATION: Synthetic Polynucleotide

<400> SEQUENCE: 140
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa ucuag 105

<210> SEQ ID NO 141
<211> LENGTH: 1991
<212> TYPE: RNA
<213> ORGANISM: Artificial Sequence
<220> FEATURE:
<223> OTHER INFORMATION: Synthetic Polynucleotide

<400> SEQUENCE: 141
ggggaaauaa gagagaaaag aagaguaaga agaaauauaa gagccaccau ggggacaguu 60
aauaaaccug uggugggcgu auugaugggg uucggaauua ucacgggaac guugcguaua 120
acgaauccgg ucagagcauc cgucuugcga uacgaugauu uucacaucga ugaagacaaa 180
cuggauacaa acuccguaua ugagccuuac uaccauucag aucaugcgga gucuucaugg 240
guaaaucggg gagagucuuc gcgaaaggcg uacgaucaua acucaccuua uauauggcca 300
cguaaugauu augauggauu cuuagagaac gcacacgaac accauggggu guauaaucag 360
ggccguggua ucgauagcgg ggaacgguua augcaaccca cacaaauguc ugcacaggag 420
gaucuugggg acgauacggg cauccacguu aucccuacgu uaaacggcga ugacagacau 480
aagauuguaa auguggacca acgucaauac ggugacgugu uuaaaggaga ucuuaaucca 540
aagccccaag gccaaagacu cauugaggug ucaguggaag agaaucaccc guuuacuuua 600
cgcgcaccga uucagcggau uuauggaguc cgguacaccg agacuuggag cuucuugccg 660
ucauuaaccu guacgggaga cgcagcgccc gccauccagc auauauguuu aaagcauaca 720
acaugcuuuc aagacguggu gguggaugug gauugcgcgg agaauacuaa agaggaucag 780
uuggccgaaa ucaguuaccg uuuucaaggu aagaaggaag cggaccaacc guggauuguu 840
guaaacacga gcacacuguu ugaugaacuc gaauuagacc cacccgagau ugaaccgggu 900
gucuugaaag uacuucggac agagaaacaa uacuugggug uguacauuug gaacaugcgc 960
ggcuccgaug guacgucuac cuacgccacg uucuugguca ccuggaaagg ggaugagaag 1020
acaagaaacc cuacgcccgc aguaacuccu caaccaagag gggcugaguu ucauaugugg 1080
aauuaccacu cgcauguauu uucaguuggu gauacguuua gcuuggcaau gcaucuucag 1140
uauaagauac augaagcgcc auuugauuug cuguuagagu gguuguaugu ccccaucgau 1200
ccuacauguc aaccaaugcg guuauauucu acguguuugu aucaucccaa cgcaccccaa 1260
ugccucucuc auaugaauuc cgguuguaca uuuaccucgc cacauuuagc ccagcguguu 1320
gcaagcacag uguaucagaa uugugaacau gcagauaacu acaccgcaua uugucuggga 1380
auaucucaua uggagccuag cuuuggucua aucuuacacg acggaggcac cacguuaaag 1440
uuuguagaua cacccgagag uuugucggga uuauacgucu uuguggugua uuuuaacggg 1500
cauguugaag ccguagcaua cacuguugua uccacaguag aucauuuugu aaacgcaauu 1560
gaagagcgug gauuuccgcc aacggccggu cagccaccgg cgacuacuaa acccaaggaa 1620
auuacgcccg uaaaccccgg aacgucacca cuucuacgau augccgcaug gaccggaggg 1680
cuugcagcag uaguacuuuu augucucgua auauucuuaa ucuguacggc uaaacgaaug 1740
aggguuaaag ccgccagggu agacaaguga uaauaggcug gagccucggu ggccaugcuu 1800
cuugccccuu gggccucccc ccagccccuc cuccccuucc ugcacccgua cccccguggu 1860
cuuugaauaa agucugagug ggcggcaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaucua g 1991

<210> SEQ ID NO 142
<211> LENGTH: 1869
<212> TYPE: RNA
<213> ORGANISM: Artificial Sequence
<220> FEATURE:
<223> OTHER INFORMATION: Synthetic Polynucleotide

<400> SEQUENCE: 142
auggggacag uuaauaaacc ugugguuggg guauugaugg gguucggaau uaucacggga 60
acguugcgua uaacgaaucc ggucagagca uccgucuugc gauacgauga uuuucacauc 120
gaugaagaca aacuggauac aaacuccgua uaugagccuu acuaccauuc agaucaugcg 180
gagucuucau ggguaaaucg gggagagucu ucgcgaaaag cguacgauca uaacucaccu 240
uauauauggc cacguaauga uuaugaugga uuuuuagaga acgcacacga acaccauggg 300
guguauaauc agggccgugg uaucgauagc ggggaacggu uaaugcaacc cacacaaaug 360
ucugcacagg aggaucuugg ggacgauacg ggcauccacg uuaucccuac guuaaacggc 420
gaugacagac auaaaaauugu aaauguggac caacgucaau acggugacgu guuuaaagga 480
gaucuuaauc caaaacccca aggccaaaga cucauugagg ugucagugga agaaaaucac 540
ccguuuacuu uacgcgcacc gauucagcgg auuuauggag uccgguacac cgagacuugg 600
agcuuuuugc cgucauuaac cuguacggga gacgcagcgc ccgccaucca gcauauaugu 660
uuaaagcaua caacaugcuu ucaagacgug gugguggaug uggauugcgc ggaaaauacu 720
aaagaggauc aguuggccga aaucaguuac cguuuucaag guaagaagga agcggaccaa 780
ccguggauug uuguaaacac gagcacacug uuugaugaac ucgaauuaga cccacccgag 840
auugaaccgg gugucuugaa aguacuucgg acagagaaac aauacuuggg uguguacauu 900
uggaacaugc gcggcuccga ugguacgucu accuacgcca cguuuuuggu caccuggaaa 960
ggggaugaga agacaagaaa cccuacgccc gcaguaacuc cucaaccaag aggggcugag 1020
uuucauaugu ggaauuacca cucgcaugua uuuucaguug gugauacguu uagcuuggca 1080
augcaucuuc aguauaagau acaugaagcg ccauuugauu ugcuguuaga gugguuguau 1140
guccccaucg auccuacaug ucaaccaaug cgguuauauu cuacguguuu guaucauccc 1200
aacgcacccc aaugccucuc ucauaugaau uccgguugua cauuuaccuc gccacauuua 1260
gcccagcgug uugcaagcac aguguaucag aauugugaac augcagauaa cuacaccgca 1320
uauugucugg gaauaucuca uauggagccu agcuuugguc uaaucuuaca cgacgggggc 1380
accacguuaa aguuuguaga uacacccgag aguuugucgg gauuauacgu uuuugugug 1440 uauuuuaacg ggcauguuga agccguagca uacacuguug uauccacagu agaucauuuu 1500
guaaacgcaa uugaagagcg uggauuuccg ccaacggccg gucagccacc ggcgacuacu 1560
aaacccaagg aaauuacccc cguaaacccc ggaacgucac cacuucuacg auaugccgca 1620
uggaccggag ggcuugcagc aguaguacuu uuaugucucg uaauauuuuu aaucuguacg 1680
gcuaaacgaa ugaggguuaa agccuacagg guagacaagu cuccuuacaa ucagucaaug 1740
uacuaugcag gacucccugu ugacgauuuc gaagacucag agaguacaga cacagaagaa 1800
gaauucggaa acgcuauagg uggcucucac ggagguagcu cguauacagu guacaucgau 1860
aaaaccaga 1869

<210> SEQ ID NO 143
<211> LENGTH: 1719
<212> TYPE: RNA
<213> ORGANISM: Artificial Sequence
<220> FEATURE:
<223> OTHER INFORMATION: Synthetic Polynucleotide

<400> SEQUENCE: 143
auggggacag uuaauaaacc ugugguggggg guauugaugg gguucggaau uaucacggga 60
acguugcgua uaacgaaucc ggucagagca uccgucuugc gauacgauga uuuucacauc 120
gaugaagaca aacuggauac aaacuccgua uaugagccuu acuaccauuc agaucaugcg 180
gagucuucau ggguaaaucg gggagagucu ucgcgaaaag cguacgauca uaacucaccu 240
uauauauggc cacguaauga uuaugaugga uuuuuagaga acgcacacga acaccauggg 300
guguauaauc agggccgugg uaucgauagc ggggaacggu uaaugcaacc cacacaaaug 360
ucugcacagg aggaucuugg ggacgauacg ggcauccacg uuaucccuac guuaaacggc 420
gaugacagac auaaaaauugu aaauguggac caacgucaau acggugacgu guuuaaagga 480
gaucuuaauc caaaacccca aggccaaaga cucauugagg ugucagugga agaaaaucac 540
ccguuuacuu uacgcgcacc gauucagcgg auuuauggag uccgguacac cgagacuugg 600
agcuuuuugc cgucauuaac cuguacggga gacgcagcgc ccgccaucca gcauauaugu 660 uuaaaaacaua caacaugcuu ucaagacgug gugguggaug uggauugcgc ggaaaauacu 720
aaagaggauc aguuggccga aaucaguuac cguuuucaag guaagaagga agcggaccaa 780
ccguggauug uuguaaacac gagcacacug uuugaugaac ucgaauuaga cccccccgag 840
auugaaccgg gugucuugaa aguacuucgg acagagaaac aauacuuggg uguguacauu 900
uggaacaugc gcggcuccga ugguacgucu accuacgcca cguuuuuggu caccuggaaa 960
ggggaugaga agacaagaaa cccuacgccc gcaguaacuc cucaaccaag aggggcugag 1020
uuucauaugu ggaauuacca cucgcaugua uuuucaguug gugauacguu uagcuuggca 1080
augcaucuuc aguauaagau acaugaagcg ccauuugauu ugcuguuaga gugguuguau 1140 gucoccaucg auccuacaug ucaaccaaug cgguuauauu cuacguguuu guaucauccc 1200
aacgcacccc aaugccucuc ucauaugaau uccgguugua cauuuaccuc gccacauuua 1260
gcccagcgug uugcaagcac aguguaucaa aauugugaac augcagauaa cuacaccgca 1320
uauugucugg gaauaucuca uauggagccu agcuuugguc uaaucuuaca cgacgggggc 1380
accacguuaa aguuuguaga uacacccgag aguuugucgg gauuauacgu uuuuguggug 1440
uauuuuaacg ggcauguuga agccguagca uacacuguug uauccacagu agaucauuuu 1500
guaaacgcaa uugaagagcg uggauuuccg ccaacggccg gucagccacc ggcgacuacu 1560
aaacccaagg aaauuacccc cguaaacccc ggaacgucac cacuucuacg auaugccgca 1620
uggaccggag ggcuugcagc aguaguacuu uuaugucucg uaauauuuuu aaucuguacg 1680
gcuaaacgaa ugaggguuaa agccgccagg guagacaag 1719

<210> SEQ ID NO 144
<211> LENGTH: 1719
<212> TYPE: RNA
<213> ORGANISM: Artificial Sequence
<220> FEATURE:
<223> OTHER INFORMATION: Synthetic Polynucleotide

<400> SEQUENCE: 144
auggggacag uuaauaaacc uguggugggg guauugaugg gguucggaau uaucacggga 60
acguugcgua uaacgaaucc ggucagagca uccgucuugc gauacgauga uuuucacauc 120
gaugaagaca aacuggauac aaacuccgua uaugagccuu acuaccauuc agaucaugcg 180
gagucuucau ggguaaaucg gggagagucu ucgcgaaaag cguacgauca uaacucaccu 240
uauauauggc cacguaauga uuaugaugga uuuuuagaga acgcacacga acaccauggg 300
guguauaauc agggccgugg uaucgauagc ggggaacggu uaaugcaacc cacacaaaug 360
ucugcacagg aggaucuugg ggacgauacg ggcauccacg uuaucccuac guuaaacggc 420
gaugacagac auaaaaauugu aaauguggac caacgucaau acggugacgu guuuaaagga 480
gaucuuaauc caaaacccca aggccaaaga cucauugagg ugucagugga agaaaaucac 540
ccguuuacuu uacgcgcacc gauucagcgg auuuauggag uccgguacac cgagacuugg 600
agcuuuuugc cgucauuaac cuguacggga gacgcagcgc ccgccaucca gcauauaugu 660
uuaaaacaua caacaugcuu ucaagacgug gugguggaug uggauugcgc ggaaaauacu 720
aaagaggauc aguuggccga aaucaguuac cguuuucaag guaagaagga agcggaccaa 780
ccguggauug uuguaaacac gagcacacug uuugaugaac ucgaauuaga cccacccgag 840
auugaaccgg gugucuugaa aguacuucgg acagagaaac aauacuuggg uguguacauu 900
uggaacaugc gcggcuccga ugguacgucu accuacgcca cguuuuuggu caccuggaaa 960
ggggaugaga agacaagaaa cccuacgccc gcaguaacuc cucaaccaag aggggcugag 1020
uuucauaugu ggaauuacca cucgcaugua uuuucaguug gugauacguu uagcuuggca 1080
augcaucuuc aguauaagau acaugaagcg ccauuugauu ugcuguuaga gugguuguau 1140 gucccaucg auccuacaug ucaaccaaug cgguuauauu cuacguguuu guaucauccc 1200
aacgcacccc aaugccucuc ucauaugaau uccgguugua cauuuaccuc gccacauuua 1260
gcccagcgug uugcaagcac aguguaucaa aauugugaac augcagauaa cuacaccgca 1320
uauugucugg gaauaucuca uauggagccu agcuuugguc uaaucuuaca cgacgggggc 1380
accacguuaa aguuuguaga uacacccgag aguuugucgg gauuauacgu uuuuguggug 1440
uauuuuaacg ggcauguuga agccguagca uacacuguug uauccacagu agaucauuuu 1500
guaaacgcaa uugaagagcg uggauuuccg ccaacggccg gucagccacc ggcgacuacu 1560
aaacccaagg aaauuacccc cguaaacccc ggaacgucac cacuucuacg auaugccgca 1620
uggaccggag ggcuugcagc aguaguacuu uuaugucucg uaauauuuuu aaucuguacg 1680
gcuaaacgaa ugaggguuaa agccgccagg guagacaag 1719

<210> SEQ ID NO 145
<211> LENGTH: 1718
<212> TYPE: RNA
<213> ORGANISM: Artificial Sequence
<220> FEATURE:
<223> OTHER INFORMATION: Synthetic Polynucleotide

<400> SEQUENCE: 145 augggacag uuaauaaacc ugugguggg guauugaugg gguucggaau uaucacggga 60
acguugcgua uaacgaaucc ggucagagca uccgucuugc gauacgauga uuuucacauc 120
gaugaagaca aacuggauac aaacuccgua uaugagccuu acuaccauuc agaucaugcg 180
gagucuucau ggguaaaucg gggagagucu ucgcgaaagg cguacgauca uaacucaccu 240
uauauauggc cacguaauga uuaugaugga uuuuuagaga acgcacacga acaccauggg 300
guguauaauc agggccgugg uaucgauagc ggggaacggu uaaugcaacc cacacaaaug 360
ucugcacagg aggaucuugg ggacgauacg ggcauccacg uuaucccuac guuaaacggc 420
gaugacagac auaagauugu aaauguggac caacgucaau acggugacgu guuuaaagga 480
gaucuuaauc caaagcccca aggccaaaga cucauugagg ugucagugga agagaaucac 540
ccguuuacuu uacgcgcacc gauucagcgg auuuauggag uccgguacac cgagacuugg 600
agcuuuuugc cgucauuaac cuguacggga gacgcagcgc ccgccaucca gcauauaugu 660
uuaaagcaua caacaugcuu ucaagacgug gugguggaug uggauugcgc ggagaauacu 720
aaagaggauc aguuggccga aaucaguuac cguuuucaag guaagaagga agcggaccaa 780
ccguggauug uuguaaacac gagcacacug uuugaugaac ucgaauuaga cccccccgag 840
auugaaccgg gugucuugaa aguacuucgg acagagaaac aauacuuggg uguguacauu 900
uggaacaugc gcggcuccga ugguacgucu accuacgcca cguuuuuggu caccuggaaa 960
ggggaugaga agacaagaaa cccuacgccc gcaguaacuc cucaaccaag aggggcugag 1020
uuucauaugu ggaauuacca cucgcaugua uuuucaguug gugauacguu uagcuuggca 1080
augcaucuuc aguauaagau acaugaagcg ccauuugauu ugcuguuaga gugguuguau 1140 gucccaucg auccuacaug ucaaccaaug cgguuauauu cuacguguuu guaucauccc 1200
aacgcacccc aaugccucuc ucauaugaau uccgguugua cauuuaccuc gccacauuua 1260
gcccagcgug uugcaagcac aguguaucag aauugugaac augcagauaa cuacaccgca 1320
uauugucugg gaauaucuca uauggagccu agcuuugguc uaaucuuaca cgacgggggc 1380
accacguuaa aguuuguaga uacacccgag aguuugucgg gauuauacgu uuuuguggug 1440
uauuuuaacg ggcauguuga agccguagca uacacuguug uauccacagu agaucauuuu 1500
guaaacgcaa uugaagagcg uggauuuccg ccaacggccg gucagccacc ggcgacuacu 1560
aaacccaagg aaauuacccc cguaaacccc ggaacgucac cacuucuacg auaugccgca 1620
uggaccggag ggcuugcagc aguaguacuu uuaugucucg uaauauuuuu aaucuguacg 1680
gcuaaacgaa ugaggguuaa agccgccagg guagacaa 1718

<210> SEQ ID NO 146
<211> LENGTH: 1719
<212> TYPE: RNA
<213> ORGANISM: Artificial Sequence
<220> FEATURE:
<223> OTHER INFORMATION: Synthetic Polynucleotide

<400> SEQUENCE: 146
auggggacag uuaauaaacc uguggugggg guauugaugg gguucggaau uaucacggga 60
acguugcgua uaacgaaucc ggucagagca uccgucuugc gauacgauga uuuucacauc 120
gaugaagaca aacuggauac aaacuccgua uaugagccuu acuaccauuc agaucaugcg 180
gagucuucau ggguaaaucg gggagagucu ucgcgaaagg cguacgauca uaacucaccu 240
uauauauggc cacguaauga uuaugaugga uuuuuagaga acgcacacga acaccauggg 300
guguauaauc agggccgugg uaucgauagc ggggaacggu uaaugcaacc cacacaaaug 360
ucugcacagg aggaucuugg ggacgauacg ggcauccacg uuaucccuac guuaaacggc 420
gaugacagac auaagauugu aaauguggac caacgucaau acggugacgu guuuaaagga 480
gaucuuaauc caaagcccca aggccaaaga cucauugagg ugucagugga agagaaucac 540
ccguuuacuu uacgcgcacc gauucagcgg auuuauggag uccgguacac cgagacuugg 600
agcuuuuugc cgucauuaac cuguacggga gacgcagcgc ccgccaucca gcauauaugu 660
uuaaagcaua caacaugcuu ucaagacgug gugguggaug uggauugcgc ggagaauacu 720
aaagaggauc aguuggccga aaucaguuac cguuuucaag guaagaagga agcggaccaa 780
ccguggauug uuguaaacac gagcacacug uuugaugaac ucgaauuaga cccacccgag 840
auugaaccgg gugucuugaa aguacuucgg acagagaaac aauacuuggg uguguacauu 900
uggaacaugc gcggcuccga ugguacgucu accuacgcca cguuuuuggu caccuggaaa 960
ggggaugaga agacaagaaa cccuacgccc gcaguaacuc cucaaccaag aggggcugag 1020
uuucauaugu ggaauuacca cucgcaugua uuuucaguug gugauacguu uagcuuggca 1080
augcaucuuc aguauaagau acaugaagcg ccauuugauu ugcuguuaga gugguuguau 1140
guccccaucg auccuacaug ucaaccaaug cgguuauauu cuacguguuu guaucauccc 1200
aacgcacccc aaugccucuc ucauaugaau uccgguugua cauuuaccuc gccacauuua 1260
gcccagcgug uugcaagcac aguguaucag aauugugaac augcagauaa cuacaccgca 1320
uauugucugg gaauaucuca uauggagccu agcuuugguc uaaucuuaca cgacgggggc 1380
accacguuaa aguuuguaga uacacccgag aguuugucgg gauuauacgu uuuuguggug 1440
uauuuuaacg ggcauguuga agccguagca uacacuguug uauccacagu agaucauuuu 1500
guaaacgcaa uugaagagcg uggauuuccg ccaacggccg gucagccacc ggcgacuacu 1560
aaacccaagg aaauuacccc cguaaacccc ggaacgucac cacuucuacg auaugccgca 1620
uggaccggag ggcuugcagc aguaguacuu uuaugucucg uaauauuuuu aaucuguacg 1680
gcuaaacgaa ugaggguuaa agccgccagg guagacaag 1719

<210> SEQ ID NO 147

<211> LENGTH: 1719
<212> TYPE: RNA
<213> ORGANISM: Artificial Sequence
<220> FEATURE:
<223> OTHER INFORMATION: Synthetic Polynucleotide

<400> SEQUENCE: 147

```
auggggacag uuaauaaacc uguggugggg guauugaugg gguucggaau uaucacggga     60
acguugcgua uaacgaaucc ggucagagca uccgucuugc gauacgauga uuuucacauc    120
gaugaagaca aacuggauac aaacuccgua uaugagccuu acuaccauuc agaucaugcg    180
gagucuucau ggguaaaucg gggagagucu ucgcgaaaag cguacgauca uaacucaccu    240
uauauauggc cacguaauga uuaugaugga uuuuuagaga acgcacacga acaccauggg    300
guguauaauc agggccgugg uaucgauagc ggggaacggu uaaugcaacc cacacaaaug    360
ucugcacagg aggaucuugg ggacgauacg ggcauccacg uuaucccuac guuaaacggc    420
gaugacagac auaaaaauugu aaauguggac caacgucaau acggugacgu guuuaaagga    480
gaucuuaauc caaaaacccca aggccaaaga cucauugagg ugucagugga agaaaaucac    540
ccguuuacuu uacgcgcacc gauucagcgg auuuauggag uccgguacac cgagacuugg    600
agcuuuuugc cgucauuaac cuguacggga gacgcagcgc ccgccaucca gcauauaugu    660
uuaaagcaua caacaugcuu ucaagacgug gugguggaug uggauugcgc ggaaaauacu    720
aaagaggauc aguuggccga aaucaguuac cguuuucaag guaagaagga agcggaccaa    780
ccguggauug uuguaaacac gagcacacug uuugaugaac ucgaauuaga cccccccgag    840
auugaaccgg gugucuugaa aguacuucgg acagagaaac aauacuuggg uguguacauu    900
uggaacaugc gcggcuccga ugguacgucu accuacgcca cguuuuuggu caccuggaaa    960
ggggaugaga agacaagaaa cccuacgccc gcaguaacuc cucaaccaag aggggcugag   1020
uuucauaugu ggaauuacca cucgcaugua uuuucaguug gugauacguu uagcuuggca   1080
augcaucuuc aguauaagau acaugaagcg ccauuugauu ugcuguuaga gugguuguau   1140
guccccaucg auccuacaug ucaaccaaug cgguuauauu cuacguguuu guaucauccc   1200
aacgcacccc aaugccucuc ucauaugaau uccgguugua cauuuaccuc gccacauuua   1260
gcccagcgug uugcaagcac aguguaucag aauugugaac augcagauaa cuacaccgca   1320
uauugucugg gaauaucuca uauggagccu agcuuugguc uaaucuuaca cgacgggggc   1380
accacguuaa aguuuguaga uacacccgag aguuugucgg gauuauacgu uuuuguggug   1440
uauuuuaacg ggcauguuga agccguagca uacacuguug uauccacagu agaucauuuu   1500
guaaacgcaa uugaagagcg uggauuuccg ccaacggccg gucagccacc ggcgacuacu   1560
aaacccaagg aaauuacccc cguaaacccc ggaacgucac cacuucuacg auaugccgca   1620
uggaccggag ggcuugcagc aguaguacuu uuaugucucg uaauauuuuu aaucuguacg   1680
gcuaaacgaa ugaggguuaa agccgccagg guagacaag                          1719
```

<210> SEQ ID NO 148
<211> LENGTH: 1719
<212> TYPE: RNA
<213> ORGANISM: Artificial Sequence
<220> FEATURE:
<223> OTHER INFORMATION: Synthetic Polynucleotide

<400> SEQUENCE: 148

```
auggggacag uuaauaaacc uguggugggg guauugaugg gguucggaau uaucacggga     60
acguugcgua uaacgaaucc ggucagagca uccgucuugc gauacgauga uuuucacauc    120
```

gaugaagaca aacuggauac aaacuccgua uaugagccuu acuaccauuc agaucaugcg 180
gagucuucau ggguaaaucg gggagagucu ucgcgaaaag cguacgauca uaacucaccu 240
uauauauggc cacguaauga uuaugaugga uuuuuagaga acgcacacga acaccauggg 300
guguauaauc agggccgugg uaucgauagc ggggaacggu uaaugcaacc cacacaaaug 360
ucugcacagg aggaucuugg ggacgauacg ggcauccacg uuaucccuac guuaaacggc 420
gaugacagac auaaaaauugu aaauguggac caacgucaau acggugacgu guuuaaagga 480
gaucuuaauc caaaacccca aggccaaaga cucauugagg ugucagugga agaaaaucac 540
ccguuuacuu uacgcgcacc gauucagcgg auuuauggag uccgguacac cgagacuugg 600
agcuuuuugc cgucauuaac cuguacggga gacgcagcgc ccgccaucca gcauauaugu 660
uuaaagcaua caacaugcuu ucaagacgug gugguggaug uggauugcgc ggaaaauacu 720
aaagaggauc aguuggccga aaucaguuac cguuuucaag guaagaagga agcggaccaa 780
ccguggauug uuguaaacac gagcacacug uuugaugaac ucgaauuaga cccacccgag 840
auugaaccgg gugucuugaa aguacuucgg acagagaaac aauacuuggg uguguacauu 900
uggaacaugc gcggcuccga ugguacgucu accuacgcca cguuuuuggu caccuggaaa 960
ggggaugaga agacaagaaa cccuacgccc gcaguaacuc cucaaccaag aggggcugag 1020
uuucauaugu ggaauuacca cucgcaugua uuuucaguug gugauacguu uagcuuggca 1080
augcaucuuc aguauaagau acaugaagcg ccauuugauu ugcuguuaga gugguuguau 1140
guccccaucg auccuacaug ucaaccaaug cgguuauauu cuacguguuu guaucauccc 1200
aacgcacccc aaugccucuc ucauaugaau uccgguugua cauuuaccuc gccacauuua 1260
gcccagcgug uugcaagcac aguguaucag aauugugaac augcagauaa cuacaccgca 1320
uauugucugg gaauaucuca uauggagccu agcuuugguc uaaucuuaca cgacgggggc 1380
accacguuaa aguuuguaga uacacccgag aguuugucgg gauuauacgu uuuuguggug 1440
uauuuuaacg ggcauguuga agccguagca uacacuguug uauccacagu agaucauuuu 1500
guaaacgcaa uugaagagcg uggauuuccg ccaacggccg gucagccacc ggcgacuacu 1560
aaacccaagg aaauuacccc cguaaacccc ggaacgucac cacuucuacg auaugccgca 1620
uggaccggag ggcuugcagc aguaguacuu uuaugucucg uaauauuuuu aaucuguacg 1680
gcuaaacgaa ugagggguuaa agccgccagg guagacaag 1719

<210> SEQ ID NO 149
<211> LENGTH: 1719
<212> TYPE: RNA
<213> ORGANISM: Artificial Sequence
<220> FEATURE:
<223> OTHER INFORMATION: Synthetic Polynucleotide

<400> SEQUENCE: 149
auggggacag uuaauaaacc ugugguggggc guauugaugg gguucggaau uaucacggga 60
acguugcgua uaacgaaucc ggucagagca uccgucuugc gauacgauga uuuucacauc 120
gaugaagaca aacuggauac aaacuccgua uaugagccuu acuaccauuc agaucaugcg 180
gagucuucau ggguaaaucg gggagagucu ucgcgaaagg cguacgauca uaacucaccu 240
uauauauggc cacguaauga uuaugaugga uucuuagaga acgcacacga acaccauggg 300
guguauaauc agggccgugg uaucgauagc ggggaacggu uaaugcaacc cacacaaaug 360
ucugcacagg aggaucuugg ggacgauacg ggcauccacg uuaucccuac guuaaacggc 420
gaugacagac auaagauugu aaauguggac caacgucaau acggugacgu guuuaaagga 480
gaucuuaauc caaagcccca aggccaaaga cucauugagg ugucagugga agagaaucac 540
ccguuuacuu uacgcgcacc gauucagcgg auuuauggag uccgguacac cgagacuugg 600
agcuucuugc cgucauuaac cuguacggga gacgcagcgc ccgccaucca gcauauaugu 660
uuaaagcaua caacaugcuu ucaagacgug gugguggaug uggauugcgc ggagaauacu 720
aaagaggauc aguuggccga aaucaguuac cguuuucaag guaagaagga agcggaccaa 780
ccguggauug uuguaaacac gagcacacug uuugaugaac ucgaauuaga cccacccgag 840
auugaaccgg gugucuugaa aguacuucgg acagagaaac aauacuuggg uguguacauu 900
uggaacaugc gcggcuccga ugguacgucu accuacgcca cguucuuggu caccuggaaa 960
ggggaugaga agacaagaaa cccuacgccc gcaguaacuc cucaaccaag aggggcugag 1020
uuucauaugu ggaauuacca cucgcaugua uuuucaguug gugauacguu uagcuuggca 1080
augcaucuuc aguauaagau acaugaagcg ccauuugauu ugcuguuaga gugguuguau 1140
guccccaucg auccuacaug ucaaccaaug cgguuauauu cuacguguuu guaucauccc 1200
aacgcacccc aaugccucuc ucauaugaau uccgguugua cauuuaccuc gccacauuua 1260
gcccagcgug uugcaagcac aguguaucag aauugugaac augcagauaa cuacaccgca 1320
uauugucugg gaauaucuca uauggagccu agcuuugguc uaaucuuaca cgacggaggc 1380
accacguuaa aguuuguaga uacacccgag aguuugucgg gauuauacgu cuuuguggug 1440
uauuuuaacg ggcauguuga agccguagca uacacuguug uauccacagu agaucauuuu 1500
guaaacgcaa uugaagagcg uggauuuccg ccaacggccg gucagccacc ggcgacuacu 1560
aaacccaagg aaauuacgcc cguaaacccc ggaacgucac cacuucuacg auaugccgca 1620
uggaccggag ggcuugcagc aguaguacuu uuaugucucg uaauauucuu aaucuguacg 1680
gcuaaacgaa ugaggguuaa agccgccagg guagacaag 1719

<210> SEQ ID NO 150
<211> LENGTH: 1719
<212> TYPE: RNA
<213> ORGANISM: Artificial Sequence
<220> FEATURE:
<223> OTHER INFORMATION: Synthetic Polynucleotide

<400> SEQUENCE: 150
augggcaccg ugaacaagcc uguugugggc gugcugaugg gcuucggcau caucacaggc 60
acccugcgga ucaccaaucc ugugcgggcu agcgugcuga gauacgacga cuuccacauc 120
gacgaggaca agcuggacac caacagcgug uacgagcccu acuaccacag cgaucacgcc 180
gagucuagcu gggucaacag aggcgagagc agcagaaagg ccuacgacca caacagcccu 240
uacaucuggc ccagaaacga cuacgacggc uuccucgaga augcccacga acaccacggc 300
guguacaauc aaggcagagg caucgacagc ggcgagagac ugaugcagcc uacacagaug 360
agcgcccaag aggaccuggg agaugauacc ggcauccacg ugaucccuac acugaacggc 420
gacgaccggc acaagaucgu gaacguggac cagagacagu acggcgacgu guucaagggc 480
gaccugaauc cuaagccuca gggccagcgc cugaucgagg uuuccgugga agagaaucac 540
ccuuucacac ugcgggcucc cauccagaga aucuacggcg ugcgcuauac cgagacaugg 600
uccuuucugc ccagccugac auguaccggc gacgccgcuc cugccaucca gcacauuugu 660
cugaagcaca ccaccuguuu ccaggacgug gugguggaug uggacugcgc cgagaacacc 720
aaagaggauc agcuggccga gaucagcuac cgguuccagg gaaagaaaga ggccgaccag 780

-continued

```
ccuuggaucg uggucaacac cagcacacug uucgacgagc uggaacugga cccuccugag    840

auugaacccg gcguccugaa ggugcugaga accgagaagc aguaccuggg aguguacauc    900

uggaacauga gaggcagcga cggcaccucu accuacgcca ccuuucuggu cacauggaag    960

ggcgacgaga agaccagaaa ucccacacca gccgugacac cucagccuag aggcgccgaa   1020

uuucacaugu ggaacuacca cucucacgug uucagcgugg gcgauaccuu cagccuggcc   1080

augcaucugc aguacaagau ccacgaggcu cccuucgacc ugcugcugga auggcuguac   1140

gugcccaucg auccuaccug ccagccuaug cggcuguacu ccaccugucu guaucacccu   1200

aacgcuccuc agugccugag ccacaugaau agcggcugca ccuucacaag cccucaccug   1260

gcucagcgag uggccagcac aguguaccag aauugcgagc acgccgacaa uuacaccgcc   1320

uacugucugg gcaucagcca cauggaaccu agcuucggcc ugauccugca cgauggcggc   1380

accacacuga aguucgugga cacaccugag agccugagcg gccuguaugu guuuguggug   1440

uacuucaacg gccacgugga agccguggcc uacaccgugg ugucuaccgu ggaccacuuc   1500

gugaacgcca ucgaggaaag aggcuucccu ccaacugcug gacagccucc ugccaccacc   1560

aagccuaaag aaaucacacc cgugaauccc ggcacuagcc cucugcuuag auacgccgcu   1620

uggacaggcg gacuggcugc uguuguucug cugugccugg ucaucuuccu gaucugcacc   1680

gccaagcgga ugagagugaa agccgccaga guggacaag                          1719
```